United States Patent
Kwak et al.

(10) Patent No.: US 9,951,270 B2
(45) Date of Patent: Apr. 24, 2018

(54) MULTICYCLIC COMPOUND AND ORGANIC ELECTRONIC DEVICE USING THE SAME

(71) Applicant: LG CHEM, LTD., Seoul (KR)

(72) Inventors: Jiwon Kwak, Daejeon (KR); Sung Kil Hong, Daejeon (KR); Seong So Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 98 days.

(21) Appl. No.: 14/925,436

(22) Filed: Oct. 28, 2015

(65) Prior Publication Data

US 2016/0126473 A1    May 5, 2016

(30) Foreign Application Priority Data

Oct. 30, 2014 (KR) .................. 10-2014-0149580
Oct. 21, 2015 (KR) .................. 10-2015-0146793

(51) Int. Cl.

| | | |
|---|---|---|
| C09K 11/00 | (2006.01) | |
| C09K 11/06 | (2006.01) | |
| C07F 9/6568 | (2006.01) | |
| H01L 51/00 | (2006.01) | |
| C07D 209/88 | (2006.01) | |

(Continued)

(52) U.S. Cl.
CPC ............ C09K 11/06 (2013.01); C07D 209/82 (2013.01); C07D 209/88 (2013.01); C07F 9/65685 (2013.01); H01L 51/0071 (2013.01); C07C 2527/14 (2013.01); C07C 2527/16 (2013.01); C09K 2211/1014 (2013.01); C09K 2211/1022 (2013.01); H01L 51/0052 (2013.01); H01L 51/0058 (2013.01); H01L 51/0061 (2013.01); H01L 51/0067 (2013.01); H01L 51/0072 (2013.01); H01L 51/0073 (2013.01); H01L 51/0074 (2013.01); H01L 51/5012 (2013.01); H01L 51/5016 (2013.01); H01L 51/5056 (2013.01); H01L 51/5072 (2013.01)

(58) Field of Classification Search
CPC .............. H01L 51/0068; H01L 51/0071; H01L 51/0067; H01L 51/0052; H01L 51/0061; H01L 51/5012; C07C 2527/14; C07C 2527/16; C07D 209/82; C07D 209/88; C09K 11/06; C09K 2211/1014; C09K 2211/1022
USPC .............. 548/418; 549/349; 564/426; 568/8; 428/690
See application file for complete search history.

(56) References Cited

U.S. PATENT DOCUMENTS 8,852,756 B2 * 10/2014 Vestweber .............. C07C 13/62
                                                          252/301.16
8,927,117 B2 *  1/2015 Buesing .................. C07C 13/62
                                                              257/40

(Continued)

FOREIGN PATENT DOCUMENTS

KR    10-2000-0051826 A    8/2000

OTHER PUBLICATIONS

Joly et al, "Organophosphorus derivatives for electronics devices", Journal of Materials Chemistry C, The Royal Society of Chemistry, 4 (17), 2016, pp. 3686-3698.*
Baba et al, "Palladium-Catalyzed Direct Synthesis of Phosphole Derivatives from Triarylphosphines through cleavage of carbon-Hydrogen and Carbon-Phosphorus Bonds", Angewandte Chem. Int. Ed., 52, 2013, pp. 11892-11895.*

(Continued)

*Primary Examiner* — Amanda C Walke
(74) *Attorney, Agent, or Firm* — Dentons US LLP

(57) ABSTRACT

The present specification describes a novel polycyclic compound and an organic electroluminescent device using the same.

13 Claims, 2 Drawing Sheets

(51) Int. Cl.
   *C07D 209/82*   (2006.01)
   *H01L 51/50*    (2006.01)

(56) References Cited

U.S. PATENT DOCUMENTS

| | | | | |
|---|---|---|---|---|
| 8,932,731 | B2* | 1/2015 | Parham | C07D 471/16 |
| | | | | 428/690 |
| 8,957,236 | B2* | 2/2015 | Zhang | C07F 9/5045 |
| | | | | 556/404 |
| 8,999,530 | B2* | 4/2015 | Shin | H01L 51/0072 |
| | | | | 257/40 |
| 2014/0225046 | A1* | 8/2014 | Jatsch | C07D 405/14 |
| | | | | 252/519.3 |
| 2015/0031896 | A1* | 1/2015 | Vestweber | C07C 13/62 |
| | | | | 548/405 |
| 2016/0072078 | A1* | 3/2016 | Lee | H01L 51/0072 |
| | | | | 257/40 |
| 2016/0087227 | A1* | 3/2016 | Kim | H01L 51/0062 |
| | | | | 257/40 |
| 2016/0190448 | A1* | 6/2016 | Kim | H01L 51/008 |
| | | | | 257/40 |
| 2016/0333037 | A1* | 11/2016 | Yamaguchi | C09B 57/008 |

OTHER PUBLICATIONS

Duffy et al., "π-Conjugated Phospholes and their Incorporation into device; A Component with a Great Deal of Potential", Chemical Society reviews, Royal Society of Chemistry, 2016, 45, pp. 5296-5310.*

* cited by examiner

[Figure 1]
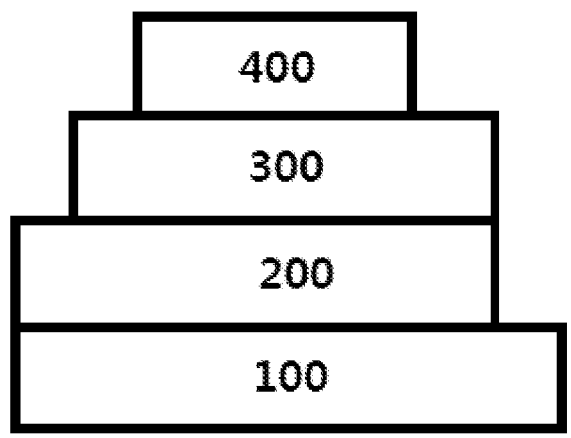
[Figure 2]
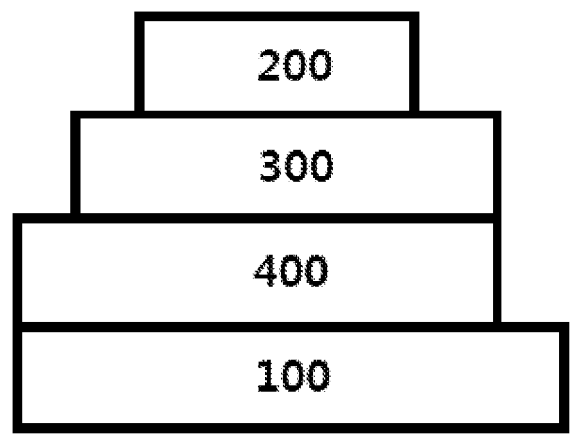

[Figure 3]
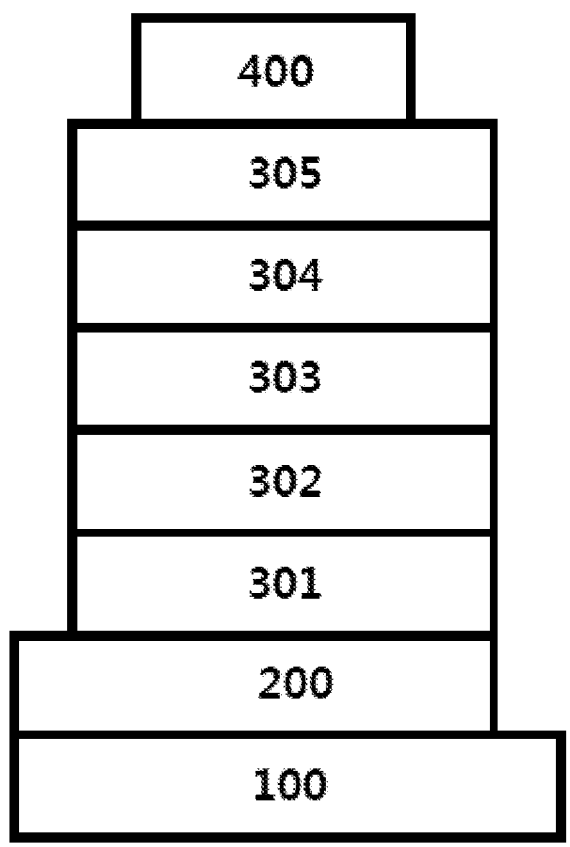

MULTICYCLIC COMPOUND AND ORGANIC ELECTRONIC DEVICE USING THE SAME

CROSS-REFERENCE TO RELATED APPLICATIONS

This application claims the benefit and priority to Korean Application No. 10-2014-0149580, filed Oct. 30, 2014 and Korean Application No. 10-2015-0146793, filed Oct. 21, 2015, both of which are incorporated by reference in their entirety for all purposes as if fully set forth herein.

TECHNICAL FIELD

The present specification relates to a polycyclic compound and an organic electroluminescent device including the same.

BACKGROUND ART

An organic electroluminescent device is a kind of self-emitting type display device, and has an advantage in that the viewing angle is wide, the contrast is excellent, and the response speed is fast.

The organic electroluminescent device has a structure in which an organic thin film is disposed between two electrodes. When a voltage is applied to an organic electroluminescent device having the structure, electrons and holes injected from the two electrodes combine with each other in an organic thin film to make a pair, and then, emit light while being extinguished. The organic thin film may be composed of a single layer or multi layers, if necessary.

A material for the organic thin film may have a light emitting function, if necessary. For example, as the material for the organic thin film, it is also possible to use a compound, which may itself constitute a light emitting layer alone, or it is also possible to use a compound, which may serve as a host or a dopant of a host-dopant-based light emitting layer. In addition to the material, as the material for the organic thin film, it is also possible to use a compound, which may serve as hole injection, hole transport, electron blocking, hole blocking, electron transport or electron injection. In order to improve the performance, service life, or efficiency of the organic electroluminescent device, there is a continuous need for developing a material for an organic thin film.

CITATION LIST

Patent Document

Official Gazette of Korean Patent Application Laid-Open No. 2000-0051826

SUMMARY OF THE INVENTION

The present specification provides a polycyclic compound and an organic electroluminescent device including the same.

The present specification provides a compound represented by the following Formula 1.

[Formula 1]

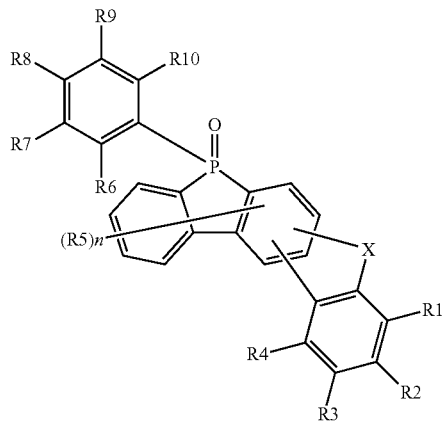

Formula 1 is represented by any one of the following Formulae 1-1 to 1-4,

[Formula 1-1]

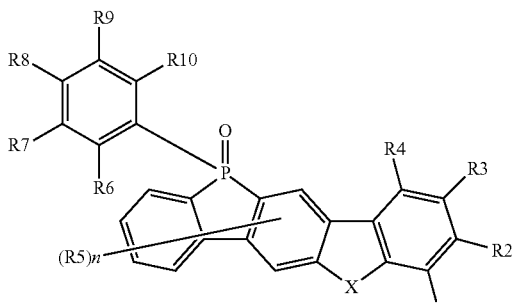

[Formula 1-2]

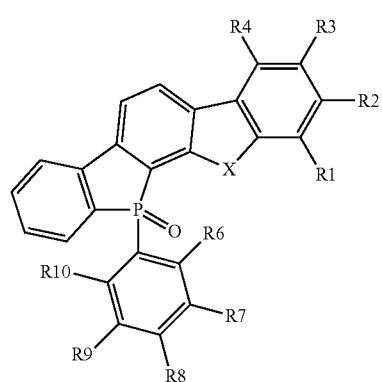

[Formula 1-3]

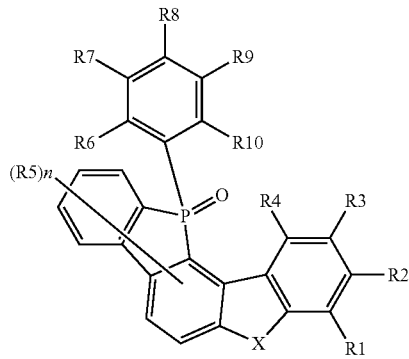

[Formula 1-4]

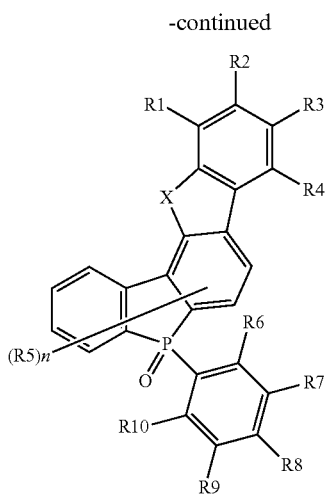

in Formulae 1-1 to 1-4,

X is O, S, or NAr, n is an integer of 0 to 6, when n is 2 or more, a plurality of R5's is the same as or different from each other, R1 to R5 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted amine group; a substituted or unsubstituted arylphosphine group; a substituted or unsubstituted phosphine oxide group; a substituted or unsubstituted aryl group; or a substituted or unsubstituted heterocyclic group, or combine with an adjacent group to form a substituted or unsubstituted ring, and R6 to R10 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted amine group; a substituted or unsubstituted arylphosphine group; a substituted or unsubstituted phosphine oxide group; a substituted or unsubstituted aryl group; or a substituted or unsubstituted heterocyclic group, or combine with two or more adjacent groups in R6 to R10 to form a substituted or unsubstituted ring, Ar is hydrogen; a substituted or unsubstituted heteroaryl alkyl group; a substituted or unsubstituted aryl group; or a substituted or unsubstituted heterocyclic group.

Further, the present specification provides an organic electroluminescent device including: a first electrode; a second electrode provided to face the first electrode; and one or more organic material layers provided between the first electrode and the second electrode, in which one or more layers of the organic material layers include the above-described compound.

The compound according to the present specification may be used as a material for the organic material layer of the organic electroluminescent device. The compound may serve as a hole injection material, a hole transporting material, an electron inhibiting material, a light emitting material, an electron transporting material, an electron injection material, a hole inhibiting material, and the like in an organic electroluminescent device. The compound according to an exemplary embodiment may also be used as a light emitting host material of an organic electroluminescent device, for example, a phosphorescent host material. The compound according to another exemplary embodiment may also be used as a material for an electron transporting layer of an organic electroluminescent device.

BRIEF DESCRIPTION OF THE DRAWINGS

FIGS. 1 to 3 illustrate a sequence of stacking electrodes and organic material layers of an organic electroluminescent device according to exemplary embodiments of the present invention.

DETAILED DESCRIPTION

Hereinafter, the present specification will be described in more detail.

In the present specification, ⵌ means a moiety linked to another substituent.

In the present specification, the term "substituted or unsubstituted" means being unsubstituted or substituted with one or more substituents selected from the group consisting of deuterium; a halogen group; a nitrile group; a nitro group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; a heteroarylamine group; an arylamine group; or a heterocyclic group, or being unsubstituted or substituted with a substituent to which two or more substituents among the substituents exemplified above are linked. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine. In the present specification, the number of carbon atoms of a carbonyl group is not particularly limited, but is preferably 1 to 40.

Specifically, the carbonyl group may be a compound having the following structures, but is not limited thereto.

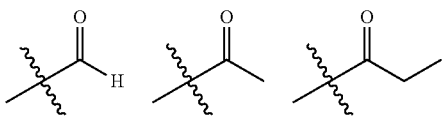

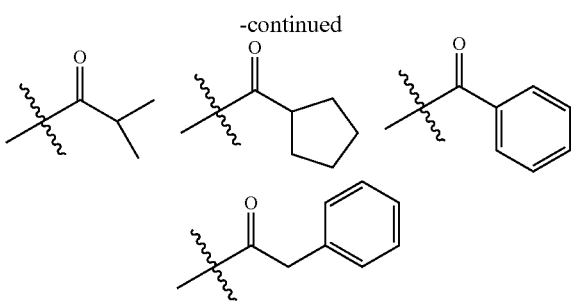

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

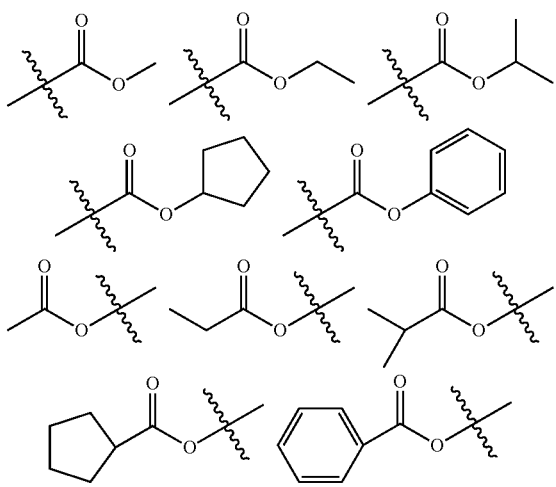

In the present specification, the number of carbon atoms of an imide group is not particularly limited, but is preferably 1 to 25. Specifically, the imide group may be a compound having the following structures, but is not limited thereto.

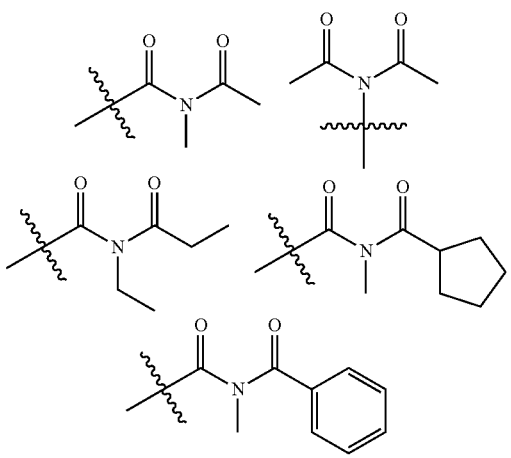

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, specific examples of a boron group include a trimethylboron group, a triethylboron group, a t-butyldimethylboron group, a triphenylboron group, a phenylboron group, and the like, but are not limited thereto.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. According to yet another exemplary embodiment, the number of carbon atoms of the alkyl group is 3 or more. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylhexyl, 2-ethylhexyl, 2-propylpentyl, n-nonyl, 2,2-dimethylheptyl, 1-ethyl-propyl, 1,1-dimethyl-propyl, isohexyl, 2-methylhexyl, 4-methylhexyl, 5-methylhexyl, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-

(naphthyl-1-yl)vinyl-1-yl, 2,2-bis(diphenyl-1-yl)vinyl-1-yl, a stilbenyl group, a styrenyl group, and the like, but are not limited thereto.

In the present specification, the number of carbon atoms of an amine group is not particularly limited, but is preferably 1 to 30. In the present specification, the amine group may be unsubstituted or substituted with one or two or more substituents selected from the group consisting of an alkyl group, an aryl group, and a heteroaryl group. Specific examples of the amine group include a methylamine group, a dimethylamine group, an ethylamine group, a diethylamine group, and the like, but are not limited thereto.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. When the aryl group is a monocyclic aryl group, examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group may be substituted, and two substituents may combine with each other to form a spiro structure.

When the fluorenyl group is substituted, the group may be

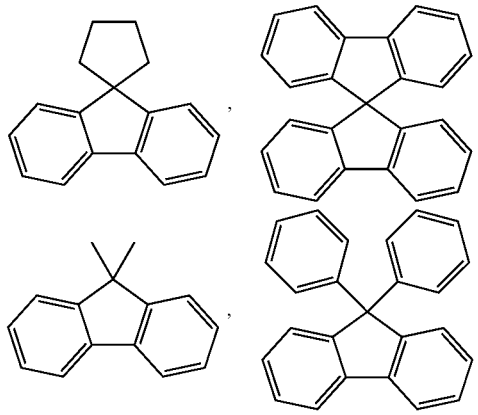

and the like. However, the group is not limited thereto.

In the present specification, a heterocyclic group is a heterocyclic group including one or more of O, N, and S as a hetero element instead of a carbon atom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isooxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aryloxy group, the arylthioxy group, the arylsulfoxy group, the arylphosphine group, the aralkyl group, the aralkylamine group, the aralkenyl group, the alkylaryl group, and the arylamine group is the same as the above-described examples of the aryl group.

In the present specification, the alkyl group in the alkylthioxy group, the alkylsulfoxy group, the aralkyl group, the aralkylamine group, the alkylaryl group, and the alkylamine group is the same as the above-described examples of the alkyl group.

In the present specification, the above-described description on the heterocyclic group may be applied to a heteroaryl group of a heteroarylamine group.

In the present specification, the alkenyl group in the aralkenyl group is the same as the above-described examples of the alkenyl group.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

The meaning that adjacent groups combine with each other to form a ring in the present specification may mean that an alkylene which is unsubstituted or substituted with a hydrocarbon or hetero ring or an alkenylene which is unsubstituted or substituted with a hydrocarbon or hetero ring combines with each other to form a ring.

In the present specification, the hydrocarbon ring may be an aliphatic ring, an aromatic ring, or a condensed ring of the aliphatic ring and the aromatic ring, and may be selected from the examples of the cycloalkyl group or the aryl group, except for the hydrocarbon ring which is not monovalent. The hetero ring may be an aliphatic ring, an aromatic ring, or a condensed ring of the aromatic ring and the aliphatic ring, and may be selected from the examples of the heterocyclic group, except for the hetero ring which is not monovalent.

In the present specification, the aliphatic hydrocarbon ring means a ring composed only of carbon and hydrogen atoms as a ring which is not an aromatic group. In the present specification, examples of the aromatic hydrocarbon ring may be selected from the above-described examples of the aryl group such as a phenyl group, a naphthyl group, and an anthracenyl group, but are not limited thereto.

In the present specification, the aliphatic hetero ring means an aliphatic ring including one or more of N, O, or S atoms as a hetero atom.

In the present specification, the aromatic hetero ring means an aromatic ring including one or more of N, O, or S atoms as a hetero atom.

In the present specification, the aliphatic hydrocarbon ring, the aromatic hydrocarbon ring, the aliphatic hetero ring, and the aromatic hetero ring may be monocyclic or polycyclic.

R1 to R5 are the same as or different from each other, and are each independently hydrogen; or combine with an adjacent group to form a substituted or unsubstituted hydrocarbon ring.

In an exemplary embodiment of the present specification, R1 is hydrogen.

In another exemplary embodiment, R2 is hydrogen.

In still another exemplary embodiment, R3 is hydrogen.

In an exemplary embodiment of the present specification, R4 is hydrogen.

In an exemplary embodiment of the present specification, R5 is hydrogen.

In an exemplary embodiment of the present specification, R1 and R2 combine with each other to form a substituted or unsubstituted ring.

In an exemplary embodiment of the present specification, R1 and R2 combine with each other to form a substituted or unsubstituted hydrocarbon ring.

In another exemplary embodiment, R1 and R2 combine with each other to form a substituted or unsubstituted aromatic hydrocarbon ring.

In an exemplary embodiment of the present specification, R1 and R2 combine with each other to form a substituted or unsubstituted benzene ring.

In one exemplary embodiment, R1 and R2 combine with each other to form a benzene ring.

In an exemplary embodiment of the present specification, R2 and R3 combine with each other to form a substituted or unsubstituted ring.

In an exemplary embodiment of the present specification, R2 and R3 combine with each other to form a substituted or unsubstituted hydrocarbon ring.

In another exemplary embodiment, R2 and R3 combine with each other to form a substituted or unsubstituted aromatic hydrocarbon ring.

In an exemplary embodiment of the present specification, R2 and R3 combine with each other to form a substituted or unsubstituted benzene ring.

In one exemplary embodiment, R2 and R3 combine with each other to form a benzene ring.

In an exemplary embodiment of the present specification, R3 and R4 combine with each other to form a substituted or unsubstituted ring.

In an exemplary embodiment of the present specification, R3 and R4 combine with each other to form a substituted or unsubstituted hydrocarbon ring.

In another exemplary embodiment, R3 and R4 combine with each other to form a substituted or unsubstituted aromatic hydrocarbon ring.

In an exemplary embodiment of the present specification, R3 and R4 combine with each other to form a substituted or unsubstituted benzene ring.

In one exemplary embodiment, R3 and R4 combine with each other to form a benzene ring.

In an exemplary embodiment of the present specification, the two adjacent R5's combine with each other to form a substituted or unsubstituted ring.

In an exemplary embodiment of the present specification, the two adjacent R5's combine with each other to form a substituted or unsubstituted hydrocarbon ring.

In another exemplary embodiment, the two adjacent R5's combine with each other to form a substituted or unsubstituted aromatic hydrocarbon ring.

In an exemplary embodiment of the present specification, the two adjacent R5's combine with each other to form a substituted or unsubstituted benzene ring. In one exemplary embodiment, the two or more adjacent R5's combine with each other to form a benzene ring.

In an exemplary embodiment of the present specification, X is O or S.

In an exemplary embodiment of the present specification, X is S.

In another exemplary embodiment, X is O.

In an exemplary embodiment of the present specification, X is NAr.

In an exemplary embodiment of the present specification, R6 is hydrogen.

In an exemplary embodiment of the present specification, R7 is hydrogen.

In an exemplary embodiment of the present specification, R8 is hydrogen.

In an exemplary embodiment of the present specification, R9 is hydrogen.

In an exemplary embodiment of the present specification, R10 is hydrogen.

In an exemplary embodiment of the present specification, R6 to R10 are simultaneously hydrogen.

In an exemplary embodiment of the present specification, Ar is an aryl group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group; or a heterocyclic group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group.

In an exemplary embodiment of the present specification, Ar is an aryl group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group.

In an exemplary embodiment of the present specification, Ar is an aryl group having 6 to 30 carbon atoms, which is unsubstituted or substituted with one or two or more substituents selected from the group consisting of deuterium, a nitrile group, a substituted or unsubstituted alkyl group having 1 to 10 carbon atoms, a substituted or unsubstituted amine group, a substituted or unsubstituted aryl group having 6 to 30 carbon atoms, and a substituted or unsubstituted heterocyclic group having 2 to 30 carbon atoms.

In an exemplary embodiment of the present specification, Ar is a heterocyclic group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group.

In an exemplary embodiment of the present specification, Ar is a heterocyclic group having 2 to 30 carbon atoms, which is unsubstituted or substituted with one or two or more substituents selected from the group consisting of deuterium, a nitrile group, a substituted or unsubstituted alkyl group having 1 to 10 carbon atoms, a substituted or unsubstituted amine group, a substituted or unsubstituted aryl group having 2 to 30 carbon atoms, and a substituted or unsubstituted heterocyclic group having 6 to 30 carbon atoms.

In another exemplary embodiment, Ar is a phenyl group; a naphthyl group; a biphenyl group; a terphenyl group; a quarterphenylene group; a fluorene group; a fluoranthene group; an anthracene group; a chrysene group; a phenanthrenyl group; a pyrene group; an amine group; a pyridine group; a pyrimidine group; a triazine group; a quinoline group; a quinazoline group; a carbazole group; a dibenzothiophene group; a dibenzofuran group; a furan group; a thiophene group; or a phenanthroline group, Ar is substituted with one or two or more substituents selected from the group consisting of deuterium; a nitrile group; an alkyl group having 1 to 10 carbon atoms; a phenyl group; a naphthyl group; a biphenyl group; a terphenyl group; a quarterphenylene group; a fluorene group; a fluoranthene group; an anthracene group; a chrysene group; a phenanthrenyl group; a pyrene group; an amine group; a pyridine group; a pyrimidine group; a triazine group; a quinoline group; a quinazoline group; a carbazole group; a dibenzothiophene group; a dibenzofuran group; a furan group; a thiophene group; and a phenanthroline group, or is unsubstituted or substituted with a substituent to which two or more substituents are linked.

In an exemplary embodiment of the present specification, Ar is an aryl group having 6 to 30 carbon atoms, which is unsubstituted or substituted with a substituted or unsubstituted aryl group having 6 to 30 carbon atoms.

In an exemplary embodiment of the present specification, Ar is a phenyl group.

In another exemplary embodiment of the present specification, Ar is a naphthyl group.

In an exemplary embodiment of the present specification, Ar is a biphenyl group.

In an exemplary embodiment of the present specification, Ar is a phenyl group which is substituted with a phenyl group.

In another exemplary embodiment, Ar is a terphenyl group.

In an exemplary embodiment of the present specification, Ar is a biphenyl group which is substituted with a phenyl group.

In an exemplary embodiment of the present specification, Ar is a terphenyl group which is substituted with a phenyl group.

In an exemplary embodiment of the present specification, Ar is a phenyl group which is substituted with a biphenyl group.

In an exemplary embodiment of the present specification, Ar is a biphenyl group which is substituted with a biphenyl group.

In another exemplary embodiment, Ar is a biphenyl group which is substituted with a naphthyl group.

In still another exemplary embodiment, Ar is a naphthyl group which is substituted with a naphthyl group.

In an exemplary embodiment of the present specification, Ar is a phenyl group which is substituted with a naphthyl group.

In an exemplary embodiment of the present specification, Ar is an anthracene group.

In an exemplary embodiment of the present specification, Ar is an anthracene group which is substituted with a phenyl group.

In another exemplary embodiment, Ar is an anthracene group which is substituted with a naphthyl group.

In still another exemplary embodiment, Ar is an anthracene group which is substituted with a fluorenyl group.

In yet another exemplary embodiment, Ar is an anthracene group which is substituted with a fluorenyl group substituted with a methyl group.

In still yet another exemplary embodiment, Ar is an anthracene group which is substituted with a fluorenyl group substituted with a methyl group and a nitrile group.

In an exemplary embodiment of the present specification, Ar is a phenyl group which is substituted with a fluorenyl group.

In an exemplary embodiment of the present specification, Ar is a phenyl group which is substituted with a fluorenyl group substituted with a methyl group.

In another exemplary embodiment, Ar is a naphthyl group which is substituted with a fluorenyl group.

In still another exemplary embodiment, Ar is a naphthyl group which is substituted with a fluorenyl group substituted with a methyl group.

In an exemplary embodiment of the present specification, Ar is a pyrenyl group.

In another exemplary embodiment, Ar is a phenanthrenyl group.

In another exemplary embodiment, Ar is a phenyl group which is substituted with an anthracene group.

In an exemplary embodiment of the present specification, Ar is a chrysene group.

In another exemplary embodiment, Ar is a fluoranthene group.

In still another exemplary embodiment, Ar is a fluoranthene group which is substituted with a phenyl group.

In the present specification, the naphthyl group is

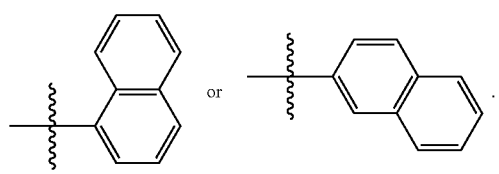 [SMILES: *c1cccc2ccccc12 ; *c1ccc2ccccc2c1]

In the present specification, the biphenyl group is

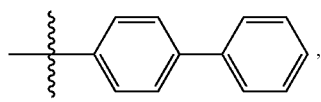

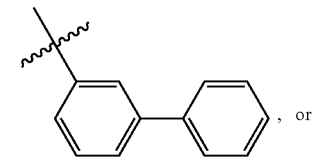

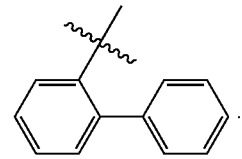

In the present specification, the pyrenyl group is

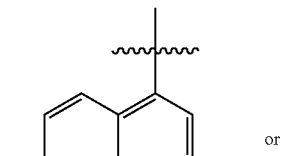

or

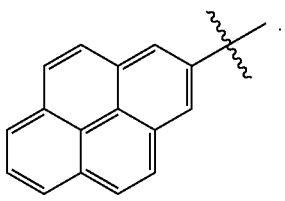

Further, in the present specification, the phenanthrenyl group is

,

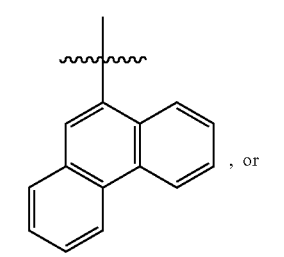, or

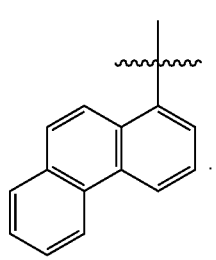.

In the present specification, the anthracene group is

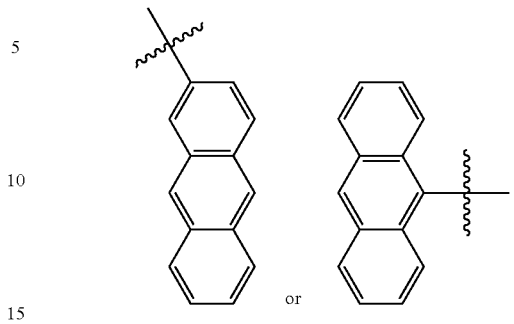

or

In an exemplary embodiment of the present specification, Ar is a phenyl group which is substituted with a nitrile group.

In an exemplary embodiment of the present specification, Ar is a phenyl group which is substituted with deuterium.

In another exemplary embodiment of the present specification, Ar is an aryl group having 6 to 30 carbon atoms, which is substituted with a substituted or unsubstituted heterocyclic group having 2 to 30 carbon atoms.

In an exemplary embodiment of the present specification, Ar is a phenyl group which is substituted with a quinoline group.

In an exemplary embodiment of the present specification, Ar is a phenyl group which is substituted with a thiophene group substituted with a phenyl group. In another exemplary embodiment, Ar is a phenyl group which is substituted with a furan group substituted with a phenyl group.

In an exemplary embodiment of the present specification, Ar is a phenyl group which is substituted with a pyridine group substituted with a phenyl group.

In another exemplary embodiment, Ar is a phenyl group which is substituted with a pyridine group substituted with a phenyl group and a biphenyl group.

In still another exemplary embodiment, Ar is a phenyl group which is substituted with a pyridine group substituted with a biphenyl group.

In yet another exemplary embodiment, Ar is a phenyl group which is substituted with a pyrimidine group substituted with a phenyl group.

In still yet another exemplary embodiment, Ar is a phenyl group which is substituted with a pyrimidine group substituted with a biphenyl group.

In another exemplary embodiment, Ar is a phenyl group which is substituted with a pyrimidine group substituted with a phenyl group and a biphenyl group.

In still another exemplary embodiment, Ar is a phenyl group which is substituted with a triazine group substituted with a phenyl group.

In yet another exemplary embodiment, Ar is a phenyl group which is substituted with a triazine group substituted with a biphenyl group.

In still yet another exemplary embodiment, Ar is a phenyl group which is substituted with a triazine group substituted with a phenyl group and a biphenyl group.

In another exemplary embodiment, Ar is a phenyl group which is substituted with a fluorenyl group.

In still another exemplary embodiment, Ar is a phenyl group which is substituted with a fluorenyl group substituted with a methyl group.

In yet another exemplary embodiment, Ar is a phenyl group which is substituted with a fluorenyl group substituted with a methyl group and a phenyl group.

In still yet another exemplary embodiment, Ar is a phenyl group which is substituted with a fluorenyl group substituted with a methyl group and a naphthyl group.

In another exemplary embodiment, Ar is a phenyl group which is substituted with a fluorenyl group substituted with a methyl group and a pyridine group.

In another exemplary embodiment of the present specification, Ar is an aryl group having 6 to 30 carbon atoms, which is unsubstituted or substituted with one or two or more substituents selected from the group consisting of a substituted or unsubstituted alkyl group having 1 to 10 carbon atoms, a substituted or unsubstituted aryl group having 6 to 30 carbon atoms, and a substituted or unsubstituted heterocyclic group having 2 to 30 carbon atoms.

In an exemplary embodiment of the present specification, Ar is a fluorenyl group.

In another exemplary embodiment, Ar is a fluorenyl group which is substituted with an alkyl group having 1 to 10 carbon atoms.

In still another exemplary embodiment, Ar is a fluorenyl group which is substituted with a methyl group.

In yet another exemplary embodiment of the present specification, Ar is a fluorenyl group which is substituted with an alkyl group having 1 to 10 carbon atoms and a phenyl group.

In another exemplary embodiment, Ar is a fluorenyl group which is substituted with an alkyl group having 1 to 10 carbon atoms and a naphthyl group.

In still another exemplary embodiment, Ar is a fluorenyl group which is substituted with an alkyl group having 1 to 10 carbon atoms and a naphthyl group.

In yet another exemplary embodiment, Ar is a fluorenyl group which is substituted with an alkyl group having 1 to 10 carbon atoms and a pyridine group.

In another exemplary embodiment of the present specification, Ar is a biphenyl group which is substituted with a quinoline group.

In another exemplary embodiment, Ar is a phenyl group which is substituted with a quinoline group.

In still another exemplary embodiment, Ar is a phenyl group which is substituted with a quinazoline group.

In yet another exemplary embodiment, Ar is a phenyl group which is substituted with a quinazoline group substituted with a phenyl group.

In still yet another exemplary embodiment, Ar is a phenyl group which is substituted with a quinazoline group substituted with a naphthyl group.

In another exemplary embodiment, Ar is a phenyl group which is substituted with a quinazoline group substituted with a biphenyl group.

In still another exemplary embodiment, Ar is a phenyl group which is substituted with a quinazoline group substituted with a phenyl group substituted with a naphthyl group.

In an exemplary embodiment of the present specification, Ar is a phenyl group which is substituted with a carbazole group.

In another exemplary embodiment, Ar is a phenyl group which is substituted with a carbazole group substituted with a phenyl group.

In an exemplary embodiment of the present specification, Ar is a phenyl group which is substituted with a dibenzothiophene group.

In another exemplary embodiment, Ar is a phenyl group which is substituted with a dibenzofuran group.

In the present specification, the fluorenyl group is

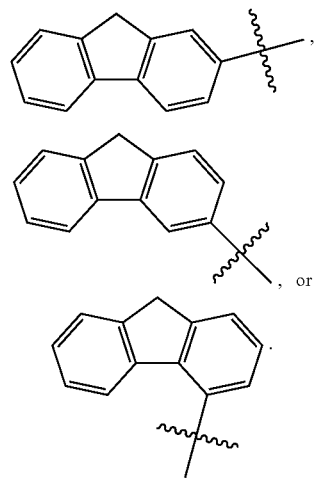

In another exemplary embodiment of the present specification, Ar is an aryl group having 6 to 30 carbon atoms, which is substituted with an amine group which is unsubstituted or substituted with one or two or more substituents selected from the group consisting of an aryl group and a heterocyclic group.

In an exemplary embodiment of the present specification, Ar is a phenyl group which is substituted with an amine group.

In an exemplary embodiment of the present specification, Ar is a phenyl group which is substituted with an amine group substituted with an aryl group.

In an exemplary embodiment of the present specification, Ar is a phenyl group which is substituted with an amine group substituted with a phenyl group.

In another exemplary embodiment, Ar is a phenyl group which is substituted with an amine group substituted with a phenyl group and a biphenyl group.

In yet another exemplary embodiment, Ar is a phenyl group which is substituted with an amine group substituted with a biphenyl group.

In an exemplary embodiment of the present specification, Ar is a biphenyl group which is substituted with an amine group.

In an exemplary embodiment of the present specification, Ar is a biphenyl group which is substituted with an amine group substituted with an aryl group.

In an exemplary embodiment of the present specification, Ar is a biphenyl group which is substituted with an amine group substituted with a phenyl group.

In another exemplary embodiment, Ar is a biphenyl group which is substituted with an amine group substituted with a phenyl group and a biphenyl group.

In yet another exemplary embodiment, Ar is a biphenyl group which is substituted with an amine group substituted with a biphenyl group.

In an exemplary embodiment of the present specification, Ar is a phenyl group which is substituted with an amine group substituted with a naphthyl group.

In another exemplary embodiment, Ar is a phenyl group which is substituted with an amine group substituted with a carbazole group substituted with a phenyl group.

In still another exemplary embodiment, Ar is a phenyl group; and a phenyl group which is substituted with an amine group substituted with a carbazole group substituted with a phenyl group.

In yet another exemplary embodiment, Ar is a phenyl group which is substituted with an amine group substituted with a dibenzothiophene group.

In still yet another exemplary embodiment, Ar is a phenyl group; and a phenyl group which is substituted with an amine group substituted with a dibenzothiophene group.

In another exemplary embodiment, Ar is a phenyl group which is substituted with an amine group substituted with a dibenzofuran group.

In still another exemplary embodiment, Ar is a phenyl group; and a phenyl group which is substituted with an amine group substituted with a dibenzofuran group.

In yet another exemplary embodiment, Ar is a biphenyl group which is substituted with an amine group substituted with a carbazole group substituted with a phenyl group.

In still yet another exemplary embodiment, Ar is a phenyl group; and a biphenyl group which is substituted with an amine group substituted with a carbazole group substituted with a phenyl group.

In another exemplary embodiment, Ar is a biphenyl group which is substituted with an amine group substituted with a dibenzothiophene group.

In still another exemplary embodiment, Ar is a phenyl group; and a biphenyl group which is substituted with an amine group substituted with a dibenzothiophene group.

In another exemplary embodiment, Ar is a biphenyl group which is substituted with an amine group substituted with a dibenzofuran group.

In still another exemplary embodiment, Ar is a phenyl group; and a biphenyl group which is substituted with an amine group substituted with a dibenzofuran group.

In yet another exemplary embodiment of the present specification, Ar is a heterocyclic group having 2 to 30 carbon atoms, which is unsubstituted or substituted with an aryl group having 6 to 30 carbon atoms.

In an exemplary embodiment of the present specification, Ar is a pyridine group.

In another exemplary embodiment, Ar is a pyridine group which is substituted with a phenyl group.

In still another exemplary embodiment, Ar is a pyridine group which is substituted with a biphenyl group.

In yet another exemplary embodiment, Ar is a pyridine group which is substituted with a phenyl group and a biphenyl group.

In still yet another exemplary embodiment, Ar is a pyrimidine group.

In another exemplary embodiment, Ar is a pyrimidine group which is substituted with a phenyl group.

In an exemplary embodiment of the present specification, Ar is a pyrimidine group which is substituted with a biphenyl group.

In another exemplary embodiment, Ar is a pyrimidine group which is substituted with a phenyl group and a biphenyl group.

In an exemplary embodiment of the present specification, Ar is a triazine group.

In another exemplary embodiment, Ar is a triazine group which is substituted with a phenyl group.

In still another exemplary embodiment, Ar is a triazine group which is substituted with a biphenyl group.

In yet another exemplary embodiment, Ar is a triazine group which is substituted with a phenyl group and a biphenyl group.

In an exemplary embodiment of the present specification, Ar is a quinoline group.

In another exemplary embodiment, Ar is a quinazoline group.

In another exemplary embodiment of the present specification, Ar is a quinazoline group which is substituted with a phenyl group.

In still another exemplary embodiment, Ar is a quinazoline group which is substituted with a naphthyl group.

In yet another exemplary embodiment, Ar is a quinazoline group which is substituted with a biphenyl group.

In still yet another exemplary embodiment, Ar is a quinazoline group which is substituted with a naphthyl group-a phenyl group.

In an exemplary embodiment of the present specification, Ar is a carbazole group.

In still another exemplary embodiment, Ar is a carbazole group which is substituted with a phenyl group.

In an exemplary embodiment of the present specification, Ar is a dibenzothiophene group.

In another exemplary embodiment, Ar is a dibenzofuran group.

In still another exemplary embodiment, Ar is a phenanthroline group.

In the present specification, the pyridine group is

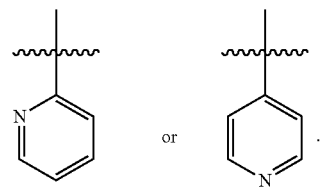 [SMILES: *c1ccccn1 ; *c1ccncc1]

In the present specification, the pyrimidine group is

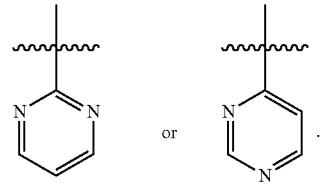 [SMILES: *c1ncccn1 ; *c1ccncn1]

In the present specification, the quinoline group is

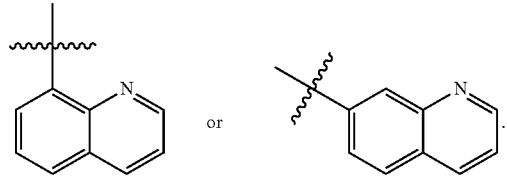 [SMILES: *c1cccc2cccnc12 ; *c1ccc2cccnc2c1]

In the present specification, the carbazole group is

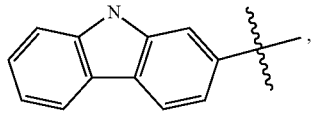

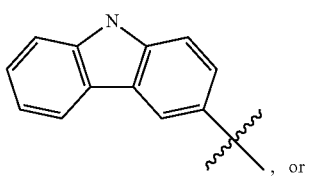

, or

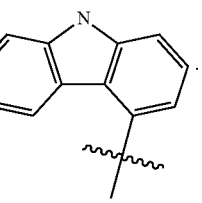

Further, in the present specification, the dibenzofuran group is

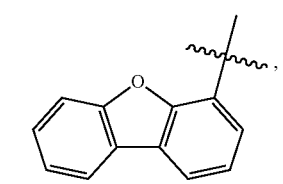

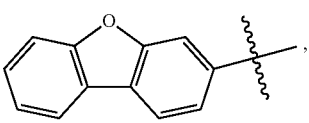

, or

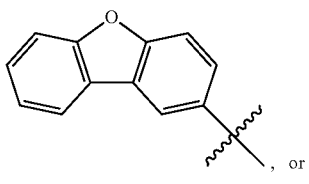

In addition, in the present specification, the dibenzothiophene group is

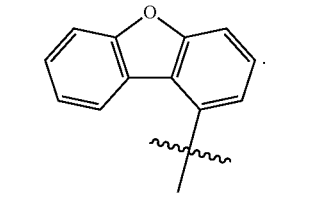

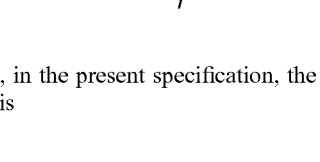

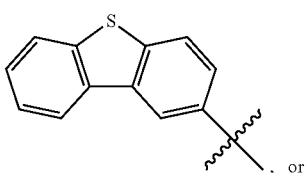

, or

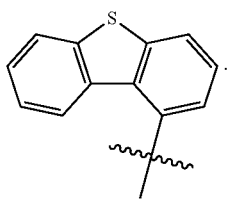

Furthermore, in the present specification, the phenanthroline group is

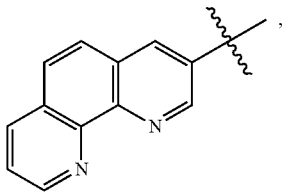

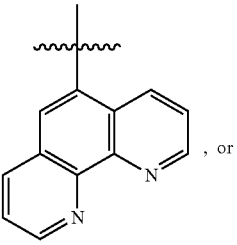

, or

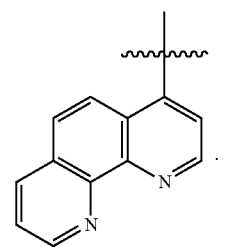

In an exemplary embodiment of the present specification, the compound represented by Formula 1 is represented by Formula 1-1.

In an exemplary embodiment of the present specification, the compound represented by Formula 1-1 is represented by any one of the following Formulae 1-1-1 to 1-1-195.

Formula 1-1-1
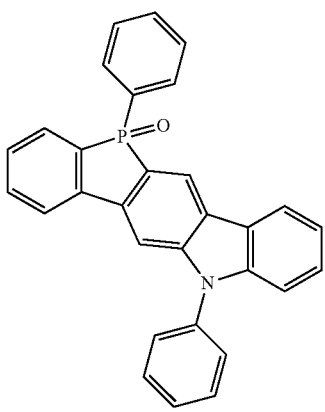
Formula 1-1-2
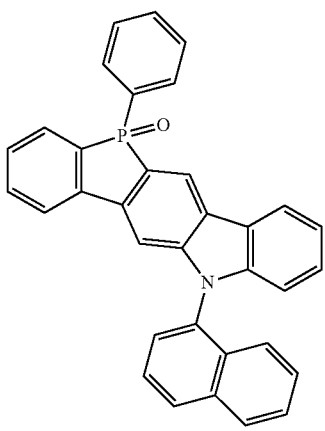
Formula 1-1-3
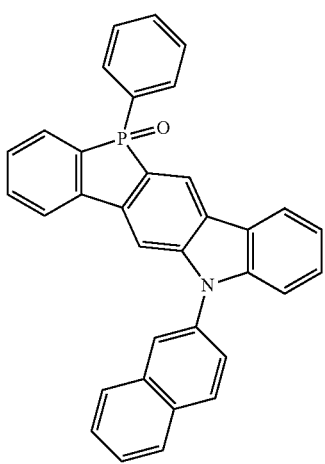
Formula 1-1-4
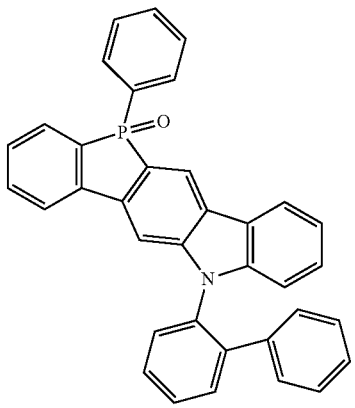
Formula 1-1-5
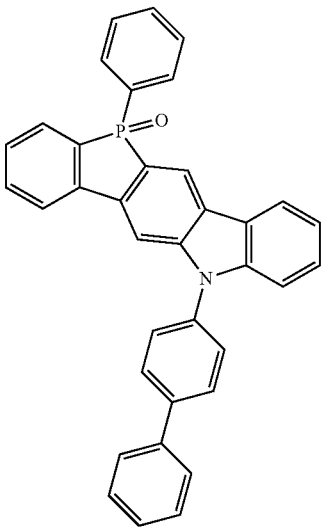
Formula 1-1-6
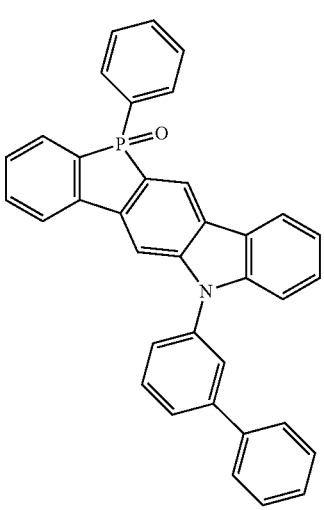

Formula 1-1-7
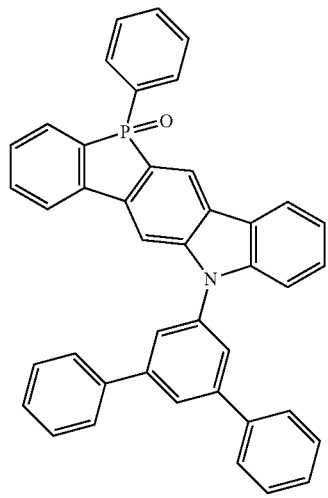
Formula 1-1-8
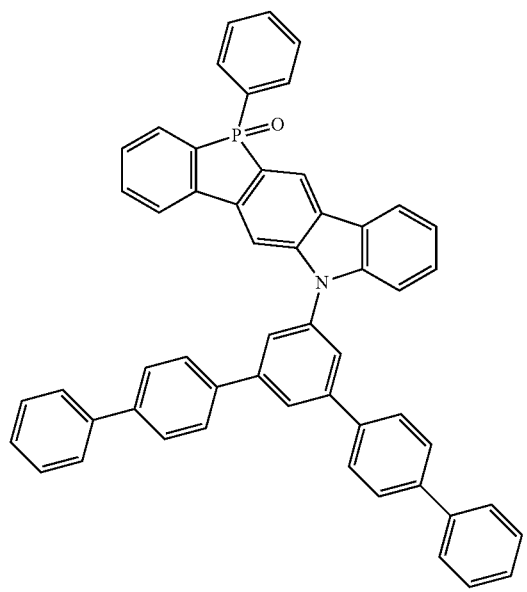
Formula 1-1-9
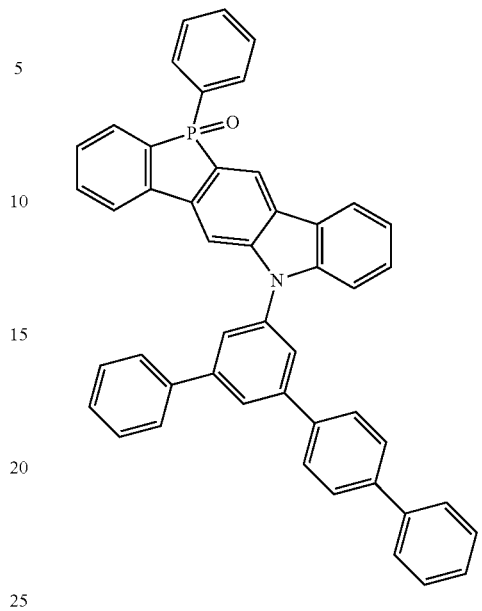
Formula 1-1-10
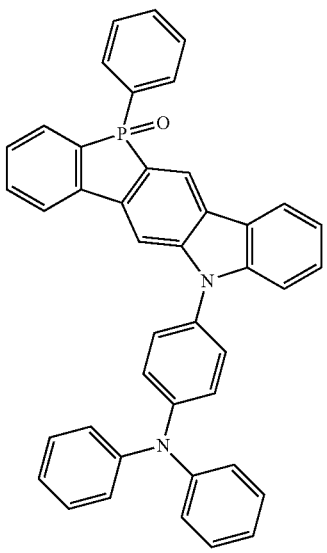

Formula 1-1-11
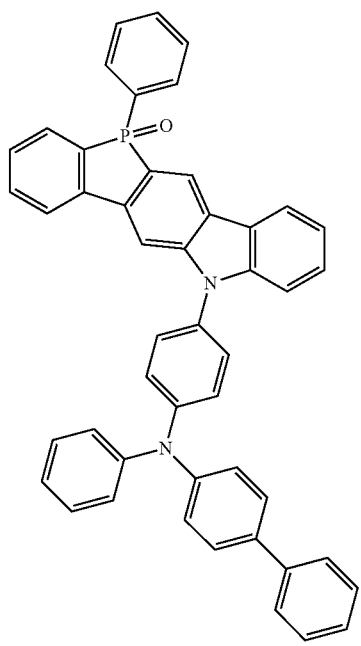
Formula 1-1-13
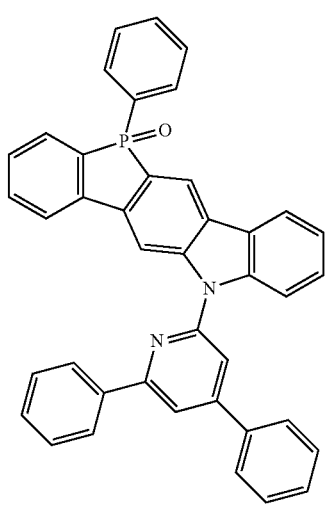
Formula 1-1-14
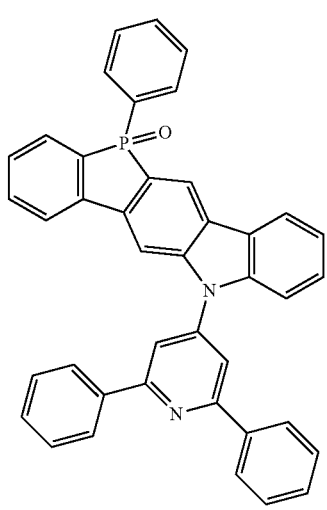
Formula 1-1-12
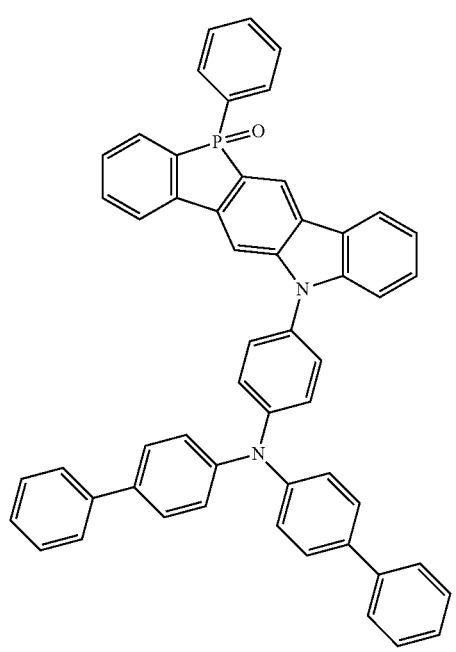
Formula 1-1-15
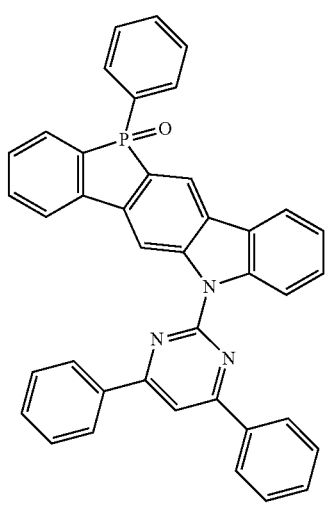

Formula 1-1-16
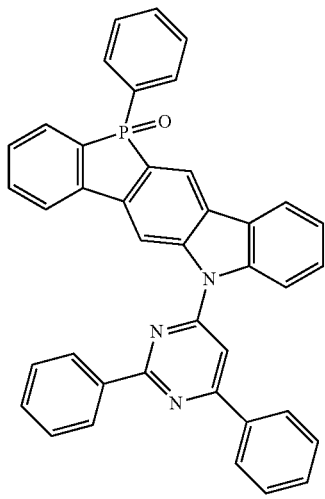
Formula 1-1-17
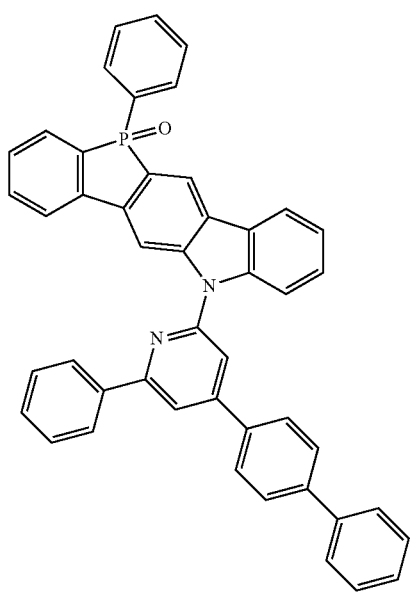
Formula 1-1-18
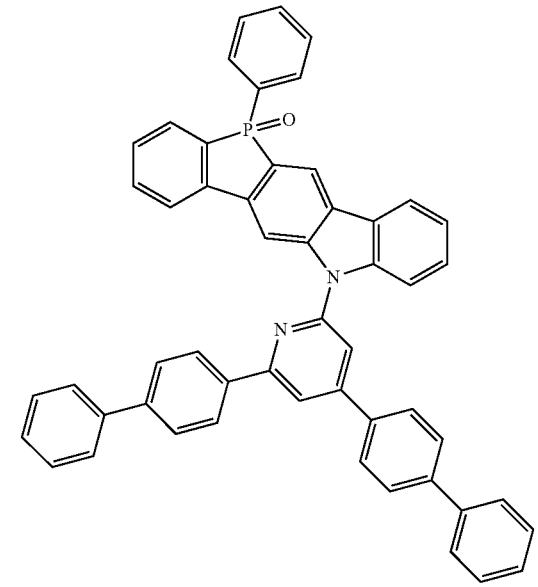
Formula 1-1-19
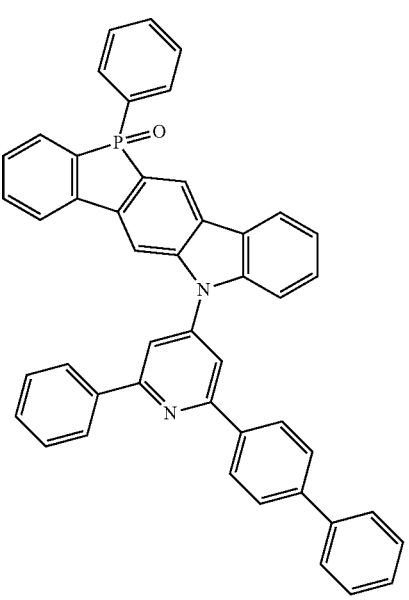

Formula 1-1-20
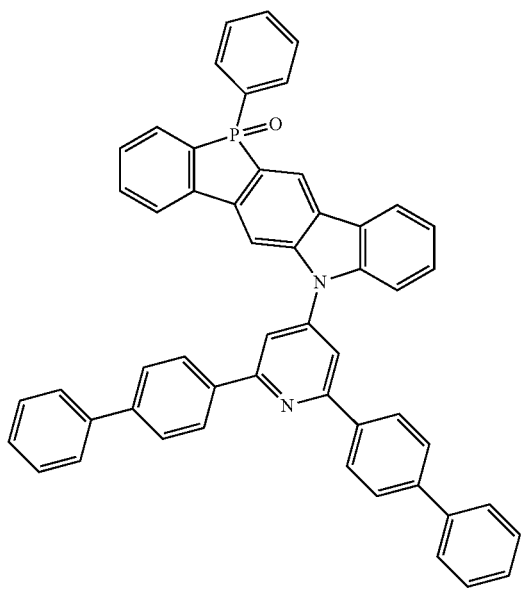
Formula 1-1-22
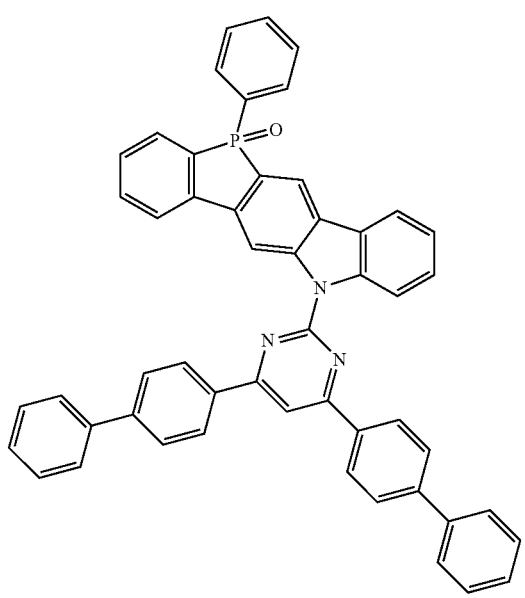
Formula 1-1-21
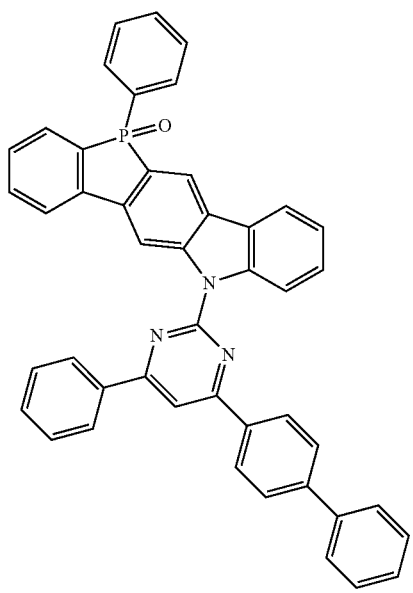
Formula 1-1-23
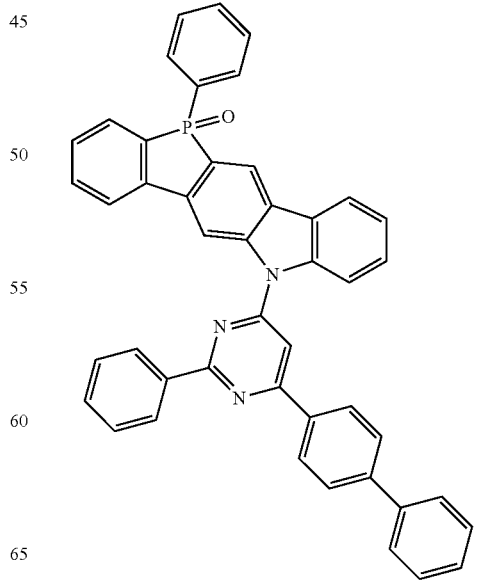

Formula 1-1-24
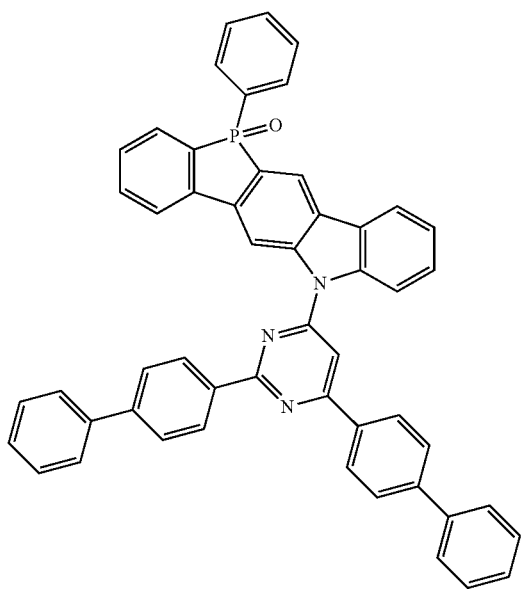
Formula 1-1-25
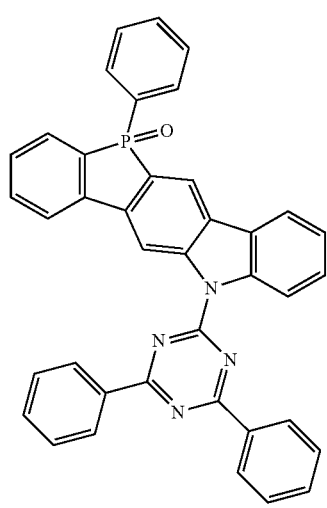
Formula 1-1-26
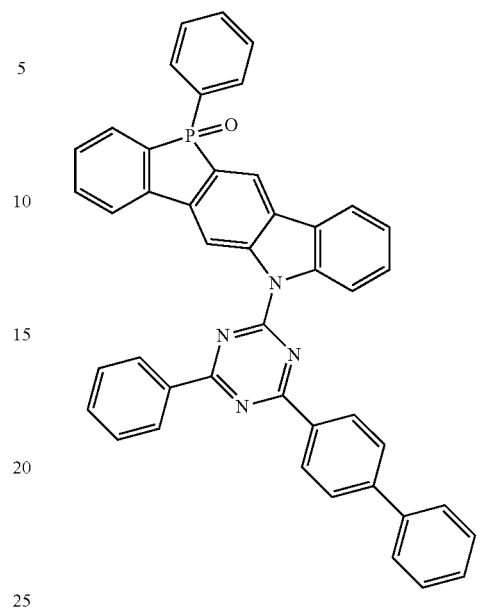
Formula 1-1-27
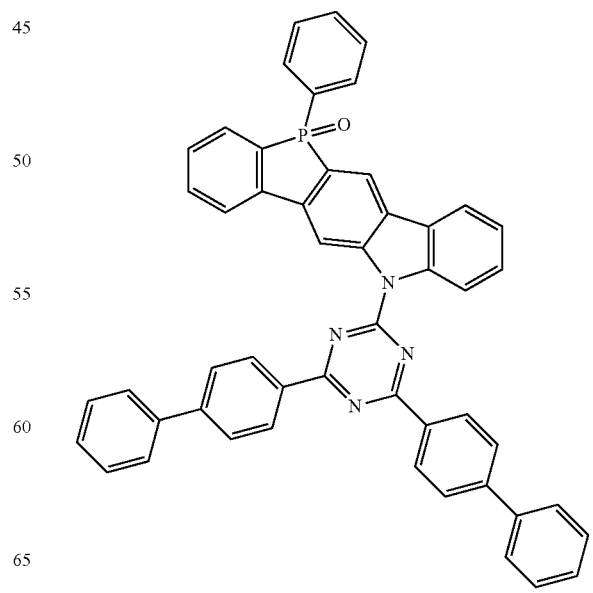

Formula 1-1-28
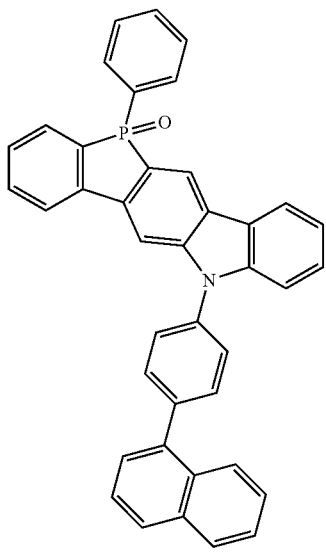
Formula 1-1-29
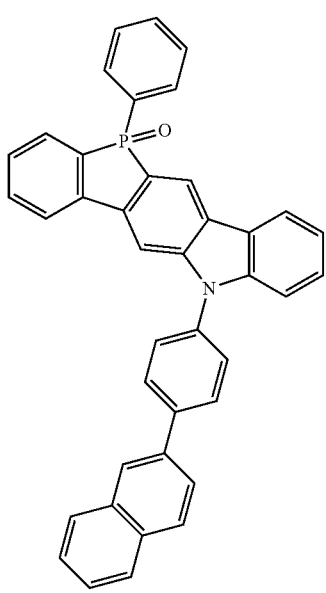
Formula 1-1-30
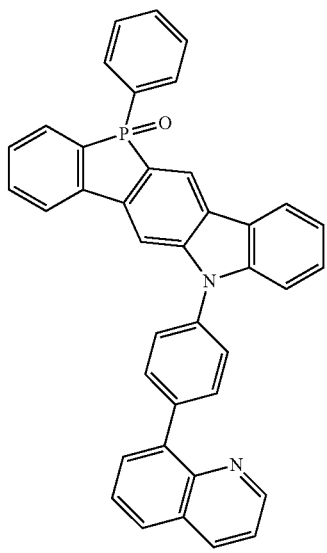
Formula 1-1-31
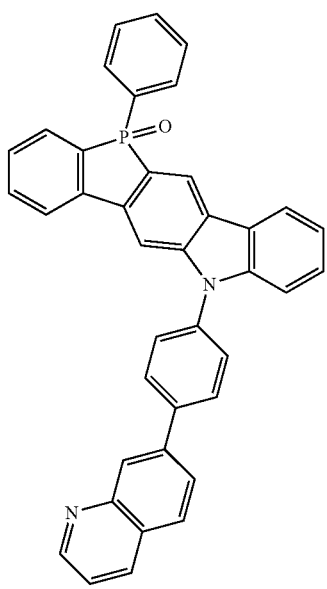
Formula 1-1-32
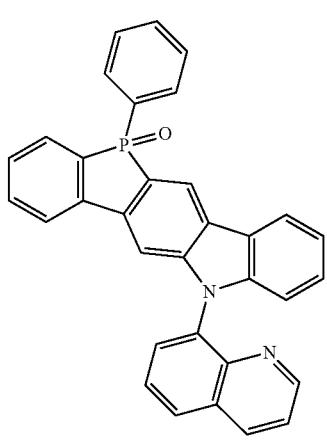

Formula 1-1-33
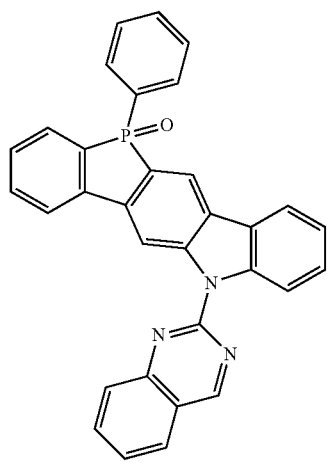
Formula 1-1-34
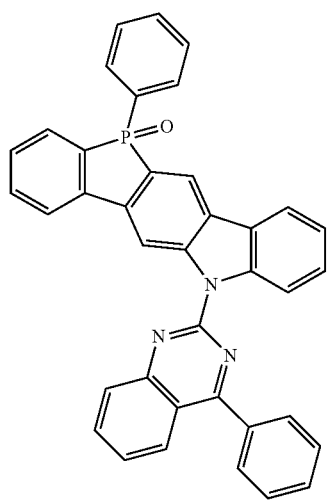
Formula 1-1-35
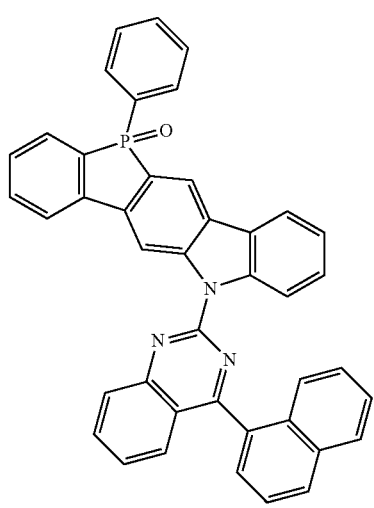
Formula 1-1-36
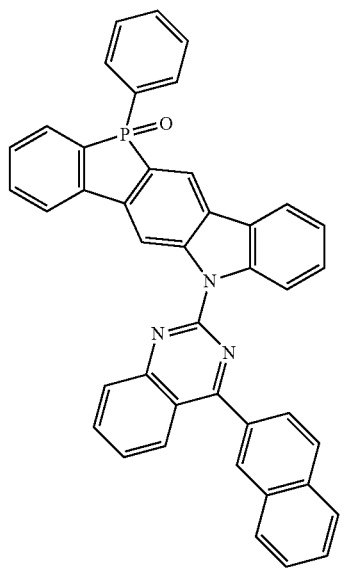
Formula 1-1-37
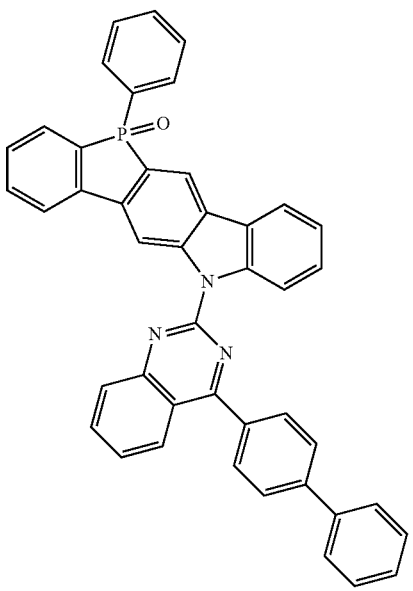

-continued
Formula 1-1-38
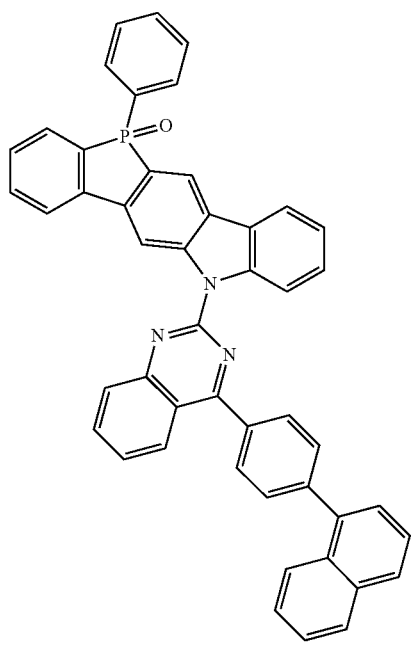
Formula 1-1-39
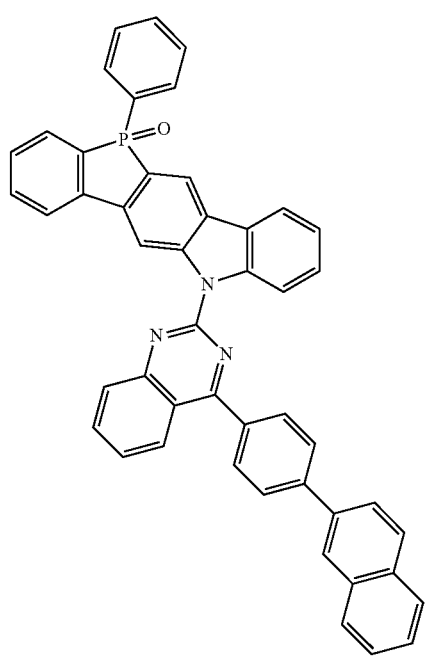
-continued
Formula 1-1-40
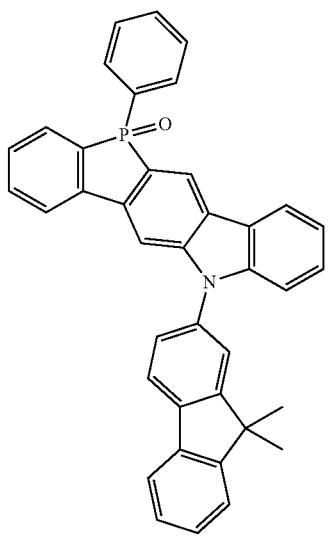
Formula 1-1-41
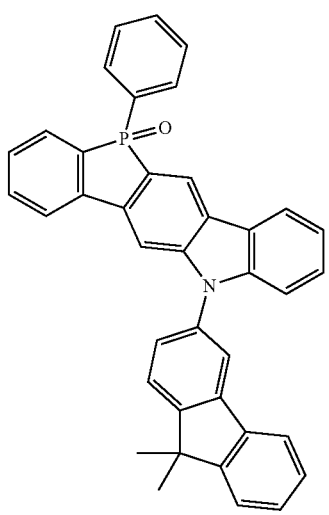
Formula 1-1-42
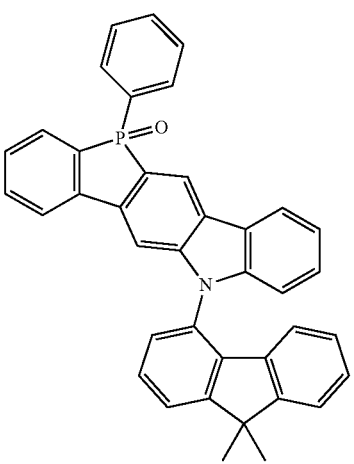

Formula 1-1-43
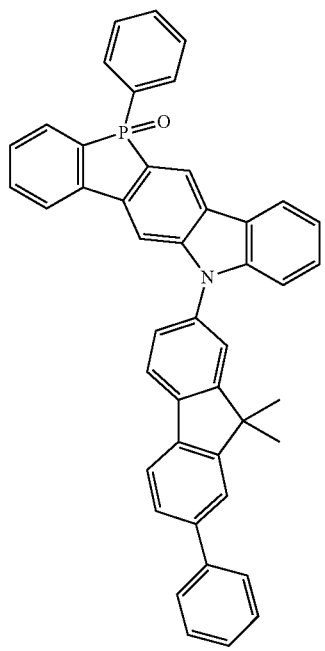
Formula 1-1-45
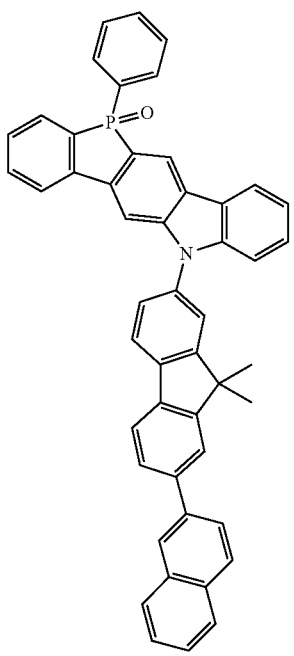
Formula 1-1-44
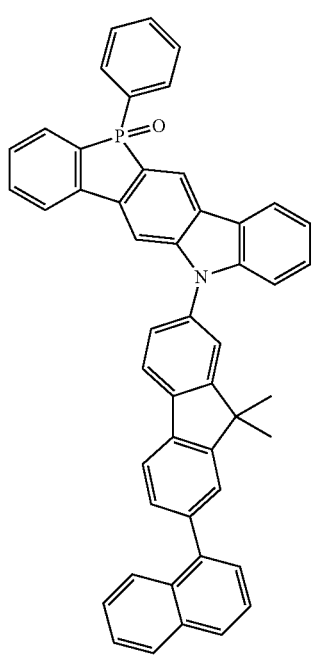
Formula 1-1-46
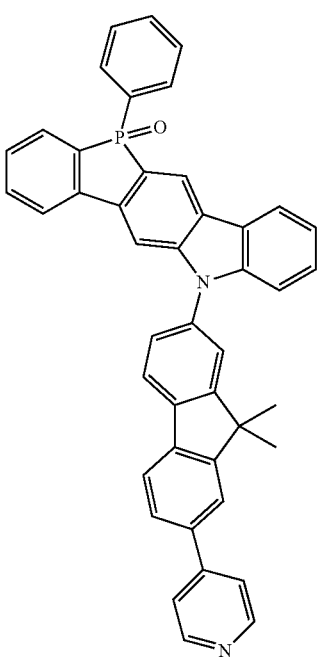

Formula 1-1-47
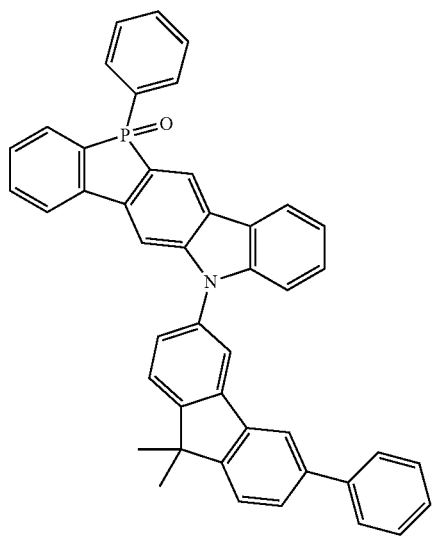
Formula 1-1-48
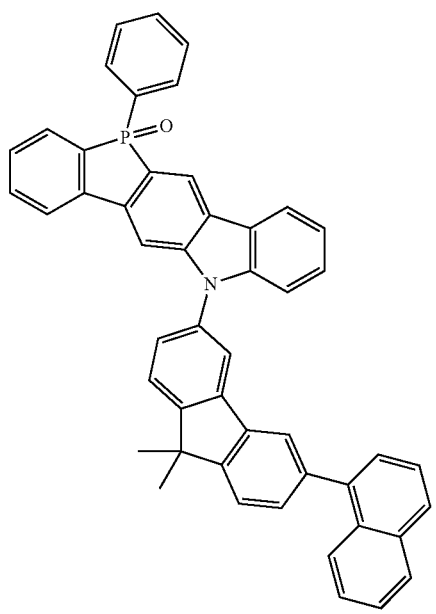
Formula 1-1-49
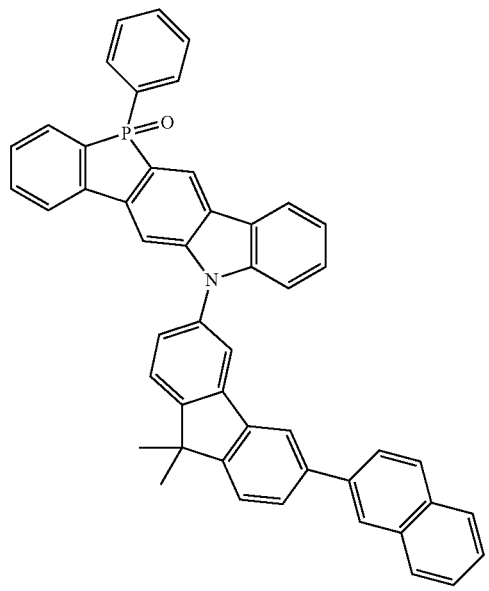
Formula 1-1-50
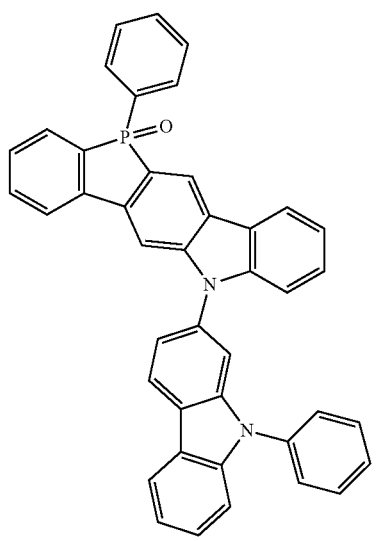

Formula 1-1-51
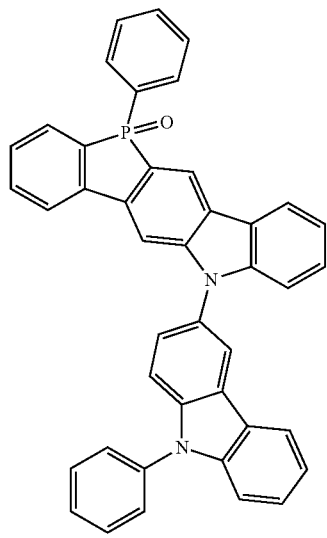
Formula 1-1-52
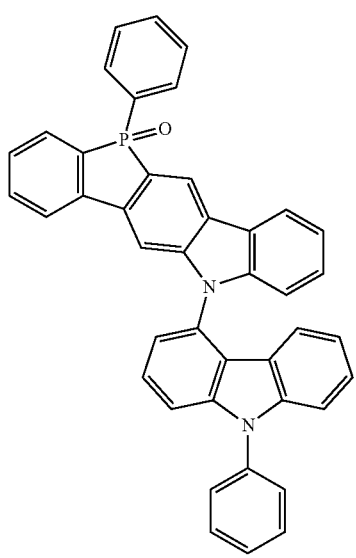
Formula 1-1-53
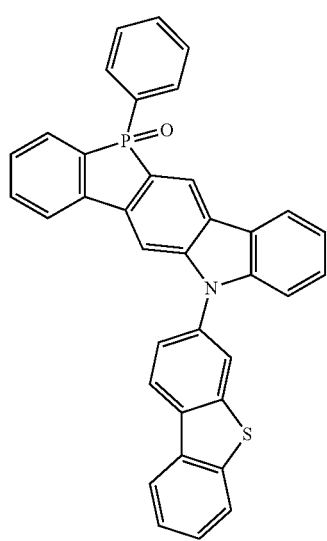
Formula 1-1-54
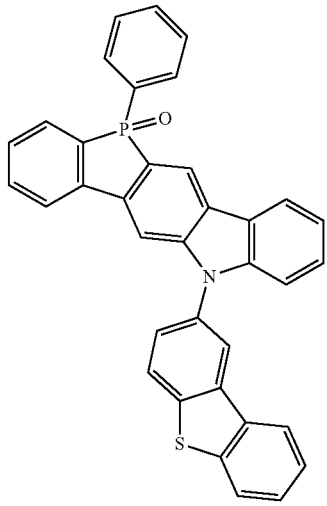
Formula 1-1-55
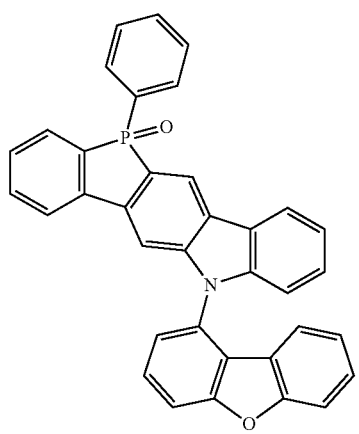
Formula 1-1-56
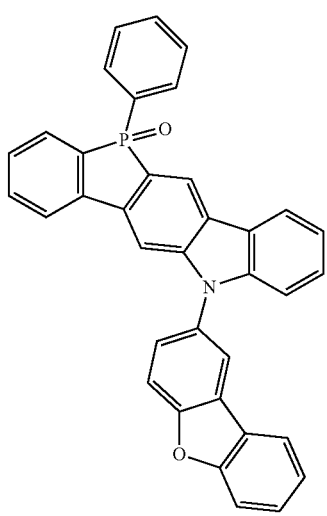

Formula 1-1-57
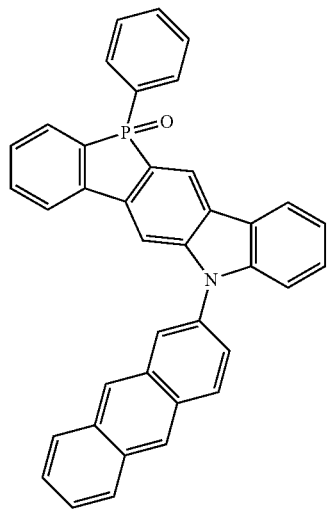
Formula 1-1-59
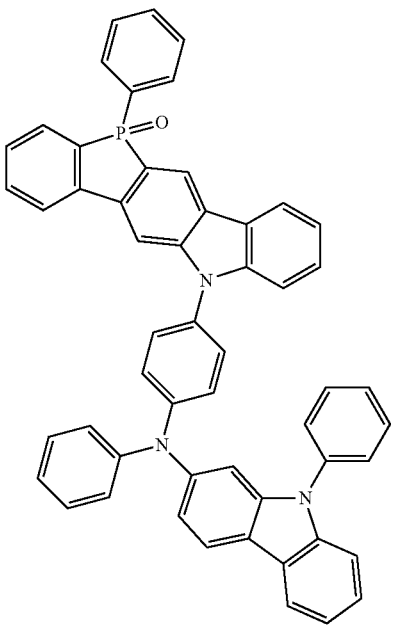
Formula 1-1-58
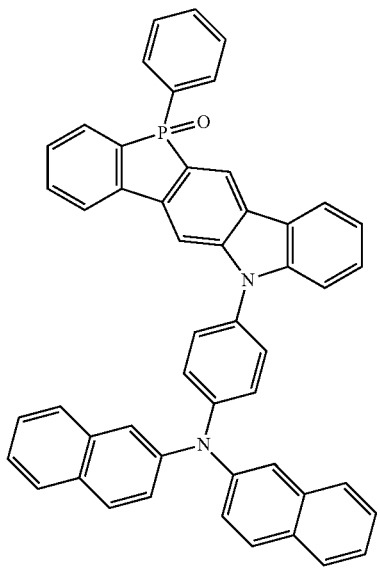
Formula 1-1-60
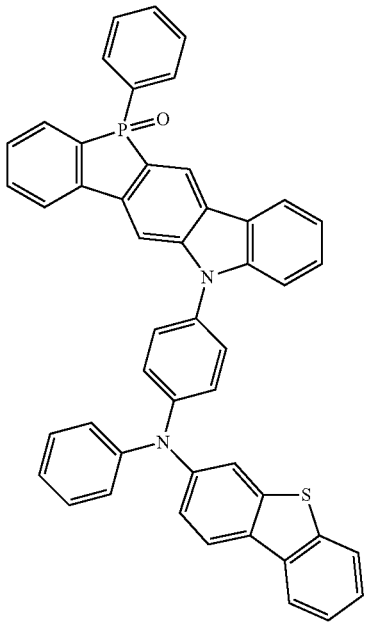

Formula 1-1-61
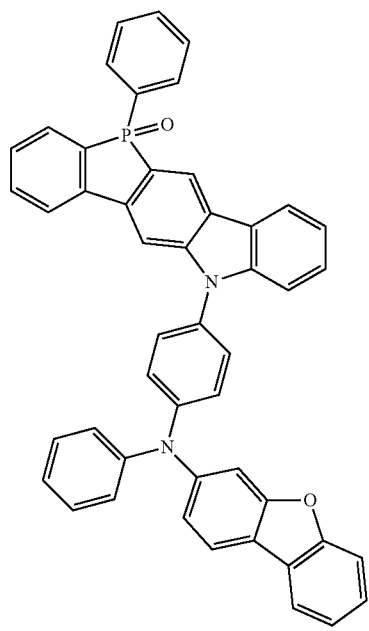
Formula 1-1-62
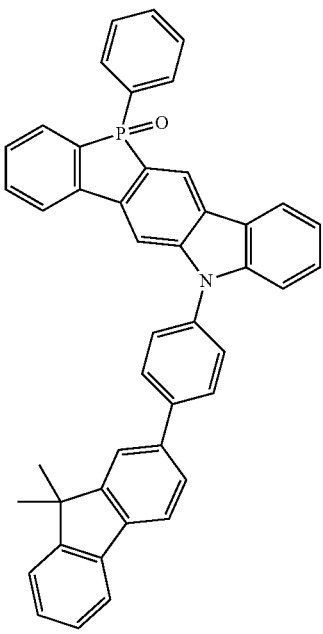
Formula 1-1-63
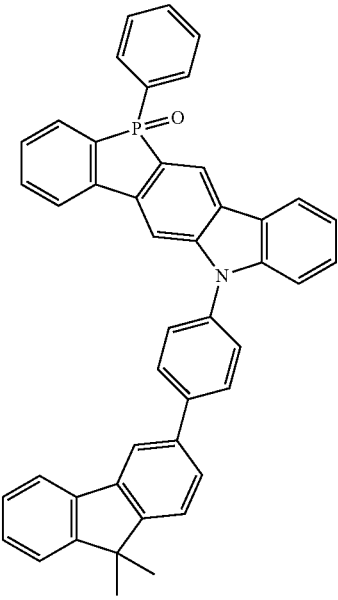
Formula 1-1-64
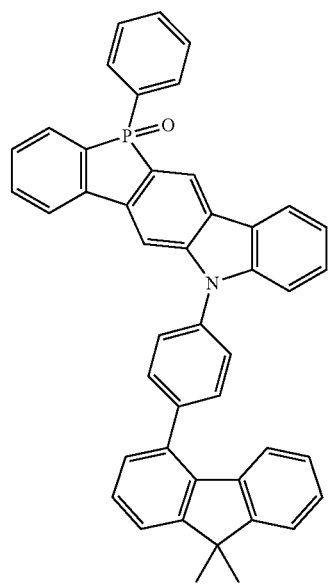

Formula 1-1-65
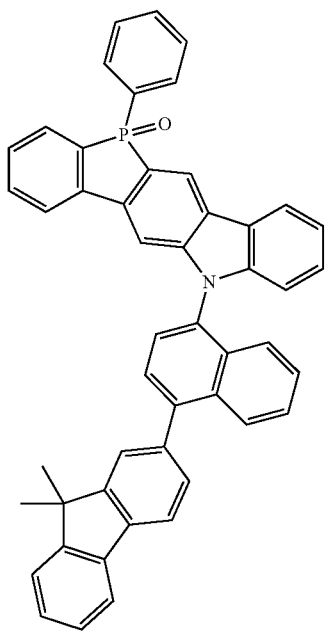
Formula 1-1-67
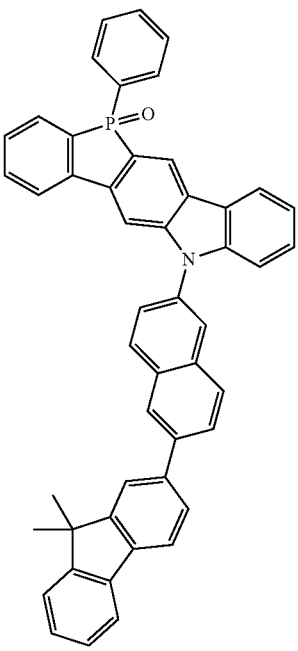
Formula 1-1-66
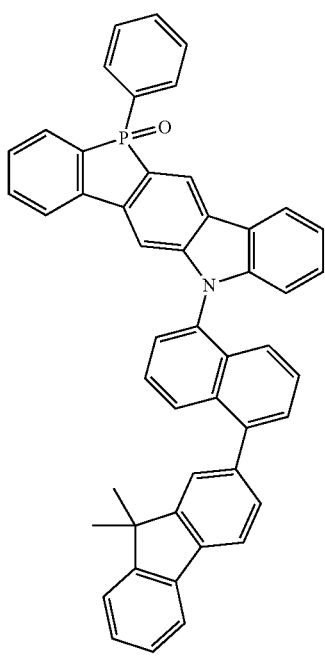
Formula 1-1-68
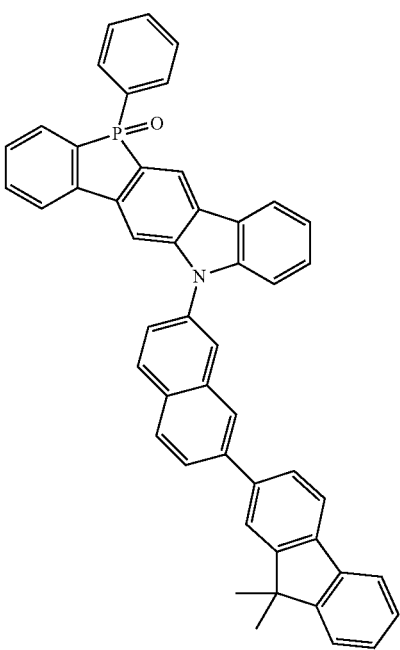

-continued
Formula 1-1-69
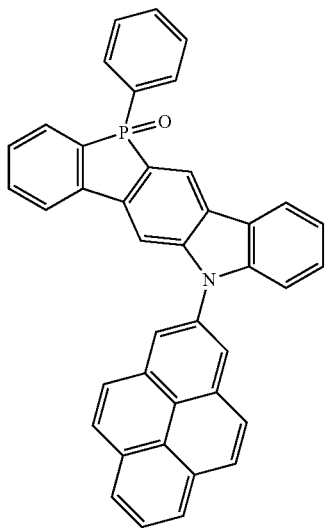
Formula 1-1-70
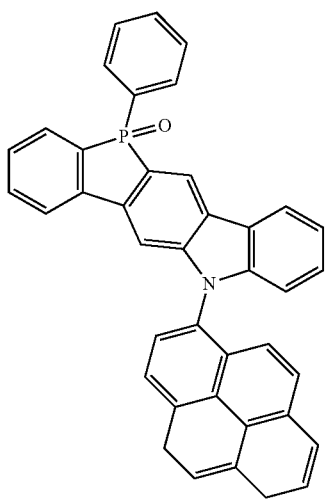
Formula 1-1-71
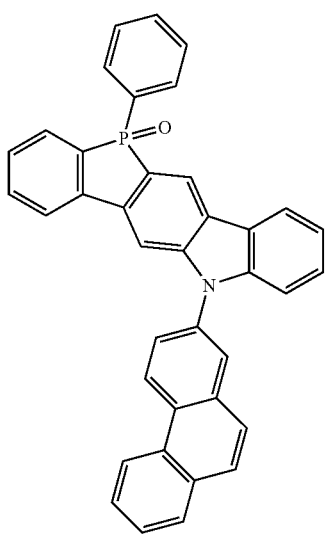
Formula 1-1-72
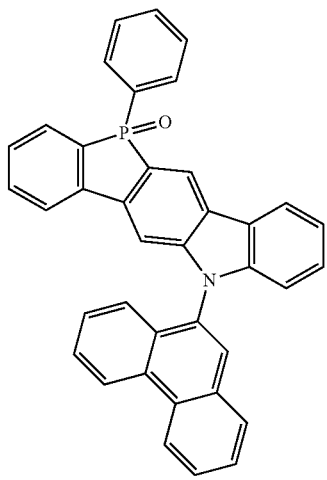
Formula 1-1-73
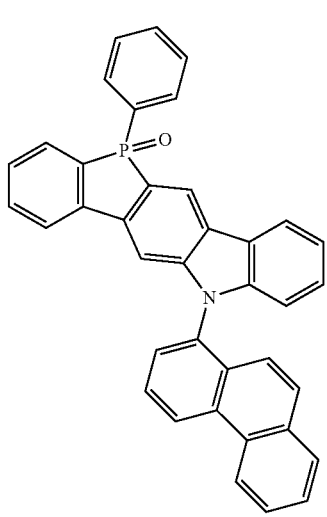
Formula 1-1-74
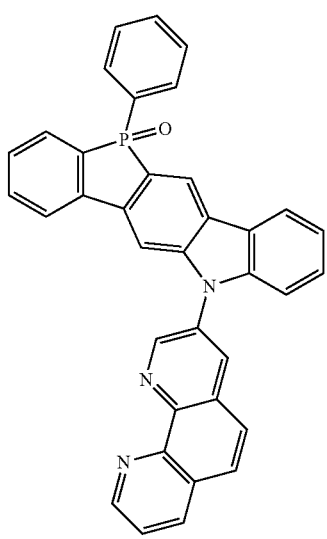

Formula 1-1-75
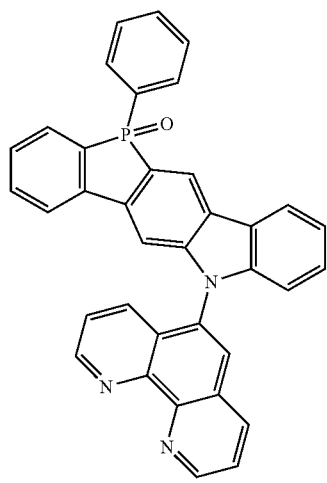
Formula 1-1-76
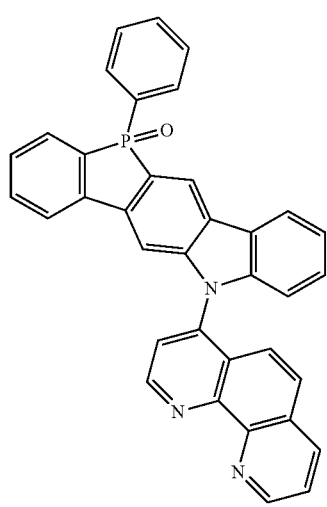
Formula 1-1-77
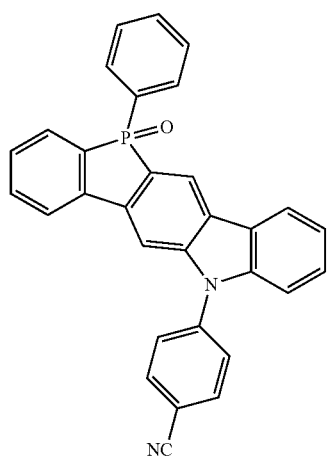
Formula 1-1-78
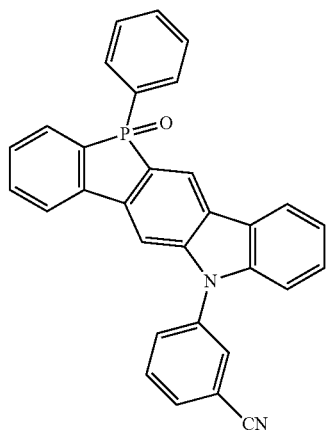
Formula 1-1-79
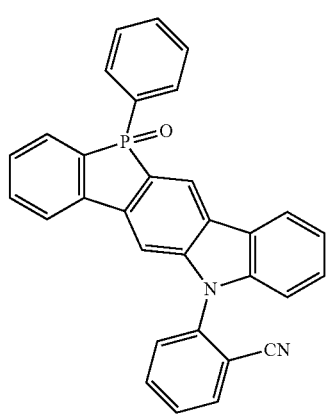
Formula 1-1-80
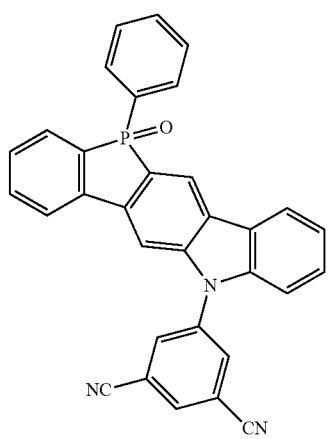

Formula 1-1-81
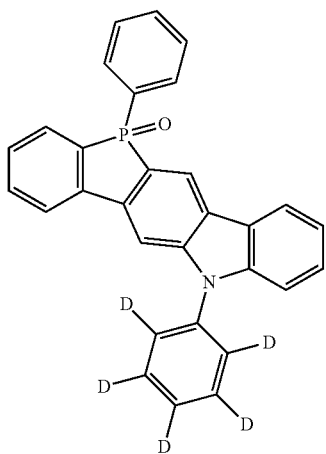
Formula 1-1-82
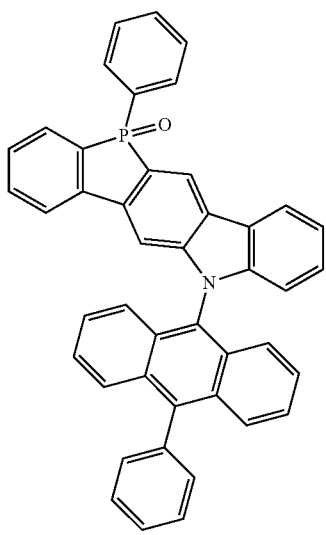
Formula 1-1-83
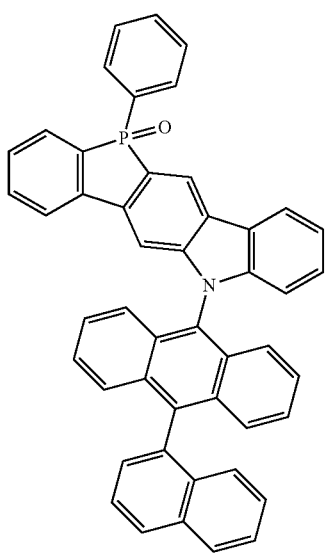
Formula 1-1-84
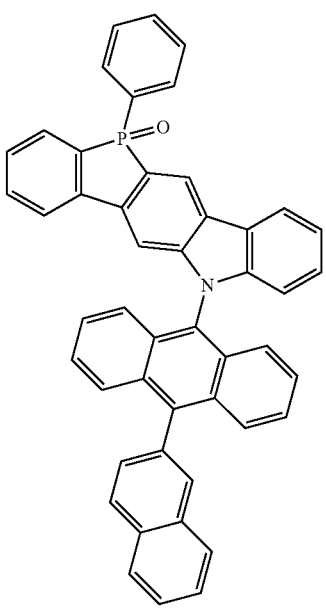
Formula 1-1-85
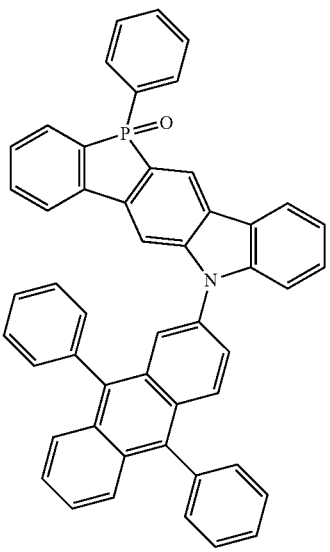

Formula 1-1-86
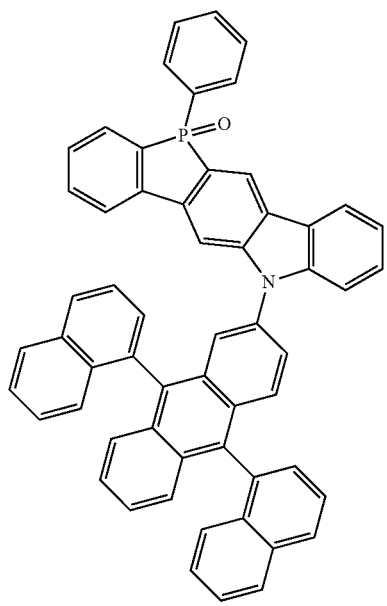
Formula 1-1-87
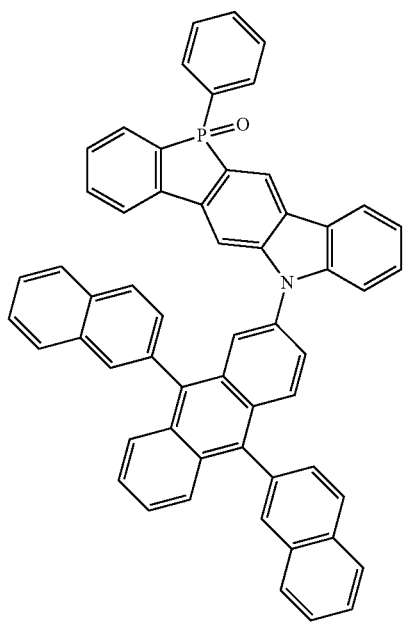
Formula 1-1-88
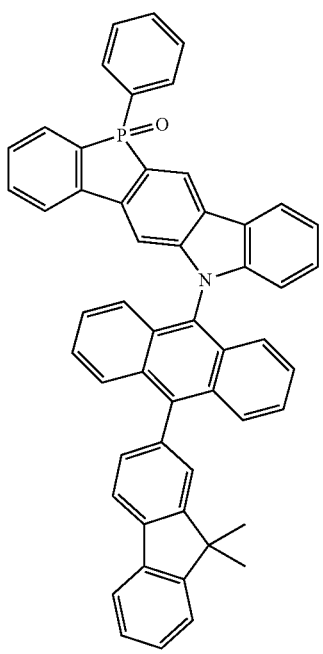
Formula 1-1-89
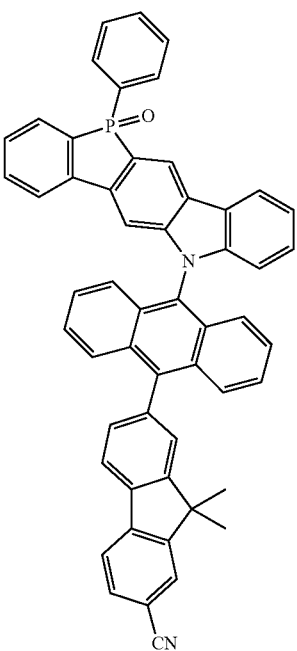

Formula 1-1-90
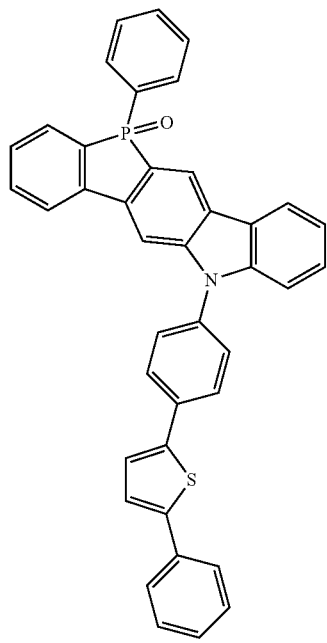
Formula 1-1-92
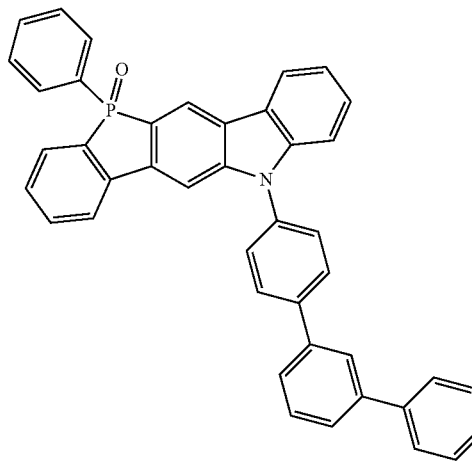
Formula 1-1-93
Formula 1-1-91
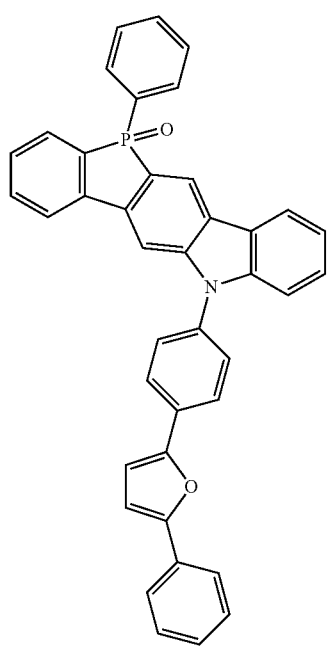
Formula 1-1-94
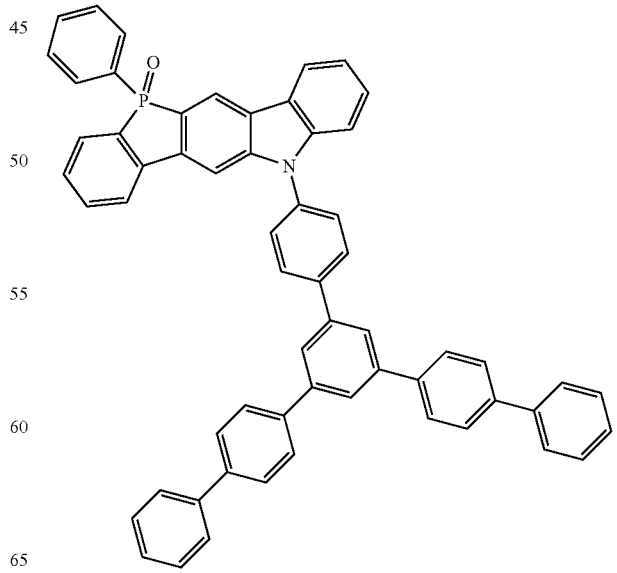

Formula 1-1-95
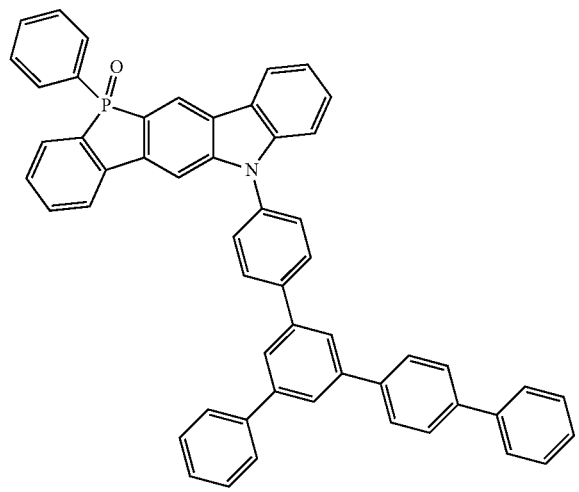
Formula 1-1-97
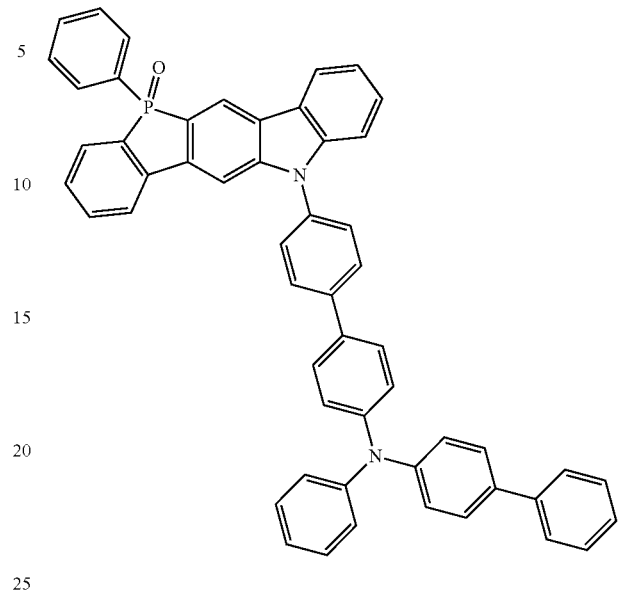
Formula 1-1-96
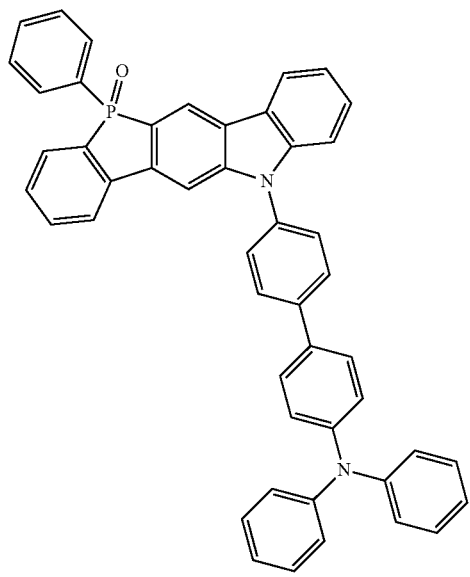
Formula 1-1-98
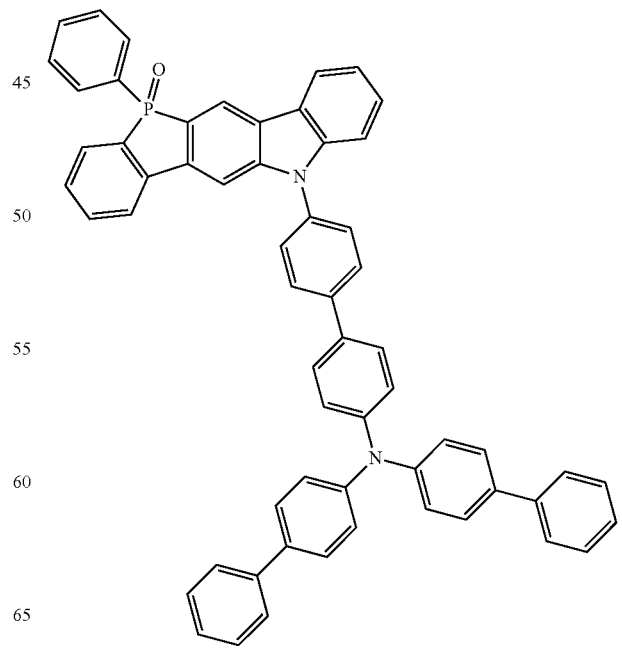

Formula 1-1-99
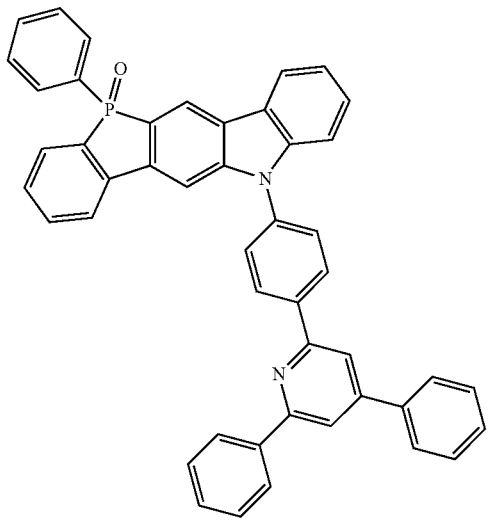
Formula 1-1-100
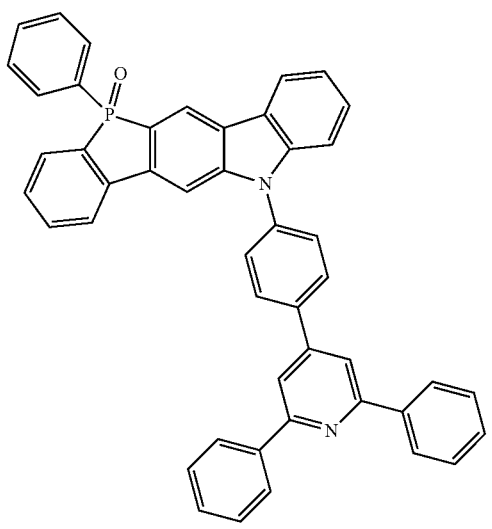
Formula 1-1-101
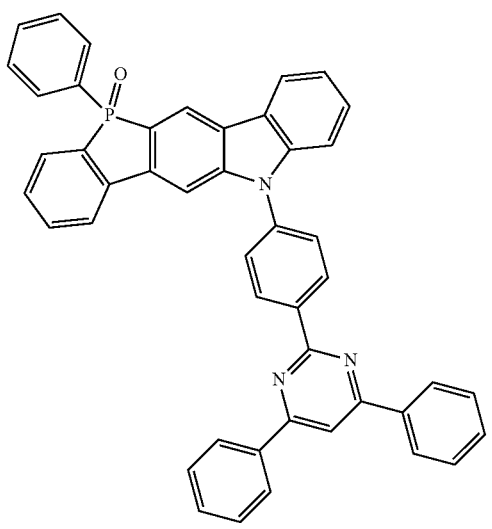
Formula 1-1-102
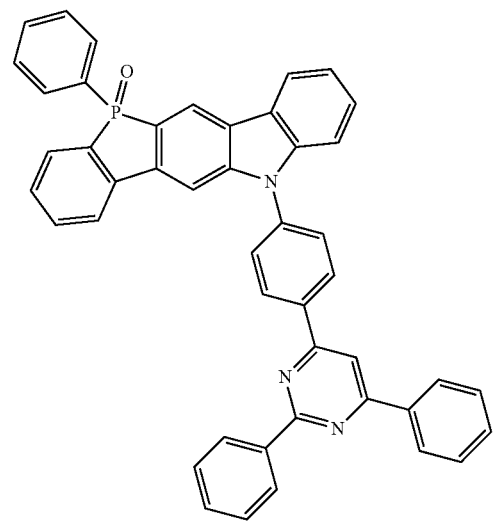
Formula 1-1-103
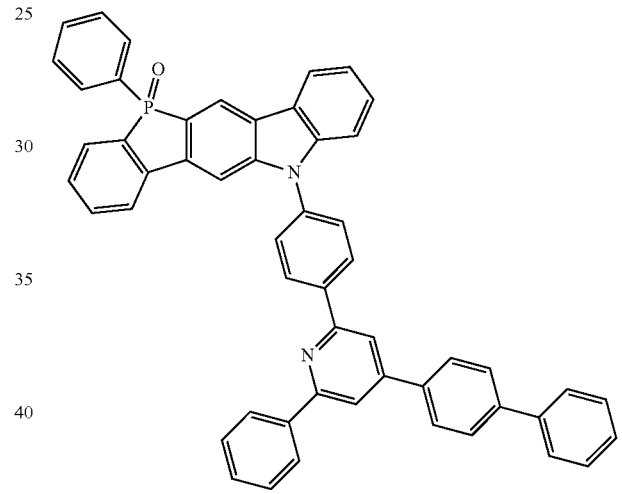
Formula 1-1-104
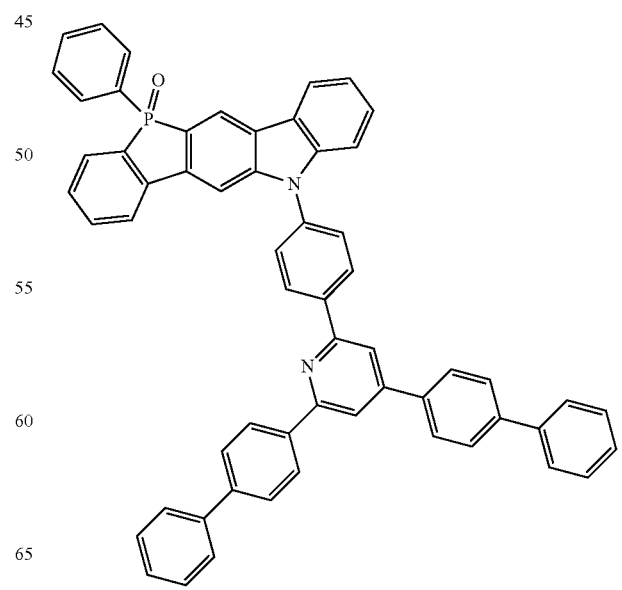

Formula 1-1-105
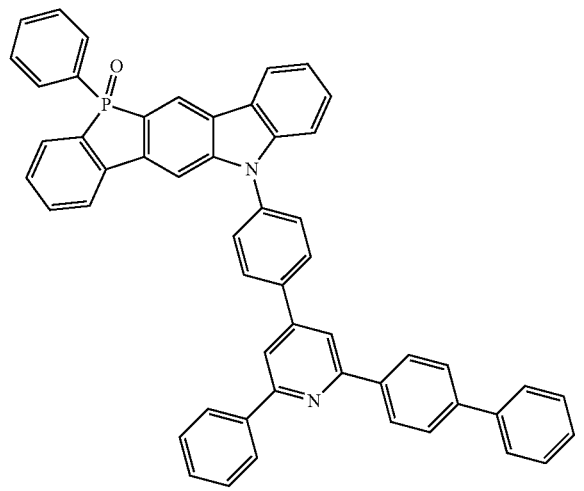
Formula 1-1-106
Formula 1-1-107
Formula 1-1-108
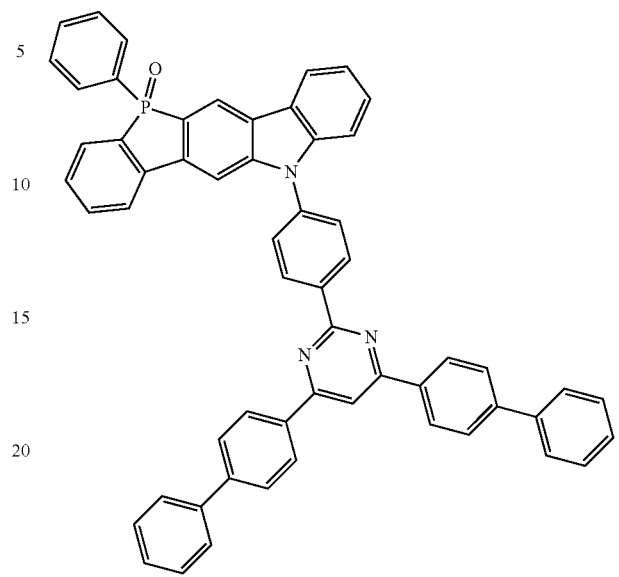
Formula 1-1-109

Formula 1-1-110
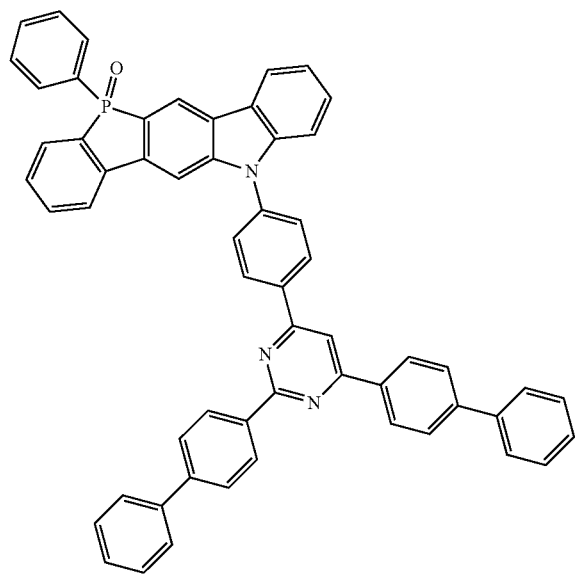
Formula 1-1-113
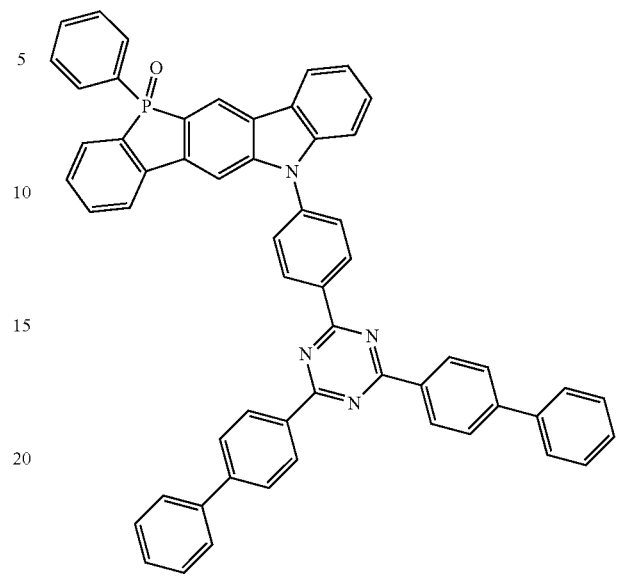
Formula 1-1-111
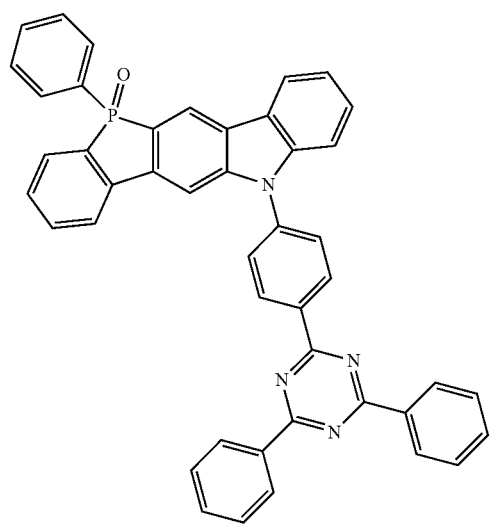
Formula 1-1-112
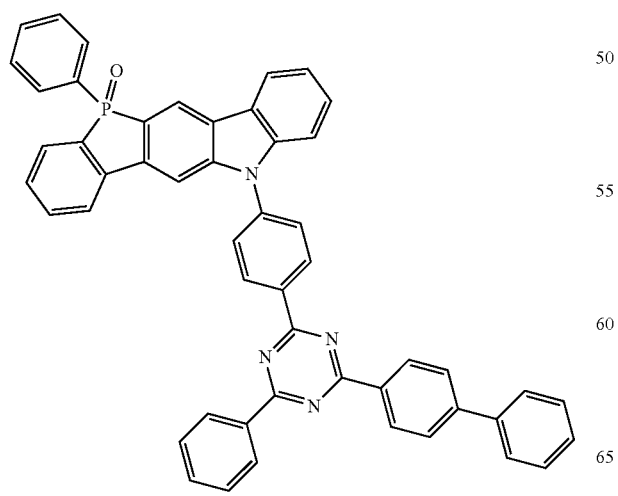
Formula 1-1-114
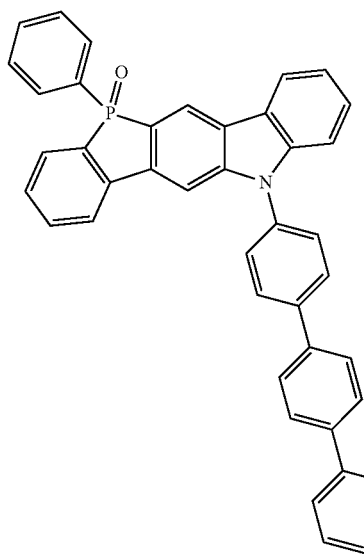

Formula 1-1-115
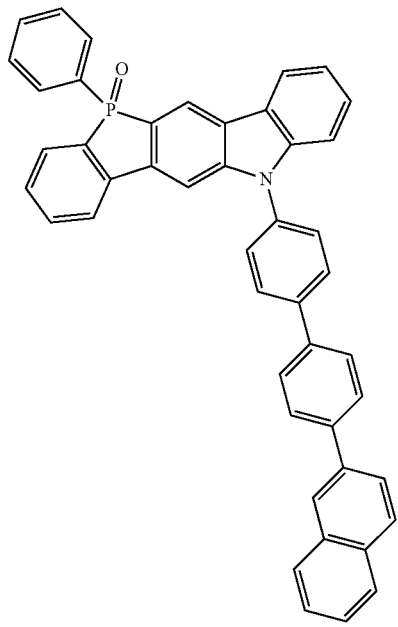
Formula 1-1-117
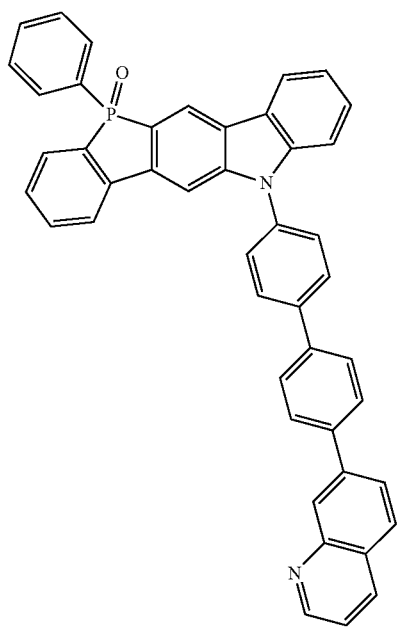
Formula 1-1-118
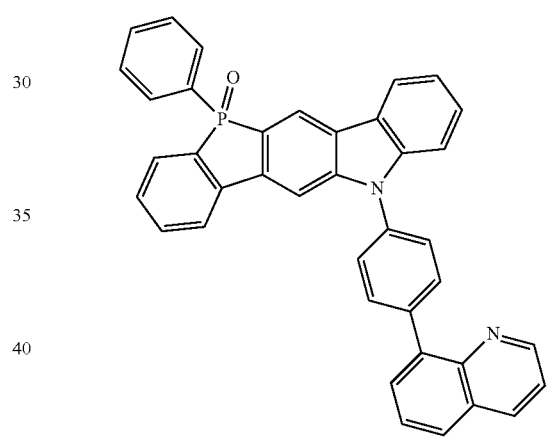
Formula 1-1-116
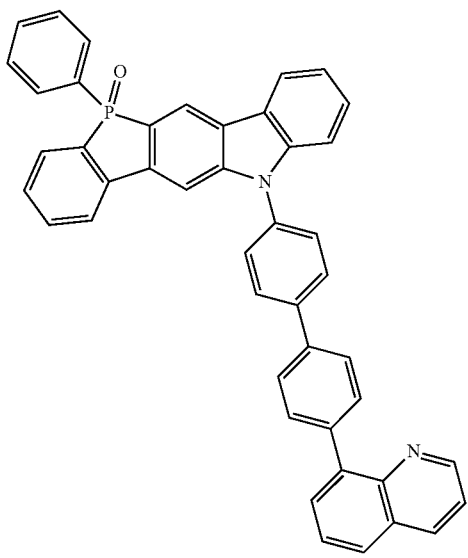
Formula 1-1-119
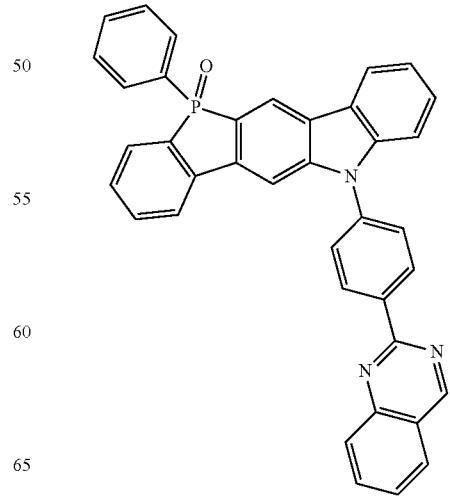

Formula 1-1-120
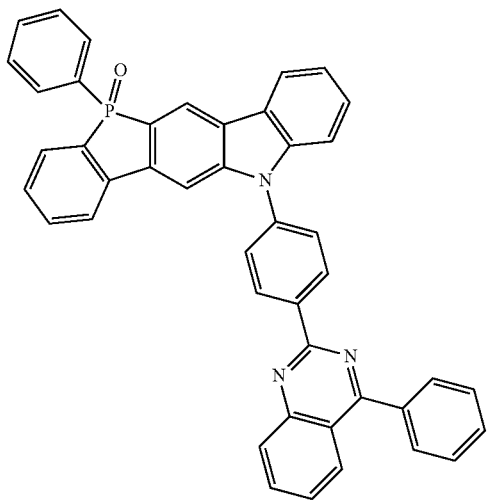
Formula 1-1-121
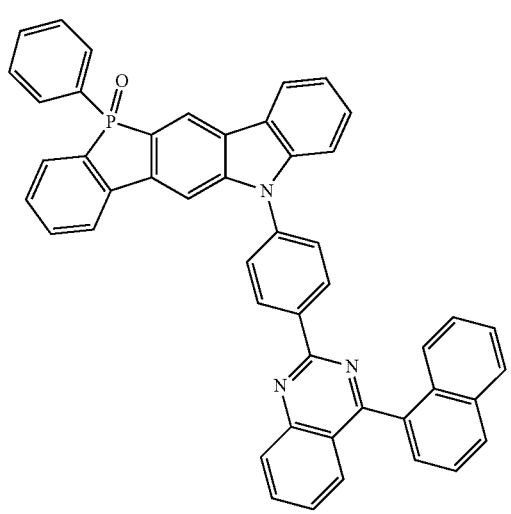
Formula 1-1-122
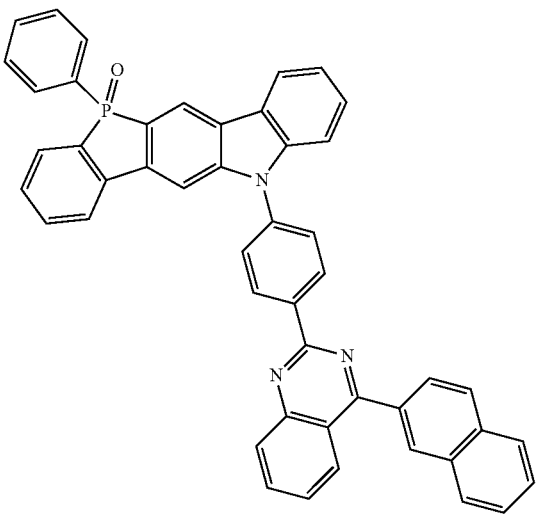
Formula 1-1-123
Formula 1-1-124
Formula 1-1-125
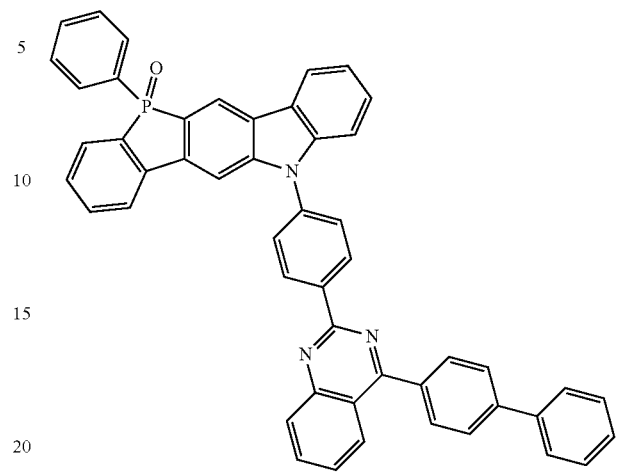

Formula 1-1-126
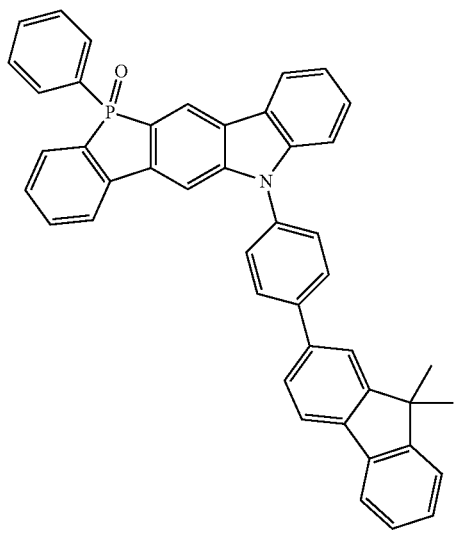
Formula 1-1-129
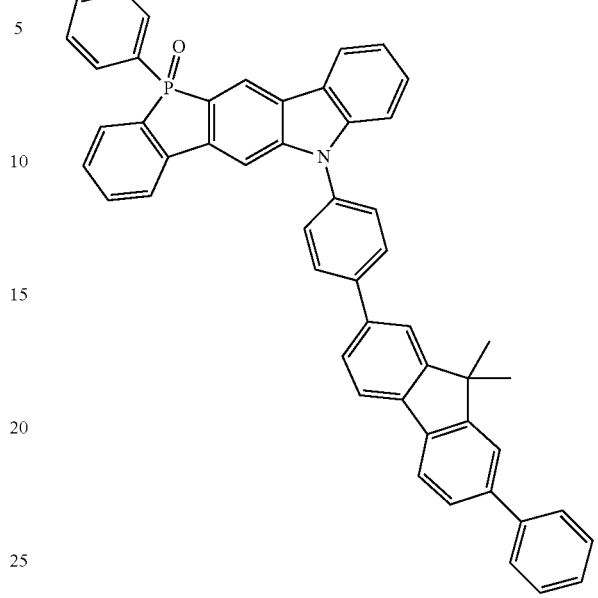
Formula 1-1-127
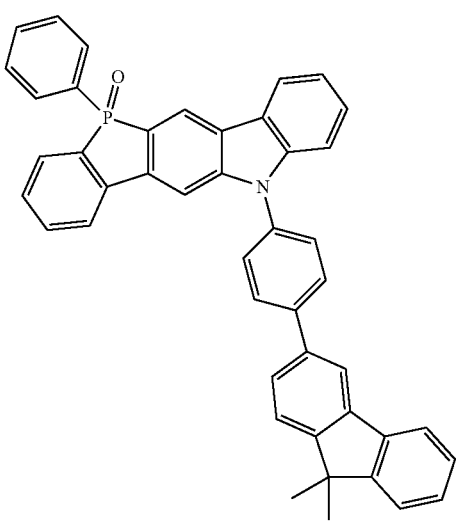
Formula 1-1-128
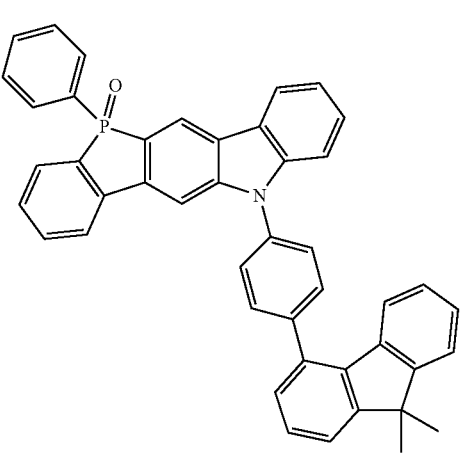
Formula 1-1-130
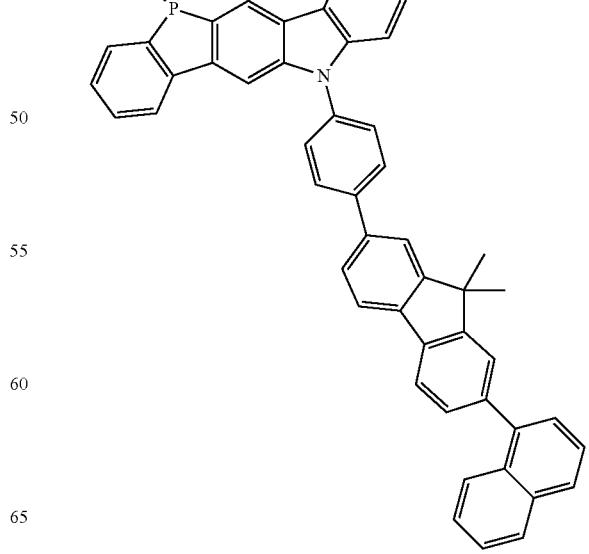

Formula 1-1-131
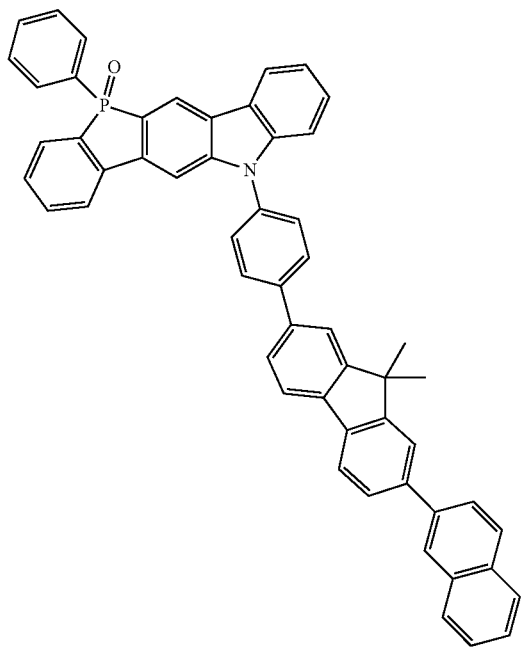
Formula 1-1-132
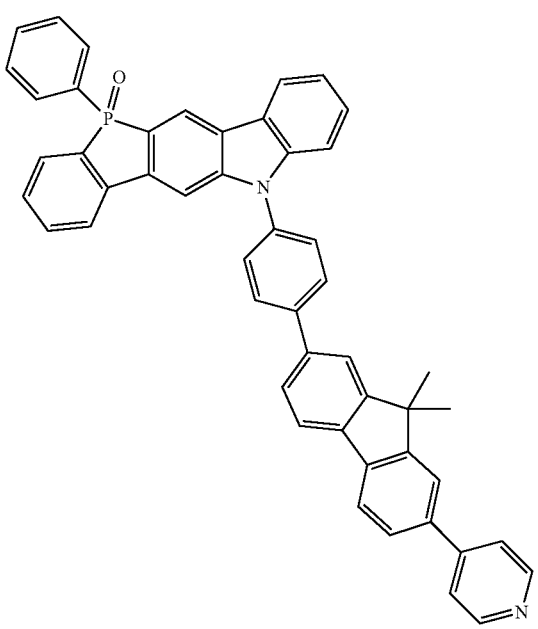
Formula 1-1-133
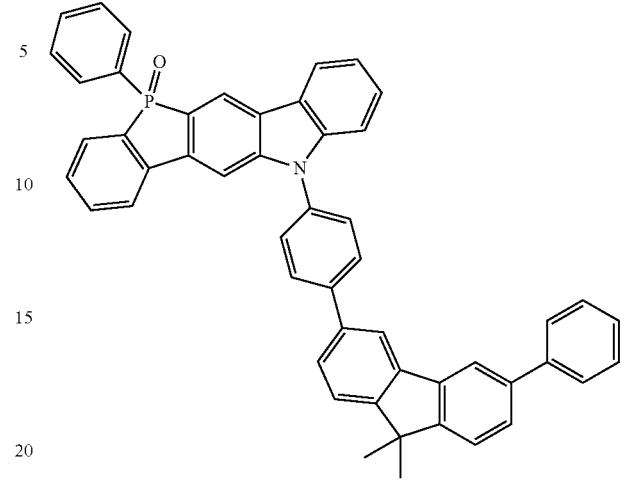
Formula 1-1-134
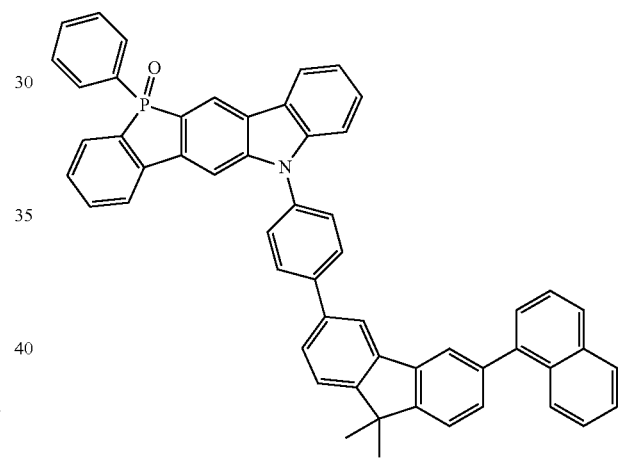
Formula 1-1-135
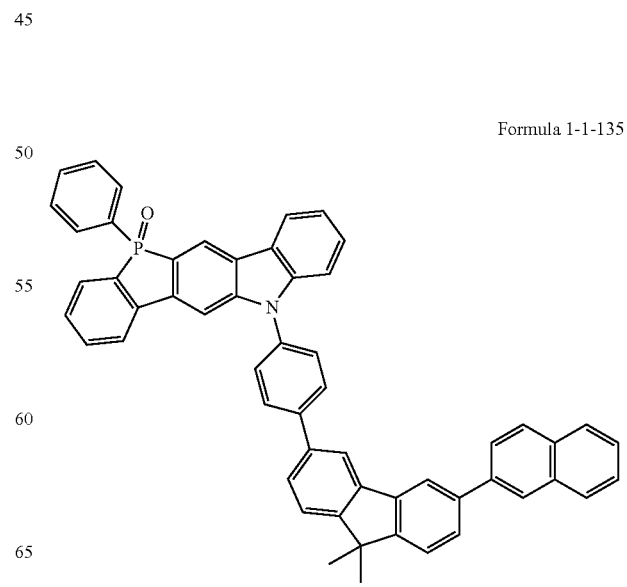

-continued
Formula 1-1-136
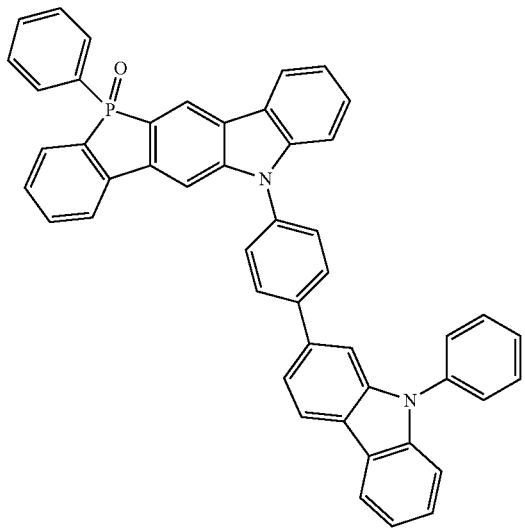
Formula 1-1-137
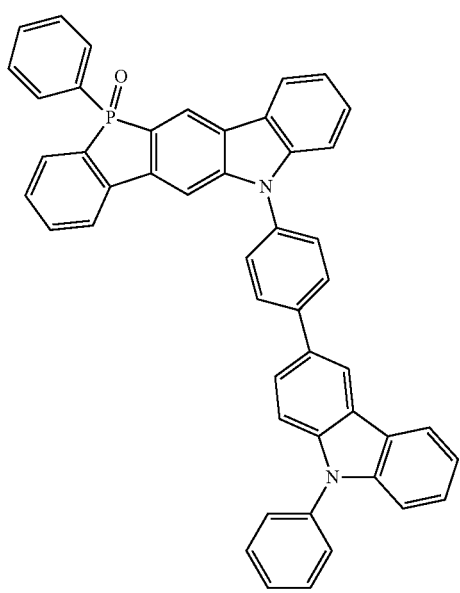
-continued
Formula 1-1-138
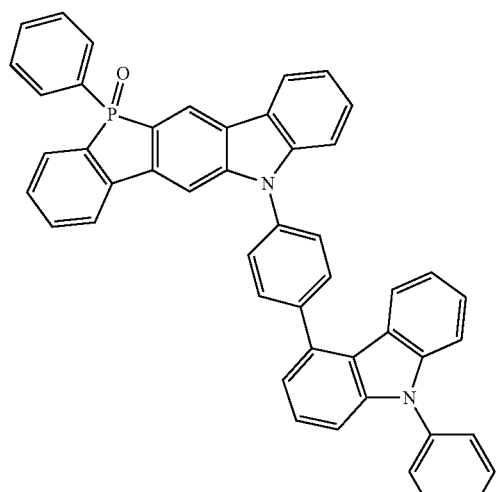
Formula 1-1-139
Formula 1-1-140
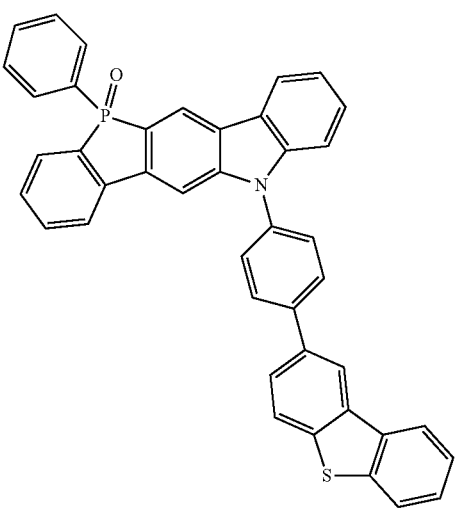

Formula 1-1-141
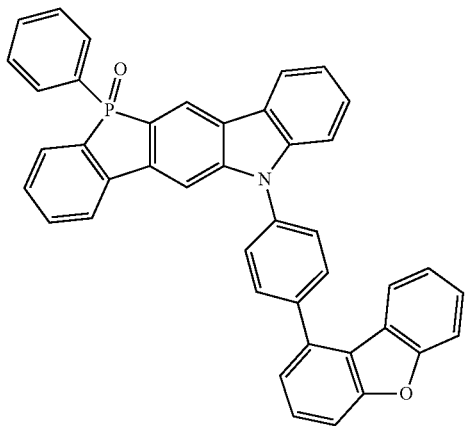
Formula 1-1-142
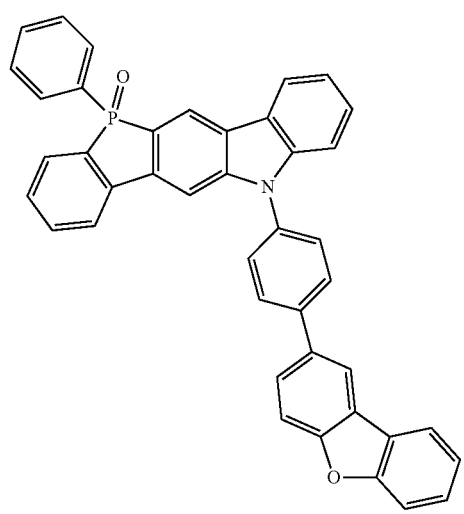
Formula 1-1-143
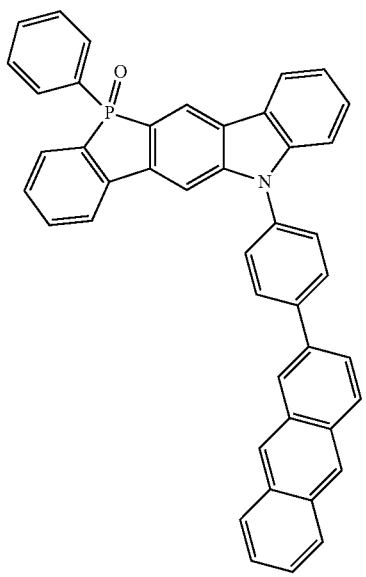
Formula 1-1-144
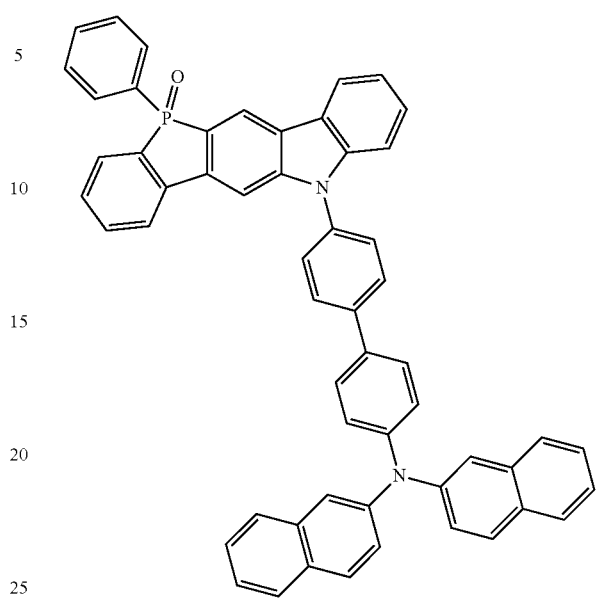
Formula 1-1-145
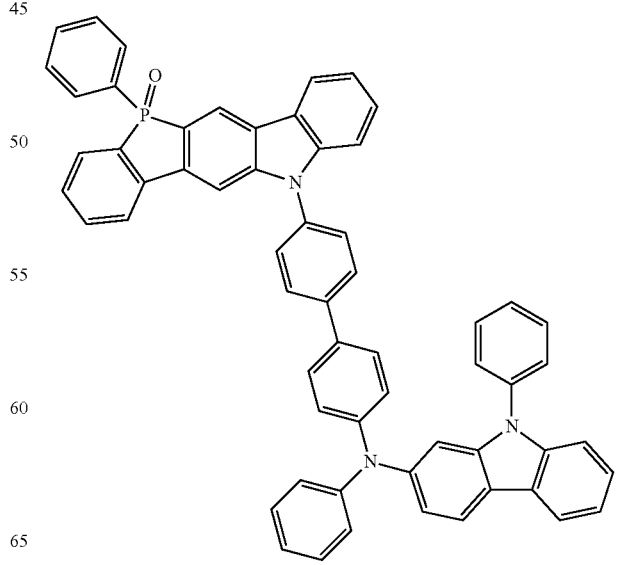

Formula 1-1-146
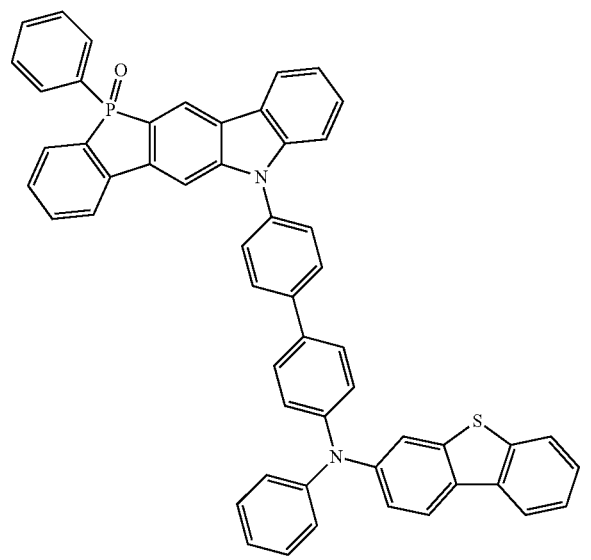
Formula 1-1-147
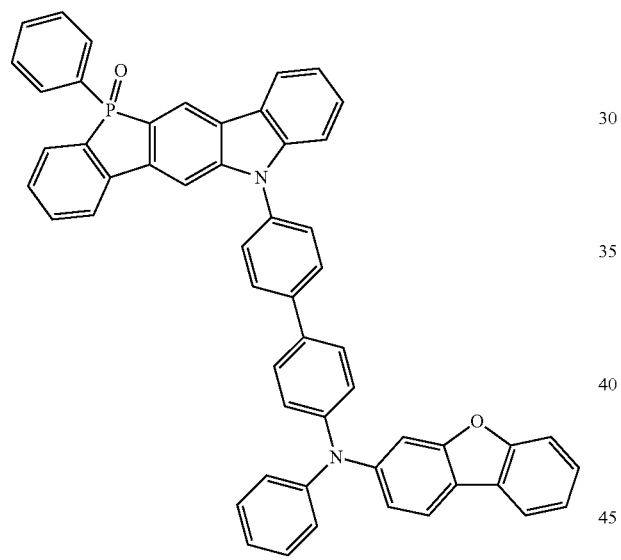
Formula 1-1-148
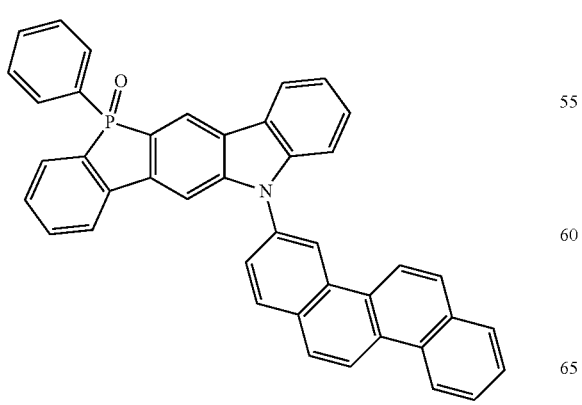
Formula 1-1-149
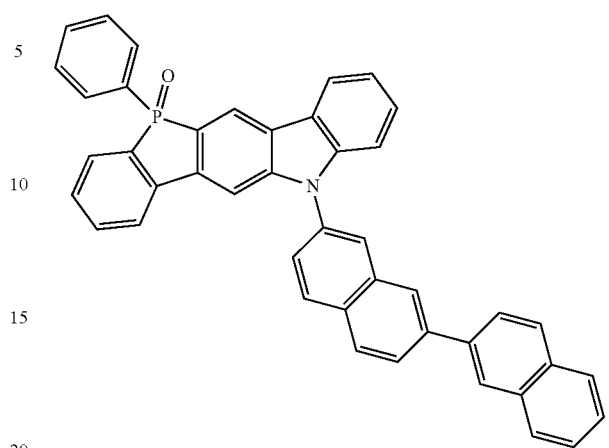
Formula 1-1-150
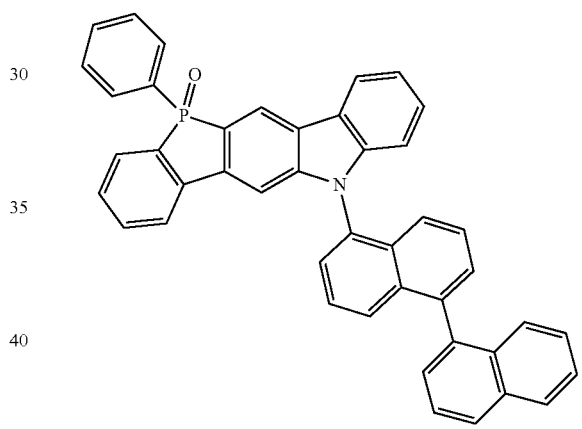
Formula 1-1-151
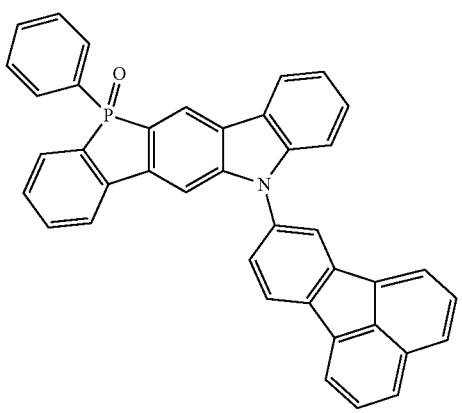

Formula 1-1-152
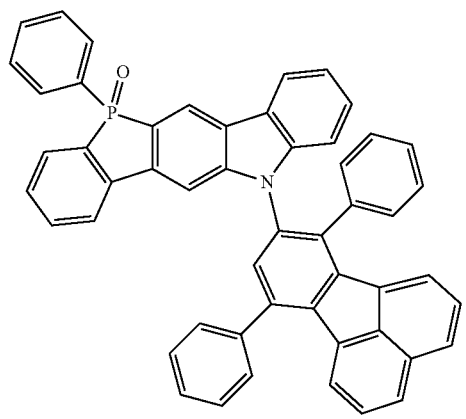
Formula 1-1-155
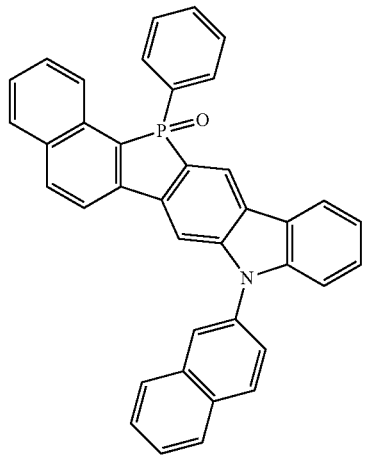
Formula 1-1-153
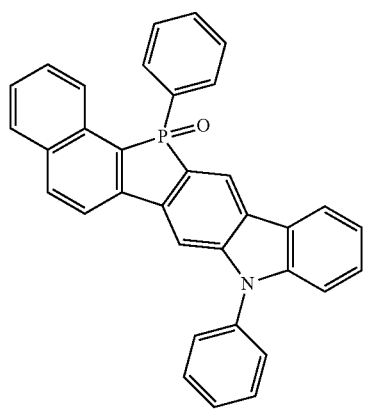
Formula 1-1-156
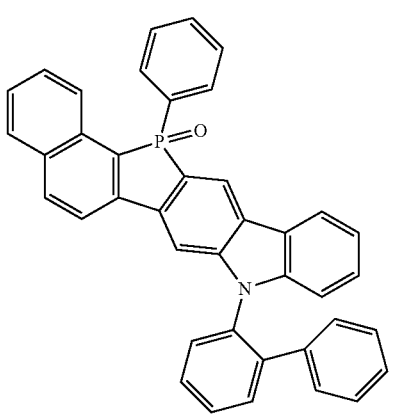
Formula 1-1-154
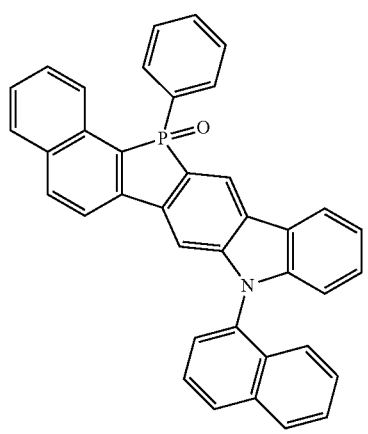
Formula 1-1-157
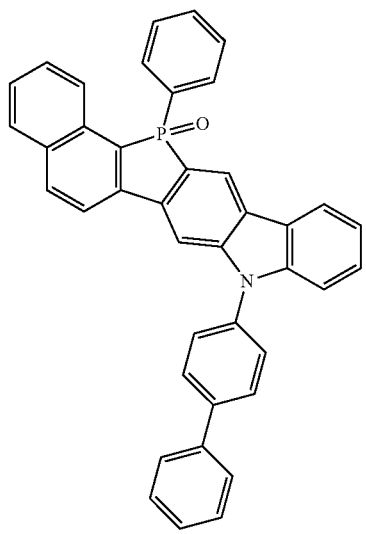

Formula 1-1-158
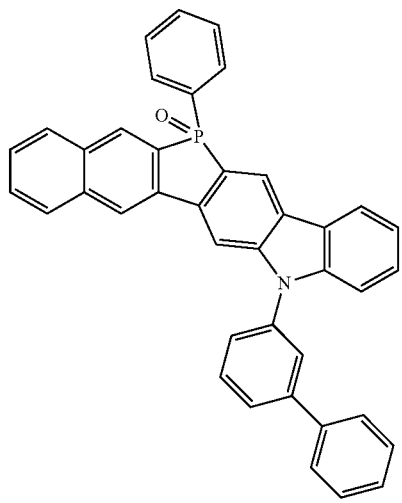
Formula 1-1-159
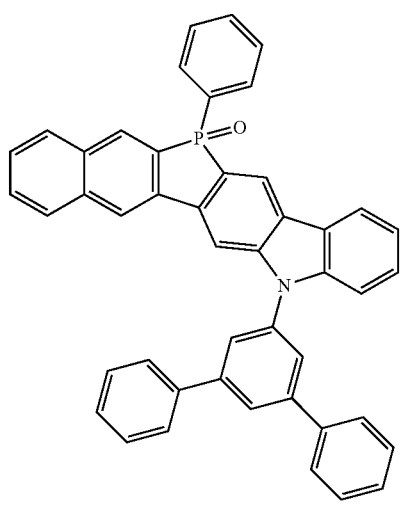
Formula 1-1-160
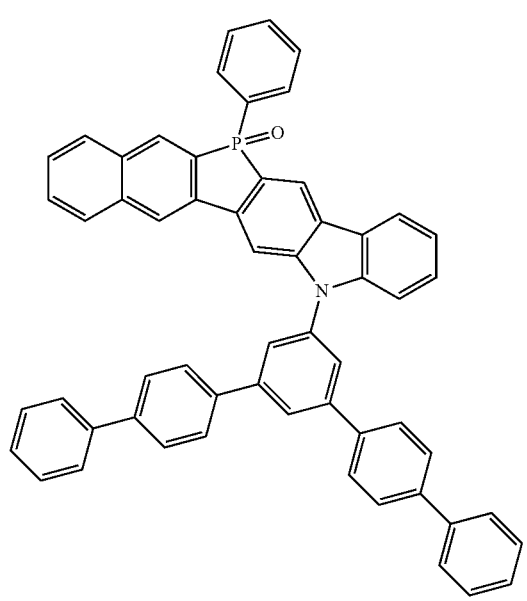
Formula 1-1-161
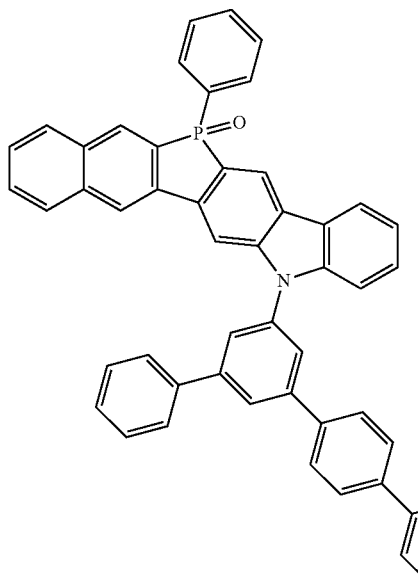
Formula 1-1-162
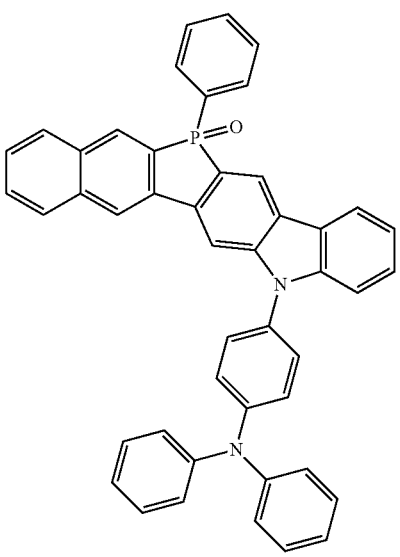

Formula 1-1-163
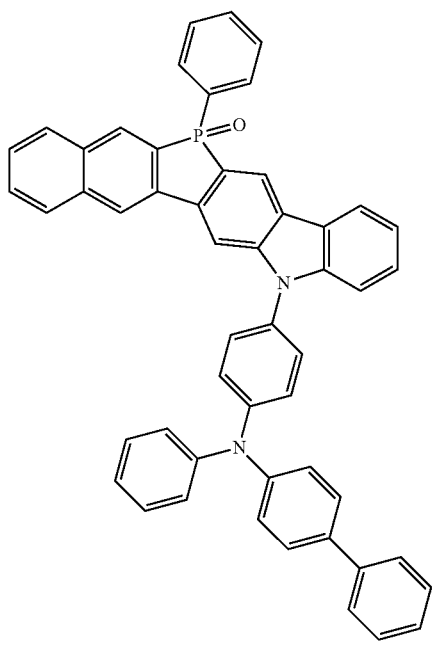
Formula 1-1-164
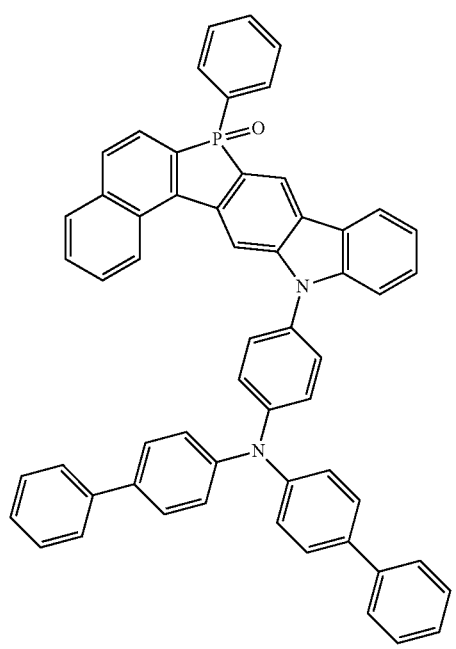
Formula 1-1-165
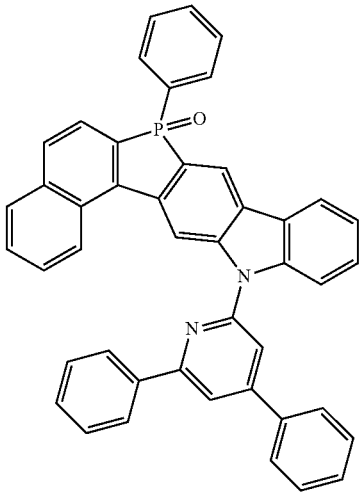
Formula 1-1-166
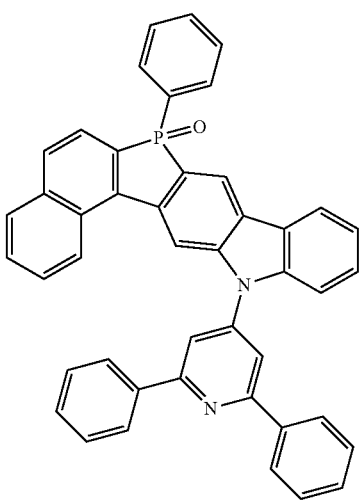
Formula 1-1-167
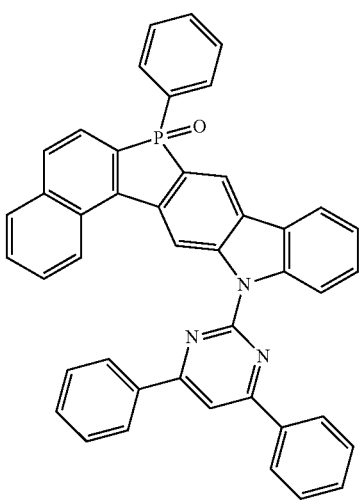

Formula 1-1-168
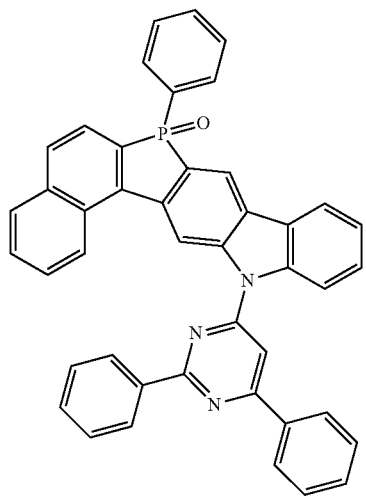
Formula 1-1-170
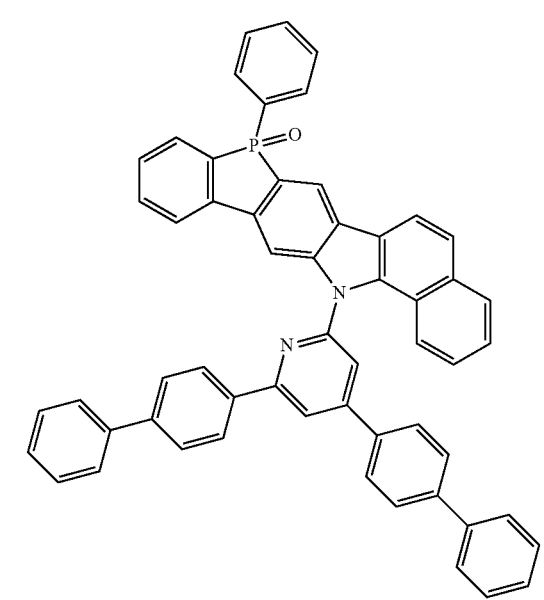
Formula 1-1-169
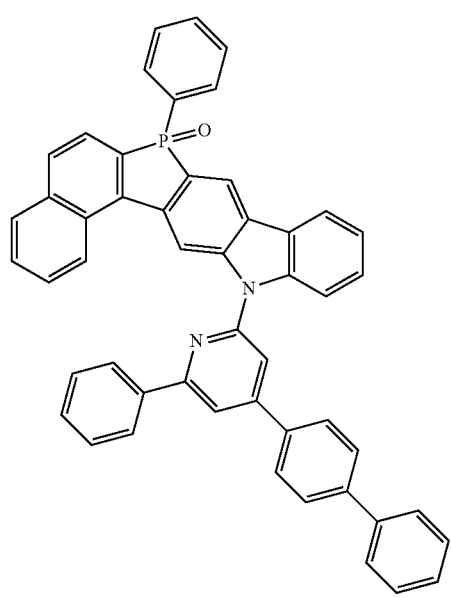
Formula 1-1-171
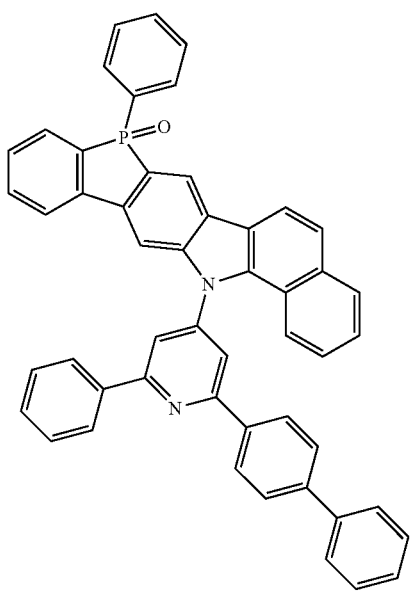

-continued
Formula 1-1-172
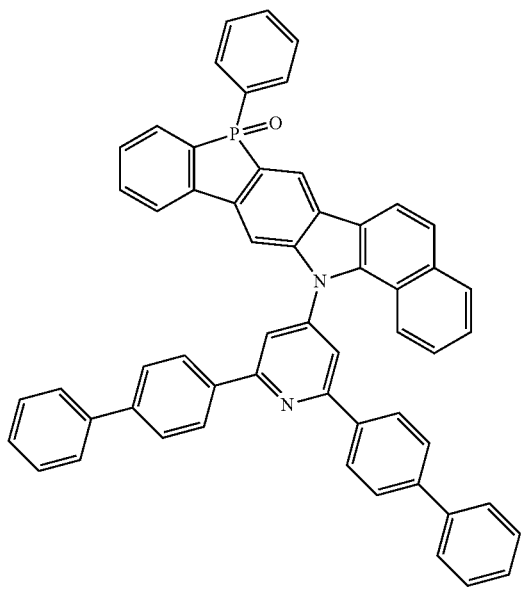
Formula 1-1-174
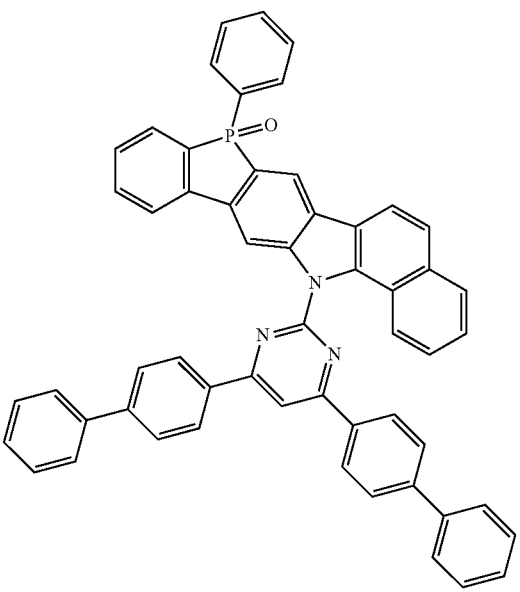
Formula 1-1-173
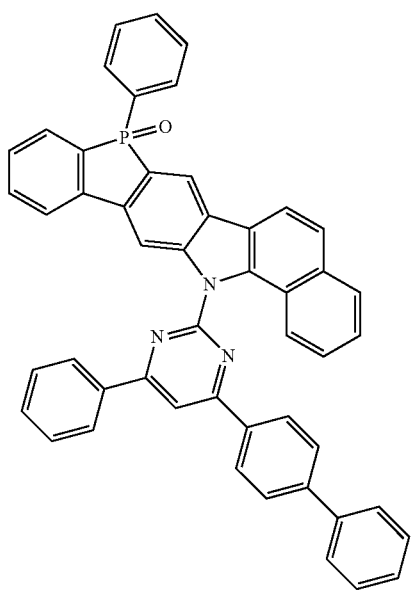
Formula 1-1-175
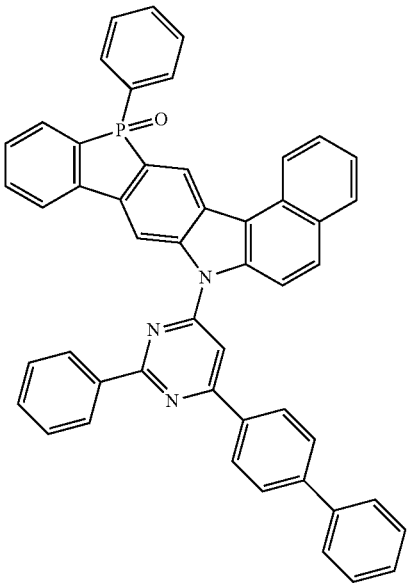

-continued
Formula 1-1-176
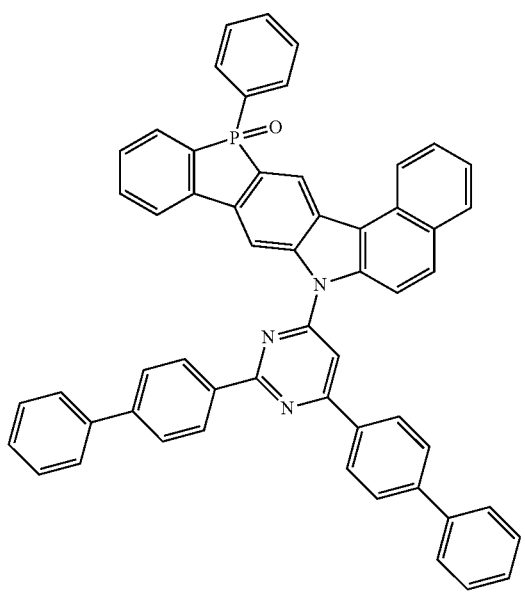
Formula 1-1-177
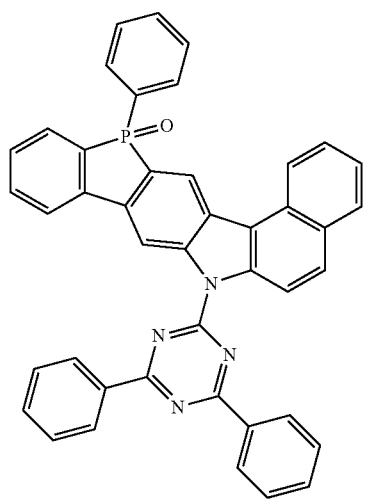
-continued
Formula 1-1-178
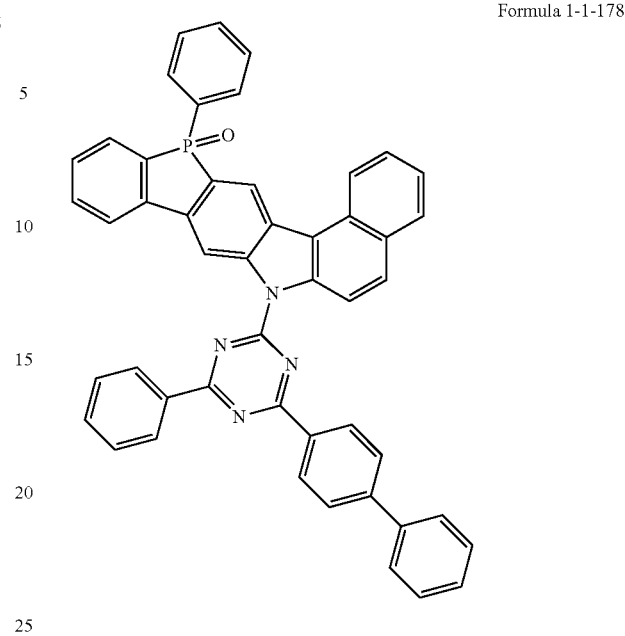
Formula 1-1-179
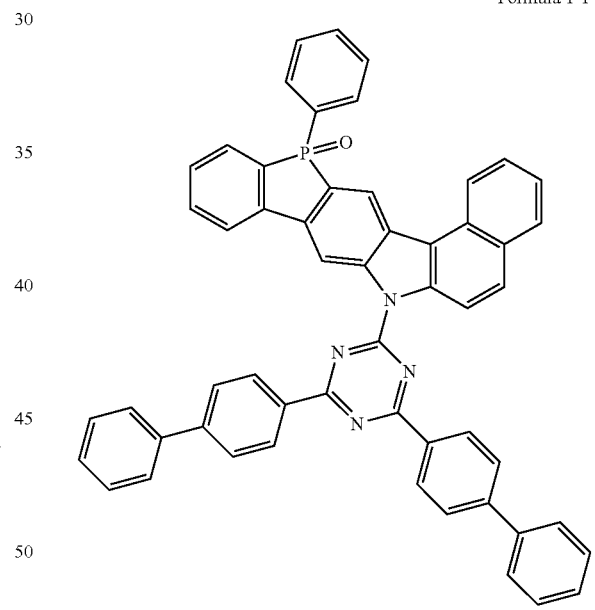
Formula 1-1-180
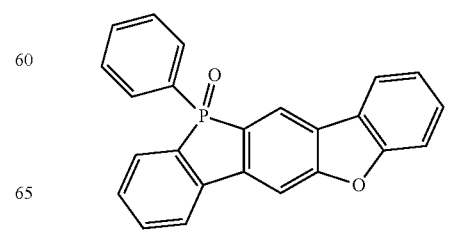

Formula 1-1-181
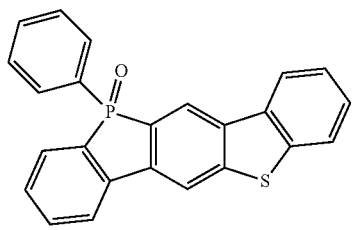
Formula 1-1-182
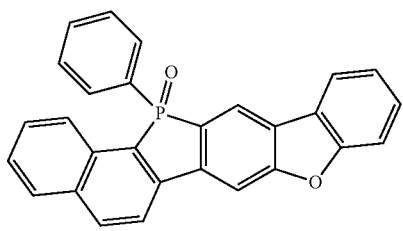
Formula 1-1-183
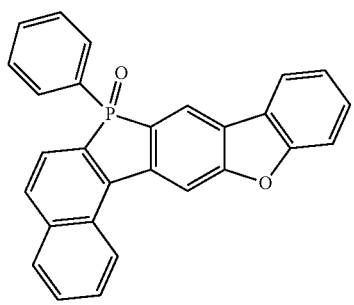
Formula 1-1-184
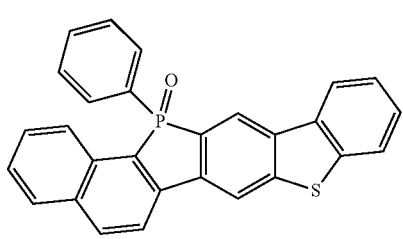
Formula 1-1-185
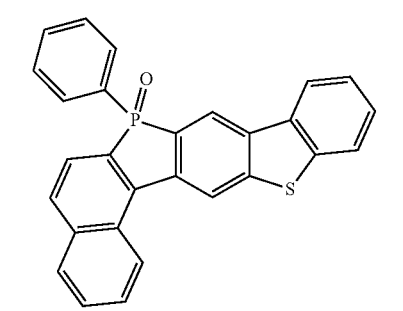
Formula 1-1-186
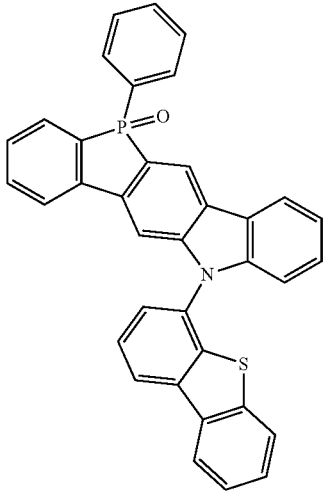
Formula 1-1-187
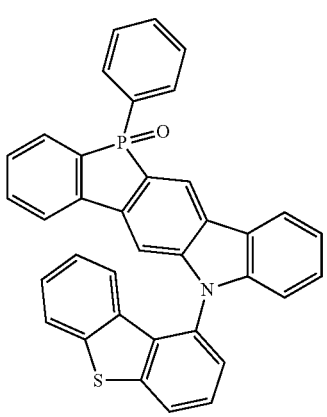
Formula 1-1-188
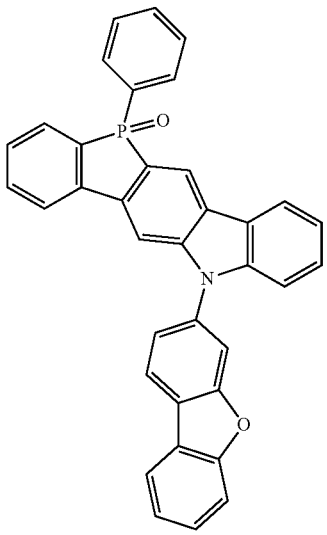

-continued
Formula 1-1-189
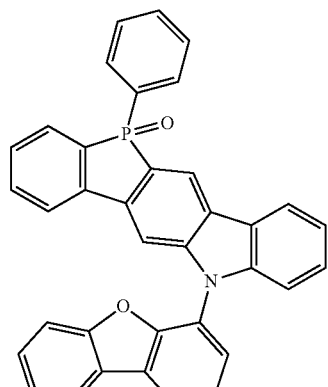
Formula 1-1-190
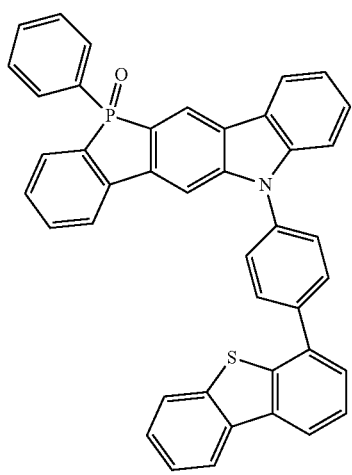
Formula 1-1-191
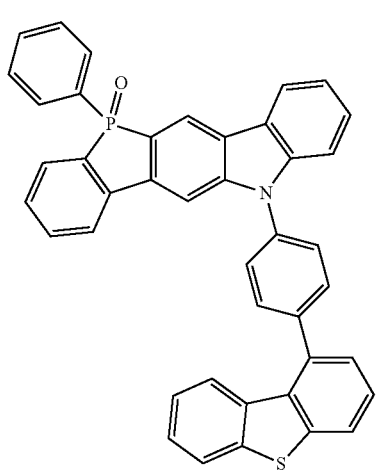
Formula 1-1-192
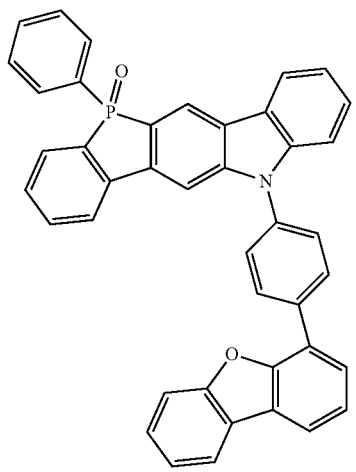
Formula 1-1-193
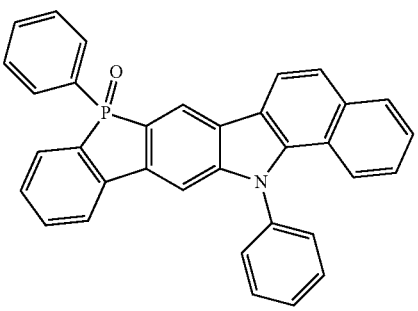
Formula 1-1-194

-continued
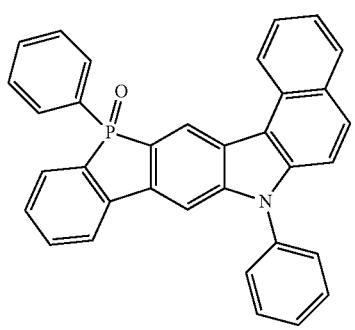
Formula 1-1-195
In an exemplary embodiment of the present specification, the compound represented by Formula 1 is represented by Formula 1-2.
In an exemplary embodiment of the present specification, the compound represented by Formula 1-2 is represented by any one of the following Formulae 1-2-1 to 1-2-195.
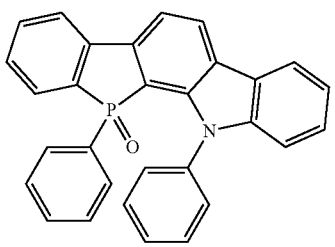
Formula 1-2-1
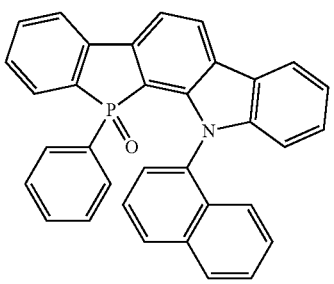
Formula 1-2-2
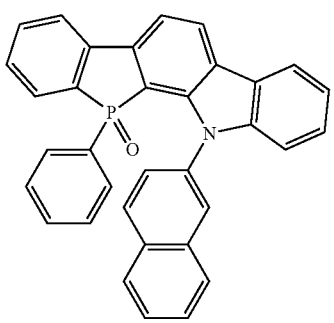
Formula 1-2-3
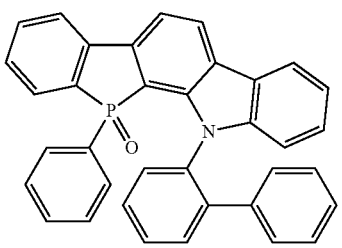
Formula 1-2-4
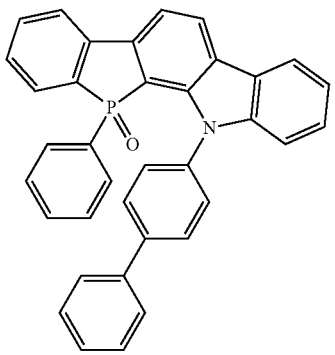
Formula 1-2-5
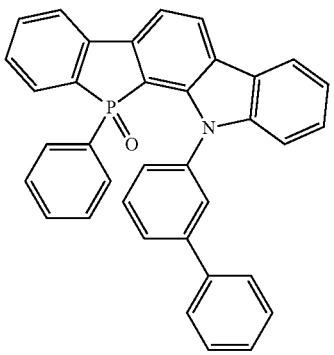
Formula 1-2-6

-continued
Formula 1-2-7
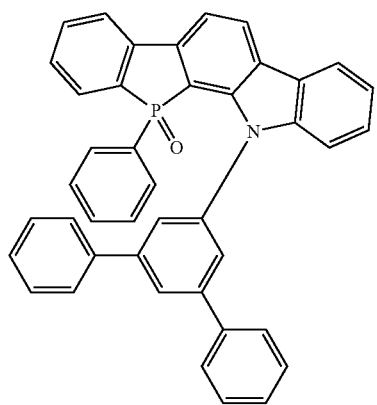
Formula 1-2-8
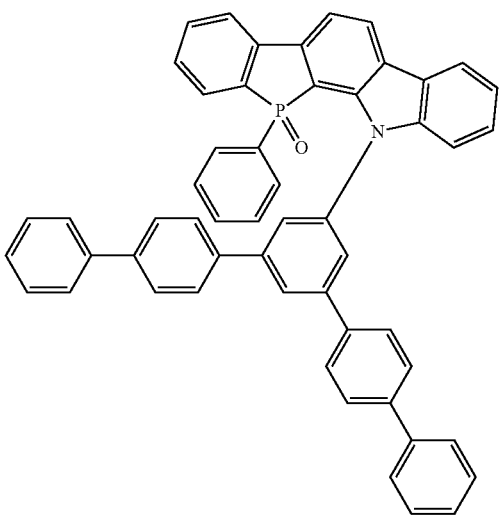
Formula 1-2-9
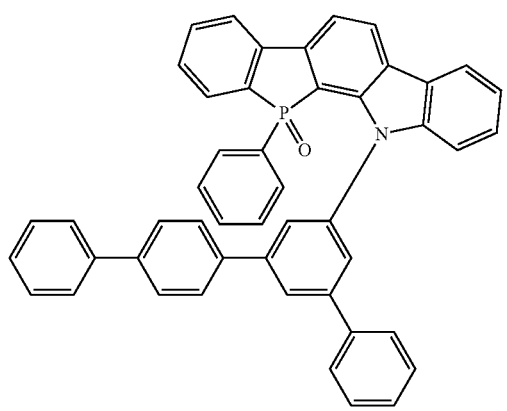
Formula 1-2-10
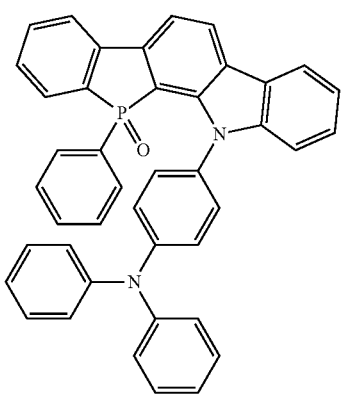
Formula 1-2-11
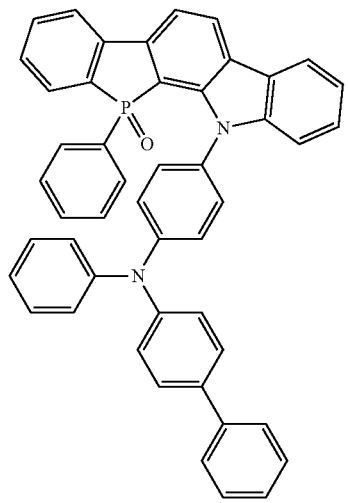
Formula 1-2-12
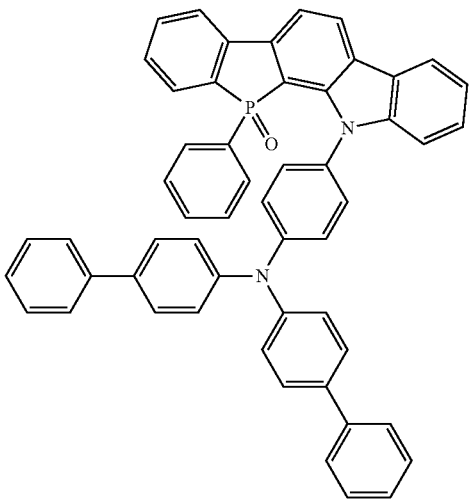

Formula 1-2-13
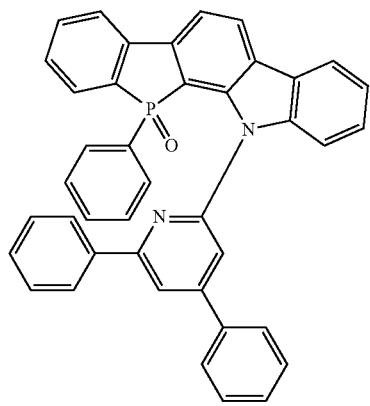
Formula 1-2-14
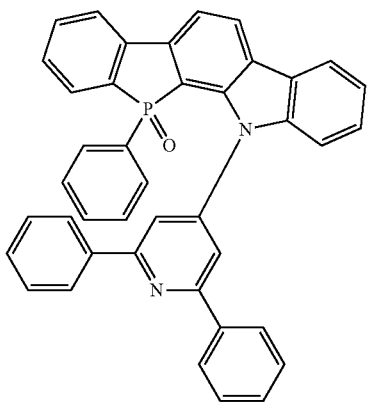
Formula 1-2-15
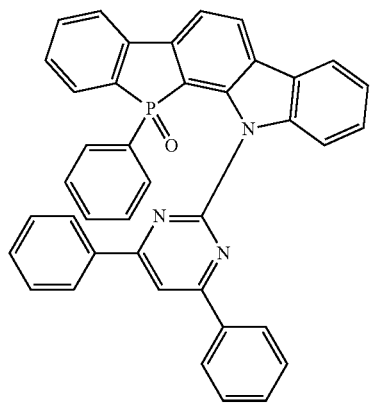
Formula 1-2-16
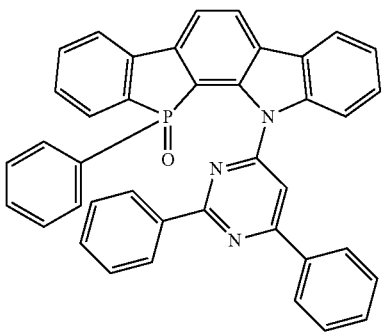
Formula 1-2-17
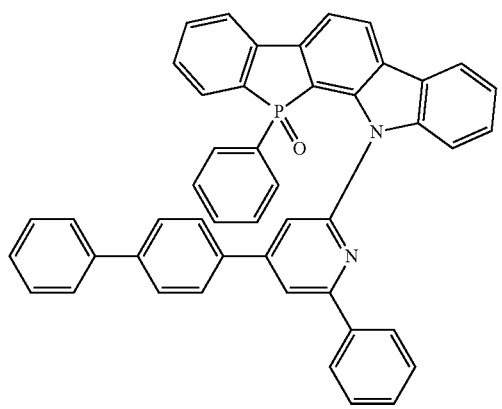
Formula 1-2-18
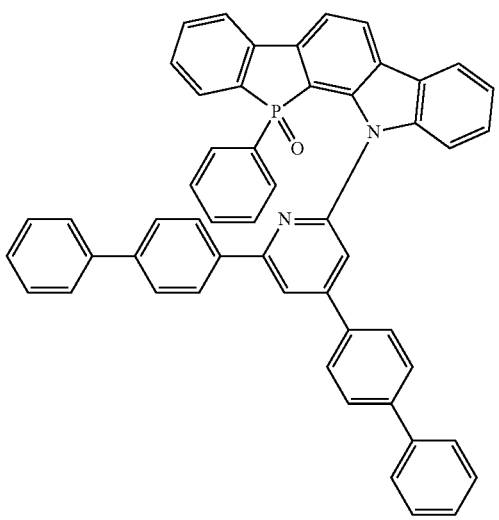

Formula 1-2-19
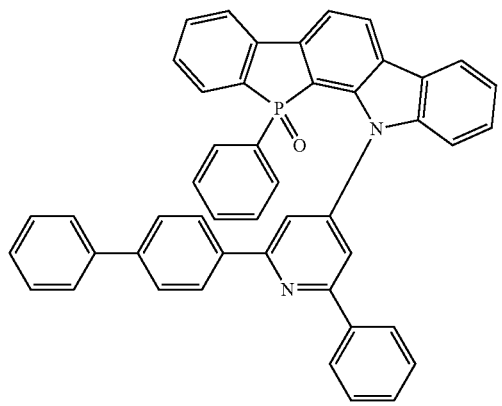
Formula 1-2-20
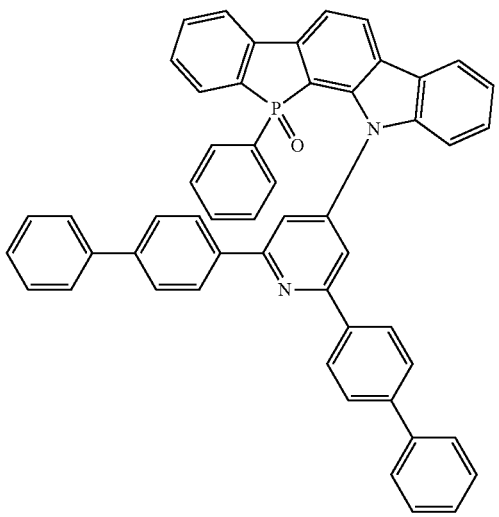
Formula 1-2-21
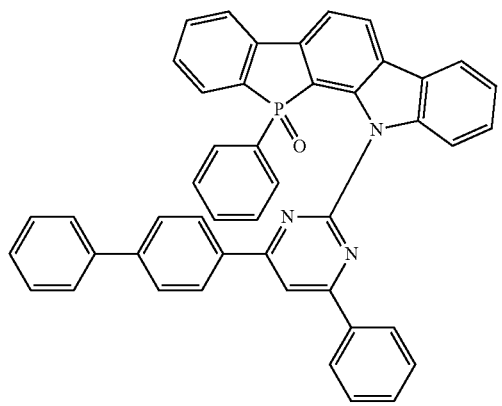
Formula 1-2-22
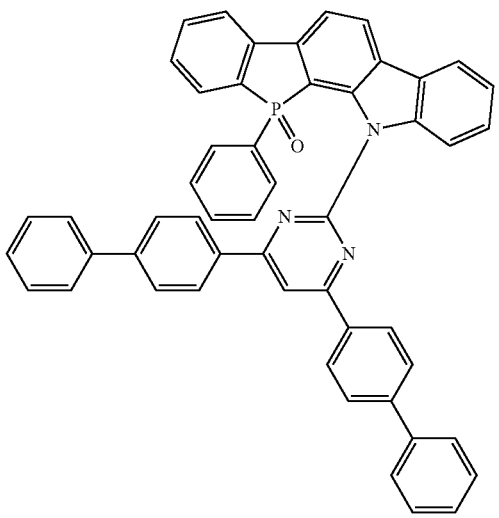
Formula 1-2-23
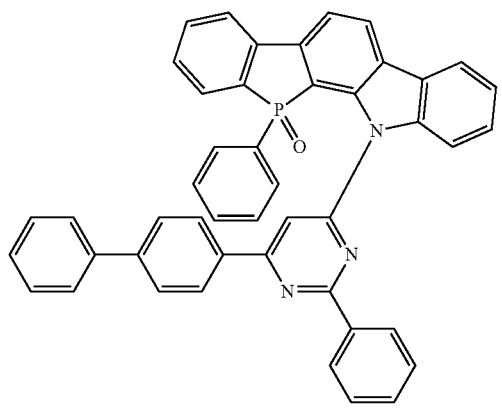
Formula 1-2-24
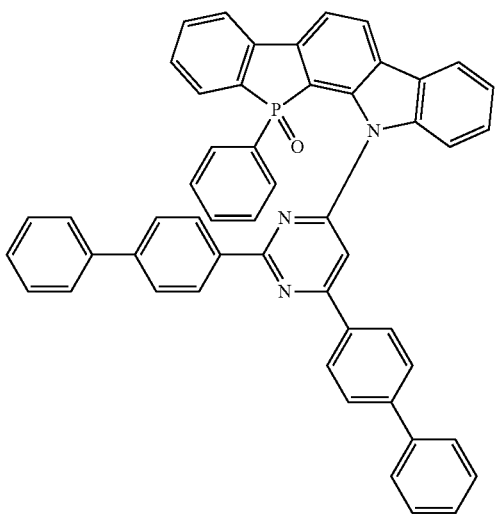

Formula 1-2-25
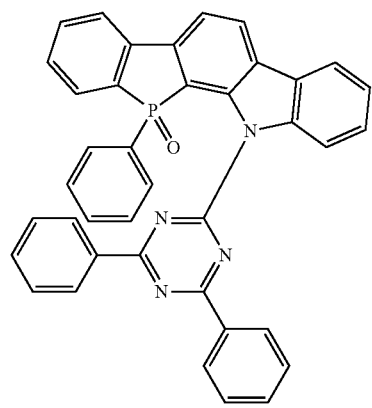
Formula 1-2-26
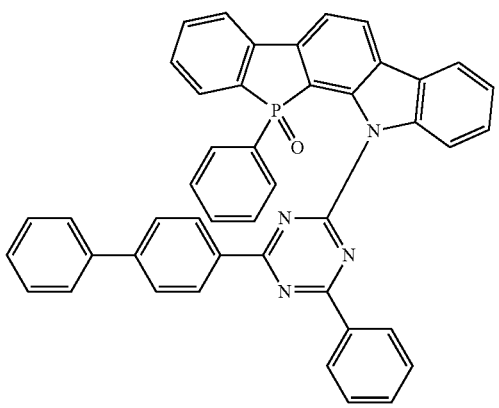
Formula 1-2-27
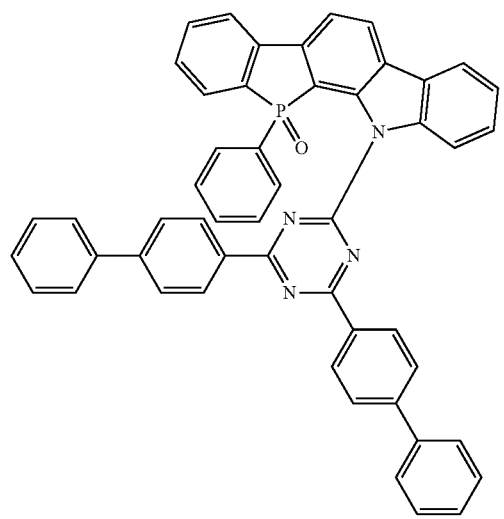
Formula 1-2-28
Formula 1-2-29
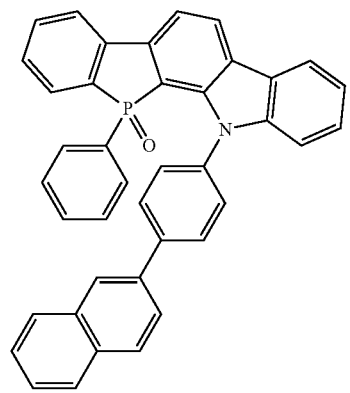
Formula 1-2-30
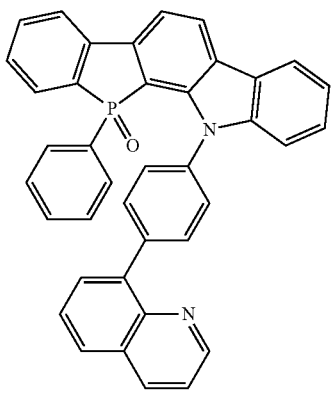

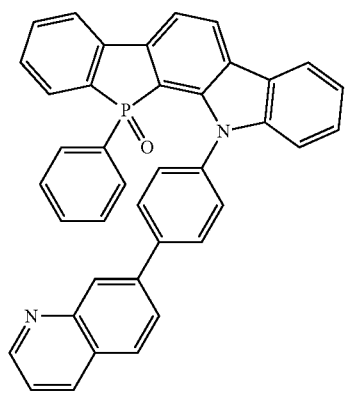
Formula 1-2-31
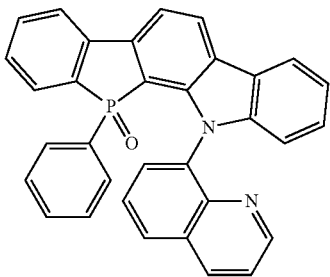
Formula 1-2-32
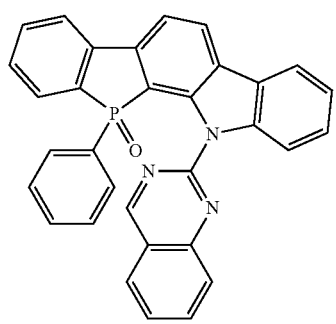
Formula 1-2-33
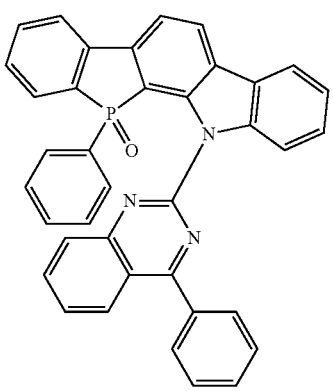
Formula 1-2-34
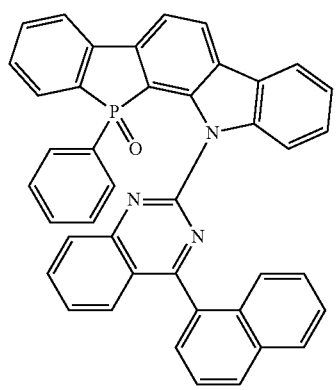
Formula 1-2-35
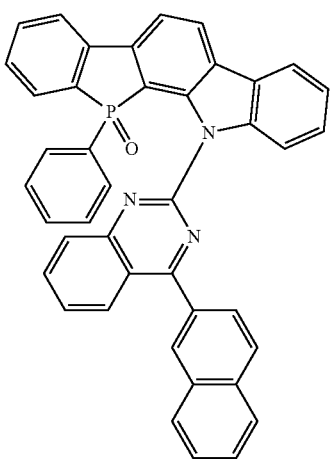
Formula 1-2-36

Formula 1-2-37
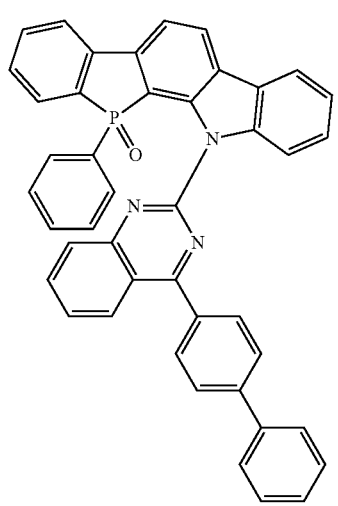
Formula 1-2-38
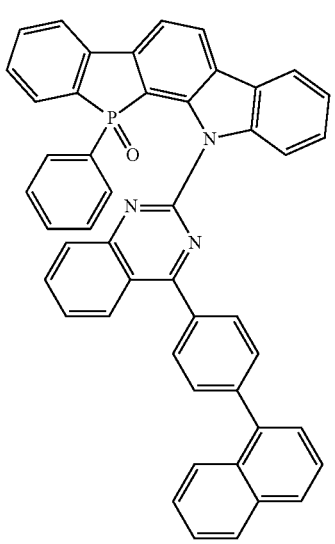
Formula 1-2-39
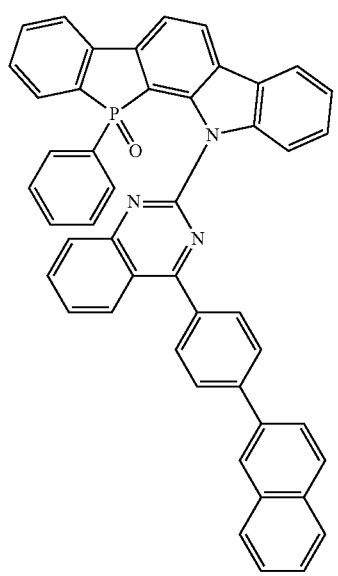
Formula 1-2-40
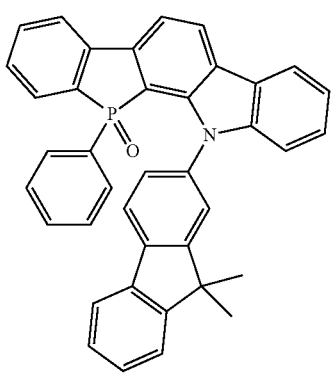
Formula 1-2-41
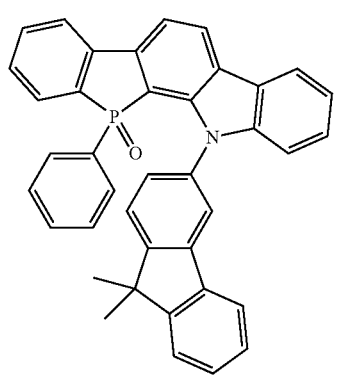
Formula 1-2-42
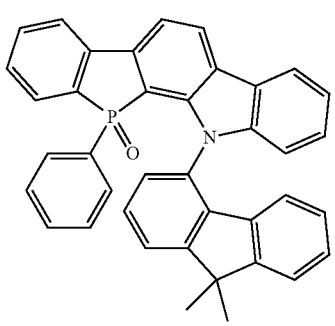

-continued
Formula 1-2-43
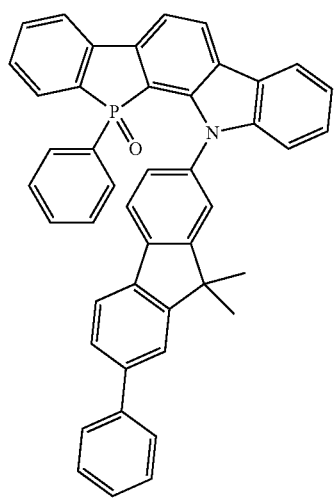
Formula 1-2-44
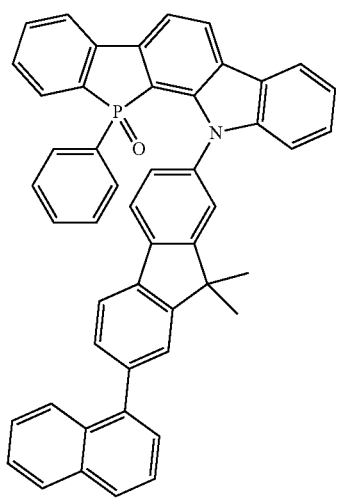
Formula 1-2-45
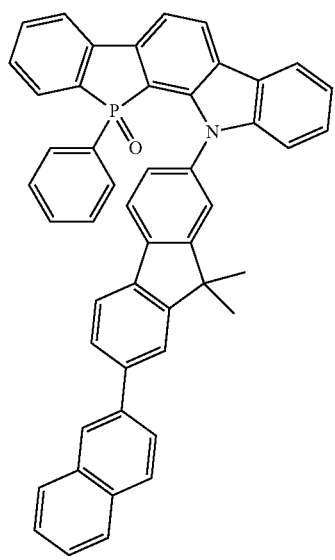
Formula 1-2-46
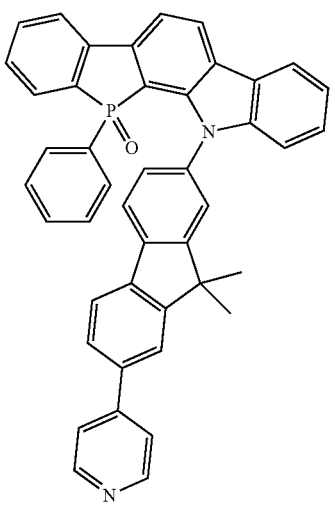
Formula 1-2-47
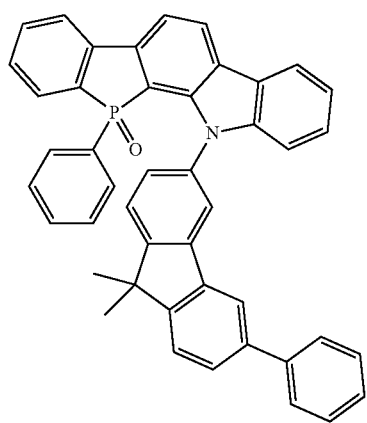
Formula 1-2-48
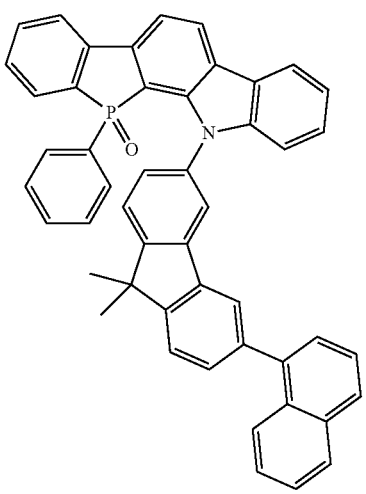

Formula 1-2-49
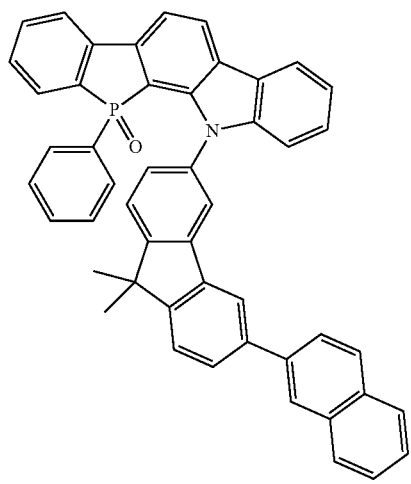
Formula 1-2-50
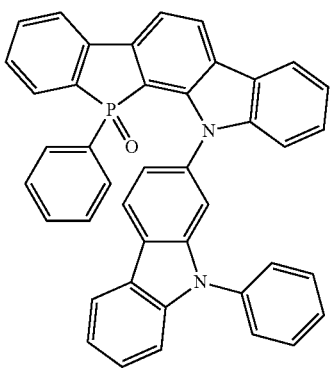
Formula 1-2-51
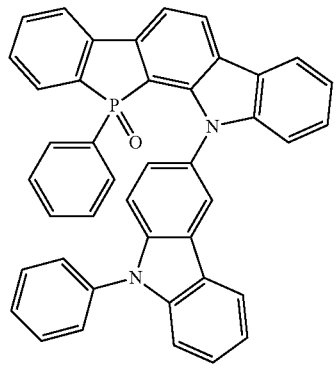
Formula 1-2-52
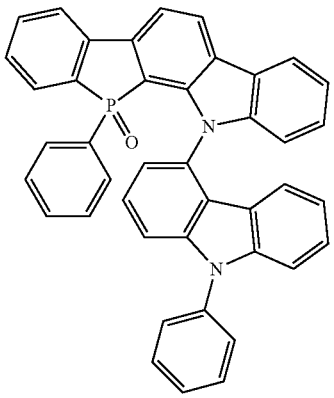
Formula 1-2-53
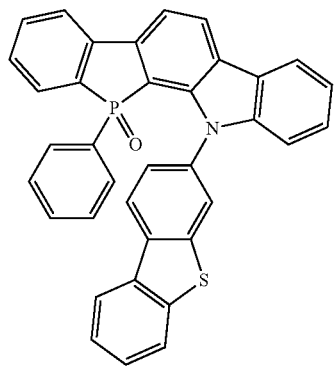
Formula 1-2-54
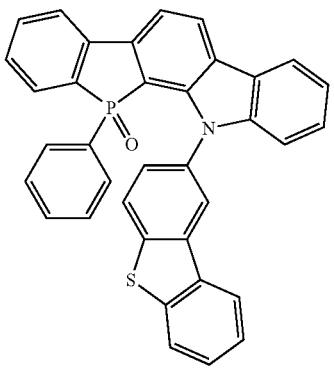
Formula 1-2-55
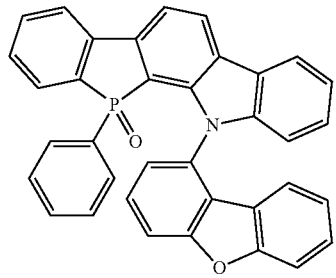
Formula 1-2-56
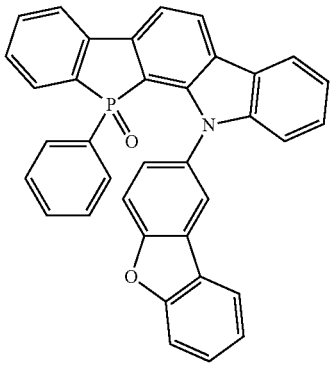

Formula 1-2-57
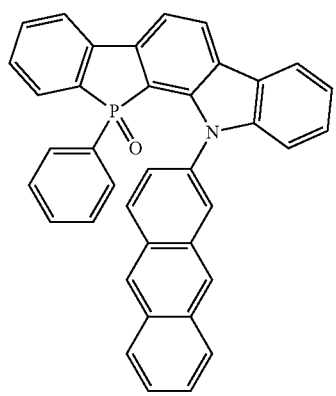
Formula 1-2-58
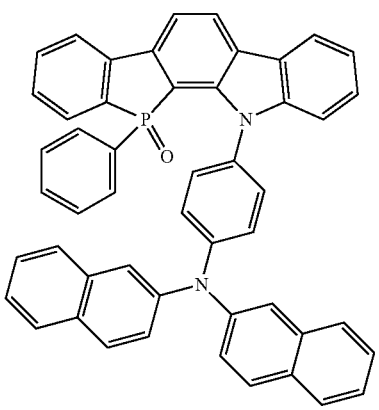
Formula 1-2-59
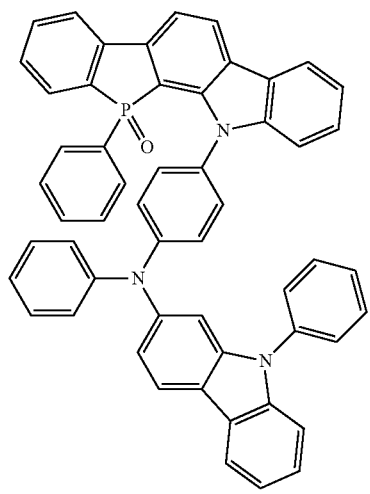
Formula 1-2-60
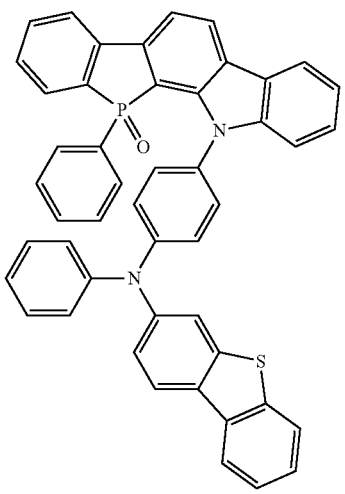
Formula 1-2-61
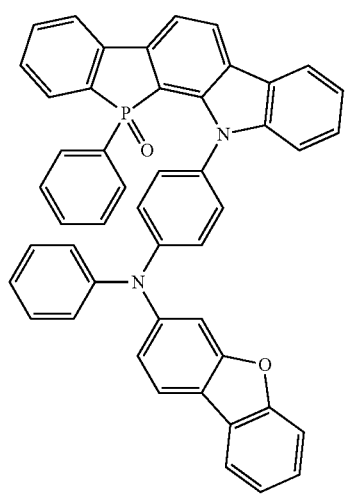
Formula 1-2-62
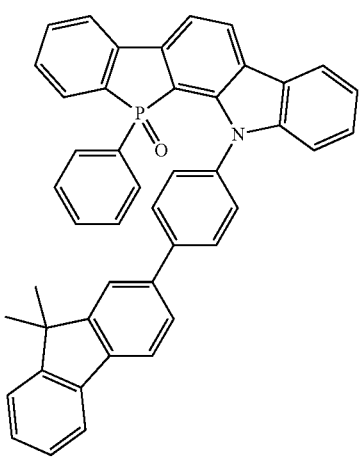

-continued
Formula 1-2-63
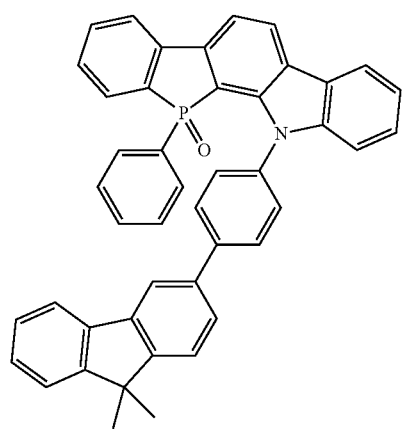
Formula 1-2-64
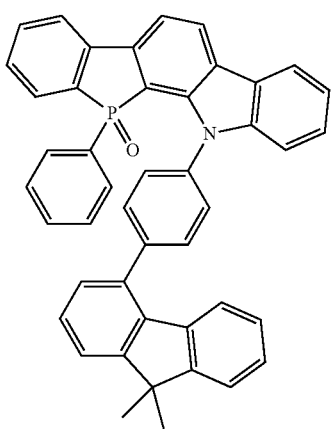
Formula 1-2-65
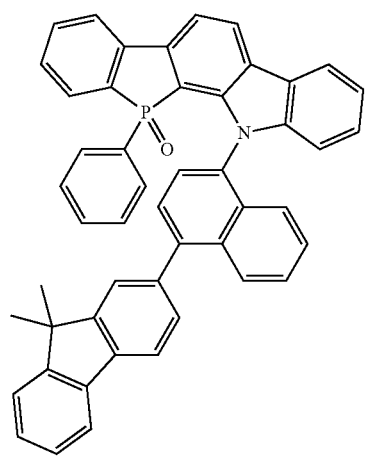
Formula 1-2-66
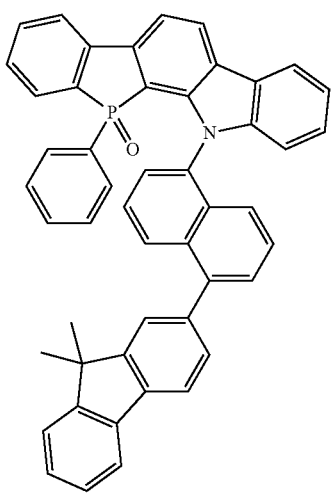
Formula 1-2-67
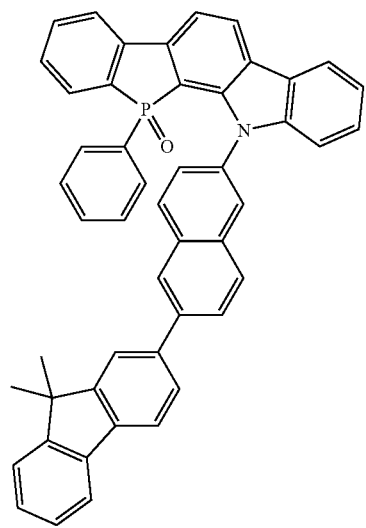
Formula 1-2-68
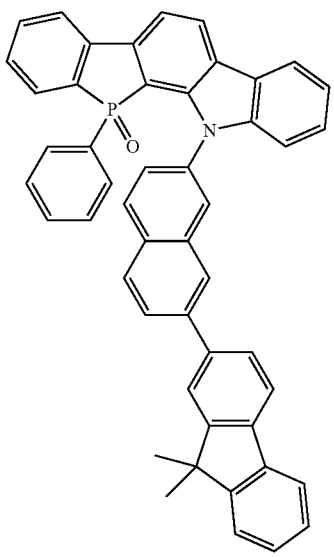

-continued
Formula 1-2-69
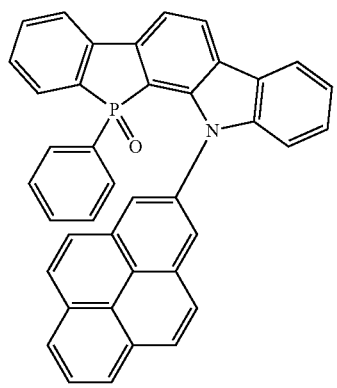
Formula 1-2-70
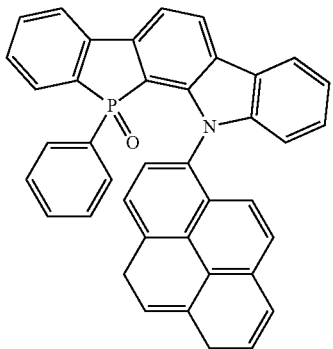
Formula 1-2-71
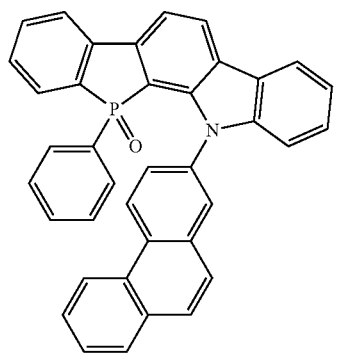
Formula 1-2-72
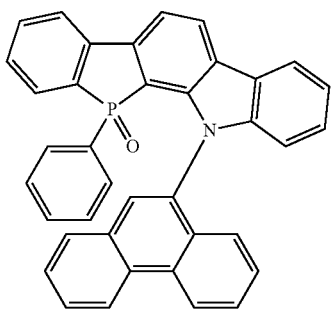
Formula 1-2-73
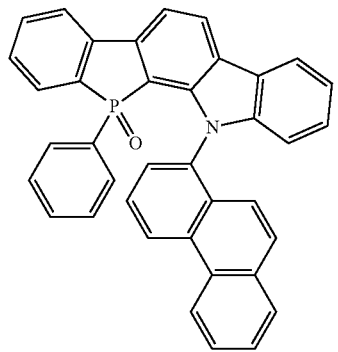
Formula 1-2-74
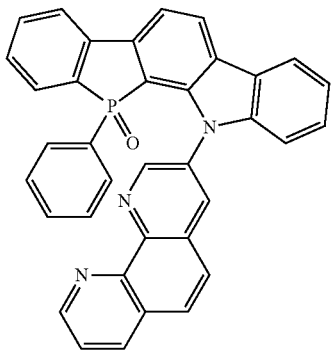
Formula 1-2-75
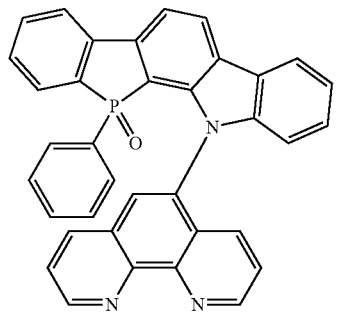
Formula 1-2-76
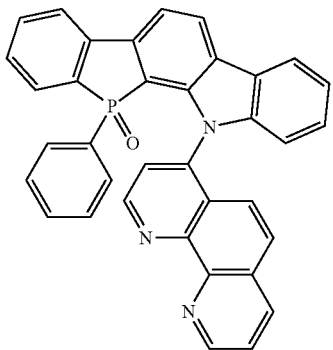

-continued
Formula 1-2-77
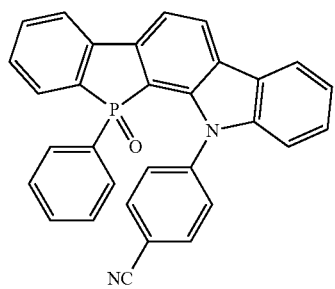
Formula 1-2-78
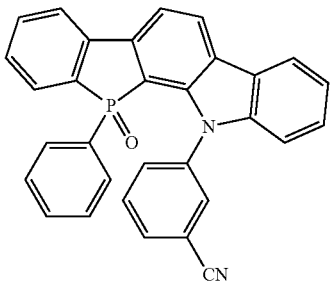
Formula 1-2-79
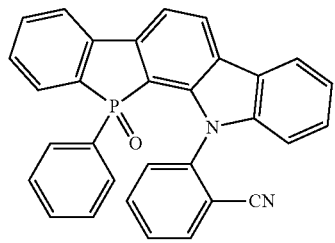
Formula 1-2-80
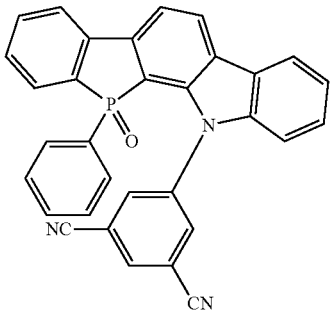
Formula 1-2-81
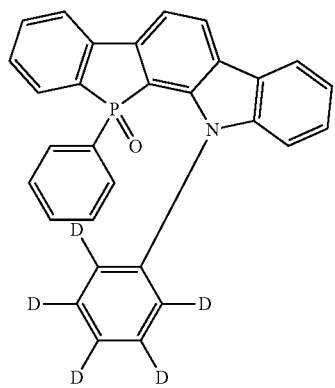
Formula 1-2-82
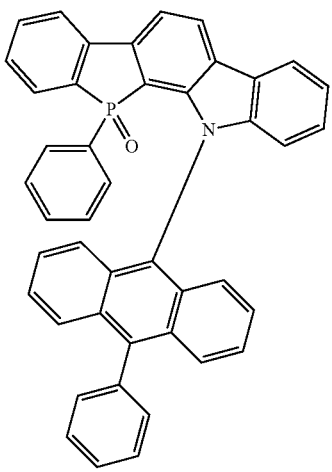
Formula 1-2-83
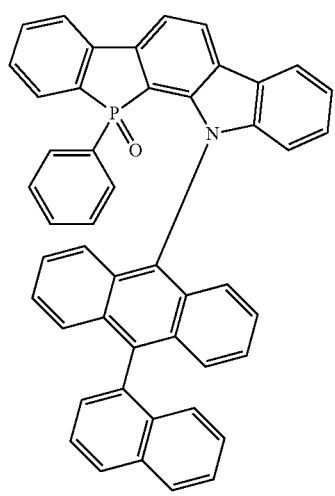
Formula 1-2-84
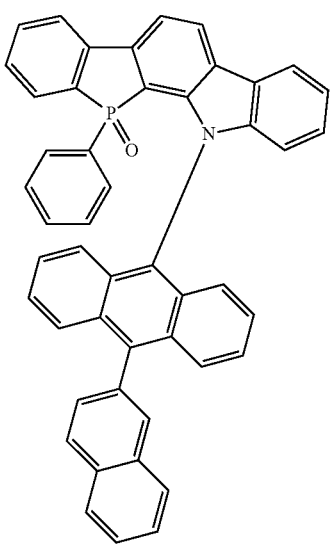

Formula 1-2-85
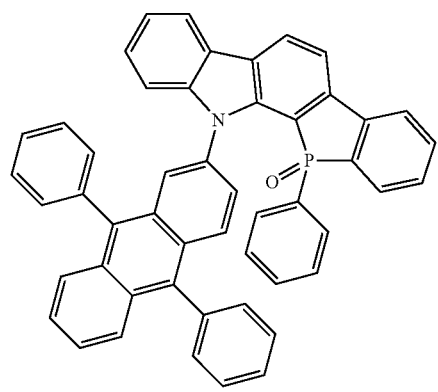
Formula 1-2-86
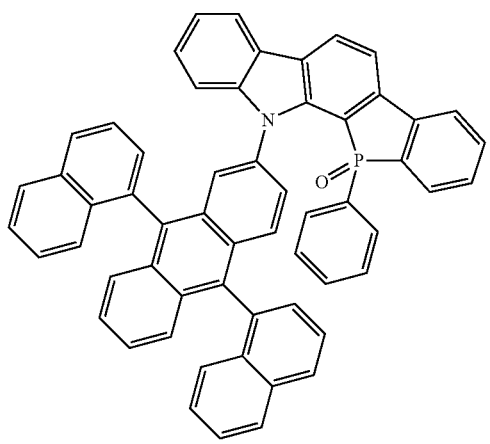
Formula 1-2-87
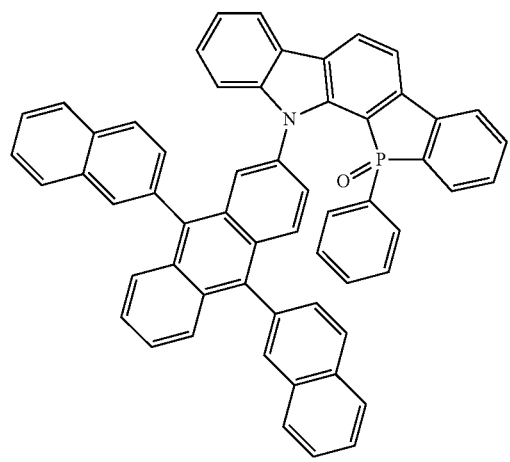
Formula 1-2-88
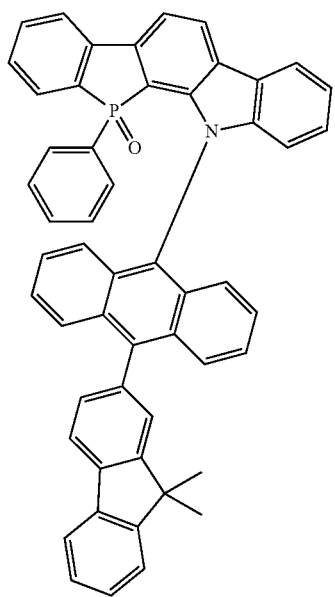

Formula 1-2-89
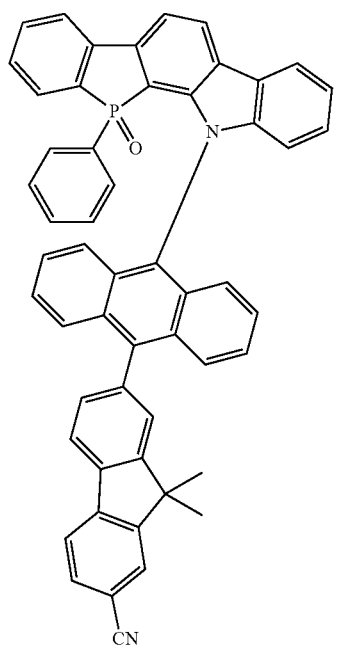
Formula 1-2-90
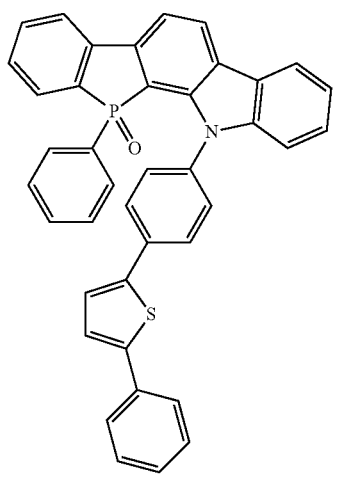
Formula 1-2-91
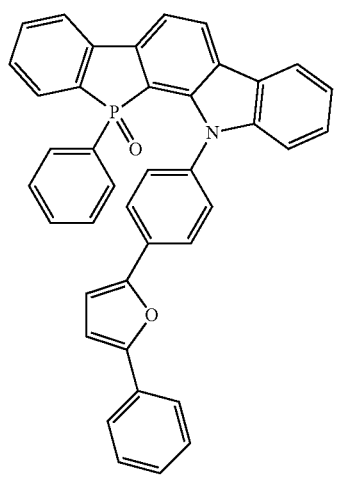
Formula 1-2-92
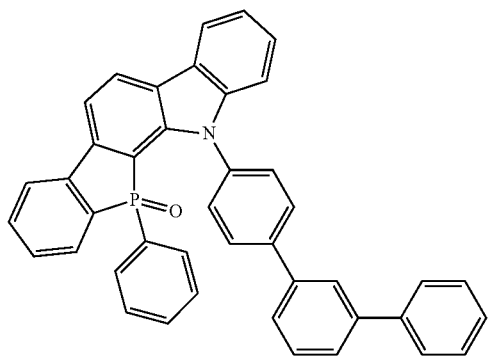
Formula 1-2-93
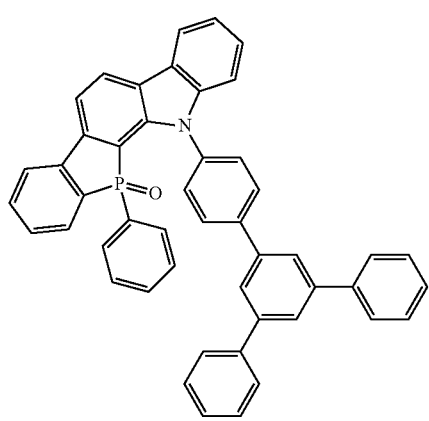
Formula 1-2-94
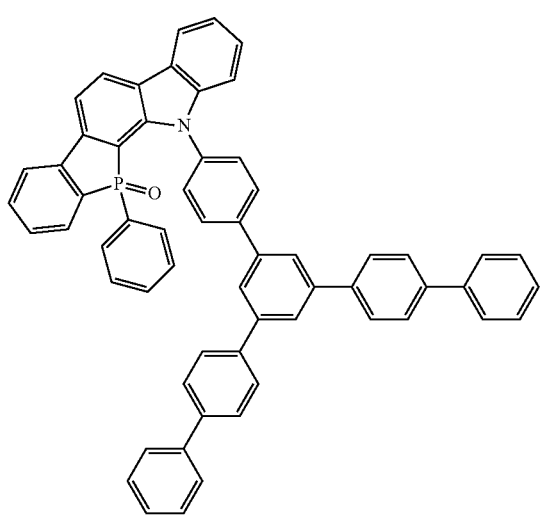

-continued
Formula 1-2-95
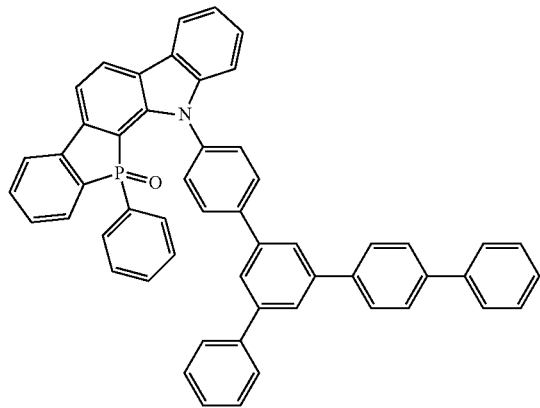
Formula 1-2-96
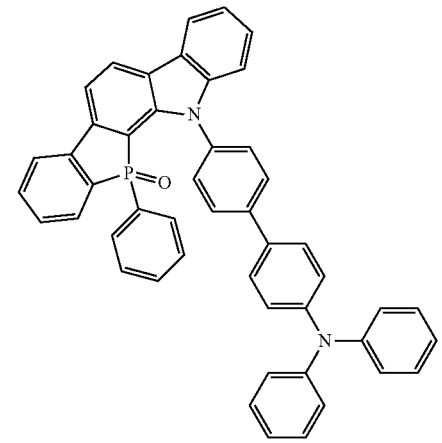
Formula 1-2-97
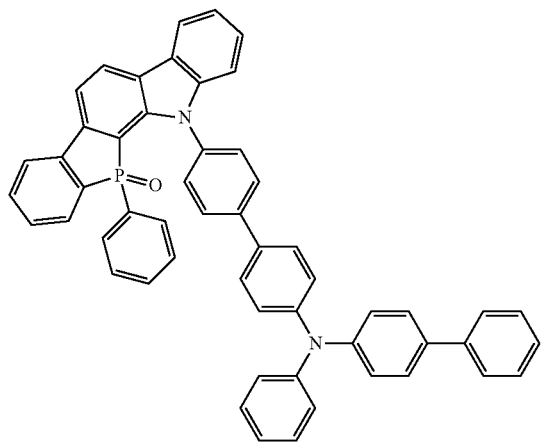
Formula 1-2-98
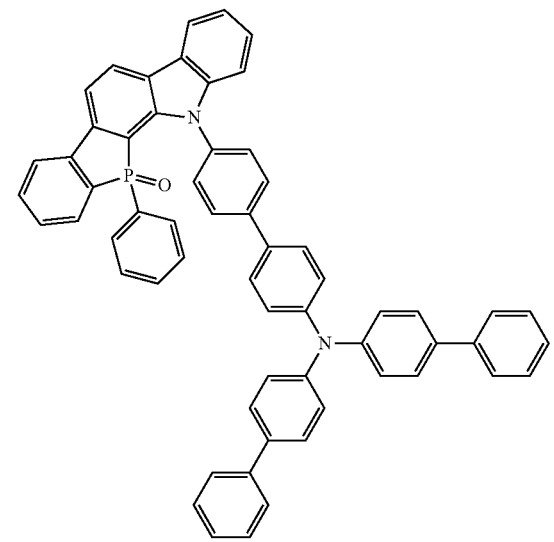
Formula 1-2-99
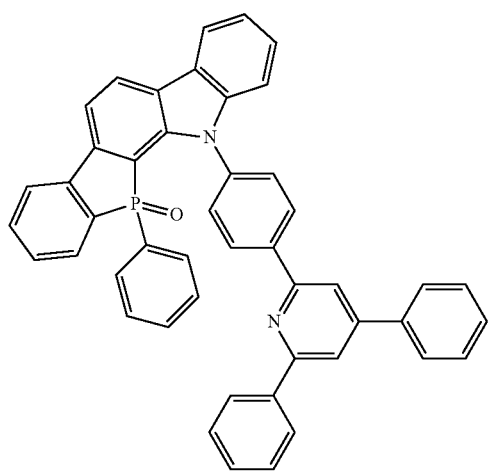
Formula 1-2-100
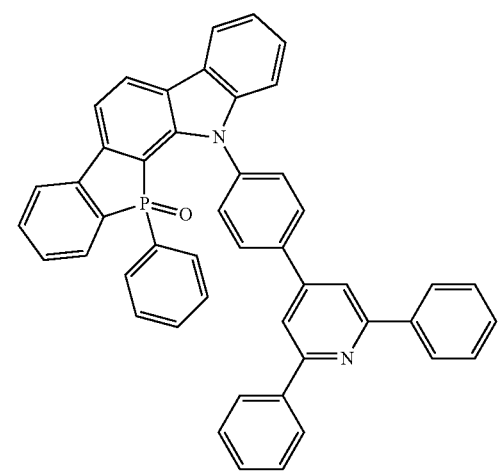

-continued
Formula 1-2-101
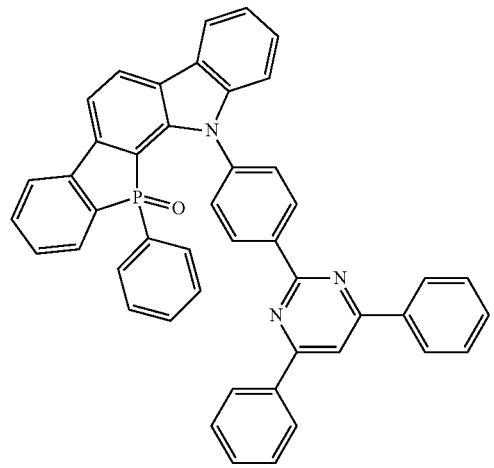
Formula 1-2-102
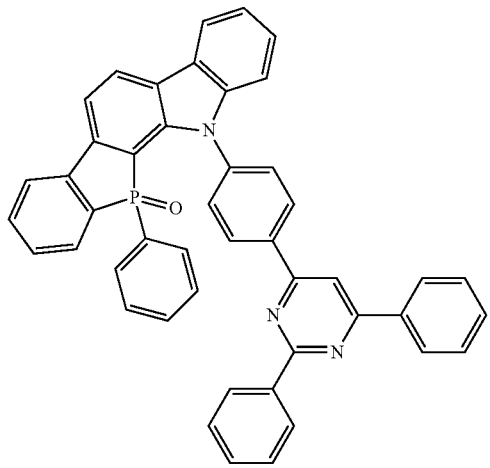
Formula 1-2-103
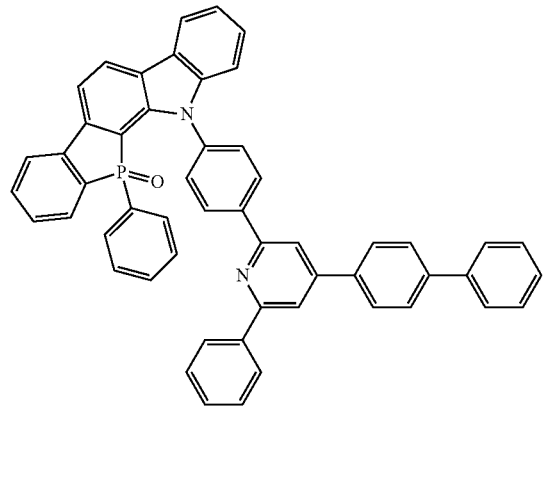
Formula 1-2-104
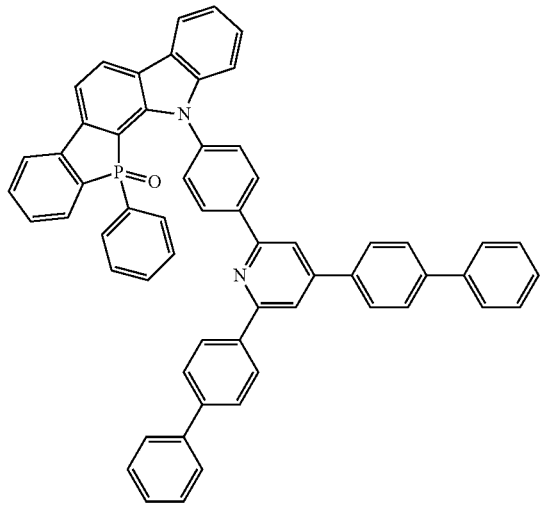
Formula 1-2-105
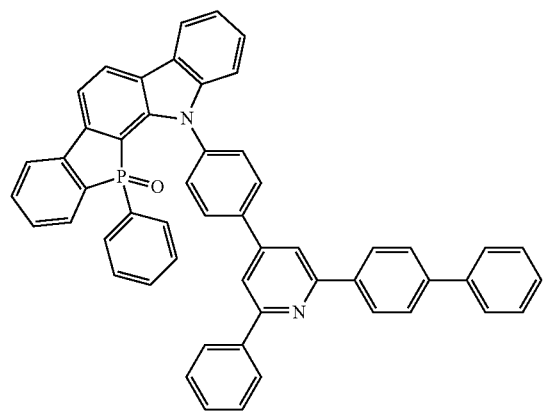
Formula 1-2-106
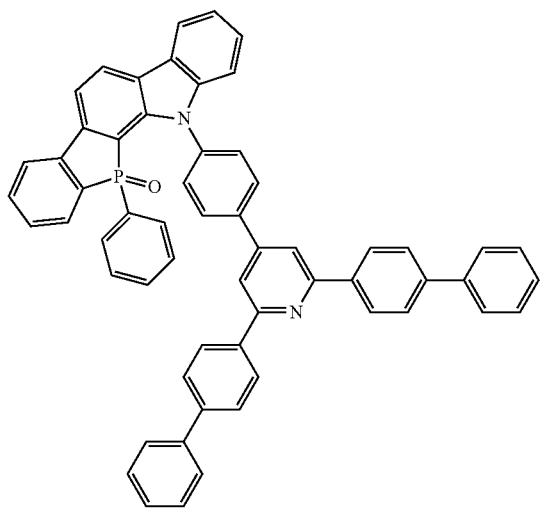

-continued
Formula 1-2-107
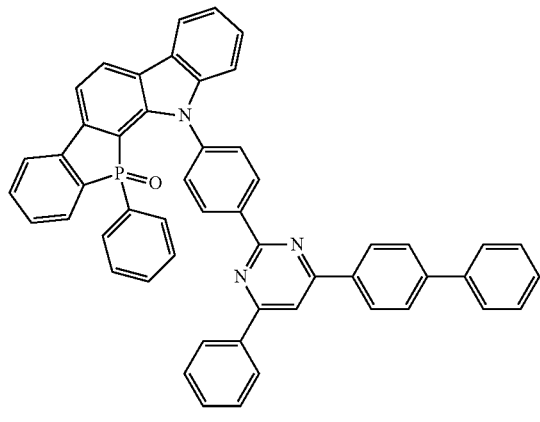
Formula 1-2-108
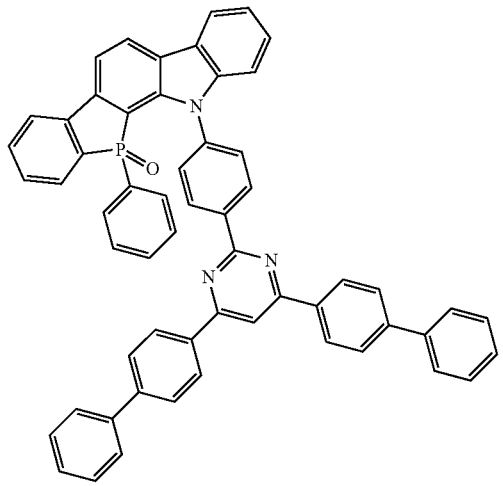
Formula 1-2-109
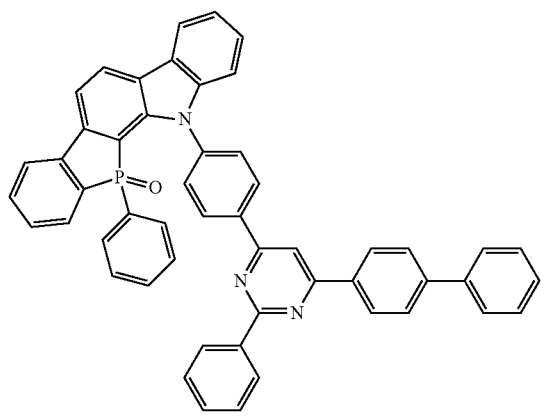
Formula 1-2-110
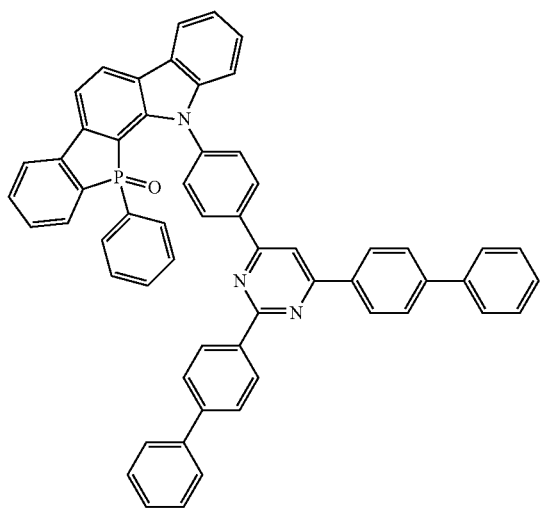
Formula 1-2-111
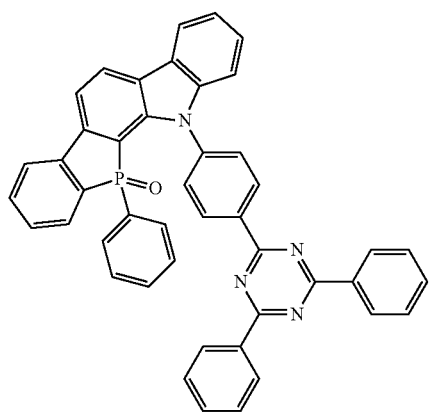
Formula 1-2-112
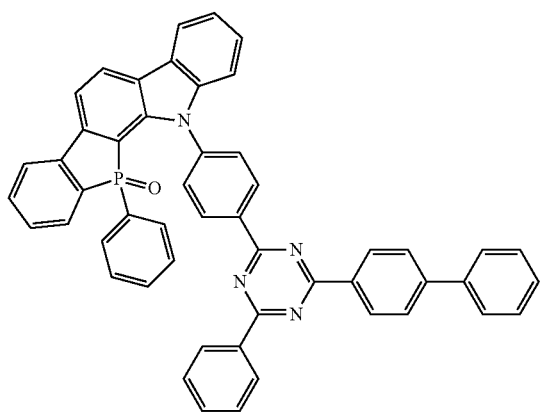

Formula 1-2-113
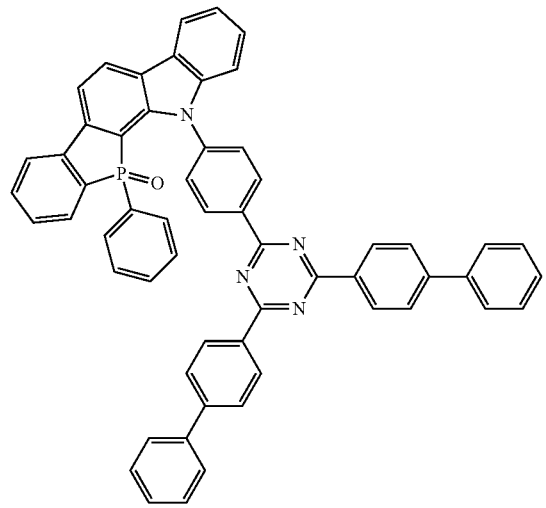
Formula 1-2-114
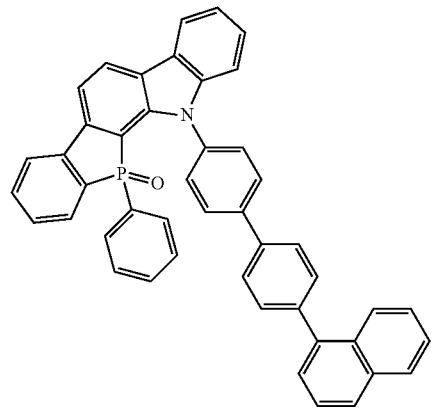
Formula 1-2-115
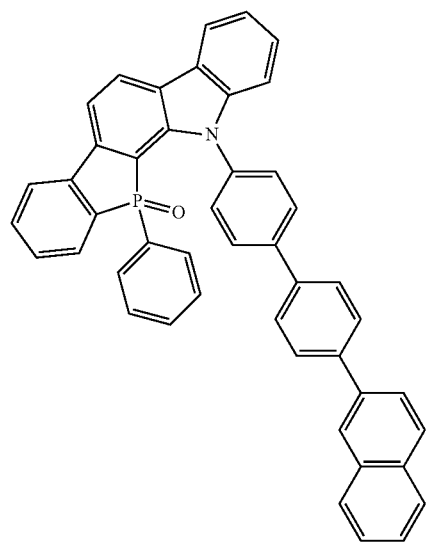
Formula 1-2-116
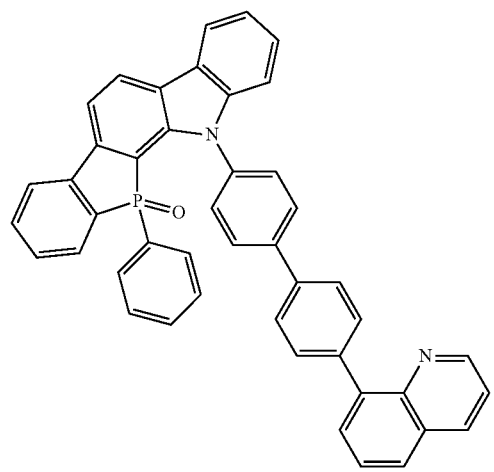
Formula 1-2-117
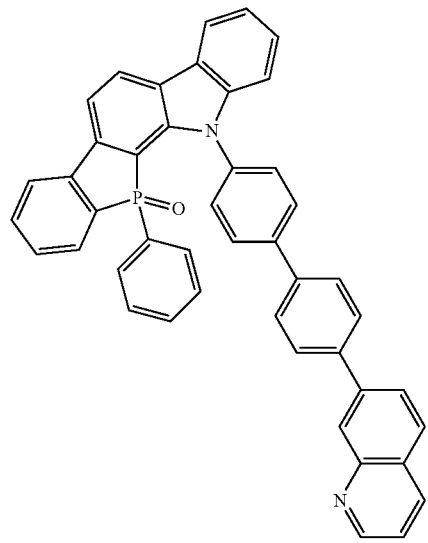
Formula 1-2-118
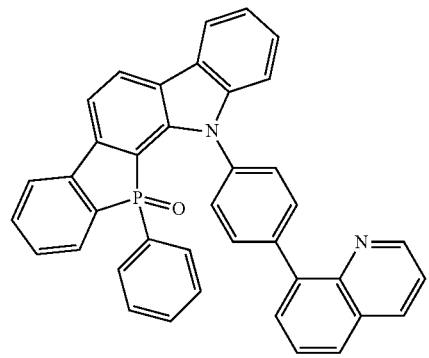

Formula 1-2-119
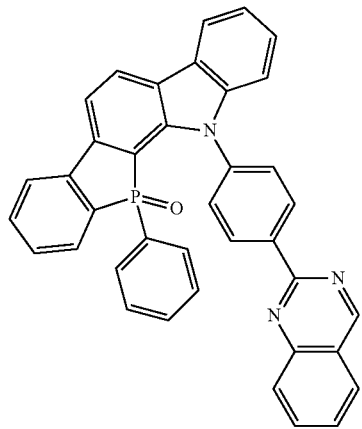
Formula 1-2-120
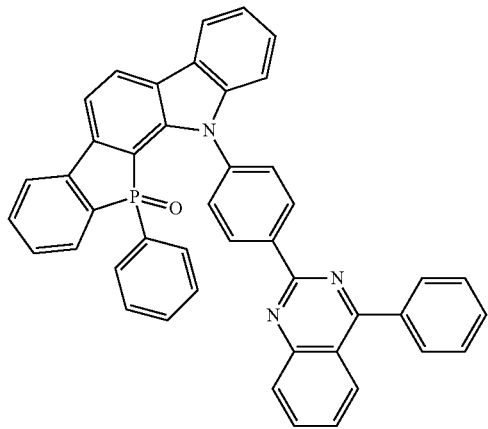
Formula 1-2-121
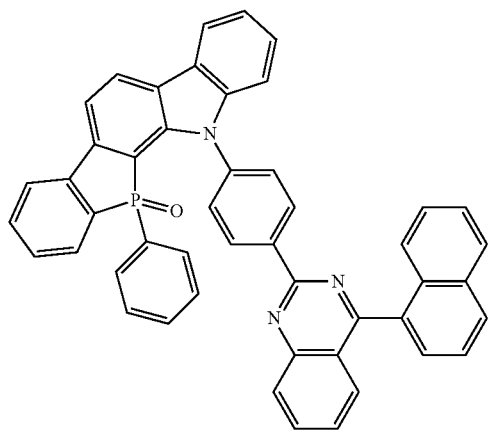
Formula 1-2-122
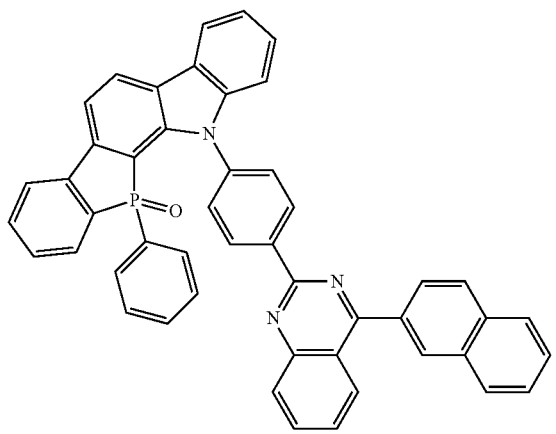
Formula 1-2-123
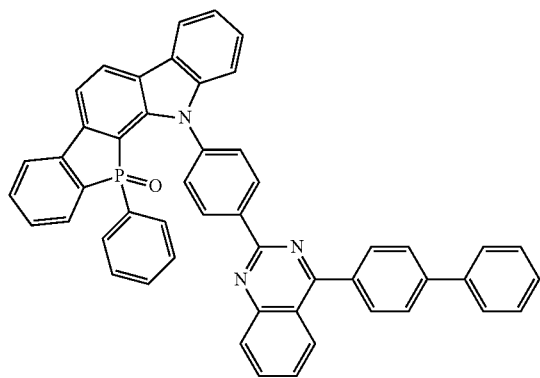
Formula 1-2-124
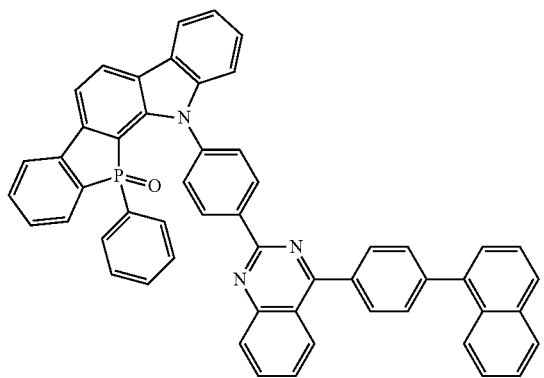

-continued
Formula 1-2-125
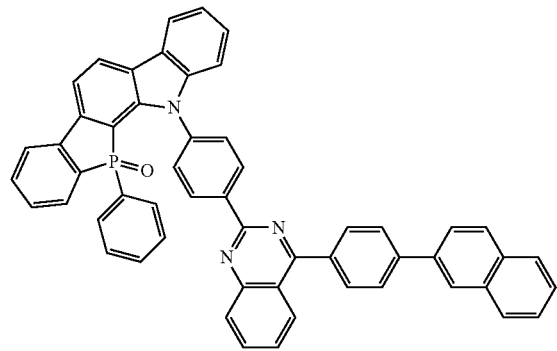
Formula 1-2-126
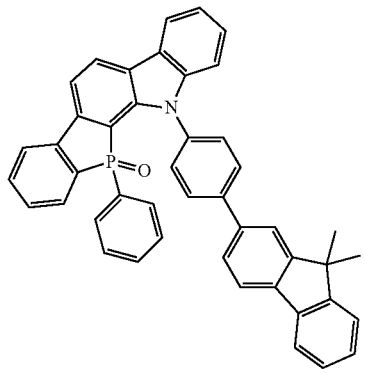
Formula 1-2-127
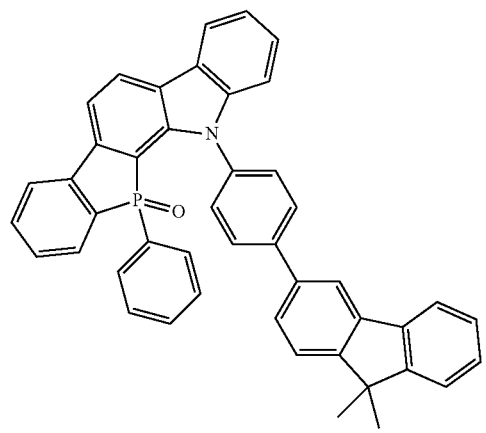
Formula 1-2-128
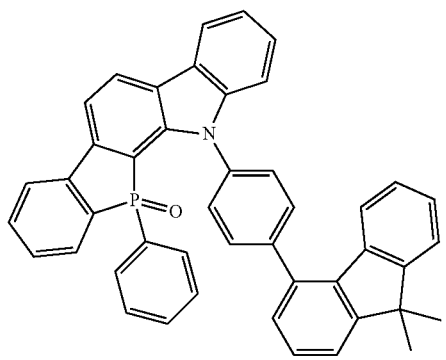
Formula 1-2-129
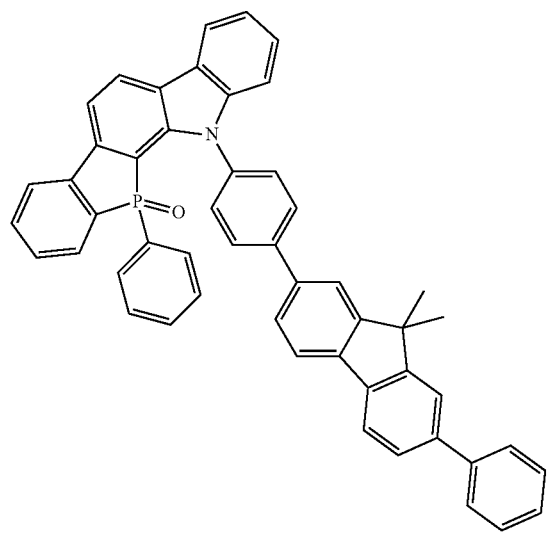
Formula 1-2-130
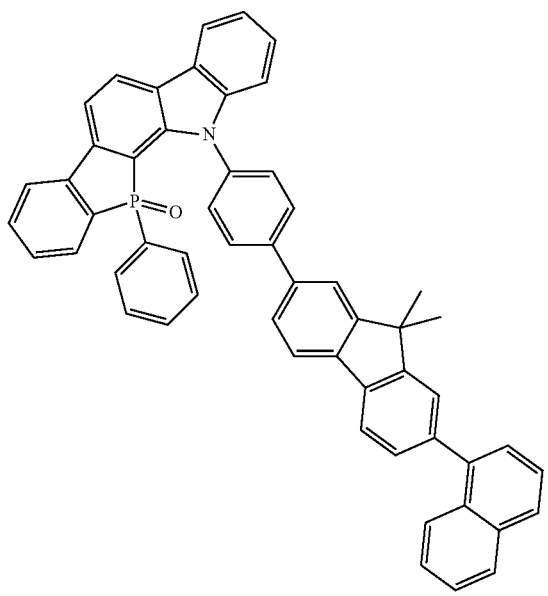

-continued
Formula 1-2-131
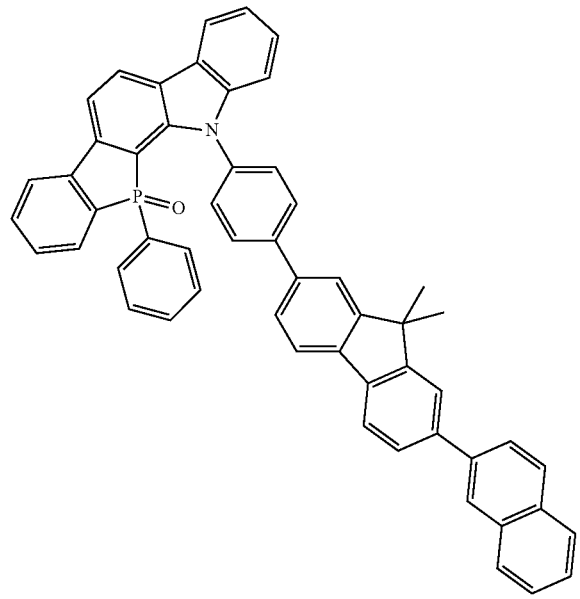
Formula 1-2-132
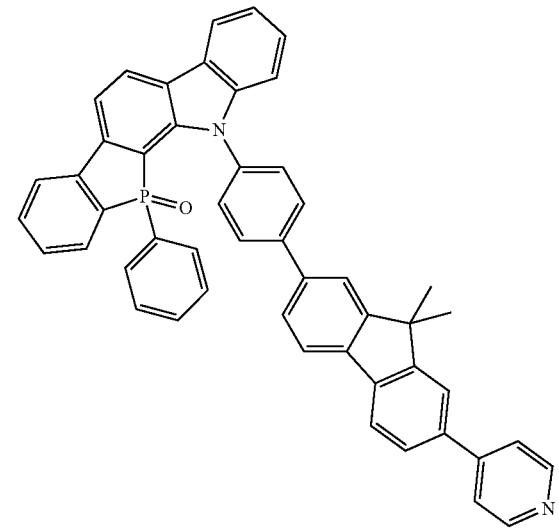
Formula 1-2-133
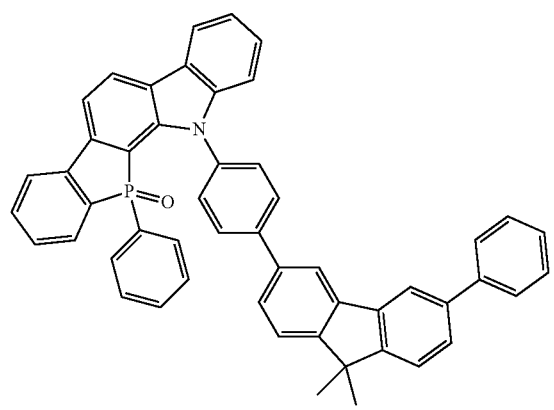
Formula 1-2-134
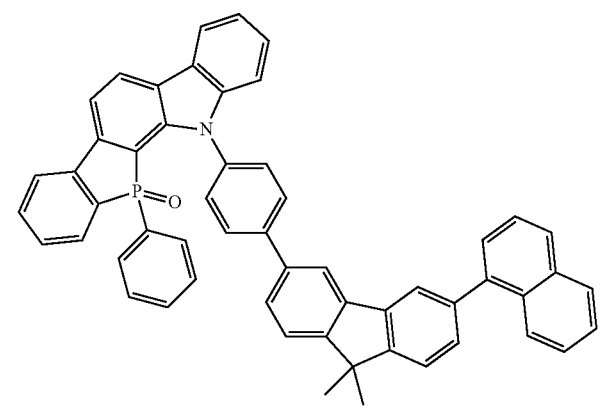
Formula 1-2-135
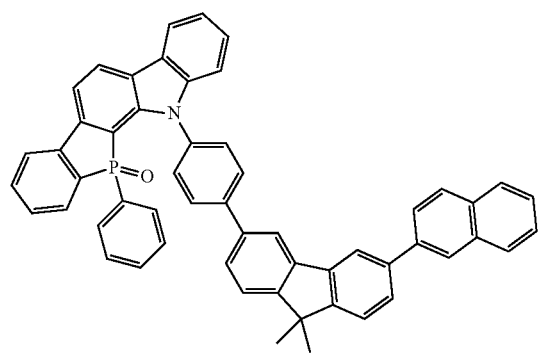
Formula 1-2-136
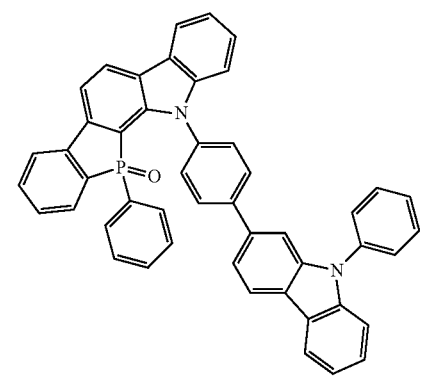

Formula 1-2-137
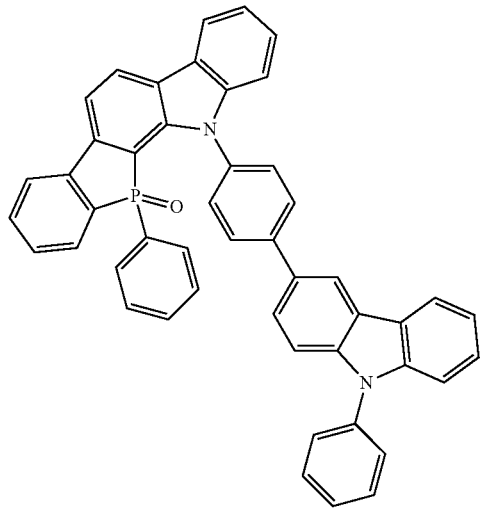
Formula 1-2-138
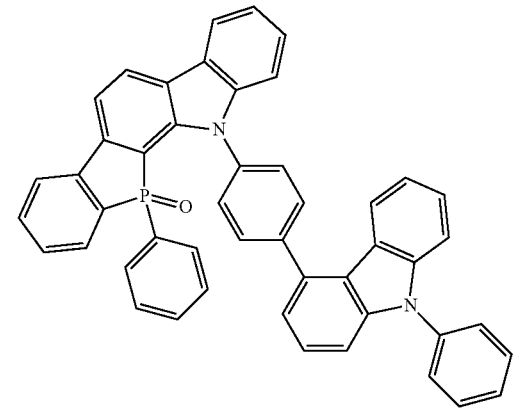
Formula 1-2-139
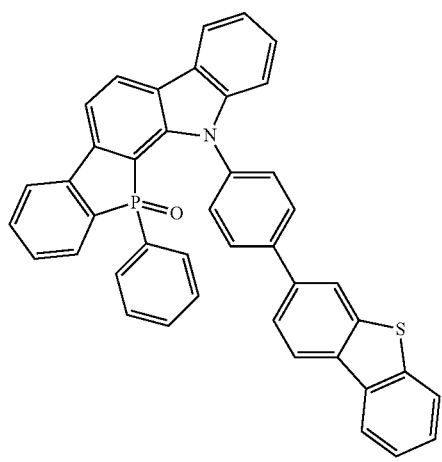
Formula 1-2-140
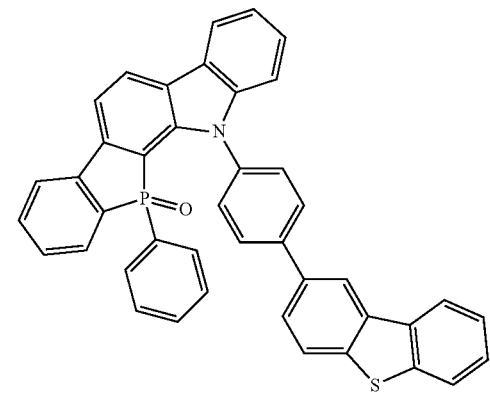
Formula 1-2-141
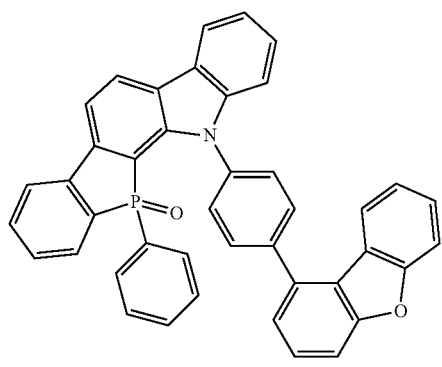
Formula 1-2-142
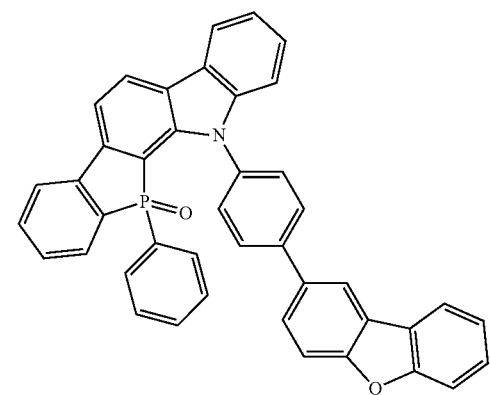

-continued
Formula 1-2-143
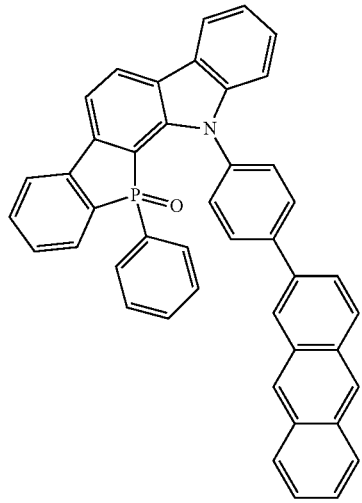
Formula 1-2-144
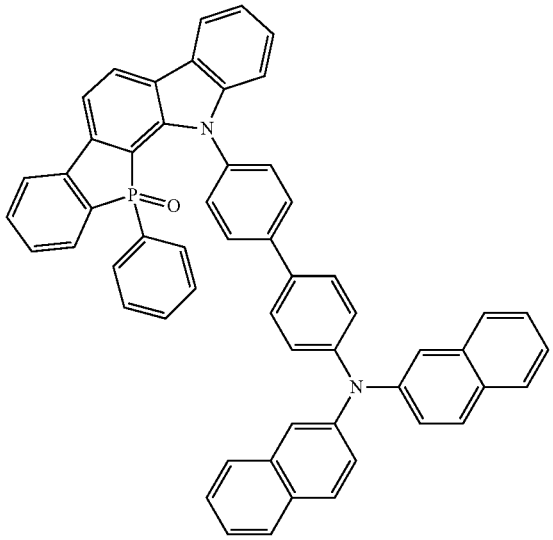
Formula 1-2-145
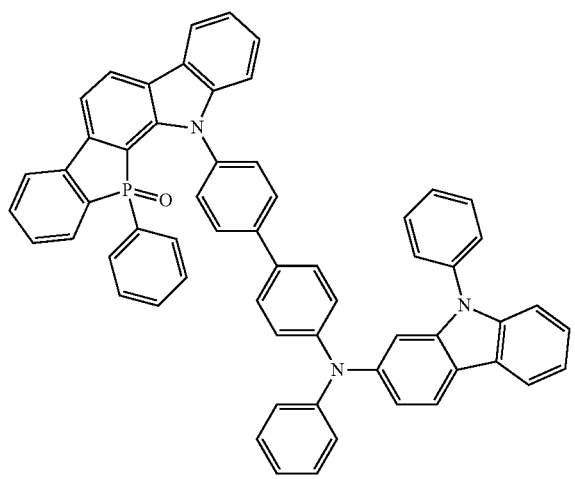
Formula 1-2-146
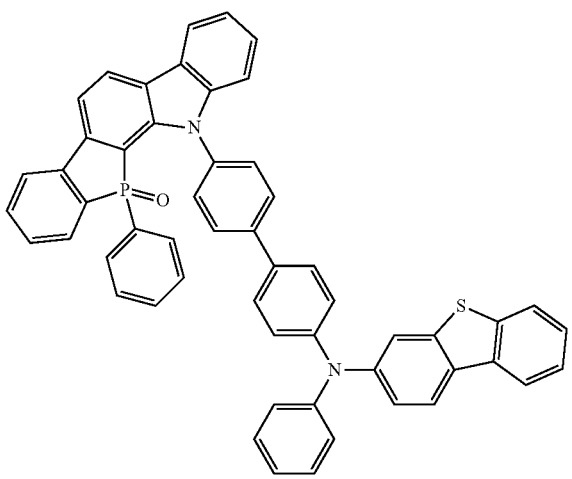
Formula 1-2-147
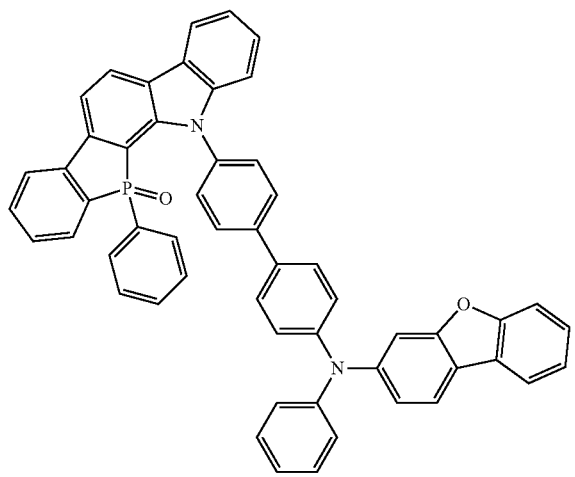
Formula 1-2-148

Formula 1-2-149
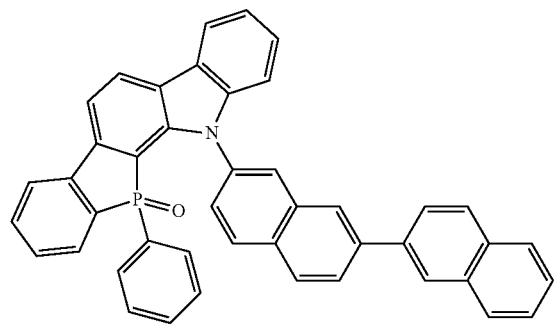
Formula 1-2-150
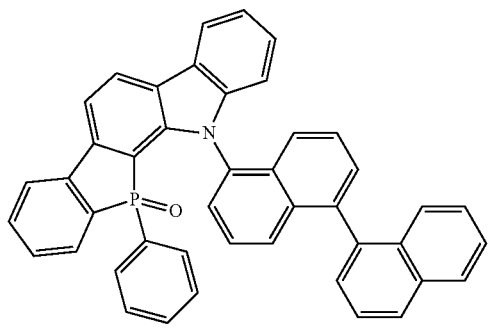
Formula 1-2-151
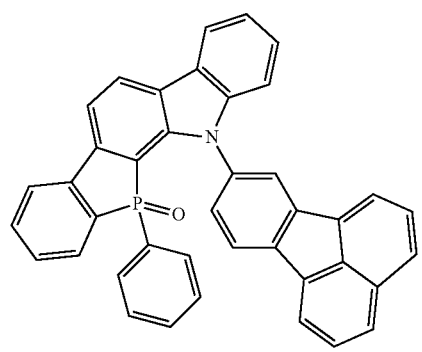
Formula 1-2-152
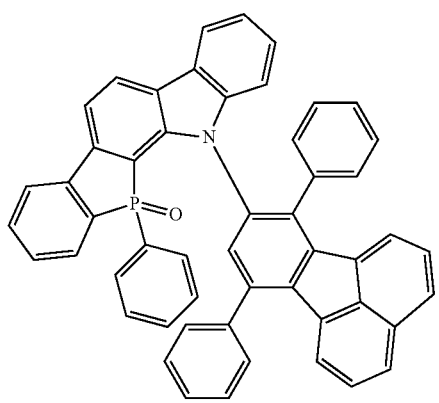
Formula 1-2-153
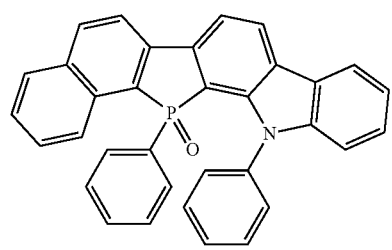
Formula 1-2-154
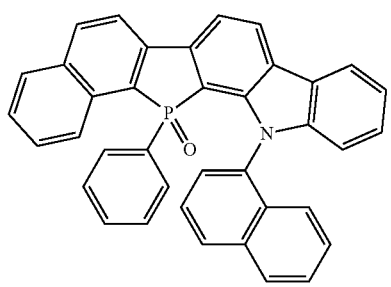
Formula 1-2-155
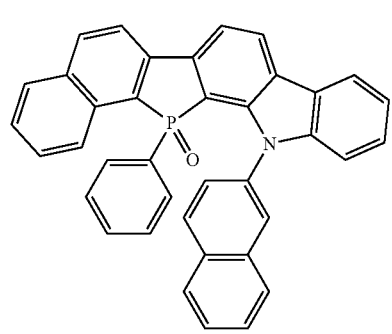
Formula 1-2-156
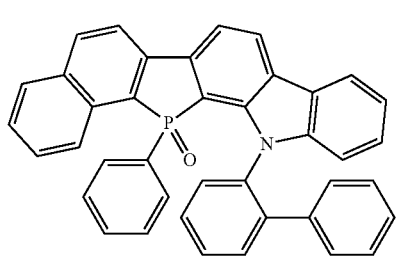

-continued
Formula 1-2-157
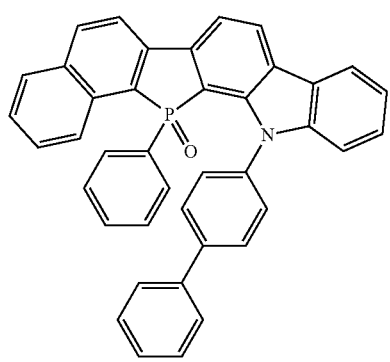
Formula 1-2-158
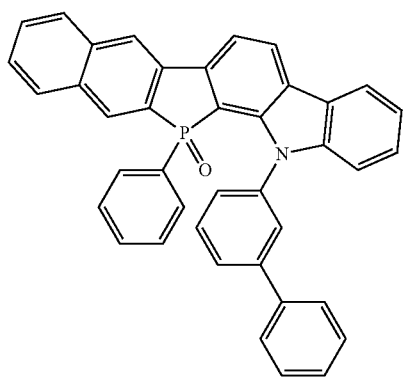
Formula 1-2-159
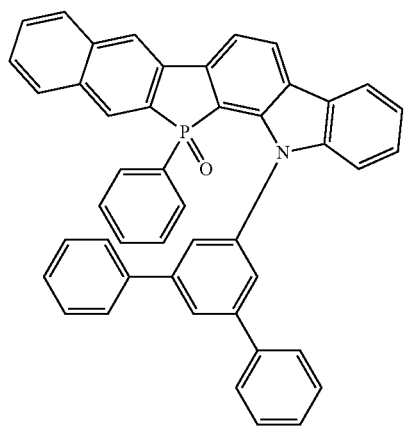
Formula 1-2-160
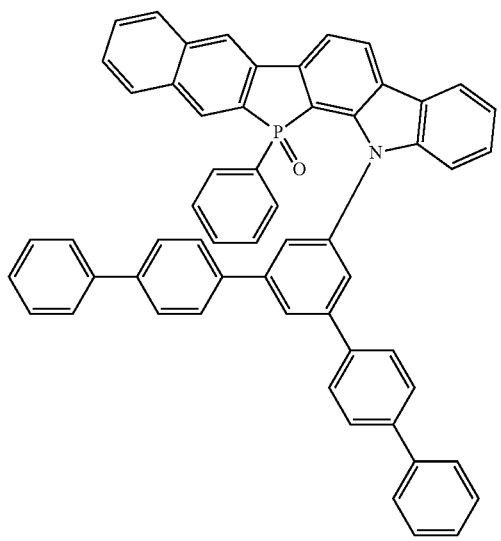
Formula 1-2-161
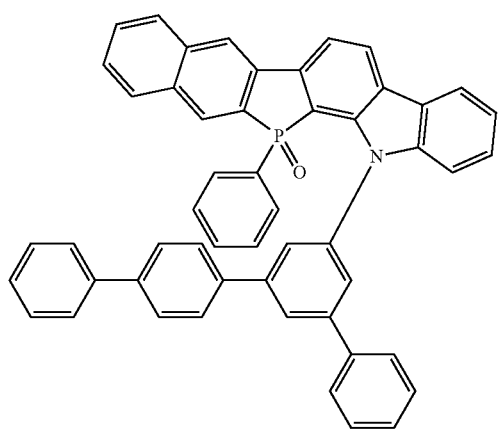
Formula 1-2-162
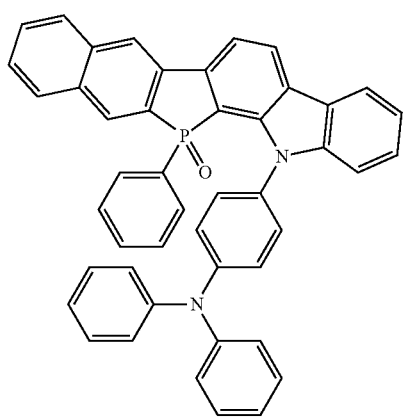

Formula 1-2-163
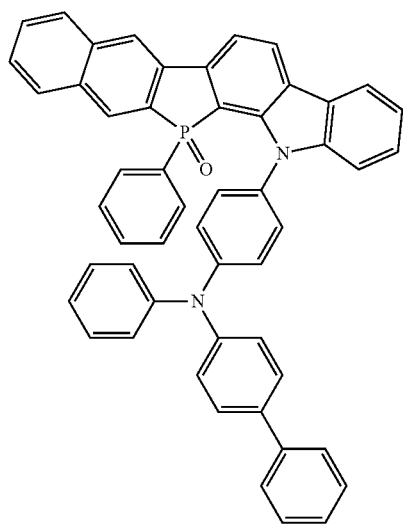
Formula 1-2-164
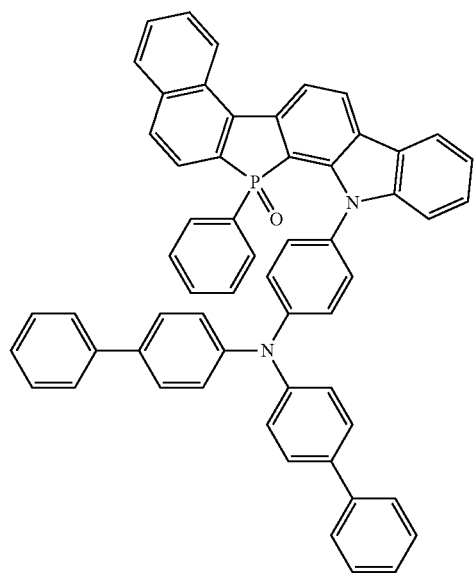
Formula 1-2-165
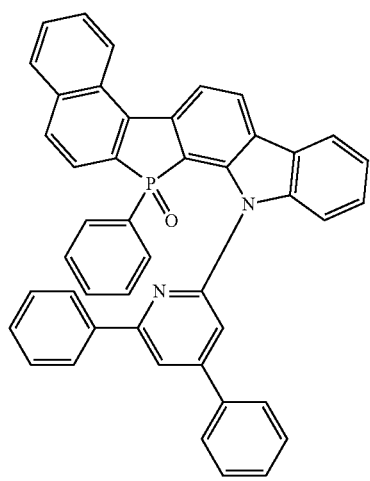
Formula 1-2-166
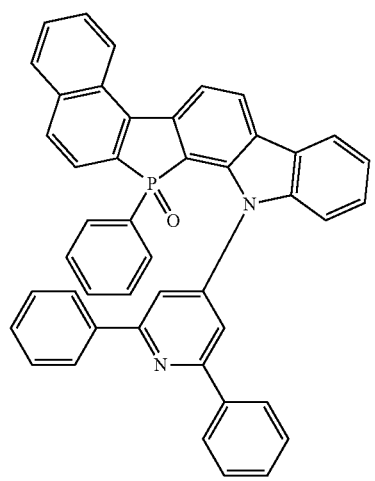
Formula 1-2-167
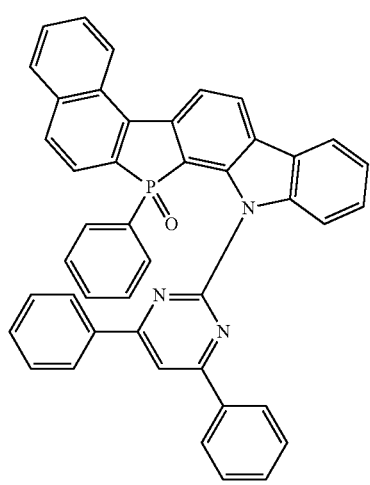
Formula 1-2-168
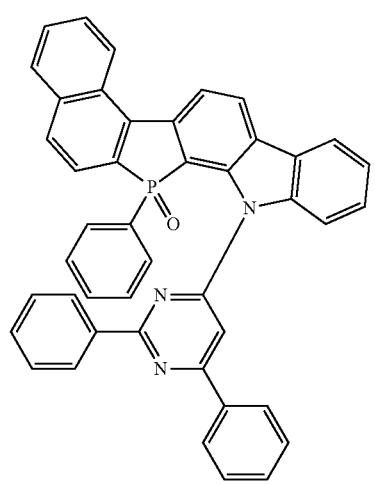

Formula 1-2-169
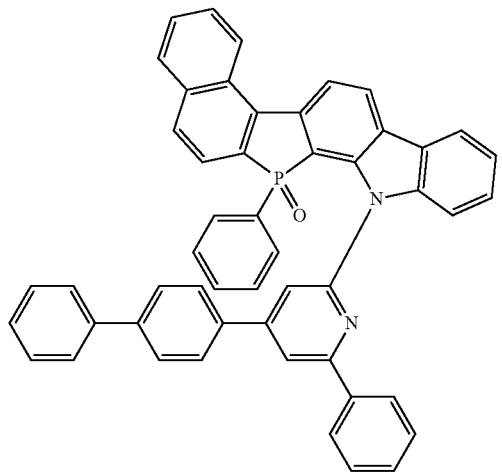
Formula 1-2-170
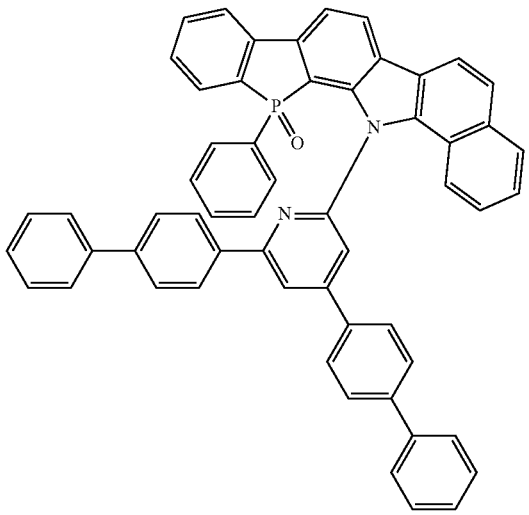
Formula 1-2-171
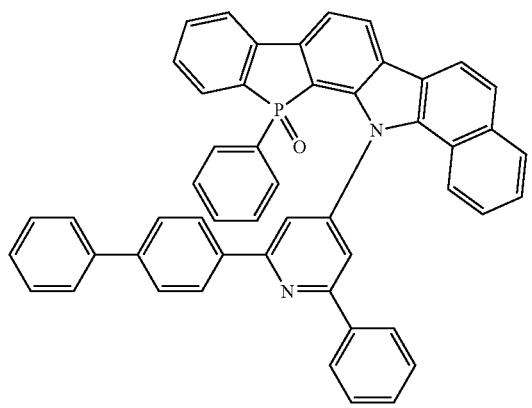
Formula 1-2-172
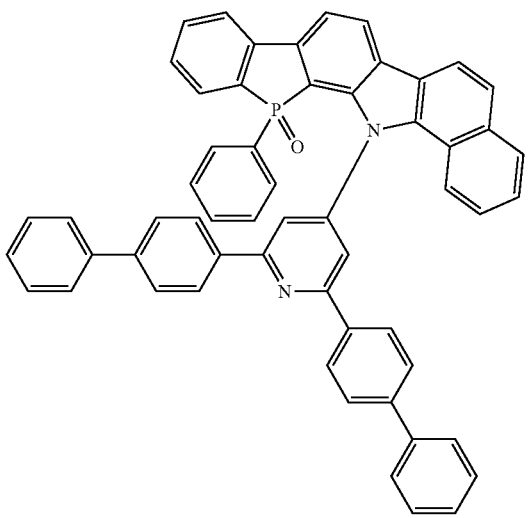
Formula 1-2-173
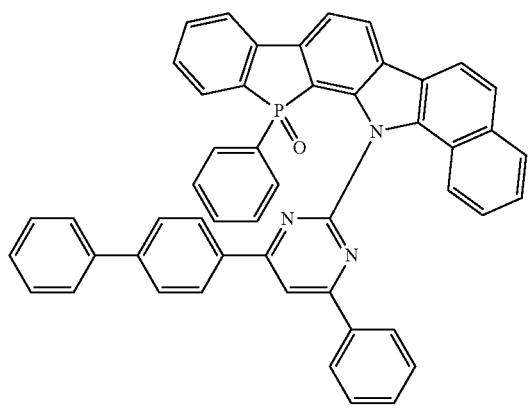
Formula 1-2-174
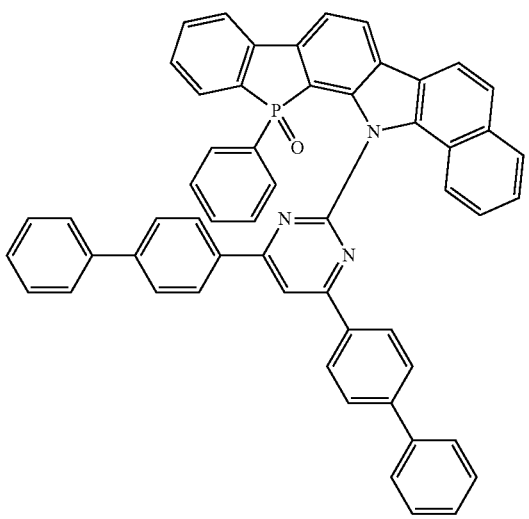

-continued
Formula 1-2-175
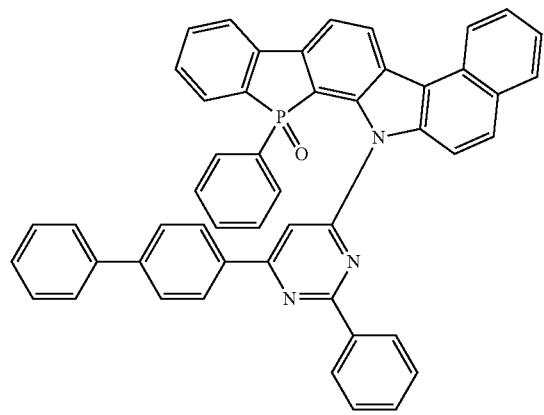
Formula-1-2-176
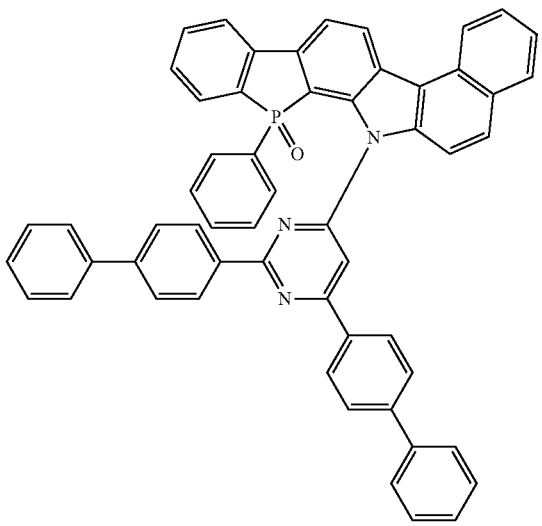
Formula 1-2-177
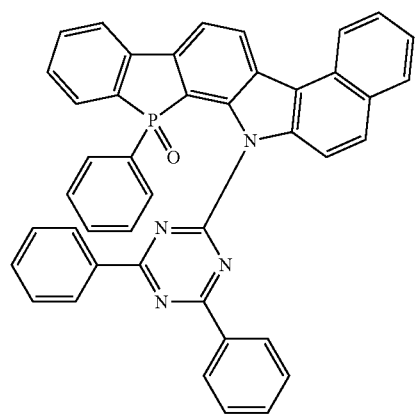
Formula 1-2-178
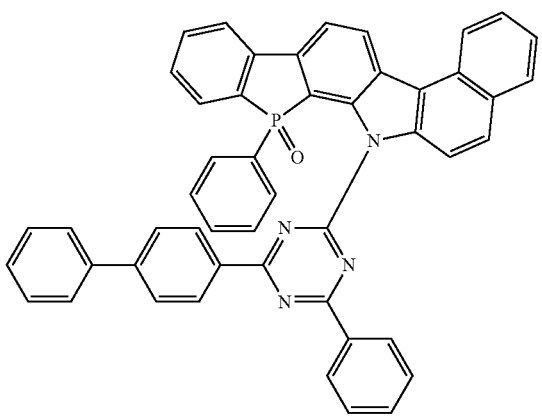
Formula 1-2-179
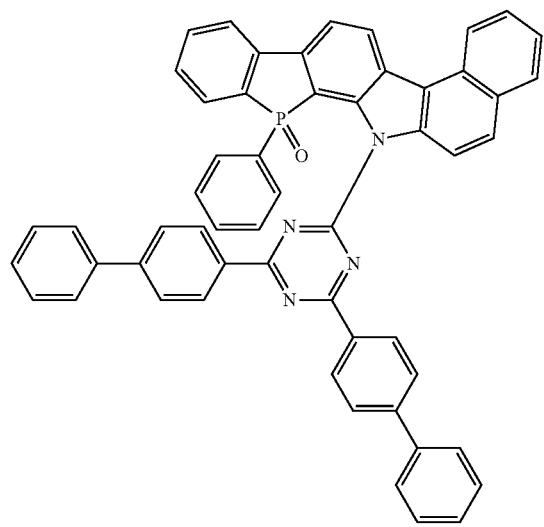
Formula 1-2-180
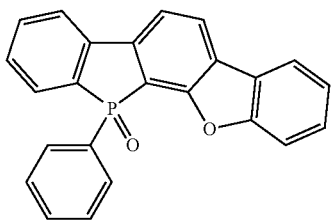

-continued
Formula 1-2-181
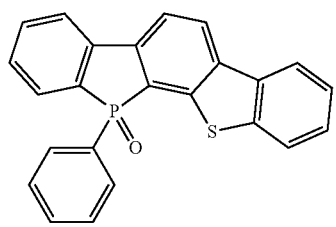
Formula 1-2-182
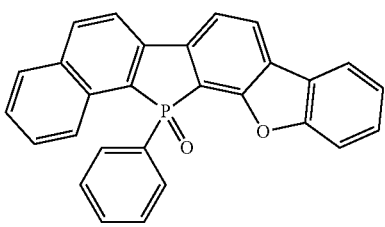
Formula 1-2-183
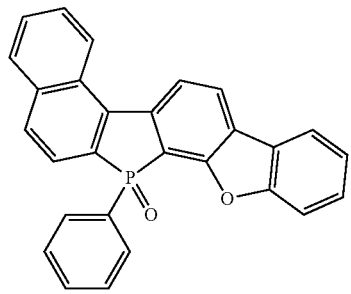
Formula 1-2-184
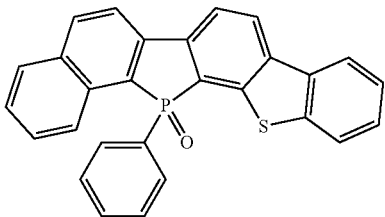
Formula 1-2-185
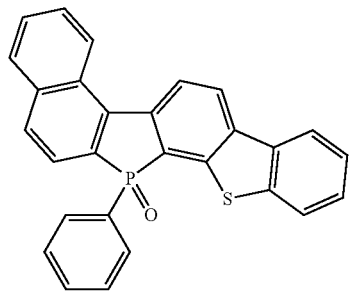
Formula 1-2-186
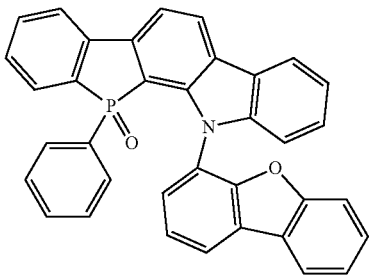
Formula 1-2-187
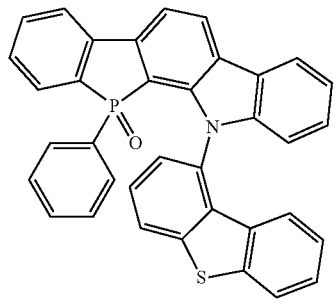
Formula 1-2-188
Formula 1-2-189
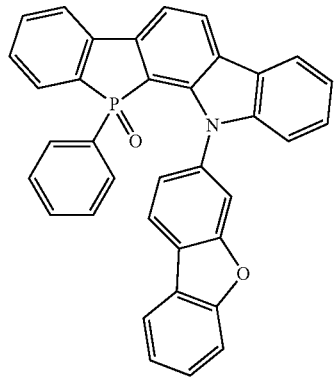
Formula 1-2-190
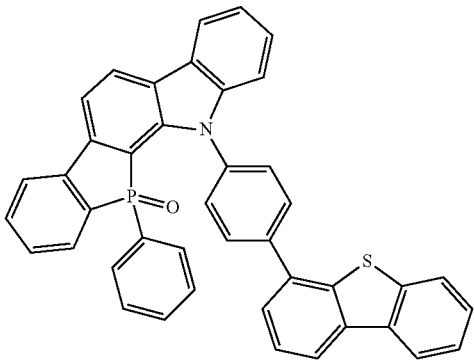

Formula 1-2-191
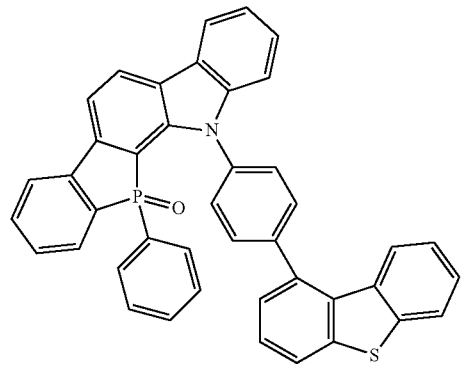
Formula 1-2-192
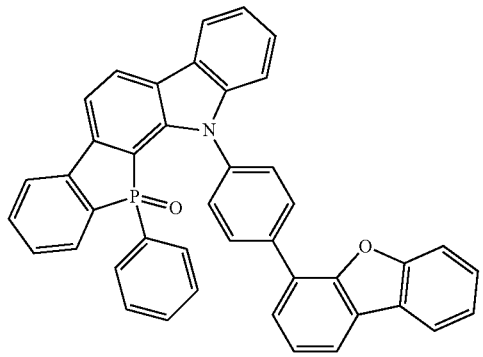
Formula 1-2-193
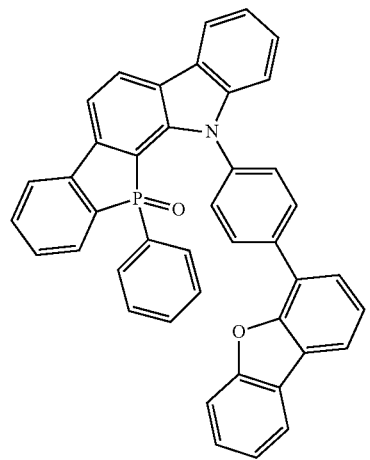
Formula 1-2-194
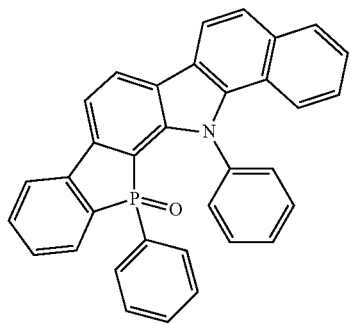
Formula 1-2-195
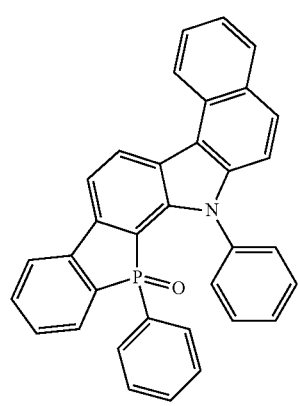
In an exemplary embodiment of the present specification, the compound represented by Formula 1 is represented by Formula 1-3.
In an exemplary embodiment of the present specification, the compound represented by Formula 1-3 is represented by any one of the following Formulae 1-3-1 to 1-3-195.

Formula 1-3-1
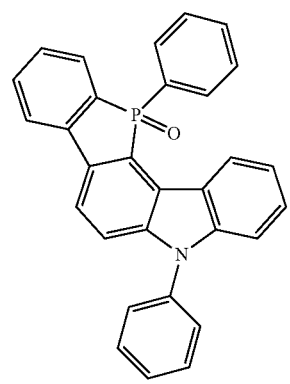
Formula 1-3-2
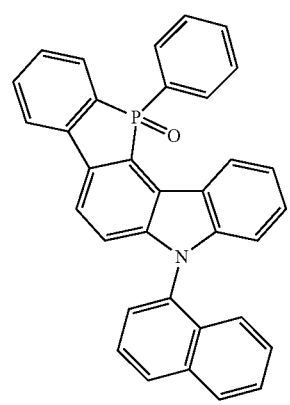
Formula 1-3-3
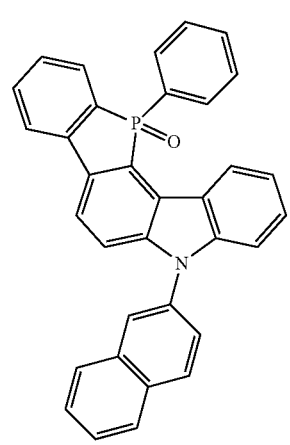
Formula 1-3-4
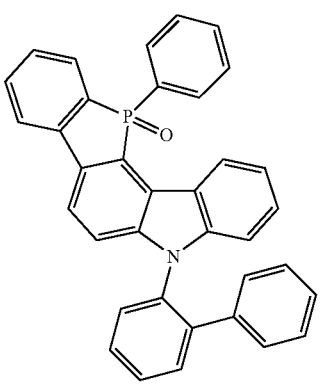
-continued
Formula 1-3-5
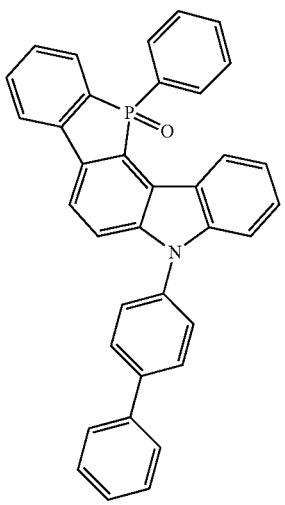
Formula 1-3-6
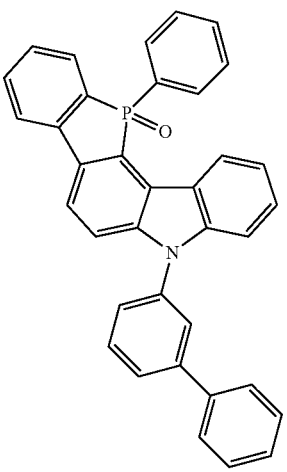
Formula 1-3-7
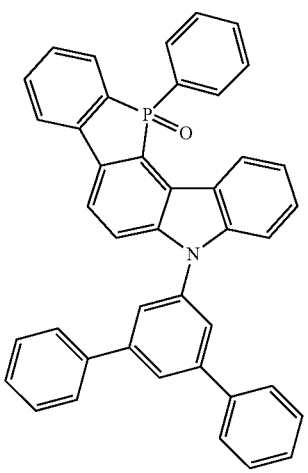

-continued
Formula 1-3-8
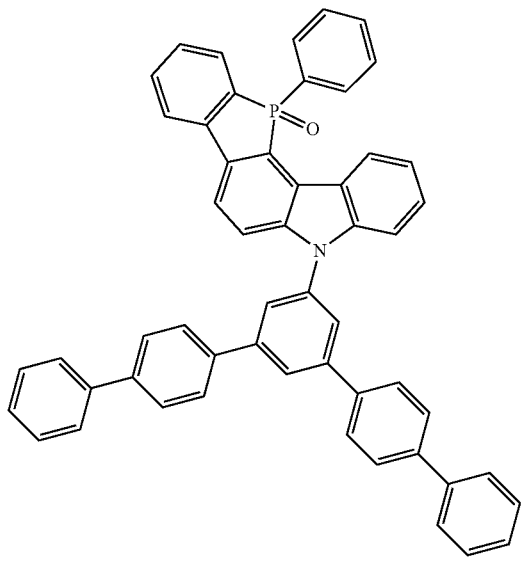
Formula 1-3-9
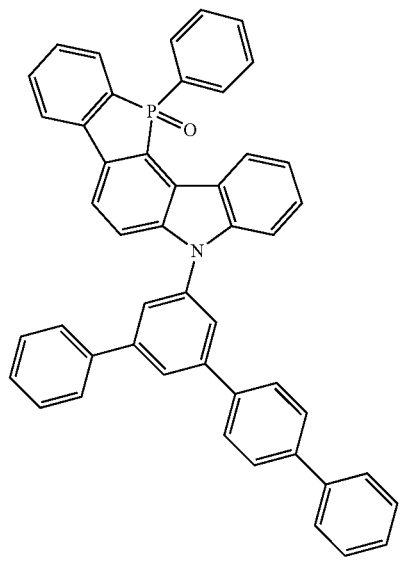
Formula 1-3-10
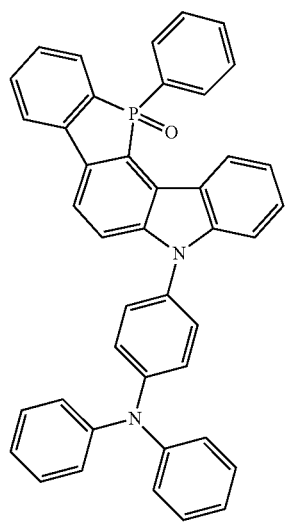
-continued
Formula 1-3-11
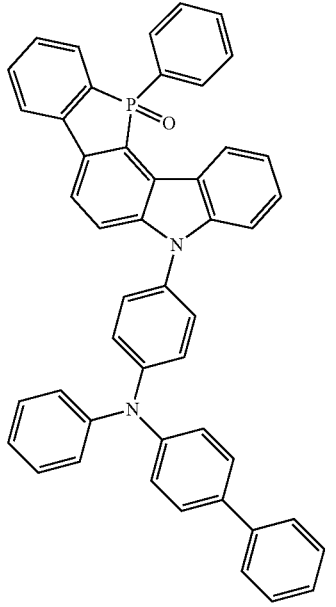
Formula 1-3-12
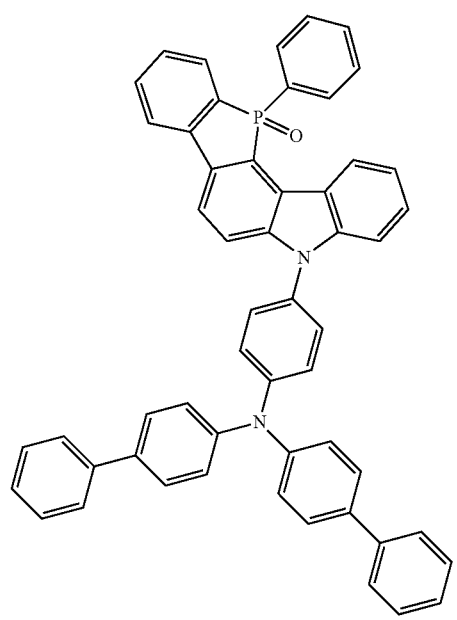

-continued
Formula 1-3-13
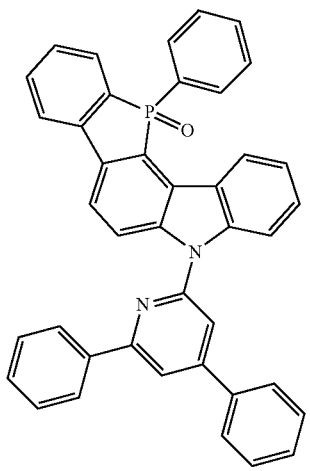
Formula 1-3-14
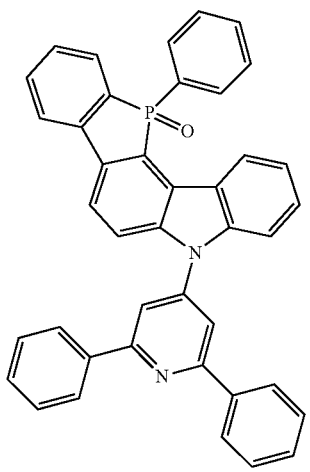
Formula 1-3-15
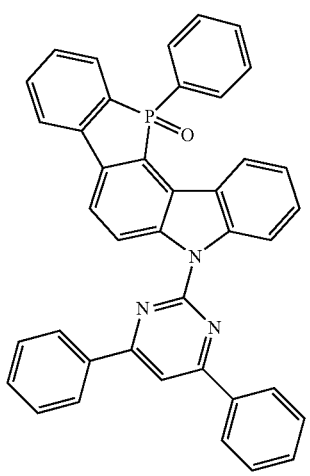
-continued
Formula 1-3-16
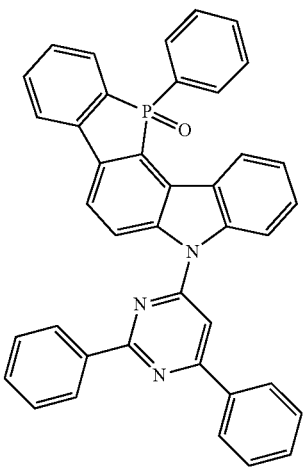
Formula 1-3-17
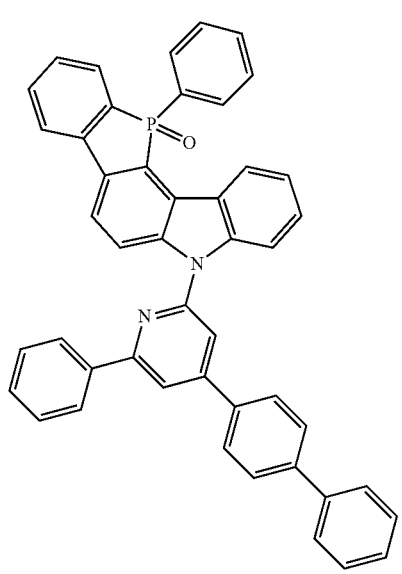
Formula 1-3-18
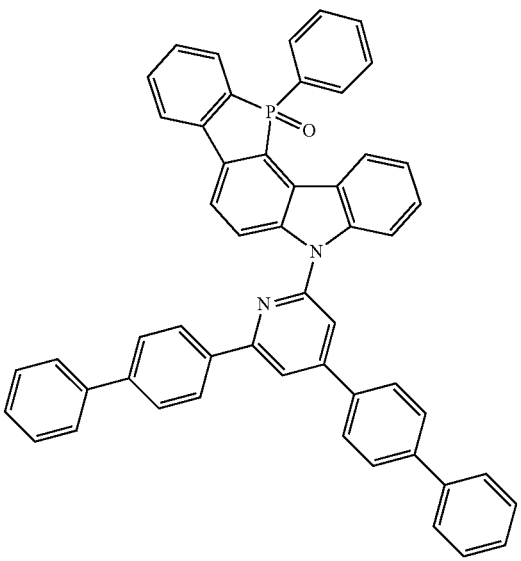

-continued
Formula 1-3-19
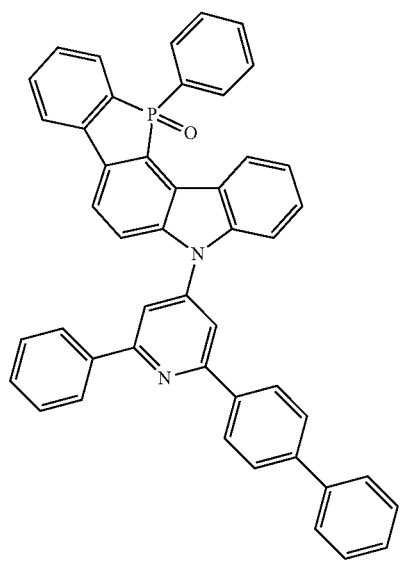
Formula 1-3-20
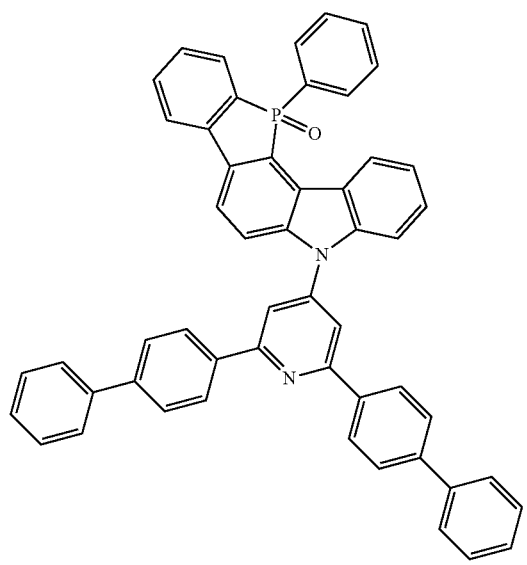
-continued
Formula 1-3-21
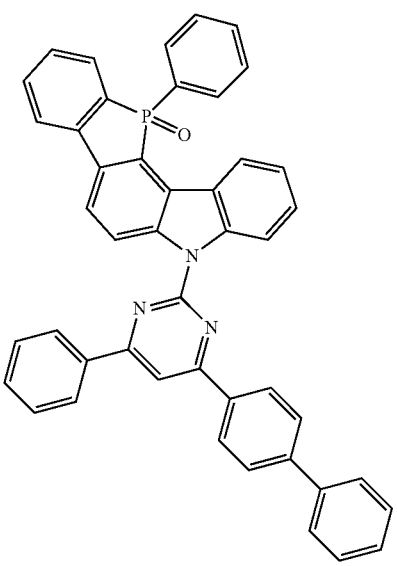
Formula 1-3-22
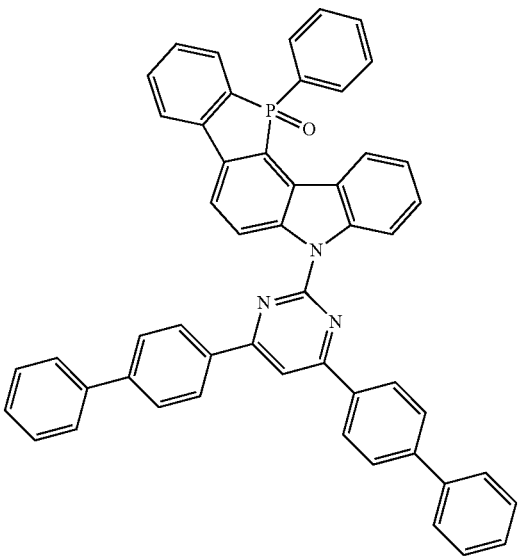

Formula 1-3-23
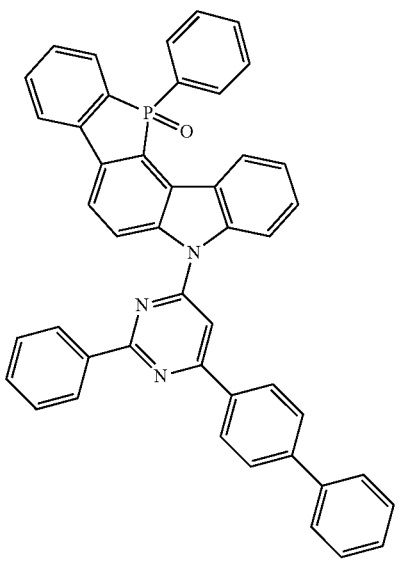
Formula 1-3-26
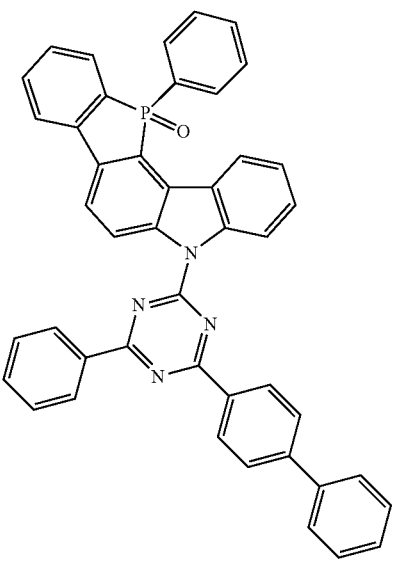
Formula 1-3-24
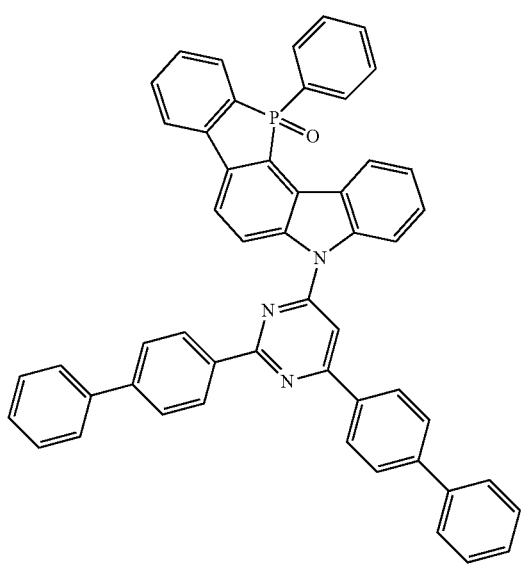
Formula 1-3-25
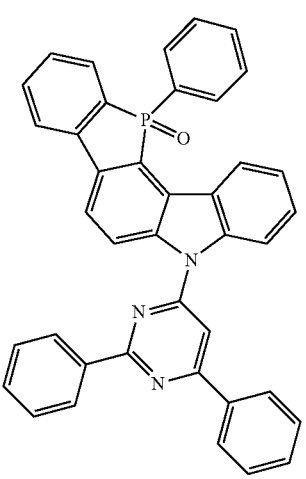
Formula 1-3-27
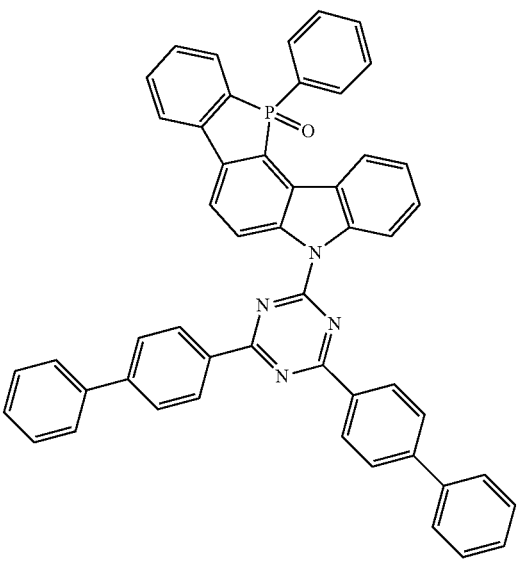

Formula 1-3-28
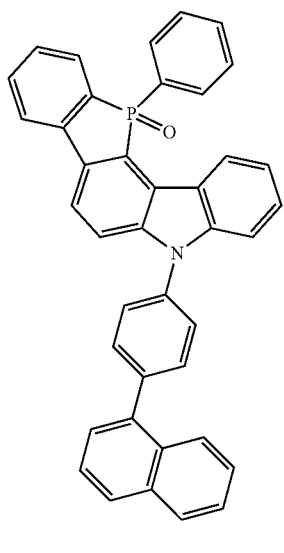
Formula 1-3-29
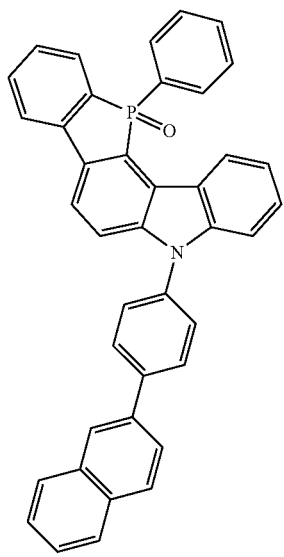
Formula 1-3-30
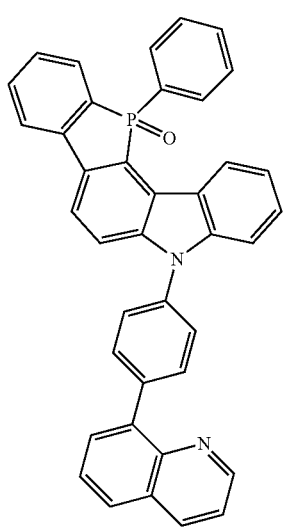
Formula 1-3-31
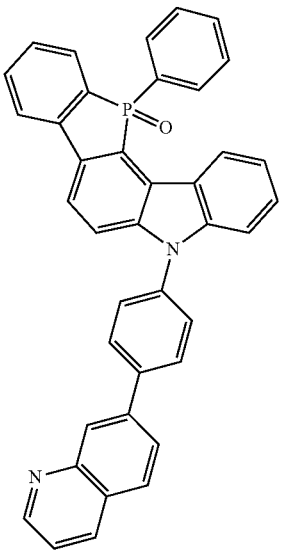
Formula 1-3-32
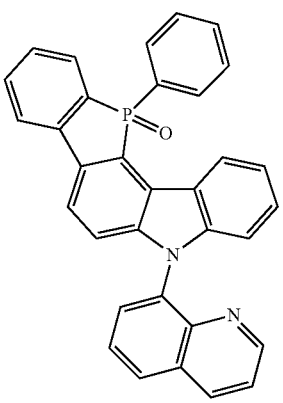
Formula 1-3-33
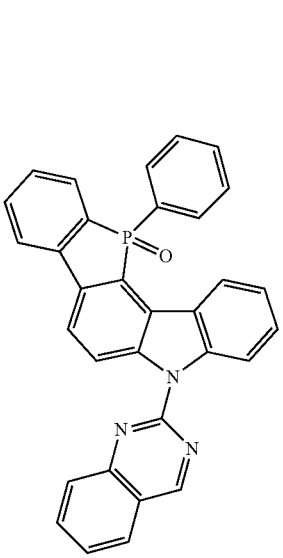

Formula 1-3-34
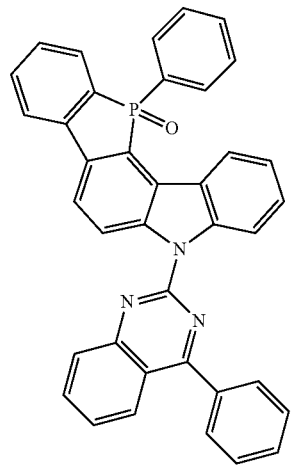
Formula 1-3-35
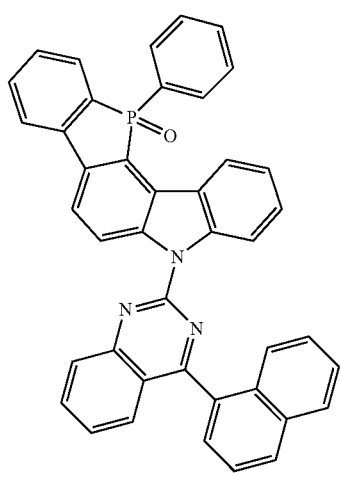
Formula 1-3-36
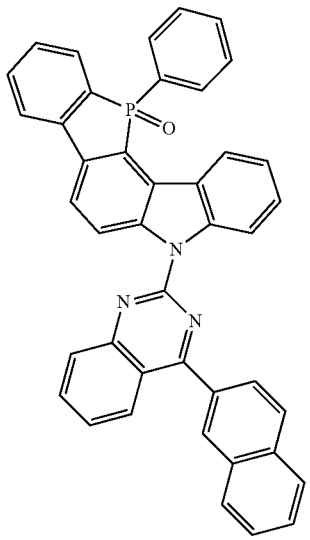
Formula 1-3-37
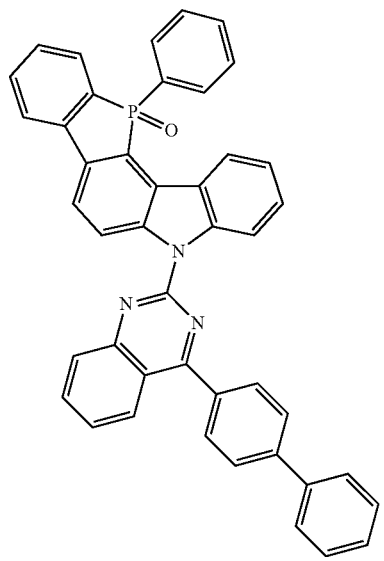
Formula 1-3-38
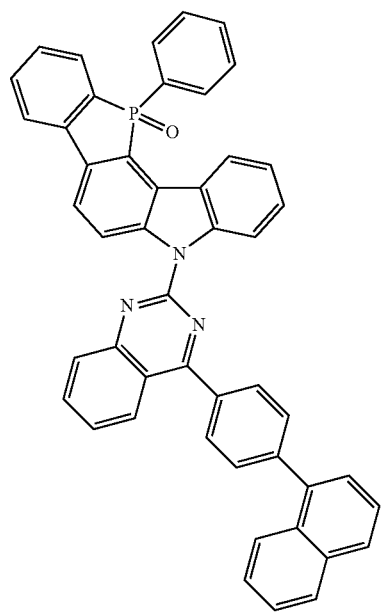

-continued
Formula 1-3-39
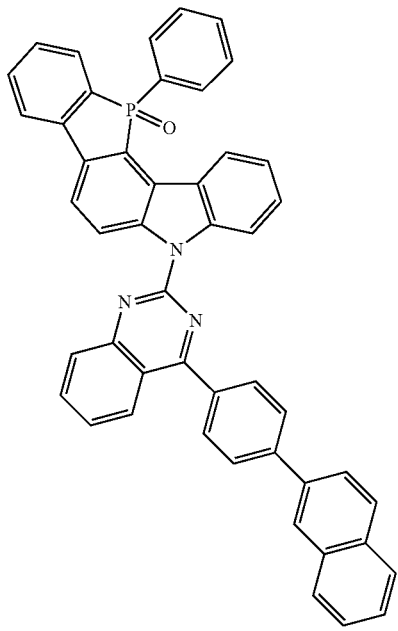
Formula 1-3-40
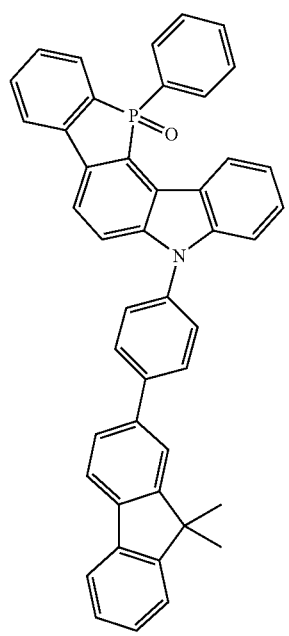
-continued
Formula 1-3-41
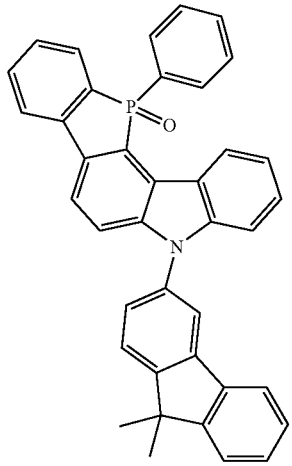
Formula 1-3-42
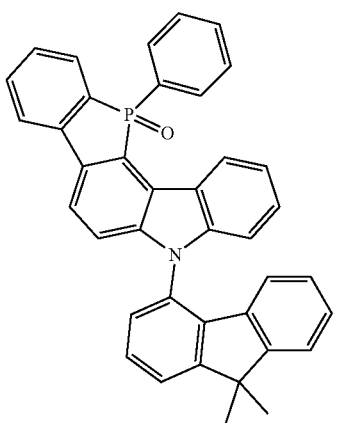
Formula 1-3-43
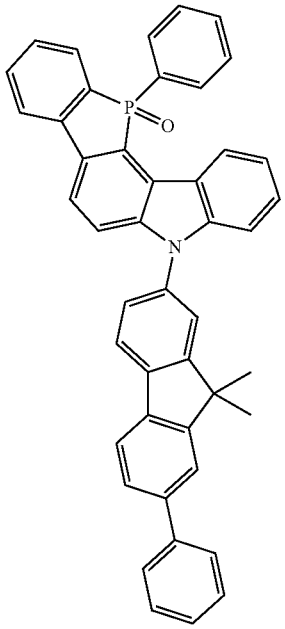

Formula 1-3-44
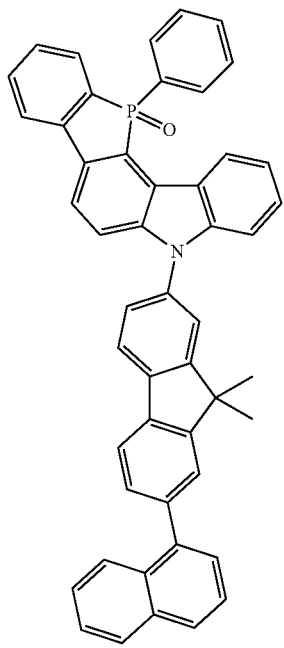
Formula 1-3-46
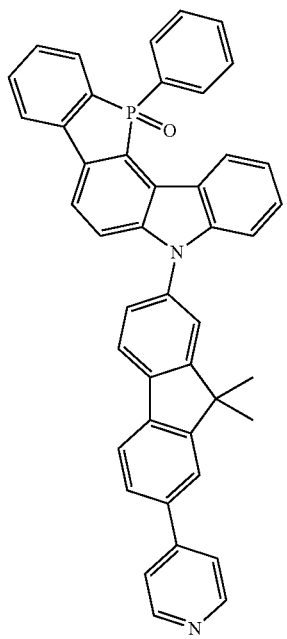
Formula 1-3-45
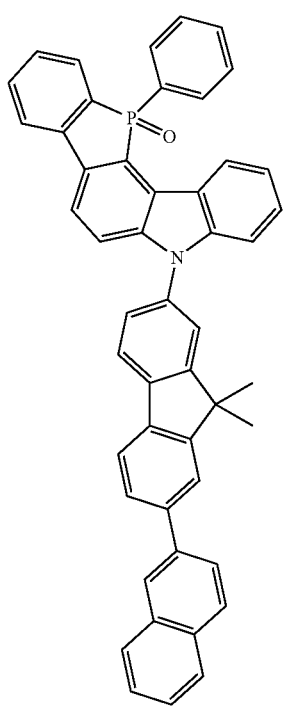
Formula 1-3-47
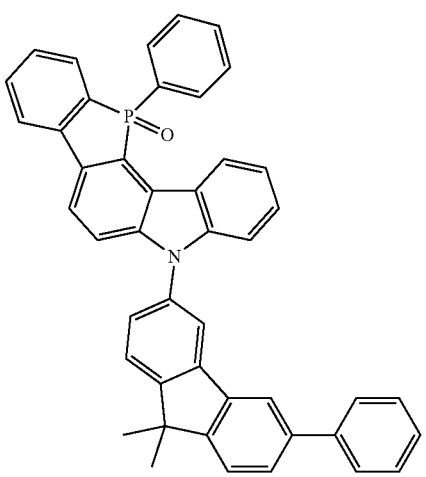

Formula 1-3-48
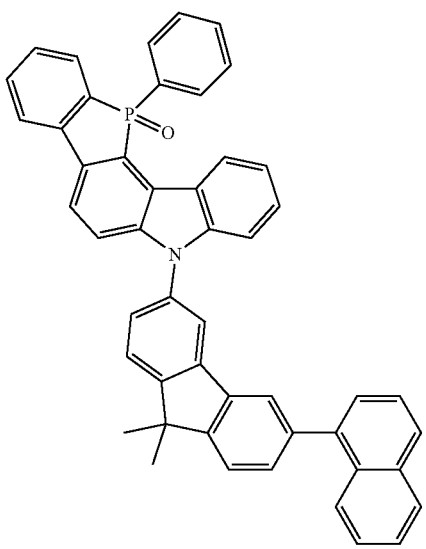
Formula 1-3-49
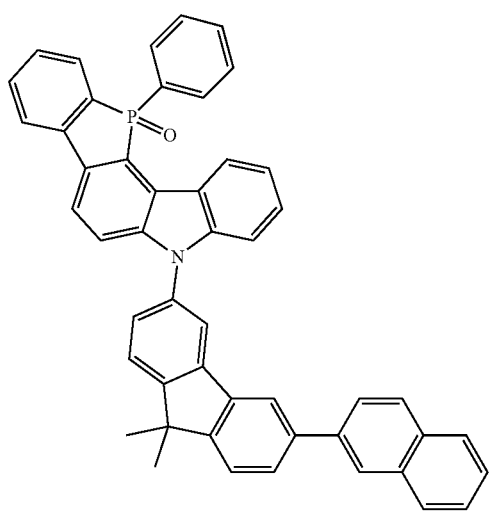
Formula 1-3-50
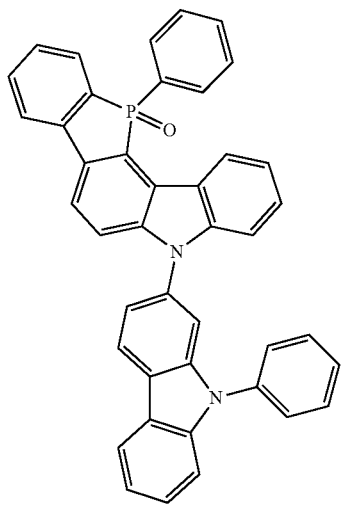
Formula 1-3-51
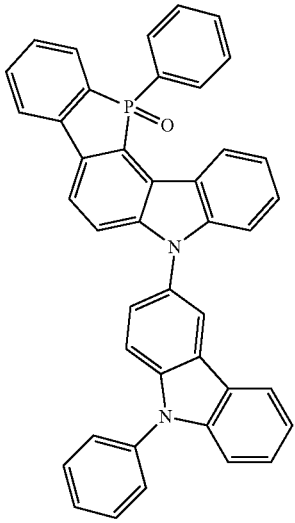
Formula 1-3-52
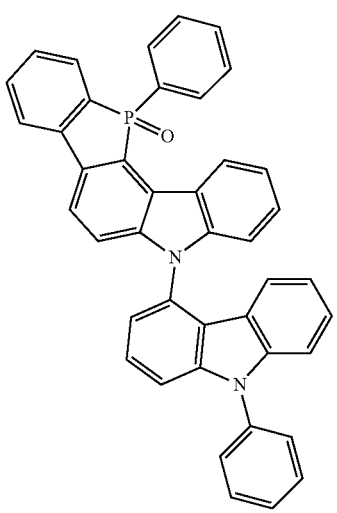
Formula 1-3-53
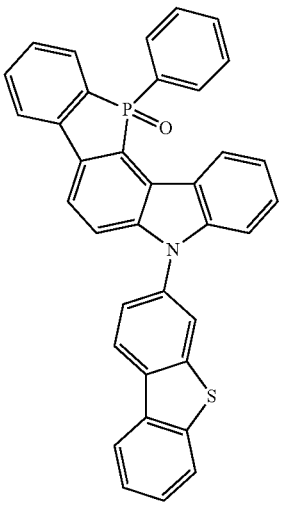

Formula 1-3-54
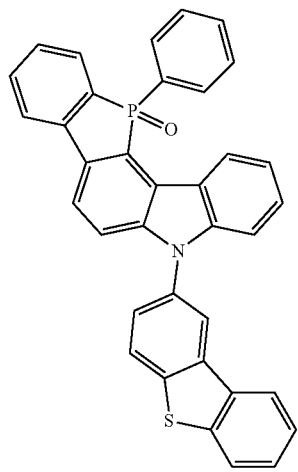
Formula 1-3-55
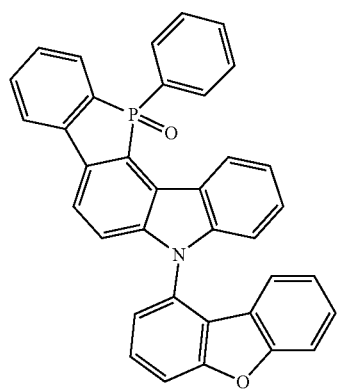
Formula 1-3-56
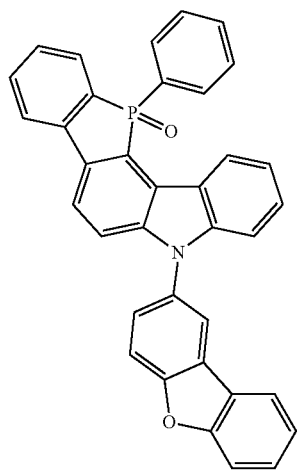
Formula 1-3-57
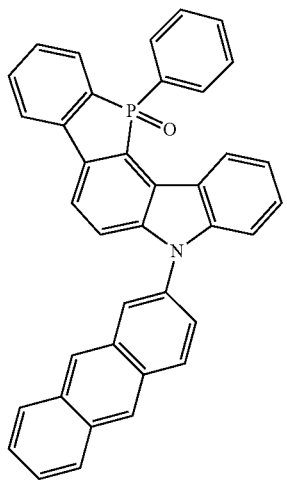
Formula 1-3-58
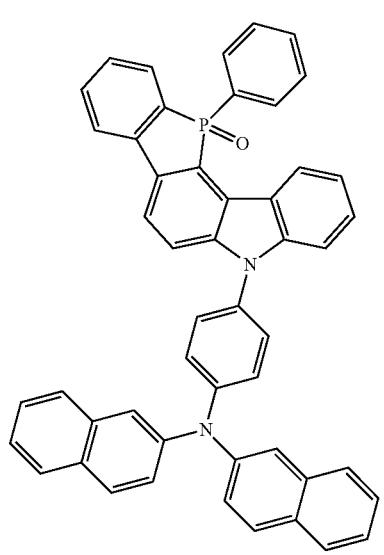
Formula 1-3-59
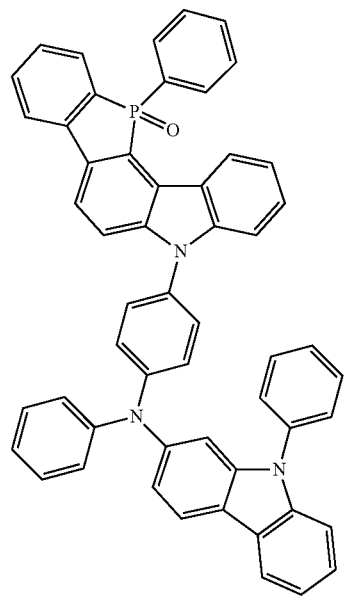

Formula 1-3-60
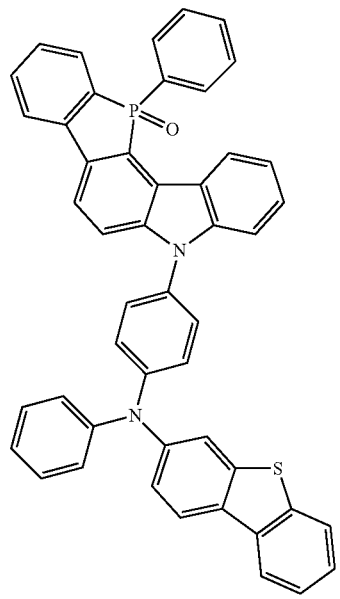
Formula 1-3-61
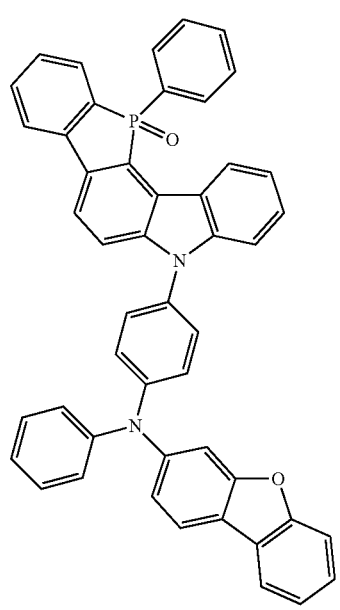
Formula 1-3-62
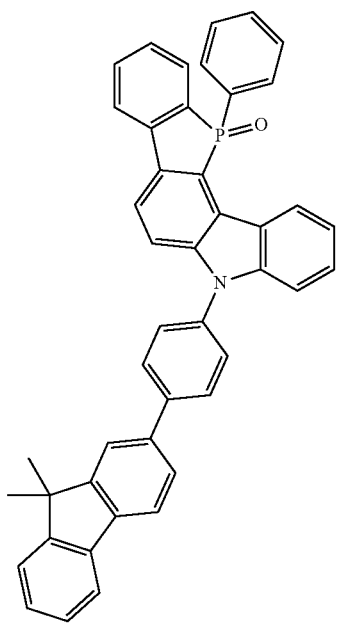
Formula 1-3-63
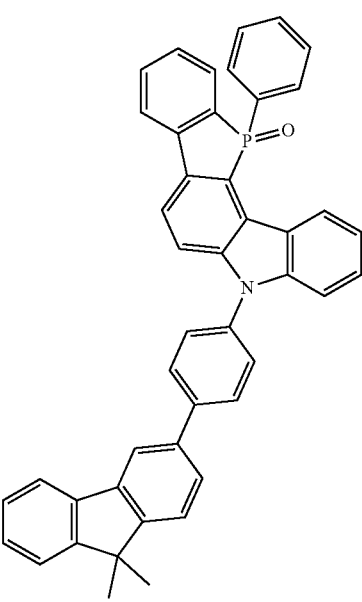

Formula 1-3-64
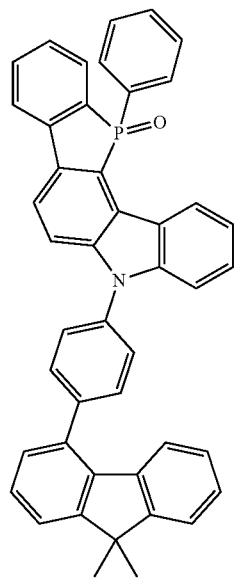
Formula 1-3-66
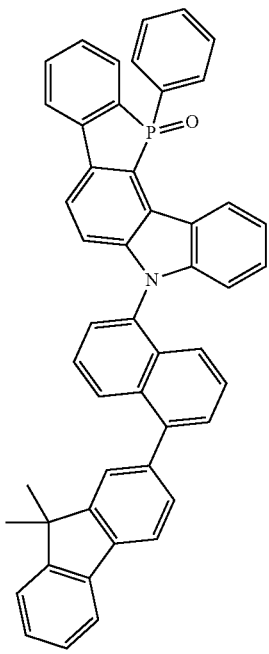
Formula 1-3-65
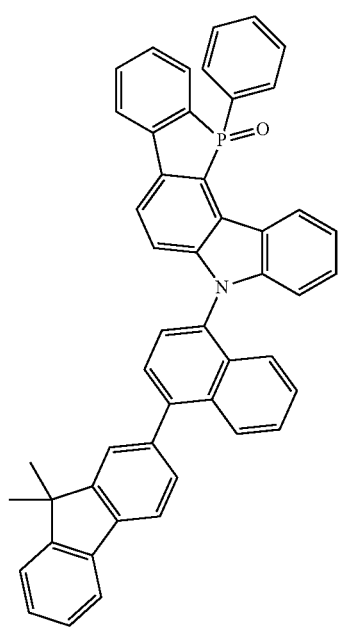
Formula 1-3-67
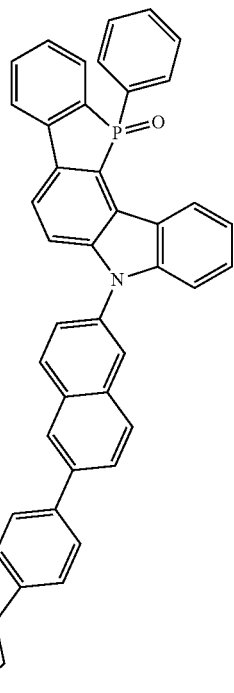

Formula 1-3-68
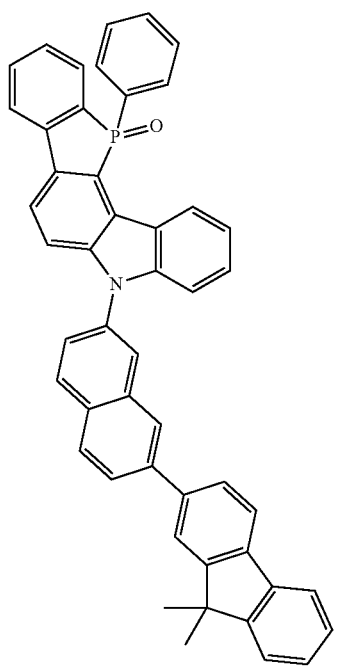
Formula 1-3-70
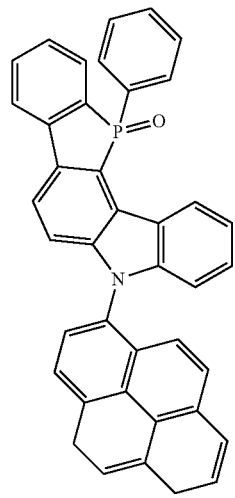
Formula 1-3-71
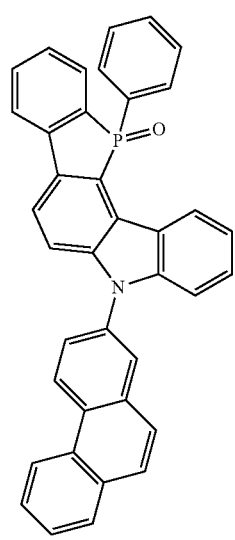
Formula 1-3-69
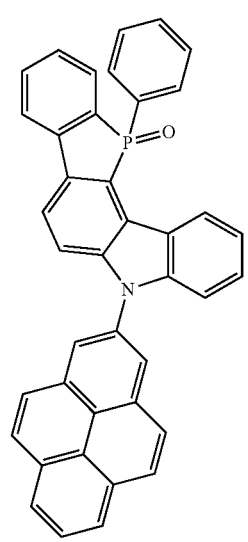
Formula 1-3-72
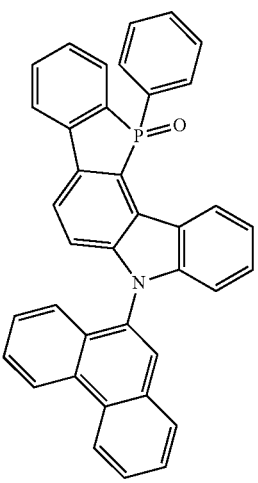

Formula 1-3-73
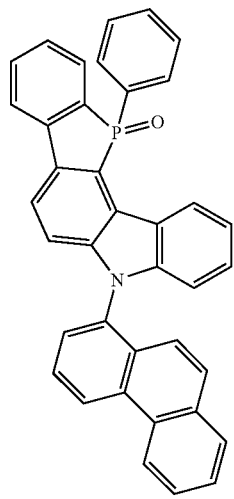
Formula 1-3-74
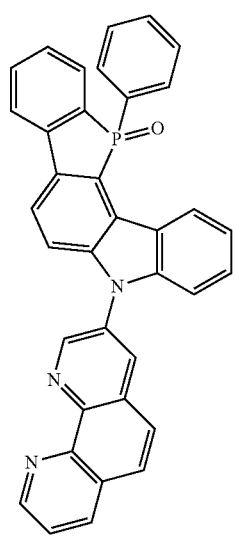
Formula 1-3-75
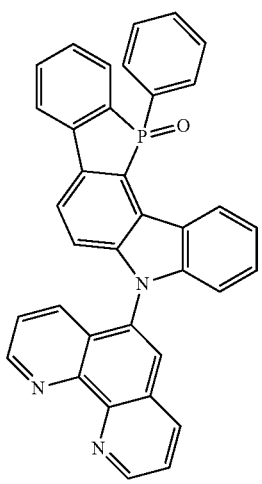
Formula 1-3-76
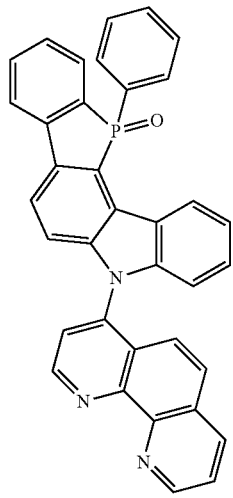
Formula 1-3-77
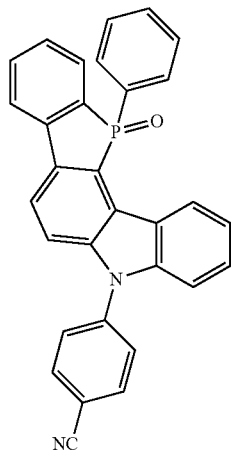
Formula 1-3-78
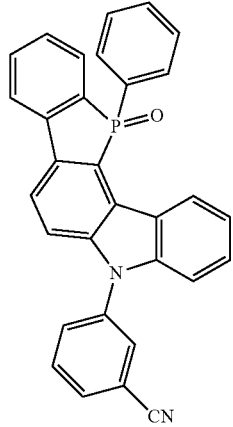

Formula 1-3-79
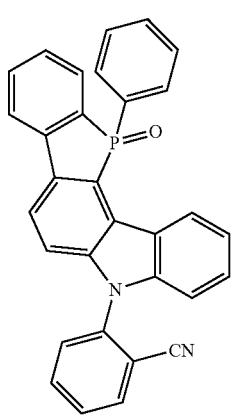
Formula 1-3-80
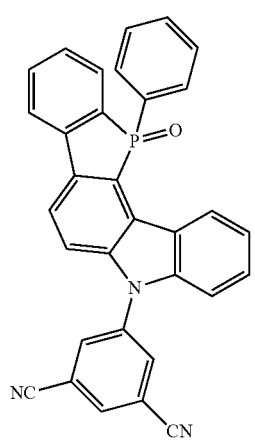
Formula 1-3-81
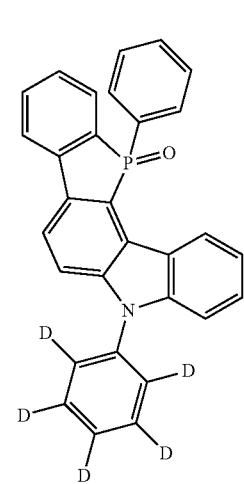
Formula 1-3-82
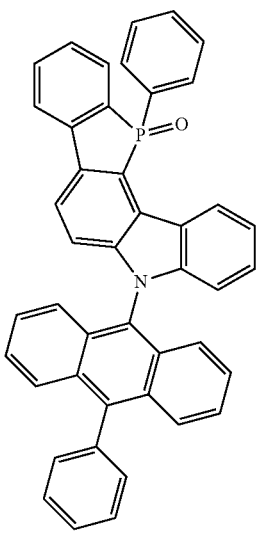
Formula 1-3-83
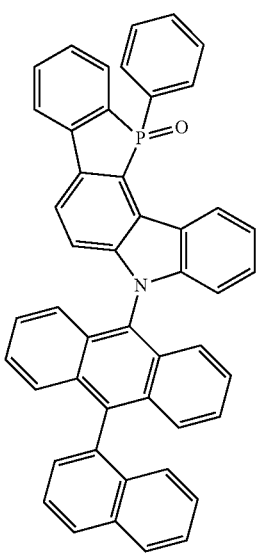

Formula 1-3-84
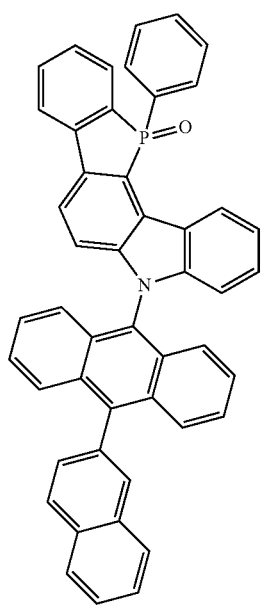
Formula 1-3-86
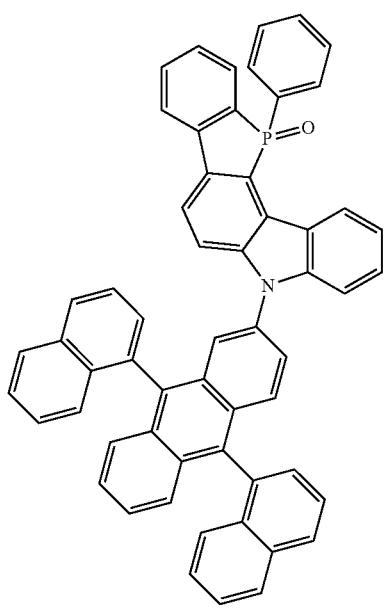
Formula 1-3-85
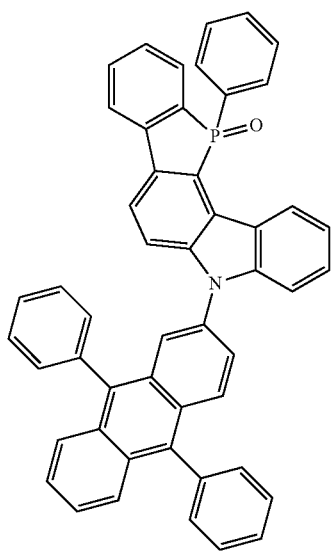
Formula 1-3-87
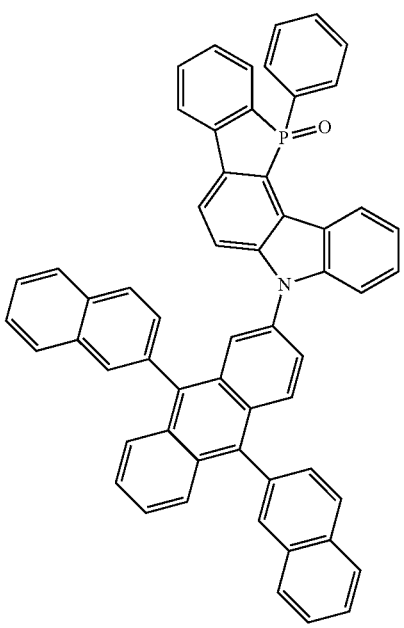

Formula 1-3-88
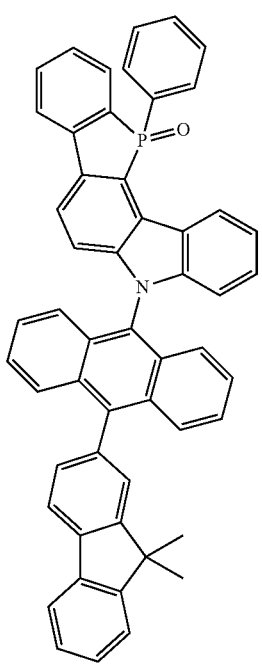
Formula 1-3-89
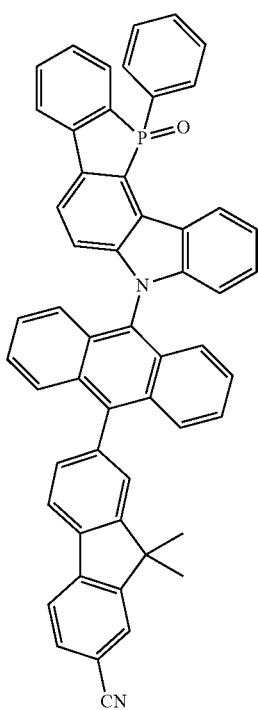
Formula 1-3-90
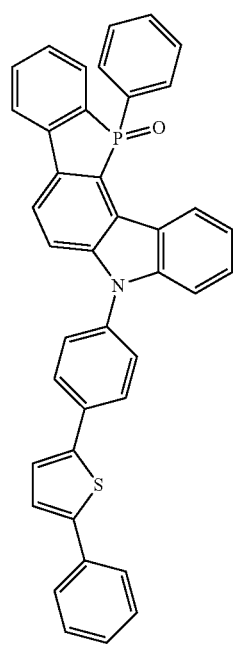
Formula 1-3-91
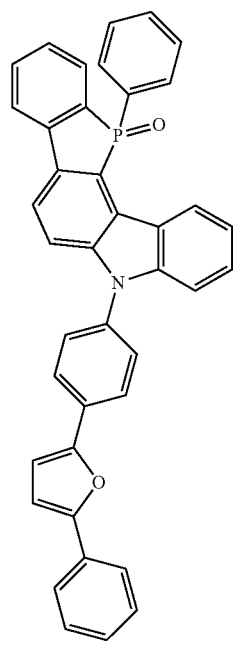

Formula 1-3-92
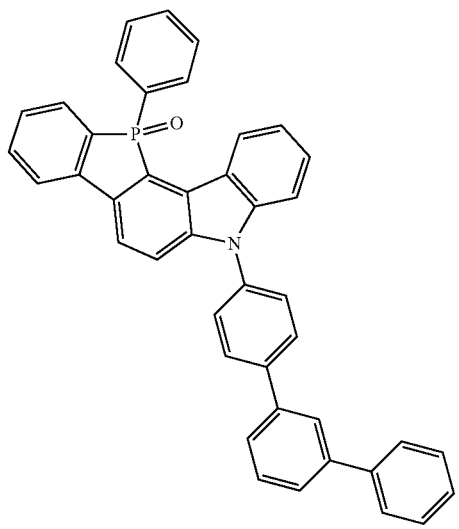
Formula 1-3-94
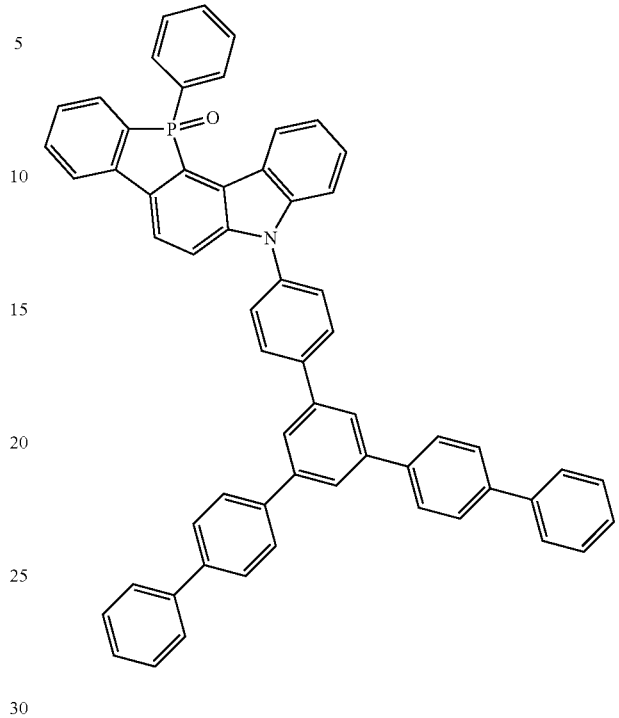
Formula 1-3-93
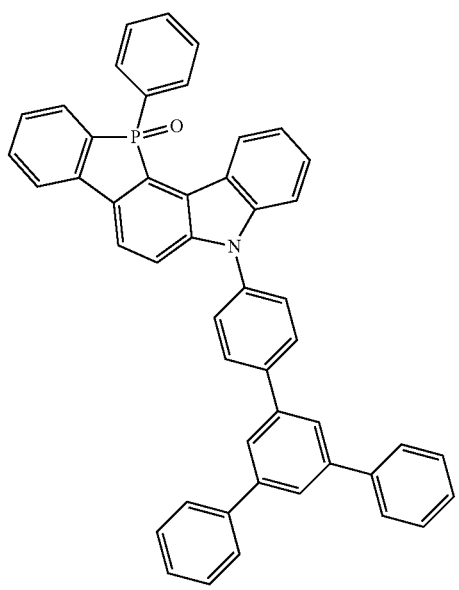
Formula 1-3-95
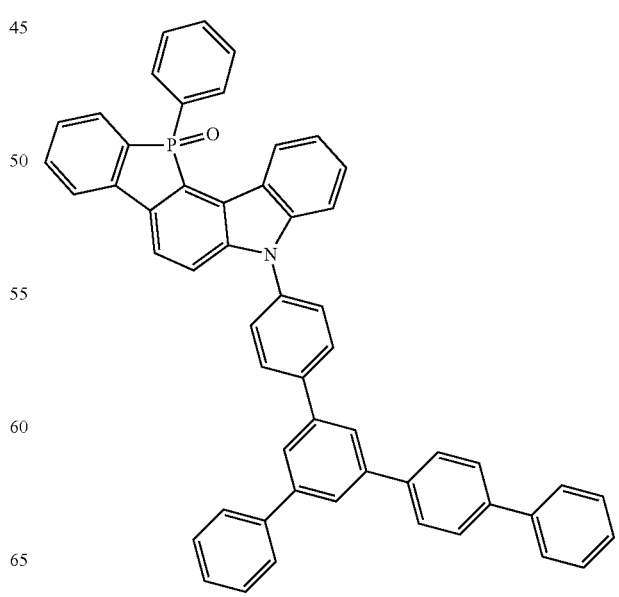

Formula 1-3-96
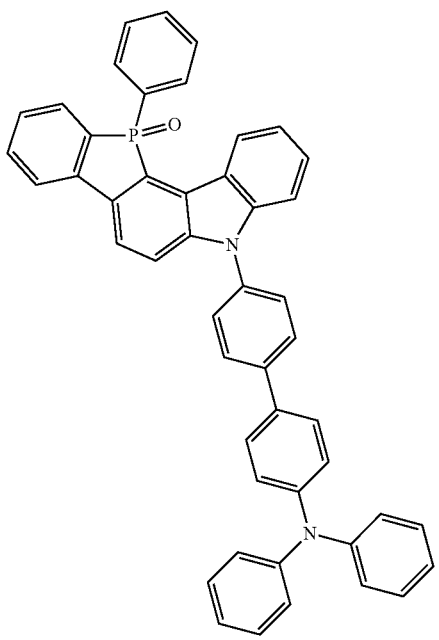
Formula 1-3-97
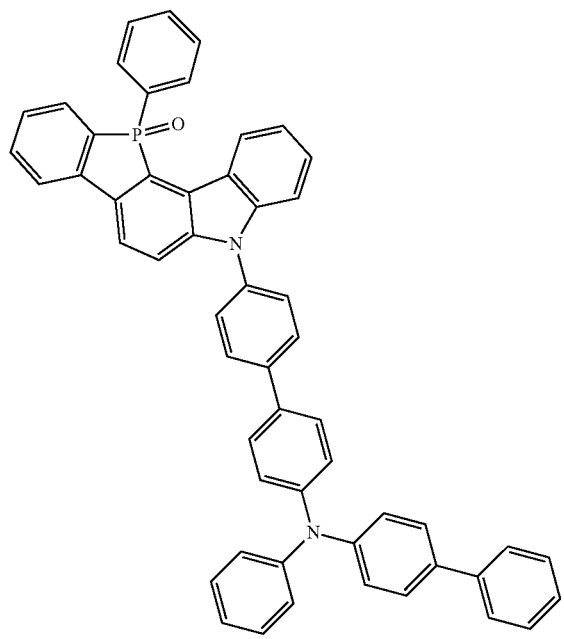
Formula 1-3-98
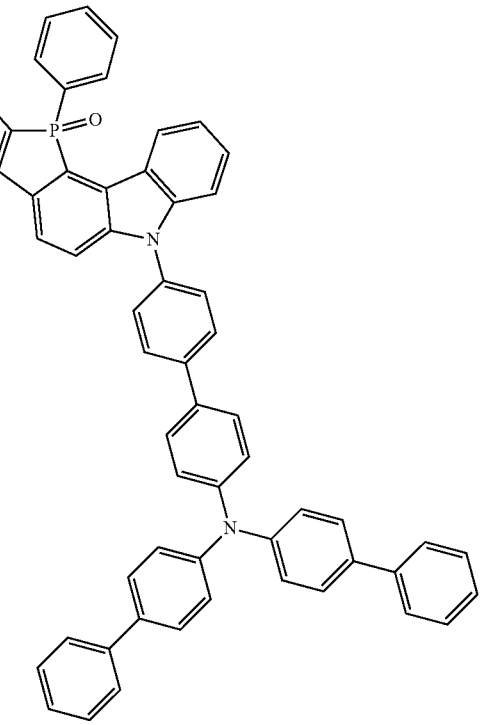
Formula 1-3-99
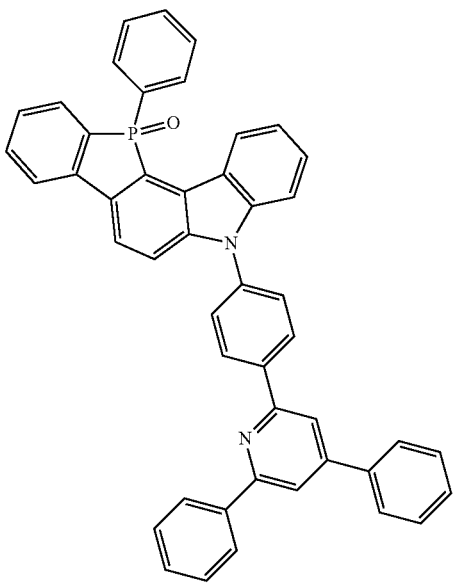

-continued
Formula 1-3-100
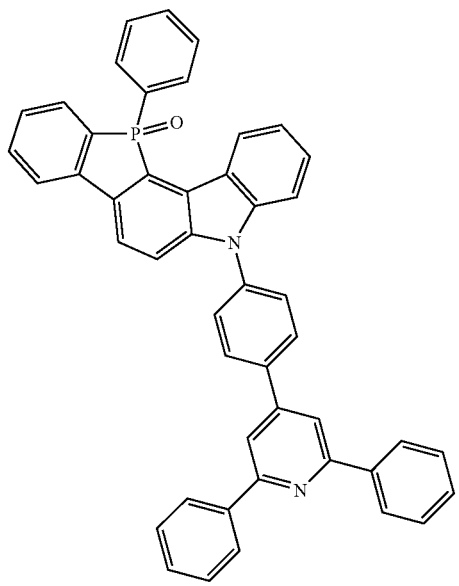
Formula 1-3-101
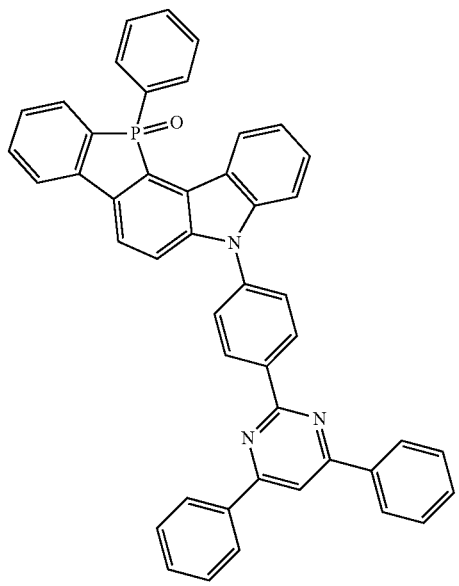
-continued
Formula 1-3-102
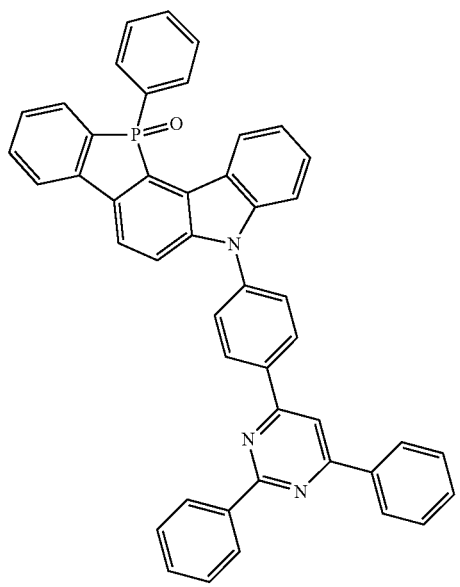
Formula 1-3-103
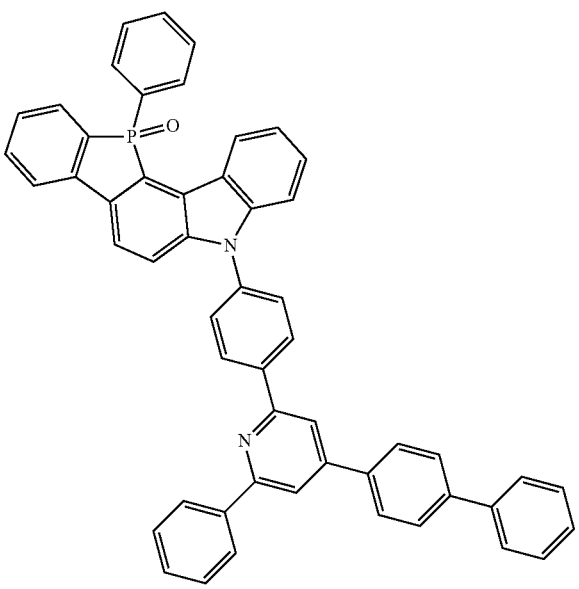

-continued
Formula 1-3-104
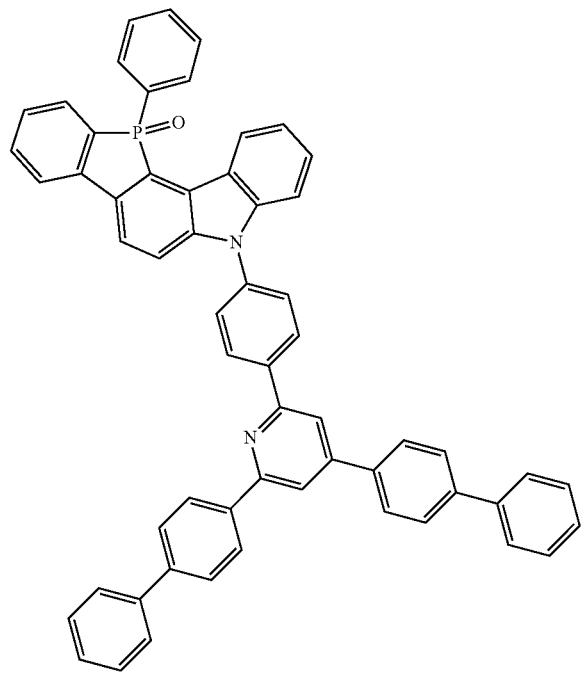
Formula 1-3-105
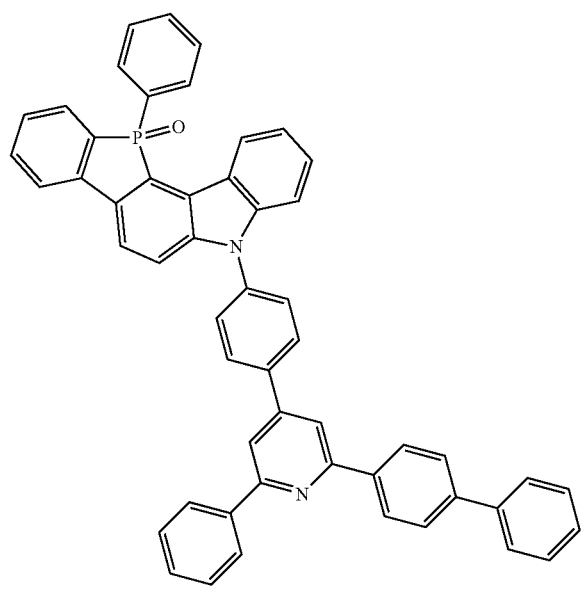
-continued
Formula 1-3-106
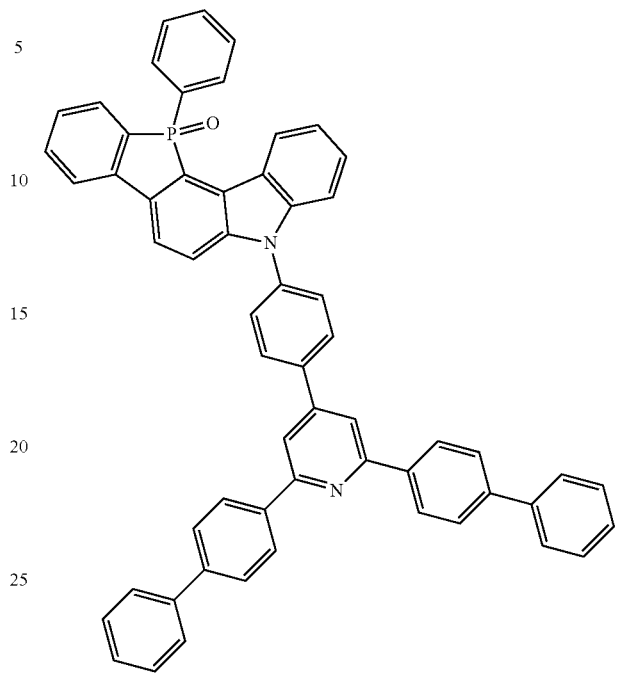
Formula 1-3-107
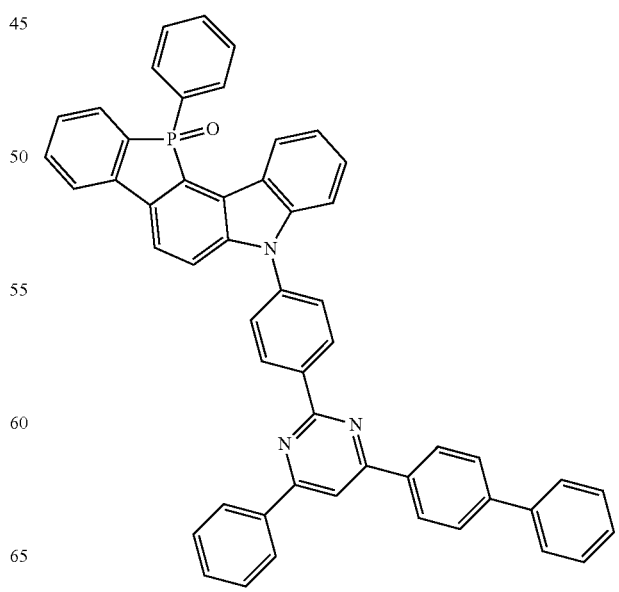

Formula 1-3-108
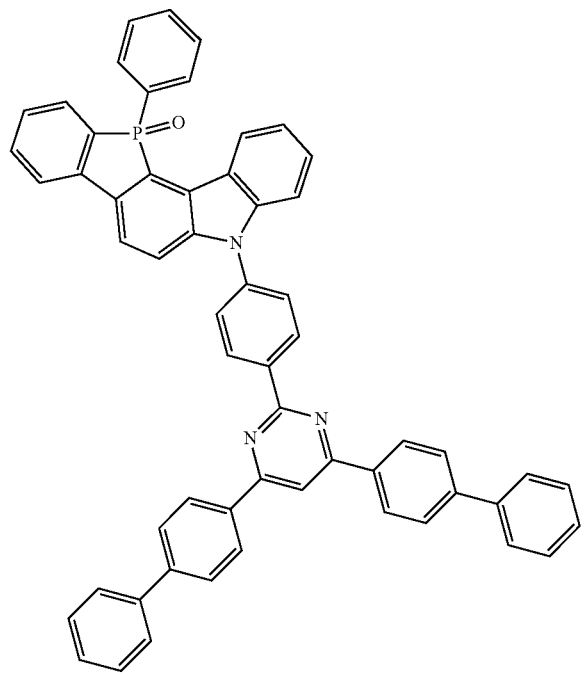
Formula 1-3-110
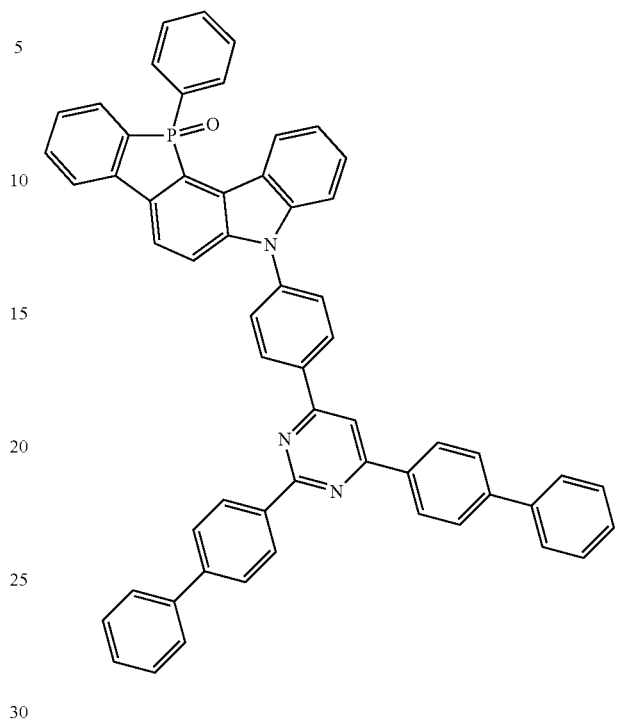
Formula 1-3-109
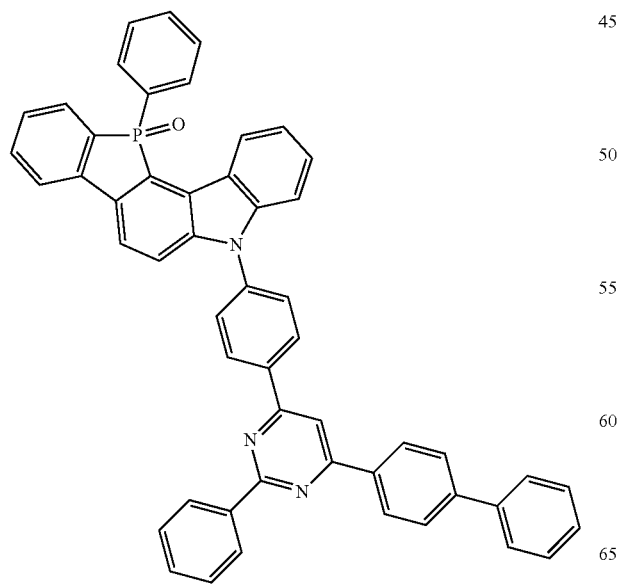
Formula 1-3-111
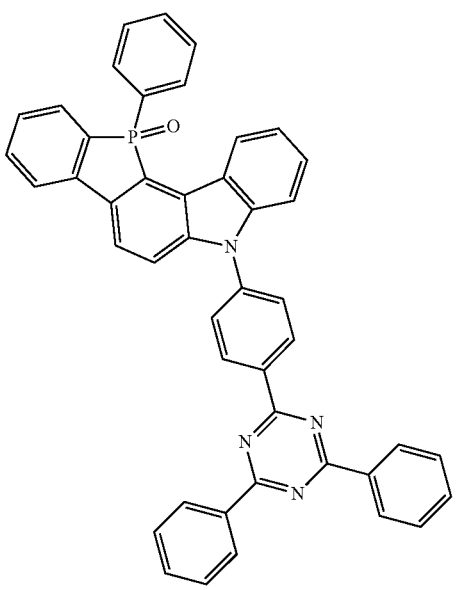

Formula 1-3-112
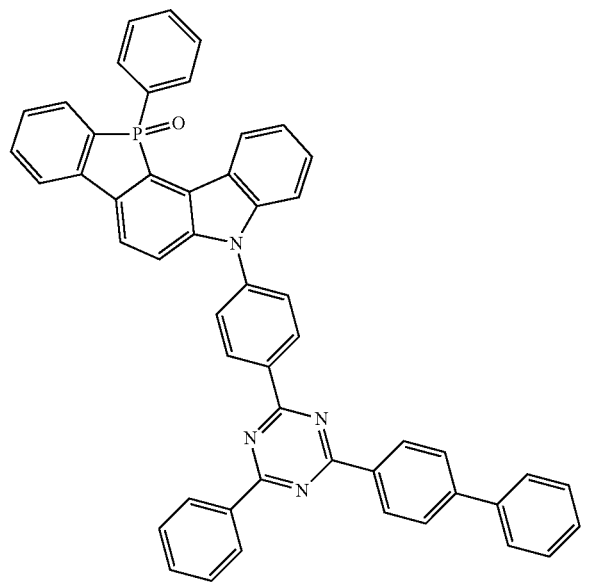
Formula 1-3-114
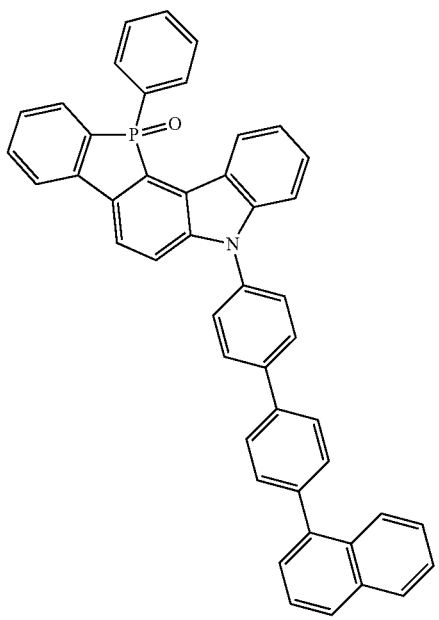
Formula 1-3-113
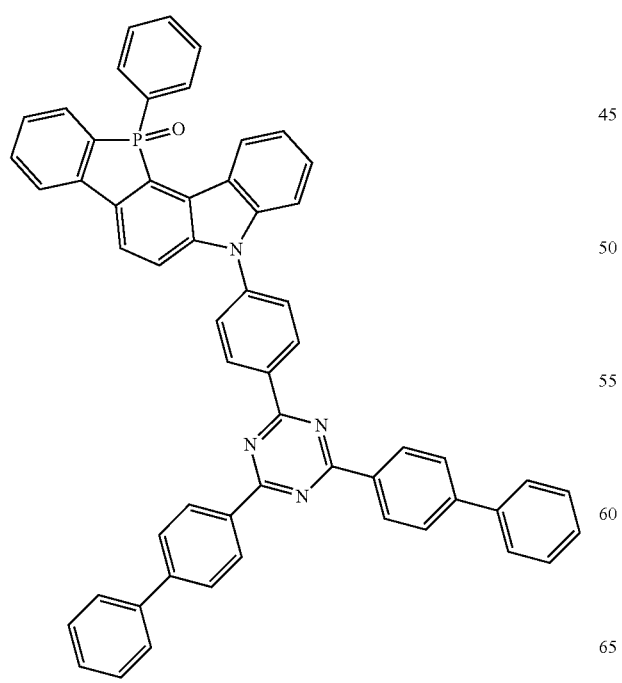
Formula 1-3-115
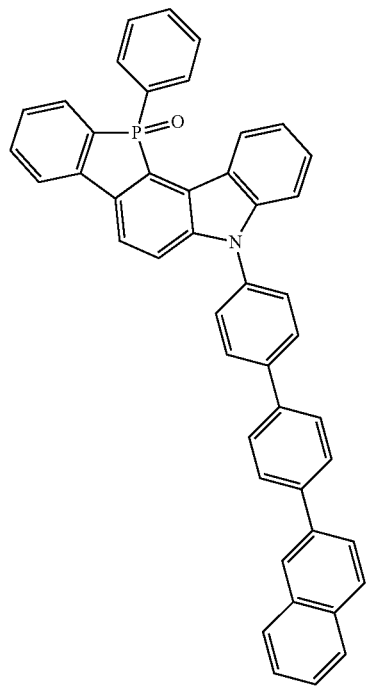

Formula 1-3-116
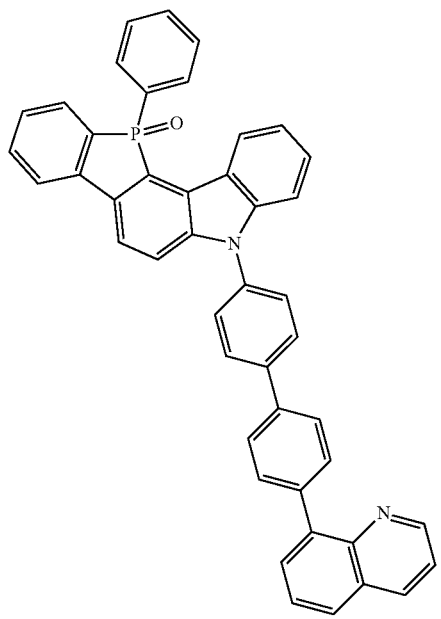
Formula 1-3-118
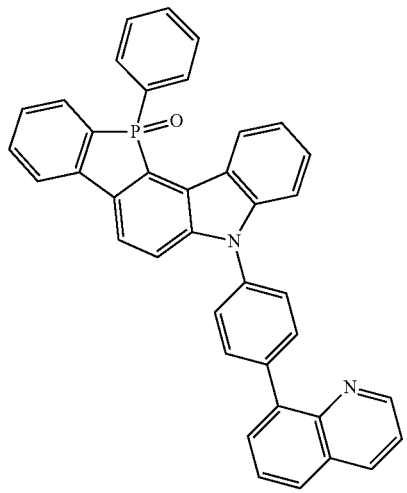
Formula 1-3-119
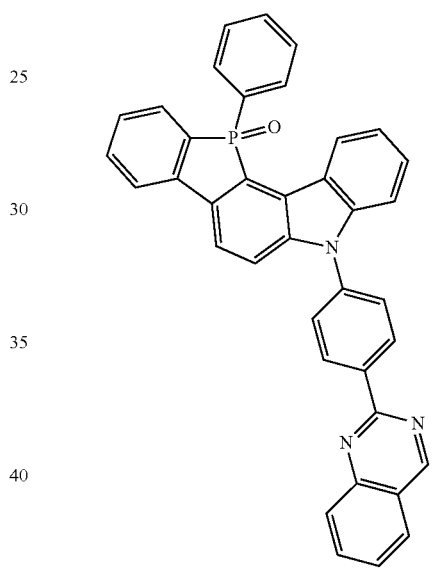
Formula 1-3-117
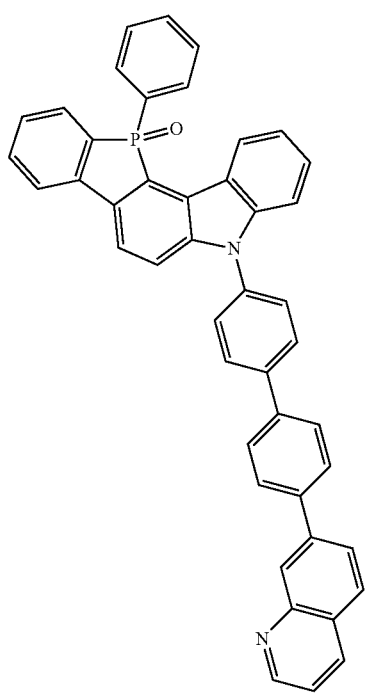
Formula 1-3-120
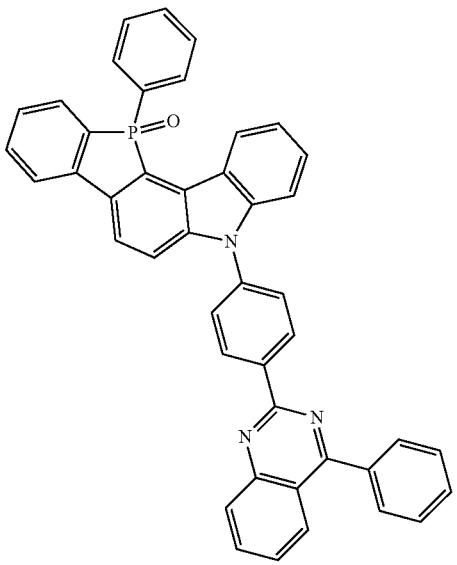

Formula 1-3-121
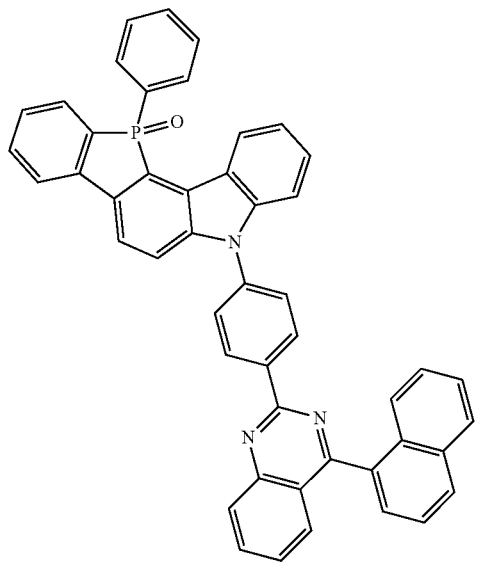
Formula 1-3-122
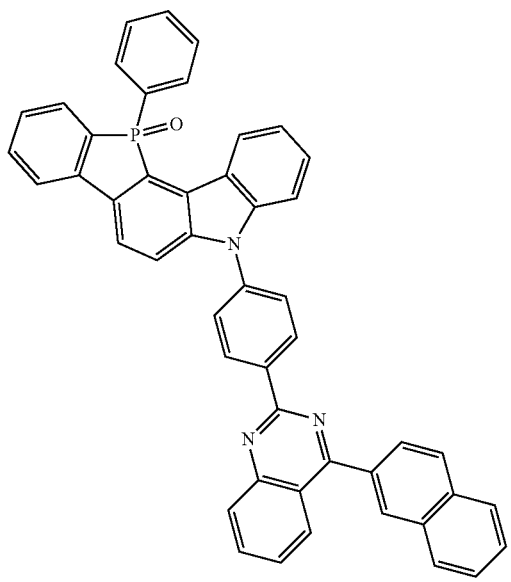
Formula 1-3-123
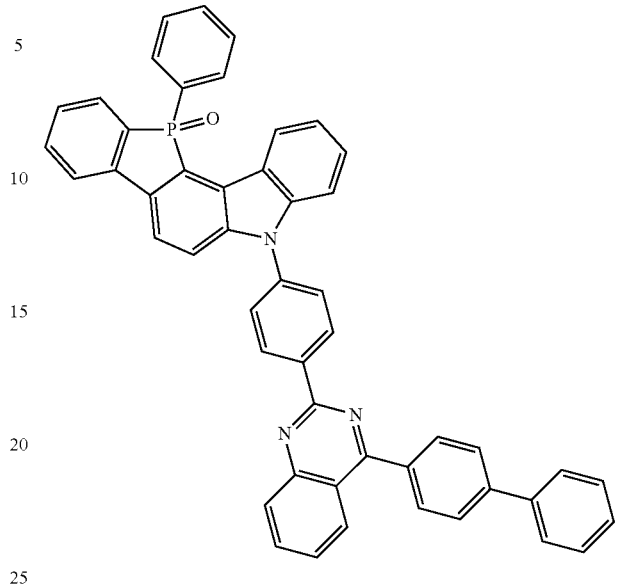
Formula 1-3-124
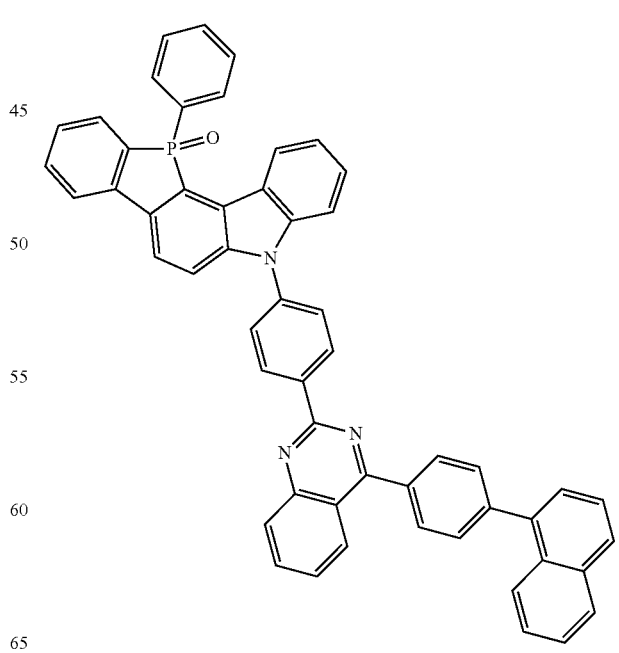

Formula 1-3-125
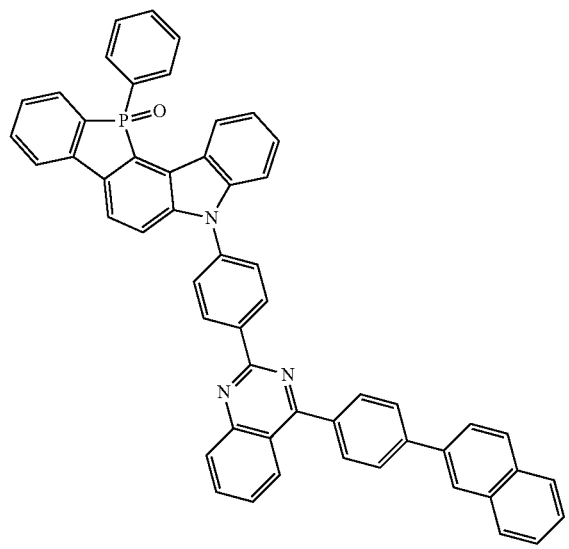
Formula 1-3-126
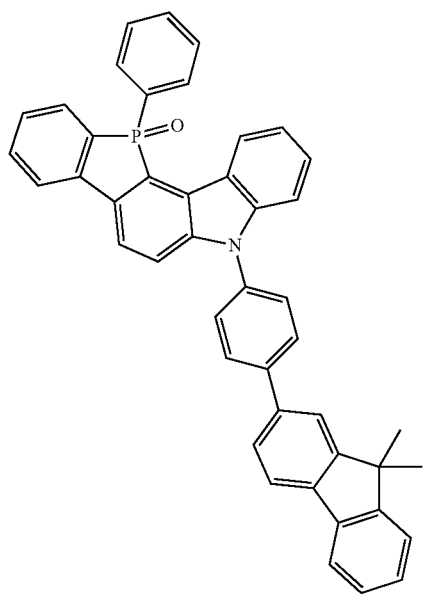
Formula 1-3-127
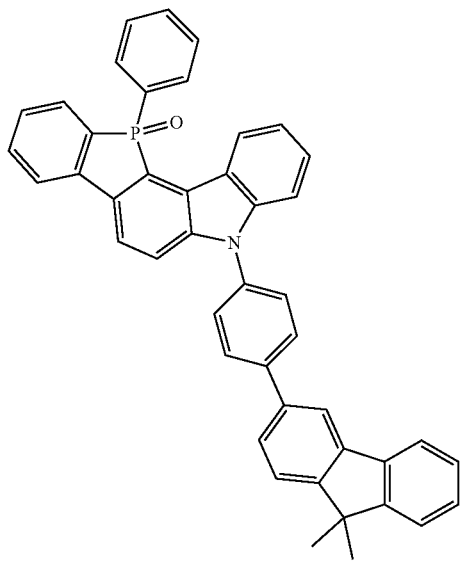
Formula 1-3-128
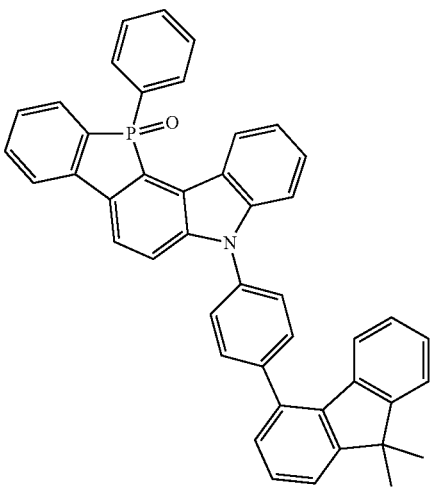

-continued
Formula 1-3-129
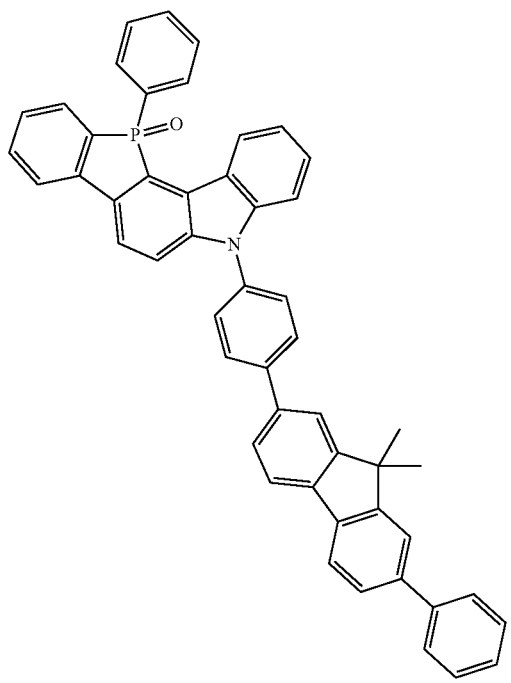
Formula 1-3-130
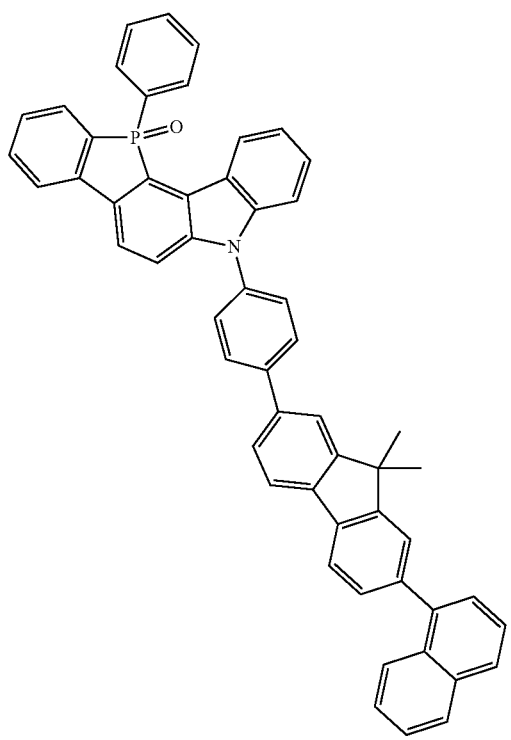
Formula 1-3-131
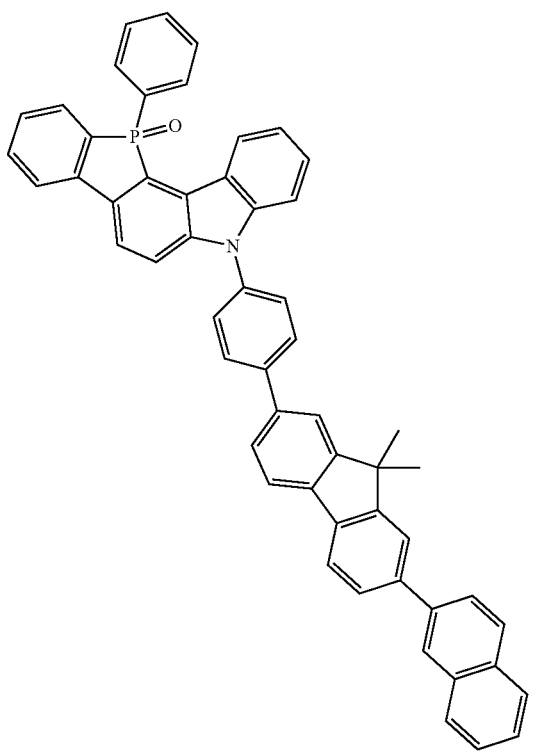
Formula 1-3-132
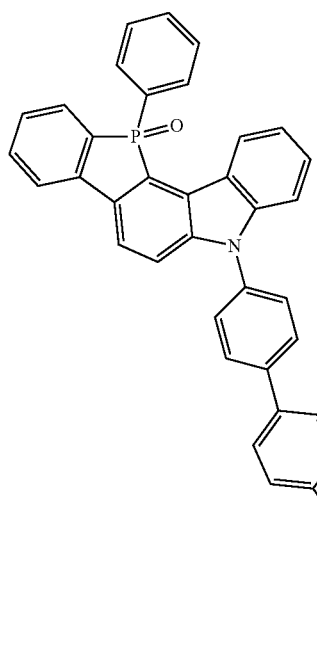

Formula 1-3-133
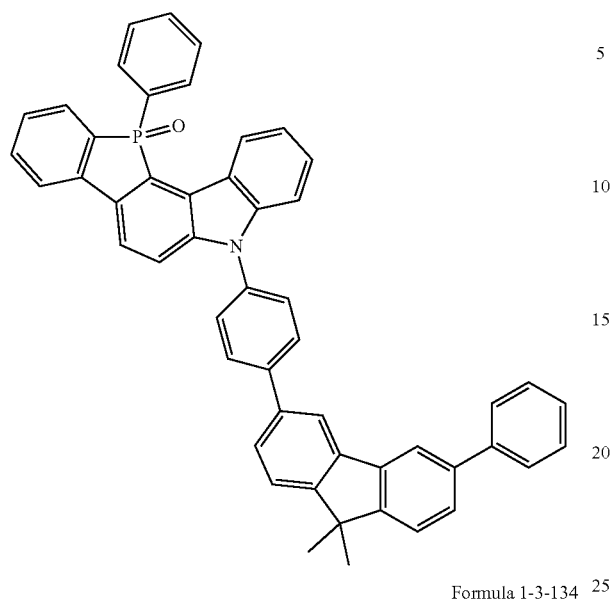
Formula 1-3-136
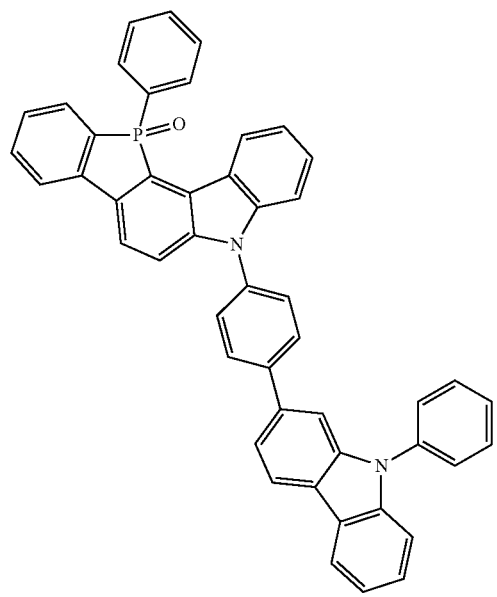
Formula 1-3-134
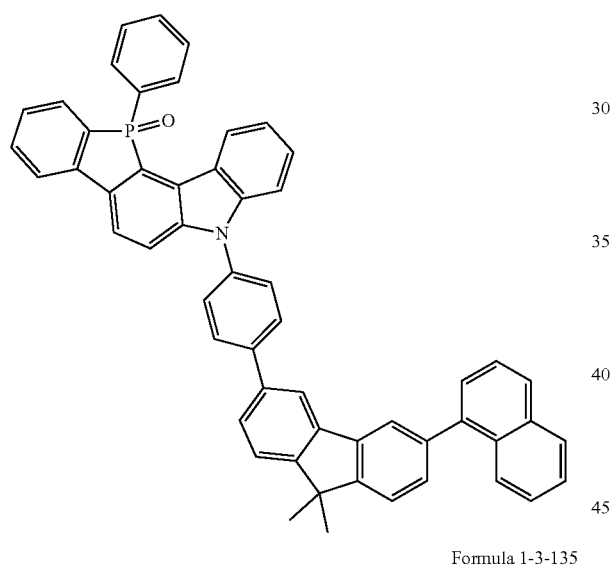
Formula 1-3-135
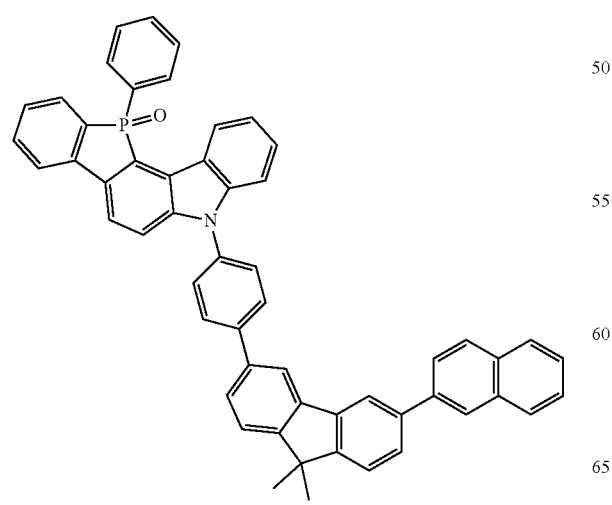
Formula 1-3-137
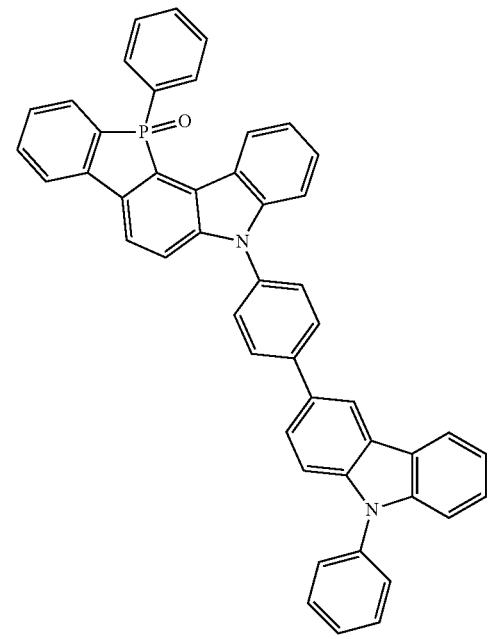

Formula 1-3-138
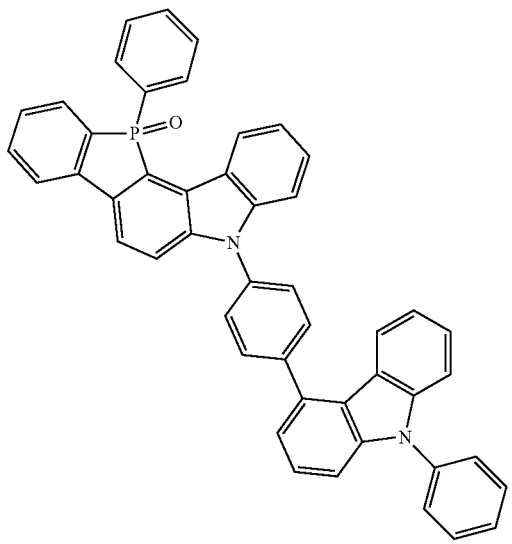
Formula 1-3-139
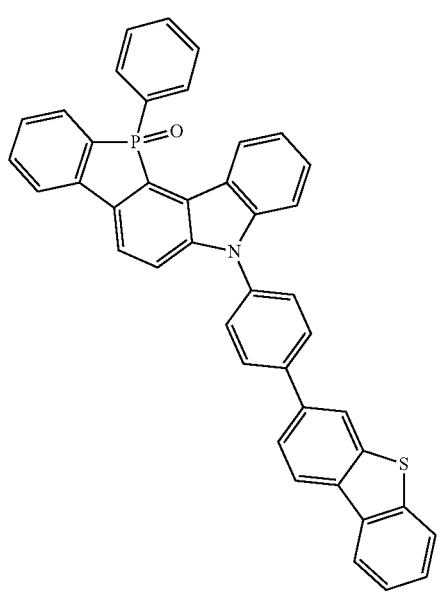
Formula 1-3-140
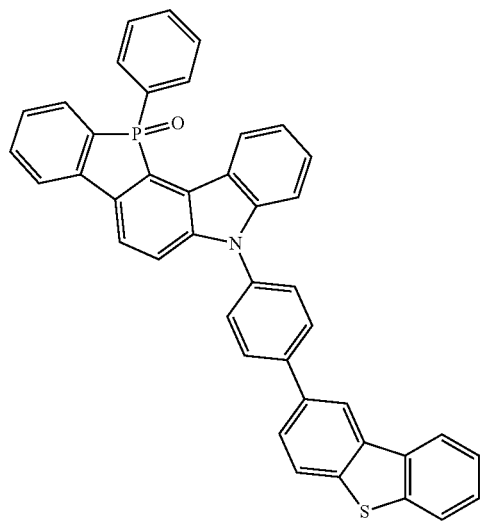
Formula 1-3-141
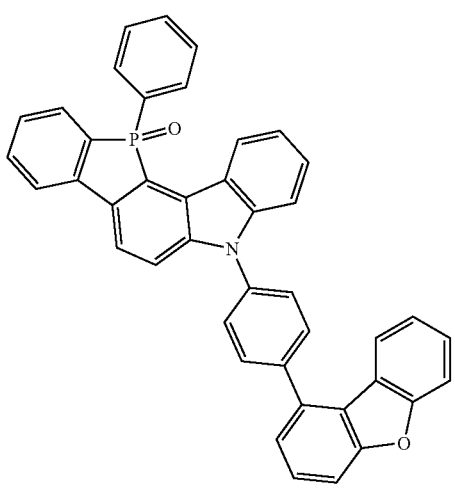
Formula 1-3-142

Formula 1-3-143
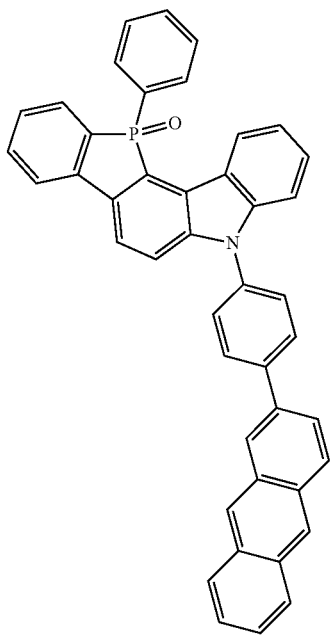
Formula 1-3-145
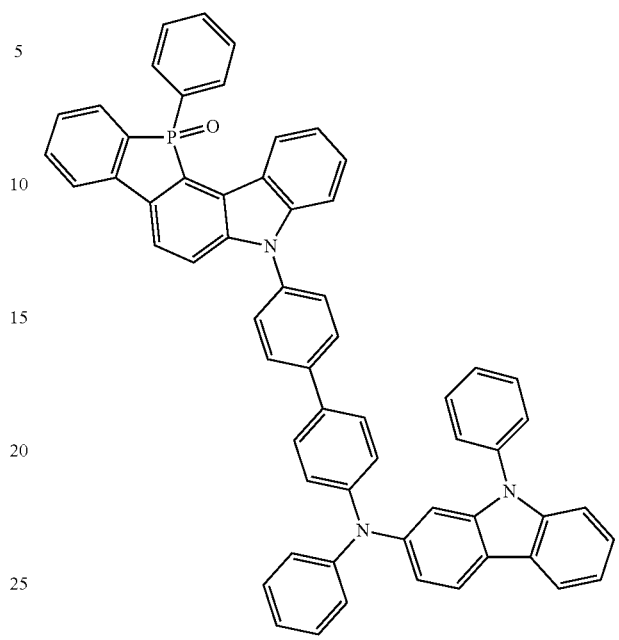
Formula 1-3-144
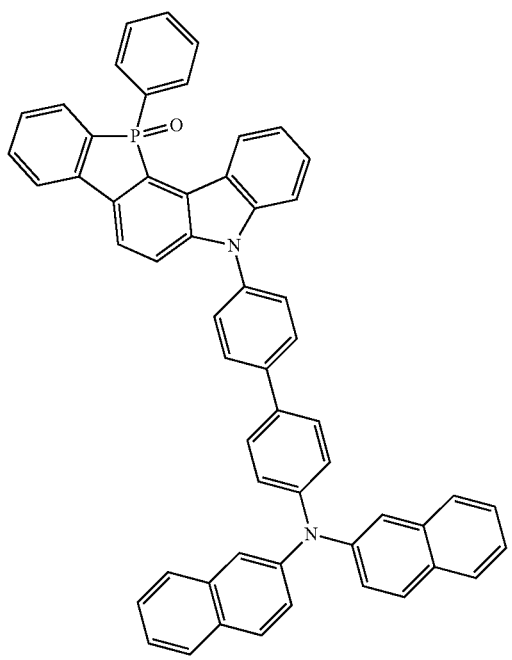
Formula 1-3-146
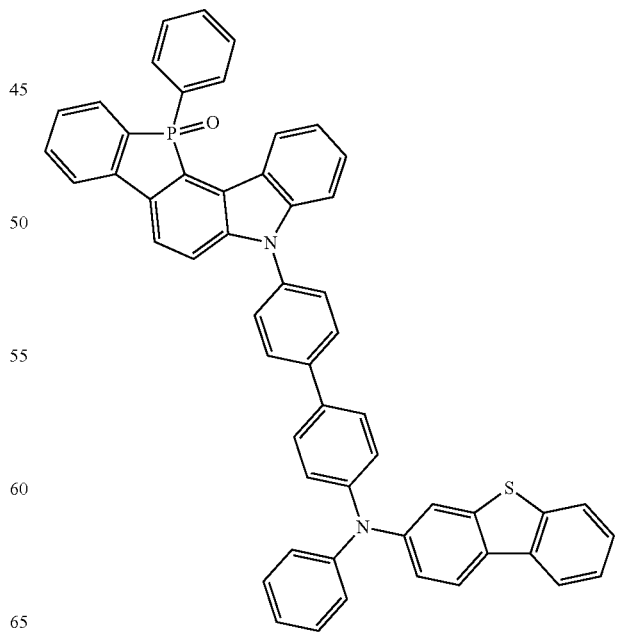

Formula 1-3-147
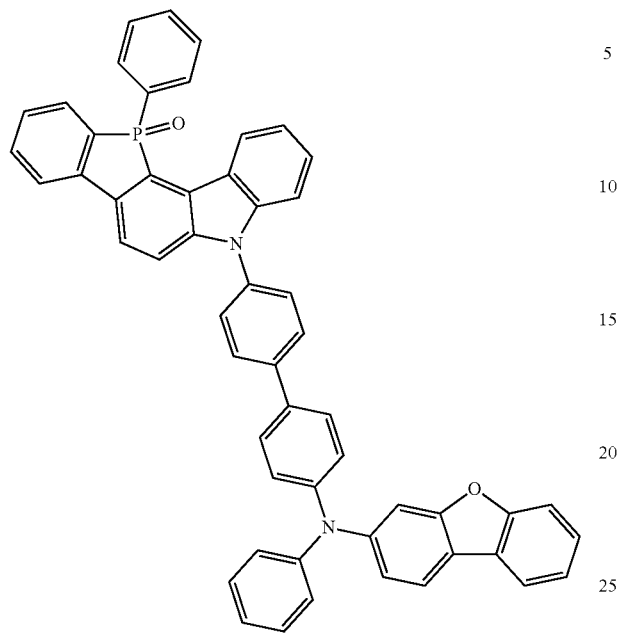
Formula 1-3-148
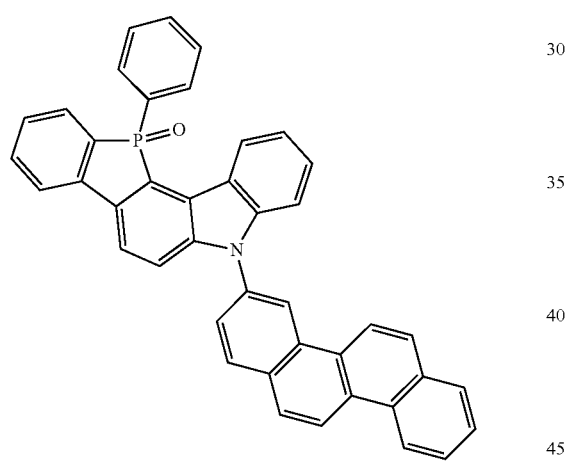
Formula 1-3-149
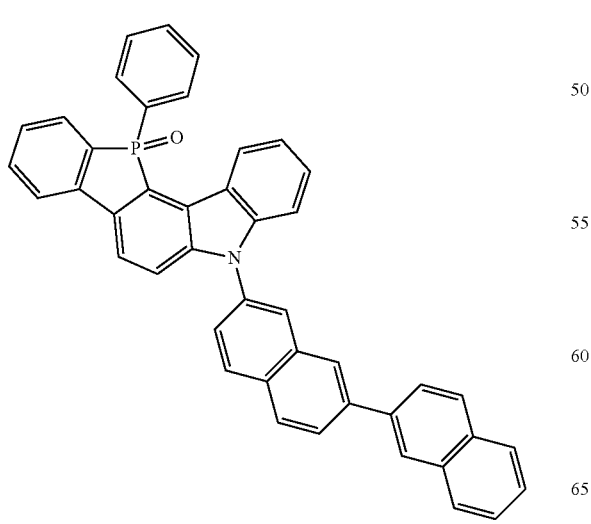
Formula 1-3-150
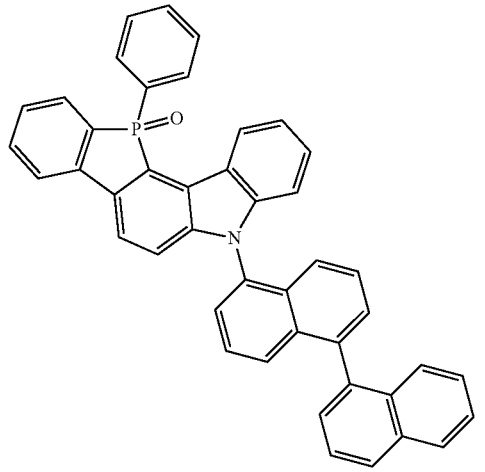
Formula 1-3-151
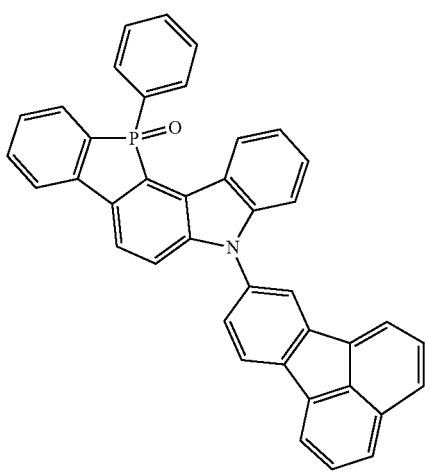
Formula 1-3-152
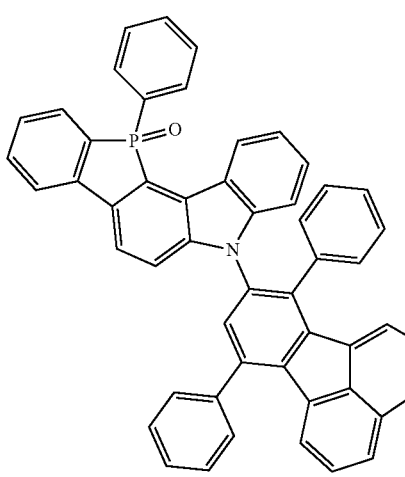

Formula 1-3-153
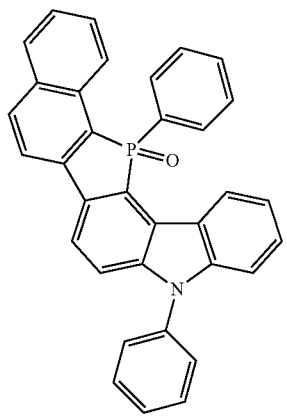
Formula 1-3-154
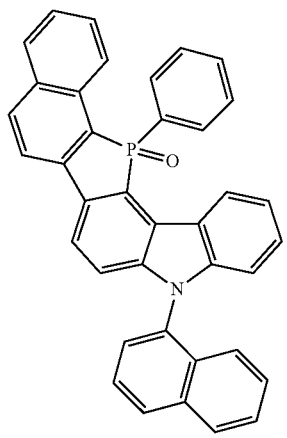
Formula 1-3-155
Formula 1-3-156
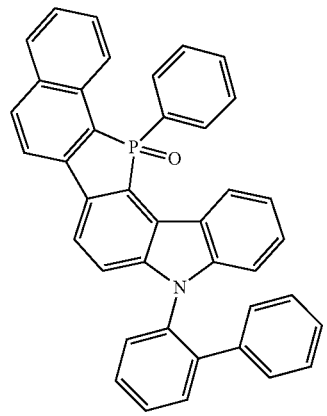
Formula 1-3-157
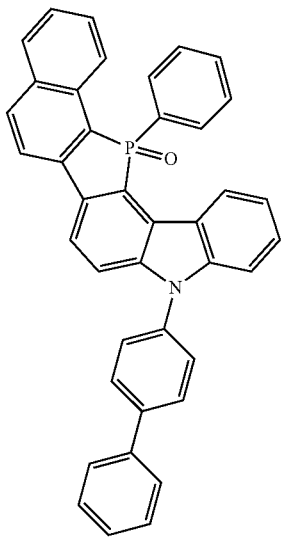
Formula 1-3-158
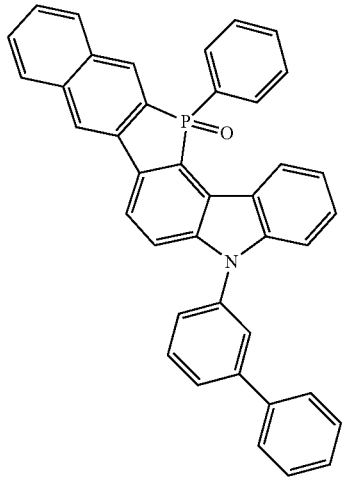

-continued
Formula 1-3-159
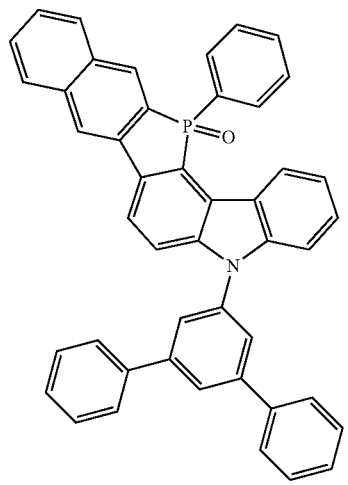
Formula 1-3-160
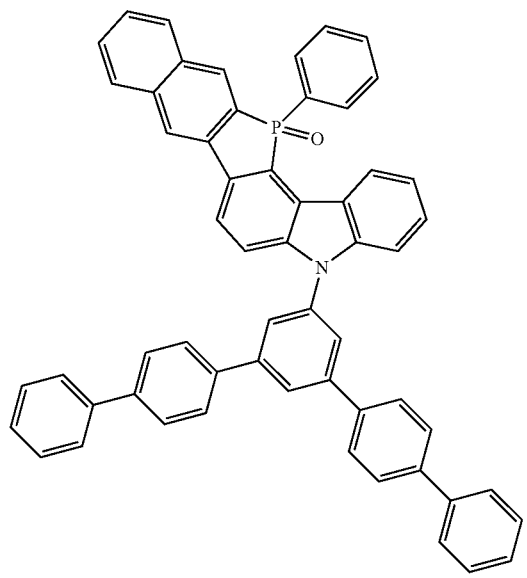
Formula 1-3-161
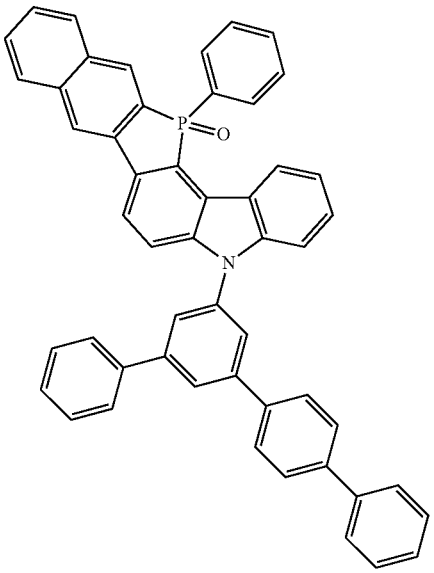
Formula 1-3-162
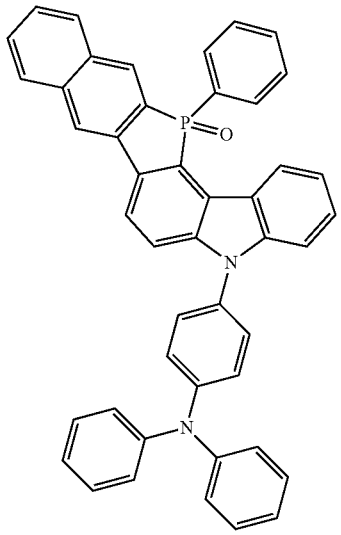

Formula 1-3-163
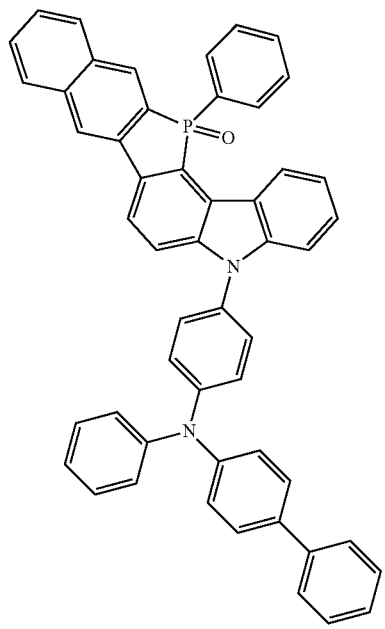
Formula 1-3-164
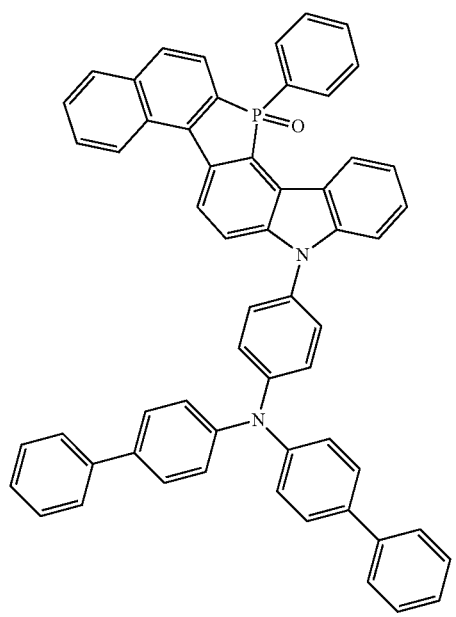
Formula 1-3-165
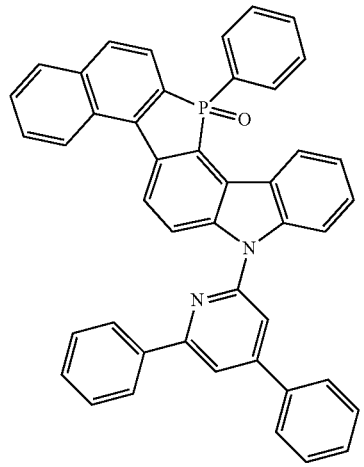
Formula 1-3-166
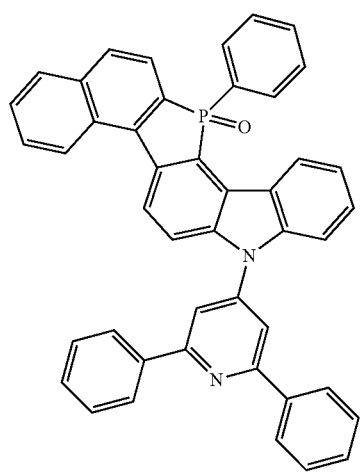
Formula 1-3-167
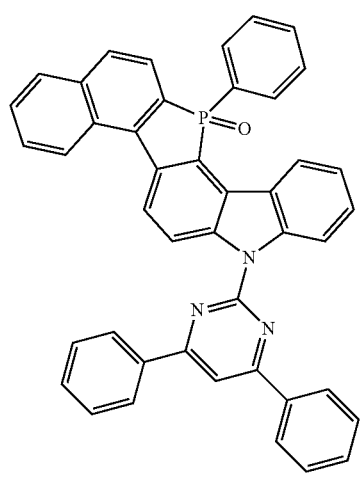

Formula 1-3-168
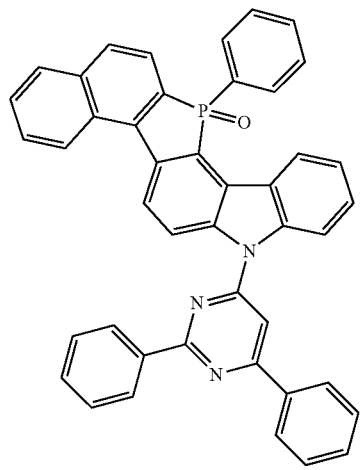
Formula 1-3-169
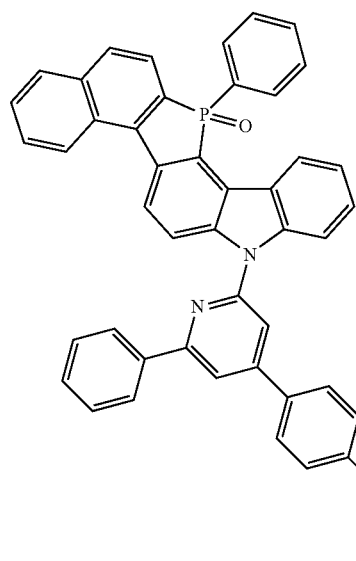
Formula 1-3-170
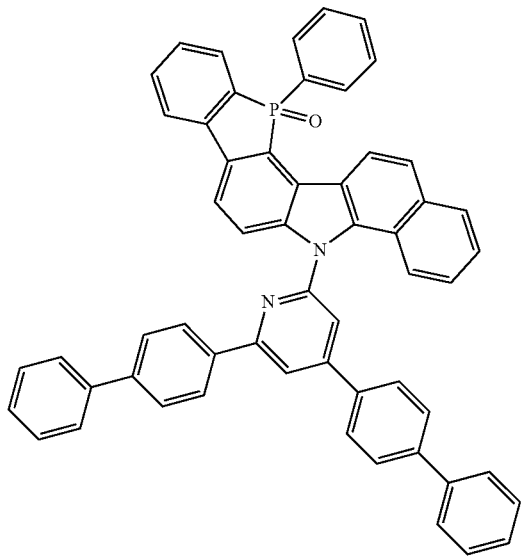
Formula 1-3-171
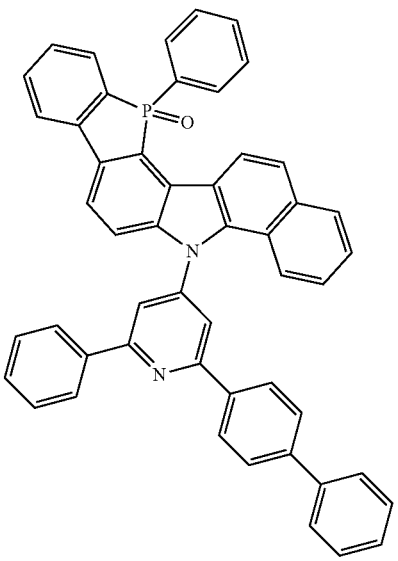
Formula 1-3-172
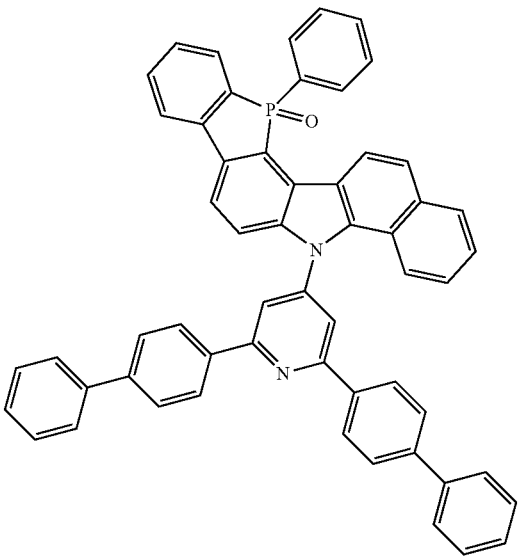

-continued
Formula 1-3-173
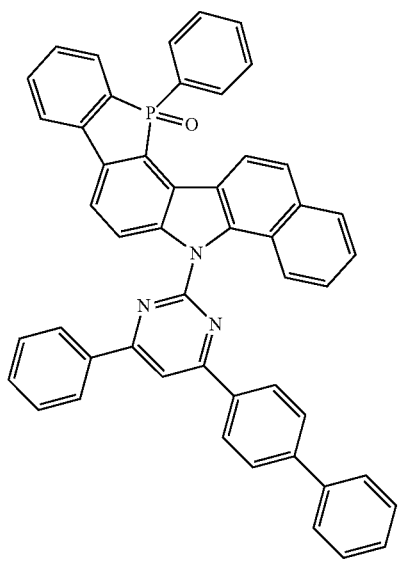
Formula 1-3-174
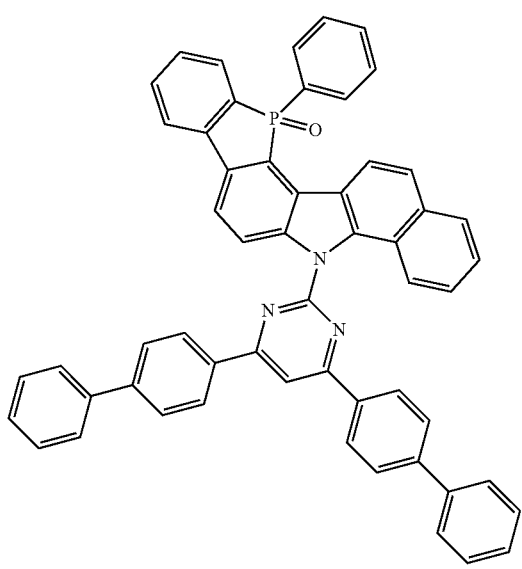
-continued
Formula 1-3-175
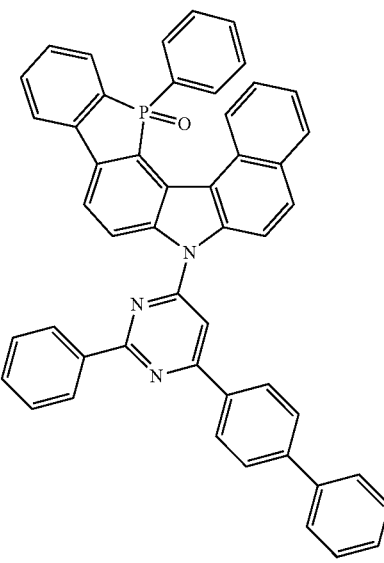
Formula 1-3-176
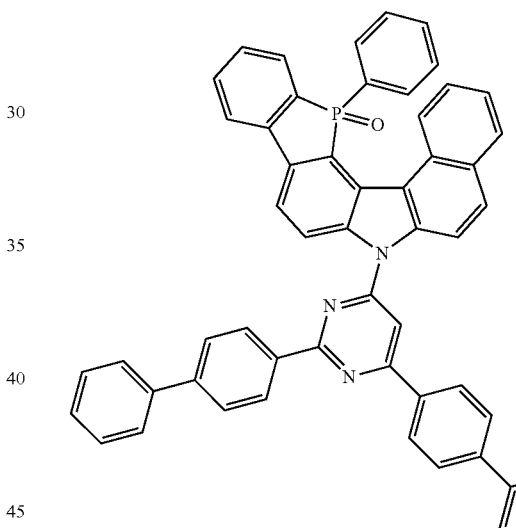
Formula 1-3-177
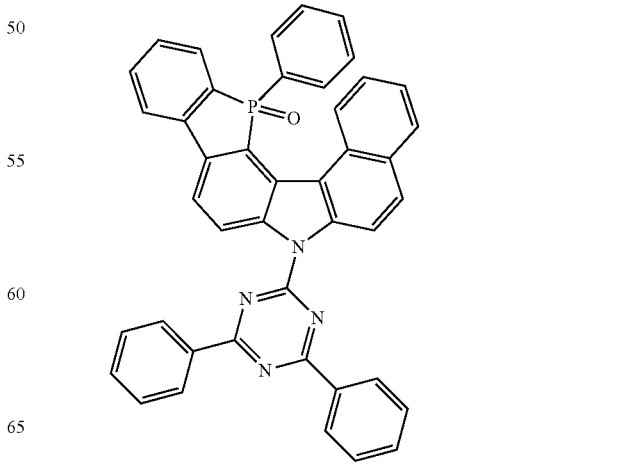

Formula 1-3-178
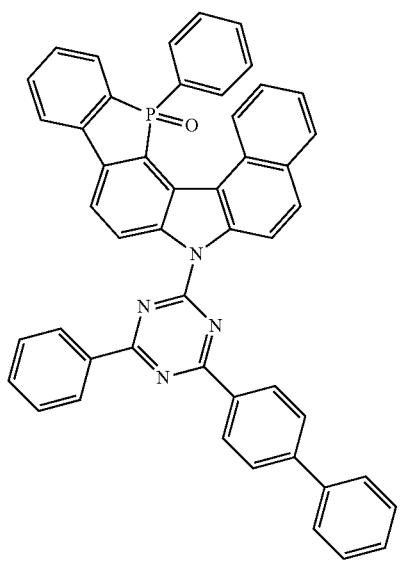
Formula 1-3-179
Formula 1-3-180
Formula 1-3-181
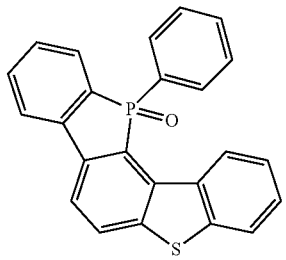
Formula 1-3-182
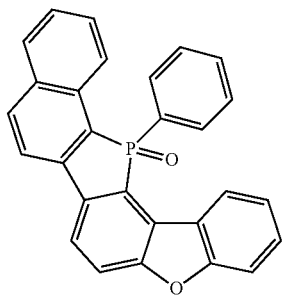
Formula 1-3-183
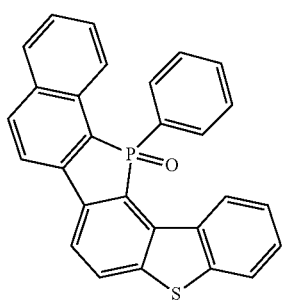
Formula 1-3-184
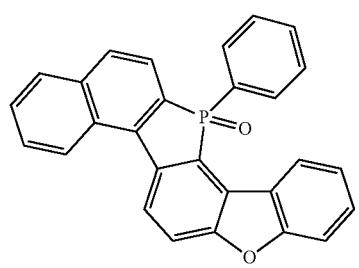
Formula 1-3-185
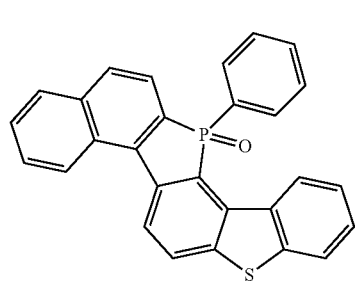

-continued
Formula 1-3-186
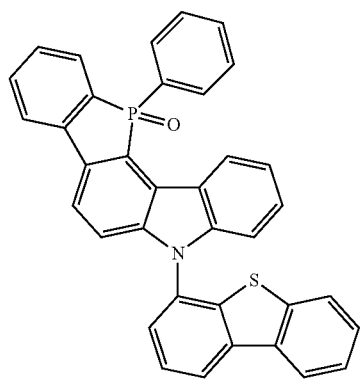
Formula 1-3-187
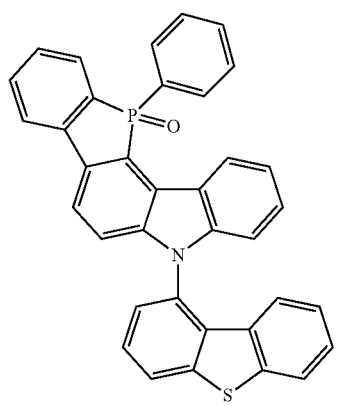
Formula 1-3-188
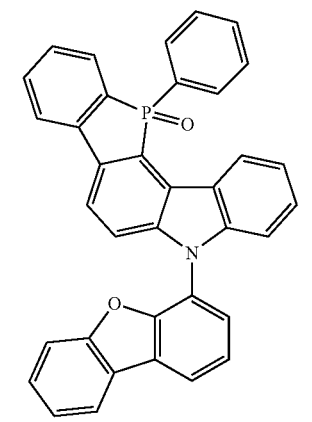
Formula 1-3-189
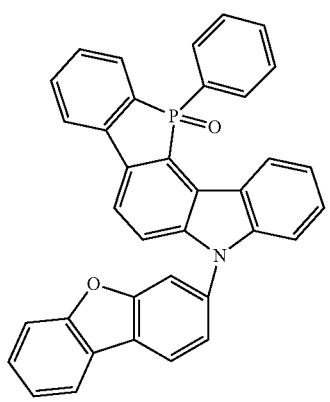
-continued
Formula 1-3-190
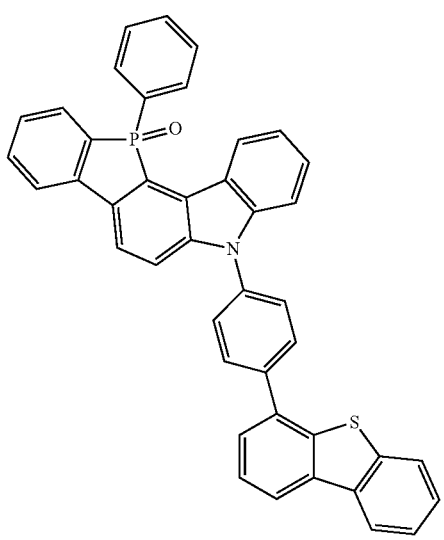
Formula 1-3-191
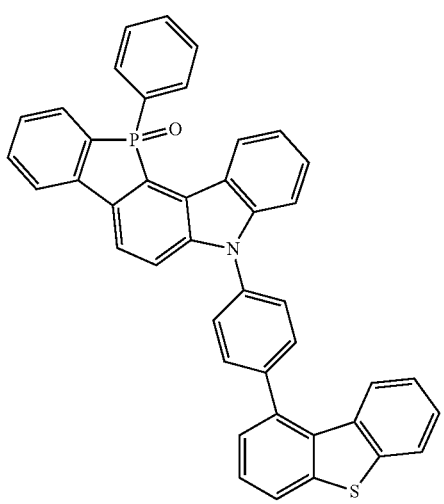
Formula 1-3-192
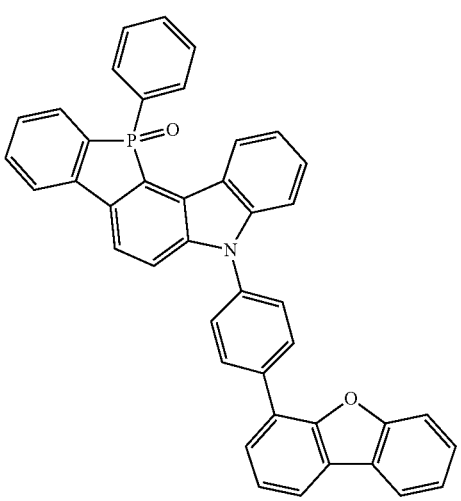

-continued
Formula 1-3-193
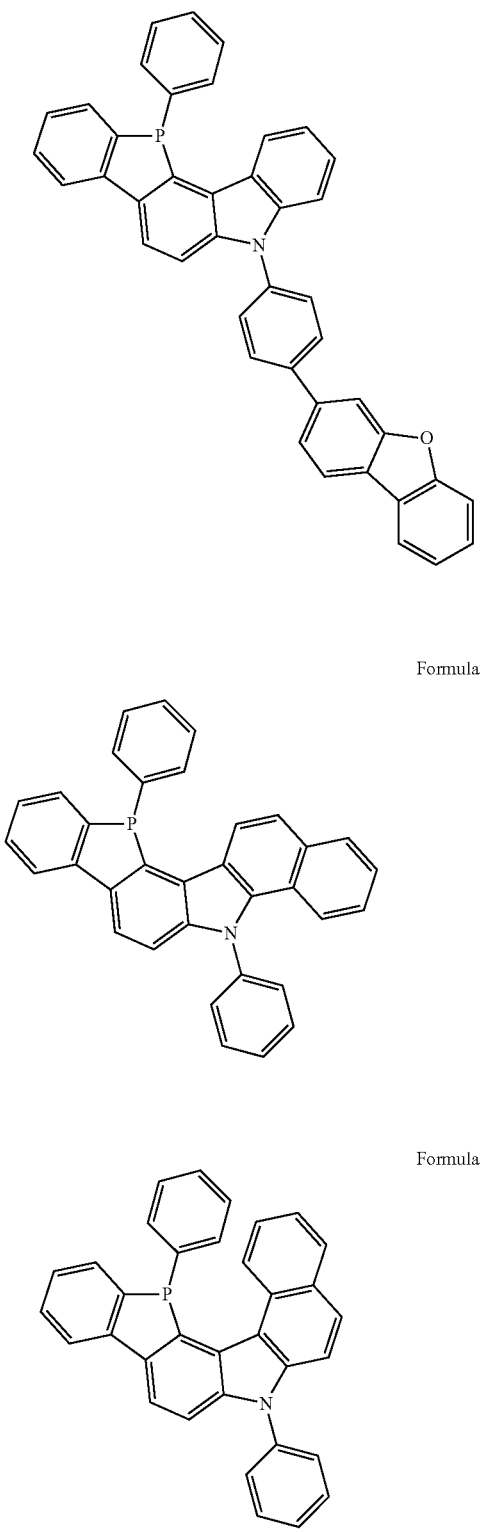
Formula 1-3-194
Formula 1-3-195
Formula 1-4-1
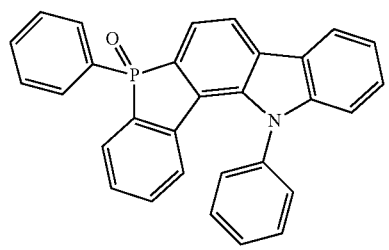
Formula 1-4-2
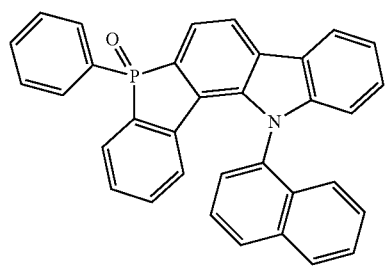
Formula 1-4-3
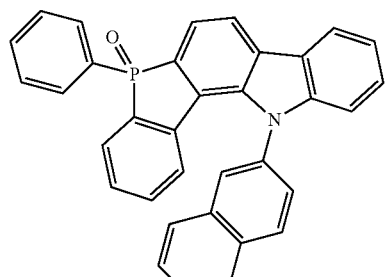
Formula 1-4-4
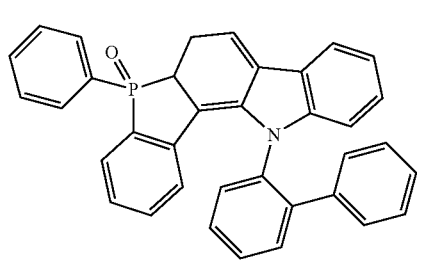
Formula 1-4-5
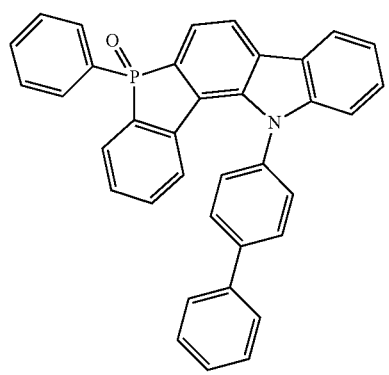
In an exemplary embodiment of the present specification, the compound represented by Formula 1 is represented by Formula 1-4.
In an exemplary embodiment of the present specification, the compound represented by Formula 1-4 is represented by any one of the following Formulae 1-4-195.

Formula 1-4-6
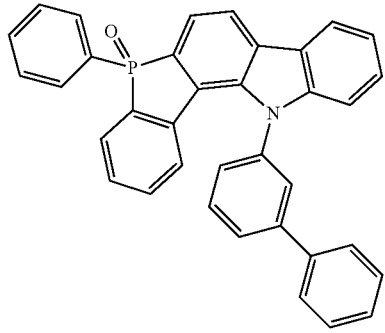
Formula 1-4-7
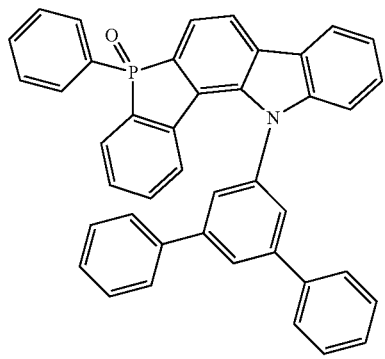
Formula 1-4-8
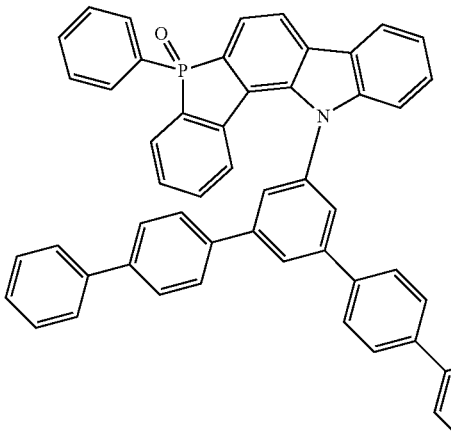
Formula 1-4-9
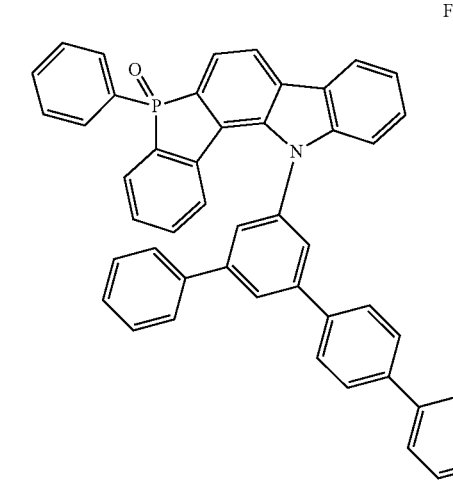
Formula 1-4-10
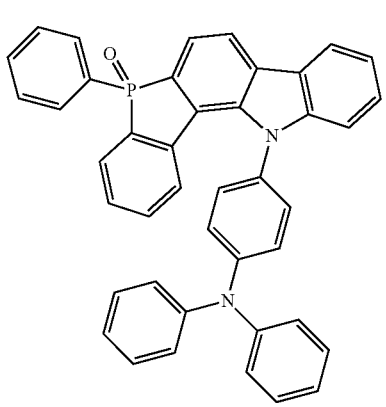
Formula 1-4-11
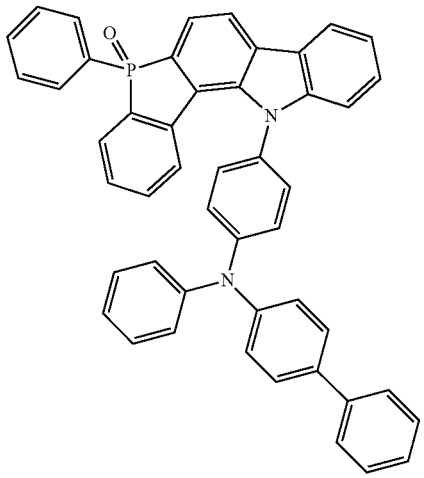
Formula 1-4-12
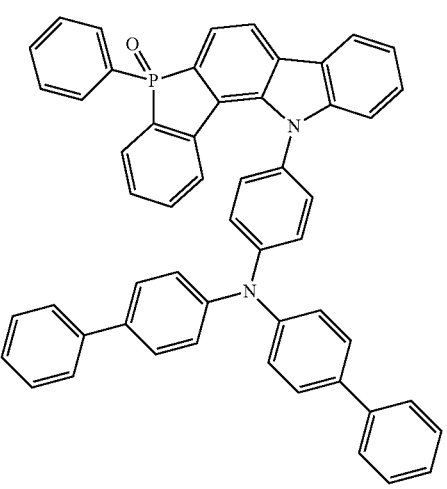

Formula 1-4-13
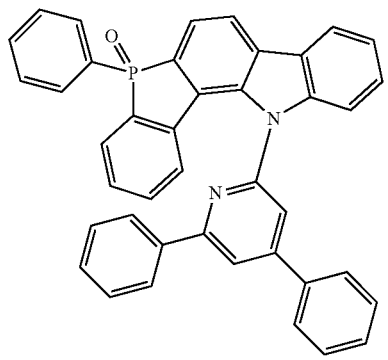
Formula 1-4-14
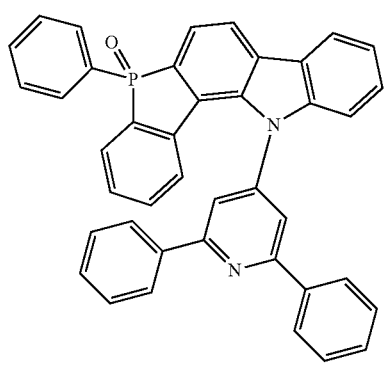
Formula 1-4-15
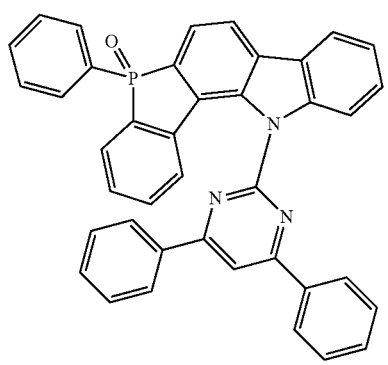
Formula 1-4-16
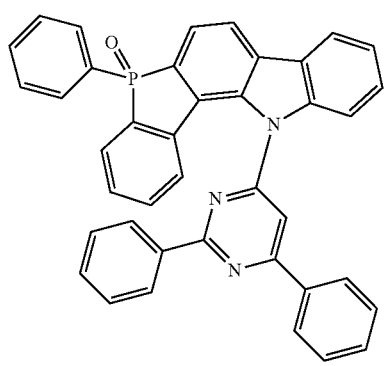
Formula 1-4-17
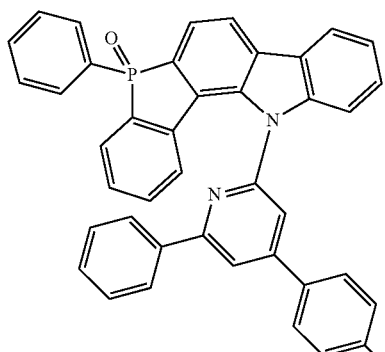
Formula 1-4-18
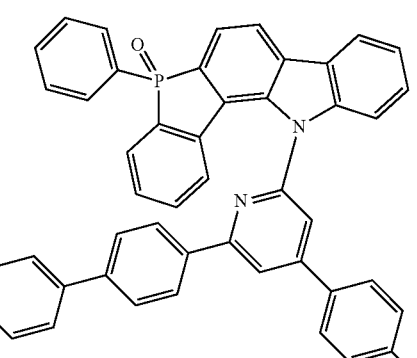
Formula 1-4-19
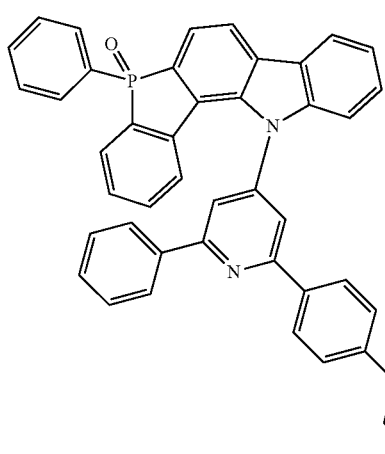

Formula 1-4-20
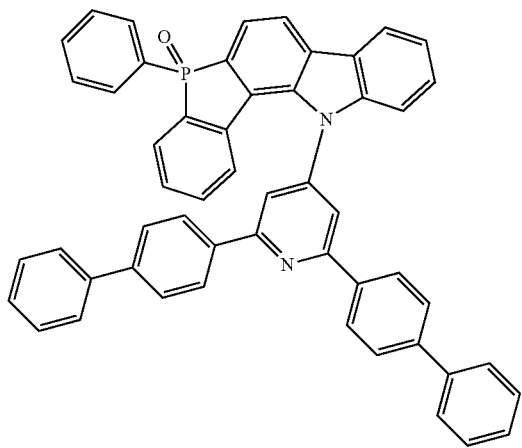
Formula 1-4-23
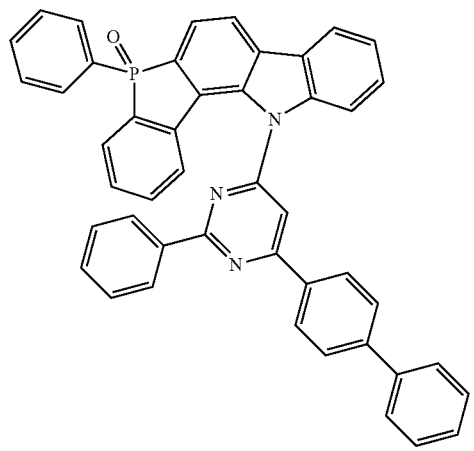
Formula 1-4-21
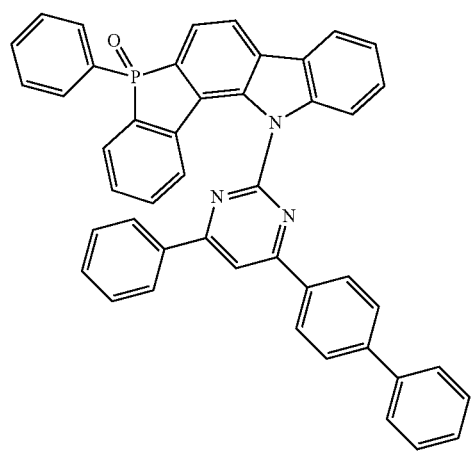
Formula 1-4-24
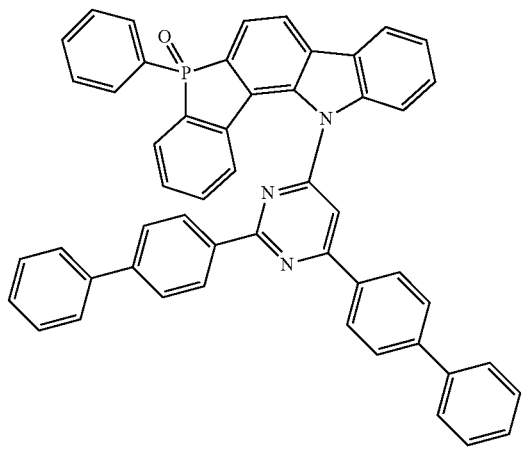
Formula 1-4-22
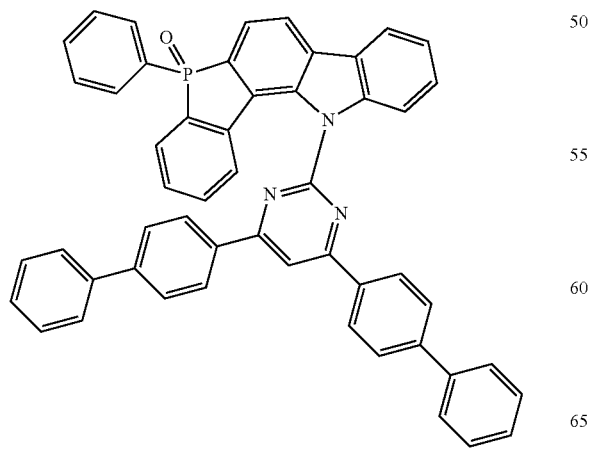
Formula 1-4-25
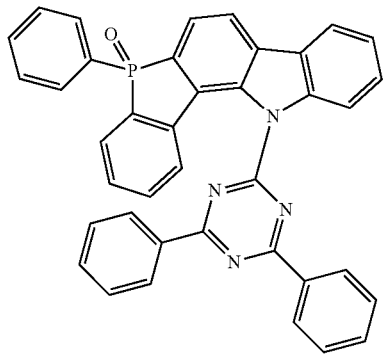

Formula 1-4-26
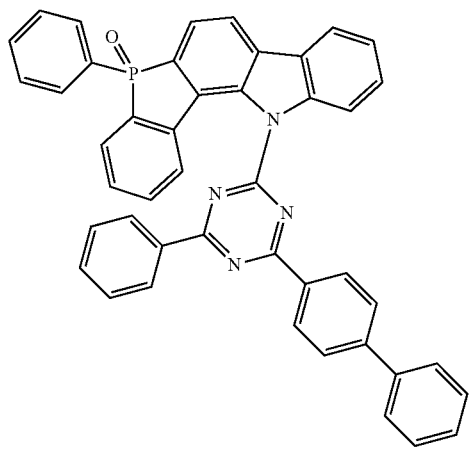
Formula 1-4-27
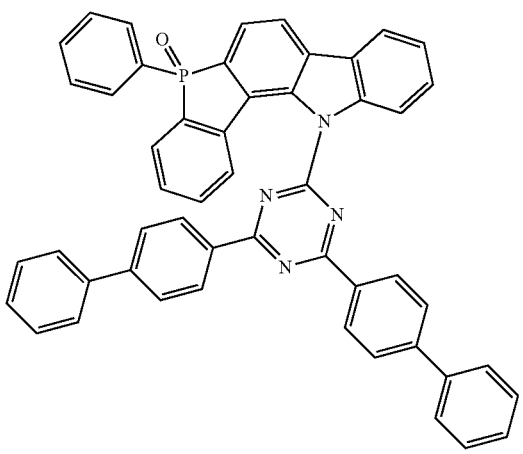
Formula 1-4-28
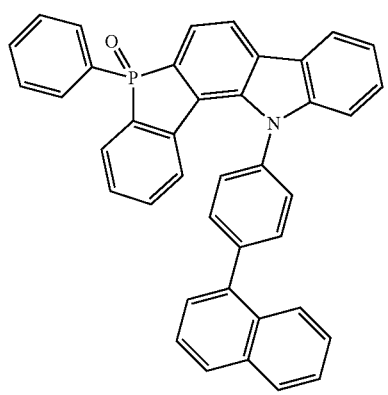
Formula 1-4-29
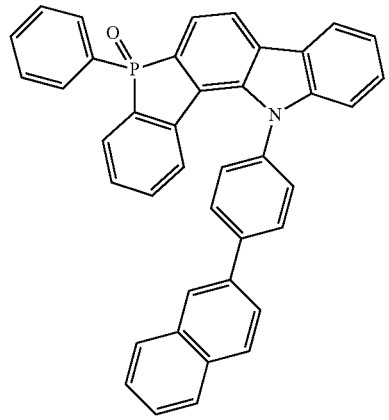
Formula 1-4-30
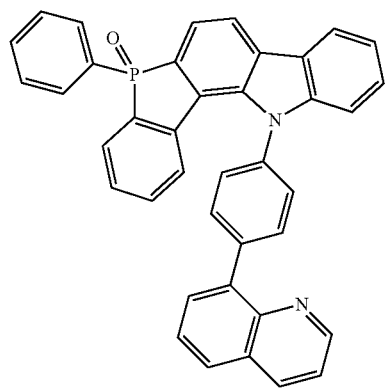
Formula 1-4-31
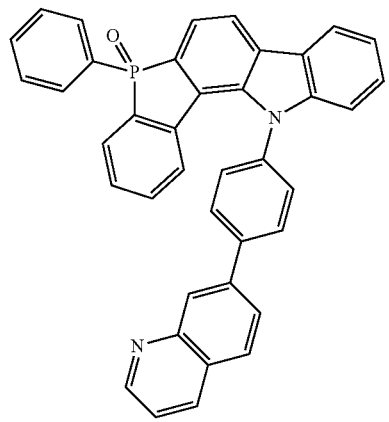
Formula 1-4-32
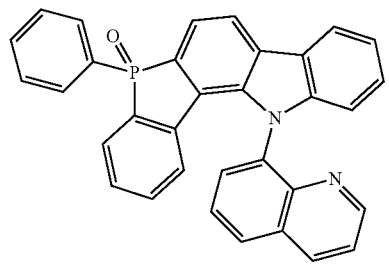

-continued
Formula 1-4-33
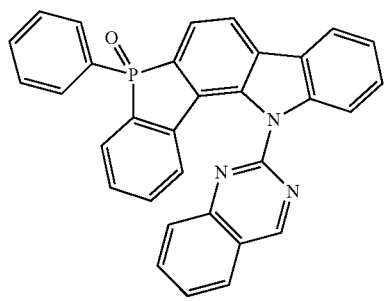
Formula 1-4-34
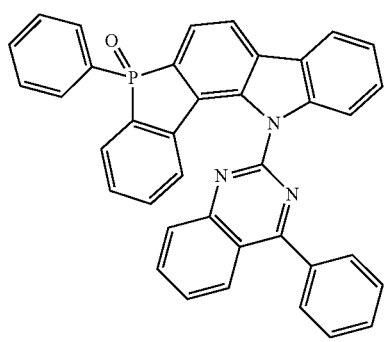
Formula 1-4-35
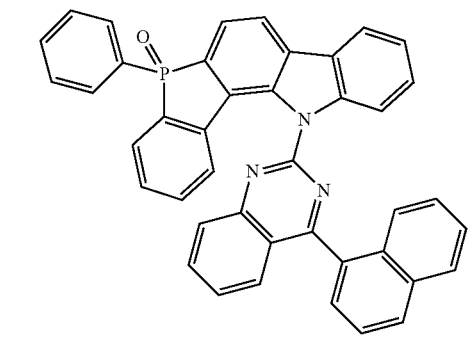
Formula 1-4-36
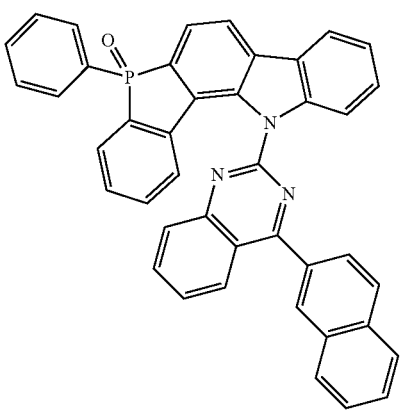
-continued
Formula 1-4-37
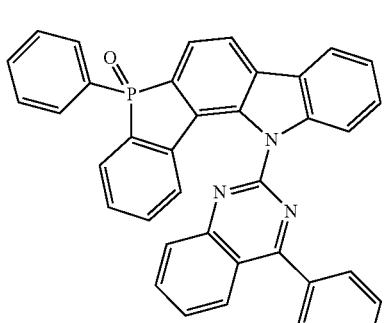
Formula 1-4-38
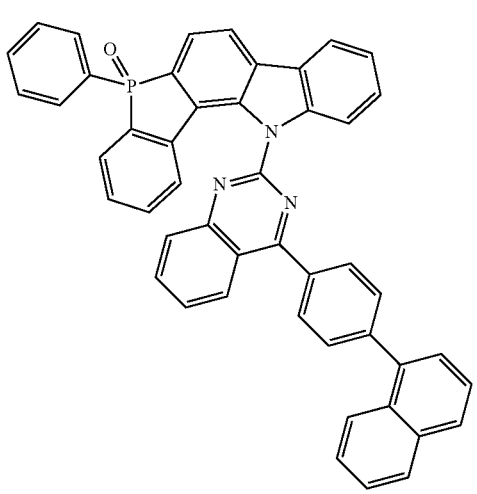
Formula 1-4-39
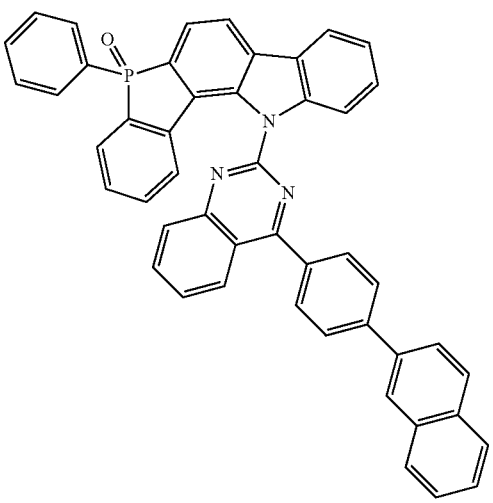

Formula 1-4-40
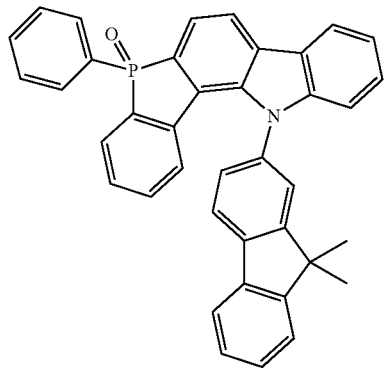
Formula 1-4-41
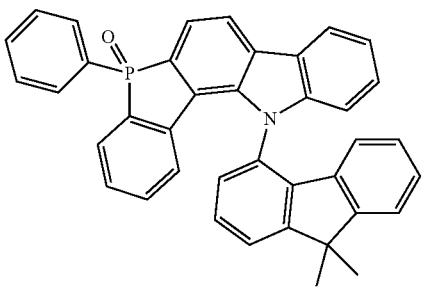
Formula 1-4-42
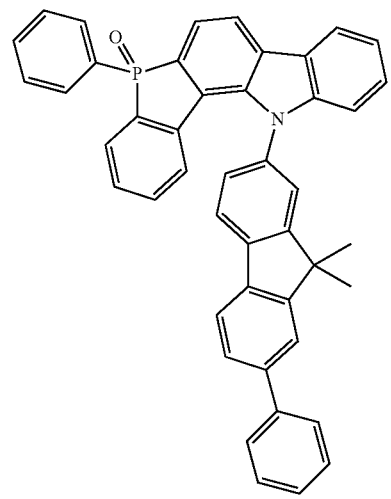
Formula 1-4-43
Formula 1-4-44
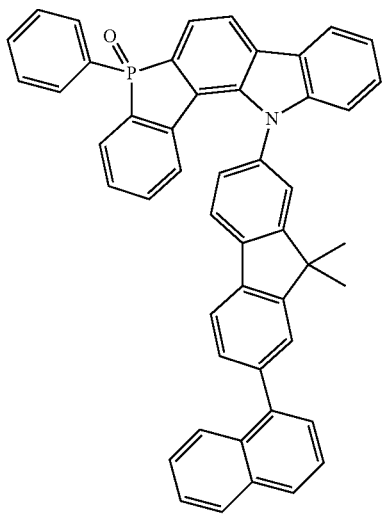
Formula 1-4-45
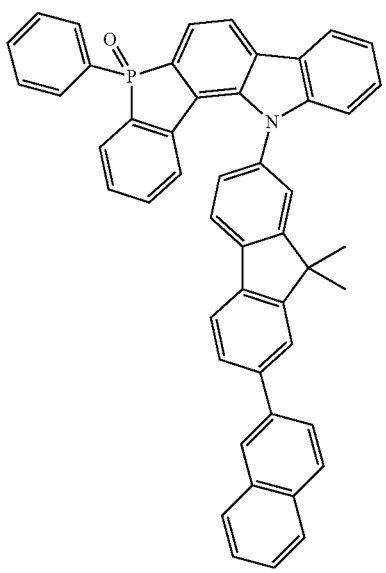
Formula 1-4-46
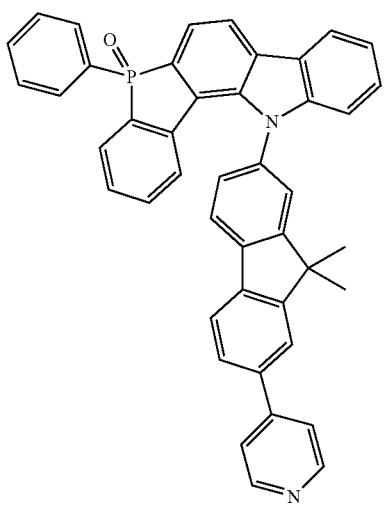

Formula 1-4-47
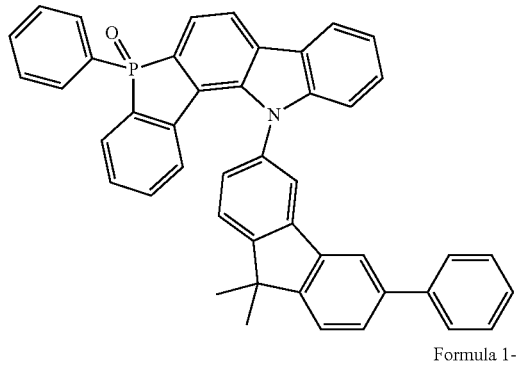
Formula 1-4-48
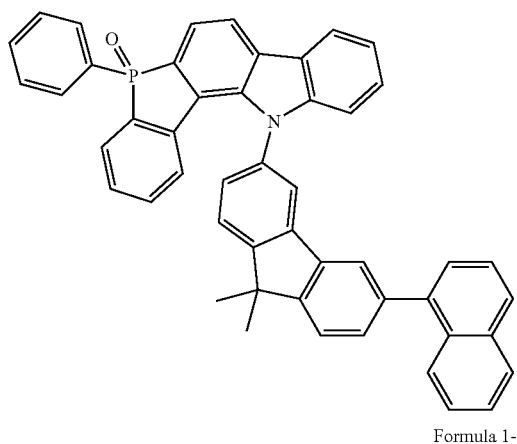
Formula 1-4-49
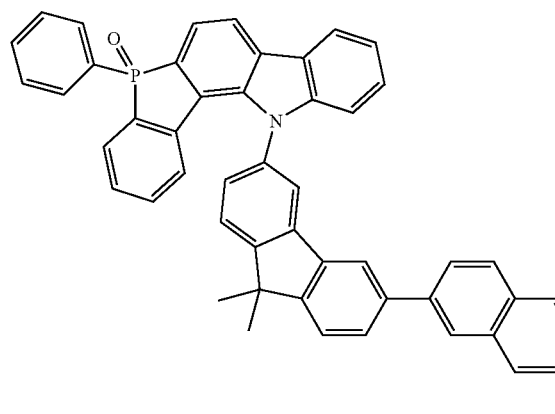
Formula 1-4-50
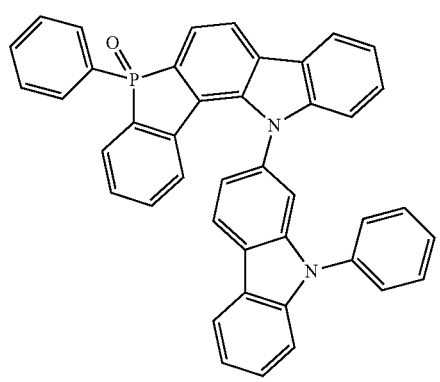
Formula 1-4-51
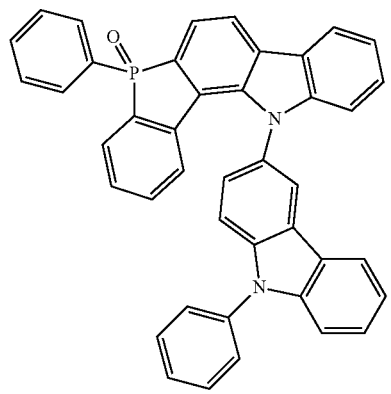
Formula 1-4-52
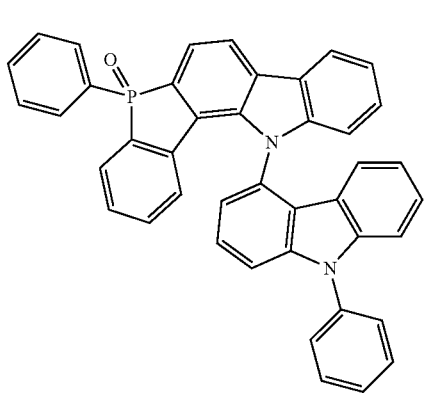
Formula 1-4-53
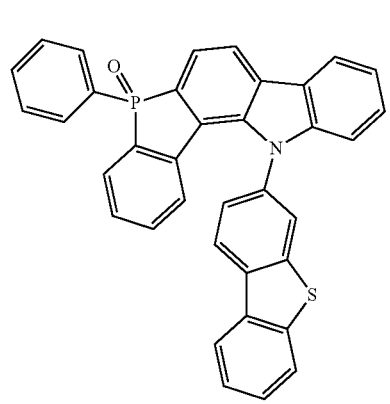
Formula 1-4-54
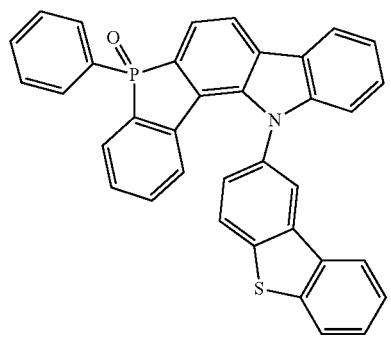

Formula 1-4-55
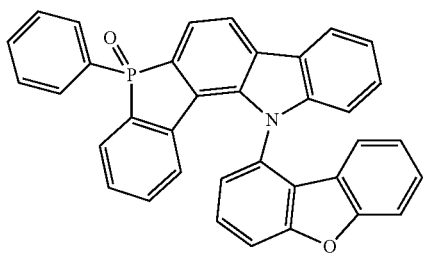
Formula 1-4-56
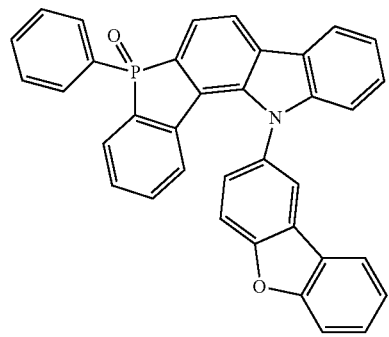
Formula 1-4-57
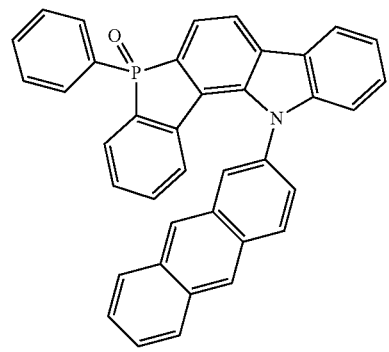
Formula 1-4-58
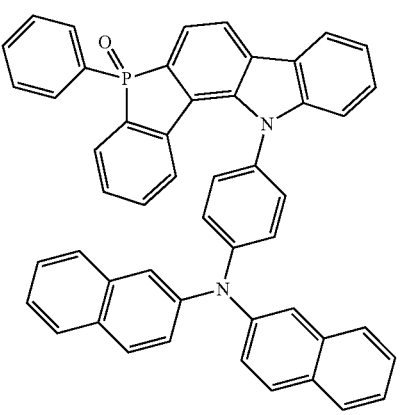
Formula 1-4-59
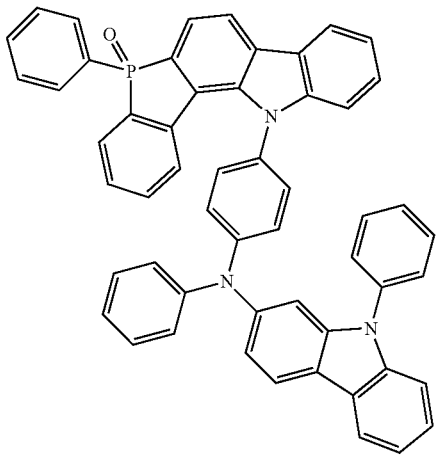
Formula 1-4-60
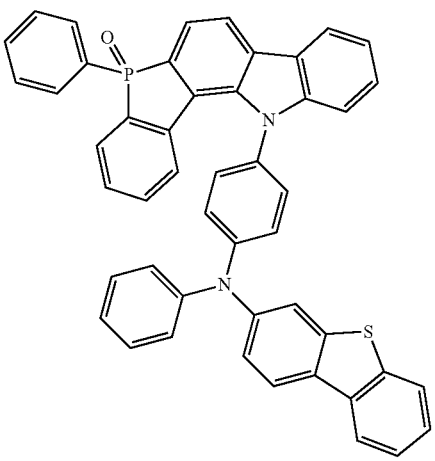
Formula 1-4-61
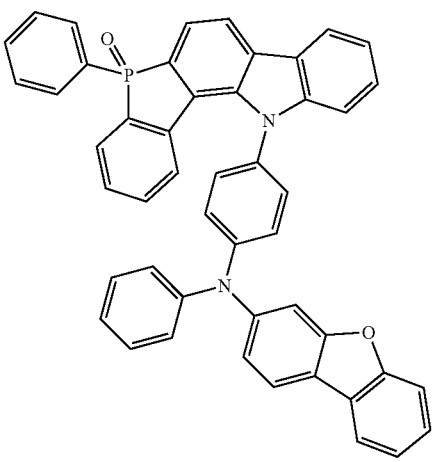

Formula 1-4-62
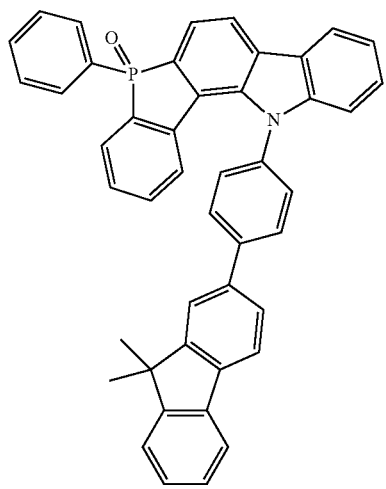
Formula 1-4-63
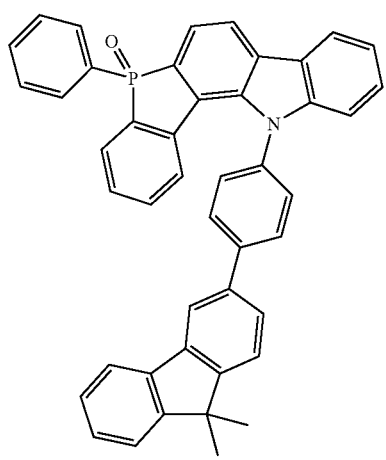
Formula 1-4-64
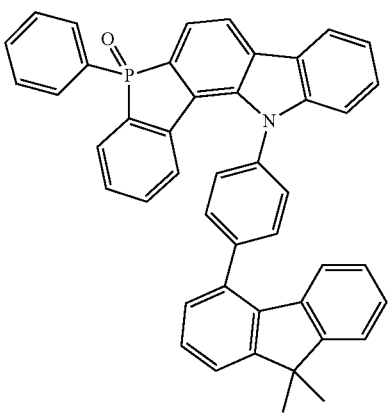
Formula 1-4-65
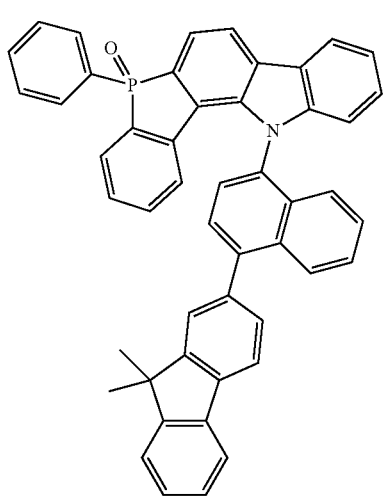
Formula 1-4-66
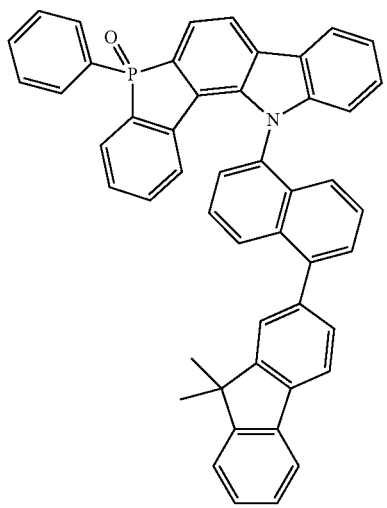
Formula 1-4-67
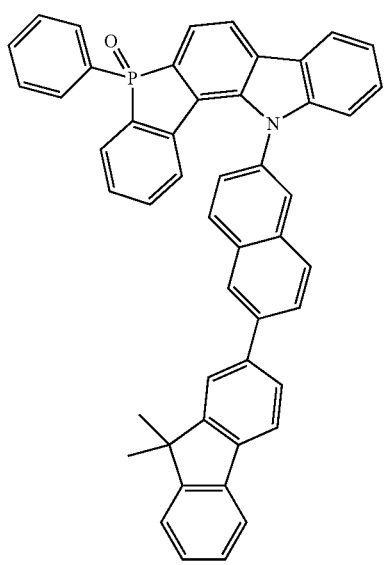

Formula 1-4-68
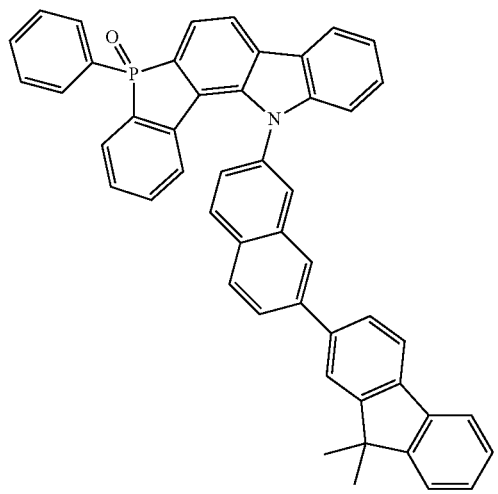
Formula 1-4-69
Formula 1-4-70
Formula 1-4-71
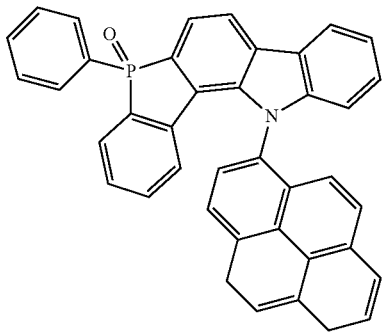
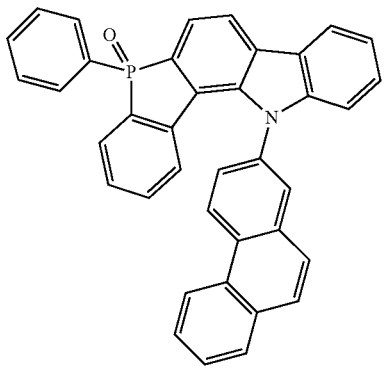
Formula 1-4-72
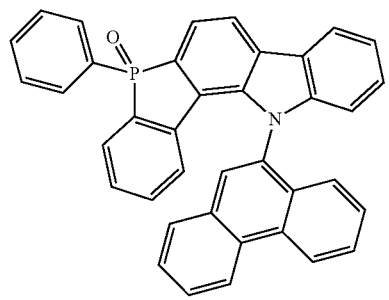
Formula 1-4-73
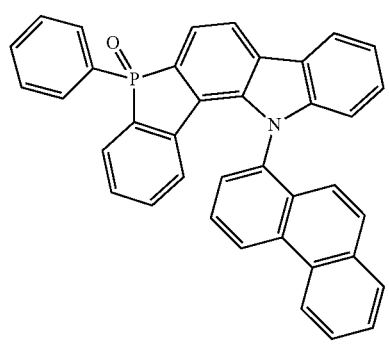
Formula 1-4-74
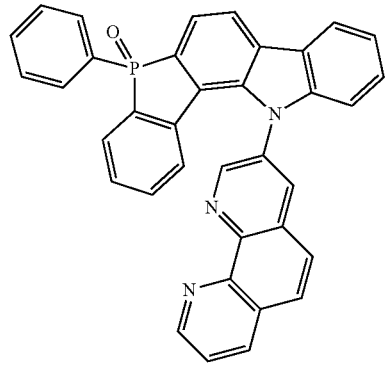
Formula 1-4-75
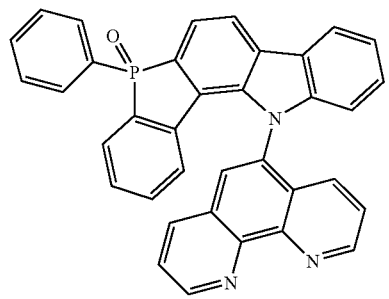

-continued
Formula 1-4-76
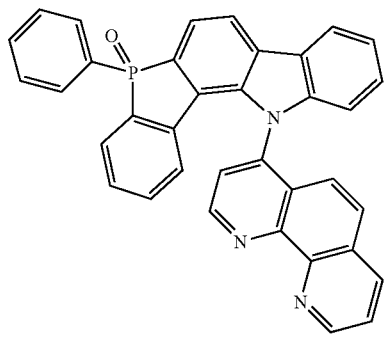
Formula 1-4-77
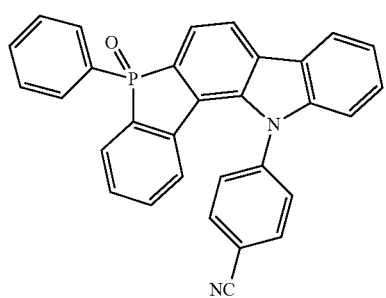
Formula 1-4-78
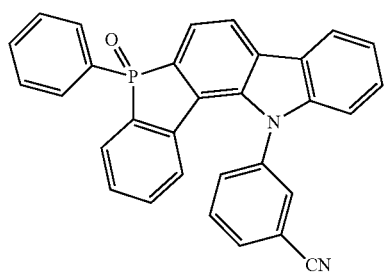
Formula 1-4-79
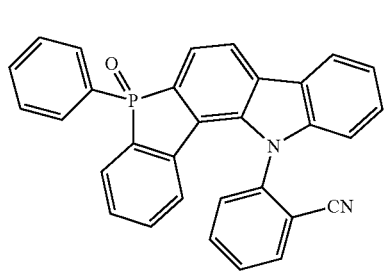
Formula 1-4-80
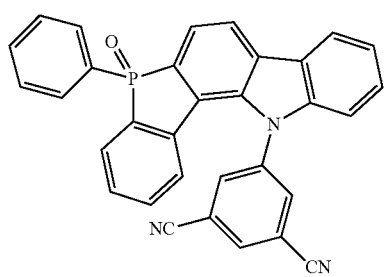
-continued
Formula 1-4-81
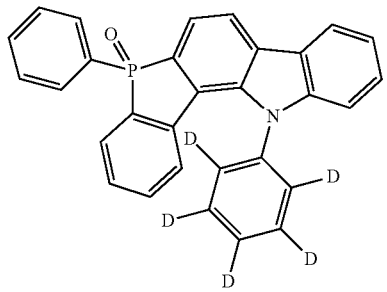
Formula 1-4-82
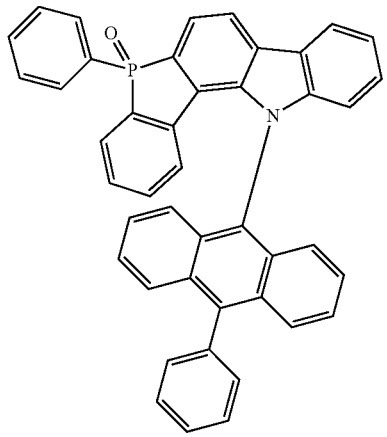
Formula 1-4-83
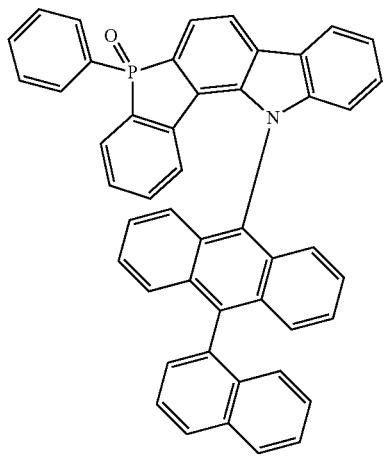

Formula 1-4-84
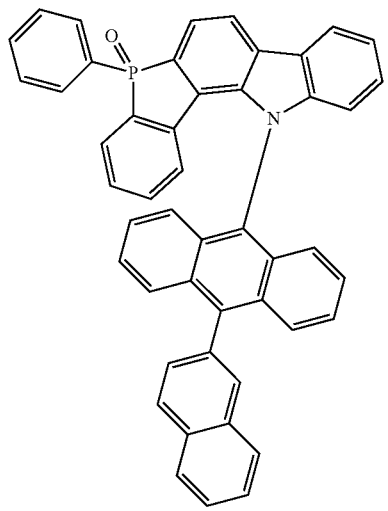
Formula 1-4-85
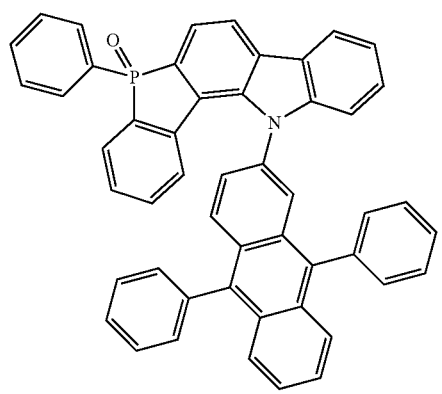
Formula 1-4-86
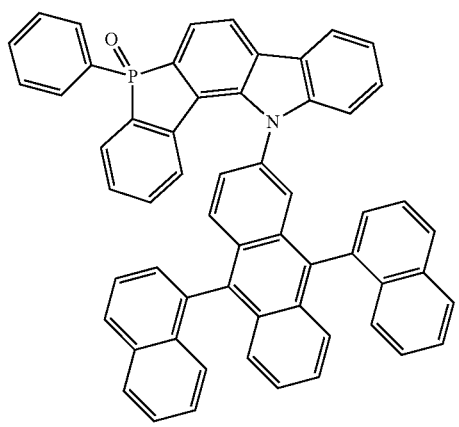
Formula 1-4-87
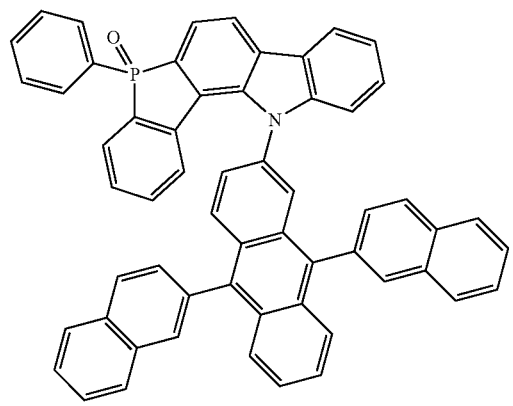
Formula 1-4-88
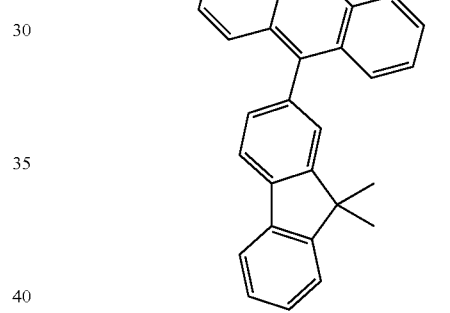
Formula 1-4-89
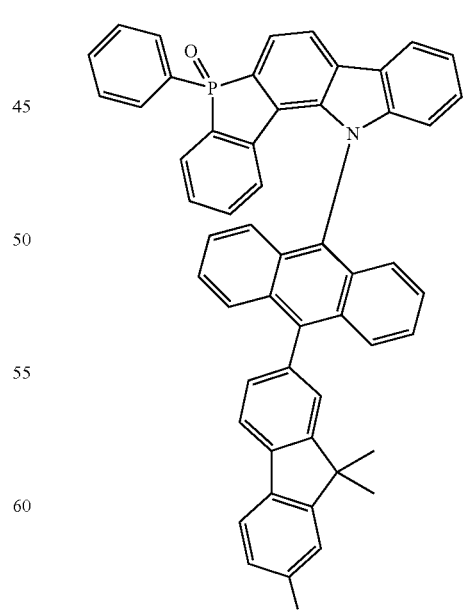

Formula 1-4-90
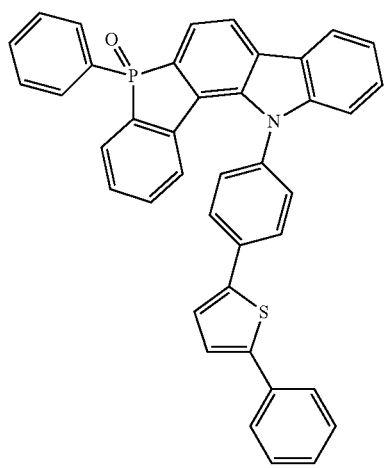
Formula 1-4-93
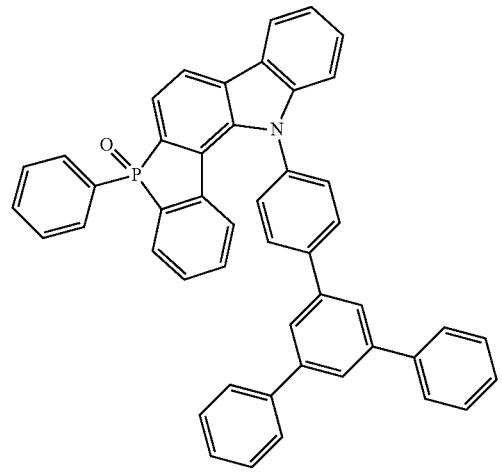
Formula 1-4-91
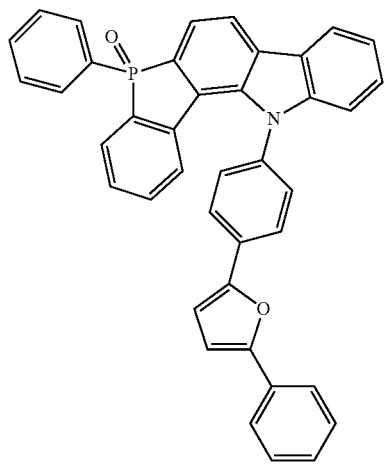
Formula 1-4-94
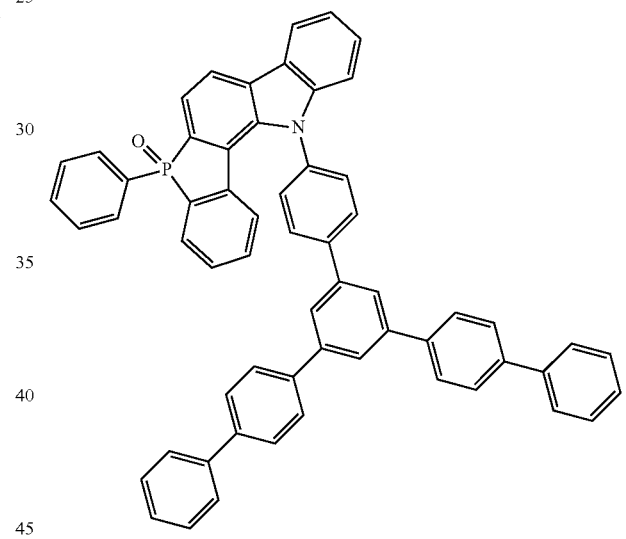
Formula 1-4-92
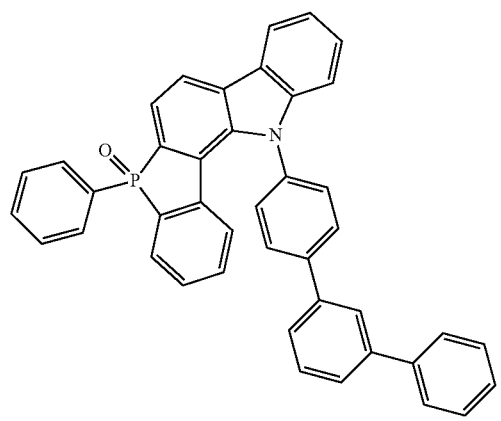
Formula 1-4-95
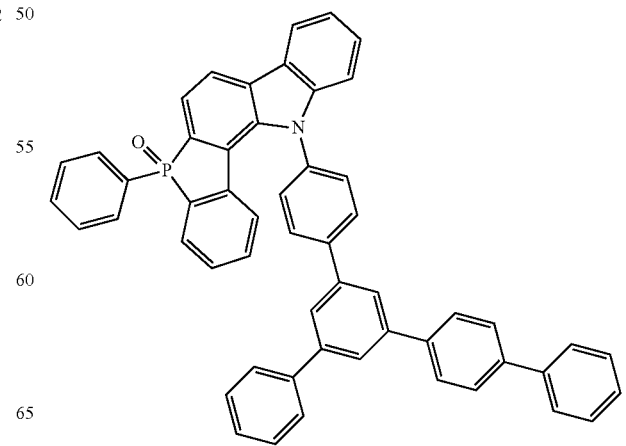

Formula 1-4-96
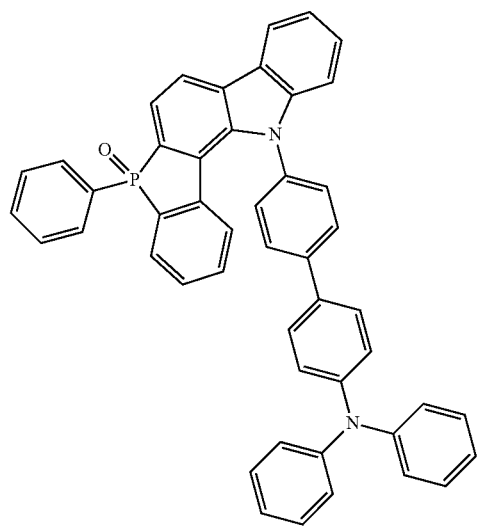
Formula 1-4-98
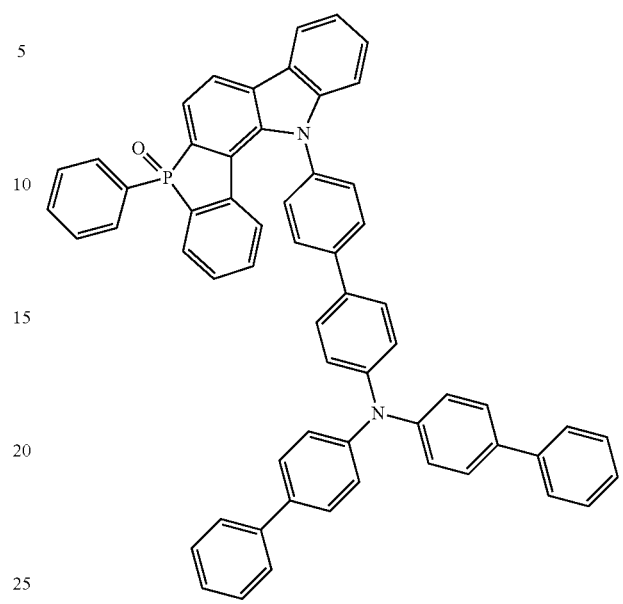
Formula 1-4-99
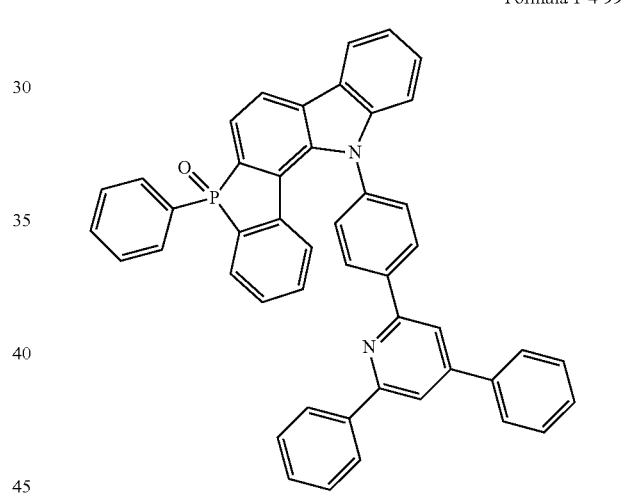
Formula 1-4-97
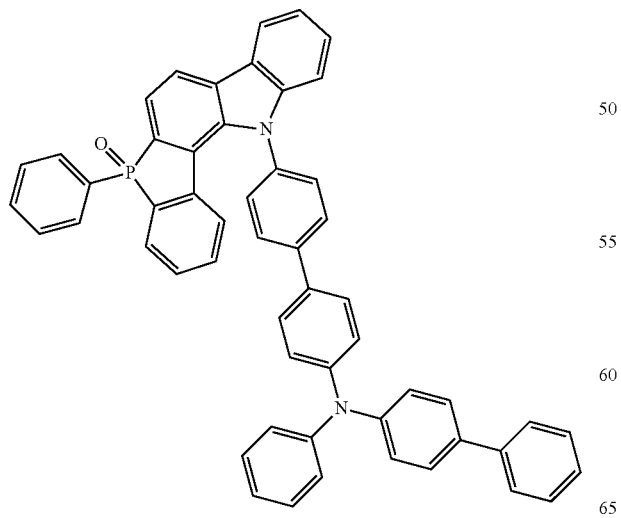
Formula 1-4-100

Formula 1-4-101
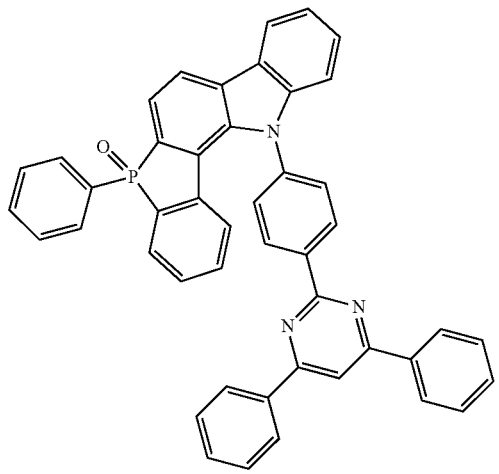
Formula 1-4-104
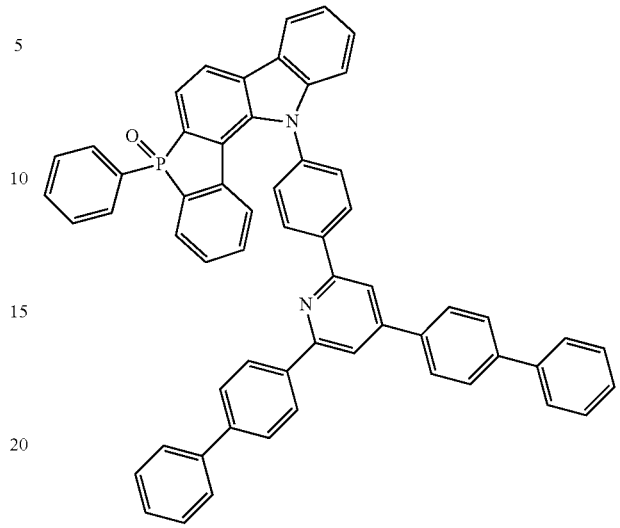
Formula 1-4-102
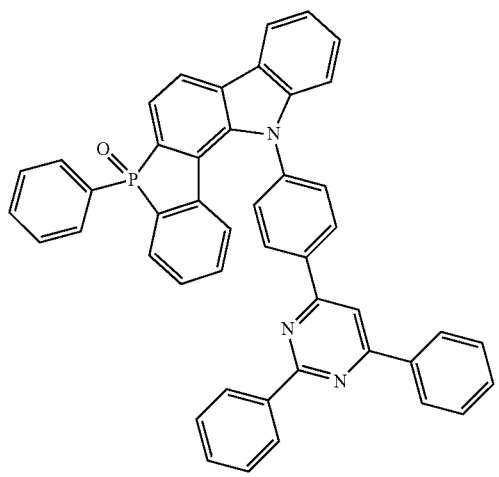
Formula 1-4-105
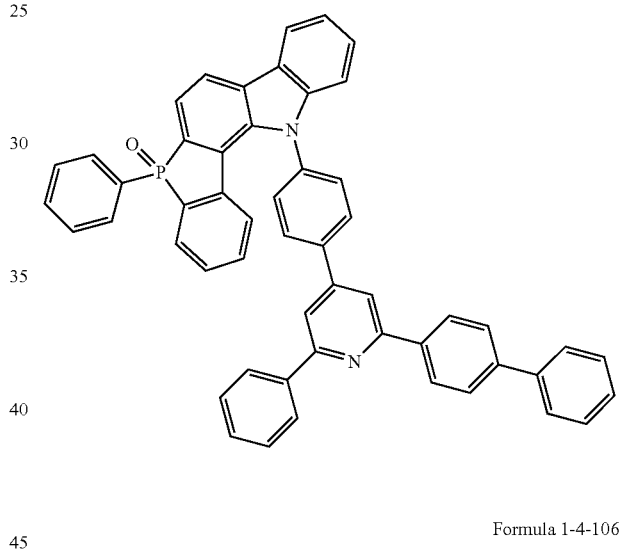
Formula 1-4-103
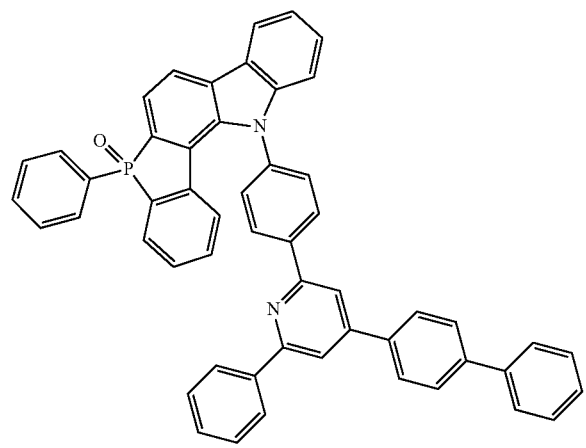
Formula 1-4-106
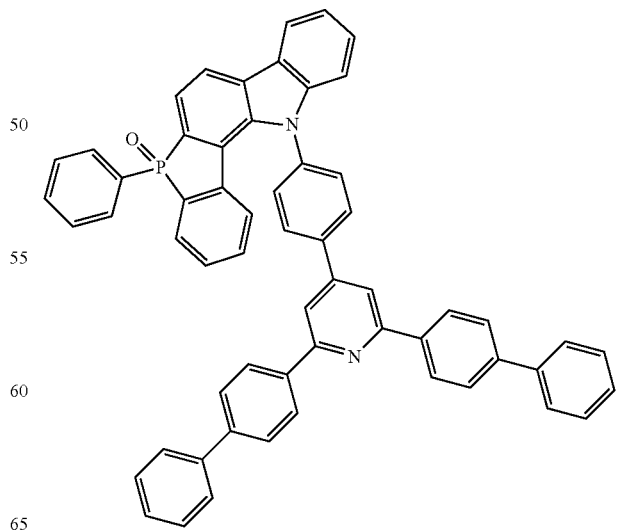

Formula 1-4-107
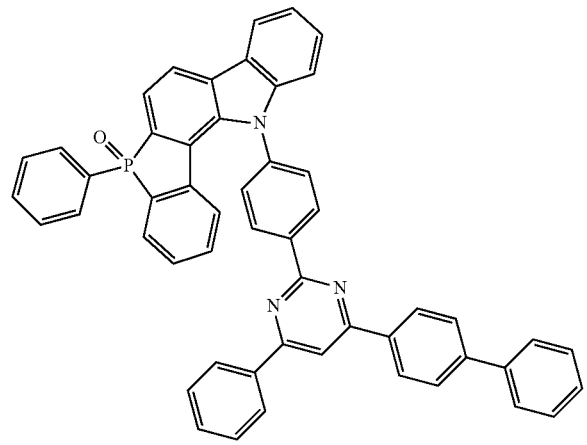
Formula 1-4-108
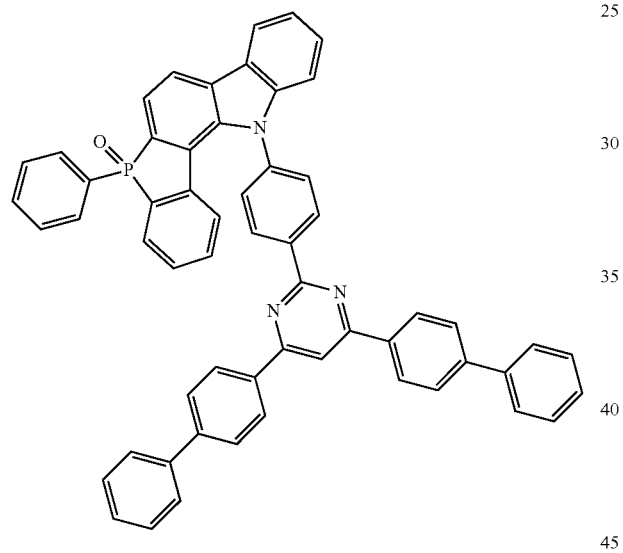
Formula 1-4-109
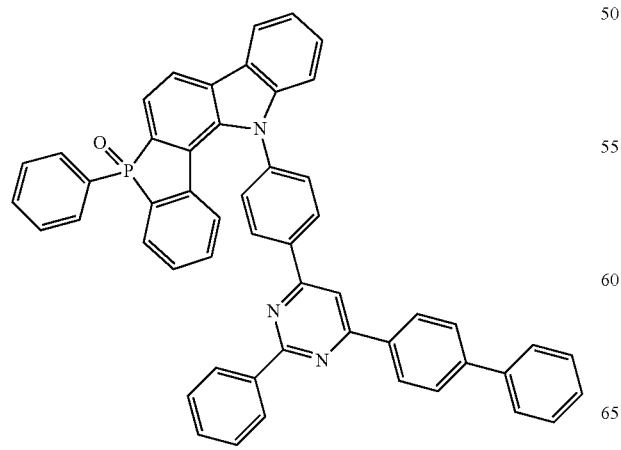
Formula 1-4-110
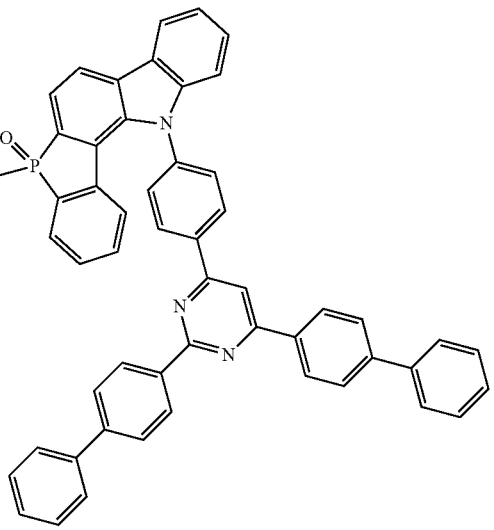
Formula 1-4-111
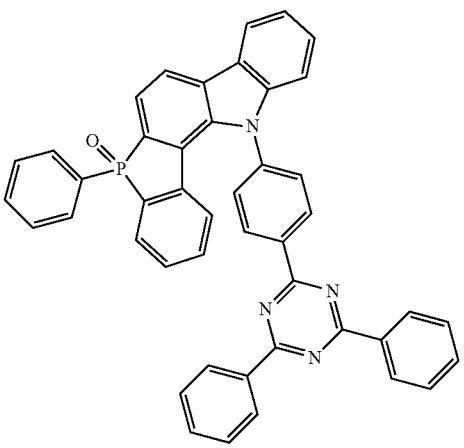
Formula 1-4-112
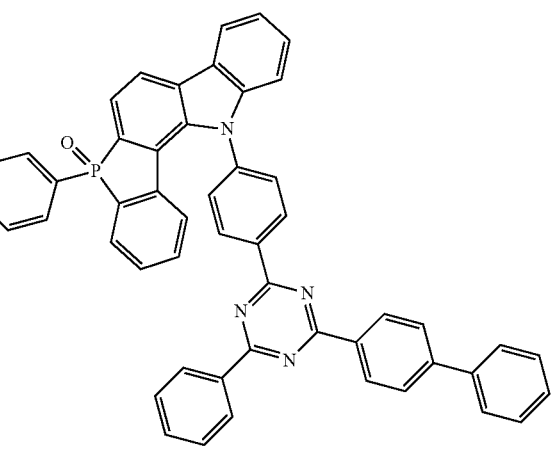

Formula 1-4-113
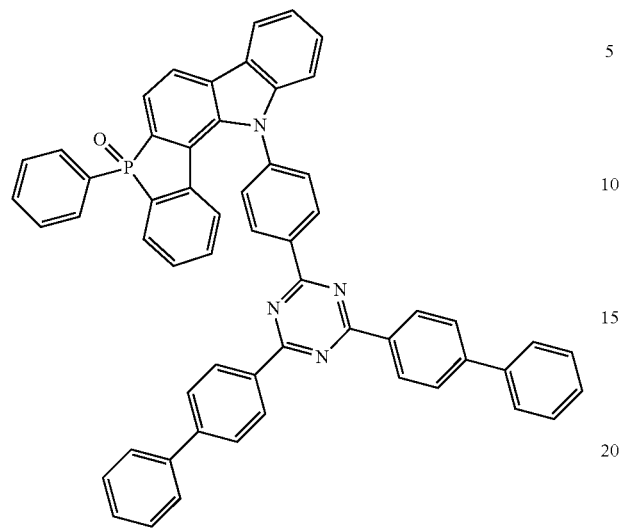
Formula 1-4-116
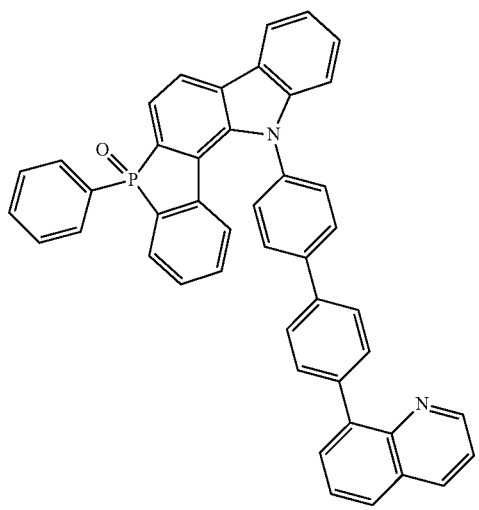
Formula 1-4-114
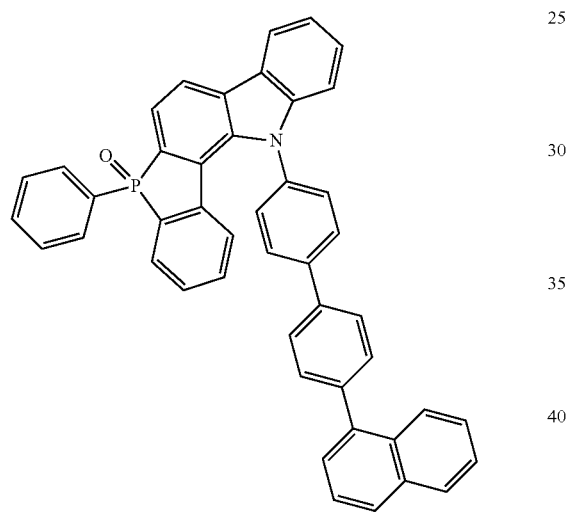
Formula 1-4-117
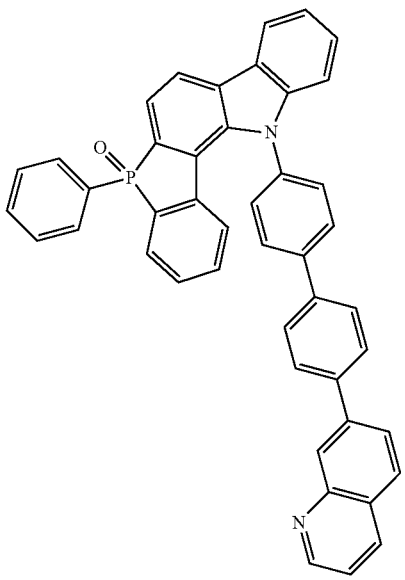
Formula 1-4-115
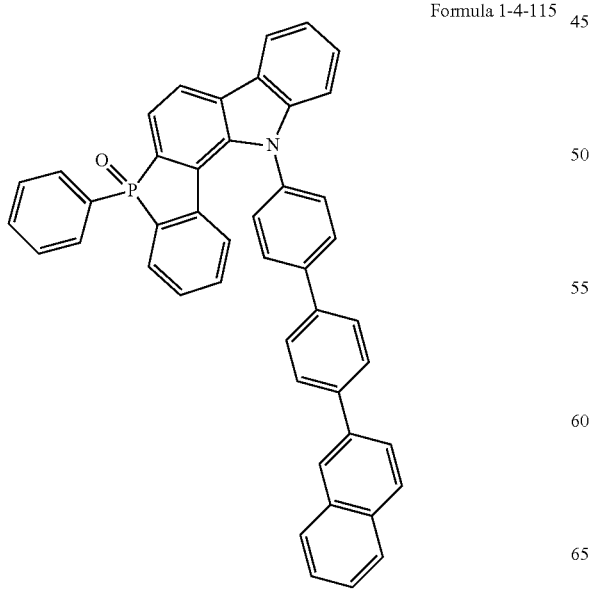
Formula 1-4-118
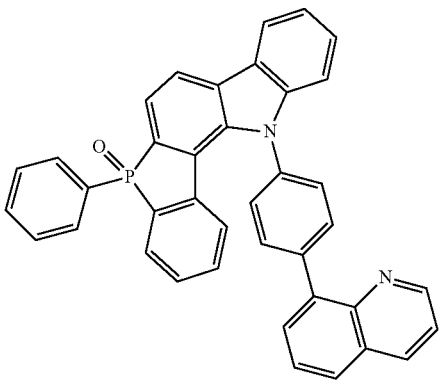

-continued
Formula 1-4-119
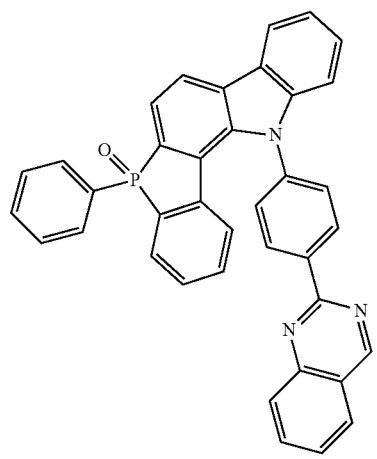
Formula 1-4-120
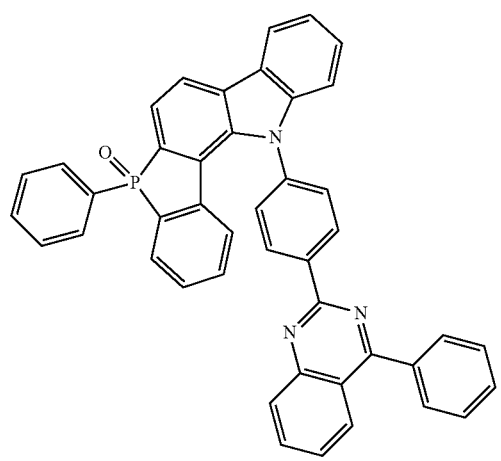
Formula 1-4-121
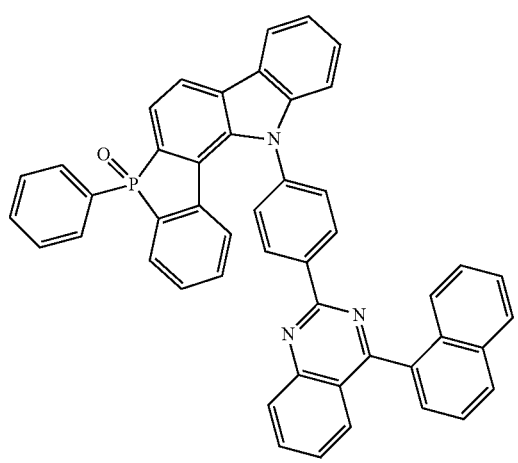
Formula 1-4-122
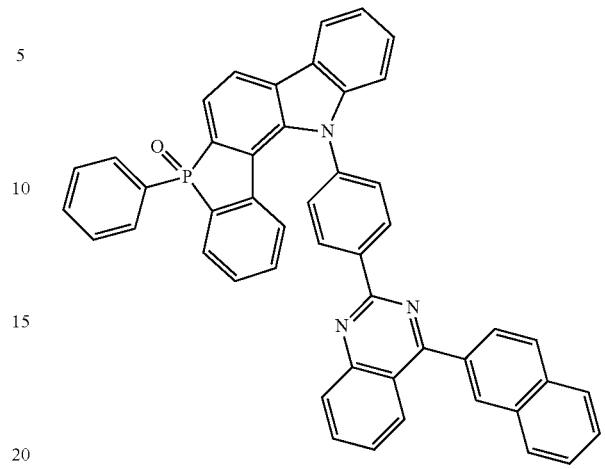
Formula 1-4-123
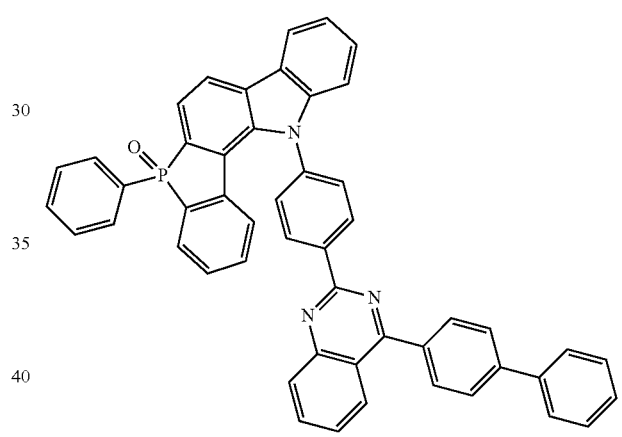
Formula 1-4-124
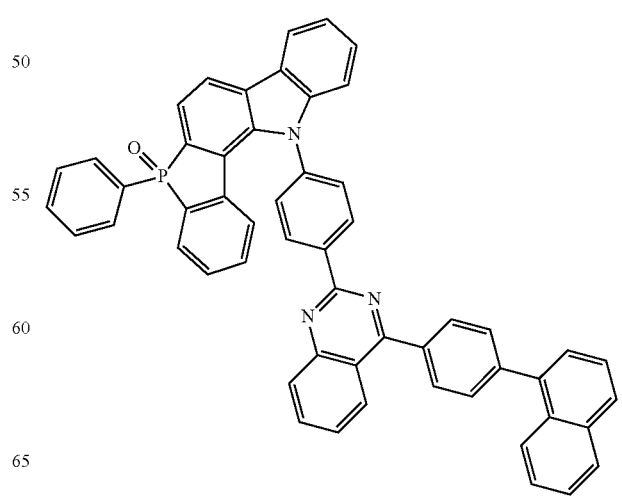

Formula 1-4-125
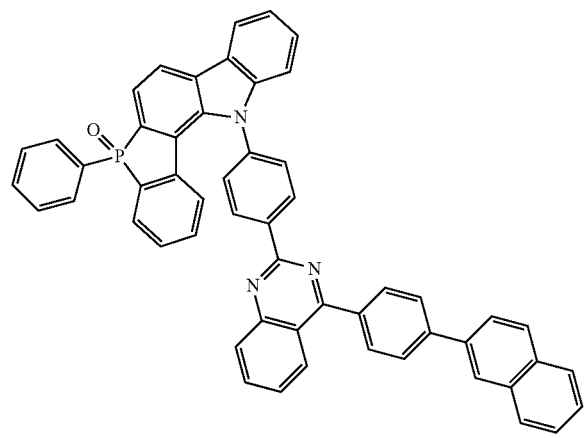
Formula 1-4-126
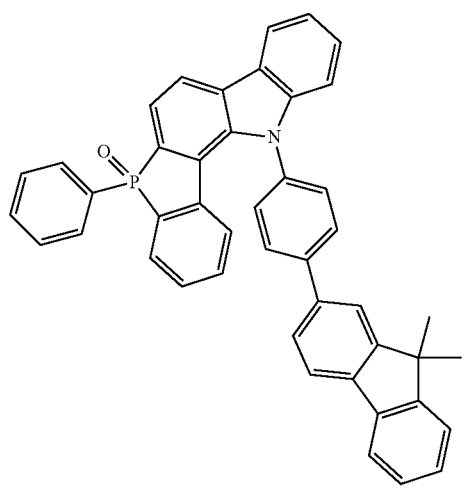
Formula 1-4-127
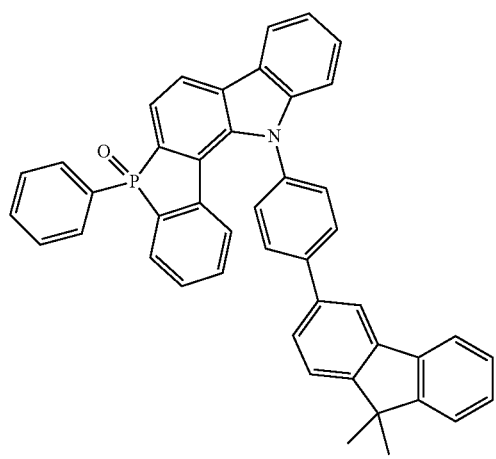
Formula 1-4-128
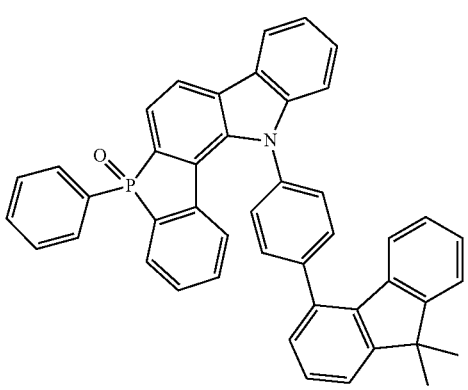
Formula 1-4-129
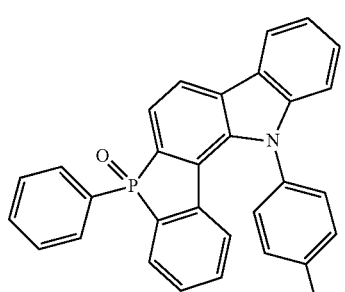
Formula 1-4-130
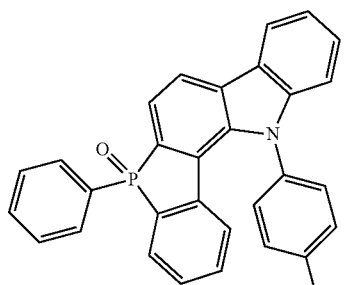

Formula 1-4-131
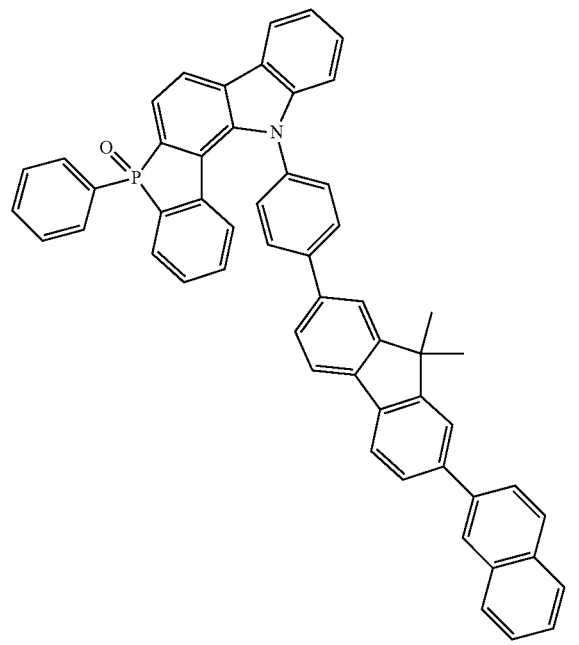
Formula 1-4-132
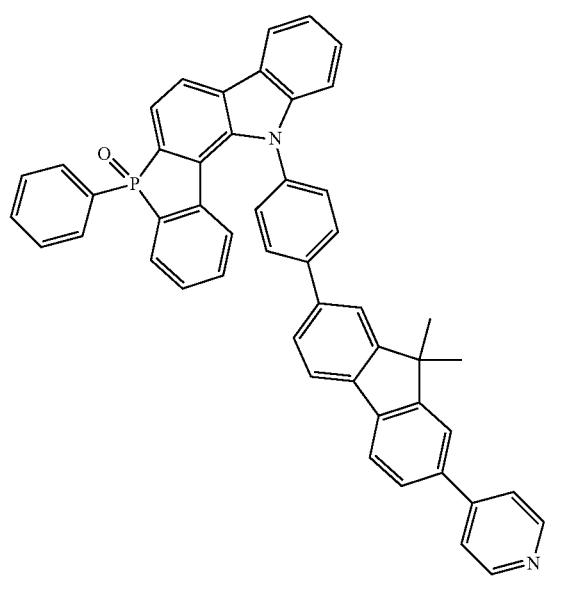
Formula 1-4-133
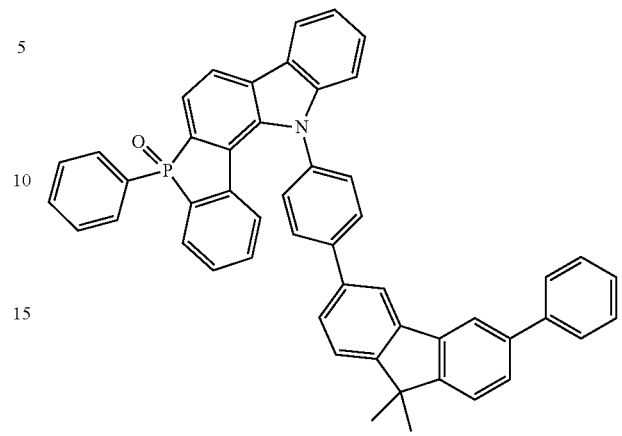
Formula 1-4-134
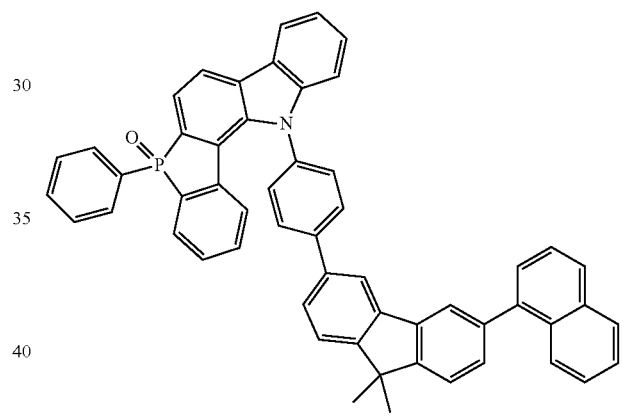
Formula 1-4-135
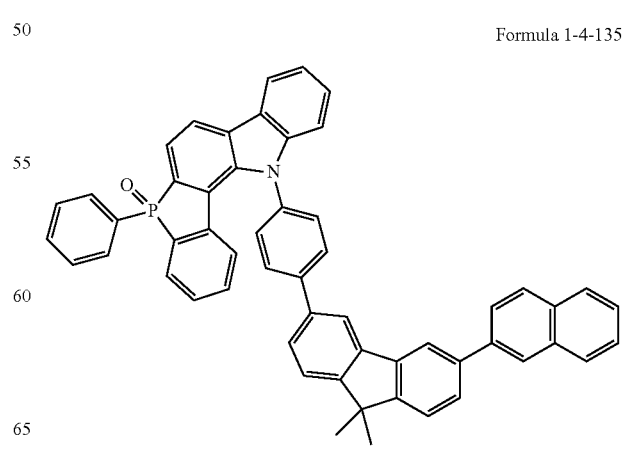

Formula 1-4-136
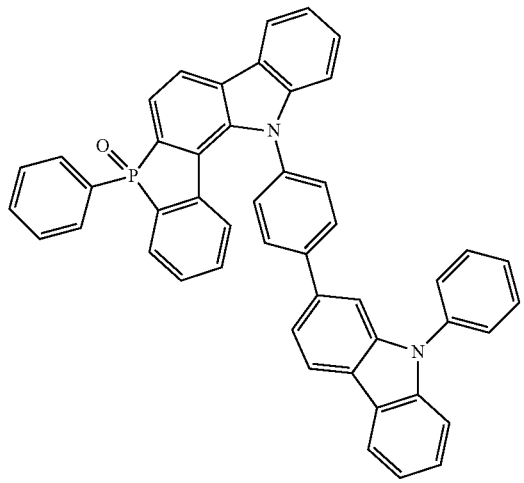
Formula 1-4-139
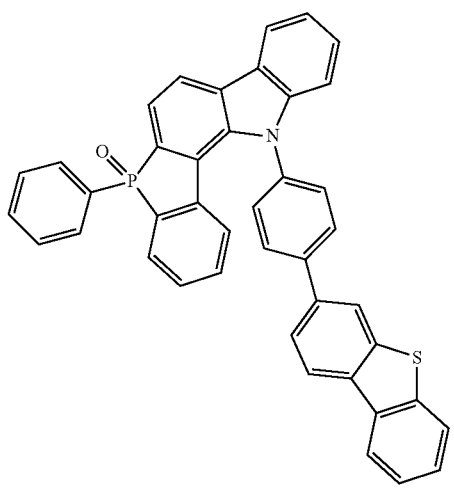
Formula 1-4-137
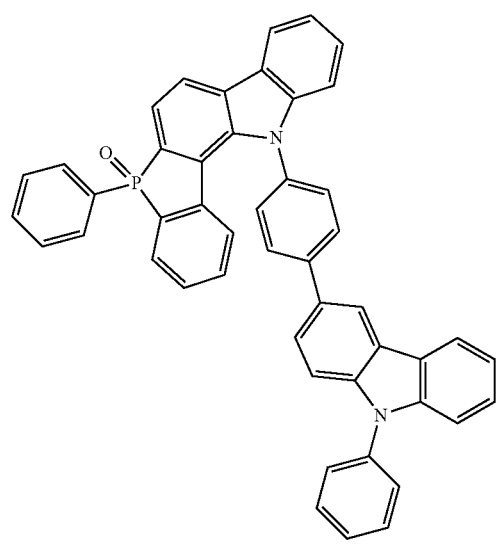
Formula 1-4-140
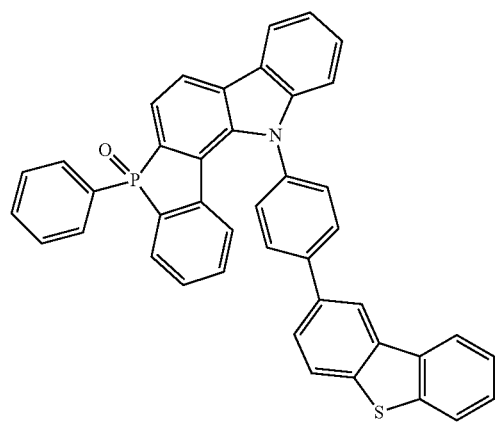
Formula 1-4-138
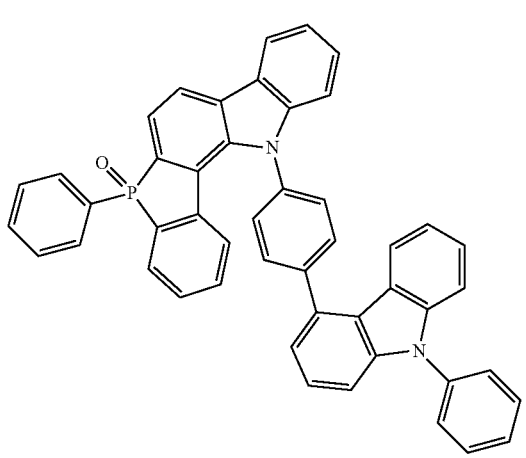
Formula 1-4-141
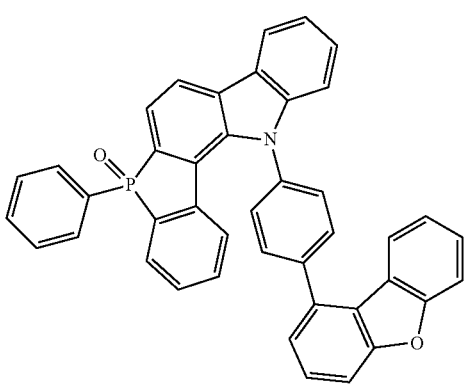

-continued
Formula 1-4-142
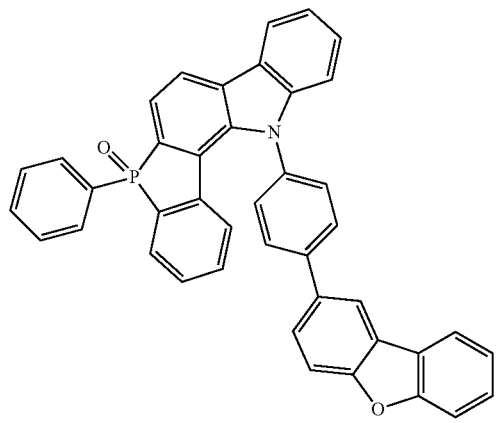
Formula 1-4-143
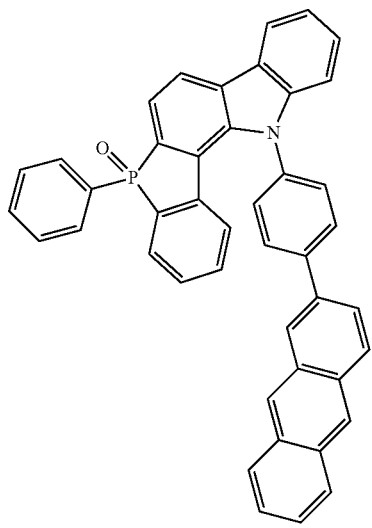
Formula 1-4-144
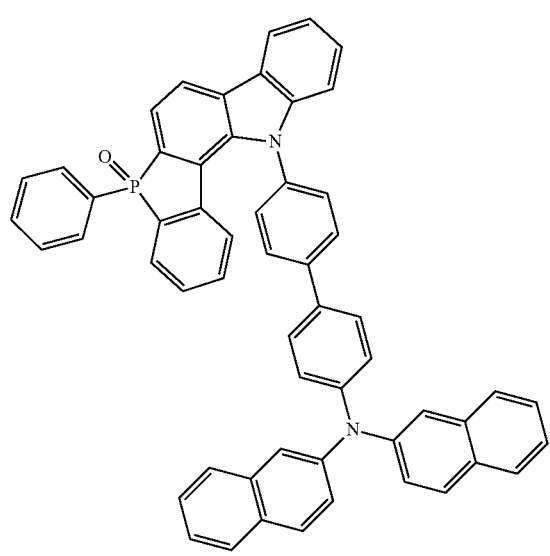
-continued
Formula 1-4-145
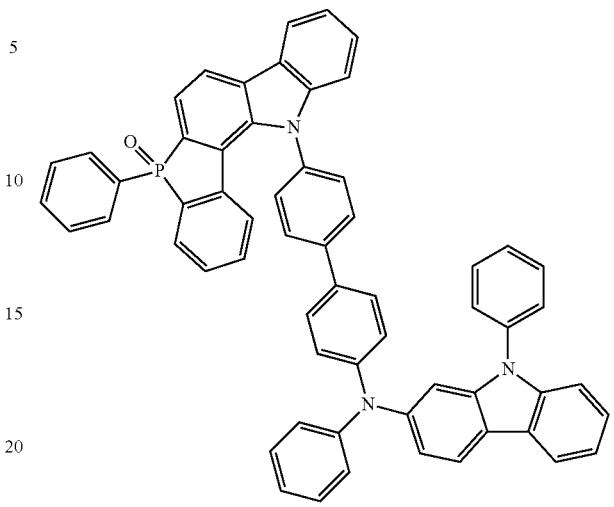
Formula 1-4-146
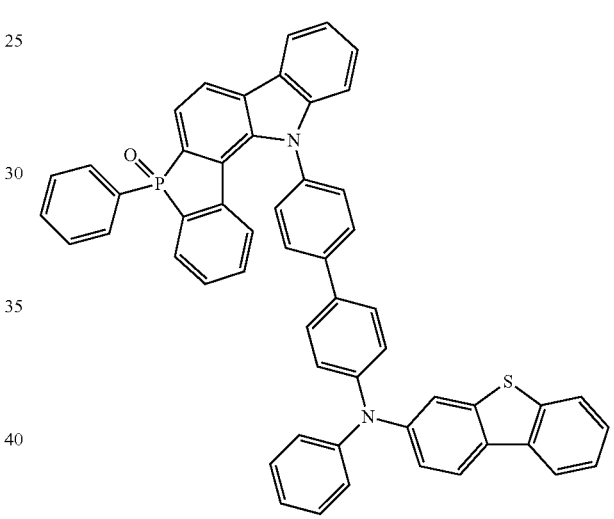
Formula 1-4-147
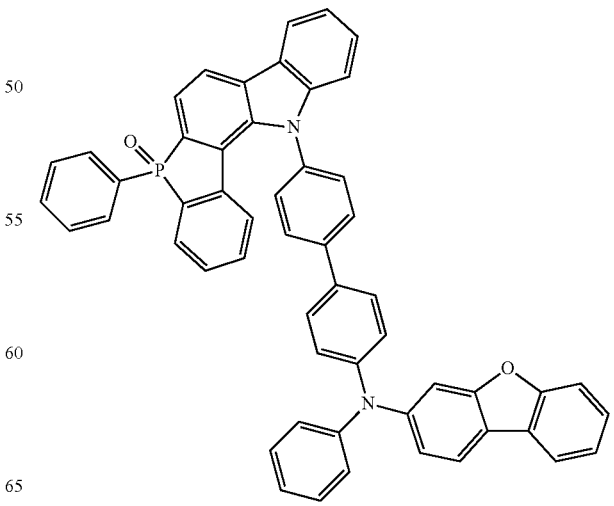

Formula 1-4-148
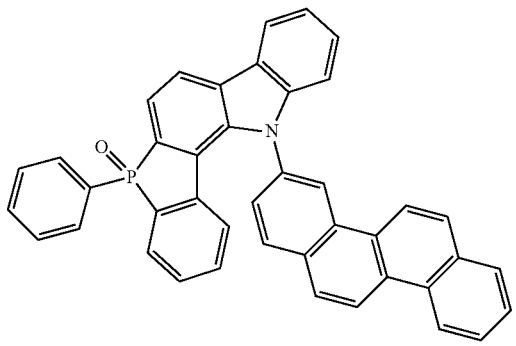
Formula 1-4-149
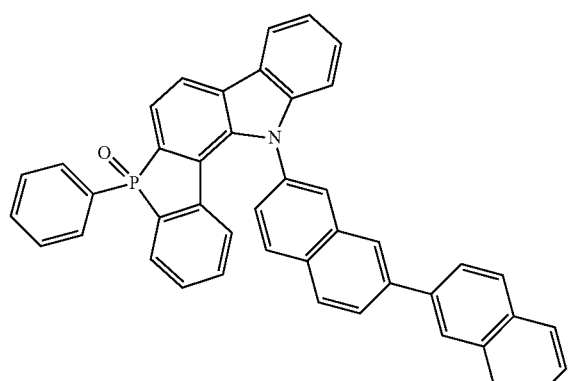
Formula 1-4-150
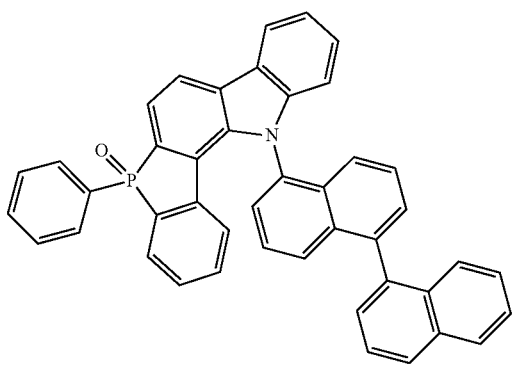
Formula 1-4-151
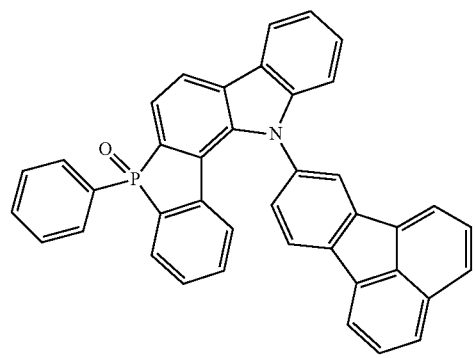
Formula 1-4-152
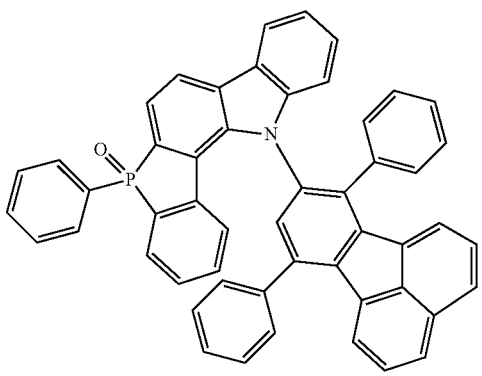
Formula 1-4-153
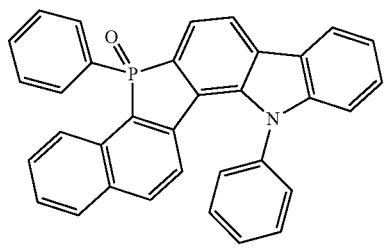
Formula 1-4-154
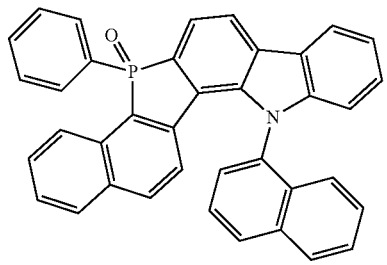
Formula 1-4-155
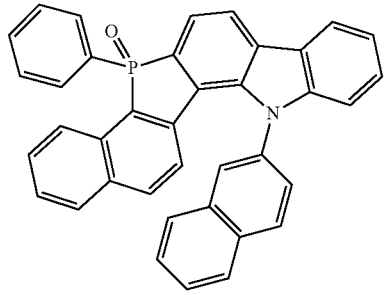
Formula 1-4-156
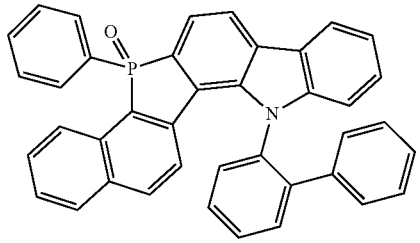

Formula 1-4-157
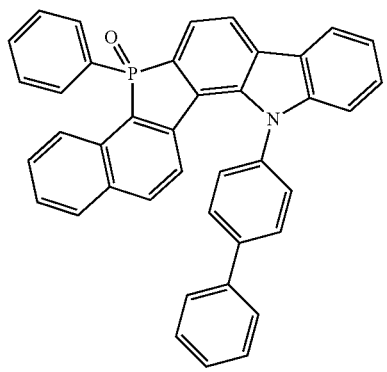
Formula 1-4-158
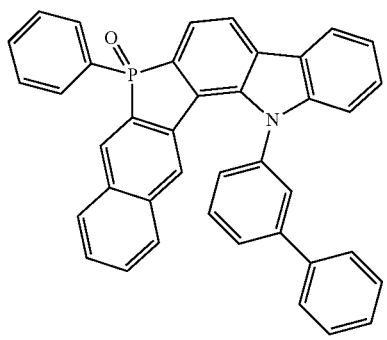
Formula 1-4-159
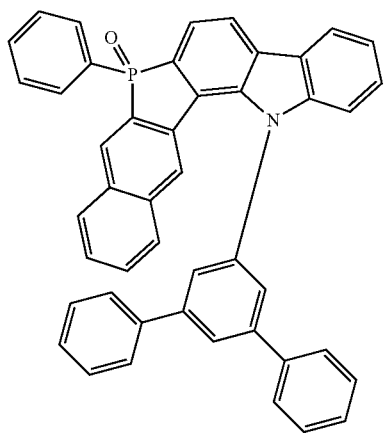
Formula 1-4-160
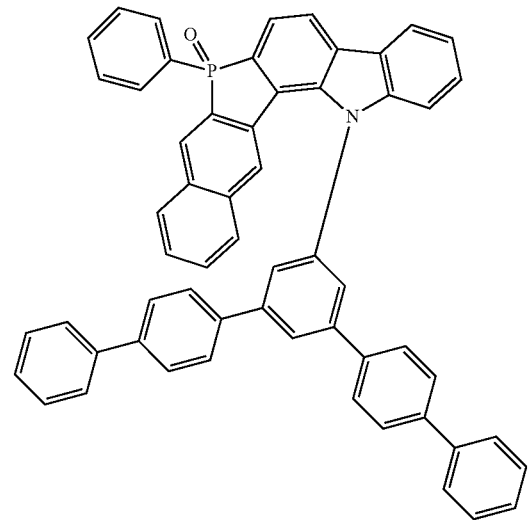
Formula 1-4-161
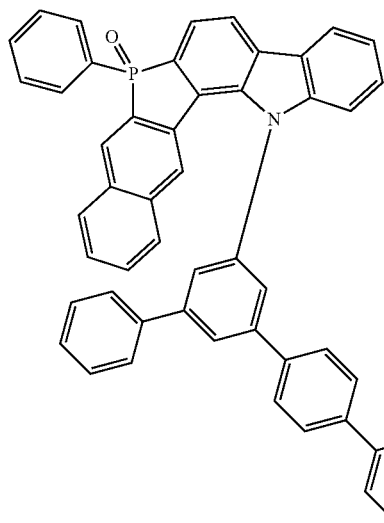
Formula 1-4-162
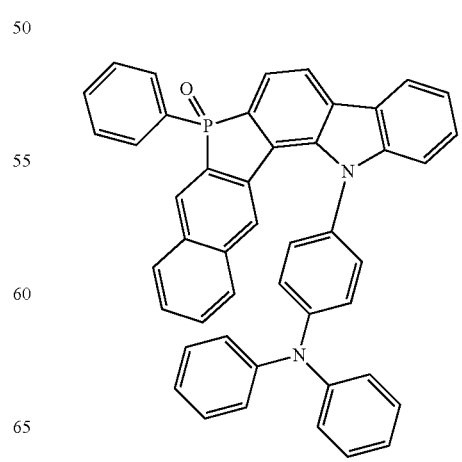

Formula 1-4-163
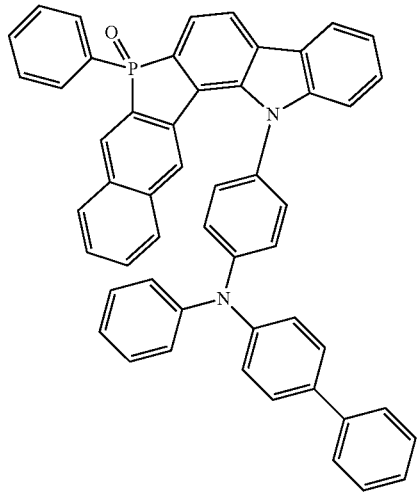
Formula 1-4-164
Formula 1-4-165
Formula 1-4-166
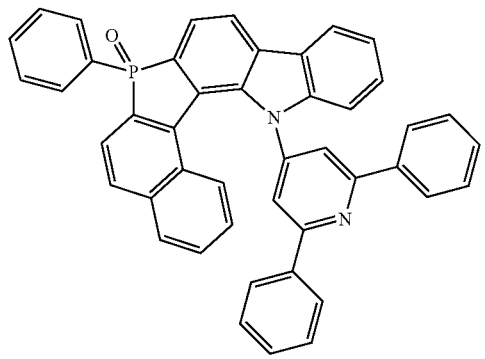
Formula 1-4-167
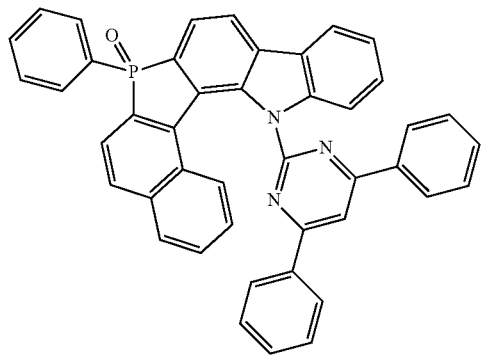
Formula 1-4-168
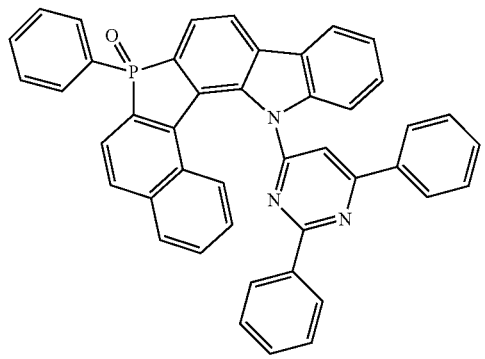
Formula 1-4-169
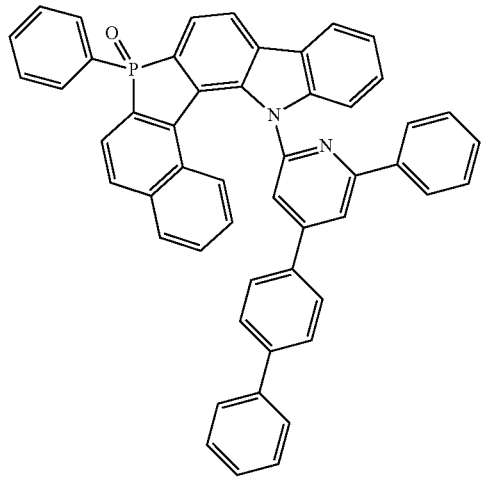

-continued
Formula 1-4-170
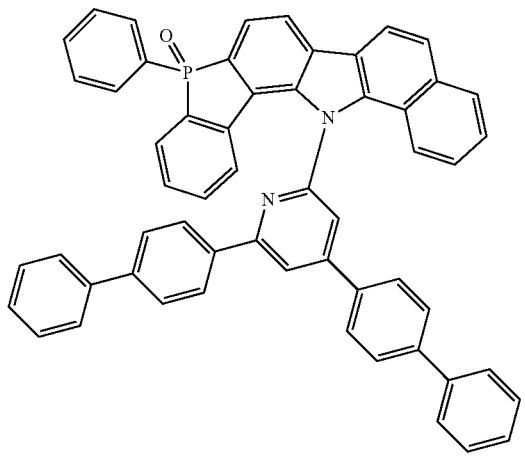
Formula 1-4-171
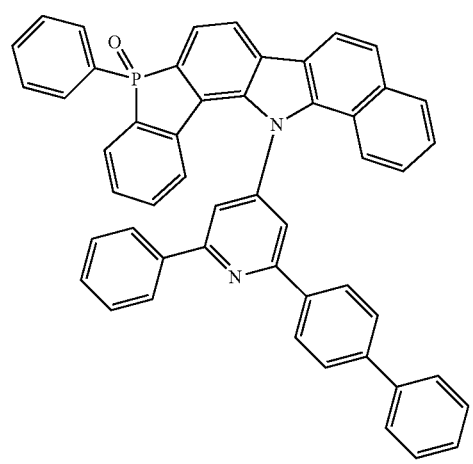
Formula 1-4-172
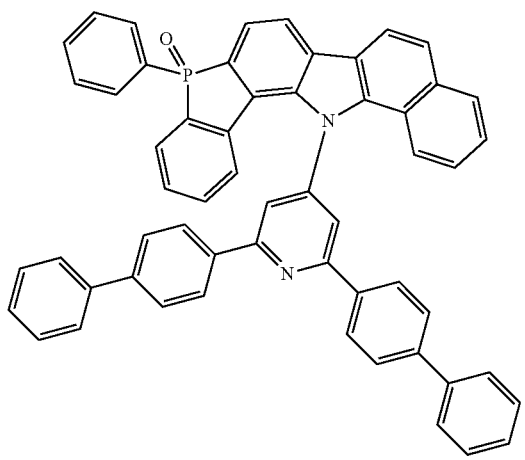
Formula 1-4-173
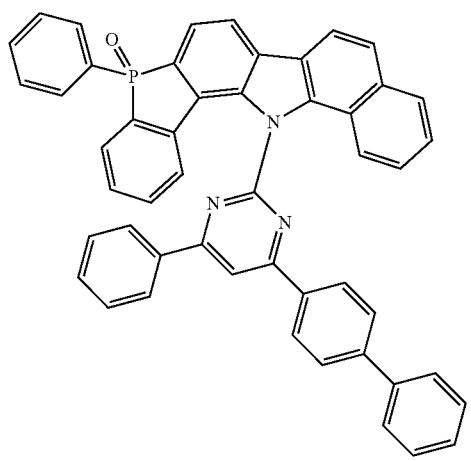
Formula 1-4-174
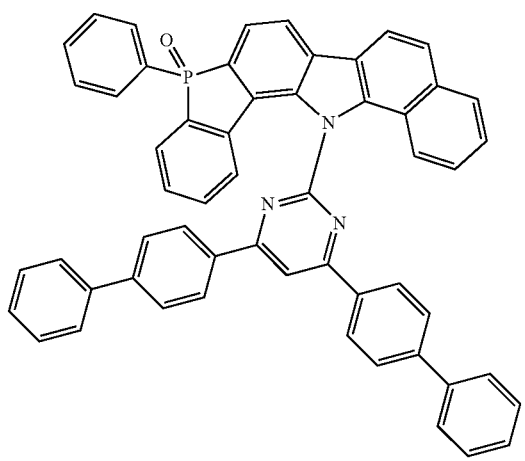
Formula 1-4-175
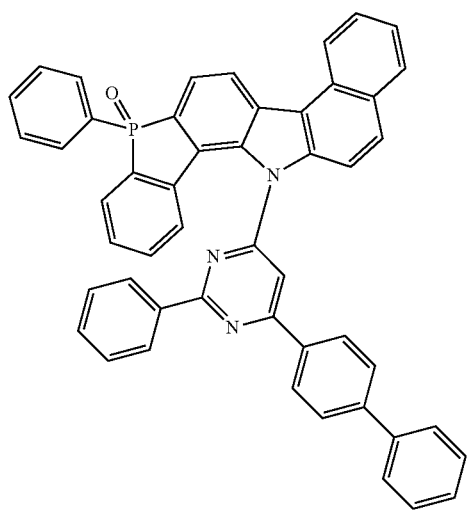

-continued
Formula 1-4-176
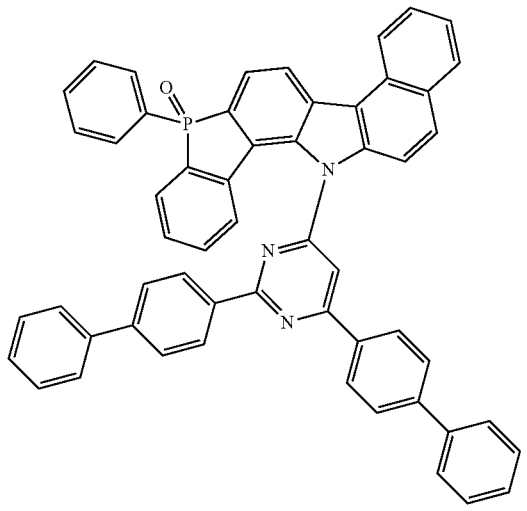
Formula 1-4-177
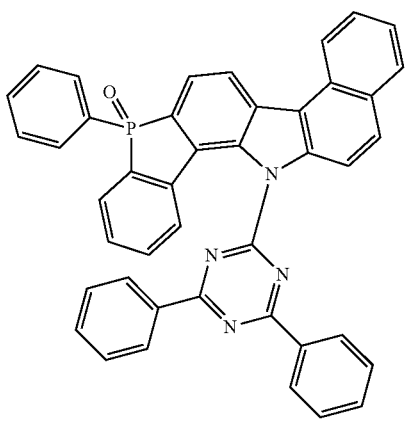
Formula 1-4-178
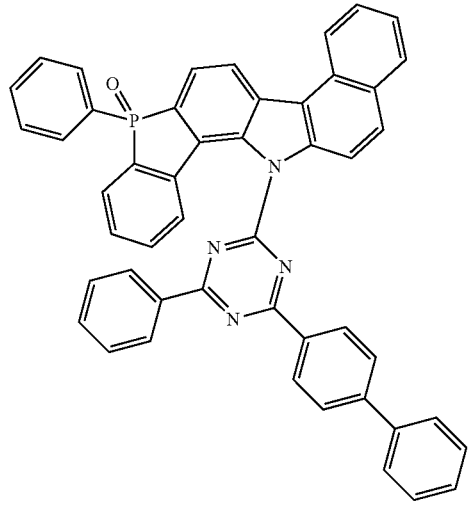
-continued
Formula 1-4-179
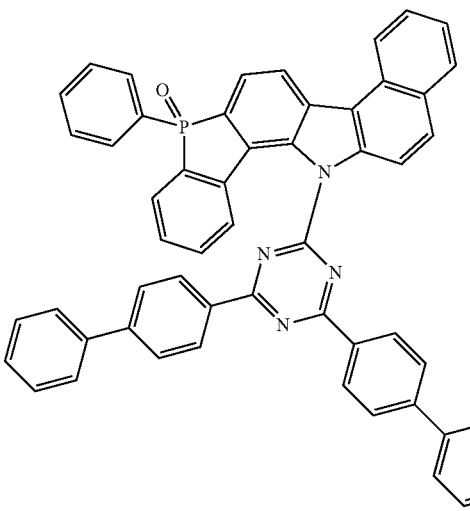
Formula 1-4-180
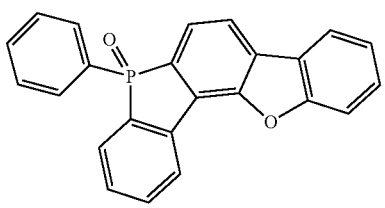
Formula 1-4-181
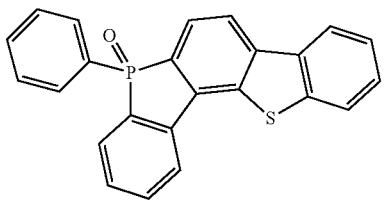
Formula 1-4-182
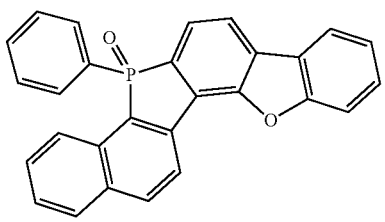
Formula 1-4-183
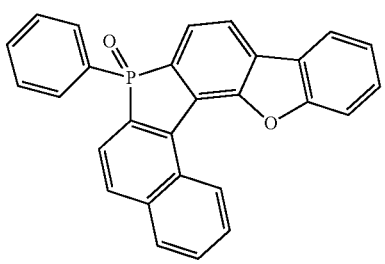

Formula 1-4-184
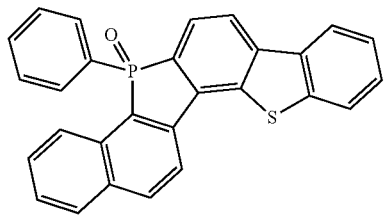
Formula 1-4-185
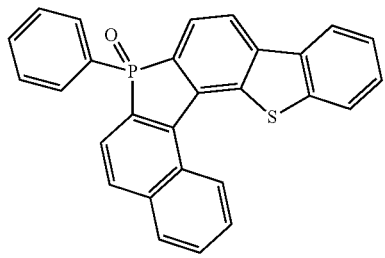
Formula 1-4-186
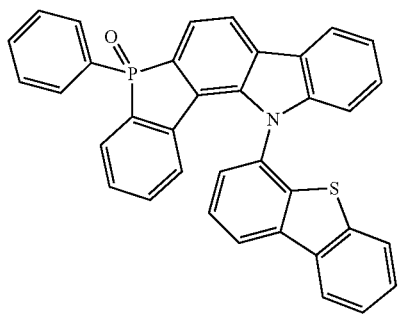
Formula 1-4-187
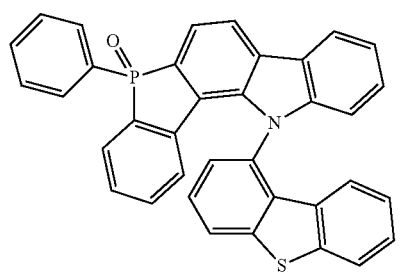
Formula 1-4-188
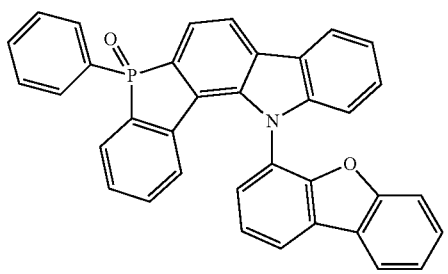
Formula 1-4-189
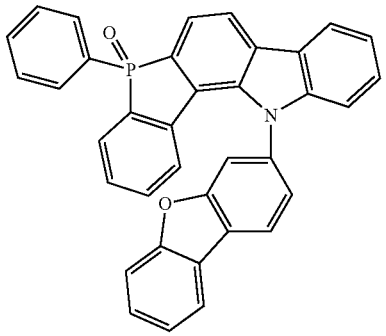
Formula 1-4-190
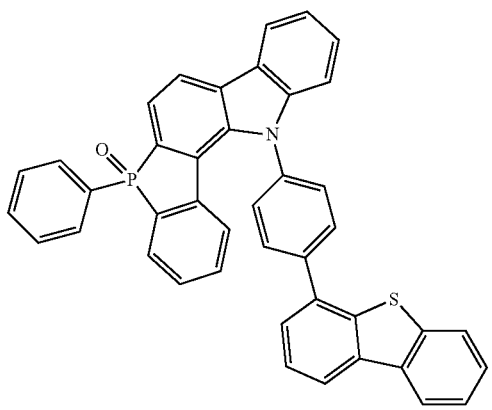
Formula 1-4-191
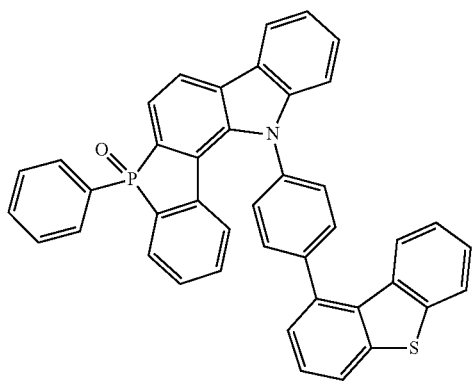
Formula 1-4-192
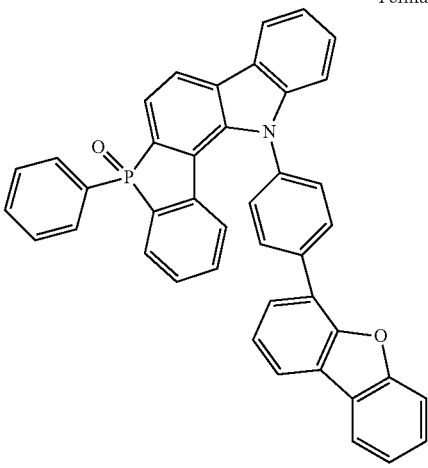

Formula 1-4-193

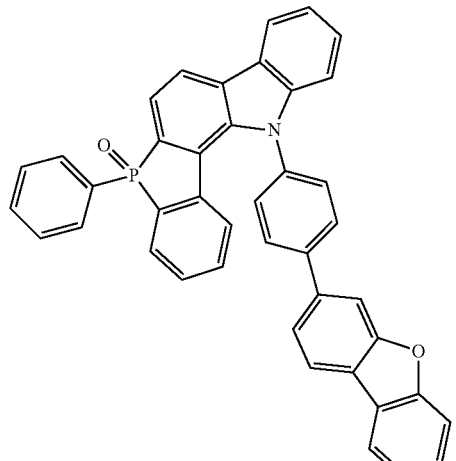

Formula 1-4-194

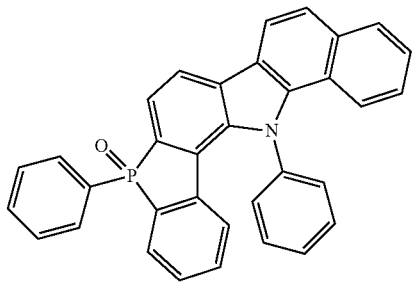

Formula 1-4-195

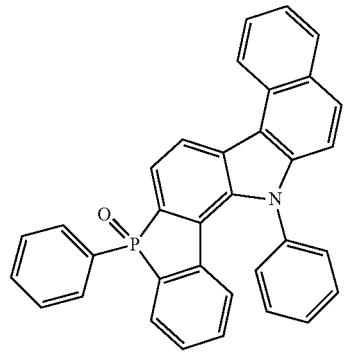

In an exemplary embodiment of the present specification, provided is an organic electroluminescent device including: a first electrode; a second electrode provided to face the first electrode; and one or more organic material layers provided between the first electrode and the second electrode, in which one or more layers of the organic material layers include the above-described compound.

The organic material layer of the organic electroluminescent device of the present specification may also be composed of a single-layered structure, but may be composed of a multi-layered structure in which two or more organic material layers are stacked. For example, the organic electroluminescent device of the present invention may have a structure including a hole injection layer, a hole transporting layer, a light emitting layer, an electron transporting layer, an electron injection layer, and the like as organic material layers. However, the structure of the organic electroluminescent device is not limited thereto, and may include a fewer number of organic layers.

In an exemplary embodiment of the present specification, the organic material layer including the compound is a hole injection layer, a hole transporting layer, or a layer which injects and transports holes simultaneously.

In another exemplary embodiment of the present specification, the organic material layer including the compound is an electron blocking layer.

In an exemplary embodiment of the present specification, the organic material layer including the compound is a light emitting layer.

In another exemplary embodiment, the compound is a phosphorescent host material or a fluorescent host material. In an exemplary embodiment of the present specification, the organic material layer includes an electron transporting layer or an electron injection layer, and the electron transporting layer or the electron injection layer includes the compound of Formula 1.

In another exemplary embodiment of the present specification, the organic material layer including the compound is an electron injection layer, an electron transporting layer, or a layer which injects and transports electrons simultaneously.

In an exemplary embodiment of the present specification, the organic electroluminescent device further includes one or two or more layers selected from the group consisting of a hole injection layer, a hole transporting layer, an electron transporting layer, an electron injection layer, an electron blocking layer, and a hole blocking layer.

In another exemplary embodiment, the organic electroluminescent device may be an organic electroluminescent device having a normal type structure in which a positive electrode, one or more organic material layers, and a negative electrode are sequentially stacked on a substrate.

In still another exemplary embodiment, the organic electroluminescent device may be an organic electroluminescent device having an inverted type structure in which a negative electrode, one or more organic material layers, and a positive electrode are sequentially stacked on a substrate.

FIGS. 1 to 3 illustrate the sequence of stacking the electrodes and the organic material layers of the organic electroluminescent device according to exemplary embodiments of the present invention. However, the scope of the present invention is not intended to be limited by these drawings, and the structure of the organic electroluminescent device known in the art may also be applied to the present invention.

According to FIG. 1, an organic electroluminescent device in which a positive electrode 200, an organic material layer 300, and a negative electrode 400 are sequentially stacked on a substrate 100 is illustrated. However, the organic electroluminescent device is not limited only to such a structure, and as illustrated in FIG. 2, an organic electroluminescent device in which a negative electrode, an organic material layer, and a positive electrode are sequentially stacked on a substrate may also be implemented.

FIG. 3 exemplifies a case where the organic material layer is a multilayer. The organic electroluminescent device according to FIG. 3 includes a hole injection layer 301, a hole transporting layer 302, a light emitting layer 303, an electron transporting layer 304, and an electron injection layer 305. However, the scope of the present invention is not limited by the stacking structure as described above, and if necessary, the other layers except for the light emitting layer may be omitted, and another necessary functional layer may be further added.

The organic electroluminescent device of the present specification may be manufactured by the materials and methods known in the art, except that one or more layers of the organic material layers include the compound of the present specification, that is, the compound of Formula 1.

When the organic electroluminescent device includes a plurality of organic material layers, the organic material layers may be formed of the same material or different materials.

The organic electroluminescent device of the present specification may be manufactured by the materials and methods known in the art, except that one or more layers of the organic material layers include the compound of Formula 1, that is, the compound represented by Formula 1.

For example, the organic electroluminescent device of the present specification may be manufactured by sequentially stacking a first electrode, an organic material layer, and a second electrode on a substrate. In this case, the organic electroluminescent device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic electroluminescent device may be made by subsequently depositing a negative electrode material, an organic material layer, and a positive electrode material on a substrate.

Further, the compound of Formula 1 may be formed as an organic material layer by not only a vacuum deposition method, but also a solution application method when an organic electroluminescent device is manufactured. Here, the solution application method means spin coating, dip coating, doctor blading, inkjet printing, screen printing, a spray method, roll coating, and the like, but is not limited thereto.

In addition to the method as described above, an organic electroluminescent device may also be made by sequentially stacking a negative electrode material, an organic material layer, and a positive electrode material on a substrate (International Patent Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structure material, such as LiF/Al or LiO$_2$/Al, and the like, but are not limited thereto.

The hole injection material is preferably a compound which has a capability of transporting holes to a layer which injects holes from an electrode, and thus has an effect of injecting holes at a positive electrode and an excellent effect of injecting holes into a light emitting layer or a light emitting material, prevents excitons, which are produced from the light emitting layer, from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer the holes to a light emitting layer, and has high mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specific examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to the light emitting layer, and is suitably a material which has high mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons, which are produced from the light emitting layer, from moving to the hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic electroluminescent device according to the present specification may be a top emission type, a bottom emission type, or a dual emission type according to the material to be used.

In an exemplary embodiment of the present specification, the compound may be included in an organic solar cell or an organic transistor in addition to the organic electroluminescent device.

Hereinafter, the present specification will be described in detail with reference to the Examples for specifically describing the present specification. However, the Examples according to the present specification may be modified in various forms, and it is not interpreted that the scope of the present specification is not limited to the Examples described below. The Examples of the present specification are provided for more completely explaining the present specification to the person with ordinary skill in the art.

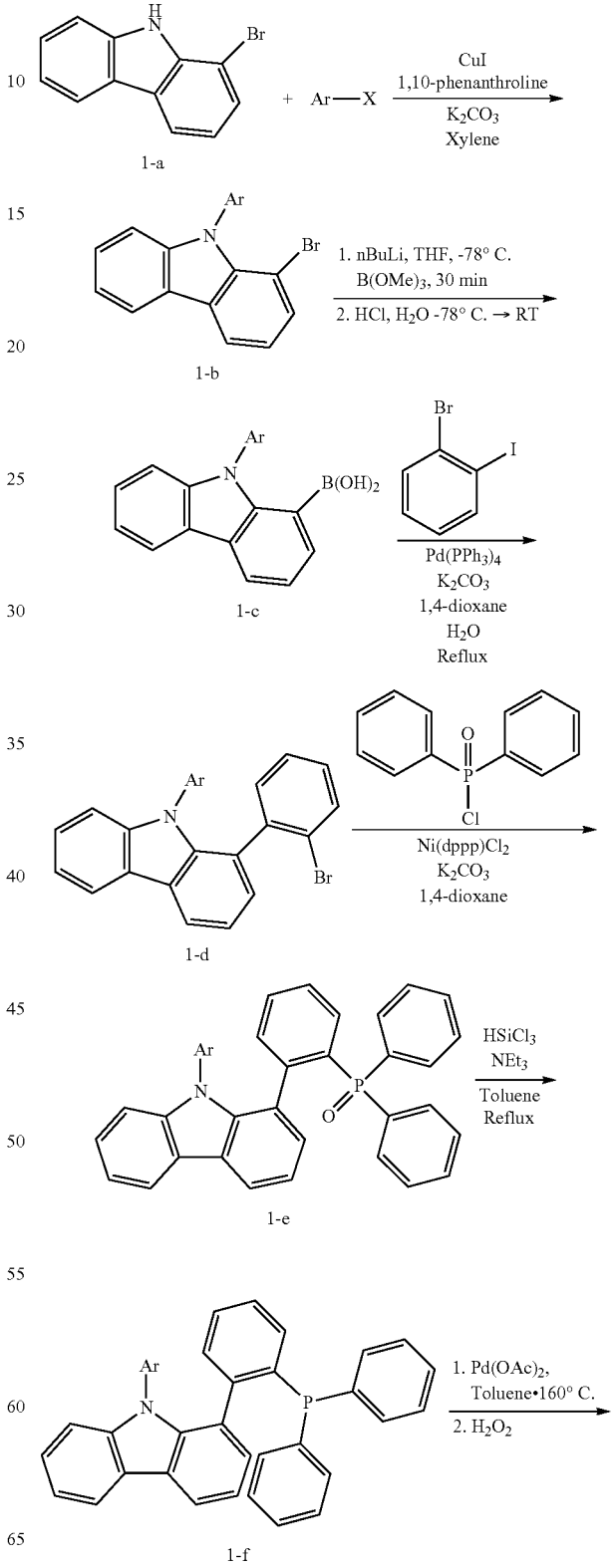

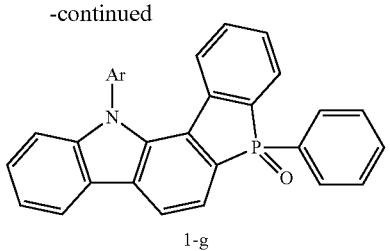
1-g

Material 1-a (Cas No. 16807-11-7, 1 eq) and Ar substituted with a halogen group (X=I or Br, 1.1 eq) were put into a two neck flask. Copper iodide (CuI) (0.2 eq), 1,10-phenanthroline (0.2 eq), and xylene were introduced into the flask, and then the resulting mixture was stirred under reflux for 6 hours. After the reaction was completed, the flask was cooled to normal temperature, the solvent was distilled under reduced pressure, and then column chromatography was used to obtain Compound 1-b.

A nitrogen atmosphere was created in the two neck flask. Compound 1-b (1 eq) was completely dissolved in tetrahydrofuran (THF), and then the temperature was maintained at −78° C. n-butyl lithium (nBuLi) (1 eq) was slowly introduced into the flask, the resulting mixture was stirred for 30 minutes after the introduction, and then B(OMe)$_3$ was slowly added dropwise thereto. The resulting mixture was stirred for 30 minutes, and then an excessive amount of 1 N HCl solution was introduced into the flask. And then, the temperature was slowly increased to normal temperature. When the reaction was completed, extraction was performed using trichloromethane (CHCl$_3$), and magnesium sulfate (MgSO$_4$) was used to remove water from the organic layer. The solvent was removed, and then ethanol recrystallization was used to obtain Compound 1-c.

Compound 1-c (1.1 eq), 2-iodo-bromobenzene (1.0 eq), Pd(PPh$_3$)$_4$ (0.02 eq), and 1,4-dioxane were added thereto, and the resulting mixture was stirred. A solution was prepared by using potassium carbonate (K$_2$CO$_3$, 3 eq) and water (H$_2$O) in the mixture, and then added thereto. The resulting mixture was stirred under reflux for 3 hours. When the reaction was completed, the temperature was cooled to normal temperature, and then the organic layer was separated. The organic solvent was completely removed through distillation under reduced pressure and column chromatography was used to obtain Compound 1-d.

Compound 1-d (1 eq), P,P-diphenyl-phosphonic chloride (Cas No. 1499-21-4)-(1.5 eq), Ni(dppp)Cl$_2$ (0.02 eq), and K$_2$CO$_3$ (3 eq) were introduced. Here, 1,4-dioxane was used to stir the mixture under reflux for 12 hours. After the reaction was completed, the temperature was cooled to normal temperature, pressure was reduced to remove the solvent, and column chromatography was used to obtain Compound 1-e.

A nitrogen atmosphere was created in the two neck flask, and then Compound 1-e (1 eq) was dissolved in anhydrous toluene, and the temperature was maintained at −116° C. Trichlorosilane (HSiCl$_3$, 5 eq) and triethylamine (NEt$_3$, 5.5 eq) were introduced to the mixture at −116° C. The temperature was slowly increased to normal temperature, and then the resulting mixture was stirred under reflux for 12 hours. When the reaction was completed, the temperature was cooled to normal temperature, a sodium carbonate (NaHCO$_3$) saturated solution was sufficiently added thereto, and the resulting mixture was stirred at normal temperature for 10 minutes. The pressure was reduced to completely remove the solvent, and column chromatography was used to obtain Compound 1-f.

Compound 1-f (1 eq), Pd(OAc)$_2$ (0.05 eq), and anhydrous toluene were introduced into a sealed tube. The sealed tube was sufficiently charged with nitrogen and sealed with a stopper, and was heated at 160° C. for 12 hours. When the reaction was completed, the temperature was cooled to normal temperature, and a few drops of hydrogen peroxide (H$_2$O$_2$, ca. 30%) were added thereto, and then the resulting mixture was stirred at normal temperature for 30 minutes. The solvent was completely removed, and column chromatography was used to obtain Compound 1-g.

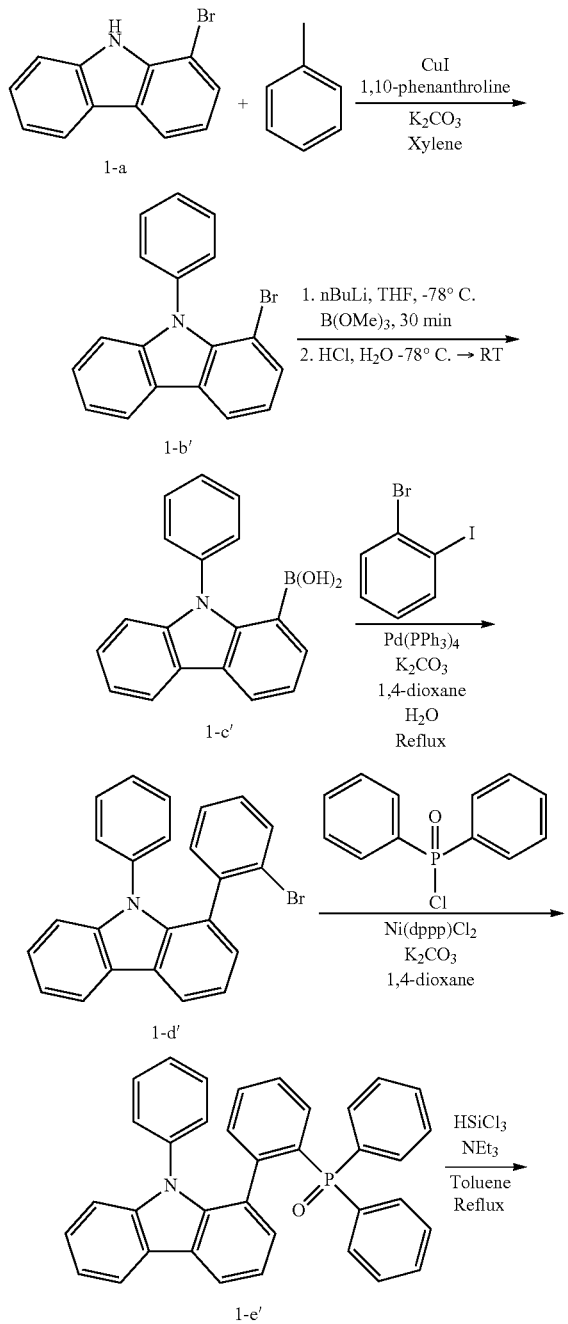

-continued

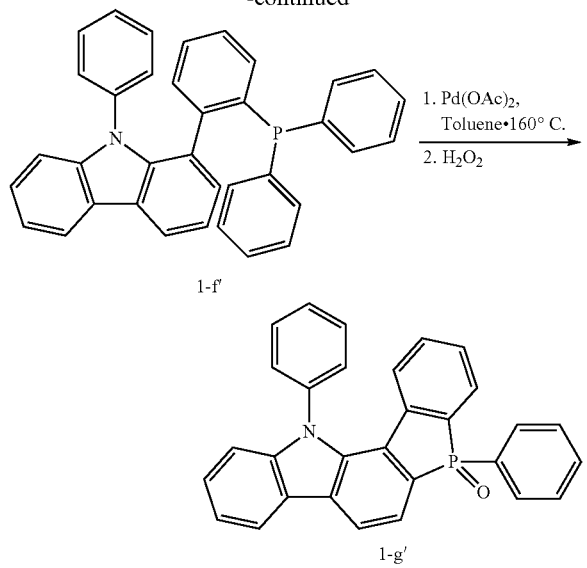

1-f'

1. Pd(OAc)₂, Toluene·160° C.
2. H₂O₂

1-g'

Material 1-a' (Cas No. 16807-11-7, 20 g, 81.3 mmol, 1 eq) and iodobenzene (18.23 g, 89.4 mmol, 1.1 eq) were put into a two neck flask. Copper iodide (CuI) (3.1 g, 16.3 mmol, 0.2 eq), 1,10-phenanthroline (3.0 g, 16.3 mmol, 0.2 eq), and 150 ml of xylene were introduced into the flask, and then the resulting mixture was stirred under reflux for 6 hours. After the reaction was completed, the flask was cooled to normal temperature, the solvent was distilled under reduced pressure, and then column chromatography was used to obtain Compound 1-b' (22.4 g, yield 86%).

A nitrogen atmosphere was created in the two neck flask. Compound 1-b' (22.4 g, 69.5 mmol, 1 eq) was completely dissolved in 150 ml of anhydrous tetrahydrofuran (THF), and then a dry ice/acetone bath was used to maintain the temperature at −78° C. n-butyl lithium (nBuLi) (27.8 ml, 69.5 mmol, 1 eq) was slowly introduced into the flask, the resulting mixture was stirred for 30 minutes after the introduction, and then B(OMe)₃ (10.8 g, 104.25 mmol, 1.5 eq) was slowly added dropwise thereto. The resulting mixture was stirred for 30 minutes, and then an excessive amount of 1 N HCl solution was introduced into the flask. And then, the temperature was slowly increased to normal temperature. Extraction was performed using trichloromethane (CHCl₃), and magnesium sulfate (MgSO₄) was used to remove water from the organic layer. Ethanol recrystallization was used to obtain Compound 1-c' (18 g, yield 90.2%).

Compound 1-c' (18 g, 62.7 mmol, 1.1 eq), 2-iodo-bromobenzene (16.1 g, 57.0 mmol, 1.0 eq), Pd(PPh₃)₄ (1.3 g, 1.14 mmol, 0.02 eq), and 150 ml of 1,4-dioxane were added thereto, and the resulting mixture was stirred. A solution was prepared by using potassium carbonate (K₂CO₃) (23.6 g, 171 mmol, 3 eq) and 60 ml of water (H₂O) thereto, and then added thereto. The resulting mixture was stirred under reflux for 3 hours. When the reaction was completed, the temperature was cooled to normal temperature, and then the organic layer was separated. The organic solvent was completely removed through distillation under reduced pressure and column chromatography was used to obtain Compound 1-d' (17.7 g, yield 78%).

Compound 1-d' (17.7 g, 44.4 mmol, 1 eq), P,P-diphenylphosphonic chloride (Cas No. 1499-21-4) (15.8 g, 66.7 mmol, 1.5 eq), Ni(dppp)Cl₂ (0.37 g, 88.8 mmol, 0.02 eq), and K₂CO₃ (18.4 g, 133.2 mmol, 3 eq) were introduced. 1,4-dioxane was used to stir the mixture under reflux for 12 hours. After the reaction was completed, the temperature was cooled to normal temperature, pressure was reduced to remove the solvent, and column chromatography was used to obtain Compound 1-e' (20.2 g, yield 87.6%).

A nitrogen atmosphere was created in the two neck flask, and then Compound 1-e' (20.2 g, 38.9 mmol, 1 eq) was dissolved in anhydrous toluene, and a liquid nitrogen/ethanol bath was used to maintain the temperature at −116° C. Trichlorosilane (HSiCl₃) (26.3 g, 194.5 mmol, 5 eq) and triethylamine (NEt₃) (21.6 g, 214.0 mmol, 5.5 eq) were introduced to the flask. The temperature was slowly increased to normal temperature, and then the resulting mixture was stirred under reflux for 12 hours. When the reaction was completed, the temperature was cooled to normal temperature, a sodium carbonate (NaHCO₃) saturated solution was sufficiently added thereto, and the resulting mixture was stirred at normal temperature for 10 minutes. The pressure was reduced to completely remove the solvent, and column chromatography was used to obtain Compound 1-f' (15.7 g, yield 80.1%).

Compound 1-f' (15.7 g, 31.2 mmol, 1 eq), Pd(OAc)₂ (0.35 g, 1.6 mmol, 0.05 eq), and 50 ml of anhydrous toluene were introduced into a sealed tube. The sealed tube was sufficiently charged with nitrogen and sealed with a stopper, and was heated at 160° C. for 12 hours. When the reaction was completed, the temperature was cooled to normal temperature, and a few drops of hydrogen peroxide (H₂O₂, ca. 30%) were added thereto, and then the resulting mixture was stirred at normal temperature for 30 minutes. The solvent was completely removed, and column chromatography was used to obtain Compound 1-g' (6.3 g, yield 45.8%).

| Formula | Ar—X | Product | m/z |
|---|---|---|---|
| 1-4-1 | I<br>CAS # 591-50-4 | | 441 |

-continued
| Formula | Ar—X | Product | m/z |
|---|---|---|---|
| 1-4-3 | 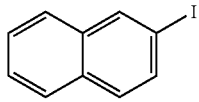<br>CAS #<br>612-55-5 | 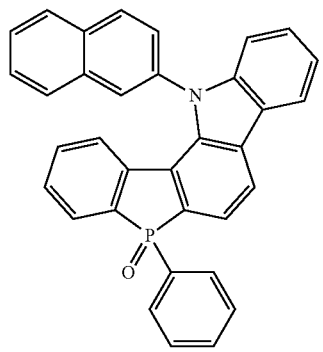 [SMILES: O=P1(c2ccccc2)c2ccccc2-c2c1ccc1c3ccccc3n(-c3ccc4ccccc4c3)c21] | 491 |
| 1-4-5 | 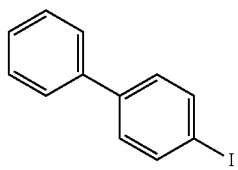<br>CAS #<br>1591-31-7 | 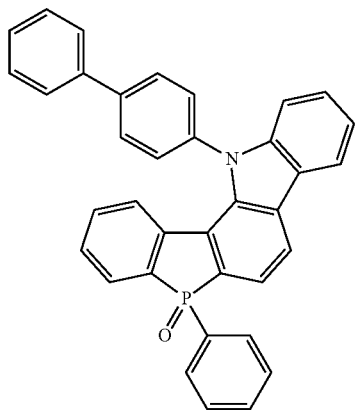 [SMILES: O=P1(c2ccccc2)c2ccccc2-c2c1ccc1c3ccccc3n(-c3ccc(-c4ccccc4)cc3)c21] | 517 |
| 1-4-10 | 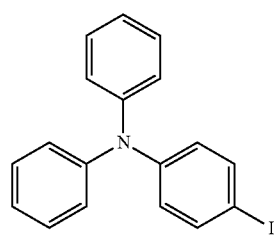<br>CAS #<br>38257-52-2 | 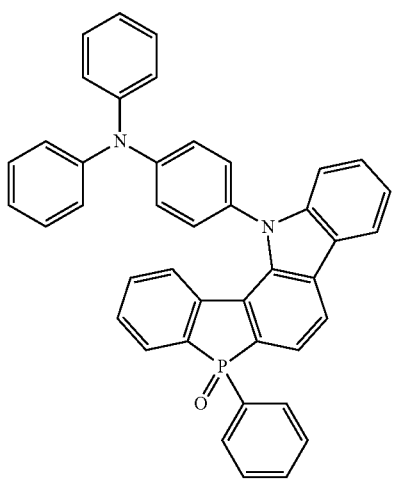 [SMILES: O=P1(c2ccccc2)c2ccccc2-c2c1ccc1c3ccccc3n(-c3ccc(N(c4ccccc4)c4ccccc4)cc3)c21] | 608 |

-continued
| Formula | Ar—X | Product | m/z |
|---|---|---|---|
| 1-4-111 | 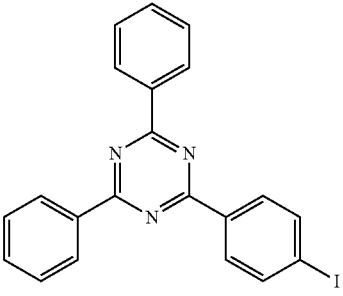<br>CAS #<br>777883-39-3 | 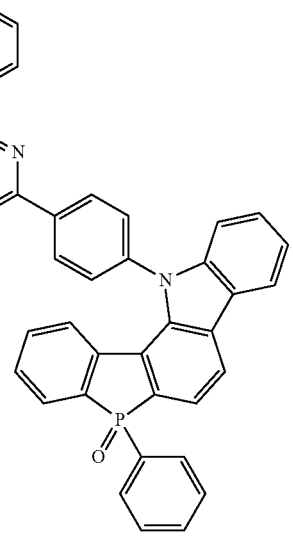 | 672 |
| 1-4-81 | 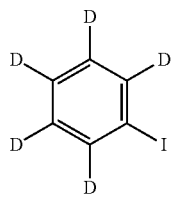<br>CAS #<br>7379-67-1 | 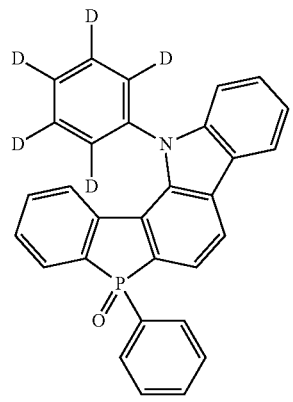 [SMILES: [2H]c1c([2H])c([2H])c(-n2c3ccccc3c3ccc4c(c32)-c2ccccc2P4(=O)c2ccccc2)c([2H])c1[2H]] | 446 |
| 1-4-34 | 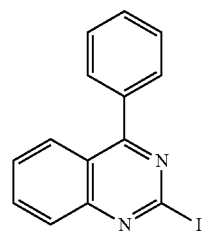<br>CAS #<br>1628067-38-8 | 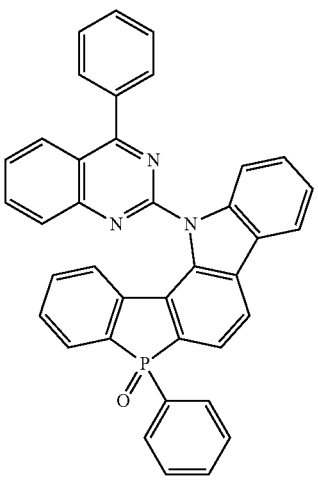 [SMILES: O=P1(c2ccccc2)c2ccccc2-c2c1ccc1c3ccccc3n(-c3nc(-c4ccccc4)c4ccccc4n3)c21] | 569 |

-continued

| Formula | Ar—X | Product | m/z |
|---|---|---|---|
| 1-4-40 | CAS # 144981-85-1 | | 557 |
| 1-4-51 | CAS # 502161-03-7 | | 606 |
| 1-4-189 | CAS # 5896-29-7 | | 531 |

-continued
| Formula | Ar—X | Product | m/z |
|---|---|---|---|
| 1-4-139 | 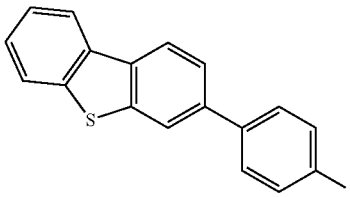 CAS # 1612853-56-1 | 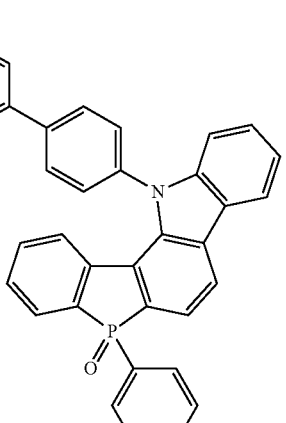 | 623 |
| 1-4-71 | 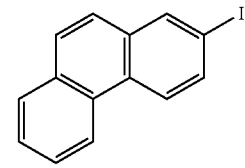 CAS # 55691-84-4 | 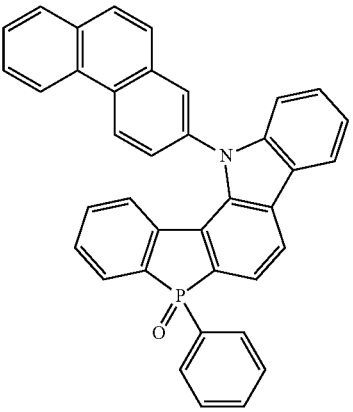 [SMILES: O=P1(c2ccccc2)c2ccccc2-c2c1ccc1c3ccccc3n(-c3ccc4c(ccc5ccccc54)c3)c21] | 541 |
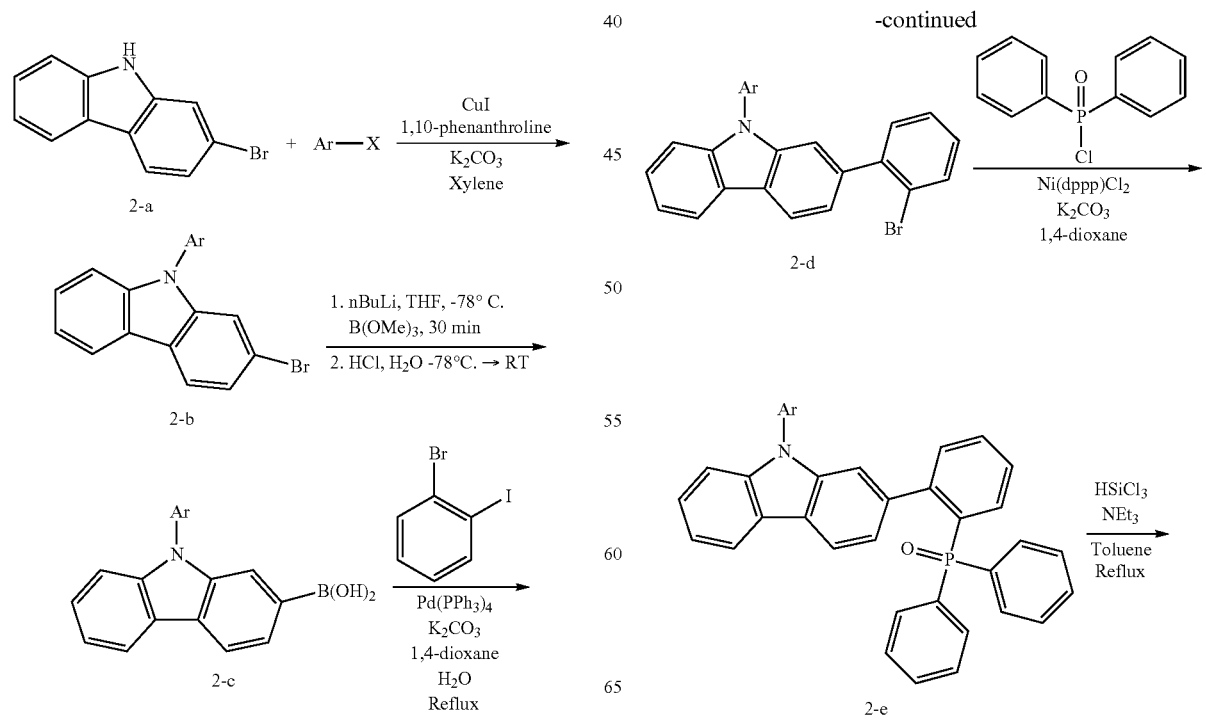

-continued
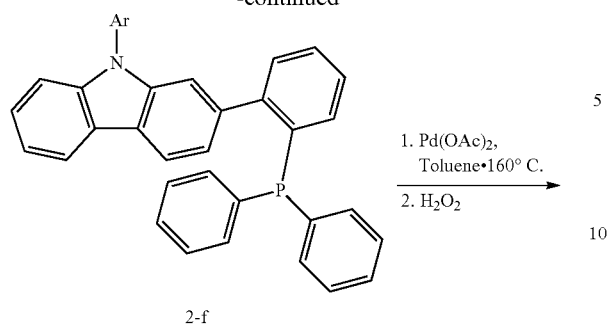
2-f
1. Pd(OAc)₂, Toluene•160° C.
2. H₂O₂
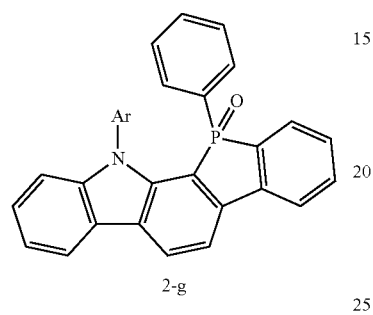
2-g
A product was synthesized in the same manner as in the method of producing Compound 1-g by using Compound 2-a (Cas No. 3652-90-2) instead of Compound 1-a.
| Formula | Ar—X | Product | m/z |
|---|---|---|---|
| 1-2-1 | 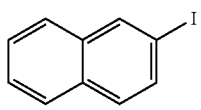<br>CAS # 591-50-4 | 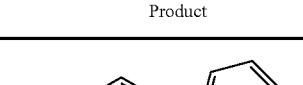 | 441 |
| 1-2-3 | 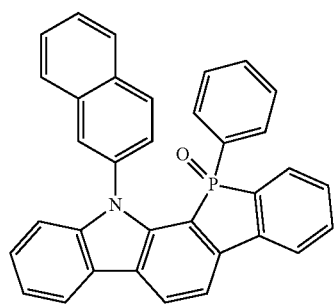<br>CAS # 612-55-5 | | 491 |

-continued
| Formula | Ar—X | Product | m/z |
|---|---|---|---|
| 1-2-5 | 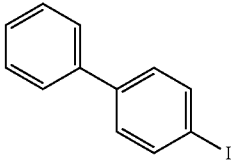<br>CAS # 1591-31-7 | 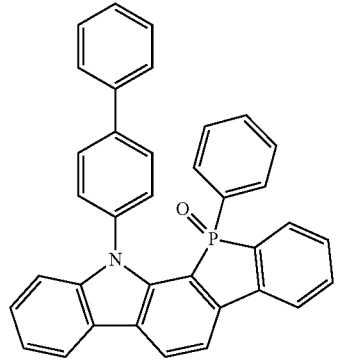 [SMILES: O=P1(c2ccccc2)c2ccccc2-c2ccc3c4ccccc4n(-c4ccc(-c5ccccc5)cc4)c3c21] | 517 |
| 1-2-10 | 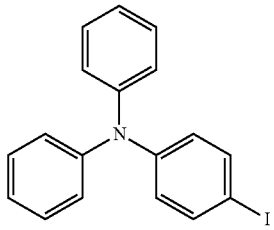<br>CAS # 38257-52-2 | 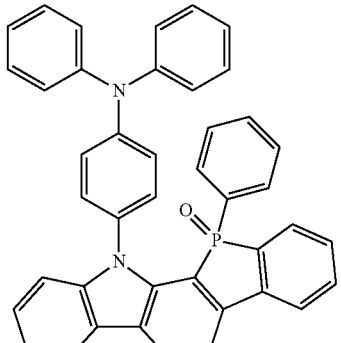 | 608 |
| 1-2-111 | 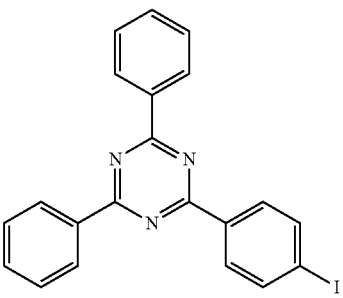<br>CAS # 777883-39-3 | 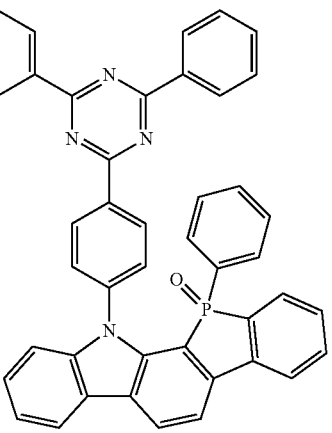 | 672 |
| 1-2-81 | 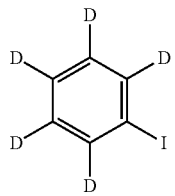<br>CAS # 7379-67-1 | 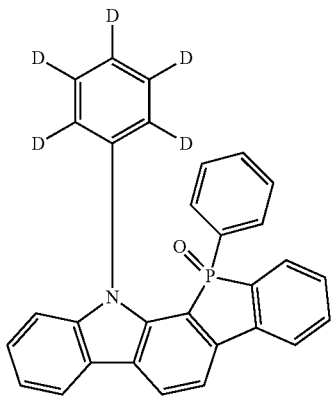 [SMILES: [2H]c1c([2H])c([2H])c(-n2c3ccccc3c3ccc4c(c32)P(=O)(c2ccccc2)c2ccccc2-4)c([2H])c1[2H]] | 446 |

-continued
| Formula | Ar—X | Product | m/z |
|---|---|---|---|
| 1-2-34 | 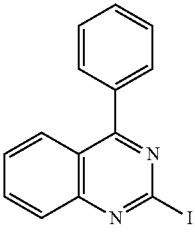<br>CAS #<br>1628067-38-8 | 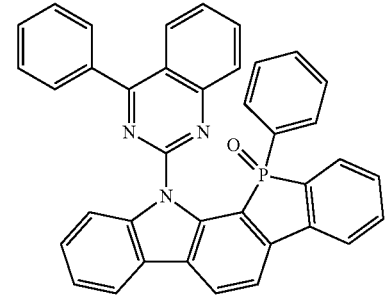 [SMILES: O=P1(c2ccccc2)c2ccccc2-c2ccc3c4ccccc4n(-c4nc(-c5ccccc5)c5ccccc5n4)c3c21] | 569 |
| 1-2-40 | 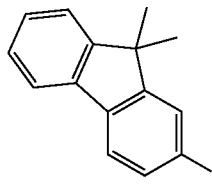<br>CAS #<br>144981-85-1 | 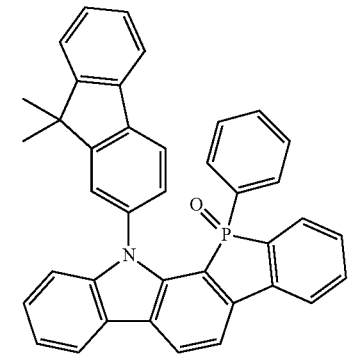 [SMILES: CC1(C)c2ccccc2-c2ccc(-n3c4ccccc4c4ccc5c(c43)P(=O)(c3ccccc3)c3ccccc3-5)cc21] | 557 |
| 1-2-51 | 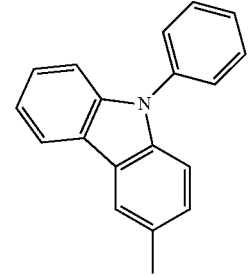<br>CAS #<br>502161-03-7 | 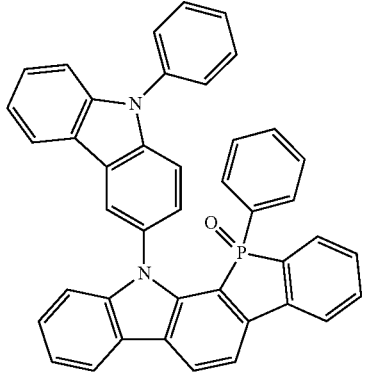 [SMILES: O=P1(c2ccccc2)c2ccccc2-c2ccc3c4ccccc4n(-c4ccc5c(c4)c4ccccc4n5-c4ccccc4)c3c21] | 606 |
| 1-2-189 | 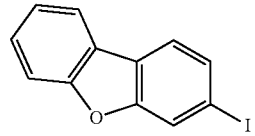<br>CAS #<br>5896-29-7 | 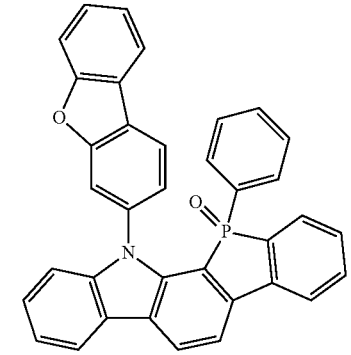 [SMILES: O=P1(c2ccccc2)c2ccccc2-c2ccc3c4ccccc4n(-c4ccc5c(c4)oc4ccccc45)c3c21] | 531 |

-continued
| Formula | Ar—X | Product | m/z |
|---|---|---|---|
| 1-2-139 | CAS # 1612853-56-1 | | 623 |
| 1-2-71 | CAS # 55691-84-4 | | 541 |
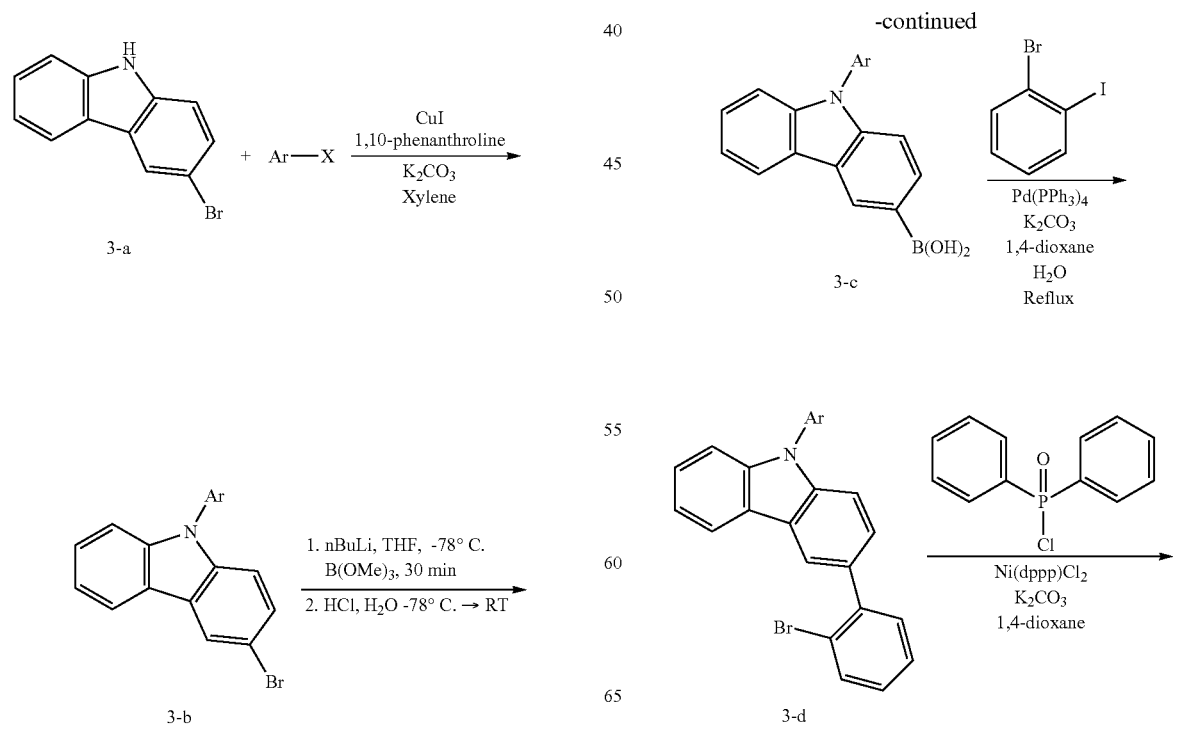

323
-continued
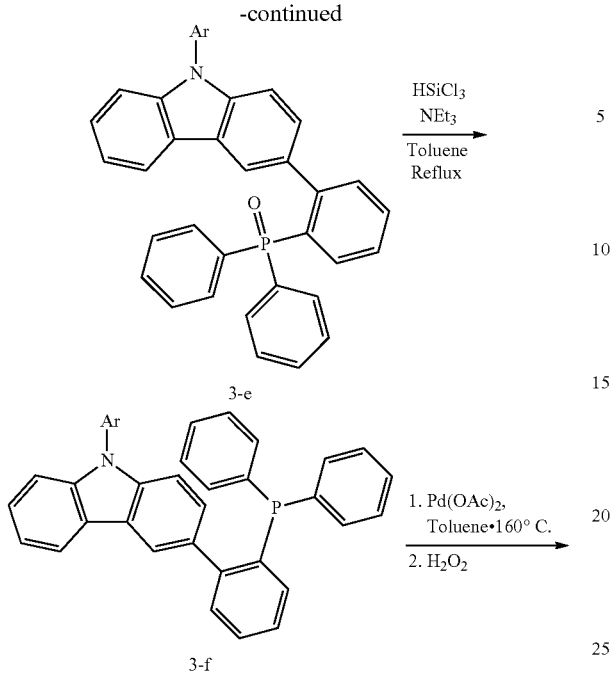
324
-continued
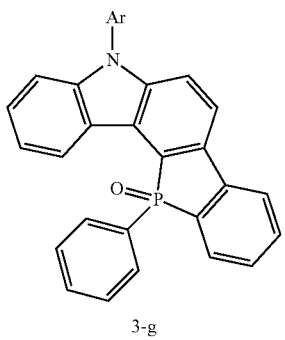
A product was synthesized in the same manner as in the method of producing Compound 1-g by using Compound 3-a (Cas No. 1592-95-6) instead of Compound 1-a.
| Formula | Ar—X | Product | m/z |
|---|---|---|---|
| 1-3-1 | ![](phenyl iodide) CAS # 591-50-4 | ![](product structure) | 441 |
| 1-3-3 | CAS # 612-55-5 | ![](product structure) | 491 |

-continued
| Formula | Ar—X | Product | m/z |
|---|---|---|---|
| 1-3-5 | 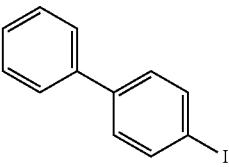 CAS # 1591-31-7 | 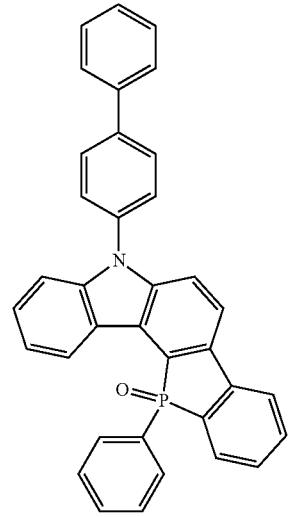 [SMILES: O=P1(c2ccccc2)c2ccccc2-c2ccc3c(c21)c1ccccc1n3-c1ccc(-c2ccccc2)cc1] | 517 |
| 1-3-10 | 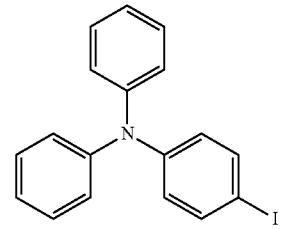 CAS # 38257-52-2 | 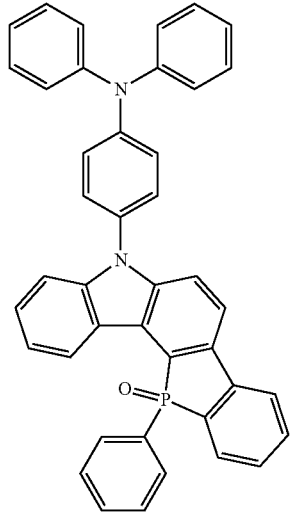 [SMILES: O=P1(c2ccccc2)c2ccccc2-c2ccc3c(c21)c1ccccc1n3-c1ccc(N(c2ccccc2)c2ccccc2)cc1] | 608 |
| 1-3-111 | 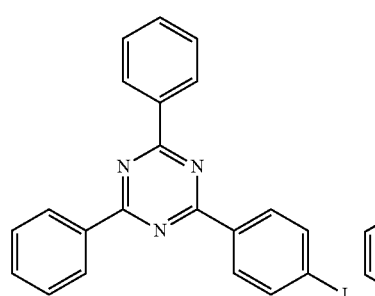 CAS # 777883-39-3 | 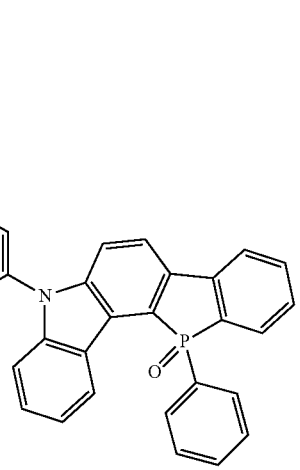 | 672 |

-continued
| Formula | Ar—X | Product | m/z |
|---|---|---|---|
| 1-3-81 | 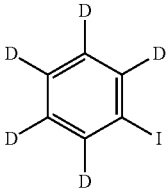<br>CAS #<br>7379-67-1 | 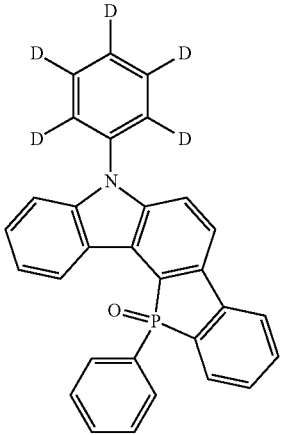 [SMILES: [2H]c1c([2H])c([2H])c(-n2c3ccccc3c3c4c(ccc32)-c2ccccc2P4(=O)c2ccccc2)c([2H])c1[2H]] | 446 |
| 1-3-34 | 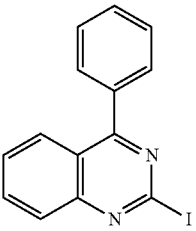<br>CAS #<br>1628067-38-8 | 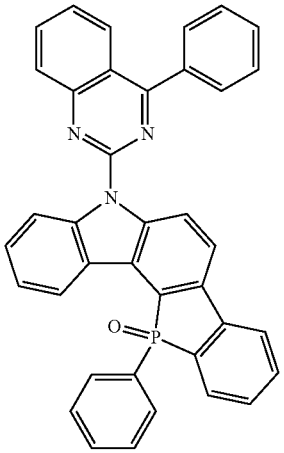 [SMILES: O=P1(c2ccccc2)c2ccccc2-c2ccc3c(c21)c1ccccc1n3-c1nc(-c2ccccc2)c2ccccc2n1] | 569 |
| 1-3-40 | 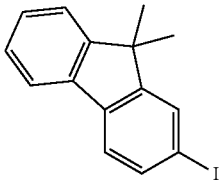<br>CAS #<br>144981-85-1 | 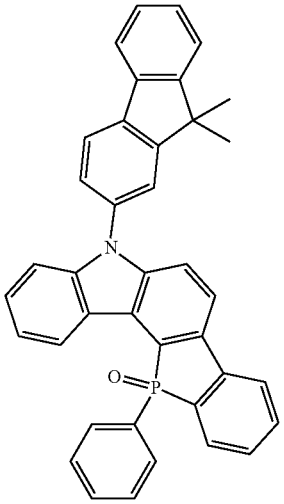 [SMILES: CC1(C)c2ccccc2-c2ccc(-n3c4ccccc4c4c5c(ccc43)-c3ccccc3P5(=O)c3ccccc3)cc21] | 557 |

| Formula | Ar—X | Product | m/z |
|---|---|---|---|
| 1-3-51 | 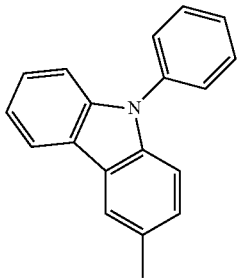<br>CAS # 502161-03-7 | 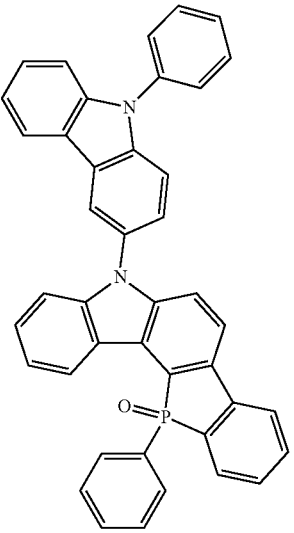 [SMILES: O=P1(c2ccccc2)c2ccccc2-c2ccc3c(c21)c1ccccc1n3-c1ccc2c(c1)c1ccccc1n2-c1ccccc1] | 606 |
| 1-3-189 | 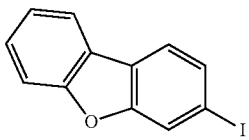<br>CAS # 5896-29-7 | 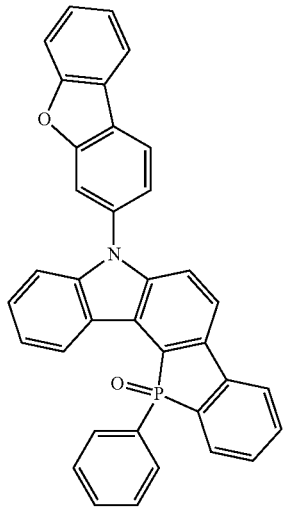 [SMILES: O=P1(c2ccccc2)c2ccccc2-c2ccc3c(c21)c1ccccc1n3-c1ccc2c(c1)oc1ccccc12] | 531 |

-continued
| Formula | Ar—X | Product | m/z |
|---|---|---|---|
| 1-3-139 | 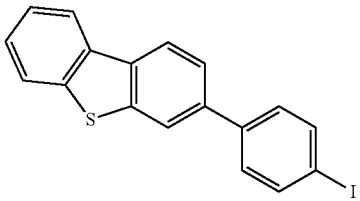<br>CAS # 1612853-56-1 | 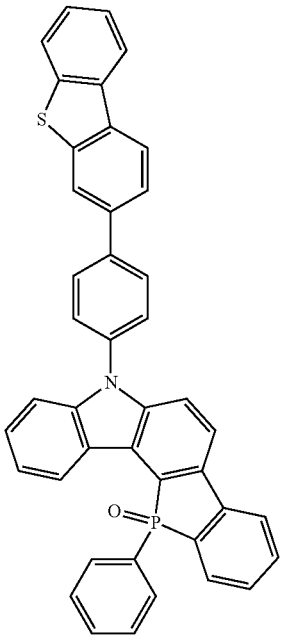 [SMILES: O=P1(c2ccccc2)c2ccccc2-c2ccc3c(c21)c1ccccc1n3-c1ccc(-c2ccc3c(c2)sc2ccccc23)cc1] | 623 |
| 1-3-71 | 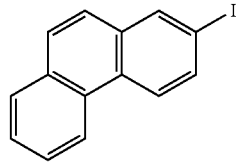<br>CAS # 55691-84-4 | 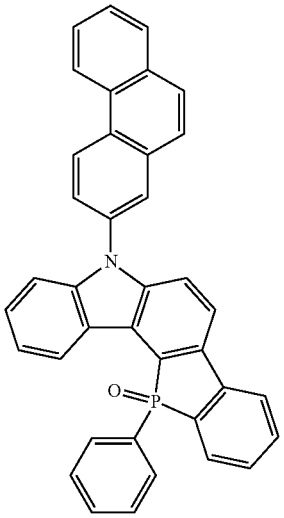 [SMILES: O=P1(c2ccccc2)c2ccccc2-c2ccc3c(c21)c1ccccc1n3-c1ccc2c(ccc3ccccc32)c1] | 541 |
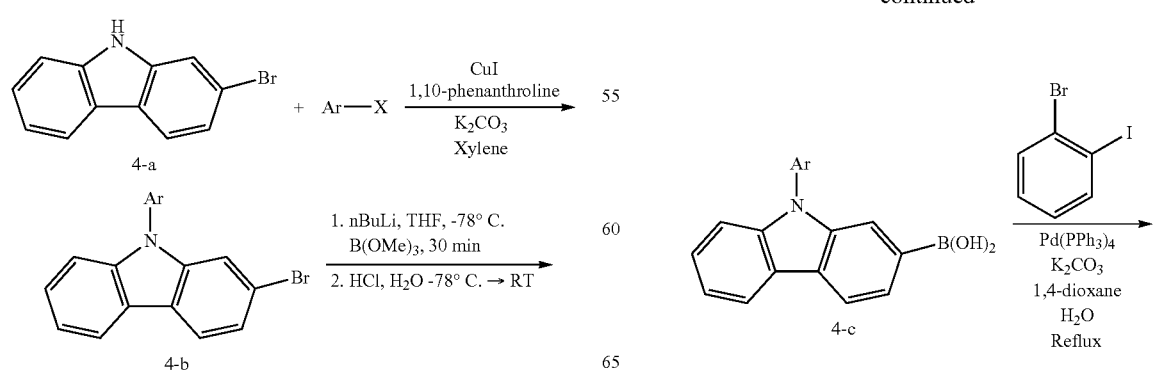

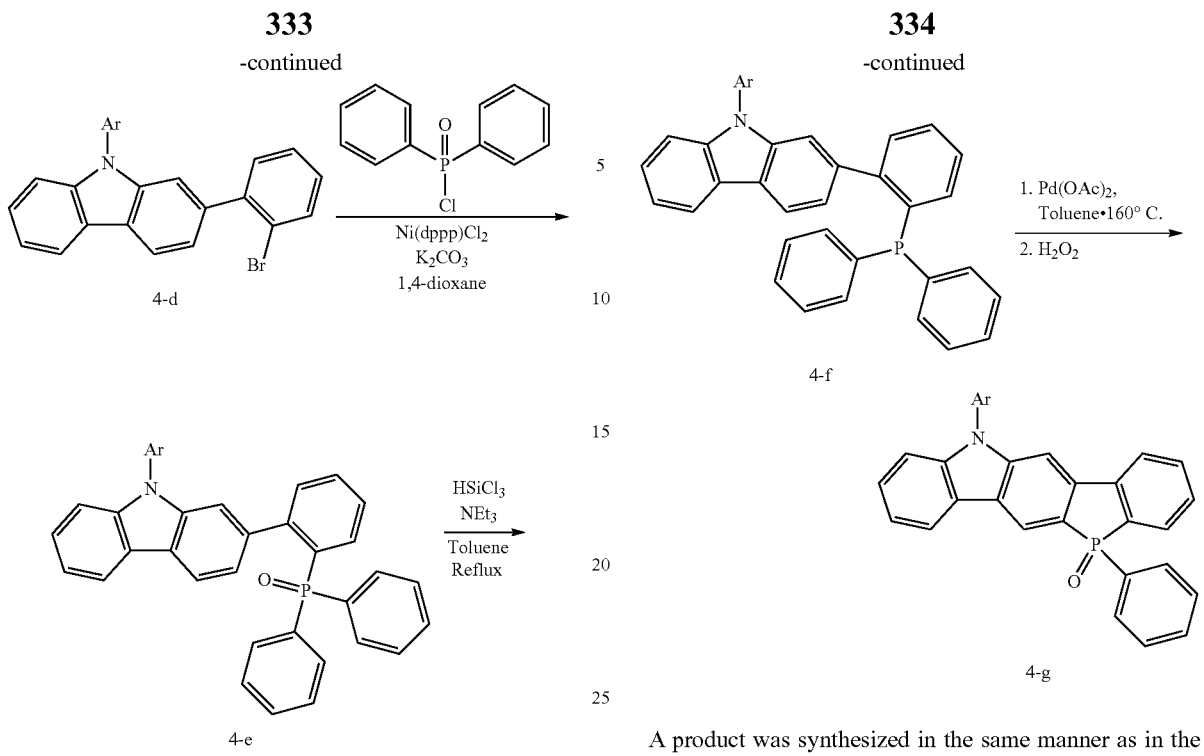
A product was synthesized in the same manner as in the method of producing Compound 1-g by using Compound 4-a (Cas No. 3652-89-9) instead of Compound 1-a.
| No. | Ar—X | Product | m/z |
|---|---|---|---|
| 1-1-1 | CAS # 591-50-4 | | 441 |
| 1-1-3 | CAS # 612-55-5 | | 491 |

-continued
| No. | Ar—X | Product | m/z |
|---|---|---|---|
| 1-1-5 | 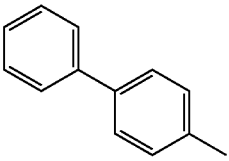<br>CAS # 1591-31-7 | 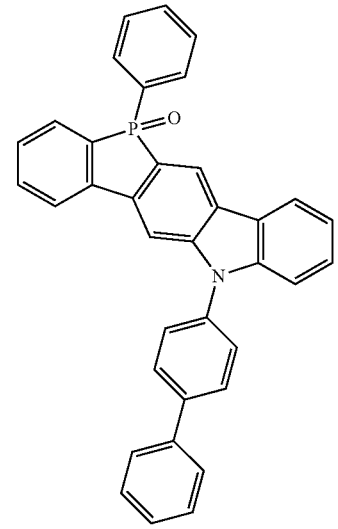 [SMILES: O=P1(c2ccccc2)c2ccccc2-c2cc3c(cc21)c1ccccc1n3-c1ccc(-c2ccccc2)cc1] | 517 |
| 1-1-10 | 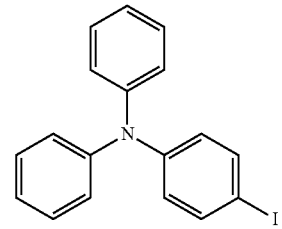<br>CAS # 38257-52-2 | 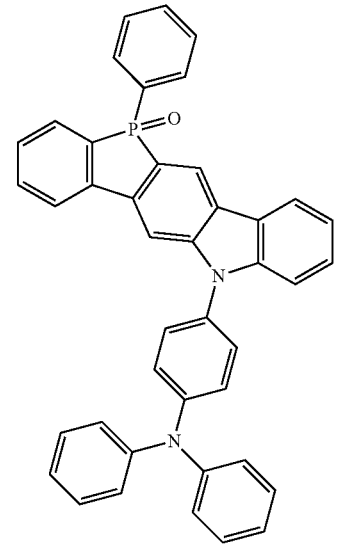 [SMILES: O=P1(c2ccccc2)c2ccccc2-c2cc3c(cc21)c1ccccc1n3-c1ccc(N(c2ccccc2)c2ccccc2)cc1] | 608 |
| 1-1-111 | 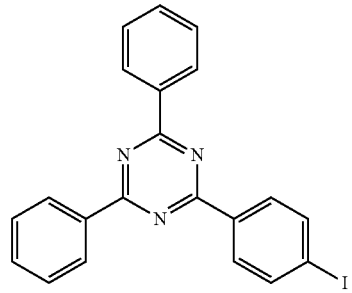<br>CAS # 777883-39-3 | 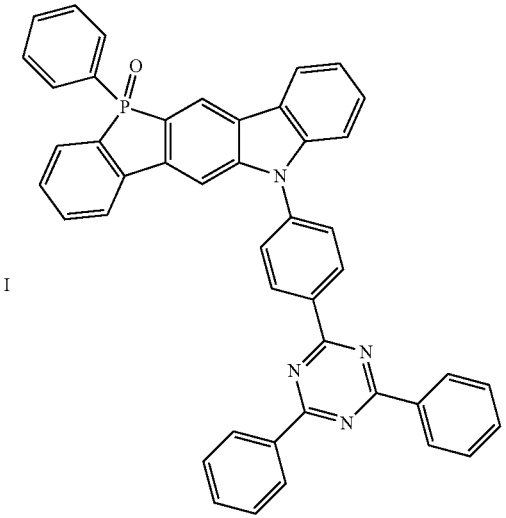 | 672 |

| No. | Ar—X | Product | m/z |
|---|---|---|---|
| 1-1-81 | 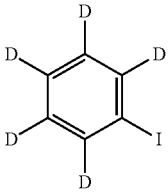<br>CAS #<br>7379-67-1 | 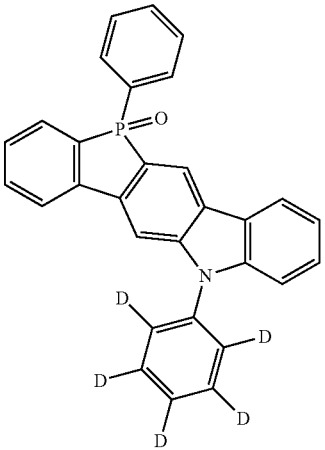 [SMILES: [2H]c1c([2H])c([2H])c(-n2c3ccccc3c3cc4c(cc32)-c2ccccc2P4(=O)c2ccccc2)c([2H])c1[2H]] | 446 |
| 1-1-34 | 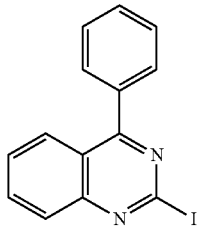<br>CAS #<br>1628067-38-8 | 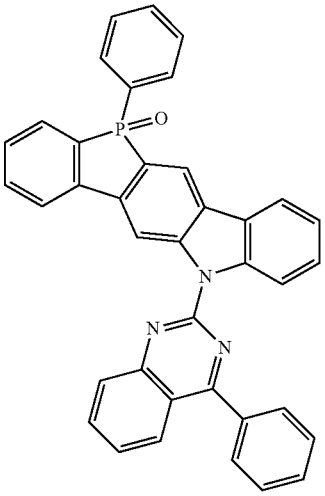 [SMILES: O=P1(c2ccccc2)c2ccccc2-c2cc3c(cc21)c1ccccc1n3-c1nc(-c2ccccc2)c2ccccc2n1] | 569 |
| 1-1-40 | 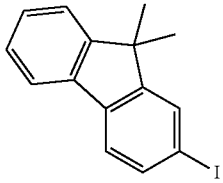<br>CAS #<br>144981-85-1 | 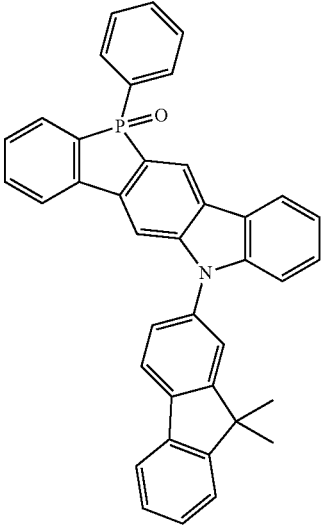 | 557 |

| No. | Ar—X | Product | m/z |
|---|---|---|---|
| 1-1-51 | CAS # 502161-03-7 | | 606 |
| 1-1-188 | CAS # 5896-29-7 | | 531 |
| 1-1-139 | CAS # 1612853-56-1 | | 623 |

-continued
| No. | Ar—X | Product | m/z |
|---|---|---|---|
| 1-1-71 | 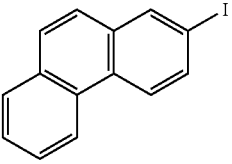<br>CAS # 55691-84-4 | 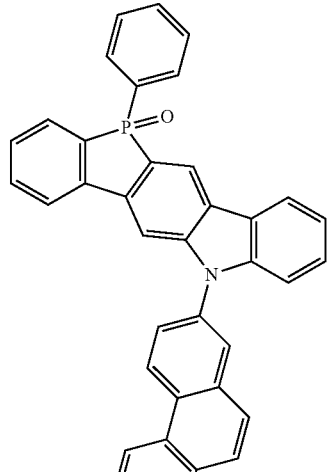 | 541 |
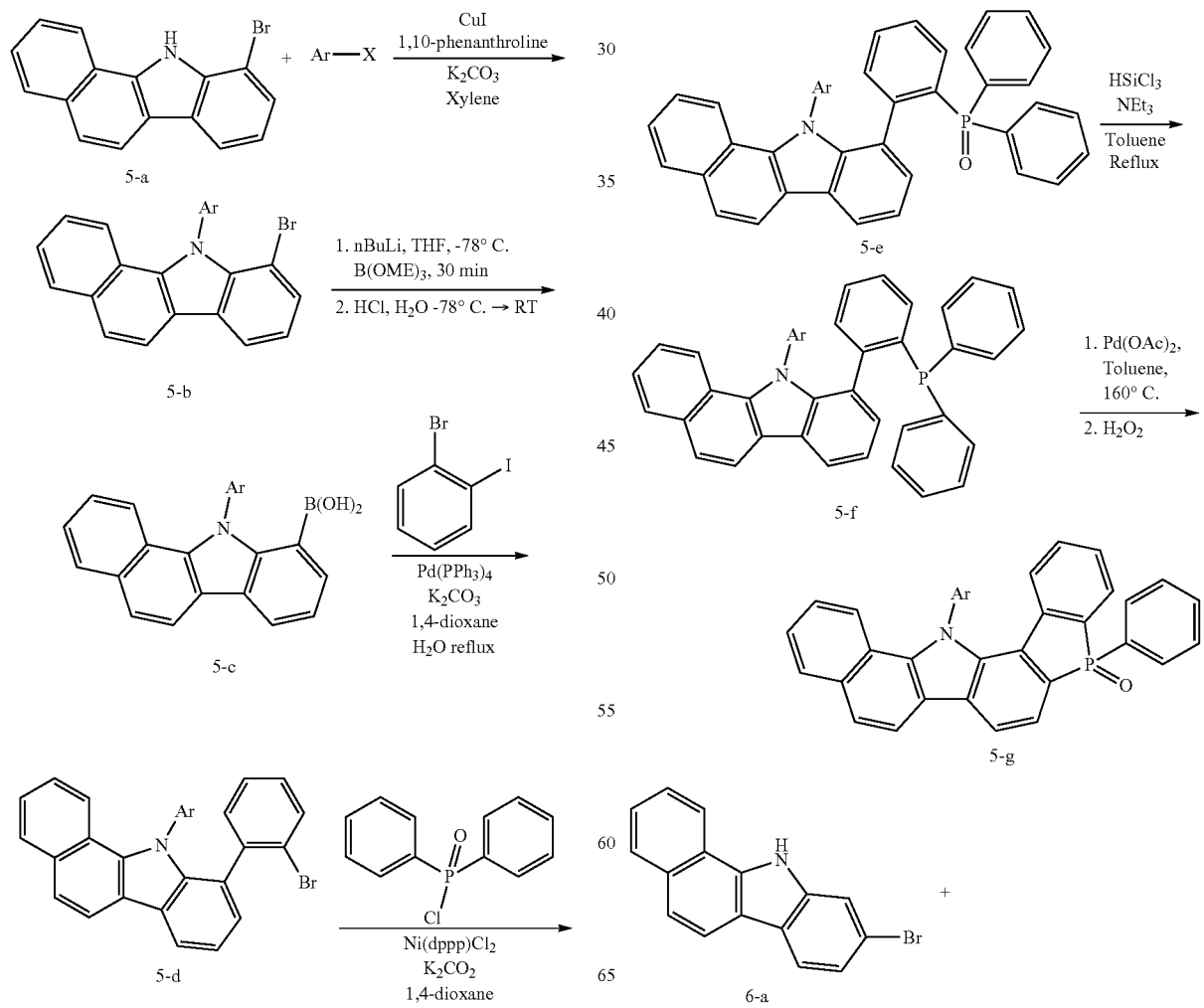

-continued
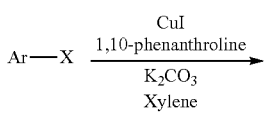
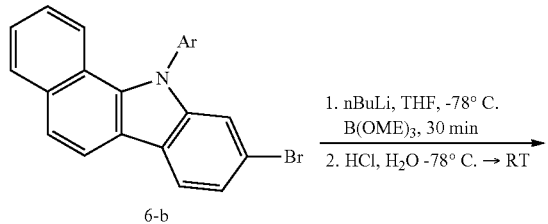
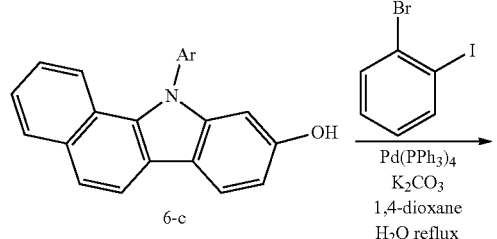
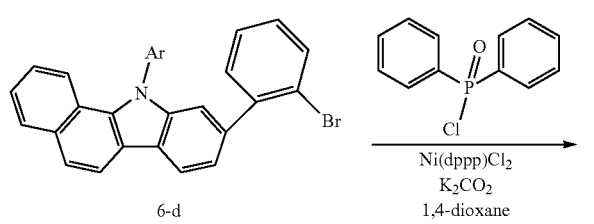
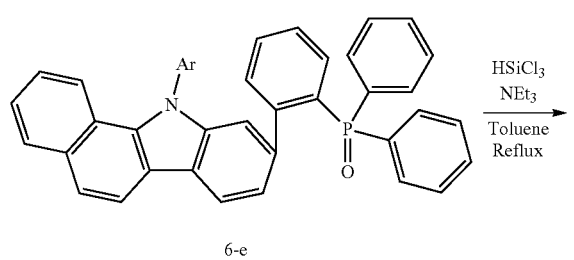
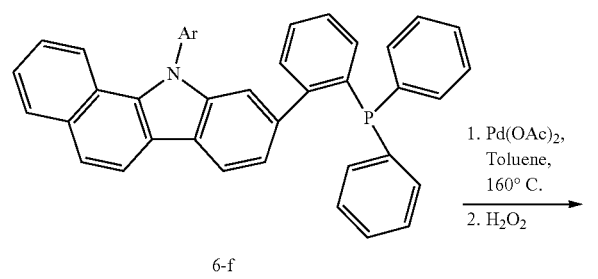
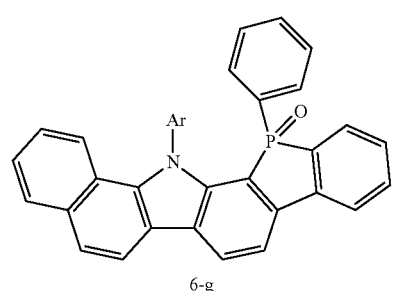
-continued
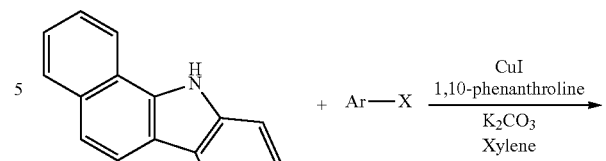
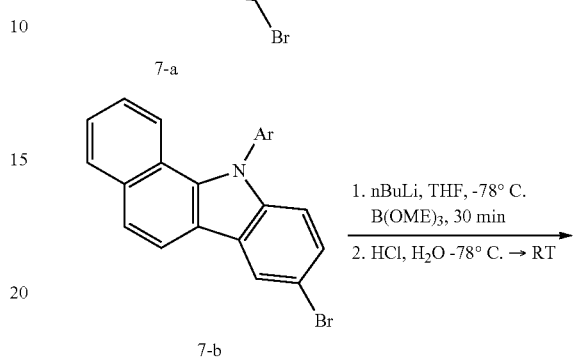
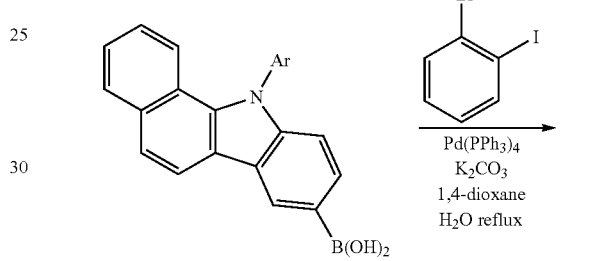
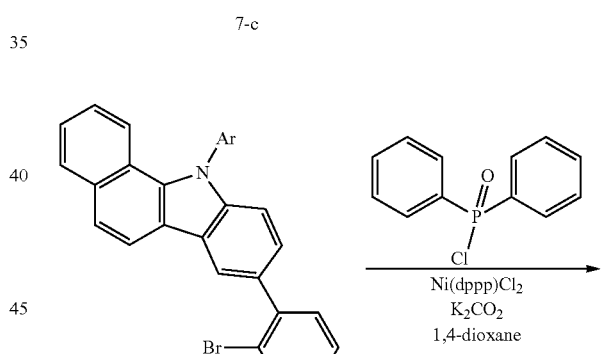

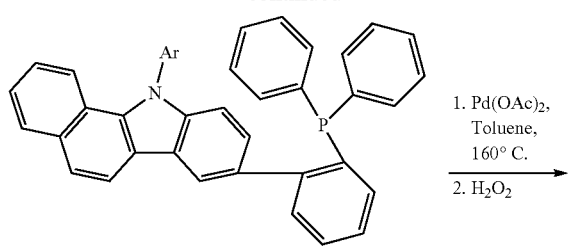
7-f
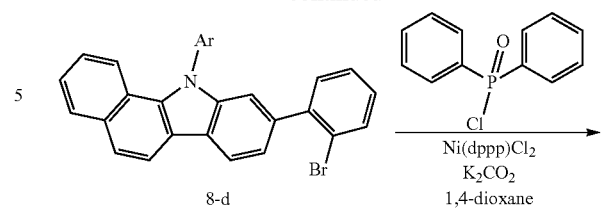
8-d
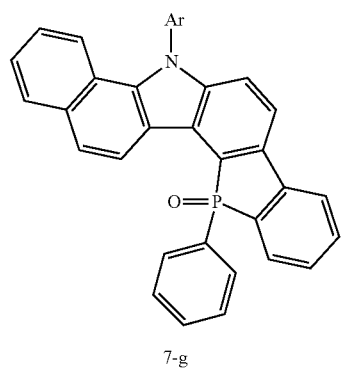
7-g
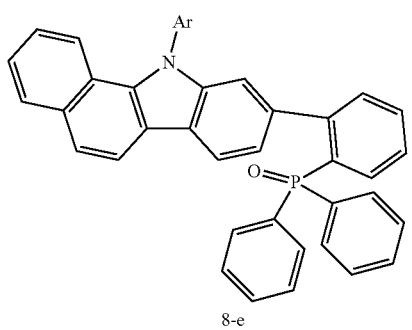
8-e
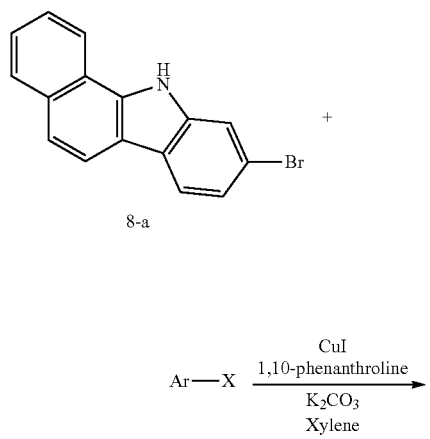
8-a
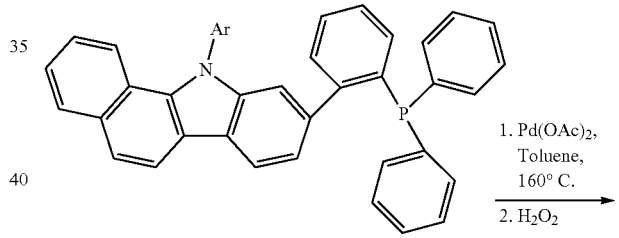
8-f
Ar—X  →  CuI, 1,10-phenanthroline, K₂CO₃, Xylene
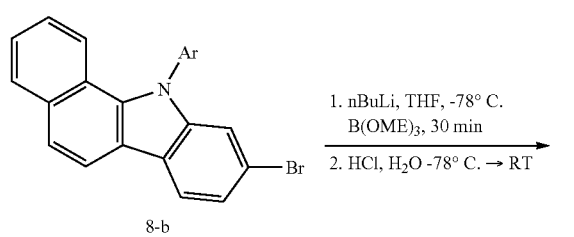
8-b  →  1. nBuLi, THF, -78° C. B(OME)₃, 30 min  2. HCl, H₂O -78° C. → RT
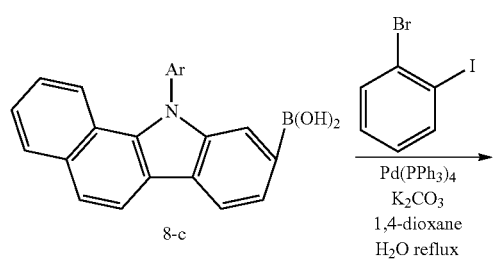
8-c  +  2-bromo-iodobenzene  →  Pd(PPh₃)₄, K₂CO₃, 1,4-dioxane, H₂O reflux
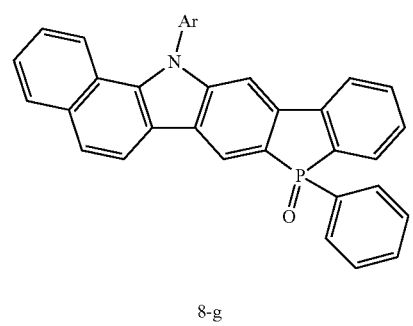
8-g
Products were synthesized in the same manner as in the method of producing Compounds 1-g to 4-g, except that the following Formulae 5-a to 8-a were used instead of Compound 1-a.

| No. | Reactant | Ar—X | Product | m/z |
|---|---|---|---|---|
| 1-4-194 | 5-a | CAS # 591-50-4 | | 491 |
| 1-2-194 | 6-a | CAS # 591-50-4 | | 491 |
| 1-3-194 | 7-a | CAS # 591-50-4 | | 491 |
| 1-1-194 | 8-a | CAS # 591-50-4 | | 491 |
-continued
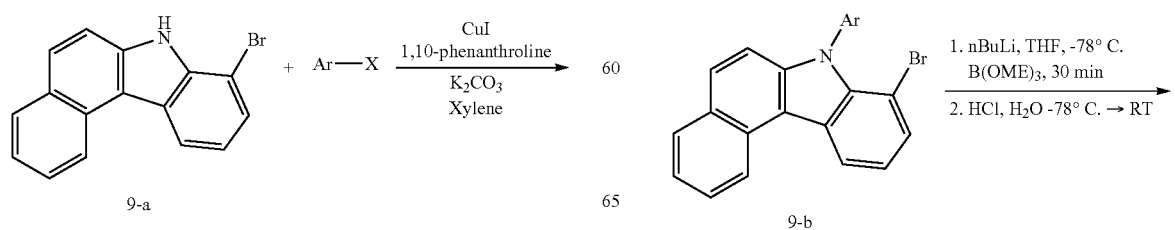

-continued
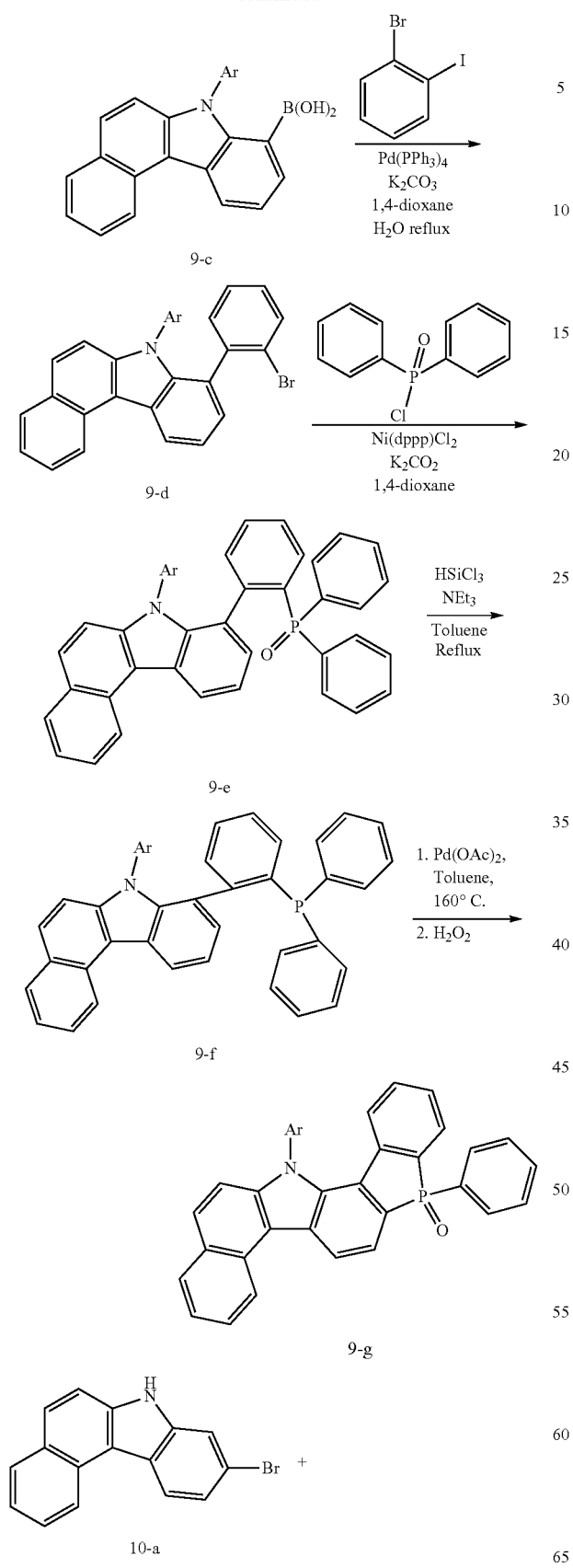
9-c
9-d
9-e
9-f
9-g
10-a
-continued
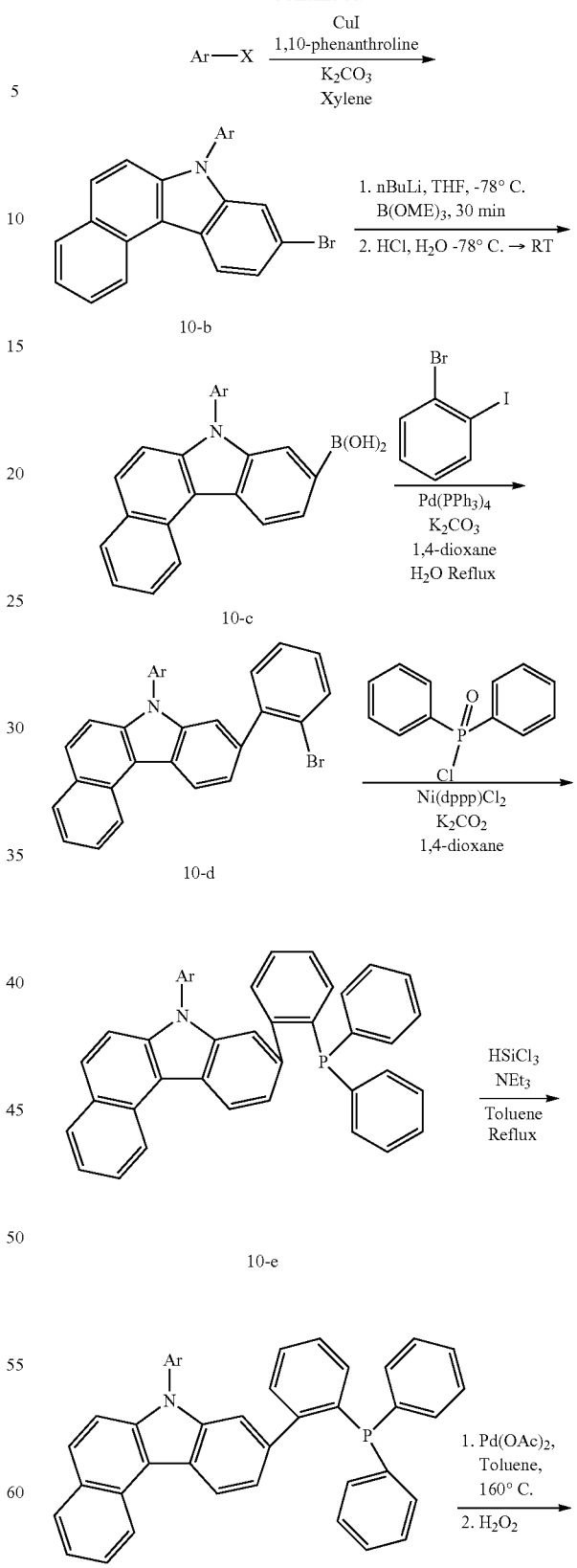
10-b
10-c
10-d
10-e
10-f

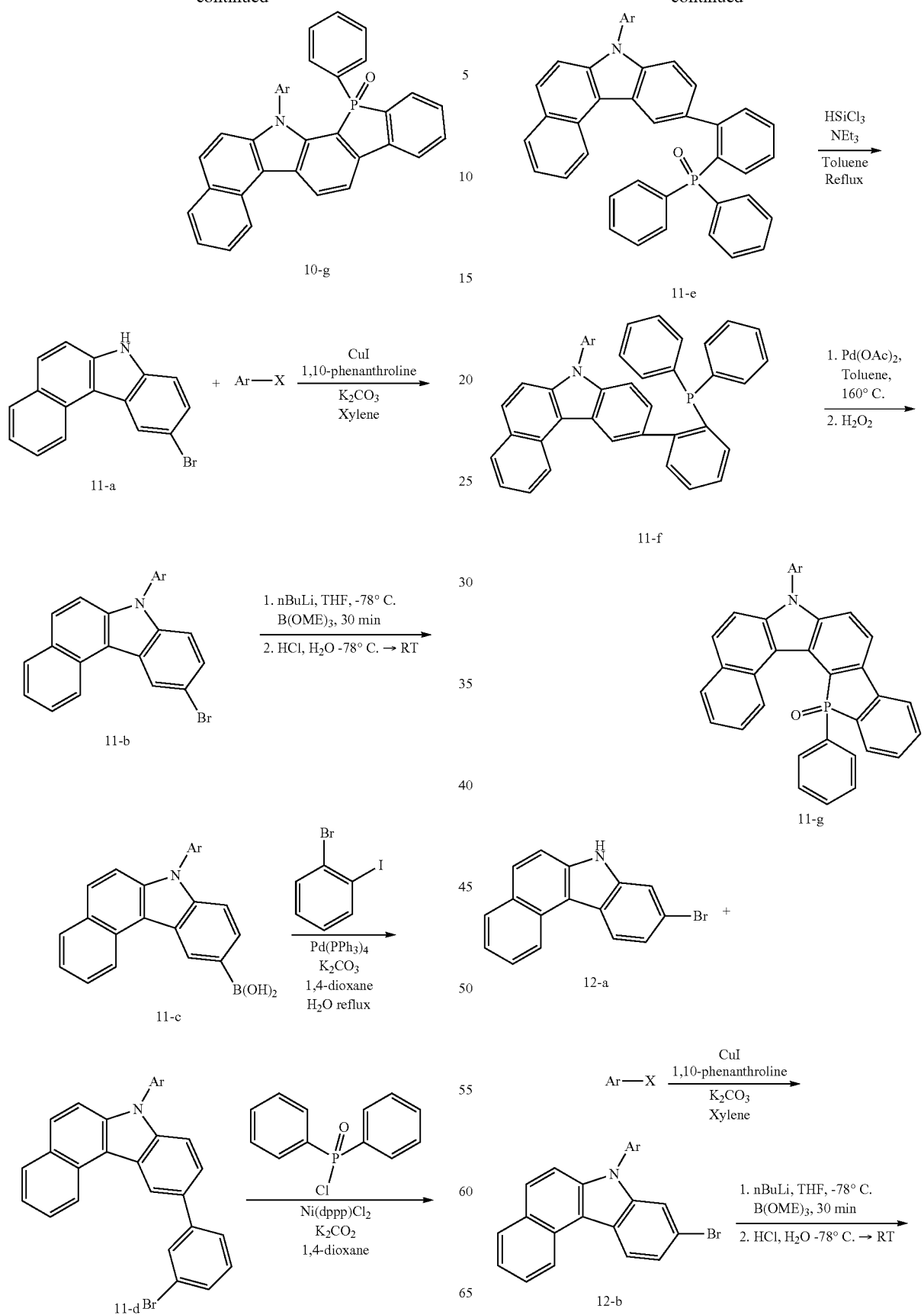

353
-continued
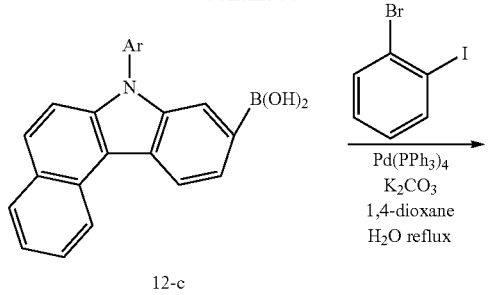
354
-continued
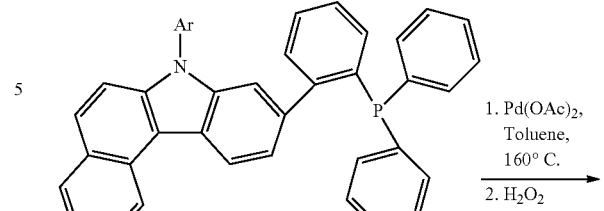
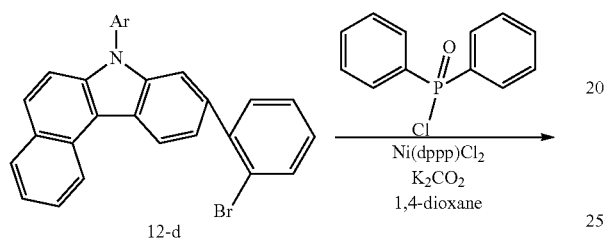
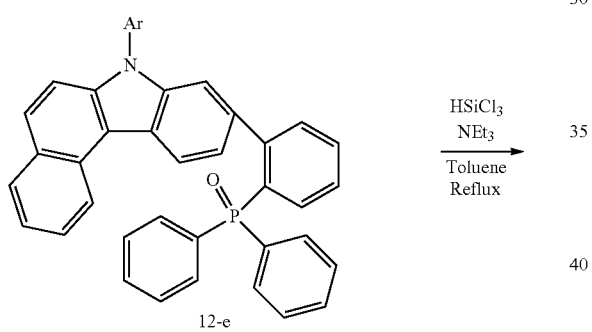
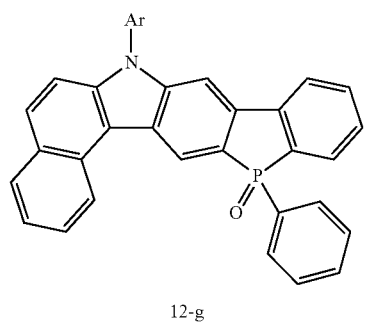
Products were synthesized in the same manner as in the method of producing Compounds 1-g to 4-g, except that the following Formulae 9-a to 12-a were used instead of Compound 1-a.
| No. | Reactant | Ar—X | Product | m/z |
|---|---|---|---|---|
| 1-4-195 | 9-a | CAS # 591-50-4 | | 491 |

-continued

| No. | Reactant | Ar—X | Product | m/z |
|---|---|---|---|---|
| 1-2-195 | 10-a | CAS # 591-50-4 | | 491 |
| 1-3-195 | 11-a | CAS # 591-50-4 | | 491 |
| 1-1-195 | 12-a | CAS # 591-50-4 | | 491 |

Comparative Example 1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice using distilled water for 10 minutes. After the washing using distilled water was completed, ultrasonic washing was conducted using isopropyl alcohol, acetone, and methanol solvents, and drying was conducted, and then the product was transferred to a plasma cleaning machine. In addition, the substrate was cleaned using oxygen plasma for 5 minutes, and then transferred to a vacuum evaporator.

Hexanitrile hexaazatriphenylene (HAT) of the following Formula was thermally vacuum deposited to have a thickness of 500 Å on a transparent ITO electrode, which was thus prepared, thereby forming a hole injection layer.

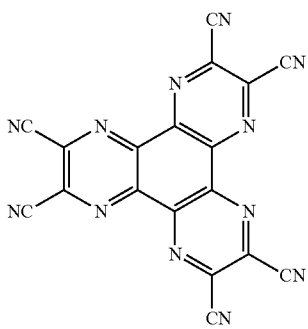

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

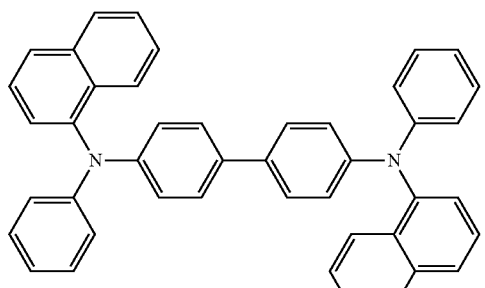

[NPB]

Subsequently, the following compound tris(4-(9H-carbazol-9-yl)phenyl)amine (TCTA) was vacuum deposited to have a film thickness of 100 Å on the hole transporting layer, thereby forming an electron blocking layer.

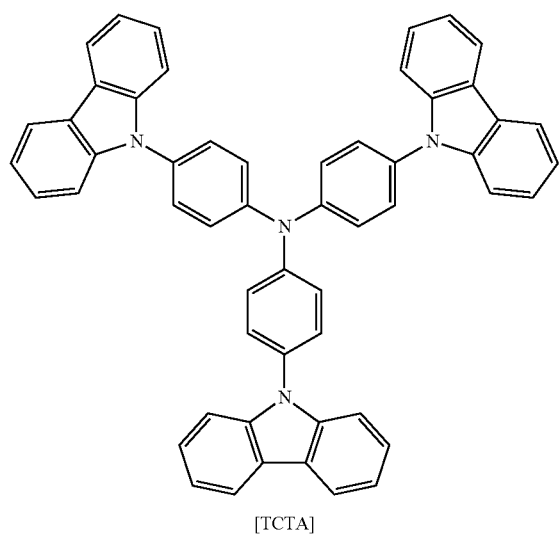

[TCTA]

Subsequently, the following BH and BD were vacuum deposited at a weight ratio of 25:1 to have a film thickness of 300 Å on the electron blocking layer, thereby forming a light emitting layer.

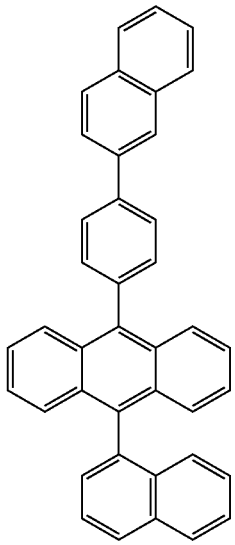

[BH]

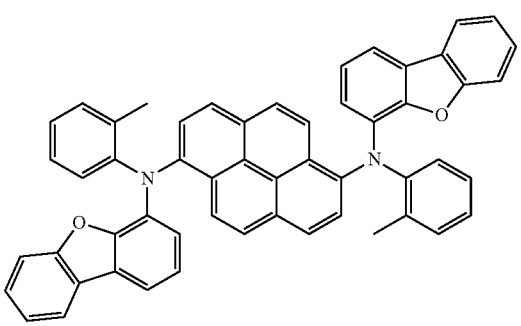

[BD]

[ET1]

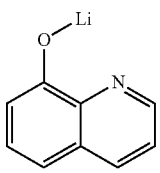

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were subsequently deposited to have a thickness of 12 Å and 2,000 Å, respectively, on the electron injection and transporting layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

Experimental Example 1-1

An organic light emitting device was manufactured in the same manner as in Experimental Example 1, except that the compound of Formula 1-4-1 was used instead of Compound ET1 in Experimental Example 1.

Experimental Example 1-2

An organic light emitting device was manufactured in the same manner as in Experimental Example 1, except that the compound of Formula 1-4-3 was used instead of Compound ET1 in Experimental Example 1.

Experimental Example 1-3

An organic light emitting device was manufactured in the same manner as in Experimental Example 1, except that the compound of Formula 1-4-40 was used instead of Compound ET1 in Experimental Example 1.

Experimental Example 1-4

An organic light emitting device was manufactured in the same manner as in Experimental Example 1, except that the compound of Formula 1-4-5 was used instead of Compound ET1 in Experimental Example 1.

Experimental Example 1-5

An organic light emitting device was manufactured in the same manner as in Experimental Example 1, except that the compound of Formula 1-4-10 was used instead of Compound ET1 in Experimental Example 1.

Experimental Example 1-6

An organic light emitting device was manufactured in the same manner as in Experimental Example 1, except that the compound of Formula 1-4-25 was used instead of Compound ET1 in Experimental Example 1.

Experimental Example 1-7

An organic light emitting device was manufactured in the same manner as in Experimental Example 1, except that the compound of Formula 1-4-81 was used instead of Compound ET1 in Experimental Example 1.

Experimental Example 1-8

An organic light emitting device was manufactured in the same manner as in Experimental Example 1, except that the compound of Formula 1-4-71 was used instead of Compound ET1 in Experimental Example 1.

Experimental Example 1-9

An organic light emitting device was manufactured in the same manner as in Experimental Example 1, except that the compound of Formula 1-2-1 was used instead of Compound ET1 in Experimental Example 1.

Experimental Example 1-10

An organic light emitting device was manufactured in the same manner as in Experimental Example 1, except that the compound of Formula 1-2-3 was used instead of Compound ET1 in Experimental Example 1.

Experimental Example 1-11

An organic light emitting device was manufactured in the same manner as in Experimental Example 1, except that the compound of Formula 1-2-40 was used instead of Compound ET1 in Experimental Example 1.

Experimental Example 1-12

An organic light emitting device was manufactured in the same manner as in Experimental Example 1, except that the compound of Formula 1-2-5 was used instead of Compound ET1 in Experimental Example 1.

Experimental Example 1-13

An organic light emitting device was manufactured in the same manner as in Experimental Example 1, except that the compound of Formula 1-2-10 was used instead of Compound ET1 in Experimental Example 1.

Experimental Example 1-14

An organic light emitting device was manufactured in the same manner as in Experimental Example 1, except that the compound of Formula 1-2-139 was used instead of Compound ET1 in Experimental Example 1.

Experimental Example 1-15

An organic light emitting device was manufactured in the same manner as in Experimental Example 1, except that the compound of Formula 1-2-81 was used instead of Compound ET1 in Experimental Example 1.

Experimental Example 1-16

An organic light emitting device was manufactured in the same manner as in Experimental Example 1, except that the compound of Formula 1-2-71 was used instead of Compound ET1 in Experimental Example 1.

Experimental Example 1-17

An organic light emitting device was manufactured in the same manner as in Experimental Example 1, except that the compound of Formula 1-3-1 was used instead of Compound ET1 in Experimental Example 1.

Experimental Example 1-18

An organic light emitting device was manufactured in the same manner as in Experimental Example 1, except that the compound of Formula 1-3-3 was used instead of Compound ET1 in Experimental Example 1.

Experimental Example 1-19

An organic light emitting device was manufactured in the same manner as in Experimental Example 1, except that the compound of Formula 1-3-40 was used instead of Compound ET1 in Experimental Example 1.

Experimental Example 1-20

An organic light emitting device was manufactured in the same manner as in Experimental Example 1, except that the compound of Formula 1-3-5 was used instead of Compound ET1 in Experimental Example 1.

Experimental Example 1-21

An organic light emitting device was manufactured in the same manner as in Experimental Example 1, except that the compound of Formula 1-3-10 was used instead of Compound ET1 in Experimental Example 1.

Experimental Example 1-22

An organic light emitting device was manufactured in the same manner as in Experimental Example 1, except that the compound of Formula 1-3-139 was used instead of Compound ET1 in Experimental Example 1.

Experimental Example 1-23

An organic light emitting device was manufactured in the same manner as in Experimental Example 1, except that the compound of Formula 1-3-81 was used instead of Compound ET1 in Experimental Example 1.

Experimental Example 1-24

An organic light emitting device was manufactured in the same manner as in Experimental Example 1, except that the compound of Formula 1-3-71 was used instead of Compound ET1 in Experimental Example 1.

Experimental Example 1-25

An organic light emitting device was manufactured in the same manner as in Experimental Example 1, except that the compound of Formula 1-1-1 was used instead of Compound ET1 in Experimental Example 1.

Experimental Example 1-26

An organic light emitting device was manufactured in the same manner as in Experimental Example 1, except that the compound of Formula 1-1-3 was used instead of Compound ET1 in Experimental Example 1.

Experimental Example 1-27

An organic light emitting device was manufactured in the same manner as in Experimental Example 1, except that the compound of Formula 1-1-40 was used instead of Compound ET1 in Experimental Example 1.

Experimental Example 1-28

An organic light emitting device was manufactured in the same manner as in Experimental Example 1, except that the compound of Formula 1-1-5 was used instead of Compound ET1 in Experimental Example 1.

Experimental Example 1-29

An organic light emitting device was manufactured in the same manner as in Experimental Example 1, except that the compound of Formula 1-1-10 was used instead of Compound ET1 in Experimental Example 1.

Experimental Example 1-30

An organic light emitting device was manufactured in the same manner as in Experimental Example 1, except that the compound of Formula 1-1-139 was used instead of Compound ET1 in Experimental Example 1.

Experimental Example 1-31

An organic light emitting device was manufactured in the same manner as in Experimental Example 1, except that the compound of Formula 1-1-81 was used instead of Compound ET1 in Experimental Example 1.

Experimental Example 1-32

An organic light emitting device was manufactured in the same manner as in Experimental Example 1, except that the compound of Formula 1-1-71 was used instead of Compound ET1 in Experimental Example 1.

Experimental Example 1-33

An organic light emitting device was manufactured in the same manner as in Experimental Example 1, except that the compound of Formula 1-4-194 was used instead of Compound ET1 in Experimental Example 1.

Experimental Example 1-34

An organic light emitting device was manufactured in the same manner as in Experimental Example 1, except that the compound of Formula 1-2-194 was used instead of Compound ET1 in Experimental Example 1.

Experimental Example 1-35

An organic light emitting device was manufactured in the same manner as in Experimental Example 1, except that the compound of Formula 1-3-194 was used instead of Compound ET1 in Experimental Example 1.

Experimental Example 1-36

An organic light emitting device was manufactured in the same manner as in Experimental Example 1, except that the compound of Formula 1-1-194 was used instead of Compound ET1 in Experimental Example 1.

Experimental Example 1-37

An organic light emitting device was manufactured in the same manner as in Experimental Example 1, except that the compound of Formula 1-4-195 was used instead of Compound ET1 in Experimental Example 1.

Experimental Example 1-38

An organic light emitting device was manufactured in the same manner as in Experimental Example 1, except that the compound of Formula 1-2-195 was used instead of Compound ET1 in Experimental Example 1.

Experimental Example 1-39

An organic light emitting device was manufactured in the same manner as in Experimental Example 1, except that the compound of Formula 1-3-195 was used instead of Compound ET1 in Experimental Example 1.

Experimental Example 1-40

An organic light emitting device was manufactured in the same manner as in Experimental Example 1, except that the compound of Formula 1-1-195 was used instead of Compound ET1 in Experimental Example 1.

When current was applied to the organic light emitting devices manufactured in Comparative Example 1 and Experimental Examples 1-1 to 1-32, the results of Table 1 were obtained.

TABLE 1

|  | Formula (Electron transporting layer) | Voltage (V@10 mA/ $cm^2$) | Efficiency (cd/A@10 mA/ $cm^2$) | Color coordinate (x, y) |
|---|---|---|---|---|
| Comparative Example 1 | ET1 | 4.19 | 5.25 | (0.138, 0.127) |
| Experimental Example 1-1 | 1-4-1 | 3.85 | 5.45 | (0.139, 0.122) |
| Experimental Example 1-2 | 1-4-3 | 3.82 | 5.48 | (0.138, 0.126) |
| Experimental Example 1-3 | 1-4-40 | 3.87 | 5.41 | (0.138, 0.127) |
| Experimental Example 1-4 | 1-4-5 | 3.88 | 5.42 | (0.137, 0.125) |
| Experimental Example 1-5 | 1-4-10 | 3.89 | 5.43 | (0.136, 0.125) |
| Experimental Example 1-6 | 1-4-25 | 3.84 | 5.47 | (0.136, 0.127) |
| Experimental Example 1-7 | 1-4-81 | 3.83 | 5.48 | (0.136, 0.125) |
| Experimental Example 1-8 | 1-4-71 | 3.84 | 5.41 | (0.137, 0.125) |
| Experimental Example 1-9 | 1-2-1 | 3.83 | 5.48 | (0.138, 0.125) |
| Experimental Example 1-10 | 1-2-3 | 3.84 | 5.42 | (0.136, 0.125) |
| Experimental Example 1-11 | 1-2-40 | 3.83 | 5.47 | (0.137, 0.125) |
| Experimental Example 1-12 | 1-2-5 | 3.84 | 5.55 | (0.136, 0.125) |
| Experimental Example 1-13 | 1-2-10 | 3.87 | 5.58 | (0.138, 0.126) |
| Experimental Example 1-14 | 1-2-139 | 3.88 | 5.51 | (0.137, 0.125) |
| Experimental Example 1-15 | 1-2-81 | 3.89 | 5.52 | (0.136, 0.127) |
| Experimental Example 1-16 | 1-2-71 | 3.87 | 5.53 | (0.135, 0.127) |
| Experimental Example 1-17 | 1-3-1 | 3.86 | 5.57 | (0.138, 0.127) |
| Experimental Example 1-18 | 1-3-3 | 3.87 | 5.58 | (0.137, 0.125) |
| Experimental Example 1-19 | 1-3-40 | 3.89 | 5.51 | (0.137, 0.125) |
| Experimental Example 1-20 | 1-3-5 | 3.85 | 5.58 | (0.136, 0.127) |
| Experimental Example 1-21 | 1-3-10 | 3.86 | 5.52 | (0.135, 0.127) |
| Experimental Example 1-22 | 1-3-139 | 3.89 | 5.57 | (0.138, 0.127) |
| Experimental Example 1-23 | 1-3-81 | 3.84 | 5.49 | (0.137, 0.125) |
| Experimental Example 1-24 | 1-3-71 | 3.87 | 5.50 | (0.137, 0.125) |
| Experimental Example 1-25 | 1-1-1 | 3.85 | 5.53 | (0.136, 0.125) |
| Experimental Example 1-26 | 1-1-3 | 3.86 | 5.56 | (0.136, 0.127) |
| Experimental Example 1-27 | 1-1-40 | 3.85 | 5.55 | (0.136, 0.125) |
| Experimental Example 1-28 | 1-1-5 | 3.88 | 5.57 | (0.137, 0.125) |
| Experimental Example 1-29 | 1-1-10 | 3.86 | 5.52 | (0.136, 0.125) |
| Experimental Example 1-30 | 1-1-139 | 3.88 | 5.52 | (0.136, 0.127) |
| Experimental Example 1-31 | 1-1-81 | 3.87 | 5.55 | (0.136, 0.125) |
| Experimental Example 1-32 | 1-1-71 | 3.84 | 5.56 | (0.137, 0.125) |
| Experimental Example 1-33 | 1-4-194 | 3.91 | 5.4 | (0.136, 0.126) |
| Experimental Example 1-34 | 1-2-194 | 3.9 | 5.42 | (0.137, 0.126) |
| Experimental Example 1-35 | 1-3-194 | 3.92 | 5.4 | (0.136, 0.127) |
| Experimental Example 1-36 | 1-1-194 | 3.91 | 5.41 | (0.137, 0.126) |
| Experimental Example 1-37 | 1-4-195 | 3.92 | 5.43 | (0.137, 0.125) |
| Experimental Example 1-38 | 1-2-195 | 3.93 | 4.45 | (0.138, 0.125) |
| Experimental Example 1-39 | 1-3-195 | 3.94 | 5.44 | (0.137, 0.127) |
| Experimental Example 1-40 | 1-1-195 | 3.94 | 5.44 | (0.136, 0.127) |

It could be confirmed that the compound derivatives of Formulae according to the present invention have excellent electron blocking capability, and thus exhibits low voltage and high efficiency characteristics, and may be applied to an organic light emitting device.

EXPLANATION OF REFERENCE NUMERALS AND SYMBOLS

100: Substrate
200: Positive electrode
300: Organic material layer
301: Hole injection layer
302: Hole transporting layer
303: Light emitting layer
304: Electron transporting layer
305: Electron injection layer
400: Negative electrode

What is claimed is:

1. A compound represented by the following Formula 1:

[Formula 1]

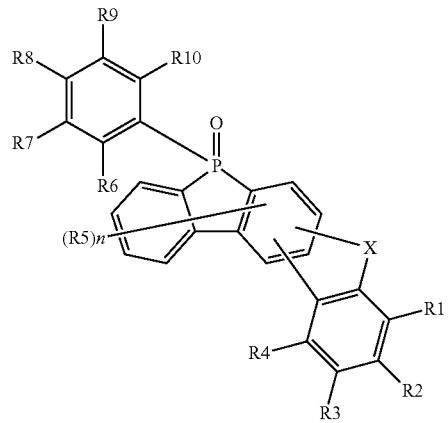

Formula 1 is represented by any one of the following Formulae 1-1 to 1-4,

[Formula 1-1]

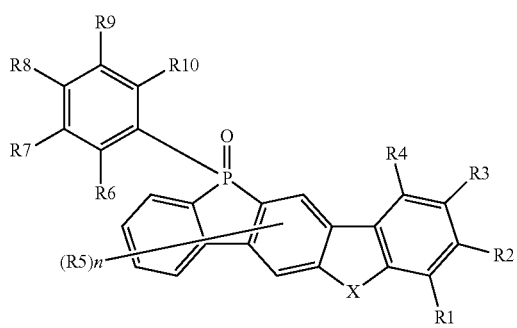

[Formula 1-2]

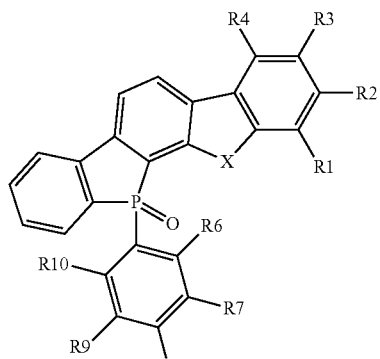

[Formula 1-3]

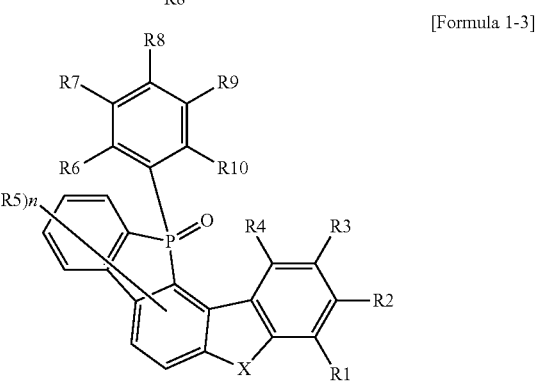

[Formula 1-4]

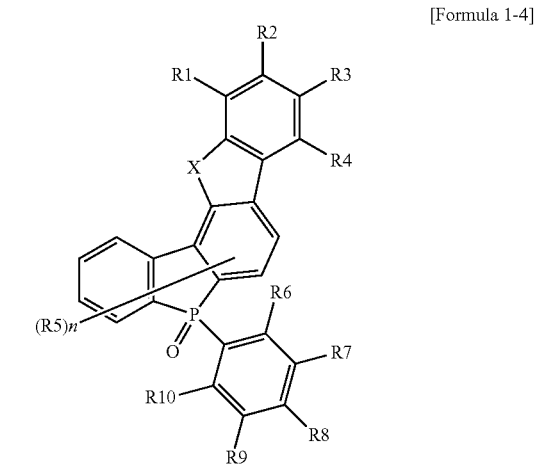

in Formulae 1-1 to 1-4,
X is O, S, or NAr,
n is an integer of 0 to 6,
when n is 2 or more, a plurality of R5's is the same as or different from each other,
R1 to R5 are the same as or different from each other, and are each independently hydrogen, or combine with an adjacent group to form a substituted or unsubstituted ring,
R6 to R10 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted amine group; a substituted or unsubstituted arylphosphine group; a substituted or unsubstituted phosphine oxide group; a substituted or unsubstituted aryl group; or a substituted or unsubstituted heterocyclic group, or combine with two or more adjacent groups in R6 to R10 to form a substituted or unsubstituted ring, and Ar is hydrogen; a substituted or unsubstituted heteroaryl alkyl group; a substituted or unsubstituted aryl group; or a substituted or unsubstituted heterocyclic group.

2. The compound of claim 1, wherein X is NAr.

3. The compound of claim 1, wherein Ar is an aryl group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group; or a heterocyclic group which is unsubstituted or substituted with one or two or more substituents selected from the group consisting of deuterium, a nitrile group, a substituted or unsubstituted alkyl group, a substituted or unsubstituted amine group, a substituted or unsubstituted aryl group, and a substituted or unsubstituted heterocyclic group.

4. The compound of claim 1, wherein Ar is a phenyl group; a naphthyl group; a biphenyl group; a terphenyl group; a quarterphenylene group; a fluorene group; a fluoranthene group; an anthracene group; a chrysene group; a phenanthrenyl group; a pyrene group; an amine group; a pyridine group; a pyrimidine group; a triazine group; a quinoline group; a quinazoline group; a carbazole group; a dibenzothiophene group; a dibenzofuran group; a furan group; a thiophene group; or a phenanthroline group, and Ar is substituted with one or two or more substituents selected from the group consisting of deuterium; a nitrile group; an alkyl group having 1 to 10 carbon atoms; a phenyl group; a naphthyl group; a biphenyl group; a terphenyl group; a quarterphenylene group; a fluorene group; a fluoranthene group; an anthracene group; a chrysene group; a phenanthrenyl group; a pyrene group; an amine group; a pyridine group; a pyrimidine group; a triazine group; a quinoline group; a quinazoline group; a carbazole group; a dibenzothiophene group; a dibenzofuran group; a furan group; a thiophene group; and a phenanthroline group, or is unsubstituted or substituted with a substituent to which two or more substituents are linked.

5. The compound of claim 1, wherein the compound represented by Formula 1-1 is represented by any one of the following Formulae 1-1-1 to 1-1-195:

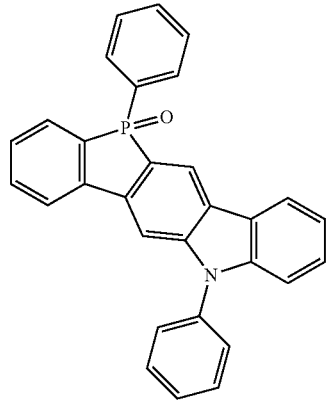

Formula 1-1-1

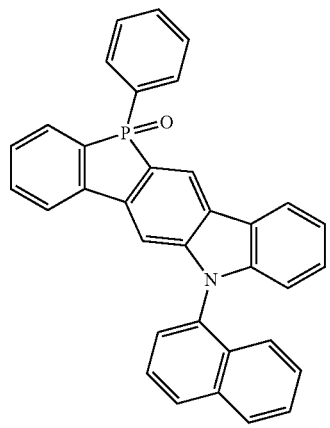

Formula 1-1-2

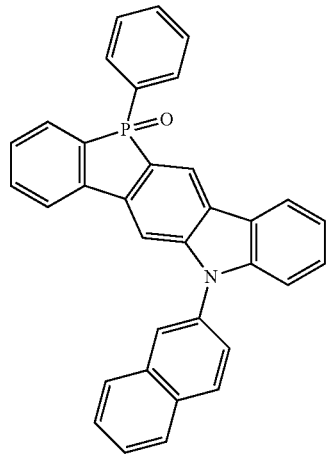

Formula 1-1-3

Formula 1-1-4
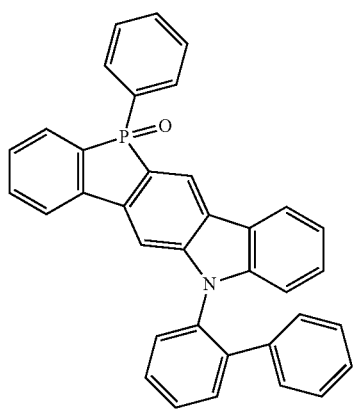
Formula 1-1-5
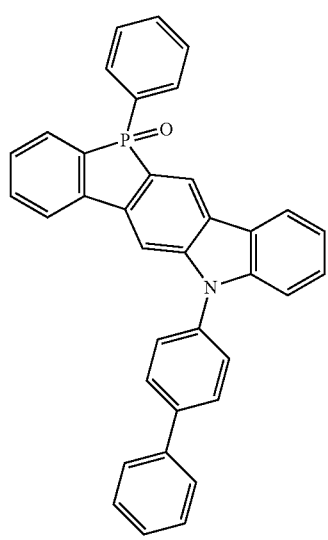
Formula 1-1-6
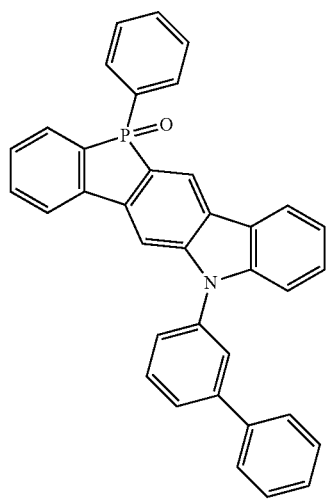
Formula 1-1-7
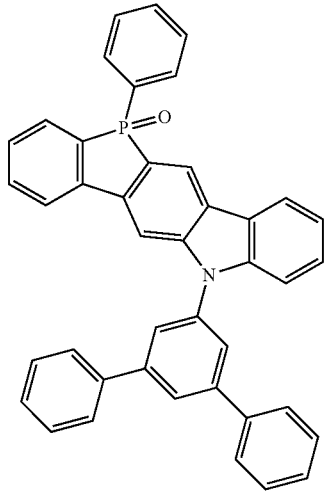
Formula 1-1-8
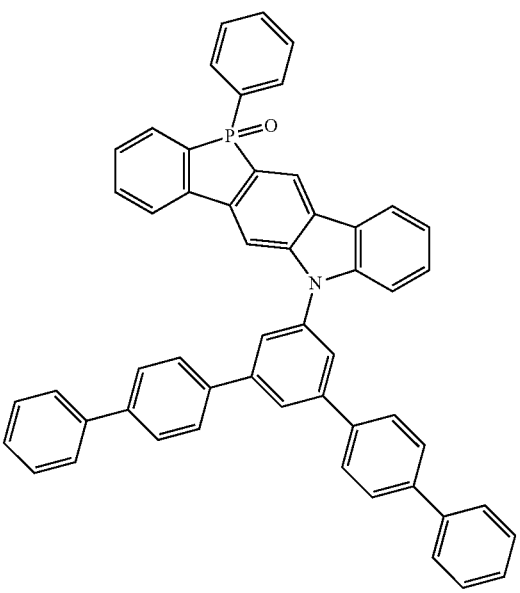

Formula 1-1-9
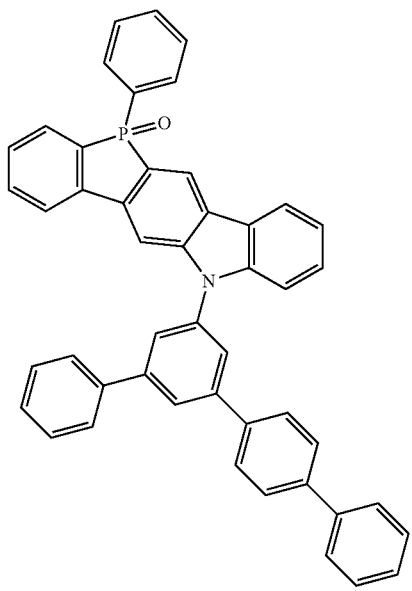
Formula 1-1-10
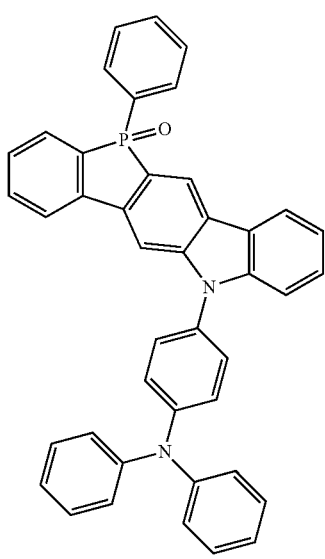
Formula 1-1-11
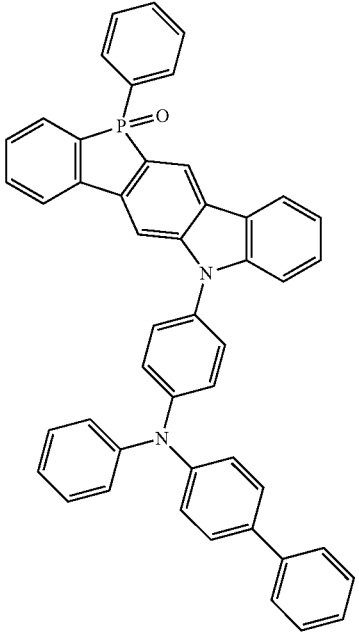
Formula 1-1-12
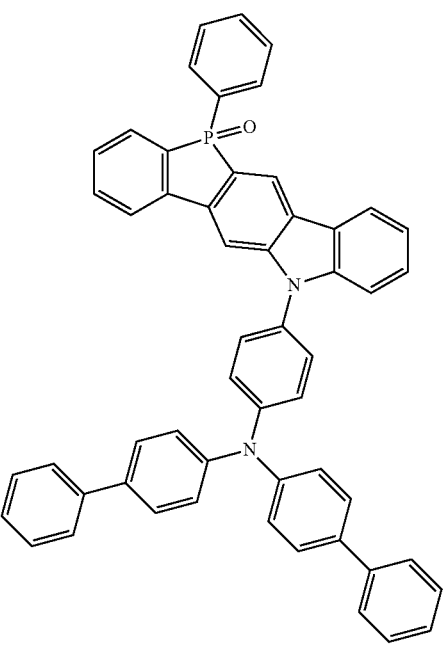

-continued
Formula 1-1-13
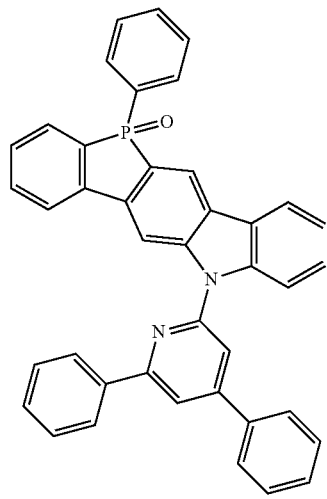
Formula 1-1-14
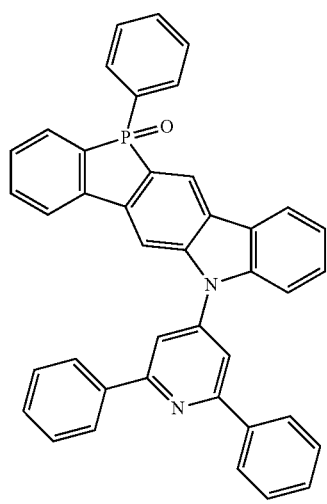
Formula 1-1-15
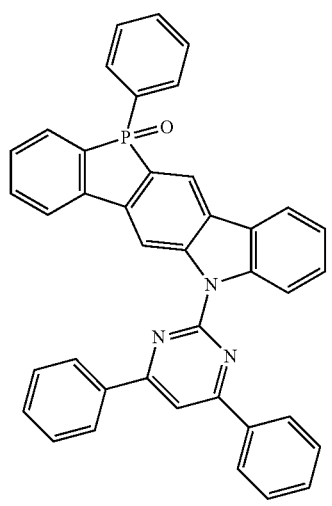
-continued
Formula 1-1-16
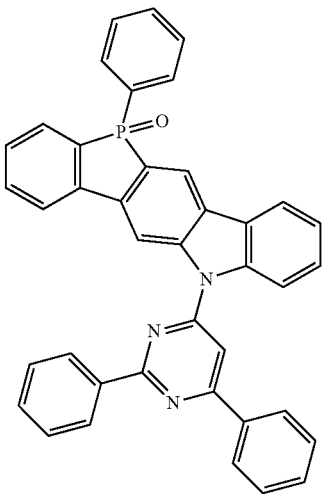
Formula 1-1-17
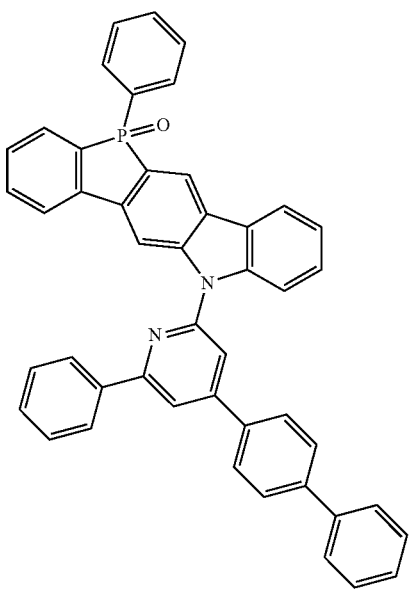

Formula 1-1-18
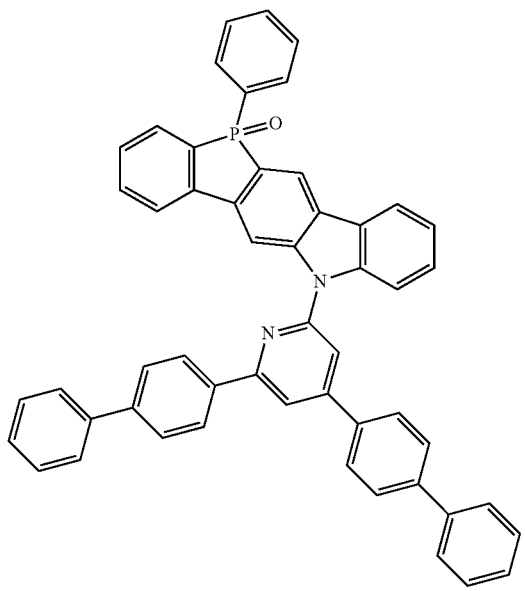
Formula 1-1-19
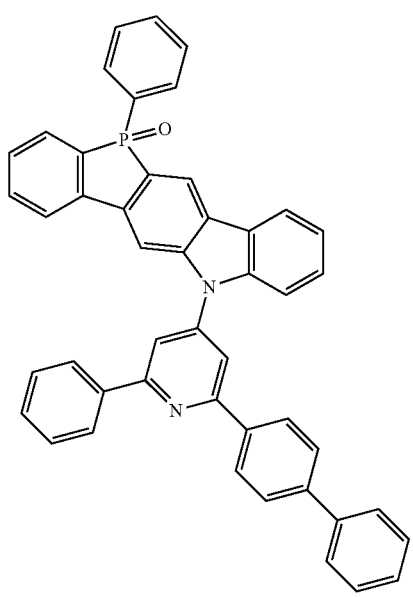
Formula 1-1-20
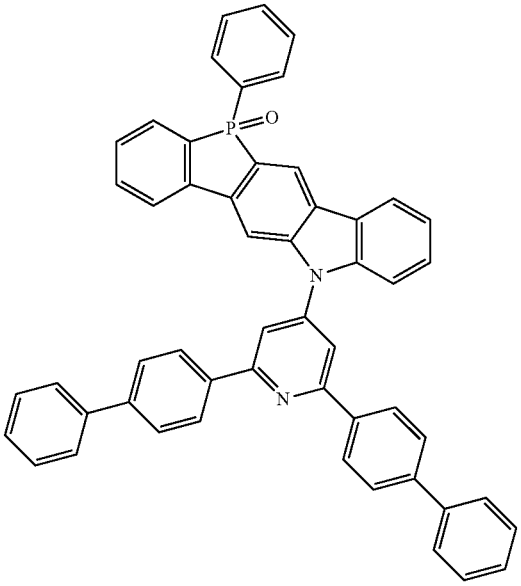
Formula 1-1-21
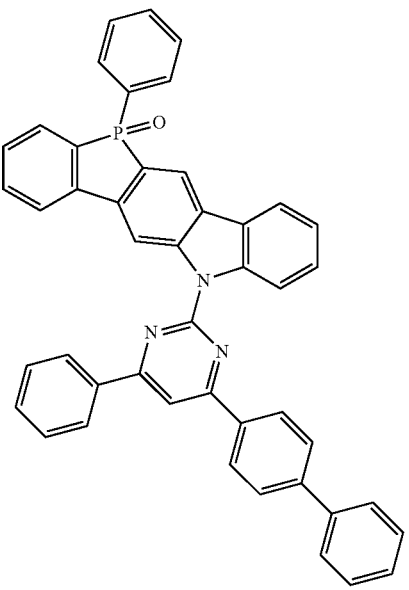

Formula 1-1-22
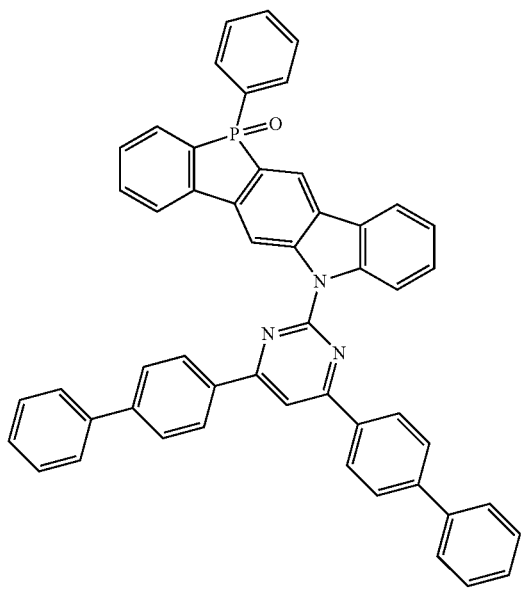
Formula 1-1-24
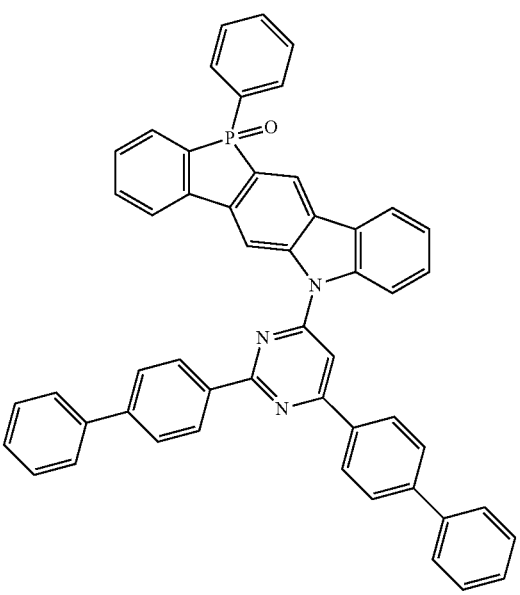
Formula 1-1-23
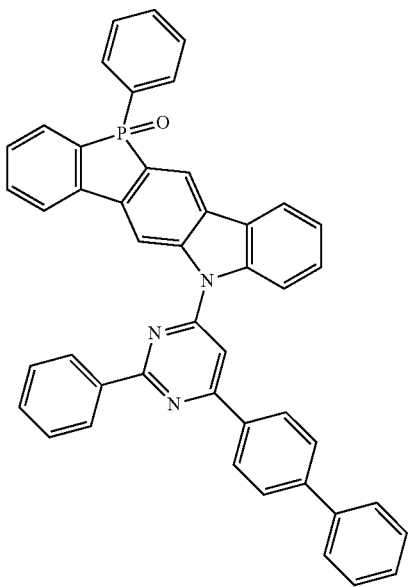
Formula 1-1-25
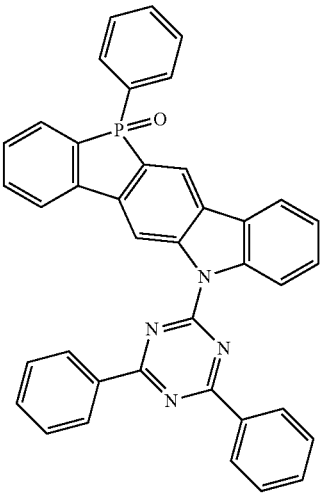

Formula 1-1-26
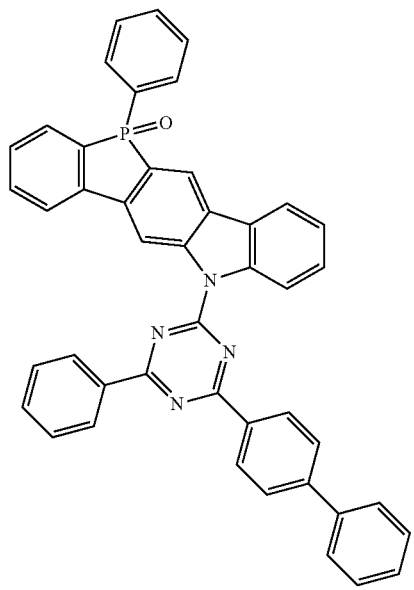
Formula 1-1-27
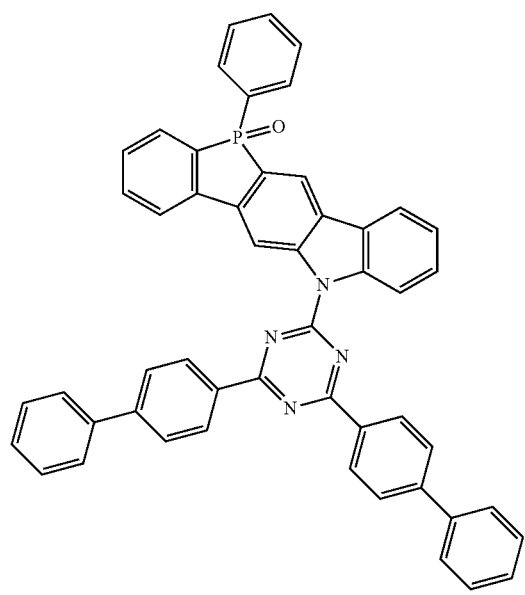
Formula 1-1-28
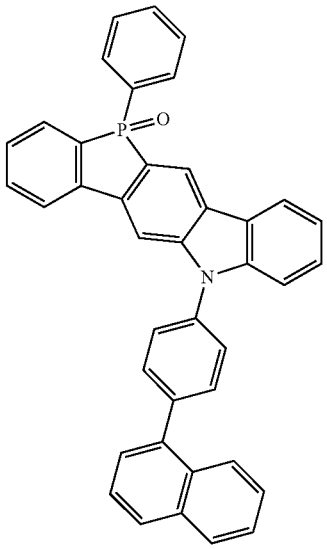
Formula 1-1-29
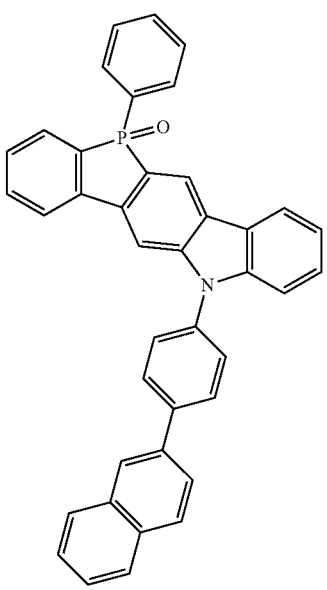

381
-continued
Formula 1-1-30
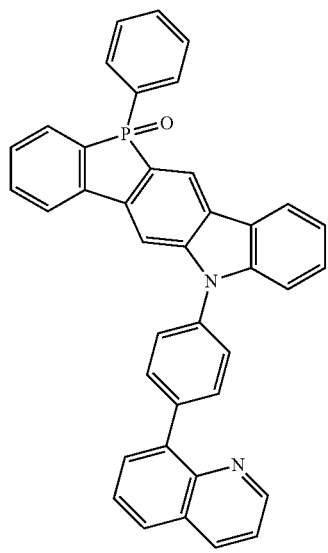
Formula 1-1-31
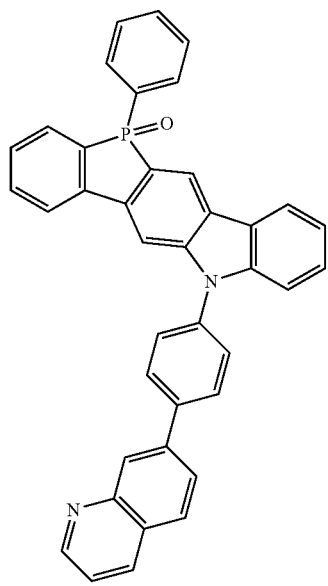
Formula 1-1-32
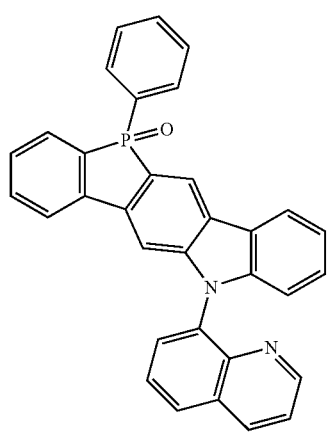
382
-continued
Formula 1-1-33
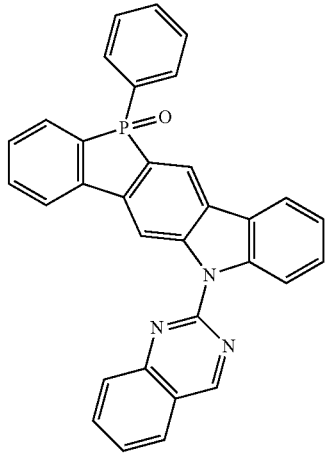
Formula 1-1-34
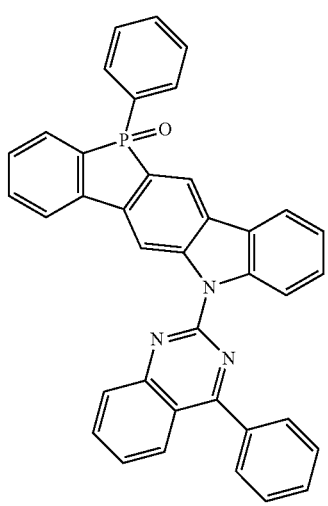
Formula 1-1-35
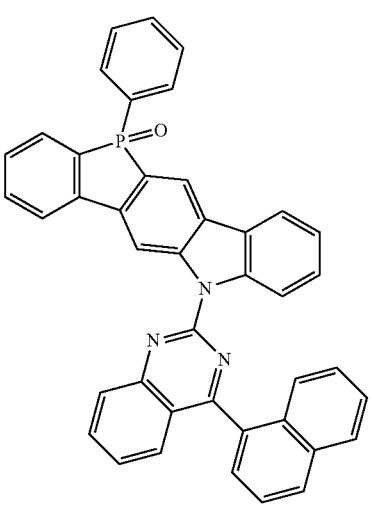

Formula 1-1-36
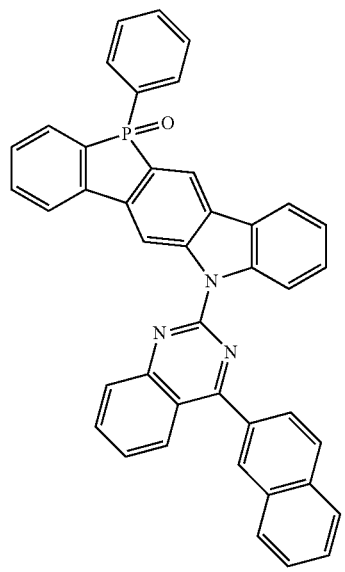
Formula 1-1-38
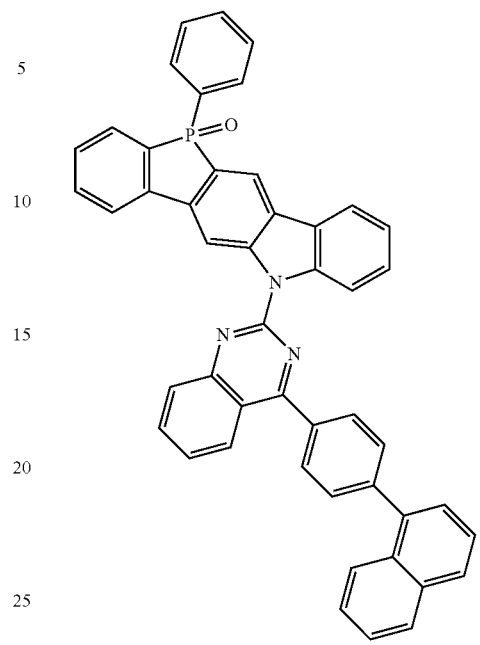
Formula 1-1-37
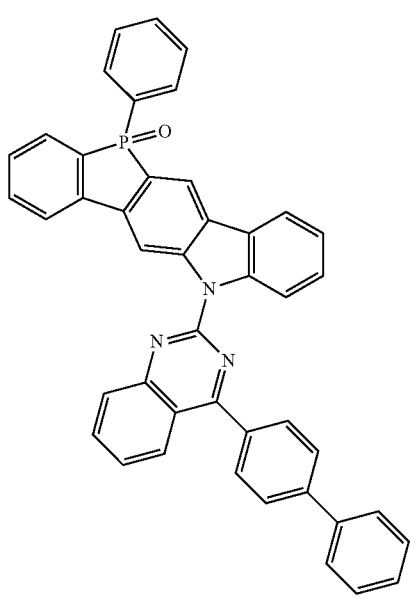
Formula 1-1-39
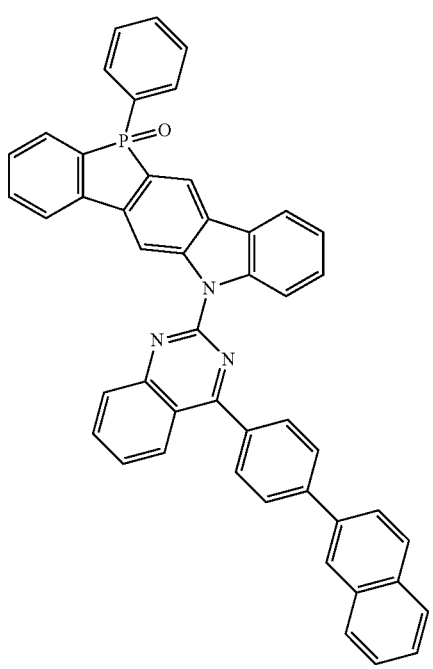

Formula 1-1-40
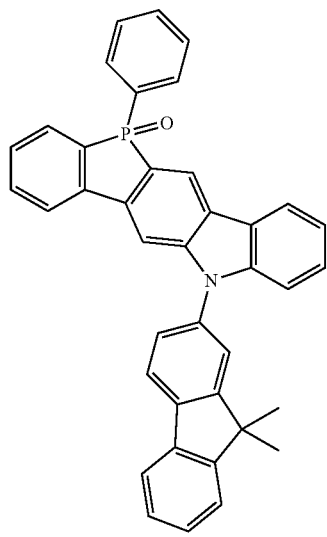 [SMILES: CC1(C)c2ccccc2-c2ccc(-n3c4ccccc4c4cc5c(cc43)-c3ccccc3P5(=O)c3ccccc3)cc21]
Formula 1-1-41
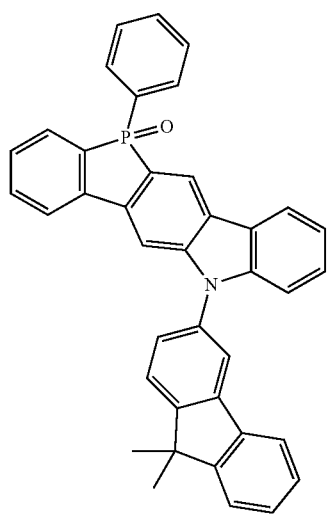
Formula 1-1-42
Formula 1-1-43
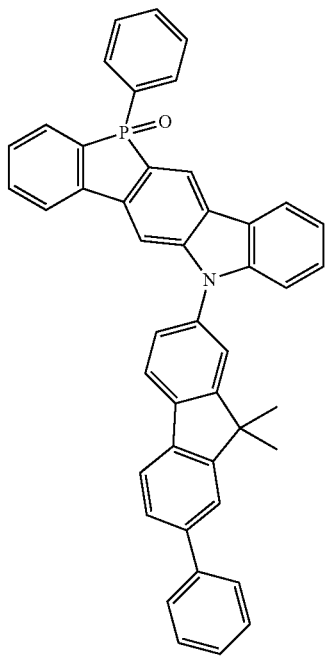
Formula 1-1-44
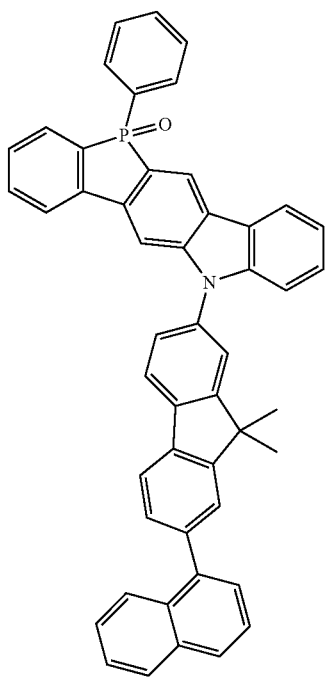

Formula 1-1-45
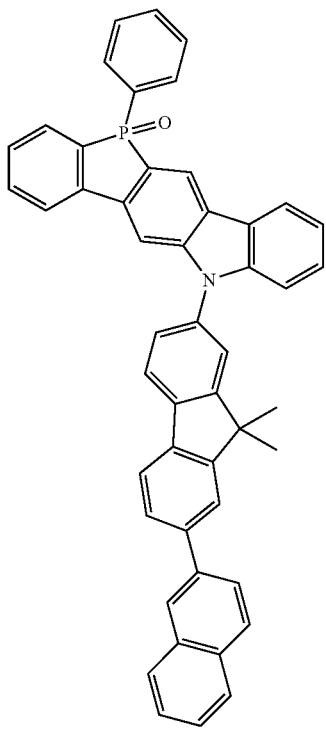
Formula 1-1-47
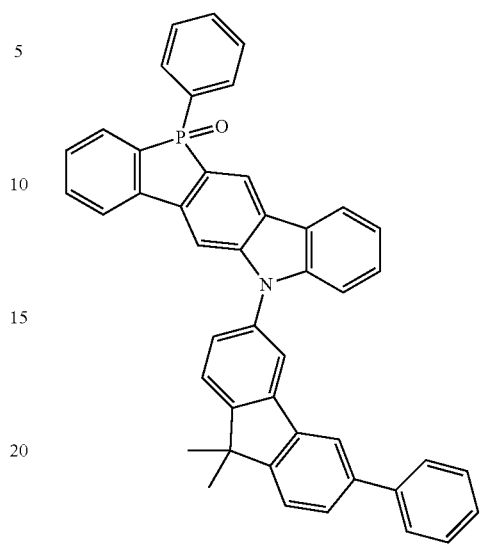
Formula 1-1-46
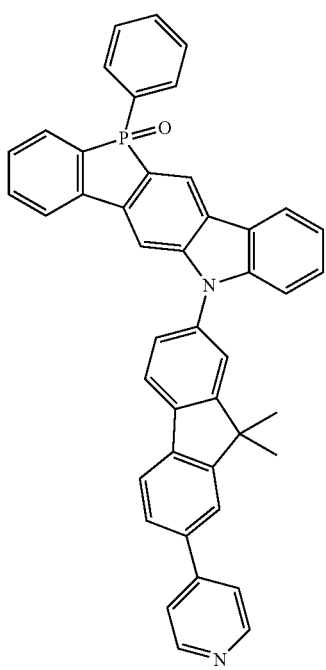
Formula 1-1-48
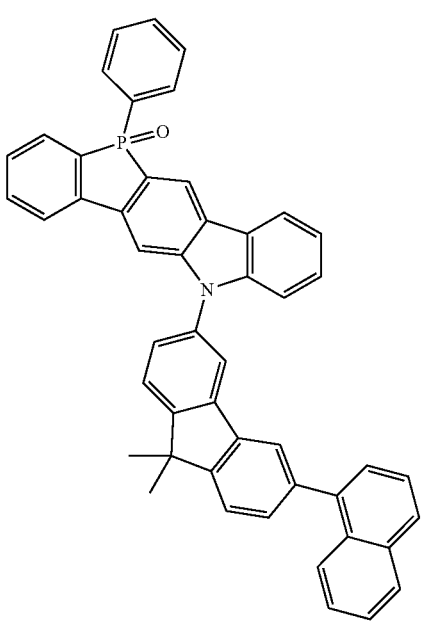

Formula 1-1-49
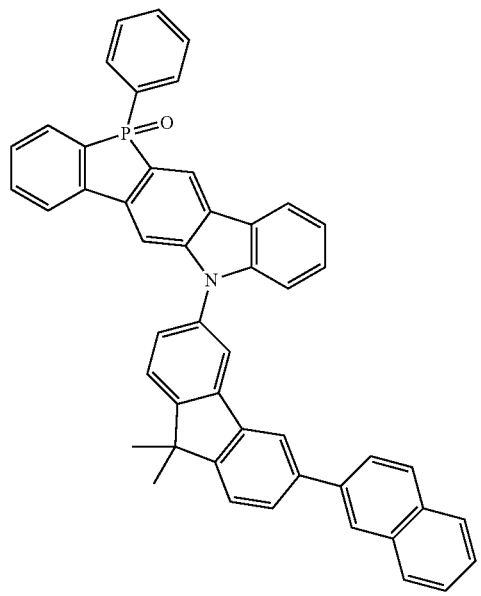
Formula 1-1-50
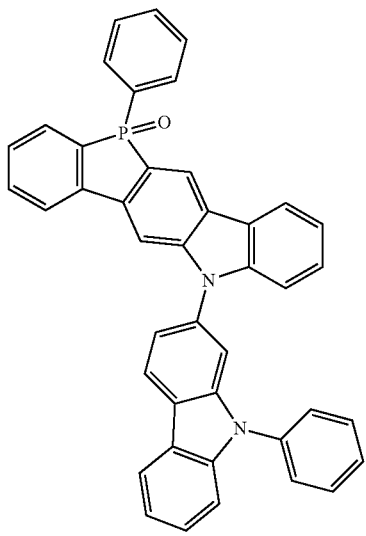
Formula 1-1-51
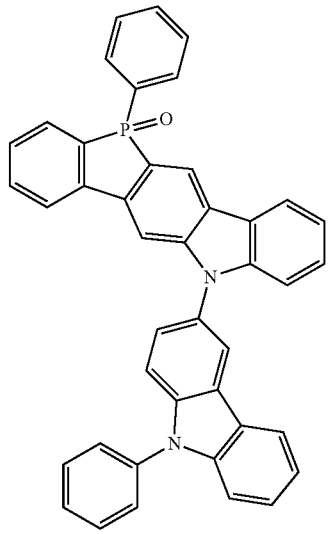 [SMILES: O=P1(c2ccccc2)c2ccccc2-c2cc3c(cc21)c1ccccc1n3-c1ccc2c(c1)c1ccccc1n2-c1ccccc1]
Formula 1-1-52
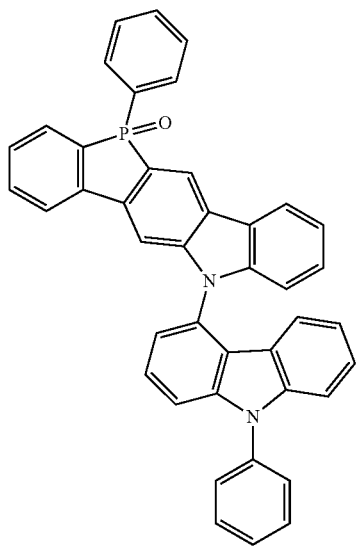
Formula 1-1-53
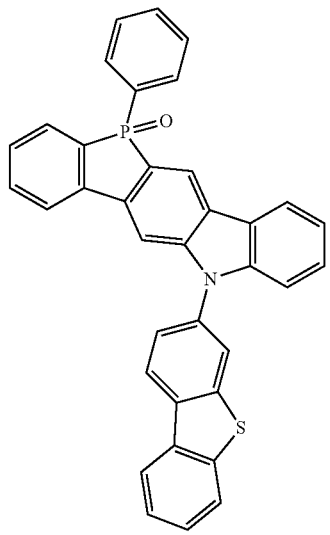 [SMILES: O=P1(c2ccccc2)c2ccccc2-c2cc3c(cc21)c1ccccc1n3-c1ccc2c(c1)oc1ccccc12]

Formula 1-1-54
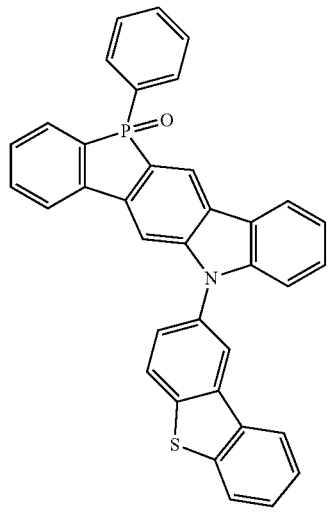
Formula 1-1-55
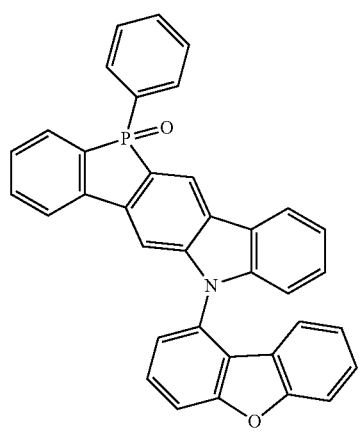
Formula 1-1-56
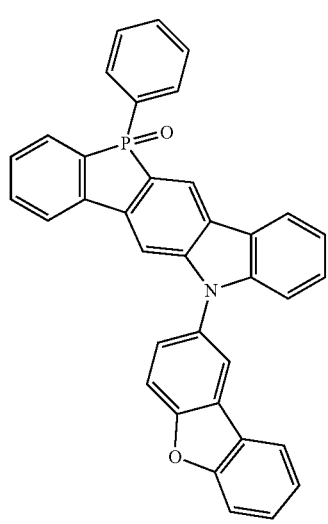
Formula 1-1-57
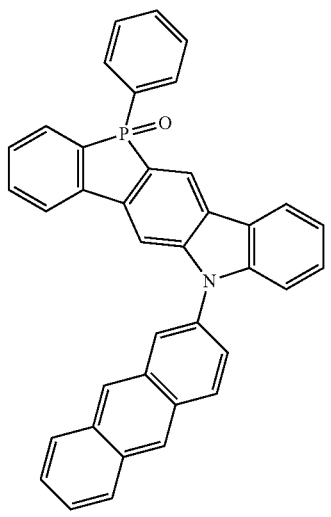
Formula 1-1-58
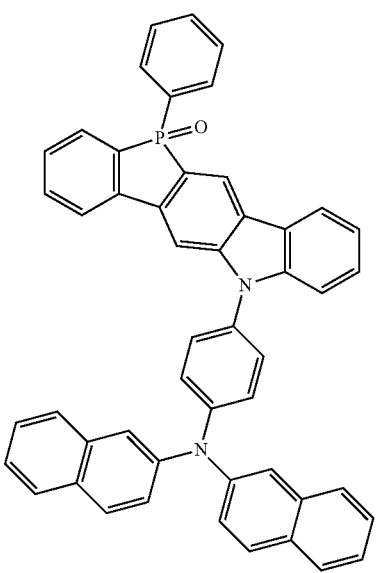

Formula 1-1-59
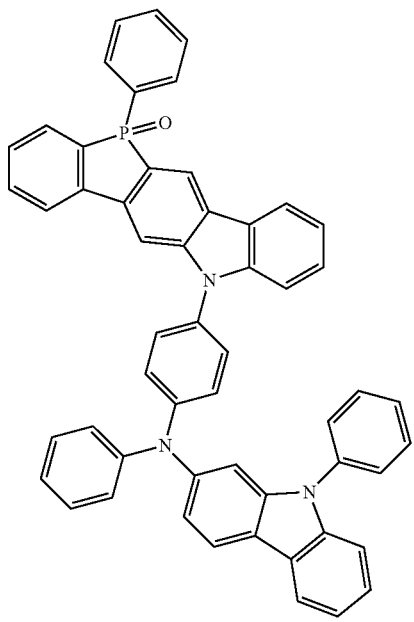
Formula 1-1-61
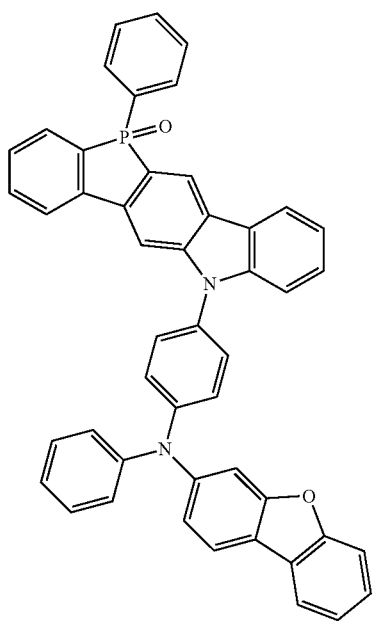
Formula 1-1-60
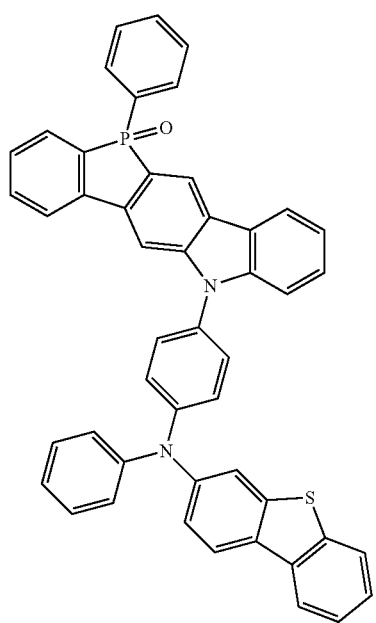
Formula 1-1-62
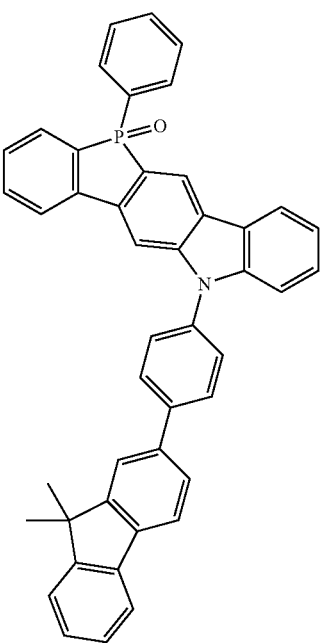

Formula 1-1-63
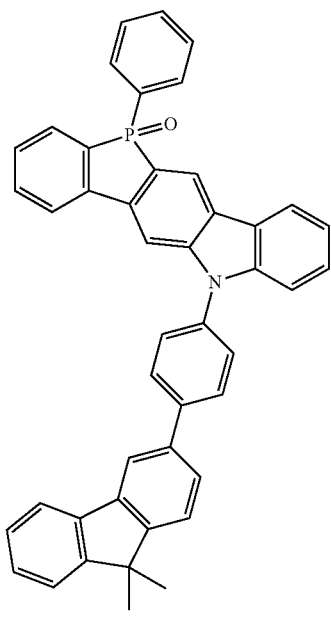
Formula 1-1-64
Formula 1-1-65
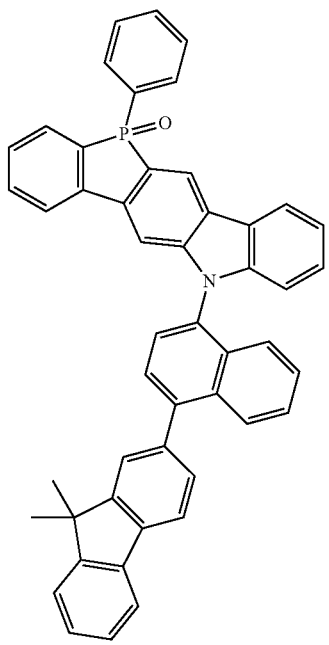
Formula 1-1-66
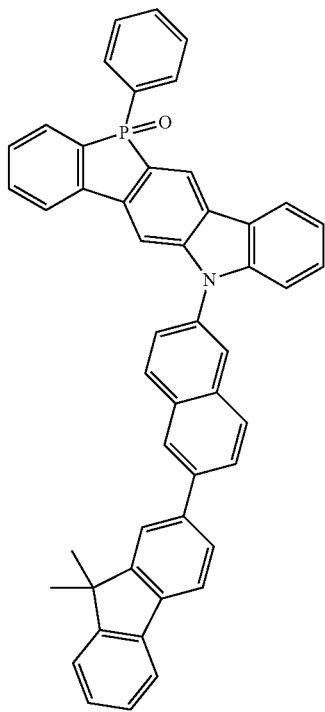

Formula 1-1-67
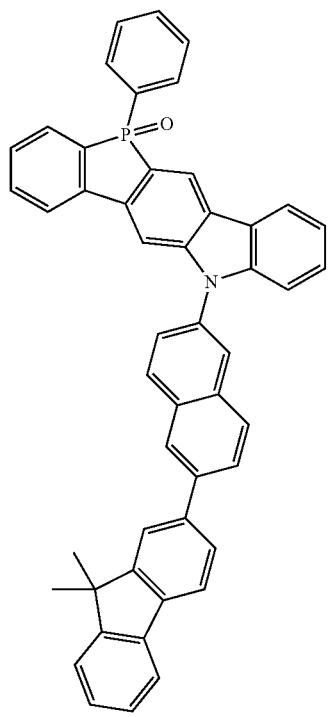
Formula 1-1-68
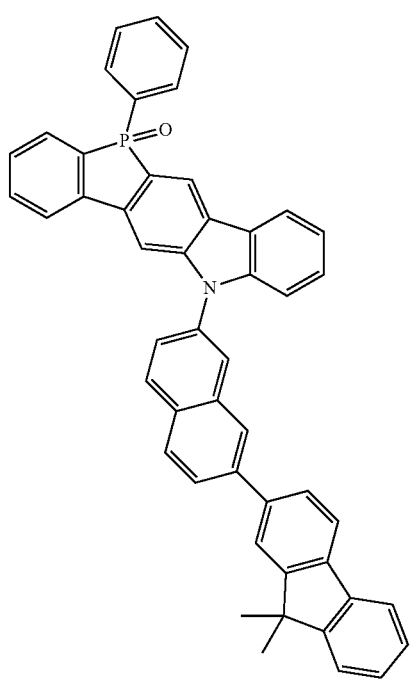
Formula 1-1-69
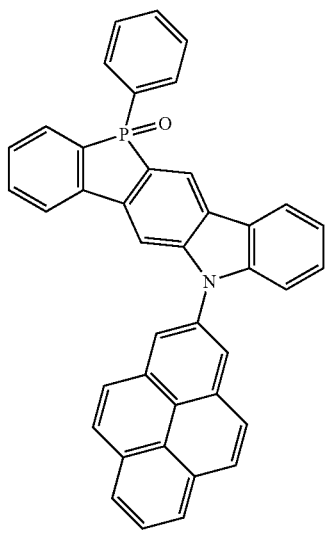
Formula 1-1-70
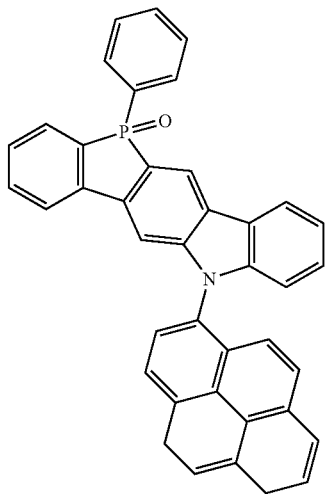
Formula 1-1-71
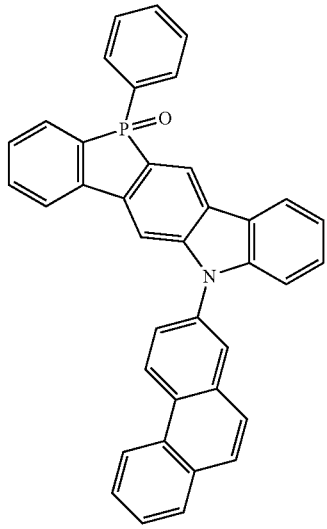

Formula 1-1-72
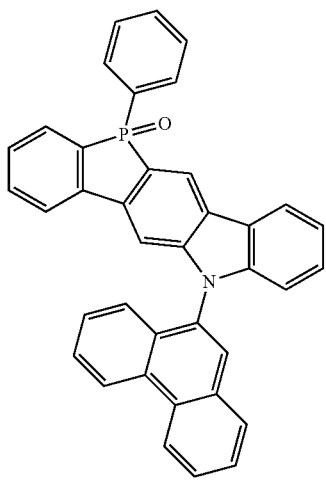
Formula 1-1-75
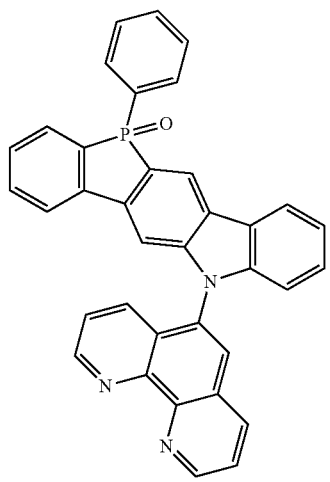
Formula 1-1-73
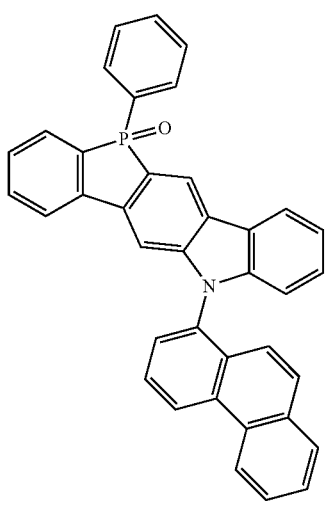
Formula 1-1-76
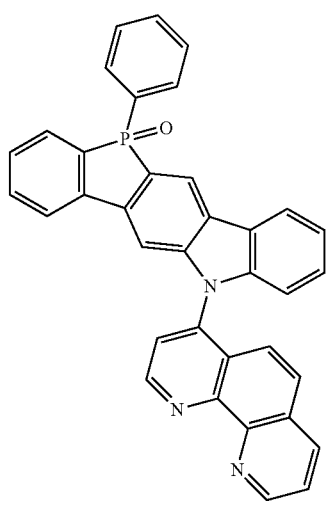
Formula 1-1-74
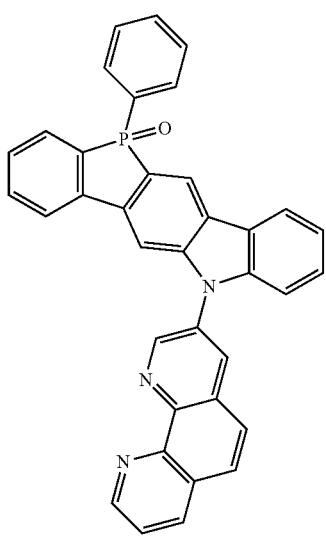
Formula 1-1-77
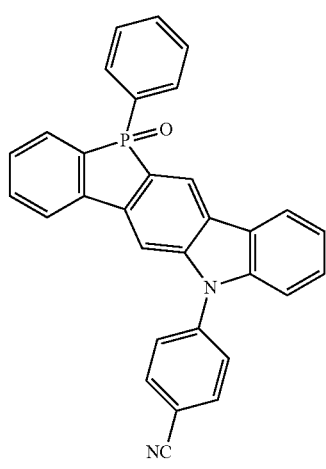

-continued
Formula 1-1-78
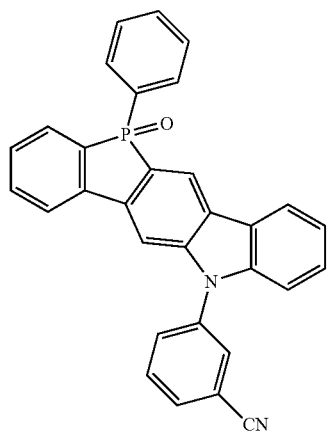
Formula 1-1-79
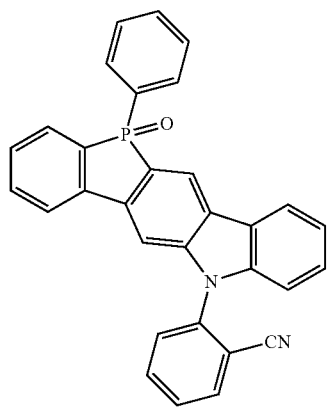
Formula 1-1-80
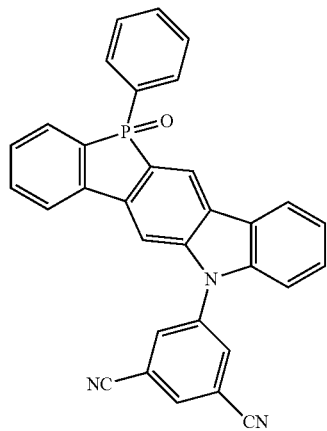
-continued
Formula 1-1-81
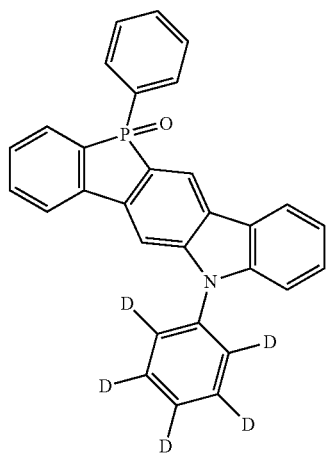
Formula 1-1-82
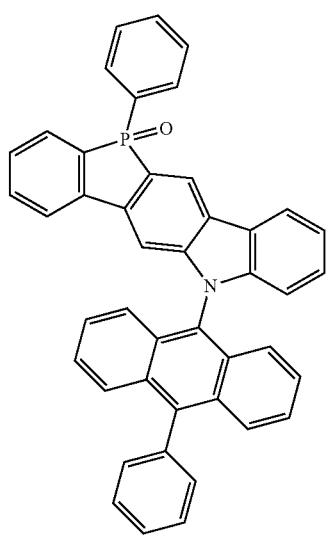
Formula 1-1-83
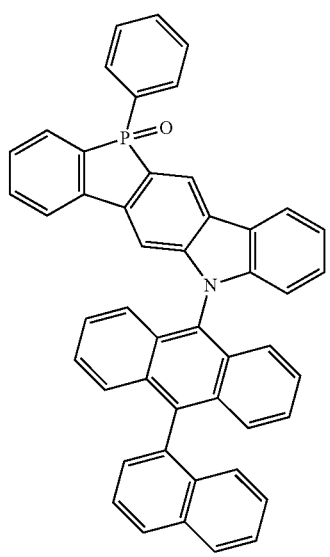

Formula 1-1-84
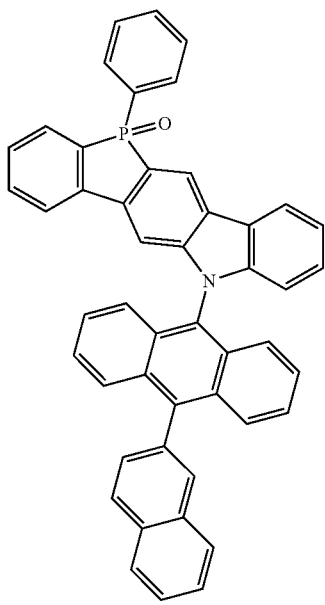
Formula 1-1-86
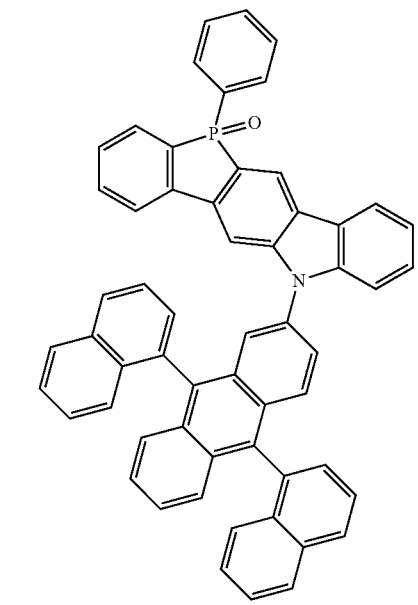
Formula 1-1-85
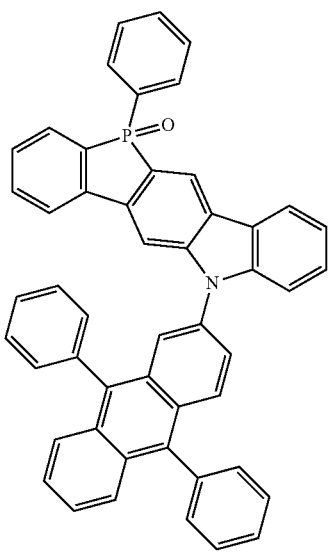
Formula 1-1-87
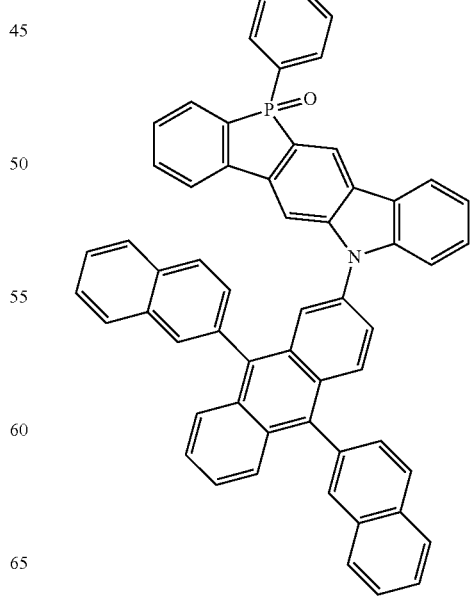

-continued
Formula 1-1-88
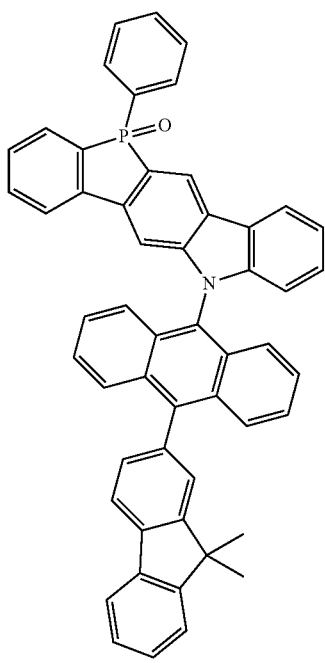
Formula 1-1-89
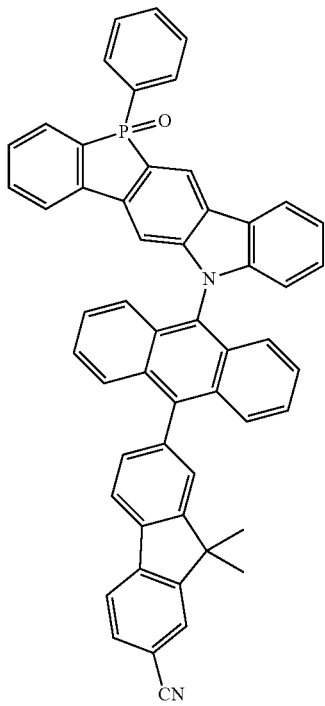
Formula 1-1-90
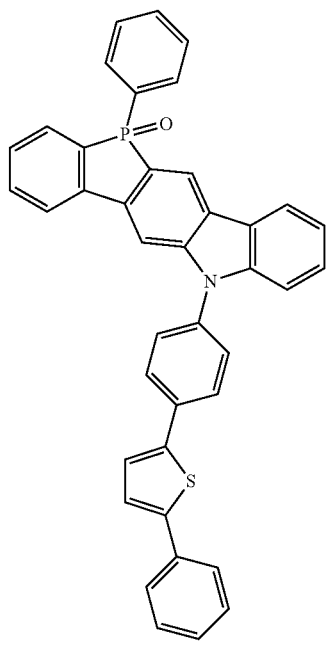
Formula 1-1-91
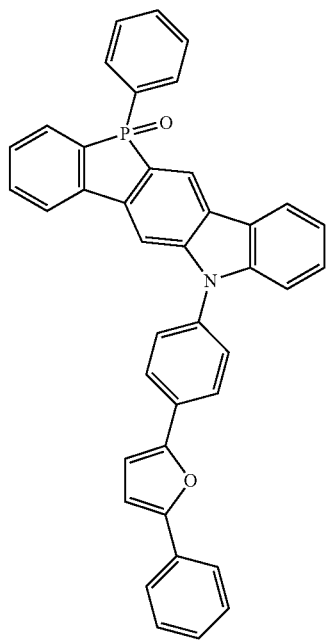

Formula 1-1-92
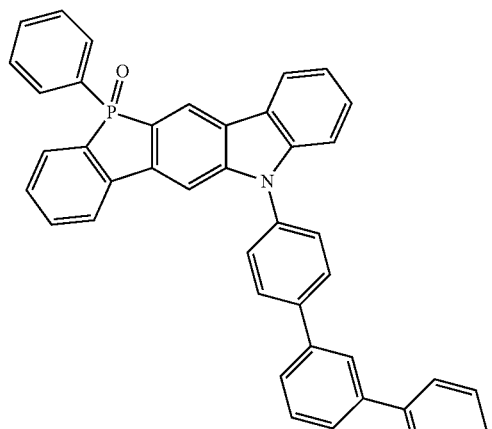
Formula 1-1-95
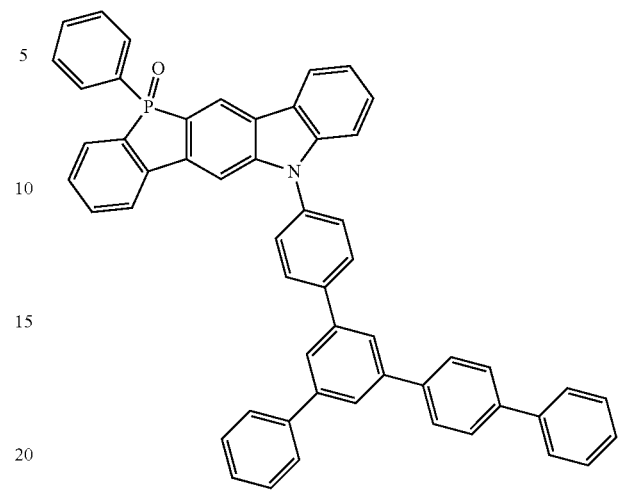
Formula 1-1-93
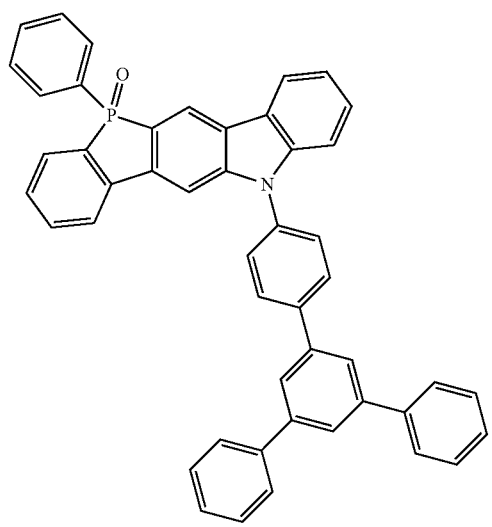
Formula 1-1-96
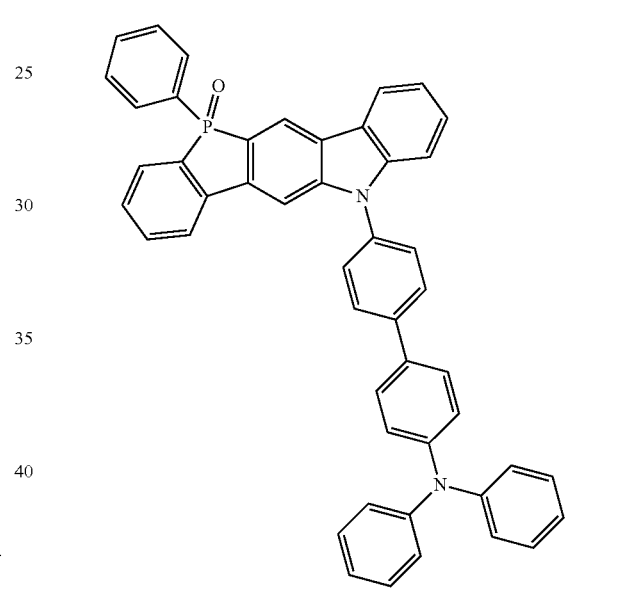
Formula 1-1-94
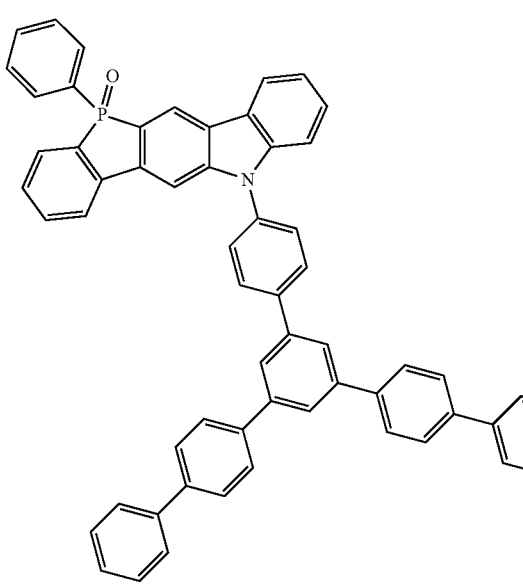
Formula 1-1-97
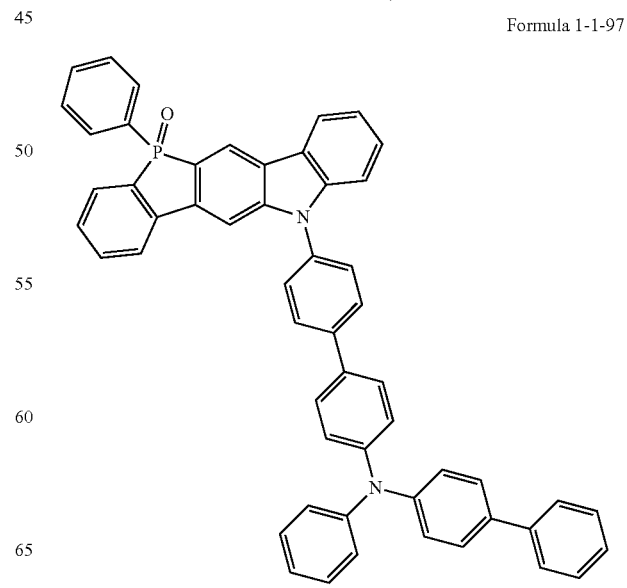

Formula 1-1-98
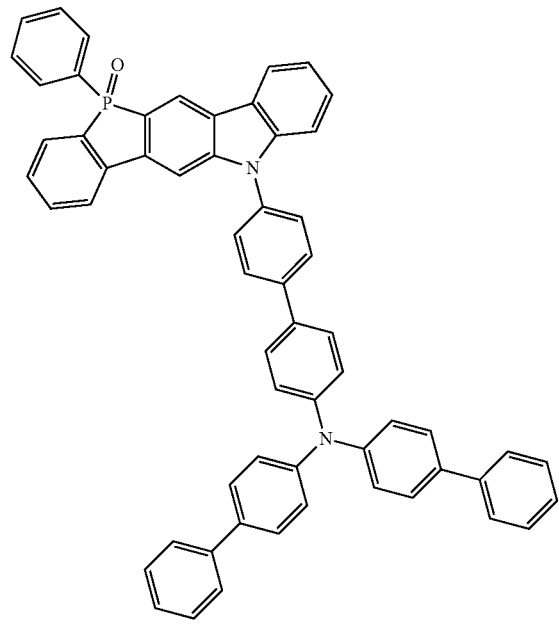
Formula 1-1-99
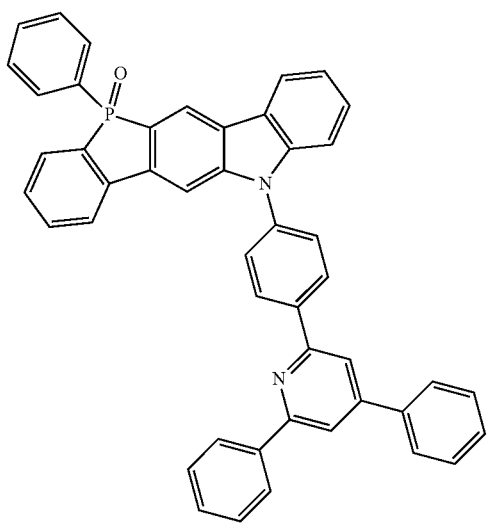
Formula 1-1-100
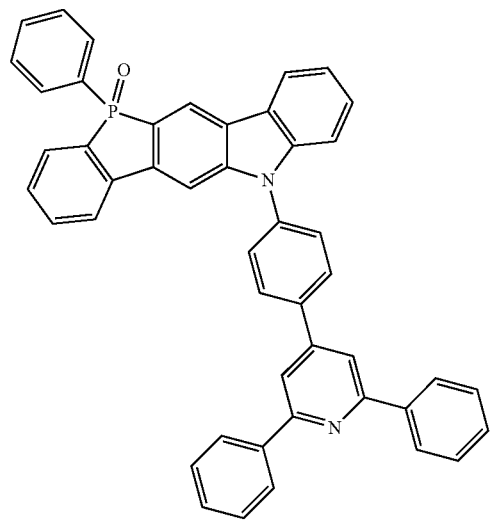
Formula 1-1-101
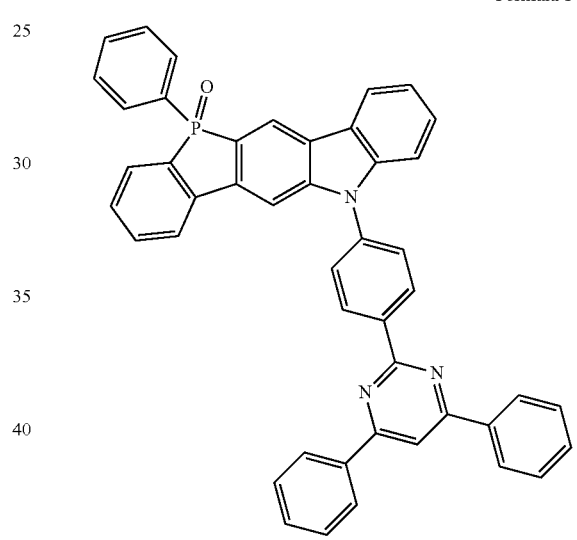
Formula 1-1-102

-continued
Formula 1-1-103
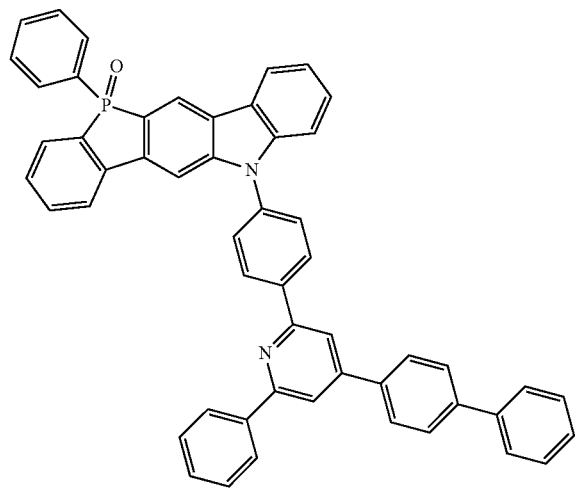
Formula 1-1-104
Formula 1-1-105
-continued
Formula 1-1-106
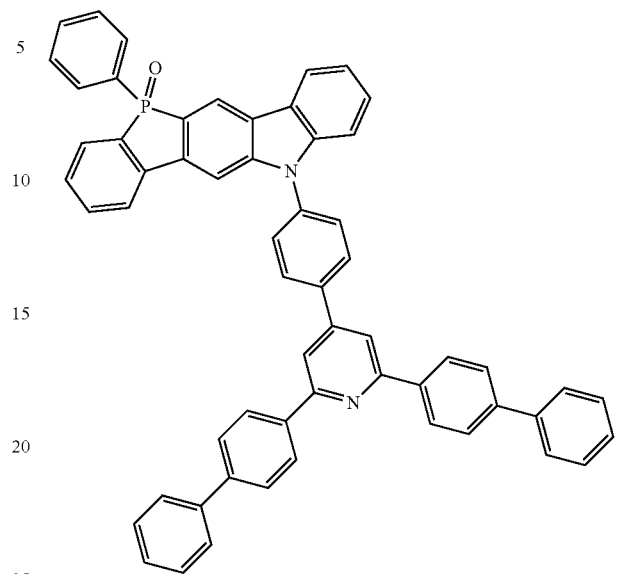
Formula 1-1-107

Formula 1-1-108
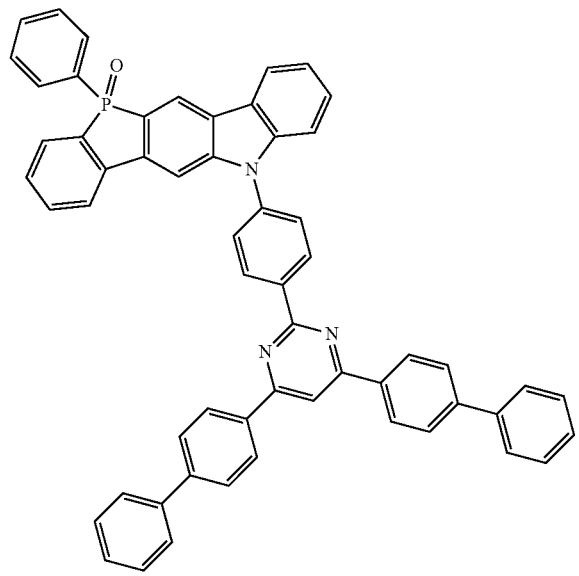
Formula 1-1-110
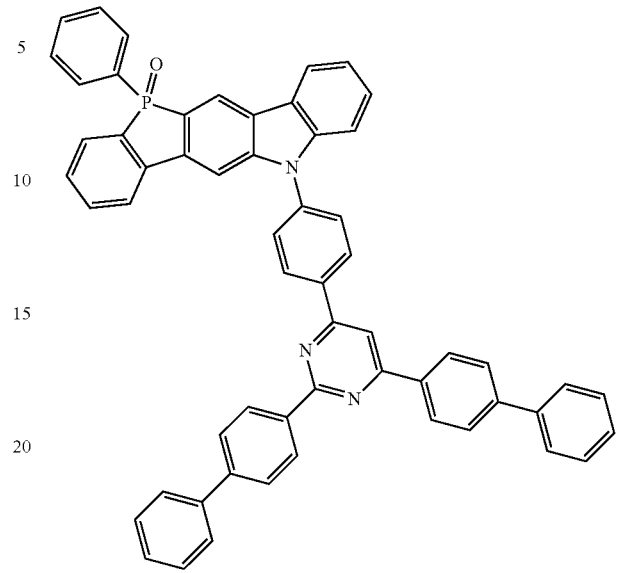
Formula 1-1-111
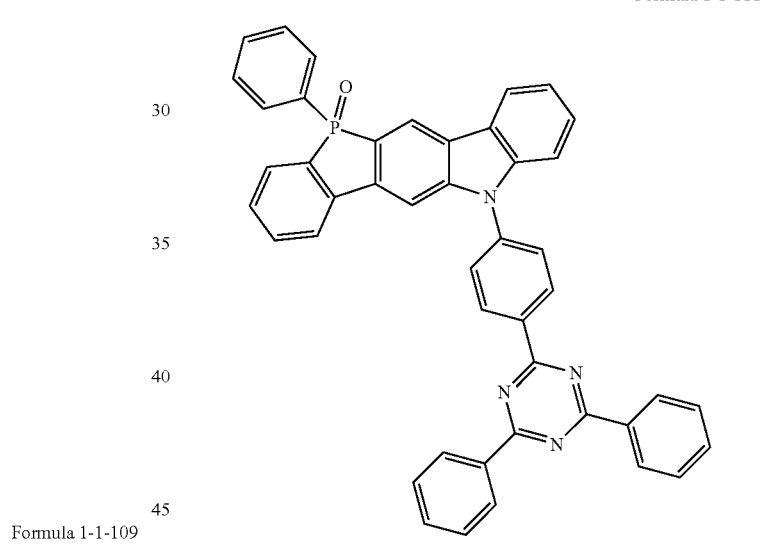
Formula 1-1-109
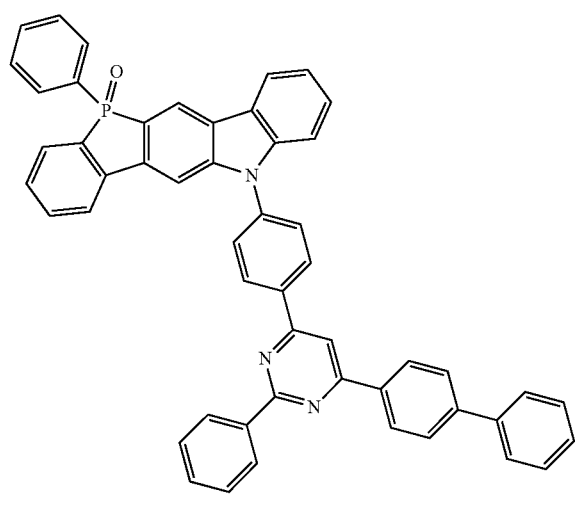
Formula 1-1-112
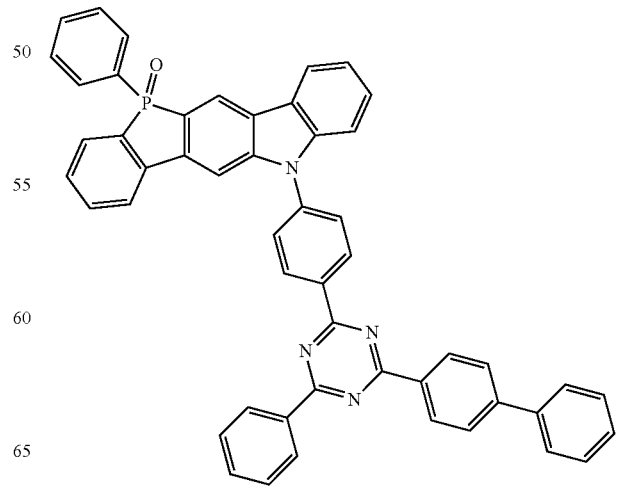

Formula 1-1-113
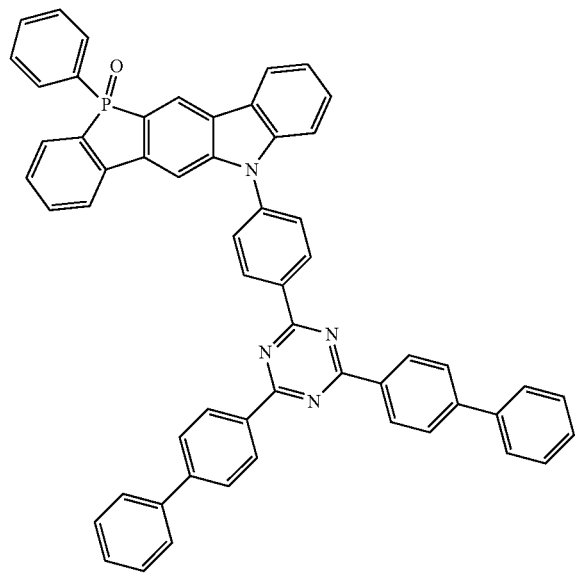
Formula 1-1-114
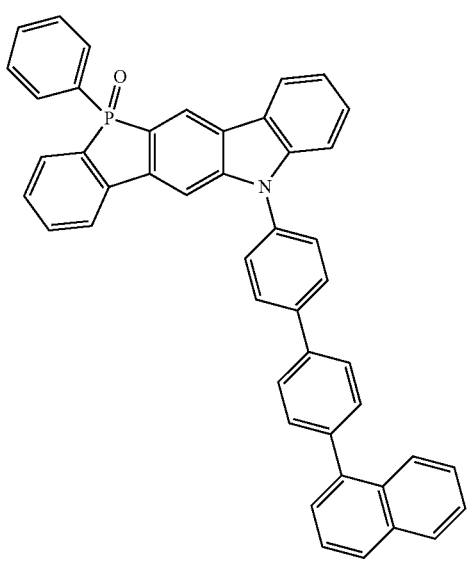
Formula 1-1-115
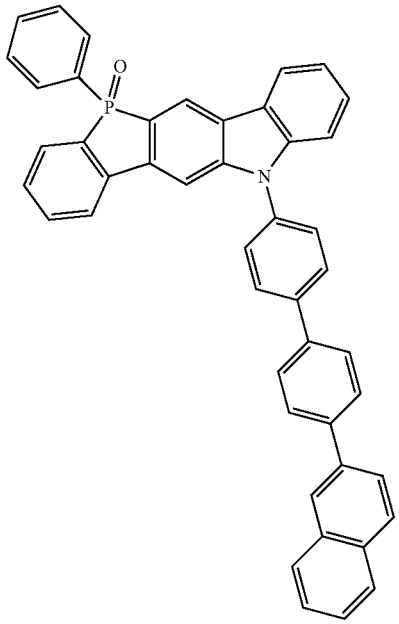
Formula 1-1-116
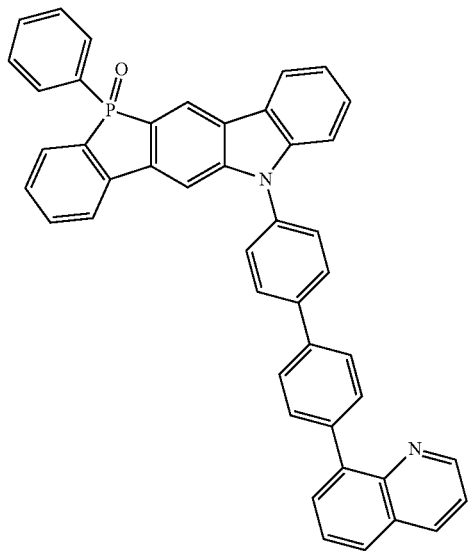

Formula 1-1-117
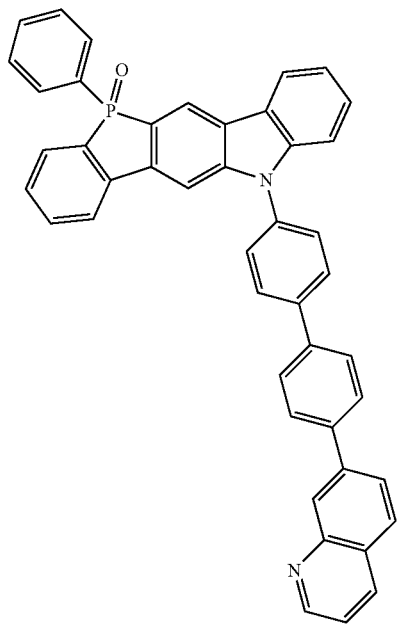
Formula 1-1-118
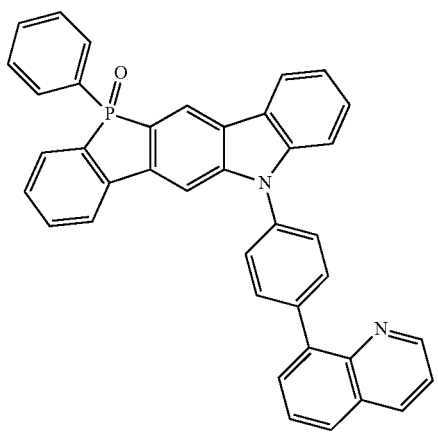
Formula 1-1-119
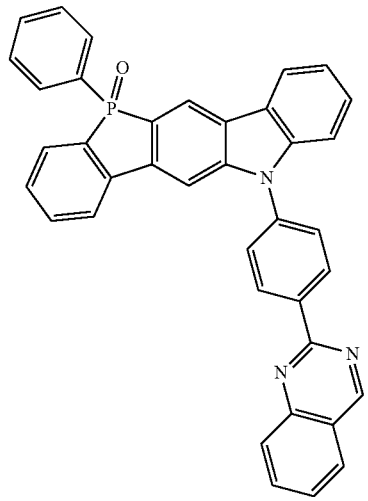
Formula 1-1-120
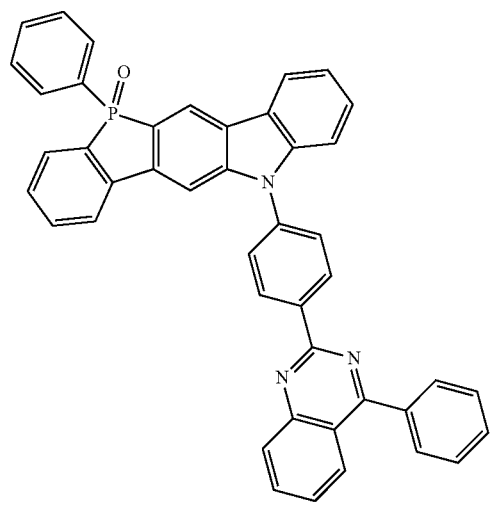
Formula 1-1-121
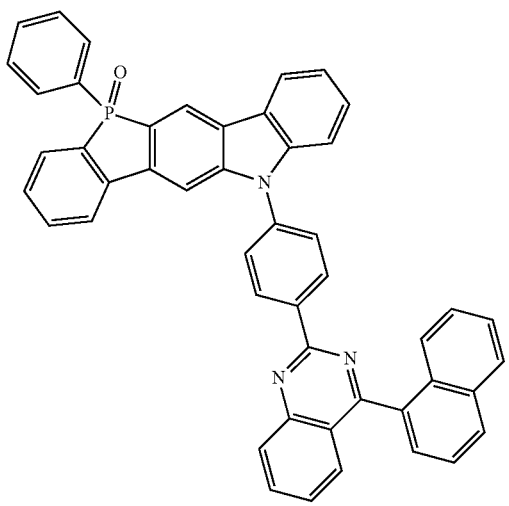
Formula 1-1-122
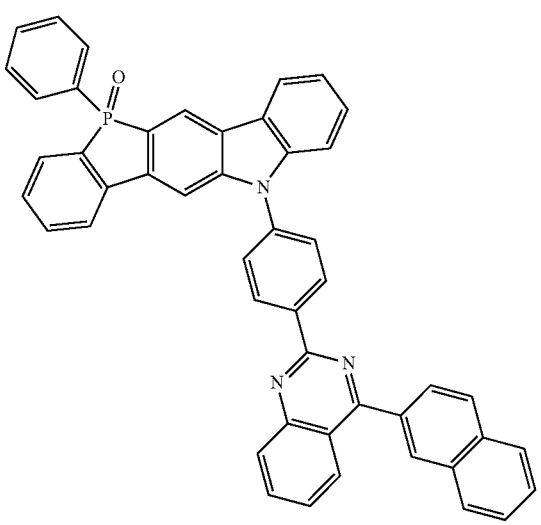

Formula 1-1-123
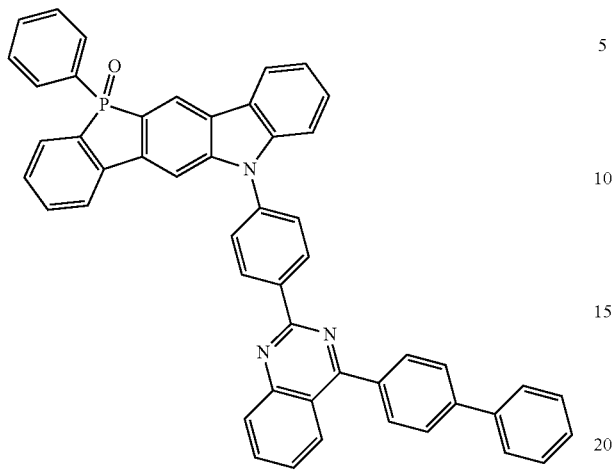
Formula 1-1-124
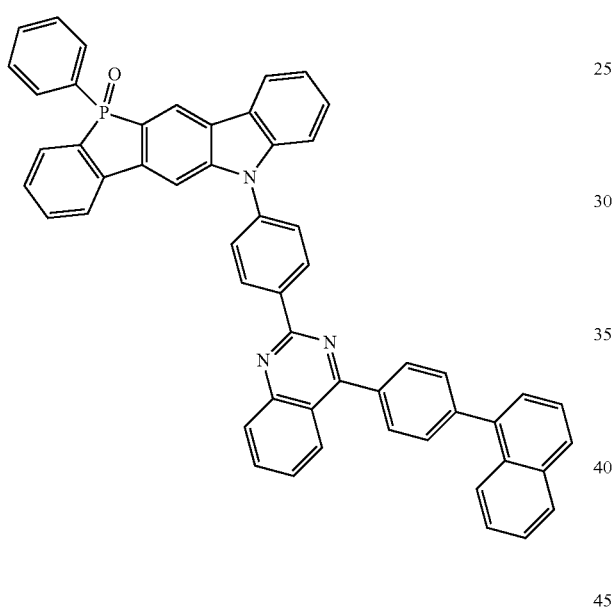
Formula 1-1-125
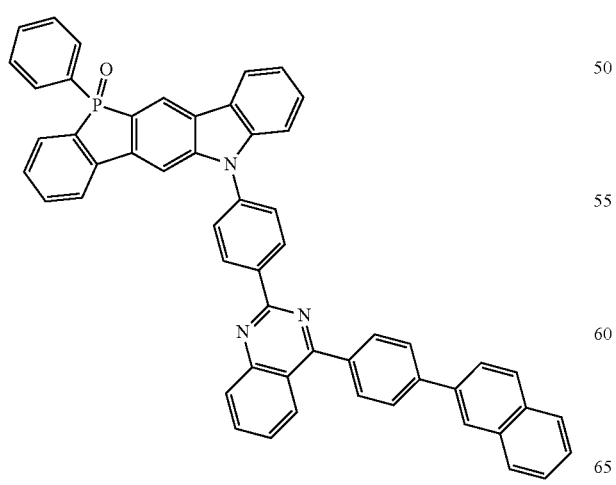
Formula 1-1-126
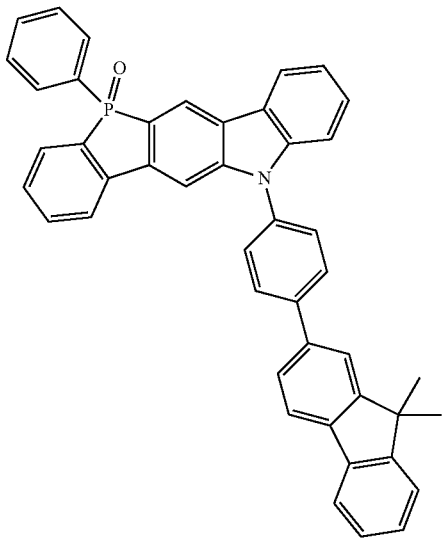
Formula 1-1-127
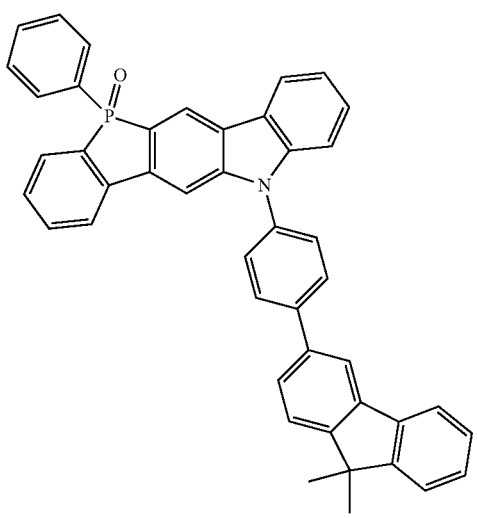
Formula 1-1-128
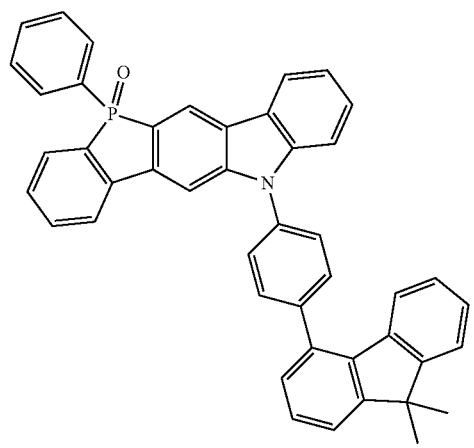

-continued
Formula 1-1-129
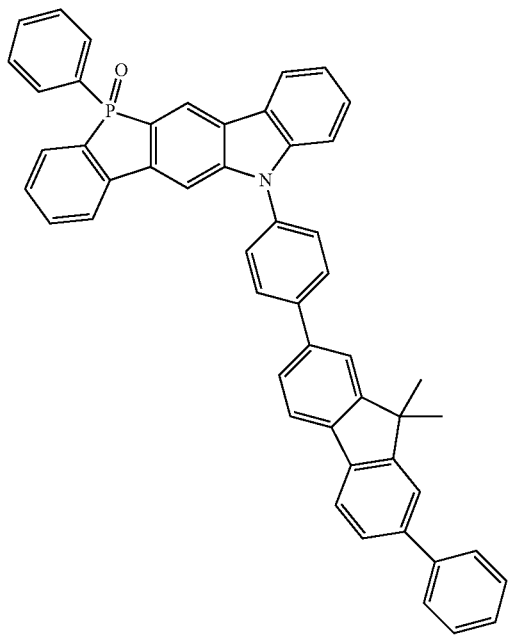
Formula 1-1-130
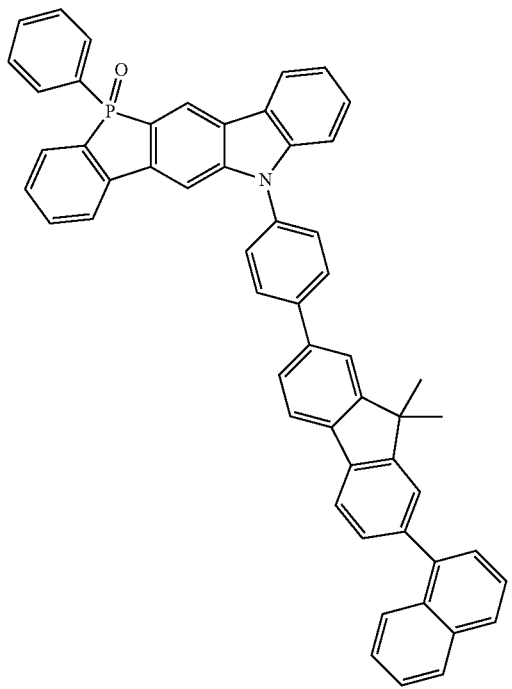
-continued
Formula 1-1-131
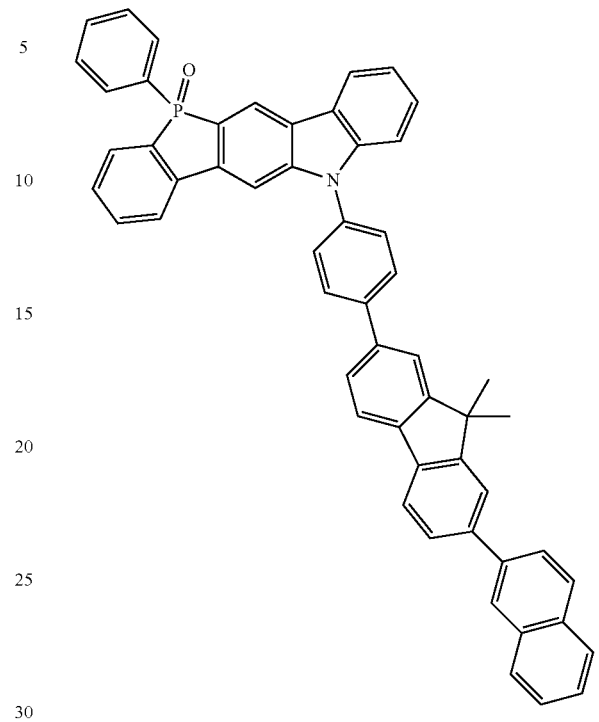
Formula 1-1-132
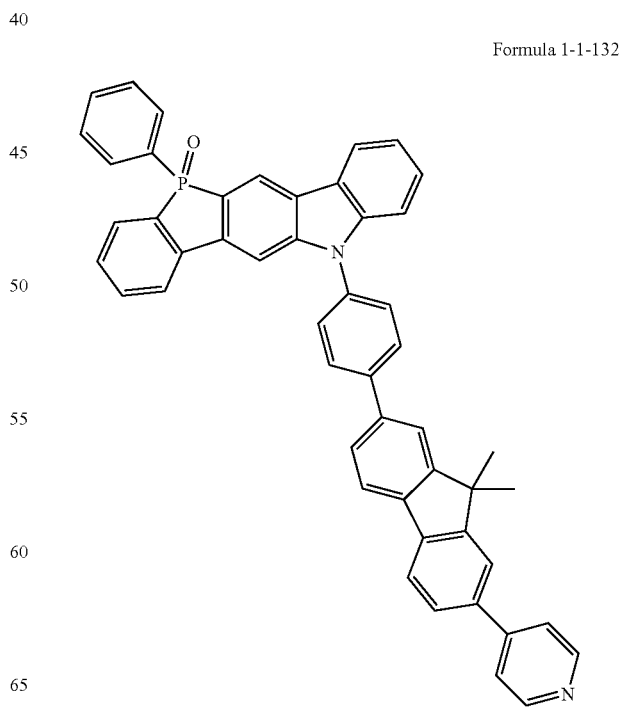

Formula 1-1-133
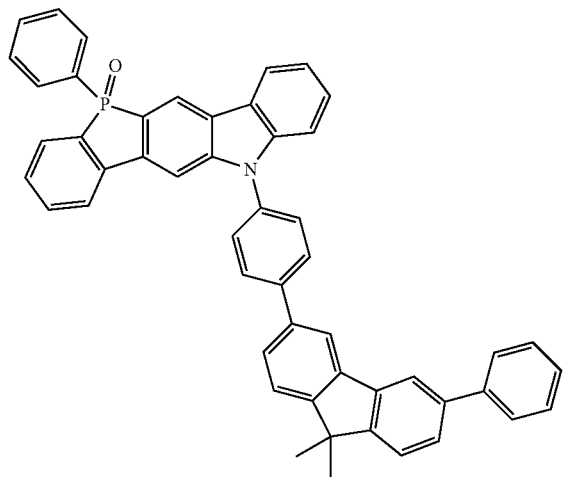
Formula 1-1-134
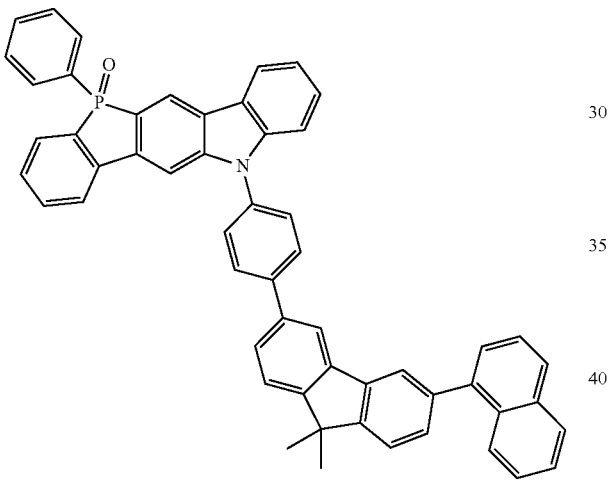
Formula 1-1-135
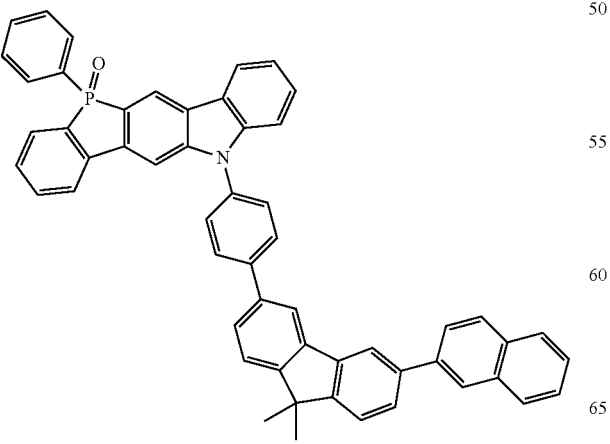
Formula 1-1-136
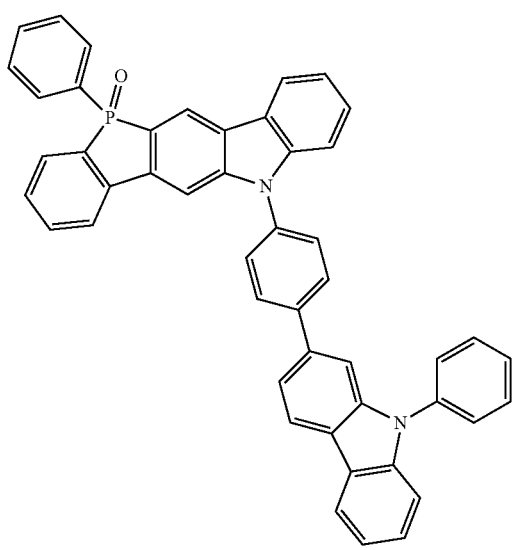
Formula 1-1-137
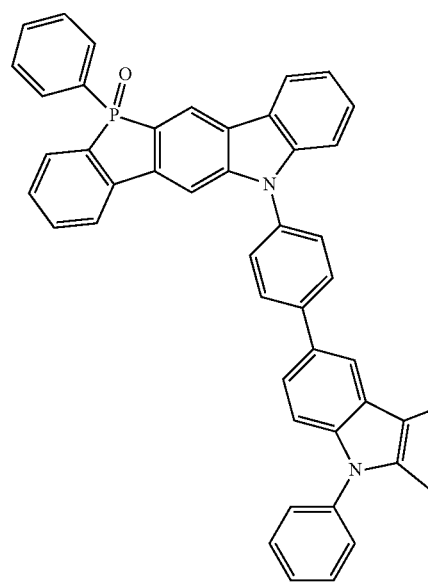

Formula 1-1-138
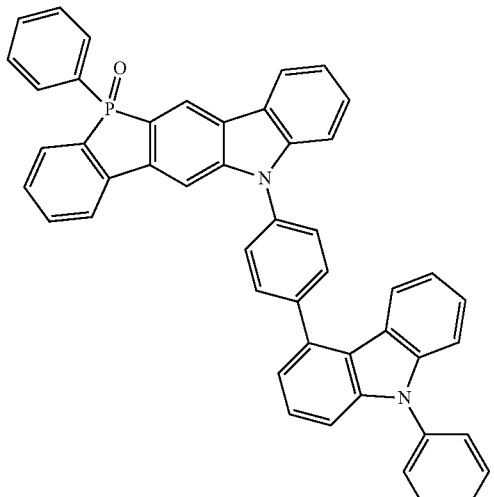
Formula 1-1-139
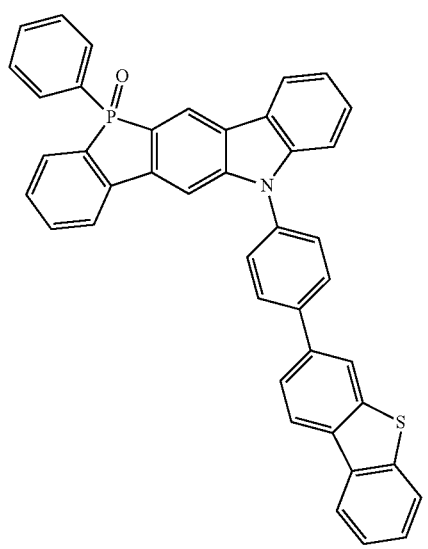 [SMILES: O=P1(c2ccccc2)c2ccccc2-c2cc3c(cc21)c1ccccc1n3-c1ccc(-c2ccc3c(c2)sc2ccccc23)cc1]
Formula 1-1-140
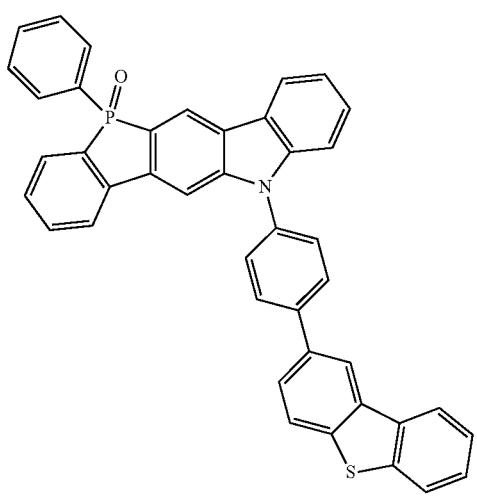
Formula 1-1-141
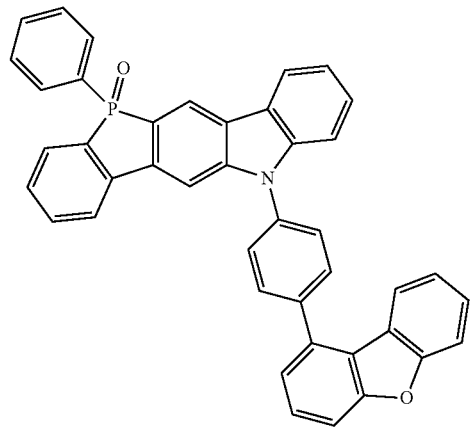
Formula 1-1-142
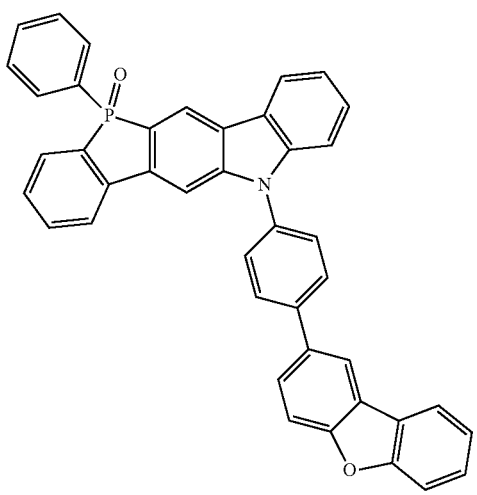
Formula 1-1-143
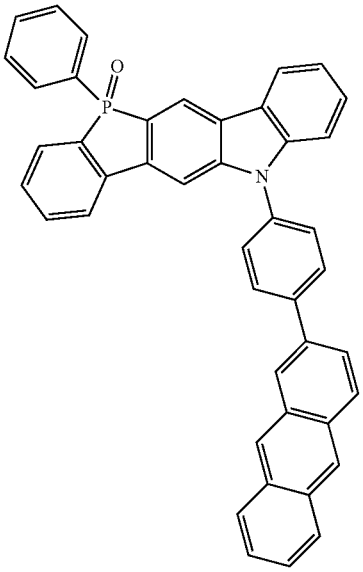

Formula 1-1-144
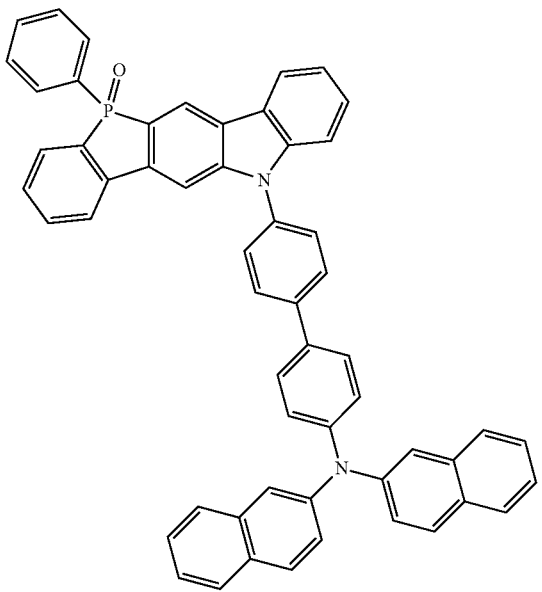
Formula 1-1-145
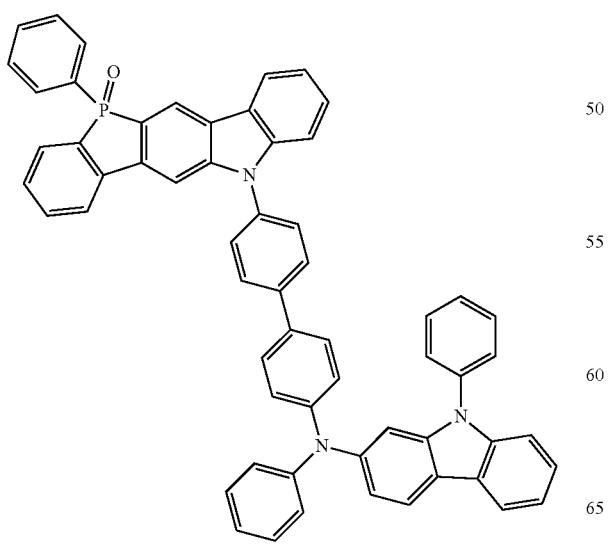
Formula 1-1-146
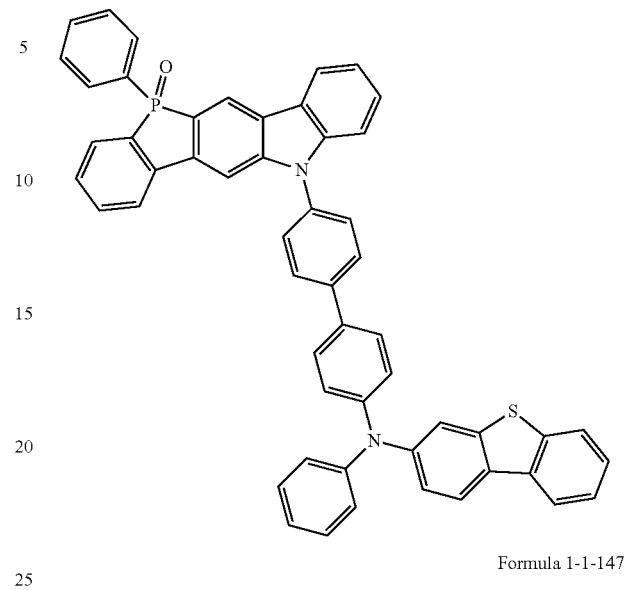
Formula 1-1-147
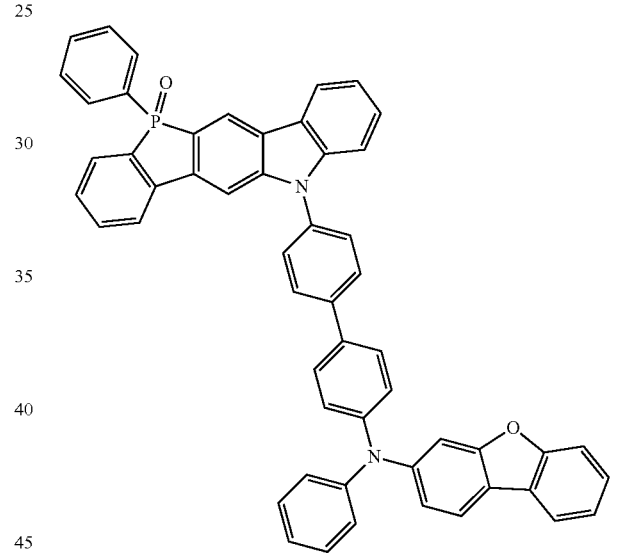
Formula 1-1-148
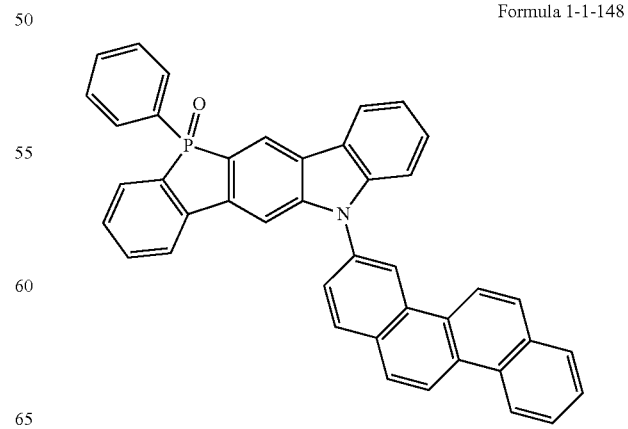

Formula 1-1-149
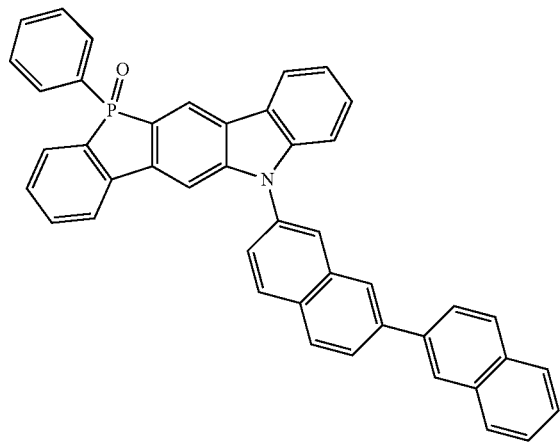
Formula 1-1-150
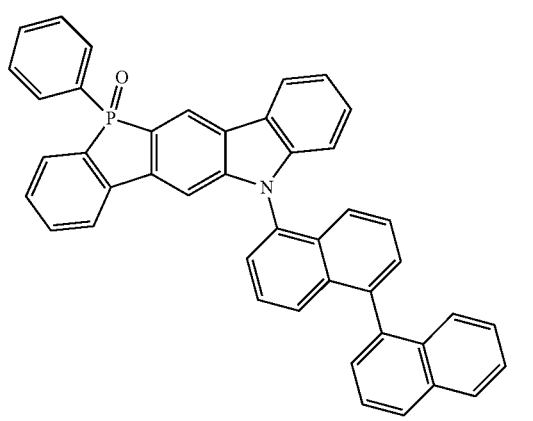
Formula 1-1-151
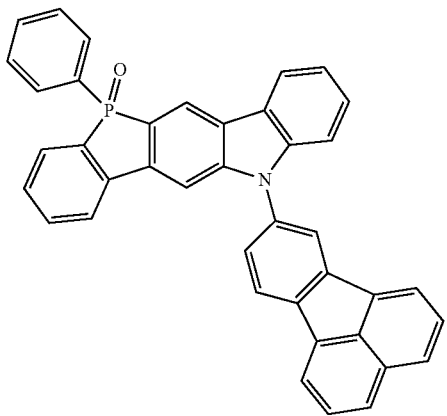
Formula 1-1-152
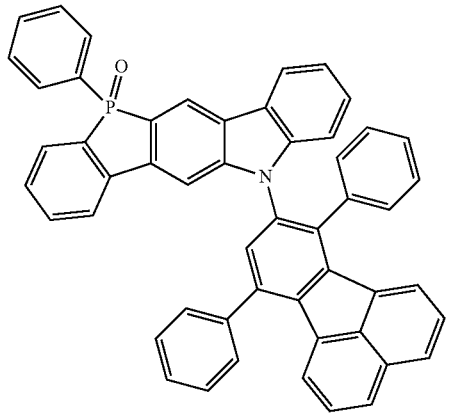
Formula 1-1-153
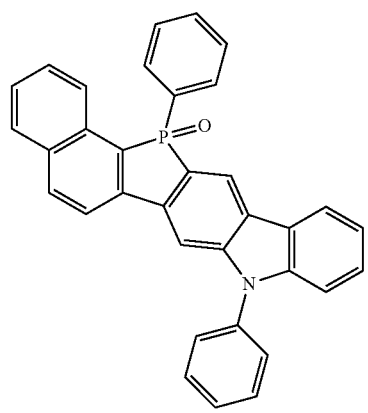
Formula 1-1-154
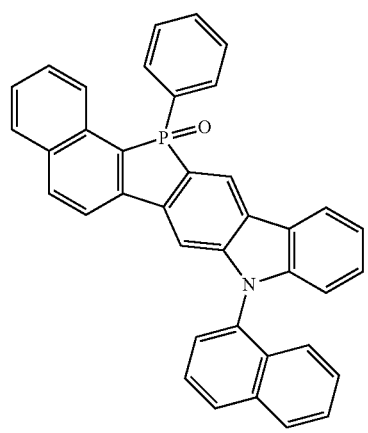

Formula 1-1-155
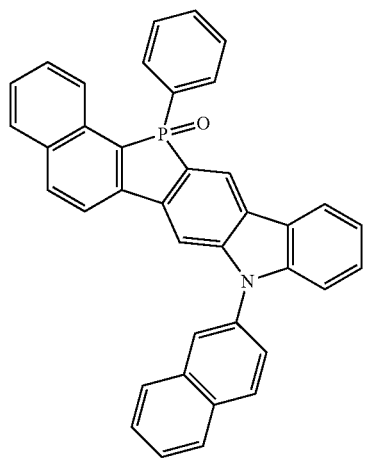
Formula 1-1-156
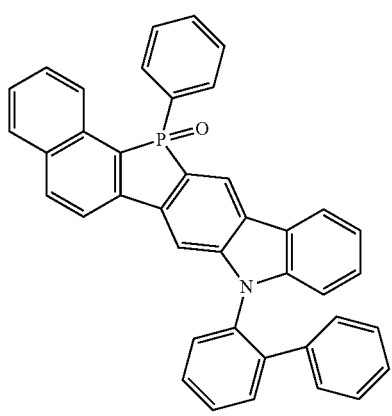
Formula 1-1-157
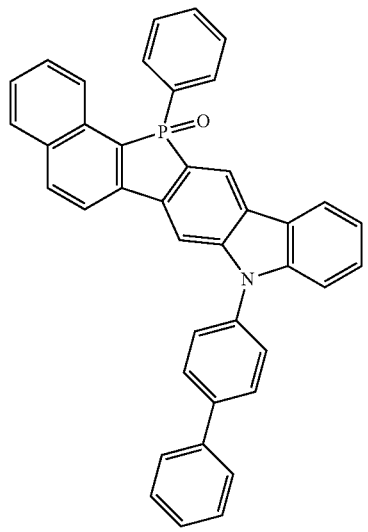
Formula 1-1-158
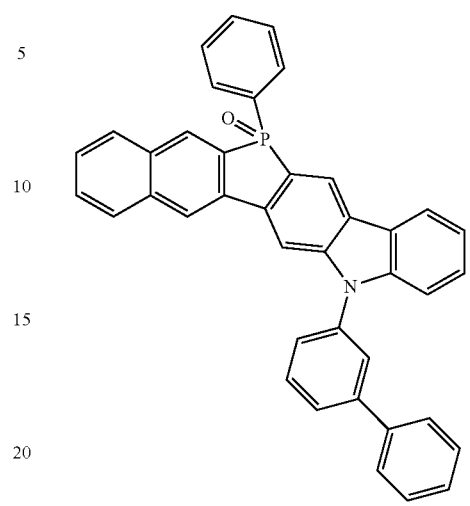
Formula 1-1-159
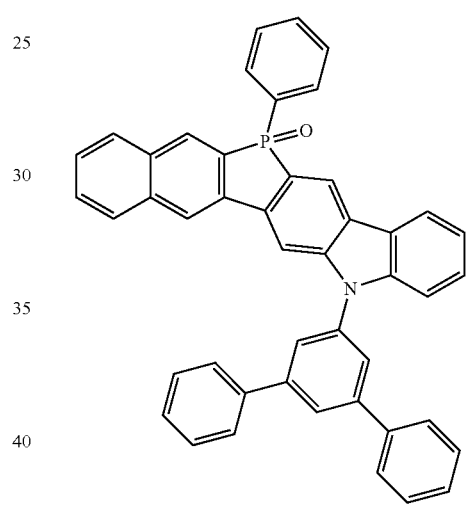
Formula 1-1-160
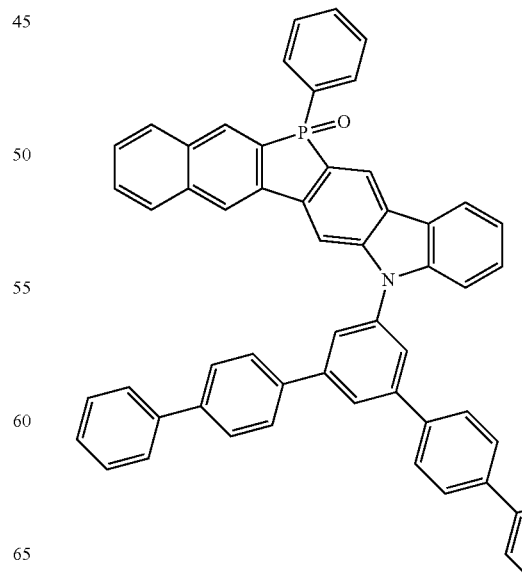

-continued
Formula 1-1-161
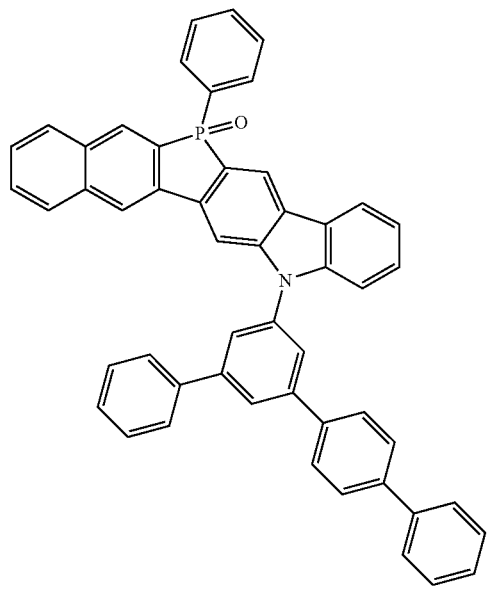
Formula 1-1-162
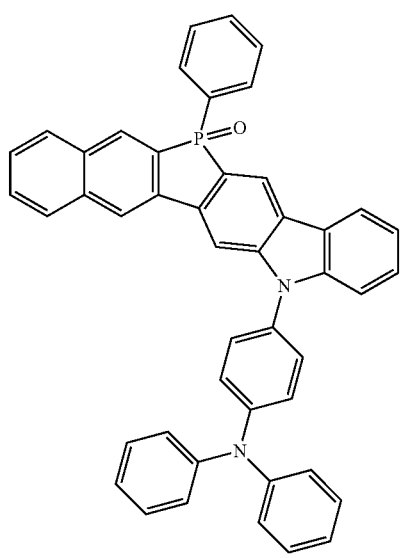
Formula 1-1-163
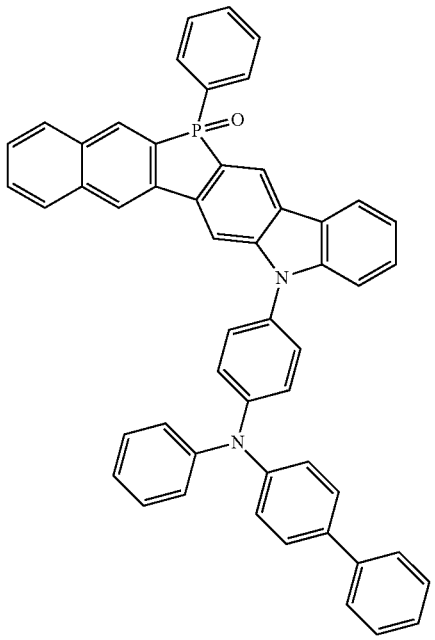
Formula 1-1-164
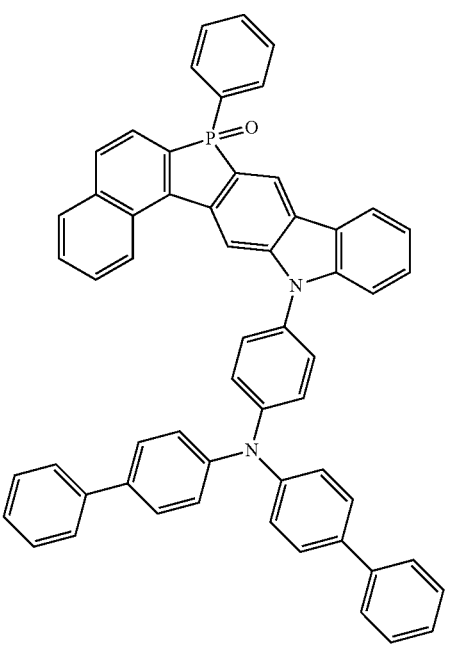

Formula 1-1-165
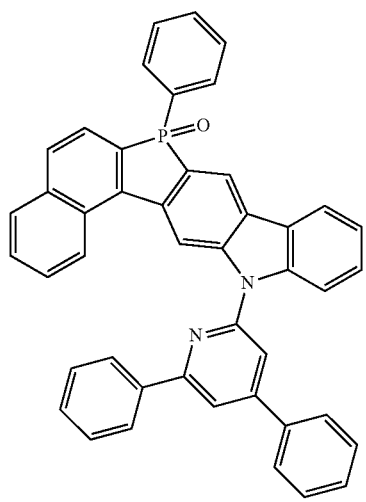
Formula 1-1-166
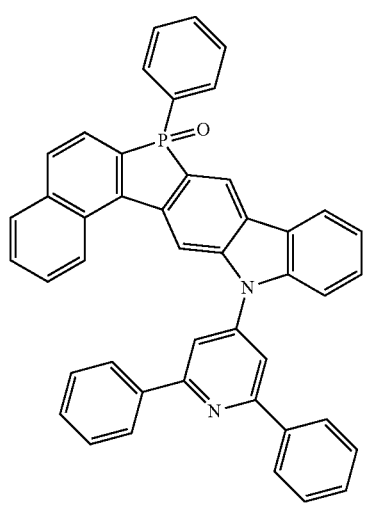
Formula 1-1-167
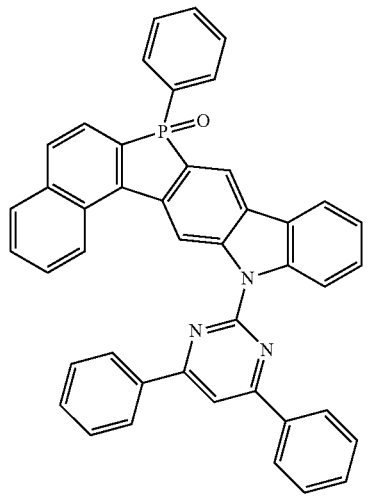
Formula 1-1-168
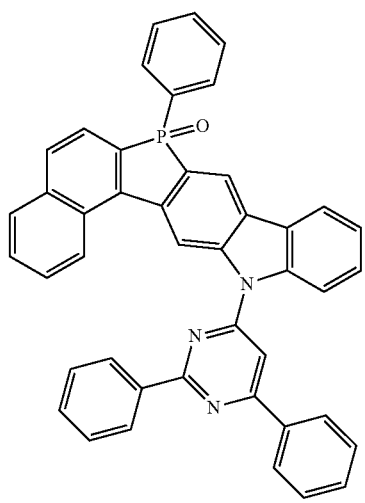
Formula 1-1-169
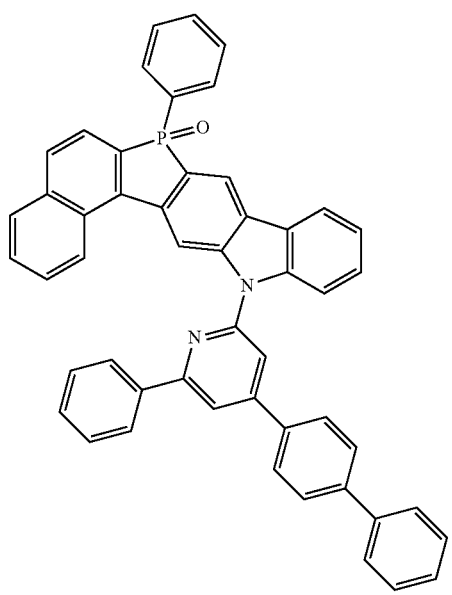

-continued
Formula 1-1-170
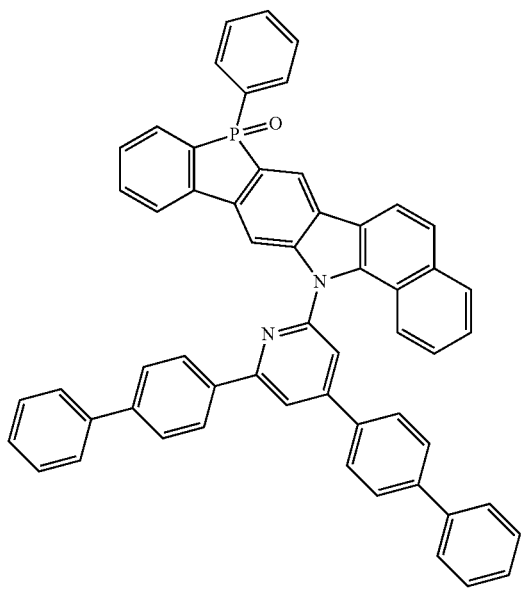
Formula 1-1-171
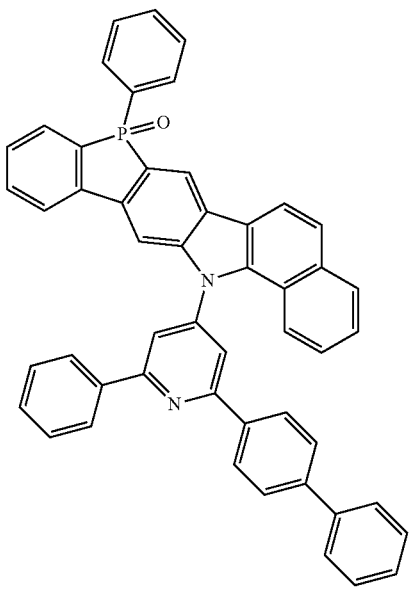
-continued
Formula 1-1-172
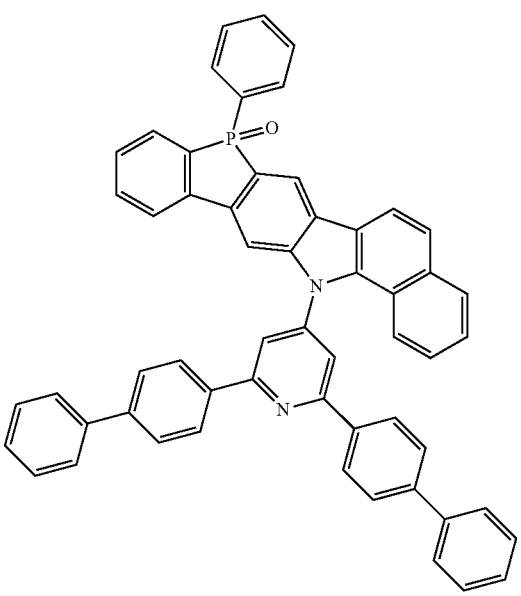
Formula 1-1-173
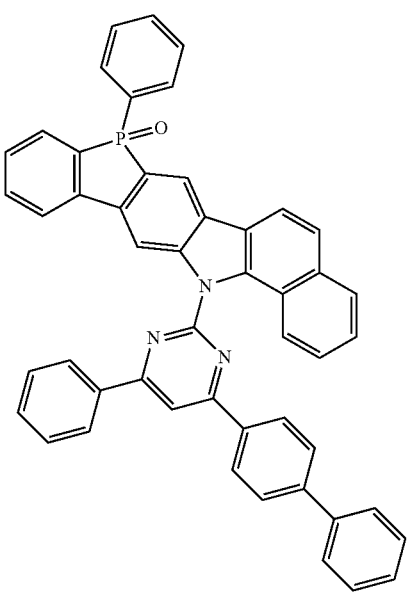

-continued
Formula 1-1-174
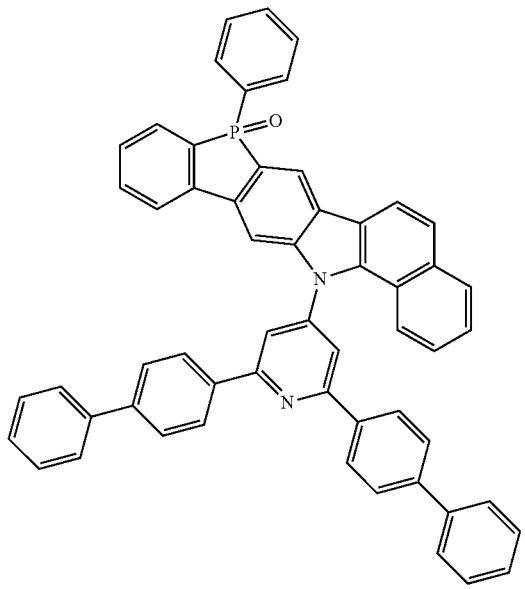
Formula 1-1-175
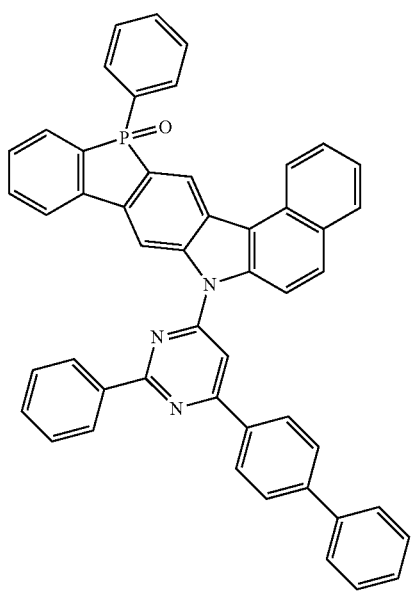
Formula 1-1-176
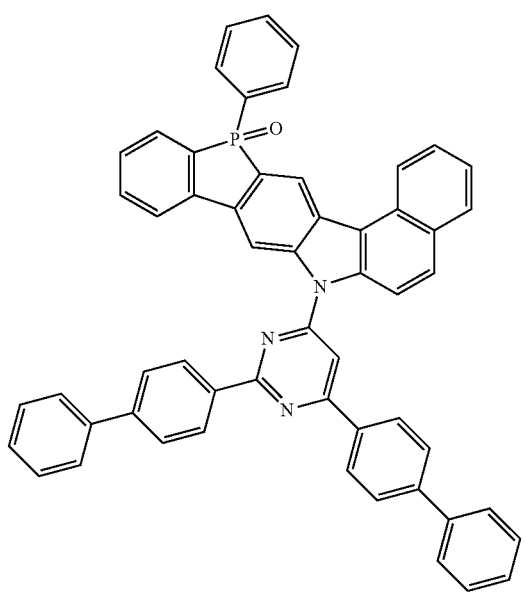
Formula 1-1-177
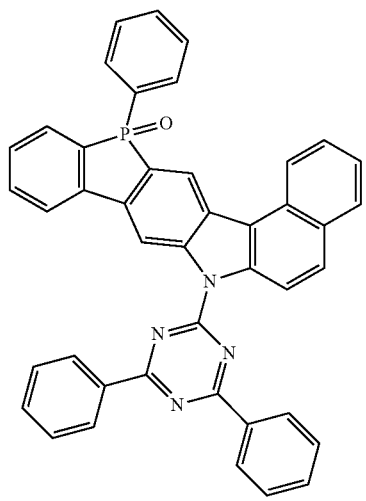

Formula 1-1-178
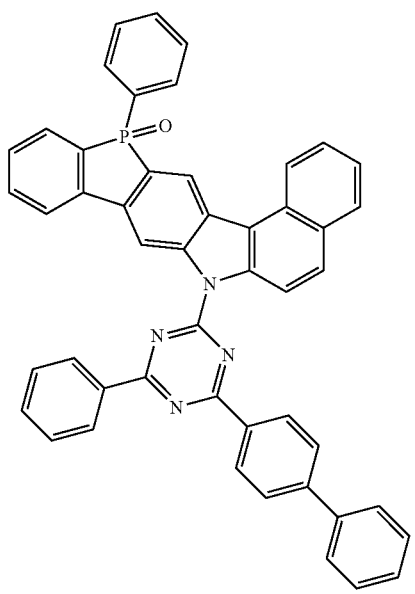
Formula 1-1-179
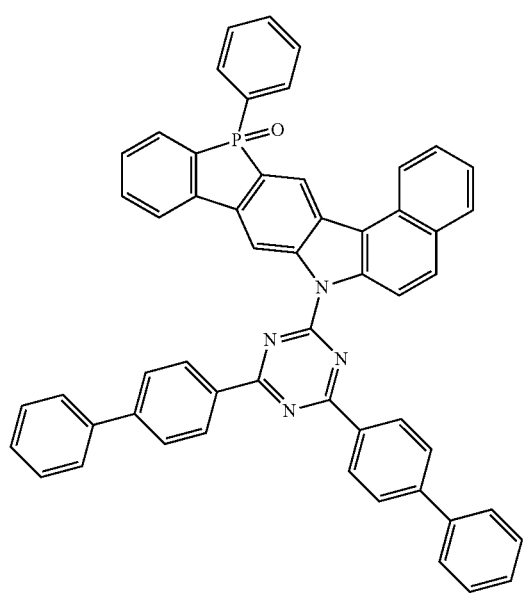
Formula 1-1-180
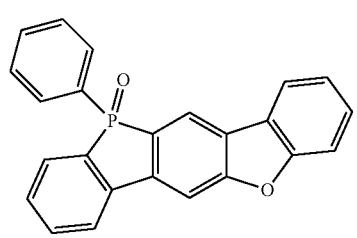
Formula 1-1-181
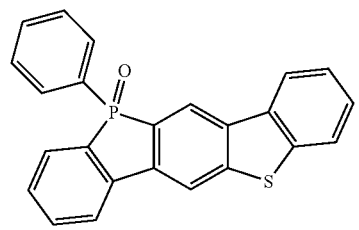
Formula 1-1-182
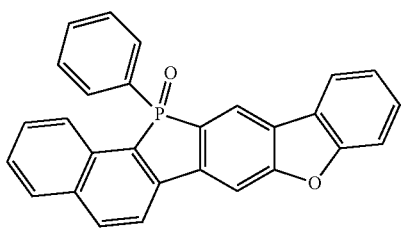
Formula 1-1-183
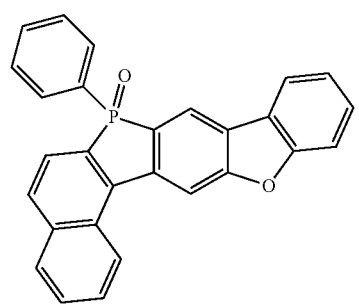
Formula 1-1-184
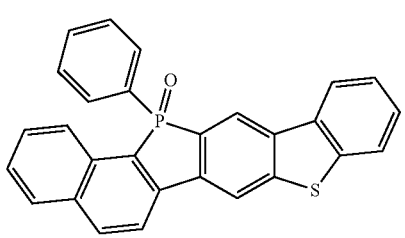
Formula 1-1-185
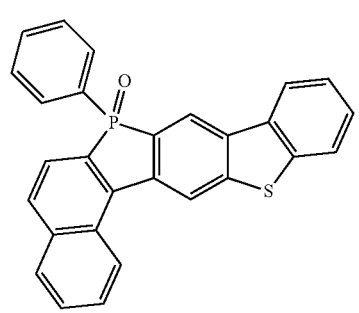

Formula 1-1-186
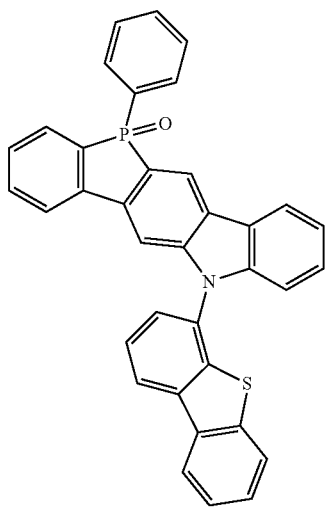
Formula 1-1-187
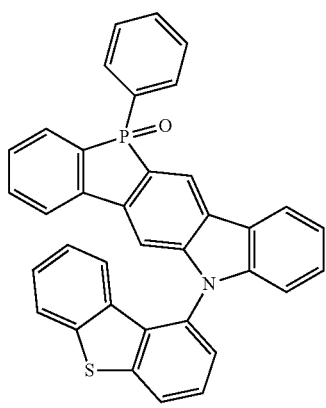
Formula 1-1-188
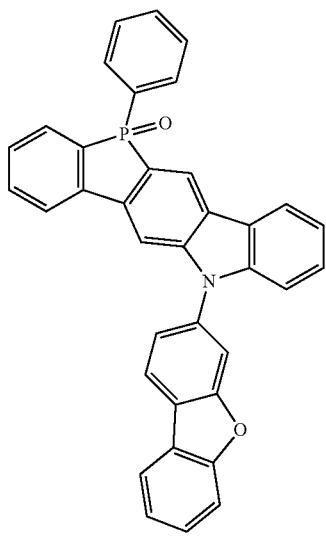
Formula 1-1-189
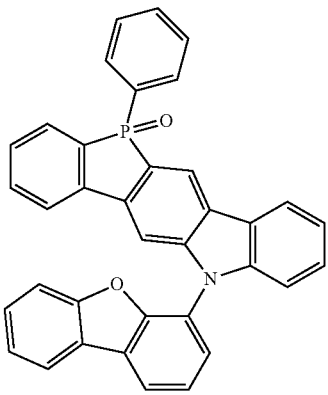
Formula 1-1-190
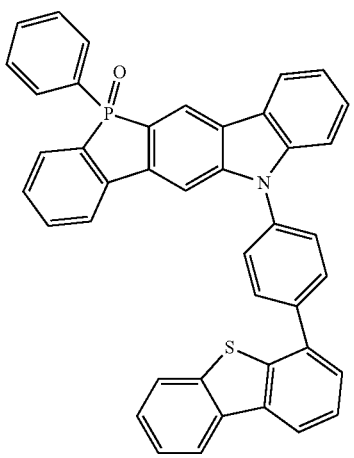
Formula 1-1-191
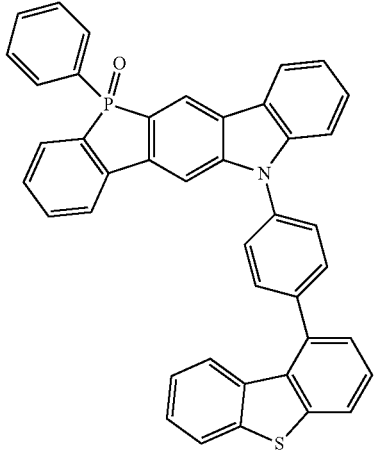

Formula 1-1-192
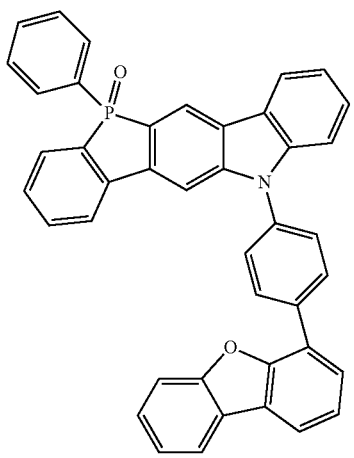
Formula 1-1-193
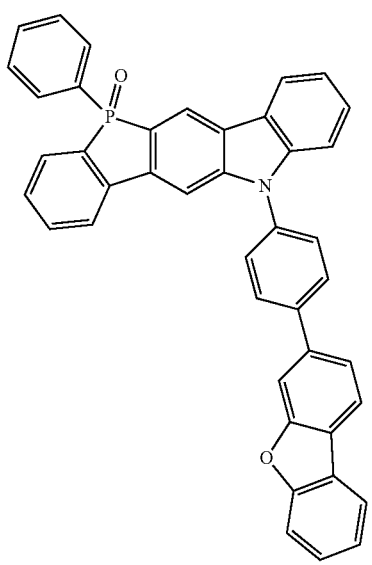
Formula 1-1-194
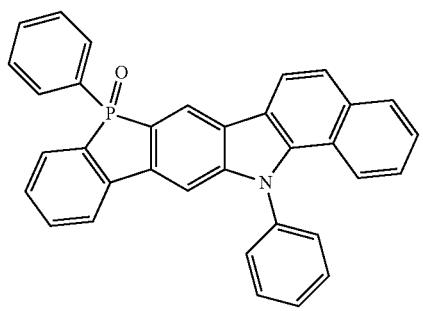 [SMILES: O=P1(c2ccccc2)c2ccccc2-c2cc3c(cc21)c1ccc2ccccc2c1n3-c1ccccc1]
Formula 1-1-195
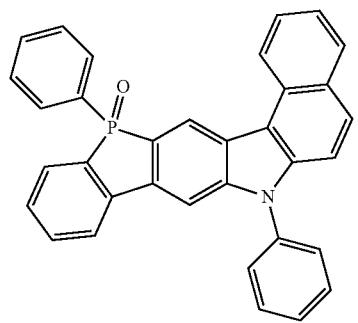 [SMILES: O=P1(c2ccccc2)c2ccccc2-c2cc3c(cc21)c1c2ccccc2ccc1n3-c1ccccc1]
6. The compound of claim 1, wherein the compound represented by Formula 1-2 is represented by any one of the following Formulae 1-2-1 to 1-2-195:
Formula 1-2-1
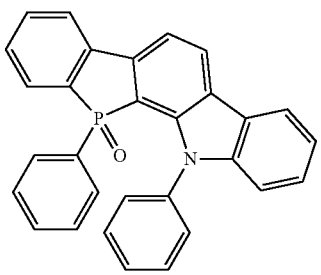
Formula 1-2-2
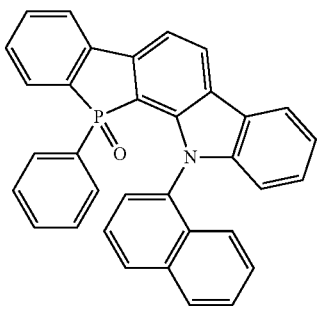
Formula 1-2-3
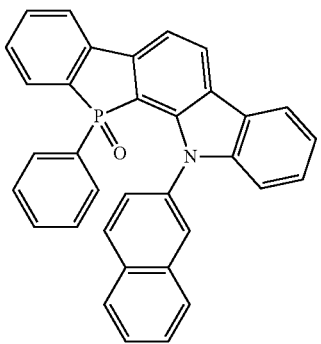

Formula 1-2-4
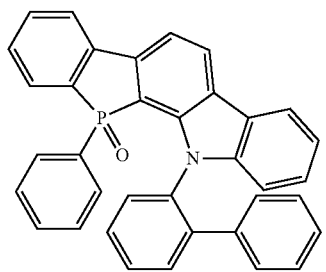
Formula 1-2-5
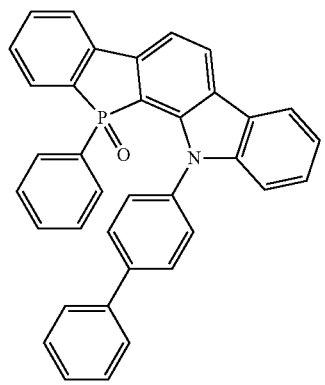
Formula 1-2-6
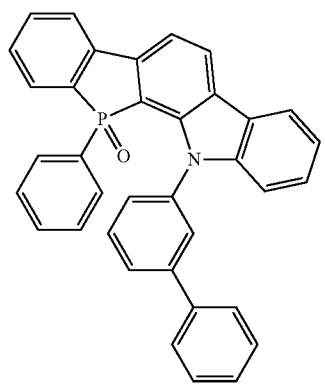
Formula 1-2-7
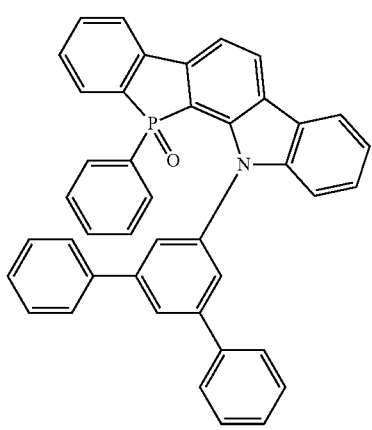
Formula 1-2-8
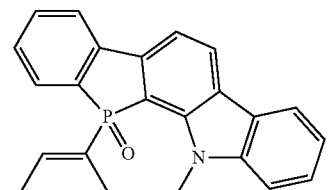
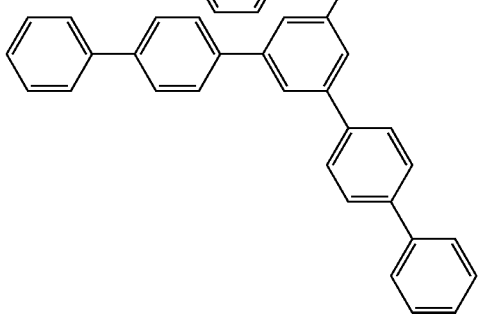
Formula 1-2-9
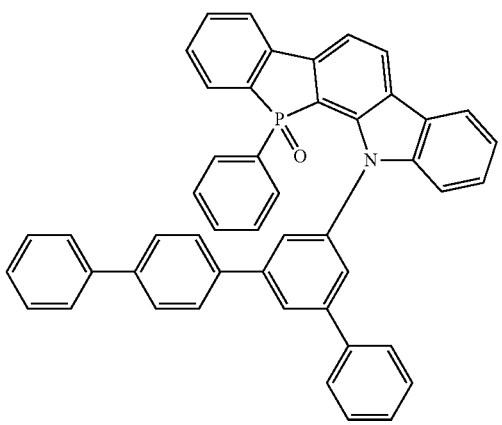
Formula 1-2-10
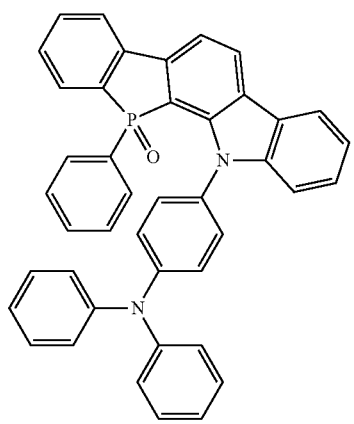

Formula 1-2-11
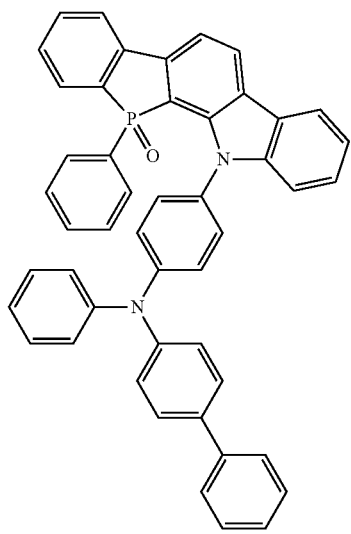
Formula 1-2-14
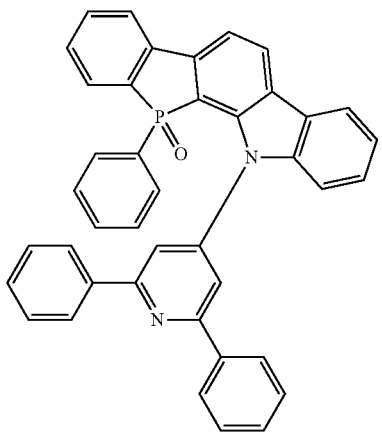
Formula 1-2-12
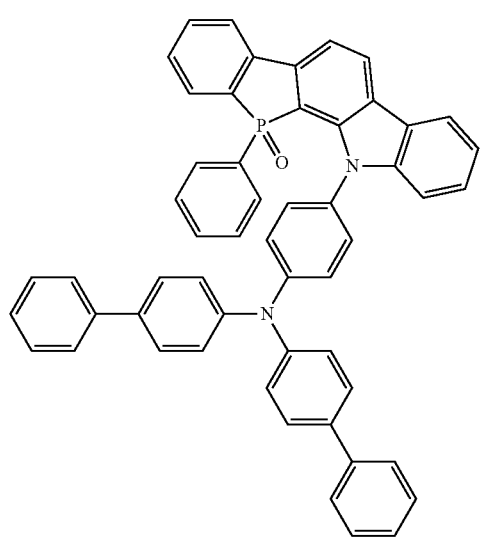
Formula 1-2-15
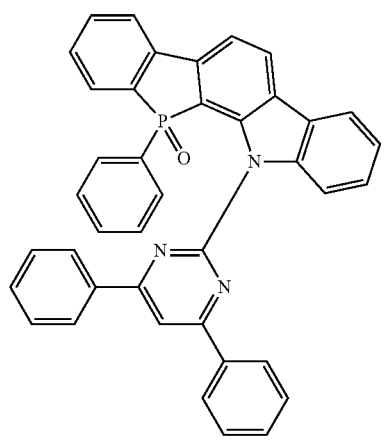
Formula 1-2-13
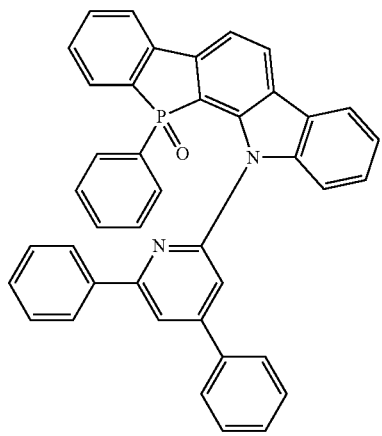
Formula 1-2-16
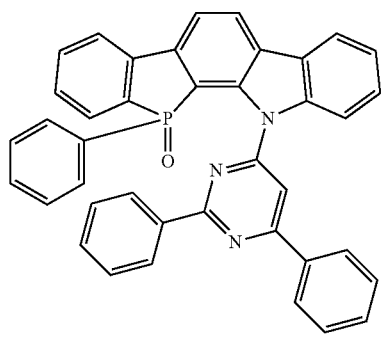

Formula 1-2-17
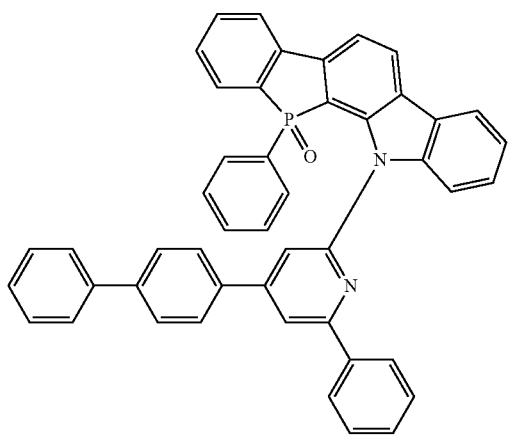
Formula 1-2-18
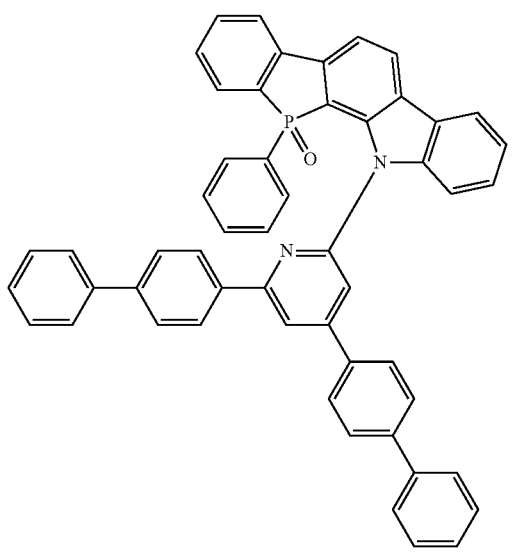
Formula 1-2-19
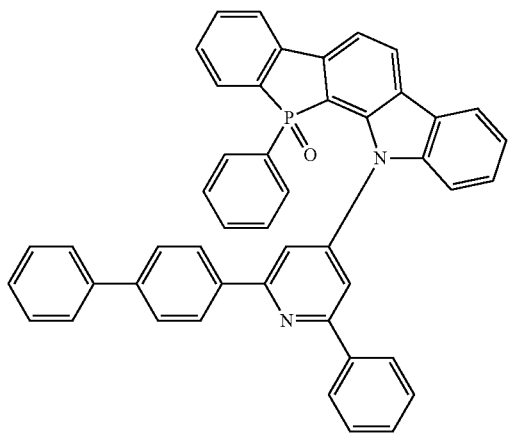
Formula 1-2-20
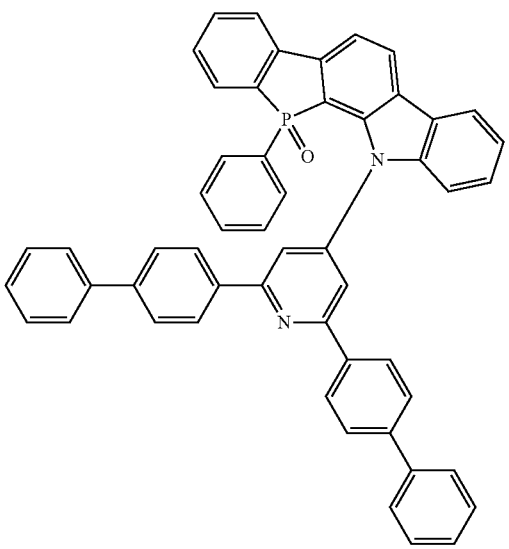
Formula 1-2-21
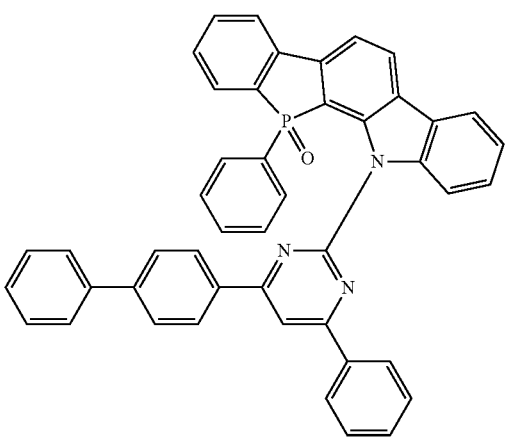
Formula 1-2-22
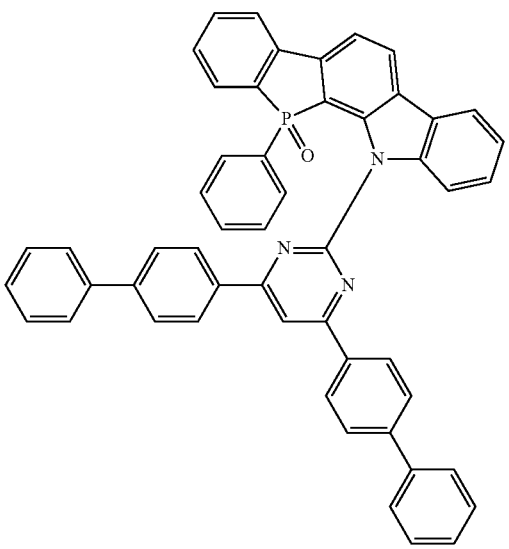

-continued
Formula 1-2-23
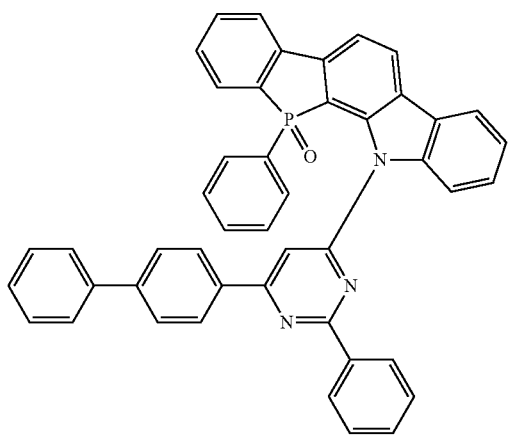
Formula 1-2-26
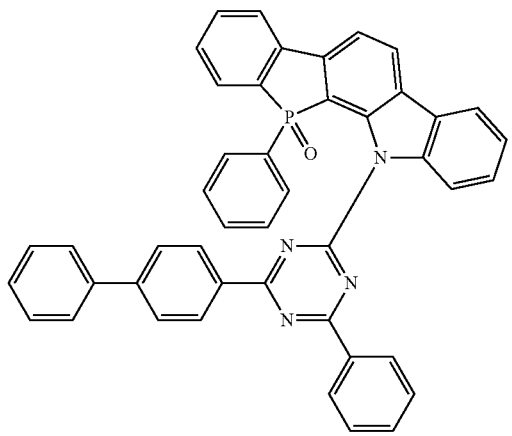
Formula 1-2-24
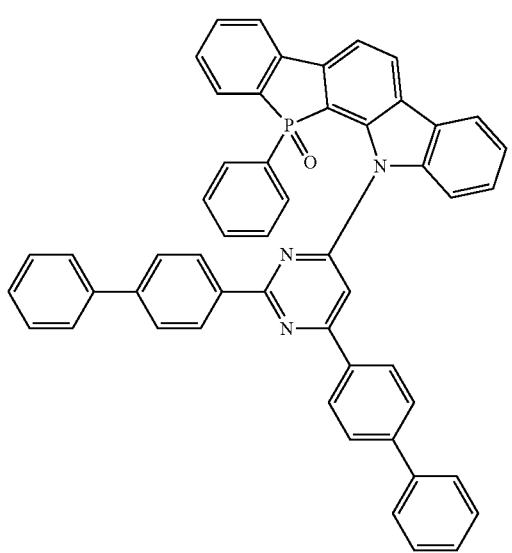
Formula 1-2-27
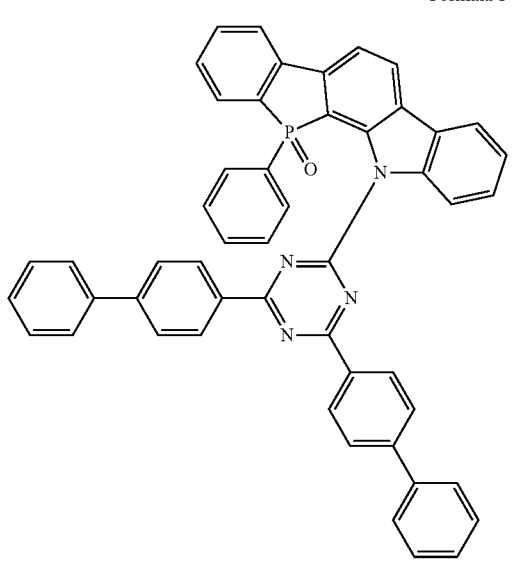
Formula 1-2-25
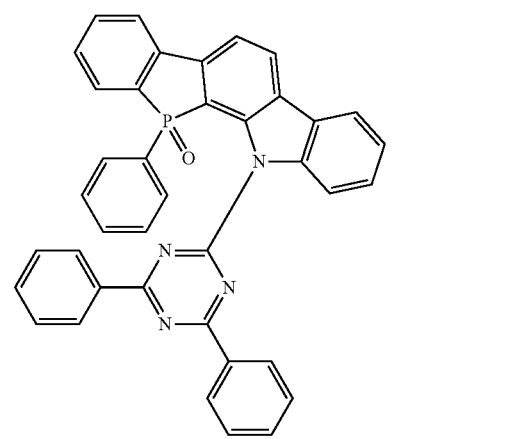
Formula 1-2-28
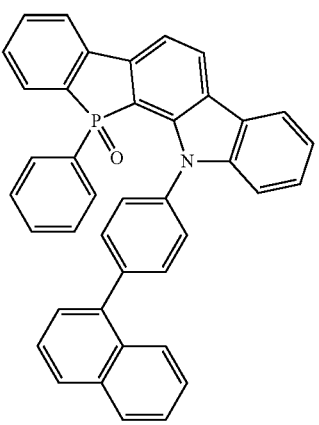

Formula 1-2-29
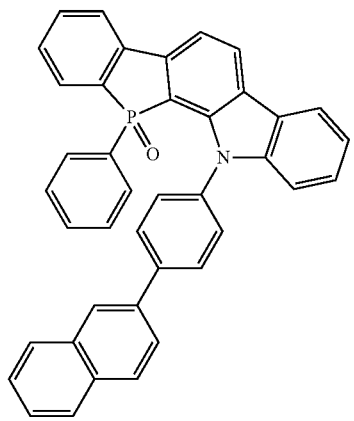
Formula 1-2-30
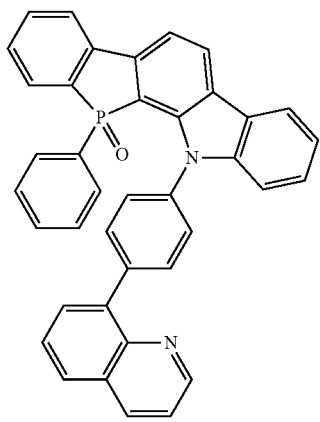
Formula 1-2-31
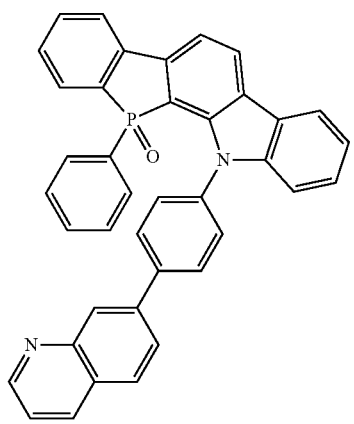
Formula 1-2-32
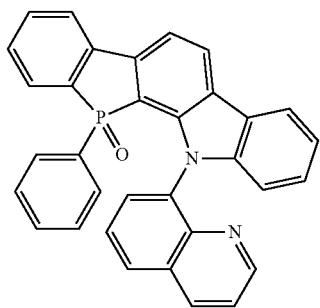
Formula 1-2-33
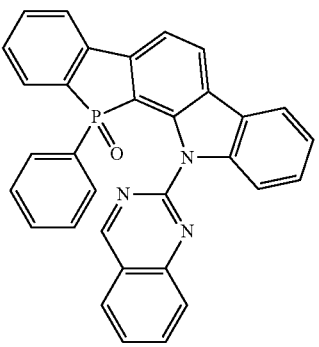
Formula 1-2-34
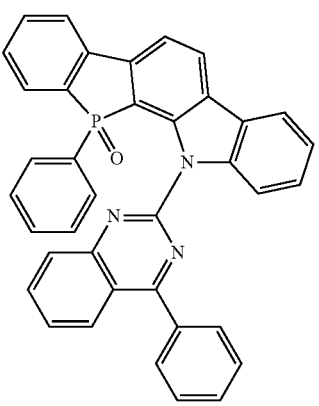
Formula 1-2-35
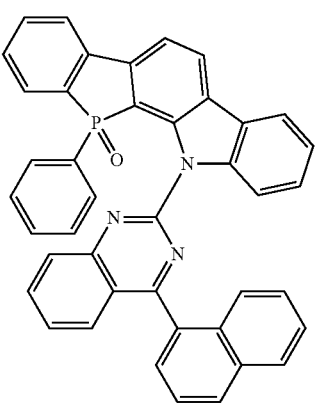

Formula 1-2-36
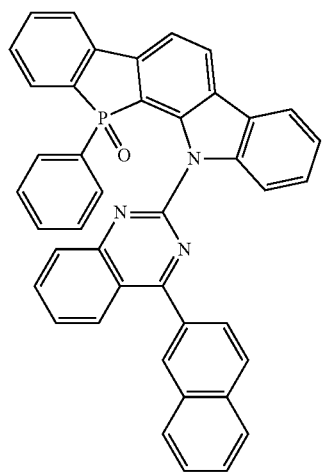
Formula 1-2-37
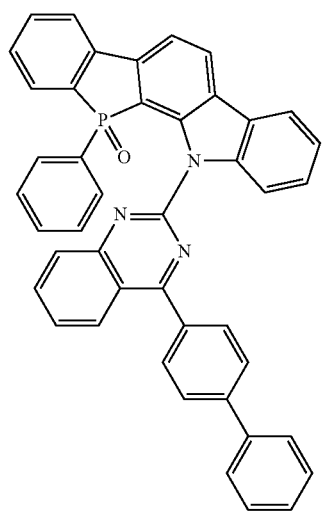
Formula 1-2-38
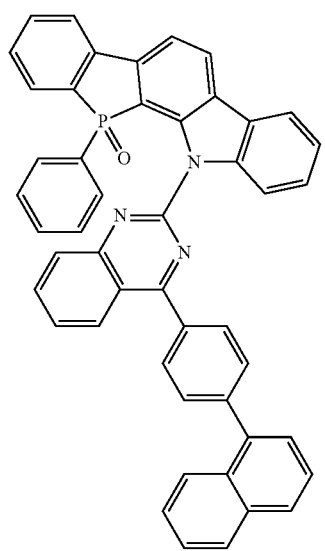
Formula 1-2-39
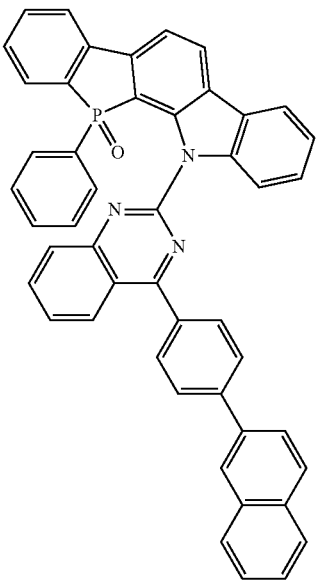
Formula 1-2-40
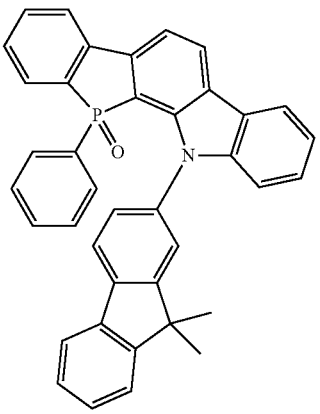
Formula 1-2-41
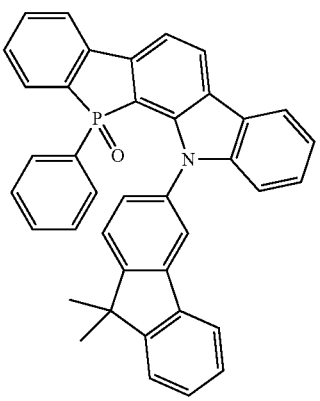

Formula 1-2-42
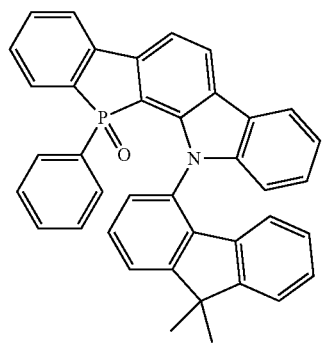
Formula 1-2-45
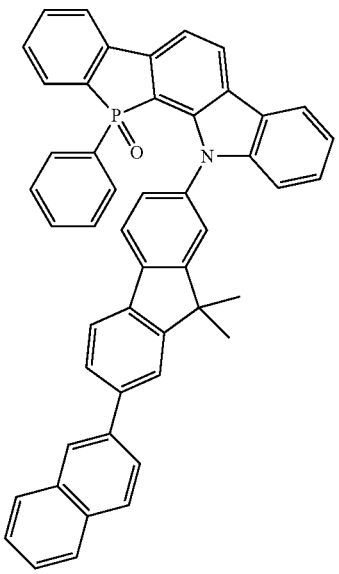
Formula 1-2-43
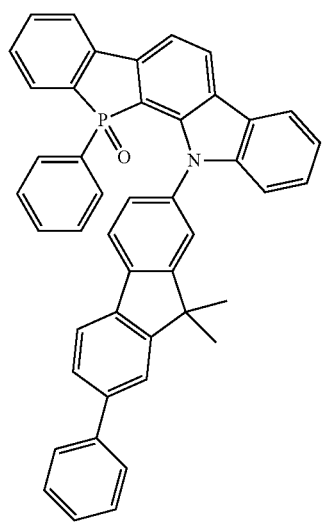
Formula 1-2-46
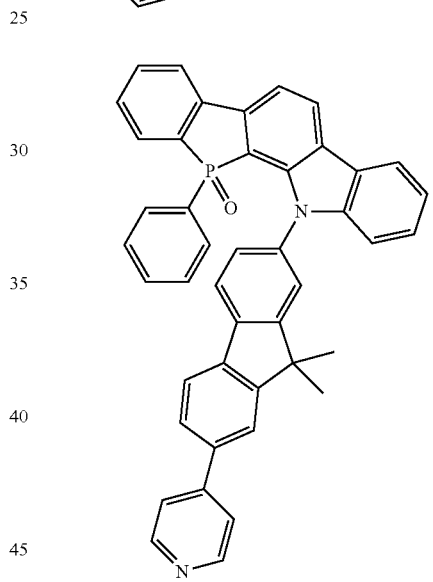
Formula 1-2-44
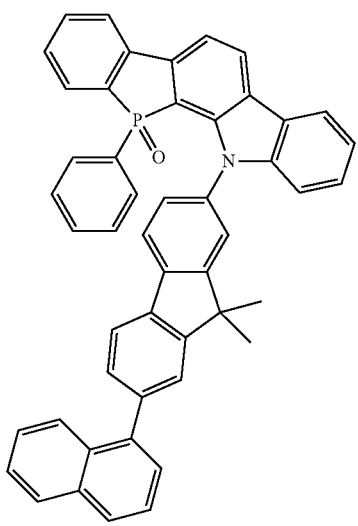
Formula 1-2-47
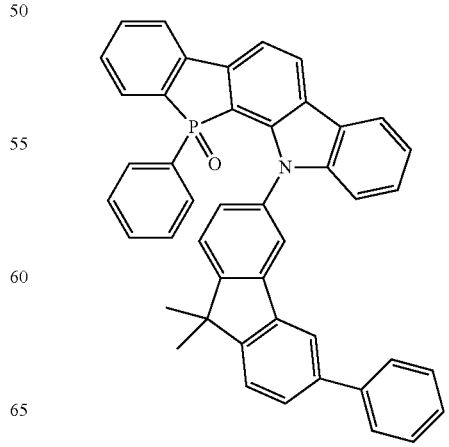

-continued
Formula 1-2-48
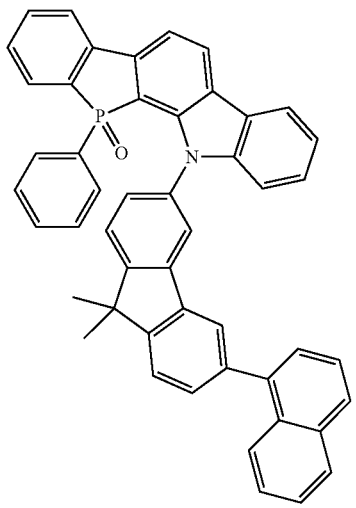
Formula 1-2-49
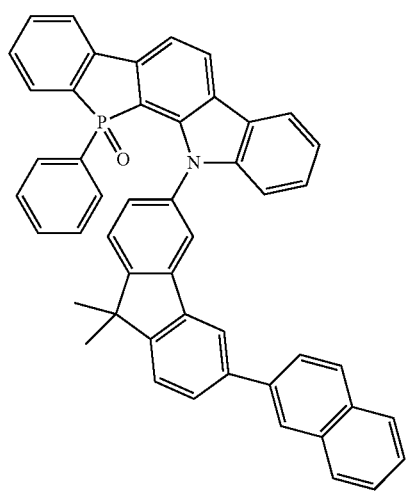
Formula 1-2-50
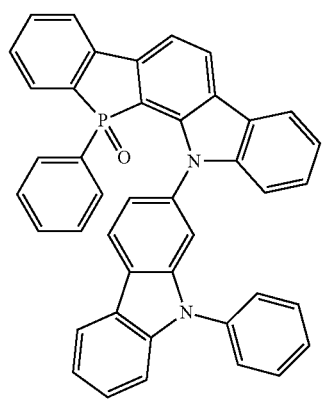
-continued
Formula 1-2-51
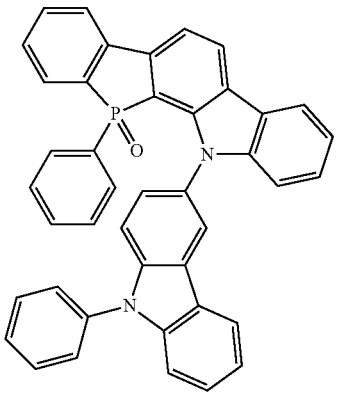
Formula 1-2-52
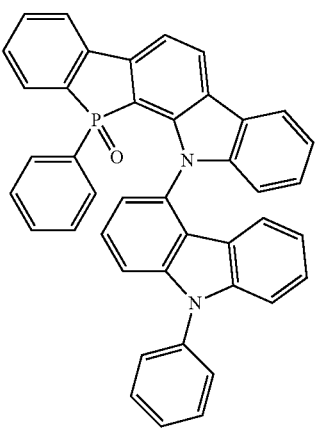
Formula 1-2-53
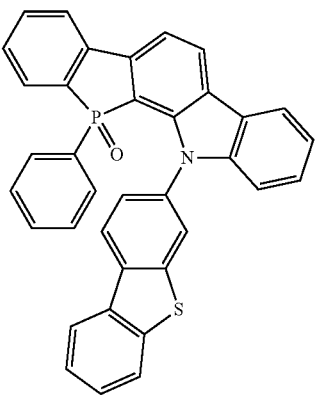
Formula 1-2-54
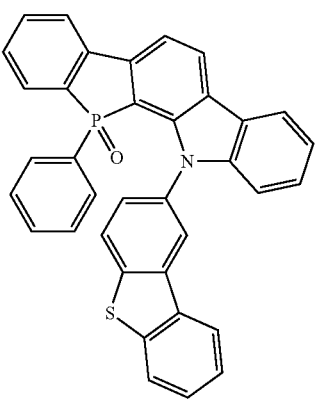

Formula 1-2-55
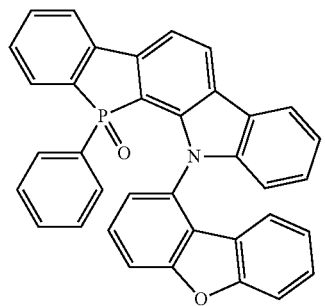
Formula 1-2-56
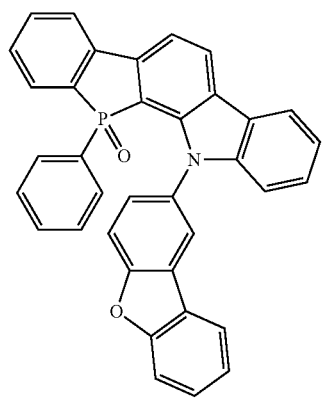
Formula 1-2-57
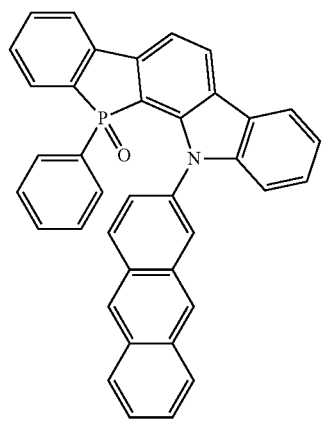
Formula 1-2-58
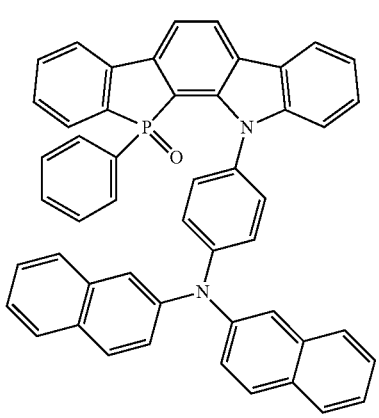
Formula 1-2-59
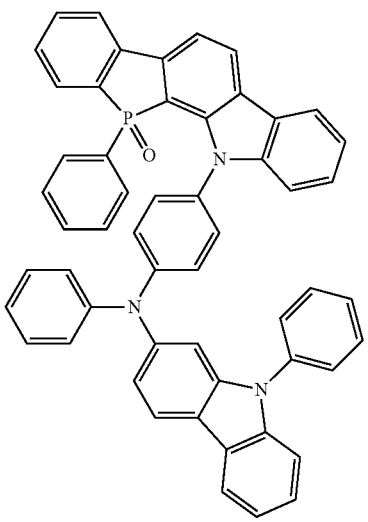
Formula 1-2-60
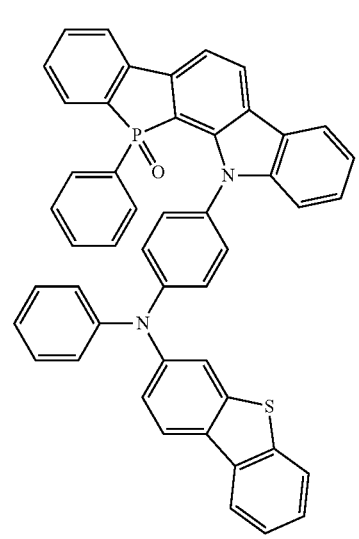
Formula 1-2-61
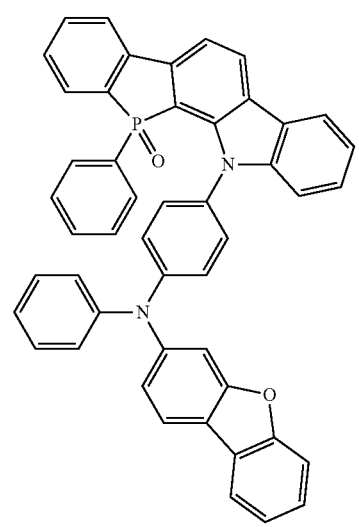

Formula 1-2-62
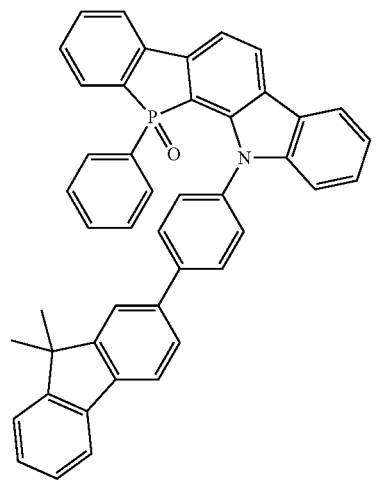
Formula 1-2-63
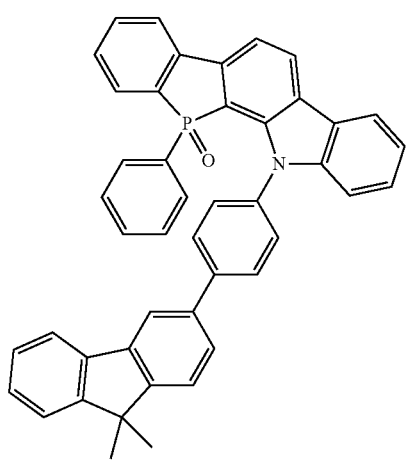
Formula 1-2-64
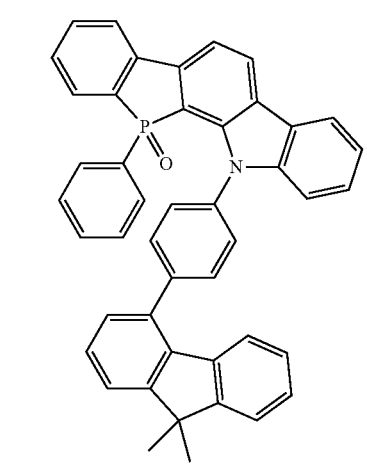
Formula 1-2-65
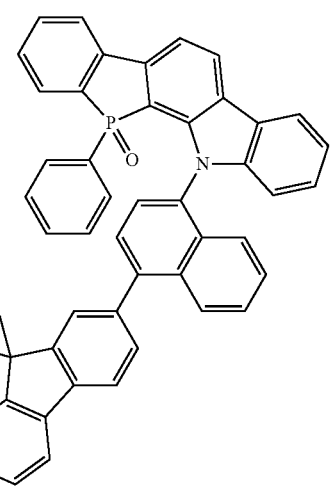
Formula 1-2-66
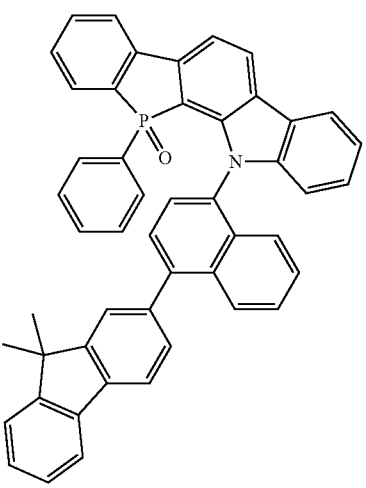
Formula 1-2-67
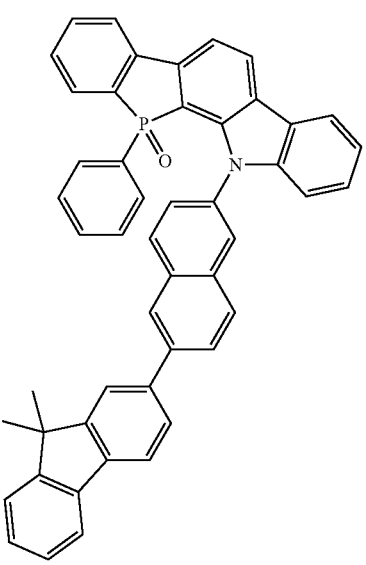

Formula 1-2-68
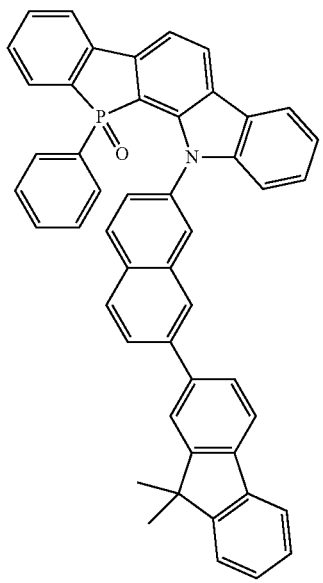
Formula 1-2-69
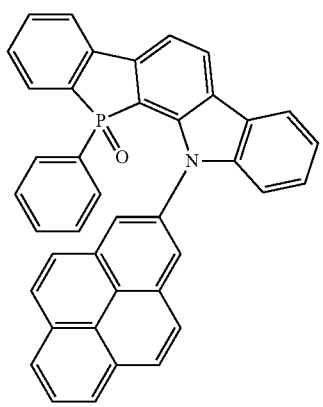
Formula 1-2-70
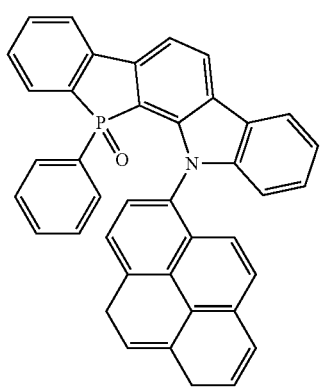
Formula 1-2-71
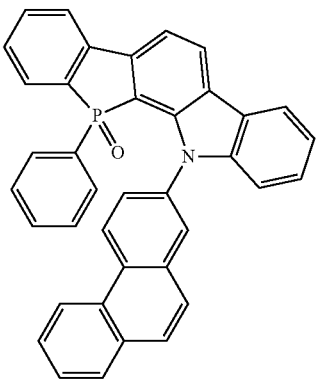
Formula 1-2-72
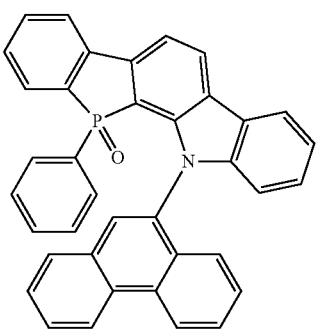
Formula 1-2-73
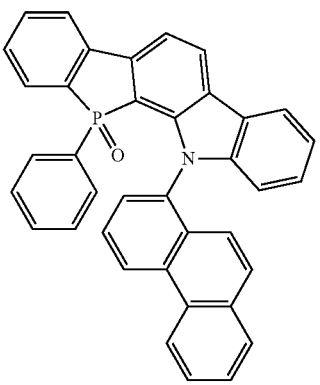
Formula 1-2-74
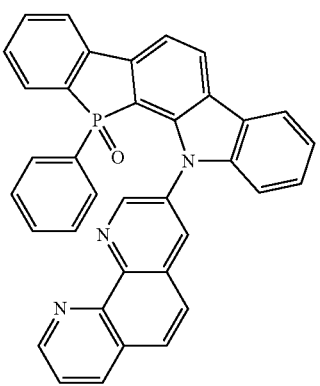

Formula 1-2-75
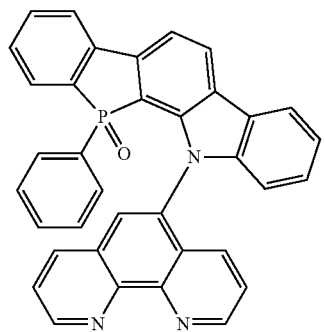
Formula 1-2-76
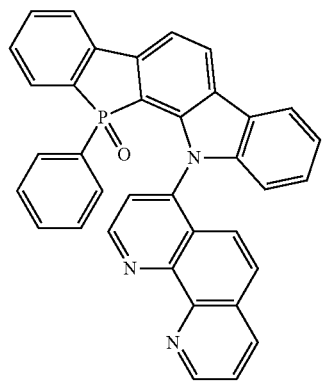
Formula 1-2-77
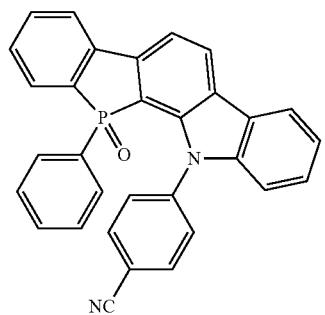
Formula 1-2-78
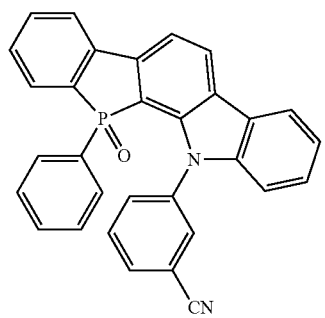
Formula 1-2-79
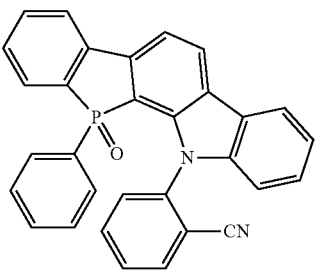
Formula 1-2-80
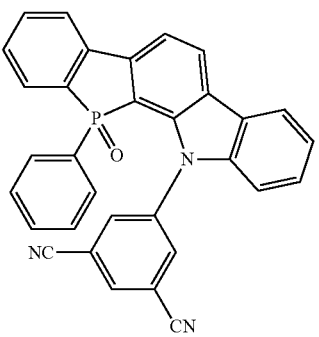
Formula 1-2-81
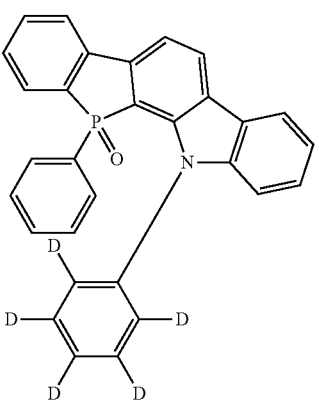
Formula 1-2-82
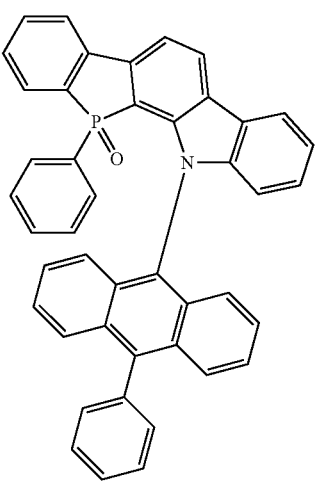

Formula 1-2-83
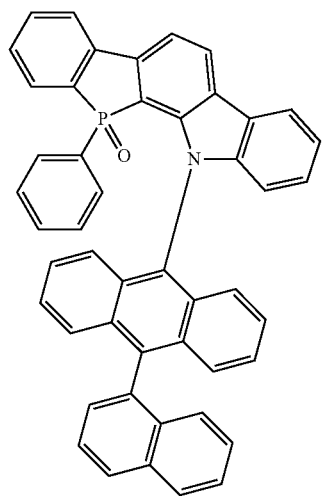
Formula 1-2-84
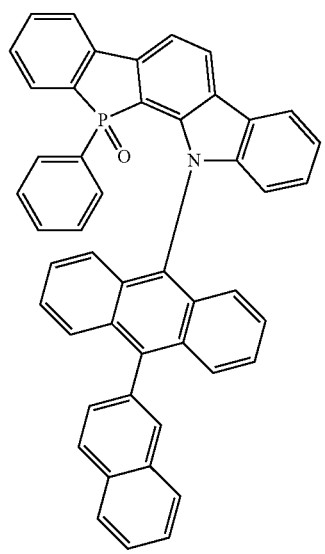
Formula 1-2-85
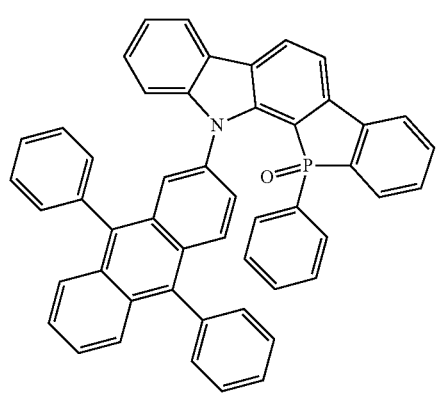
Formula 1-2-86
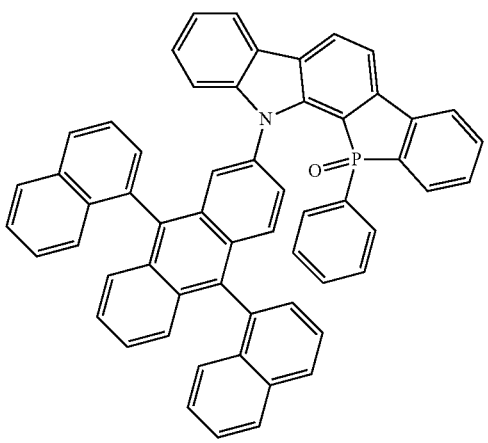
Formula 1-2-87
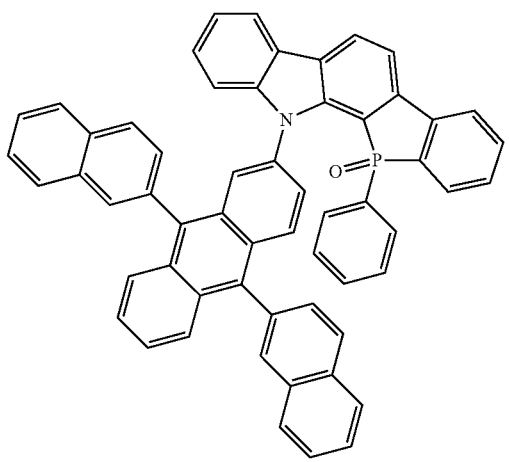
Formula 1-2-88
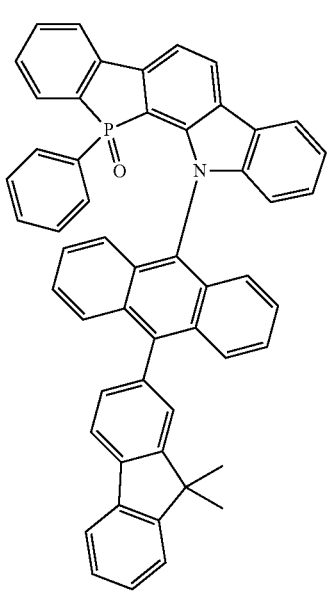

473
-continued
Formula 1-2-89
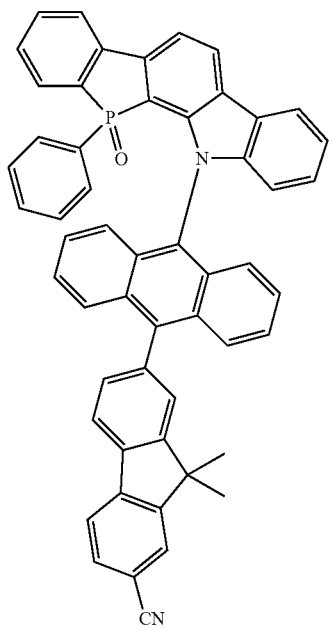
Formula 1-2-90
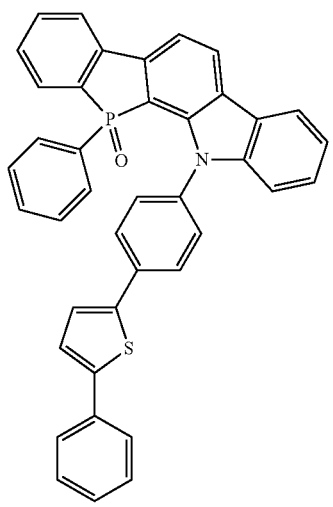
Formula 1-2-91
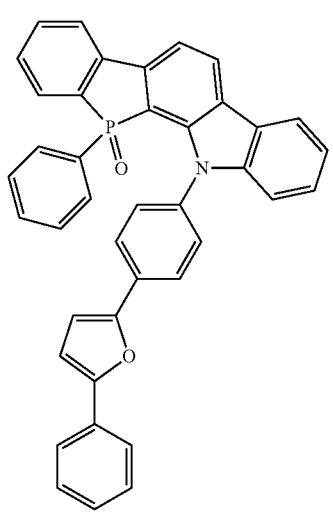
474
-continued
Formula 1-2-92
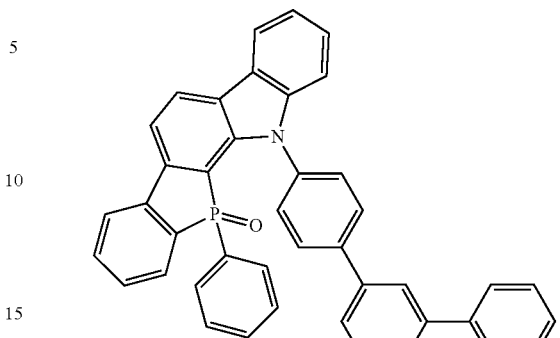
Formula 1-2-93
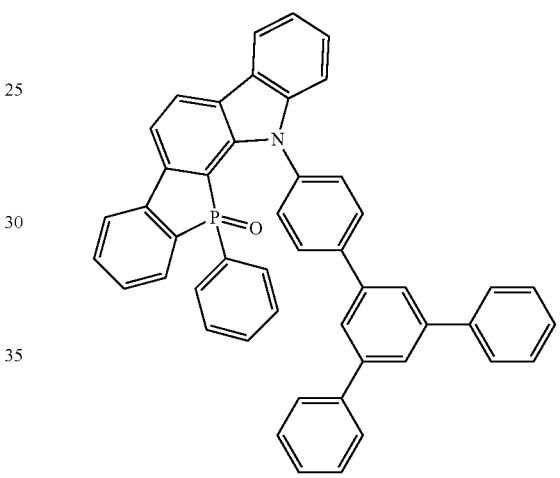
Formula 1-2-94
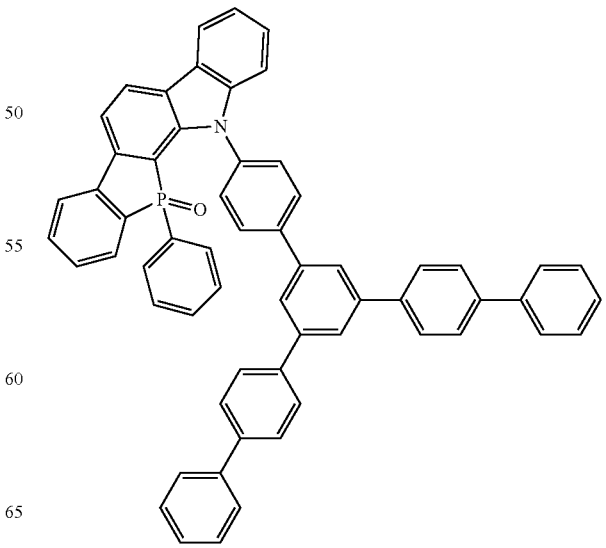

Formula 1-2-95
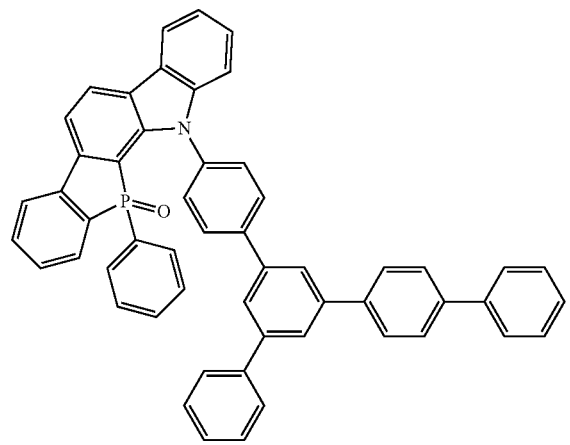
Formula 1-2-96
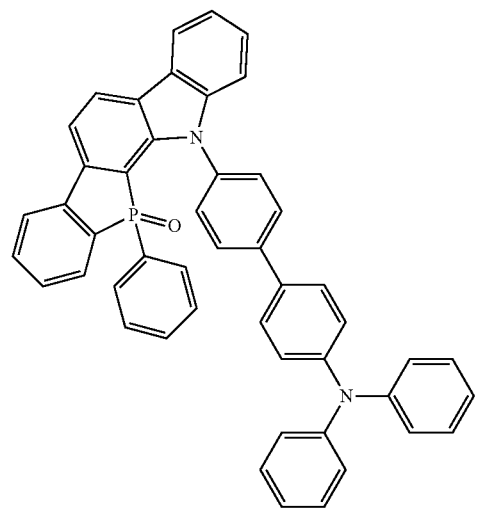
Formula 1-2-97
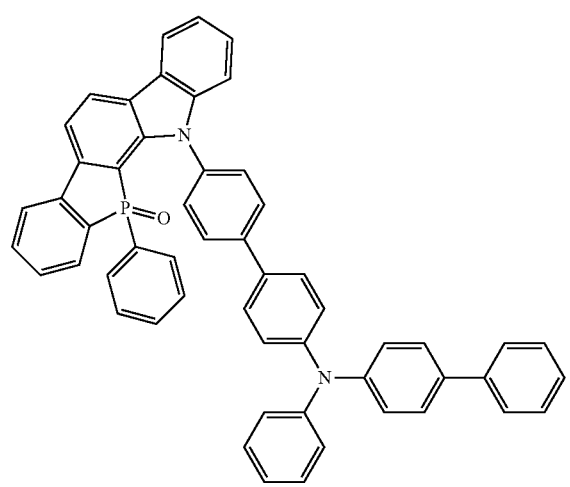
Formula 1-2-98
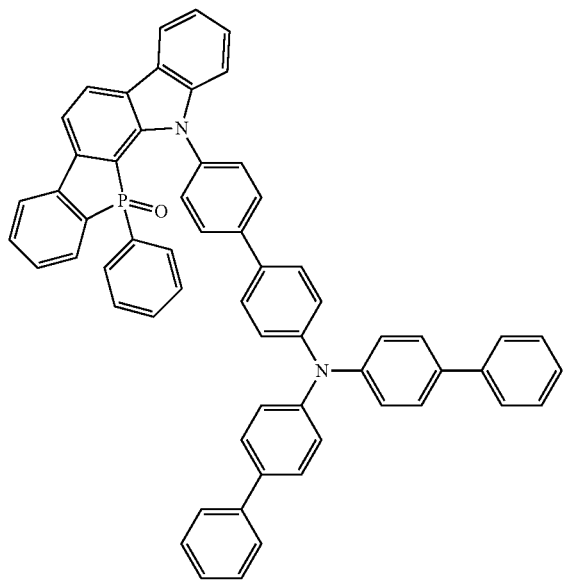
Formula 1-2-99
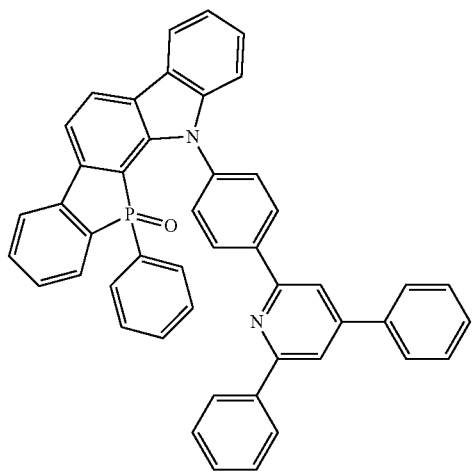
Formula 1-2-100
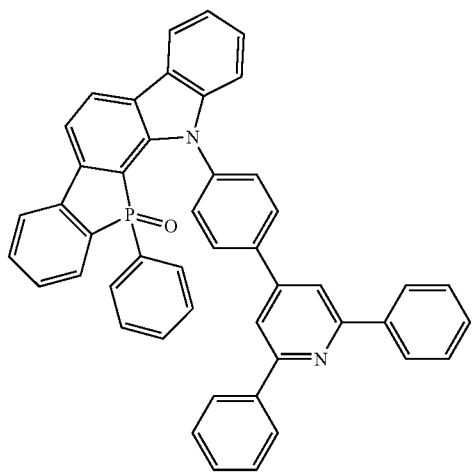

-continued
Formula 1-2-101
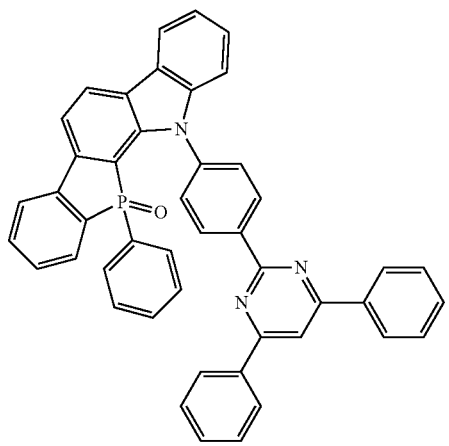
Formula 1-2-102
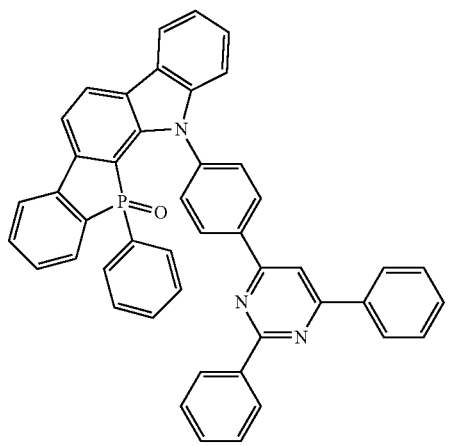
Formula 1-2-103
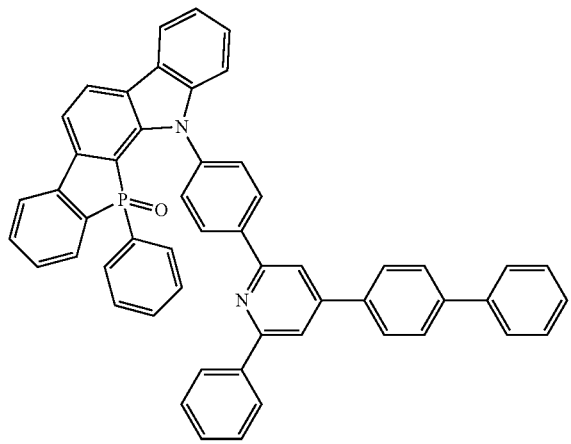
-continued
Formula 1-2-104
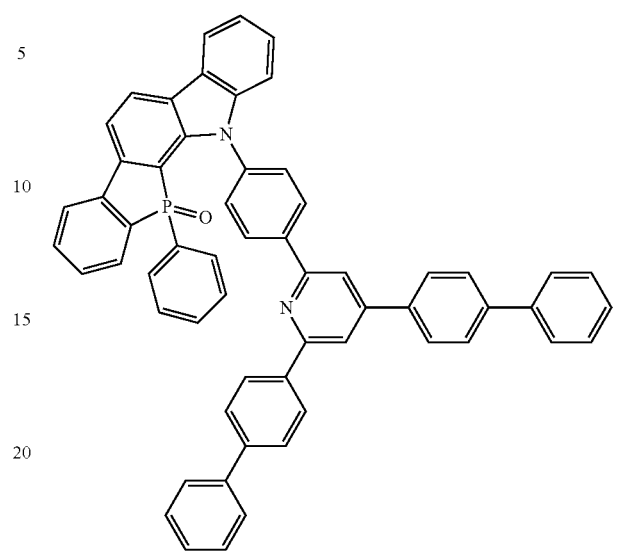
Formula 1-2-105
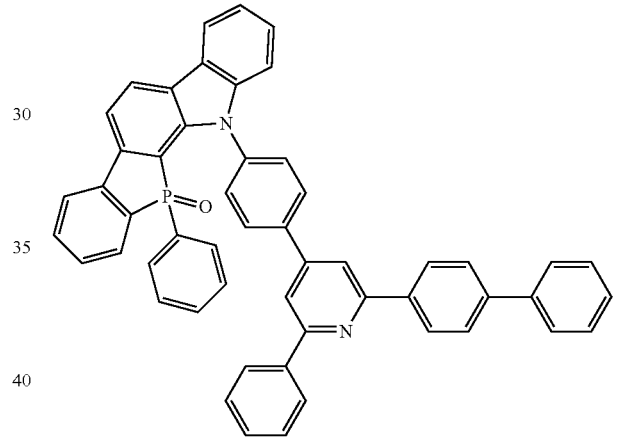
Formula 1-2-106
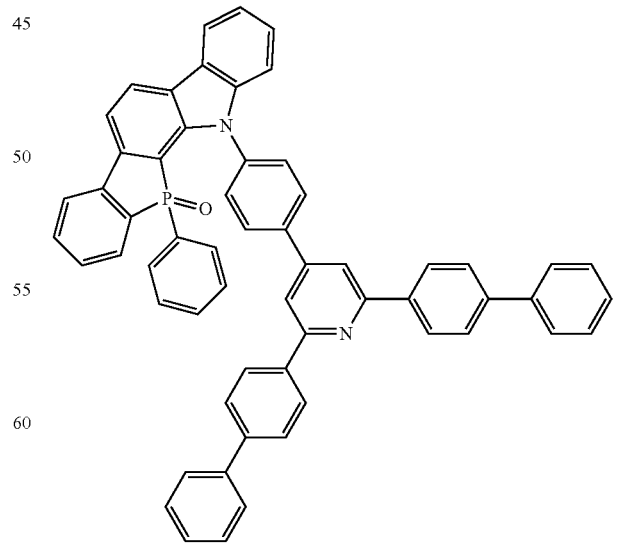

Formula 1-2-107
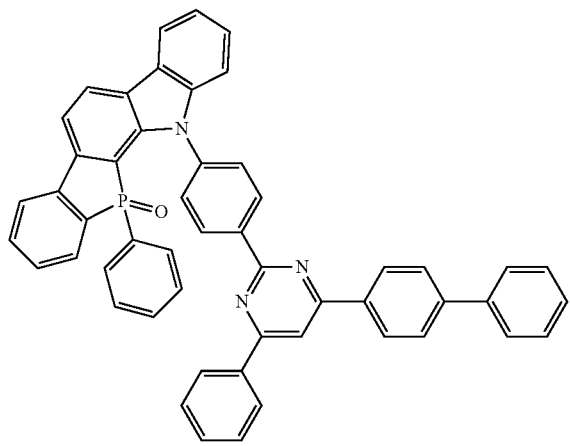
Formula 1-2-108
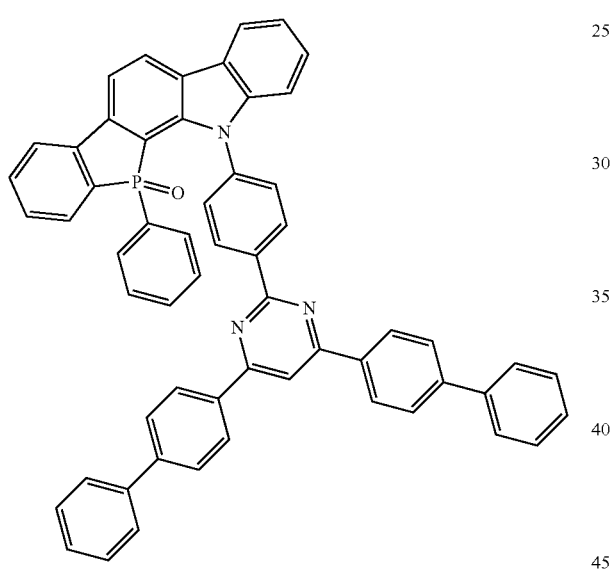
Formula 1-2-109
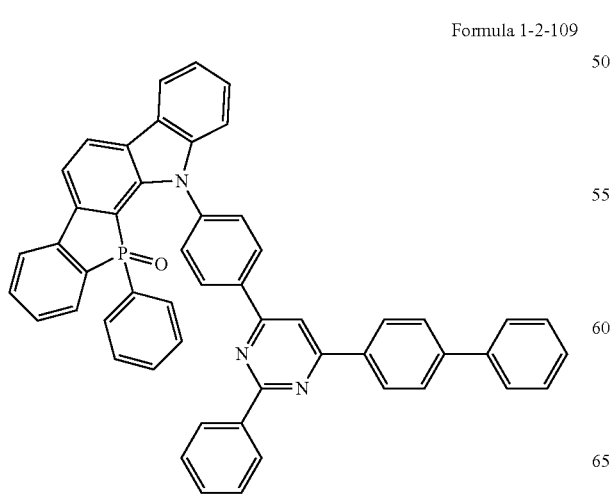
Formula 1-2-110
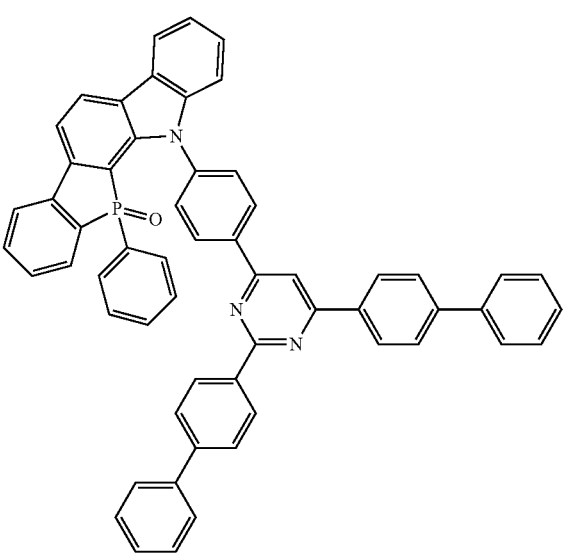
Formula 1-2-111
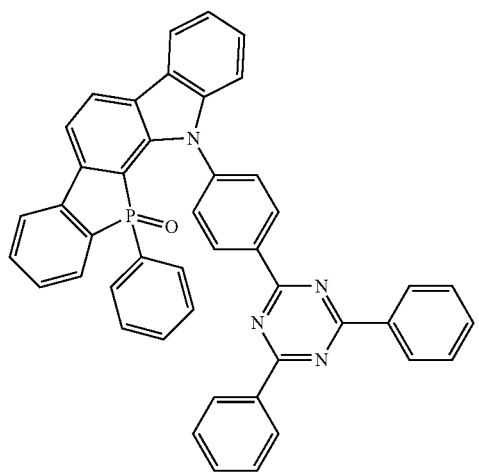
Formula 1-2-112
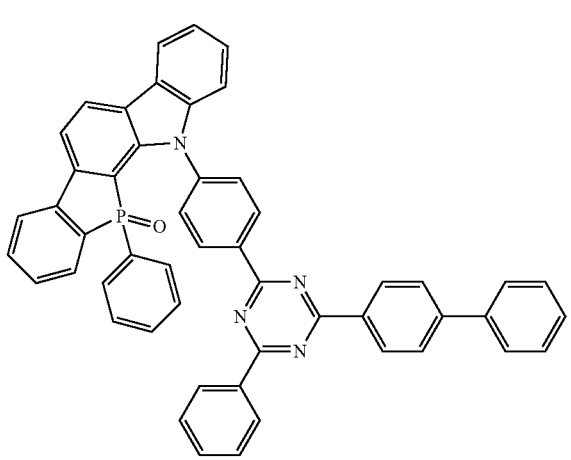

Formula 1-2-113
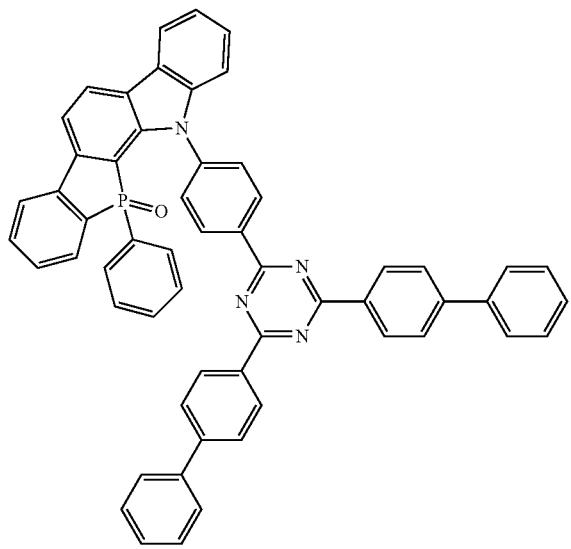
Formula 1-2-114
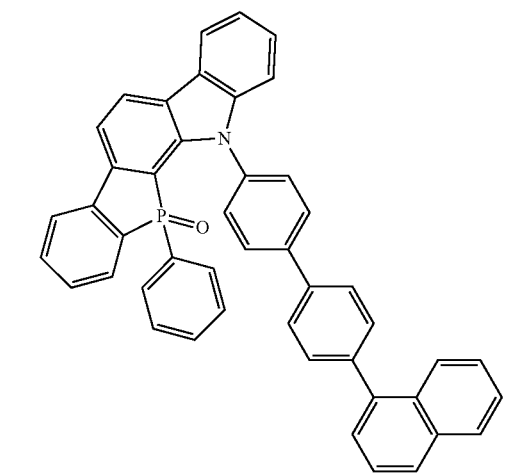
Formula 1-2-115
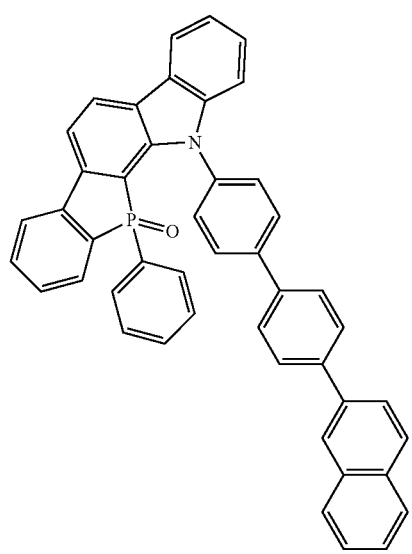
Formula 1-2-116
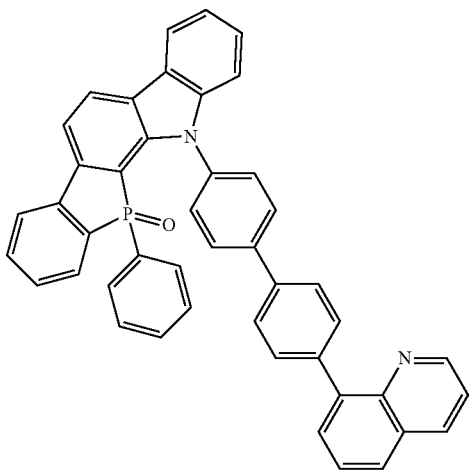
Formula 1-2-117
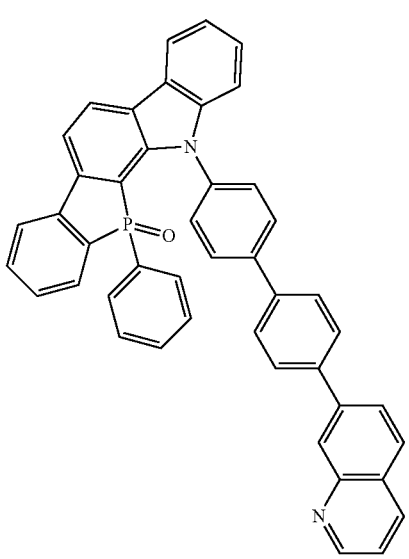
Formula 1-2-118

Formula 1-2-119
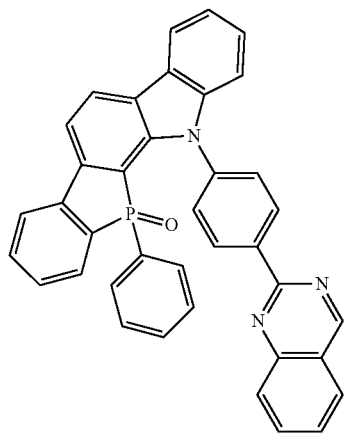
Formula 1-2-122
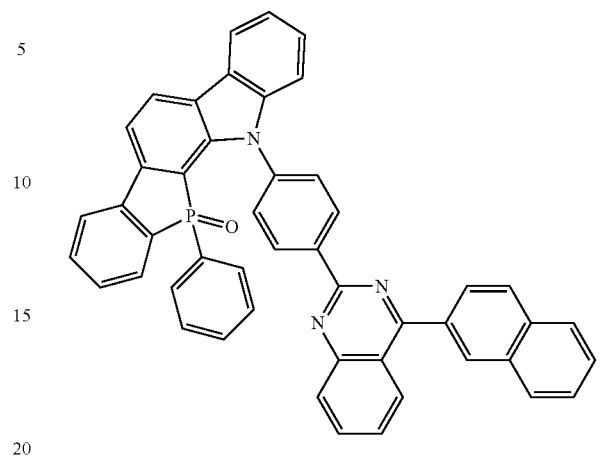
Formula 1-2-120
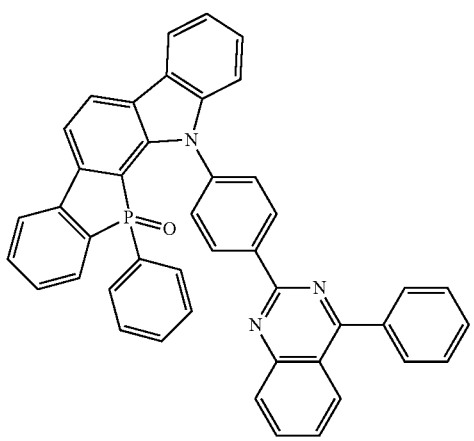
Formula 1-2-123
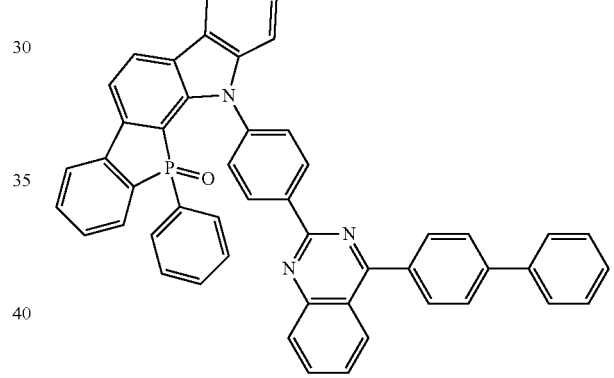
Formula 1-2-121
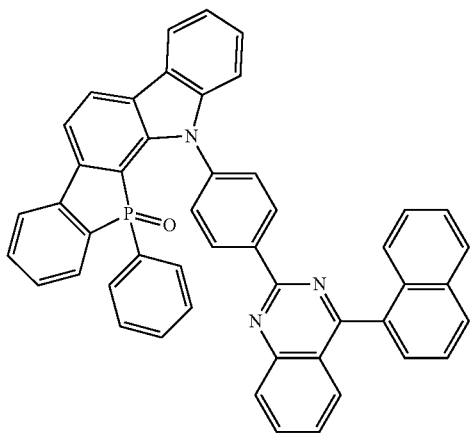
Formula 1-2-124
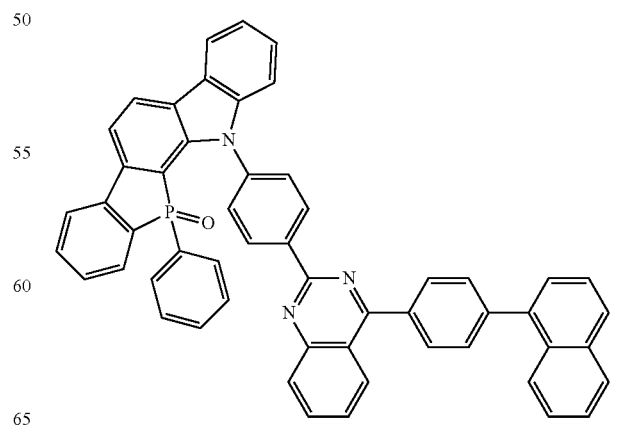

Formula 1-2-125
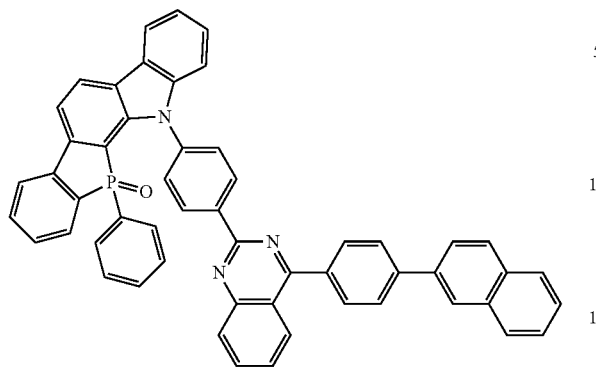
Formula 1-2-128
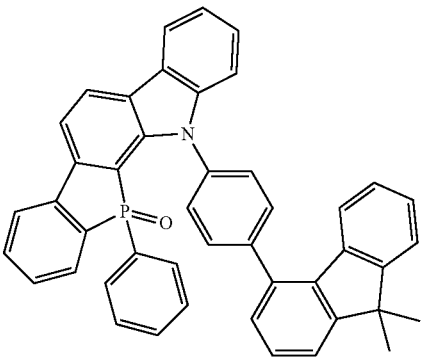
Formula 1-2-126
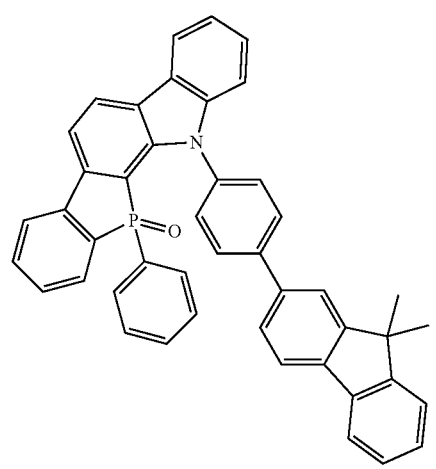
Formula 1-2-129
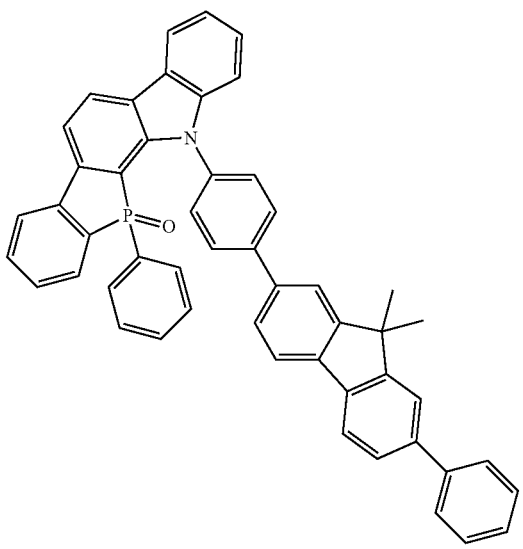
Formula 1-2-127
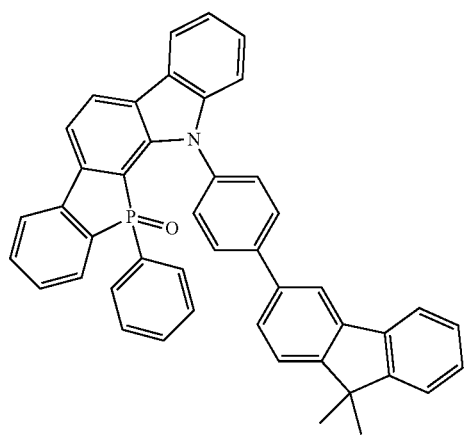
Formula 1-2-130
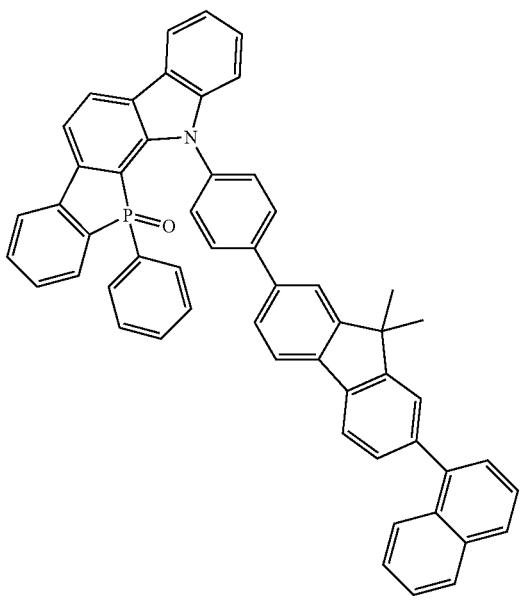

-continued
Formula 1-2-131
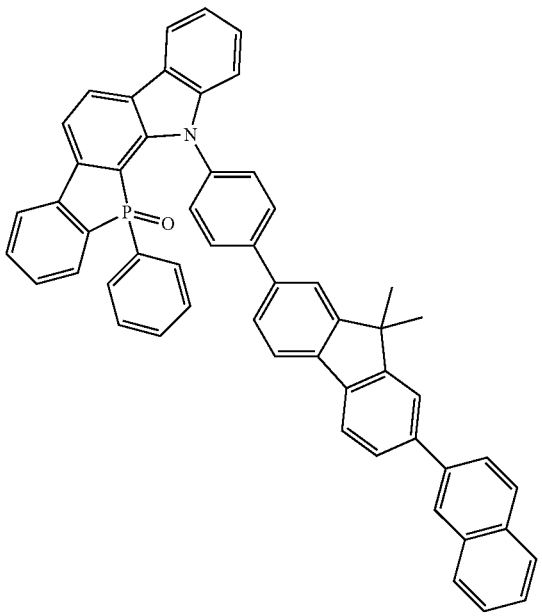
Formula 1-2-132
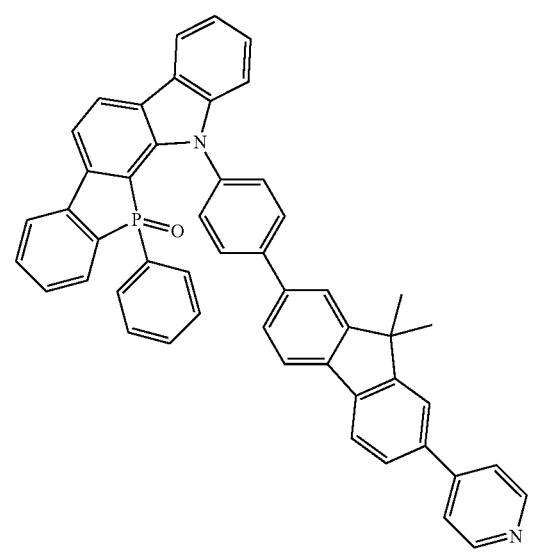
Formula 1-2-133
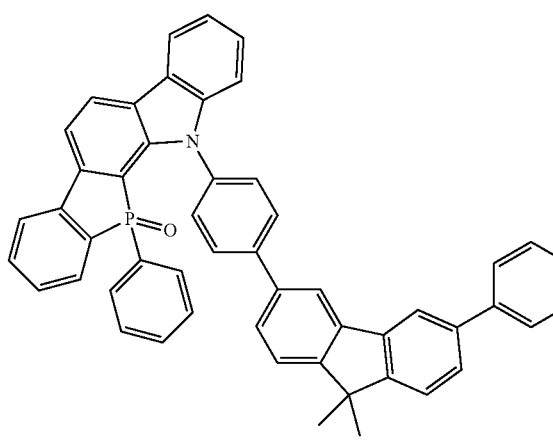
-continued
Formula 1-2-134
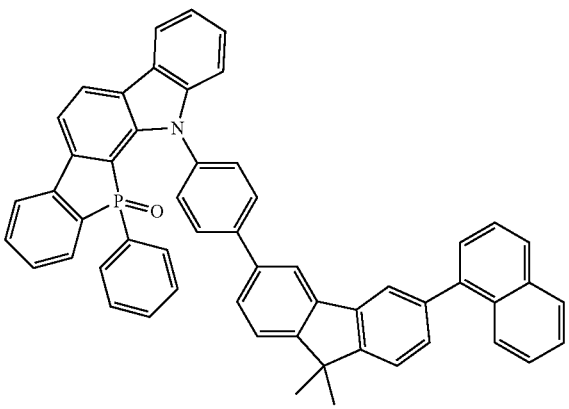
Formula 1-2-135
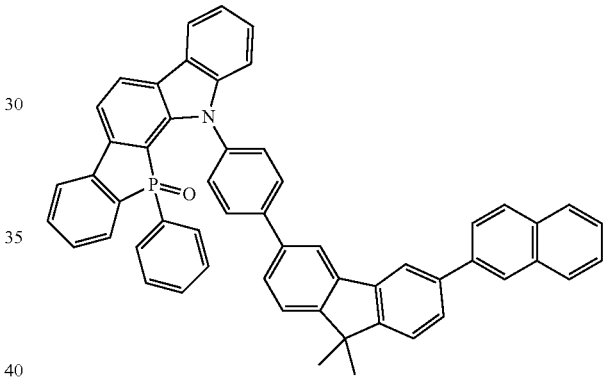
Formula 1-2-136
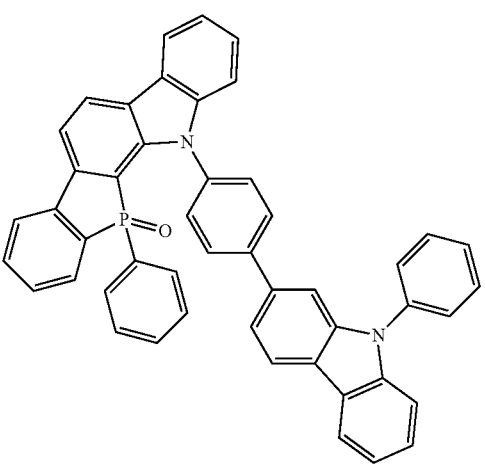

Formula 1-2-137
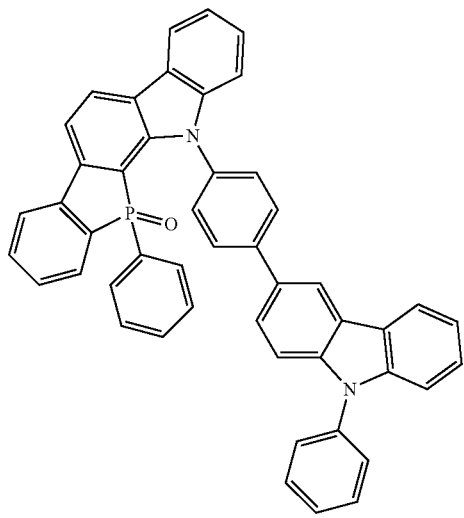
Formula 1-2-138
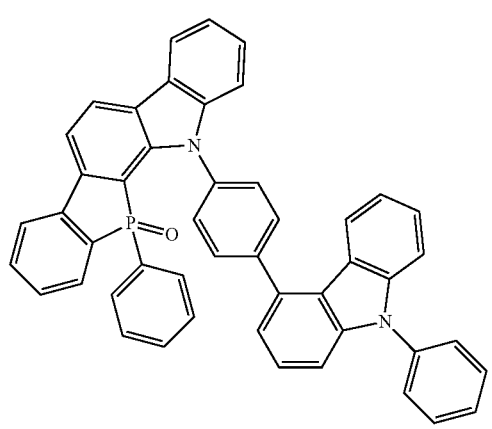
Formula 1-2-139
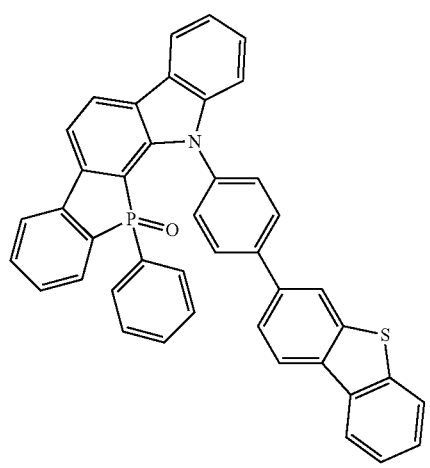
Formula 1-2-140
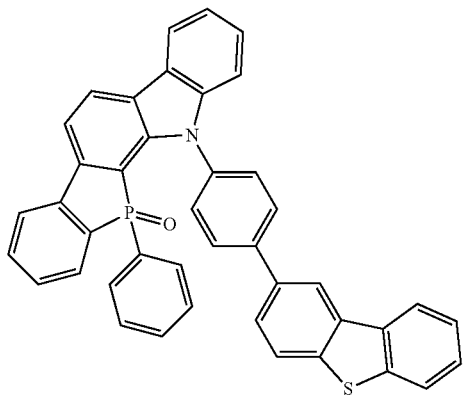
Formula 1-2-141
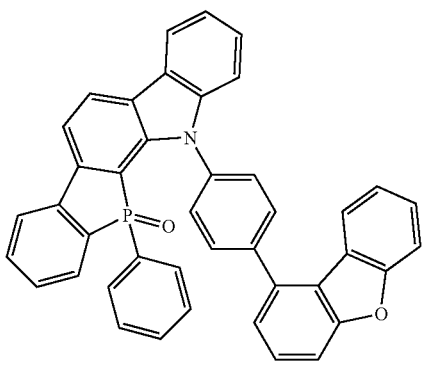
Formula 1-2-142
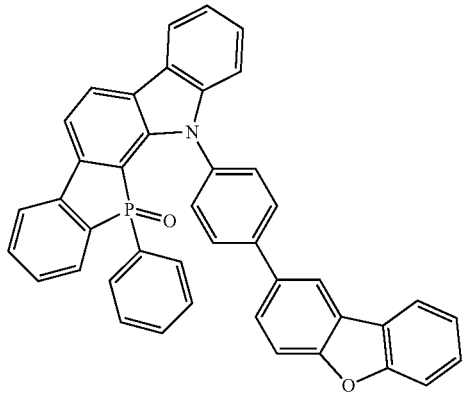

Formula 1-2-143
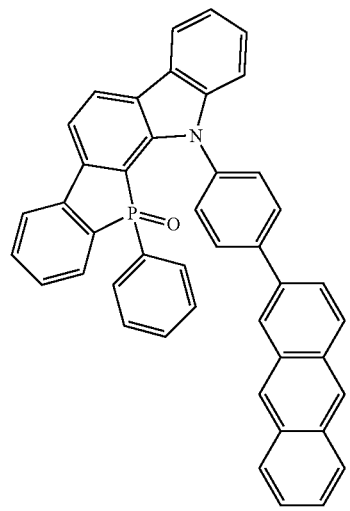
Formula 1-2-144
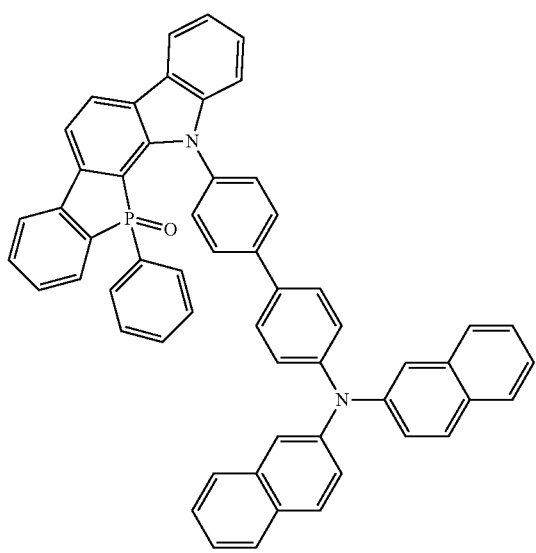
Formula 1-2-145
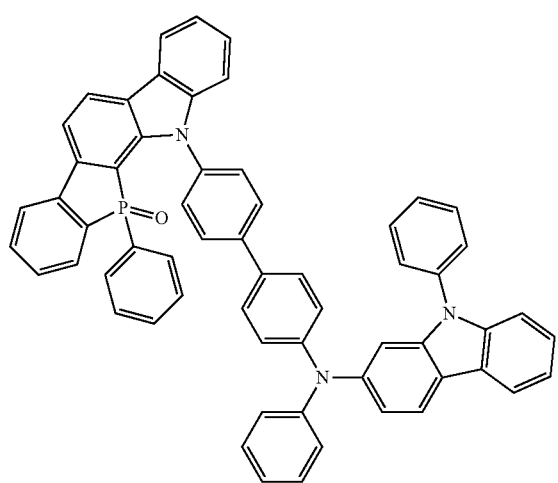
Formula 1-2-146
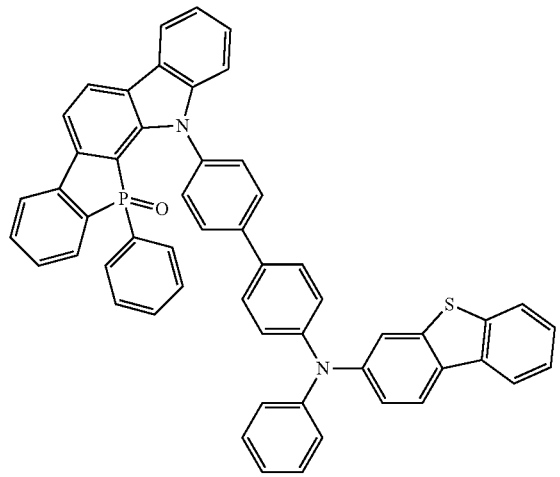
Formula 1-2-147
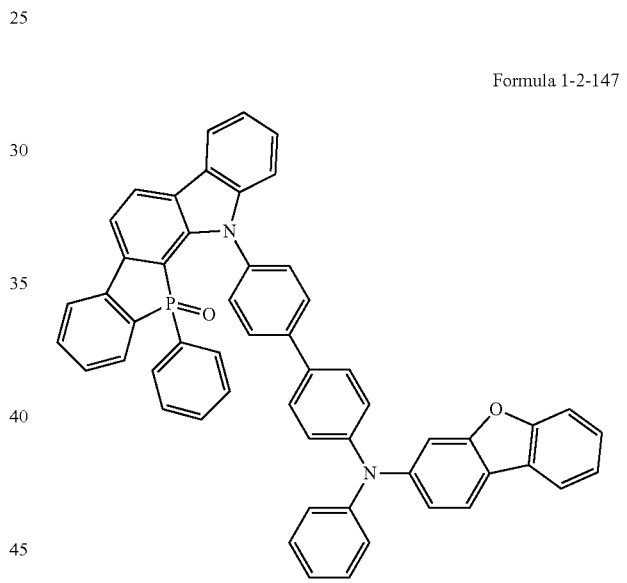
Formula 1-2-148
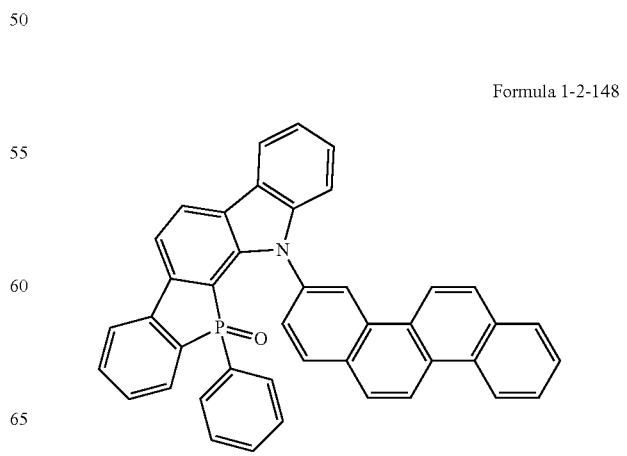

Formula 1-2-149
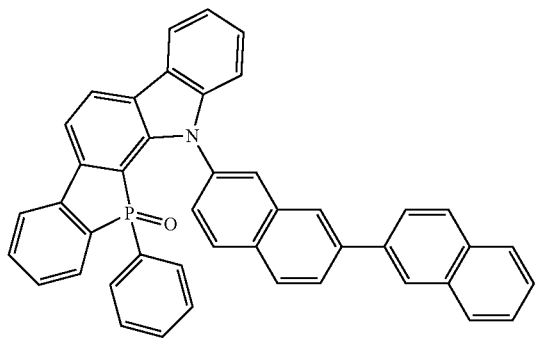
Formula 1-2-150
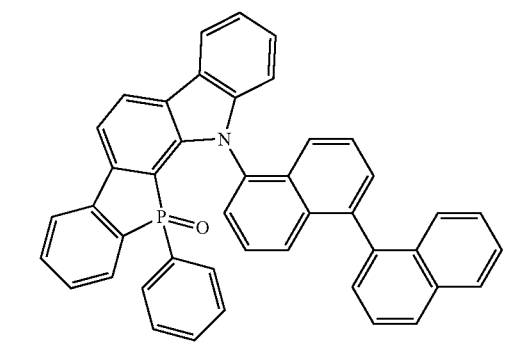
Formula 1-2-151
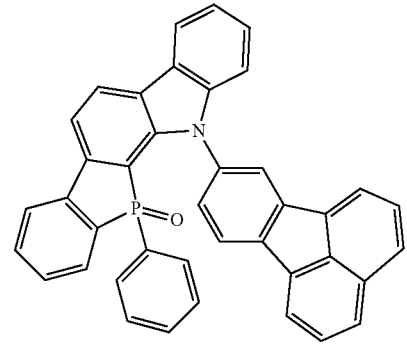
Formula 1-2-152
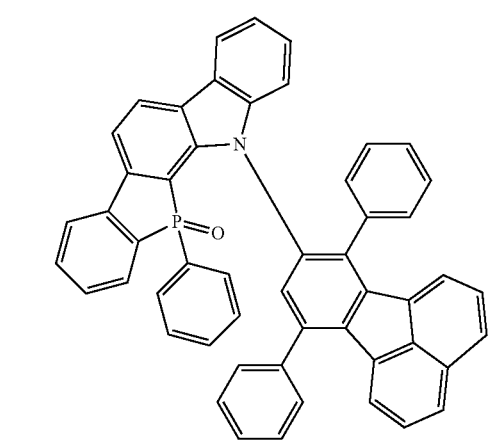
Formula 1-2-153
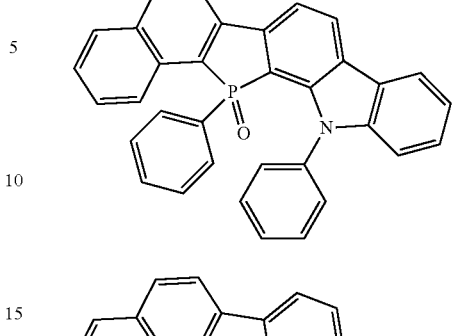
Formula 1-2-154
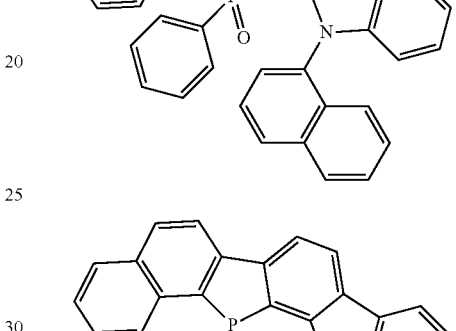
Formula 1-2-155
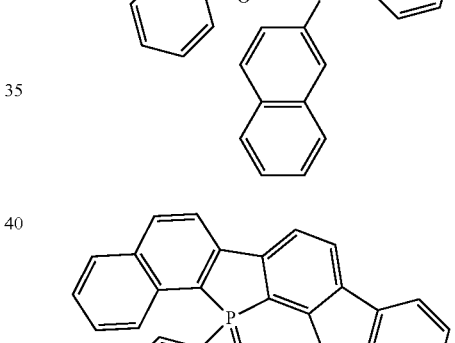
Formula 1-2-156
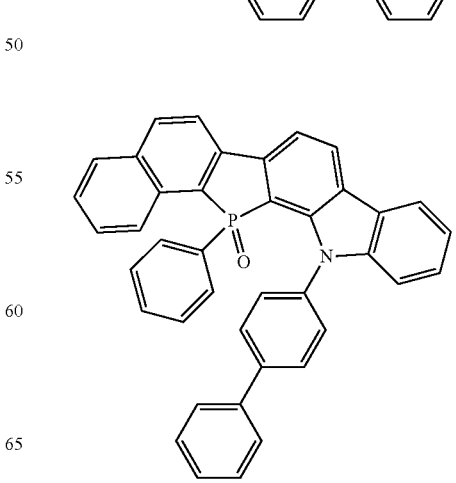
Formula 1-2-157

Formula 1-2-158
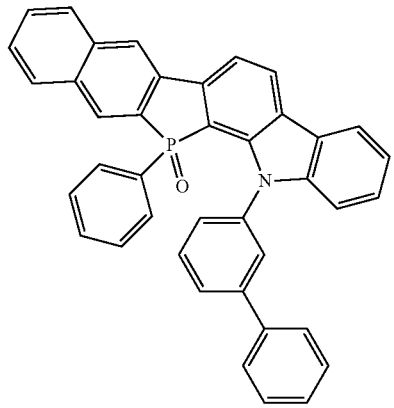
Formula 1-2-161
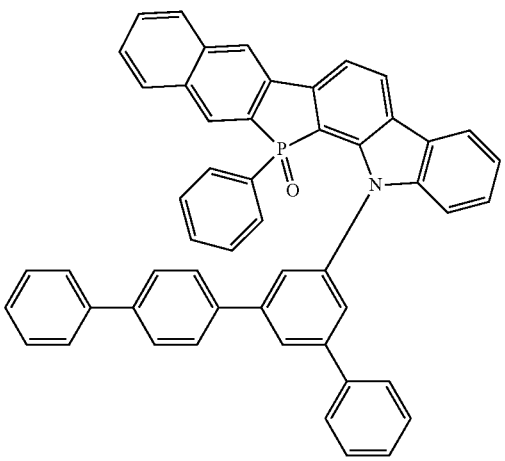
Formula 1-2-159
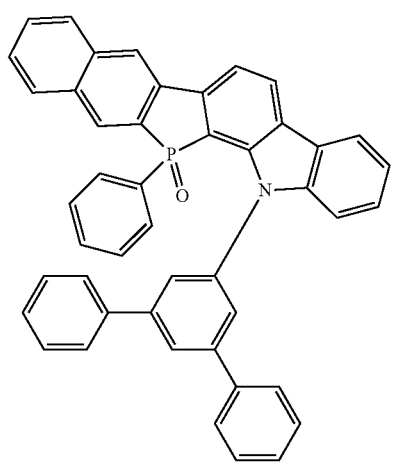
Formula 1-2-162
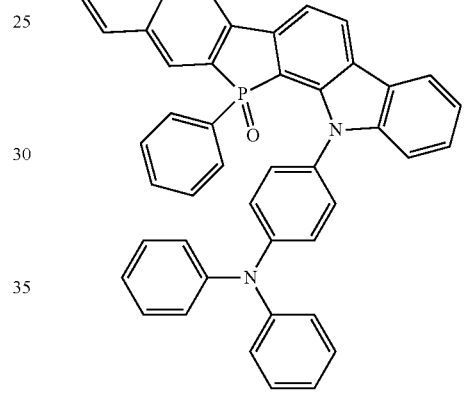
Formula 1-2-160
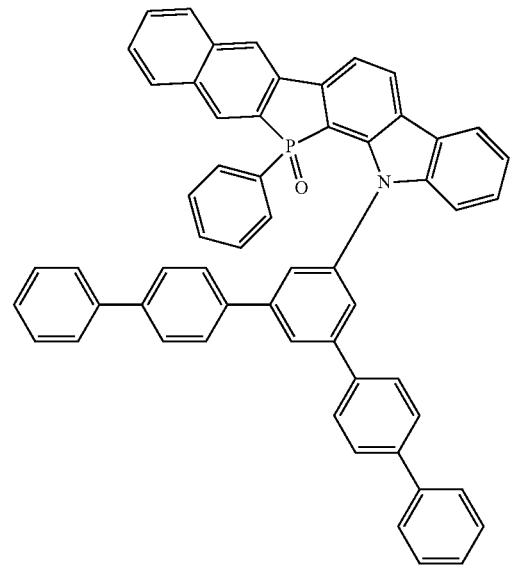
Formula 1-2-163
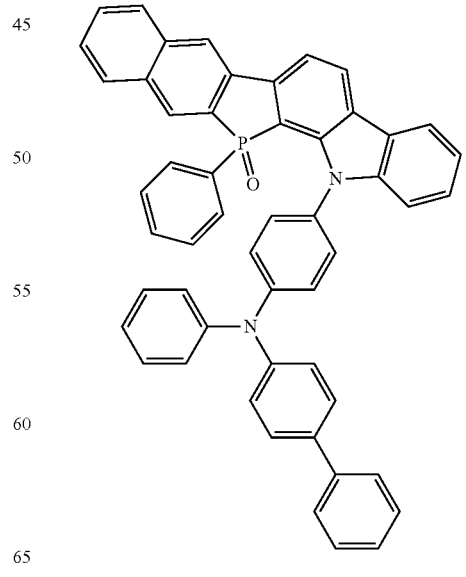

Formula 1-2-164
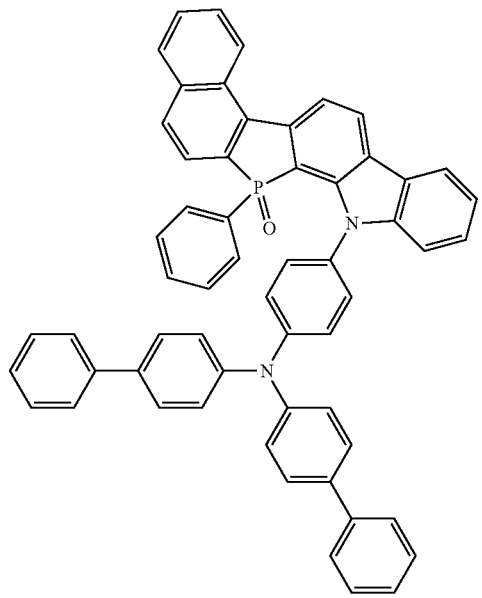
Formula 1-2-167
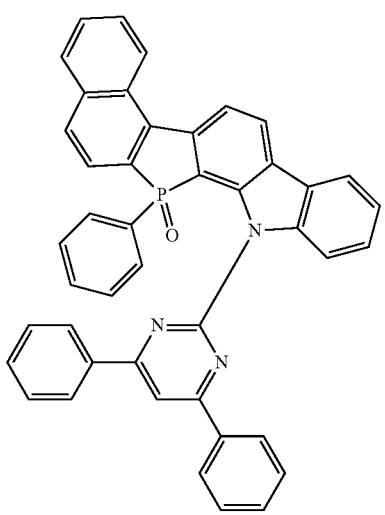
Formula 1-2-165
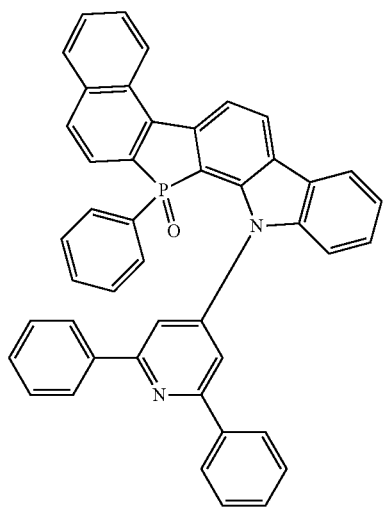
Formula 1-2-168
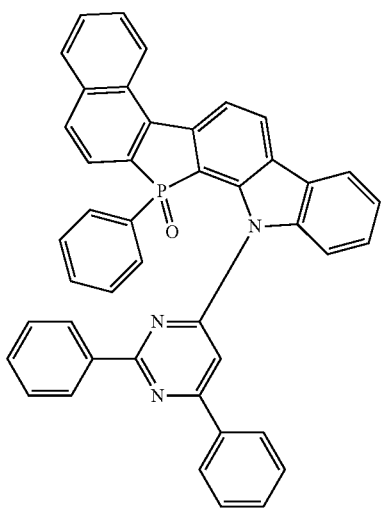
Formula 1-2-166
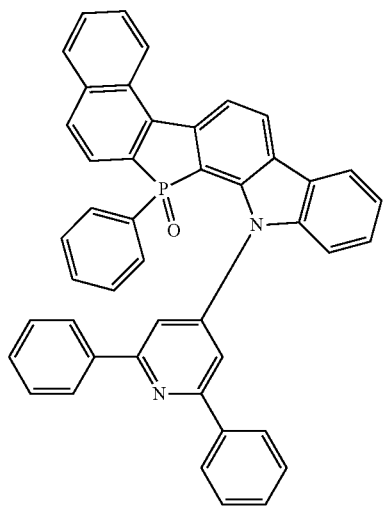
Formula 1-2-169
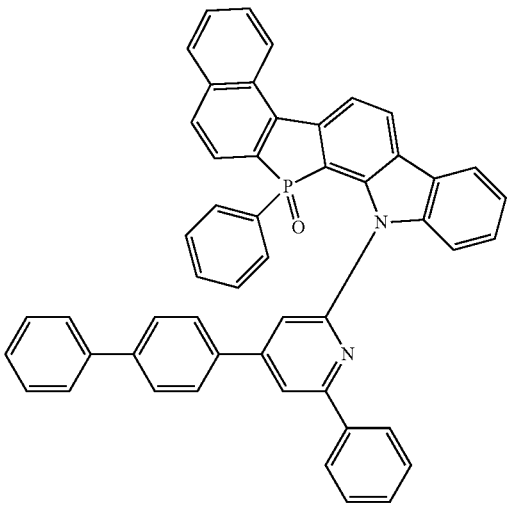

Formula 1-2-170
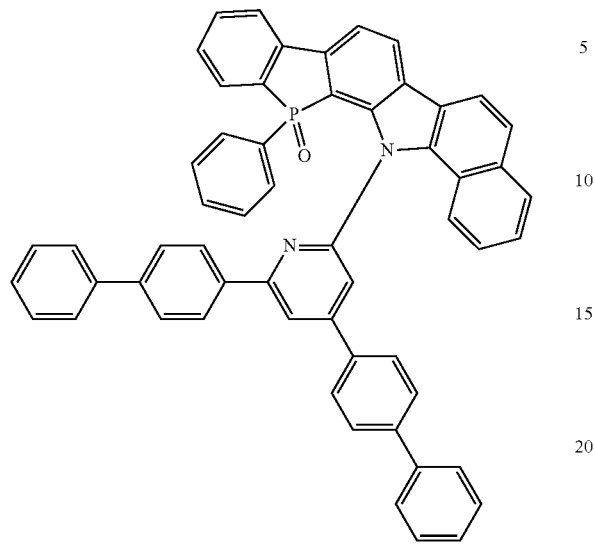
Formula 1-2-171
Formula 1-2-172
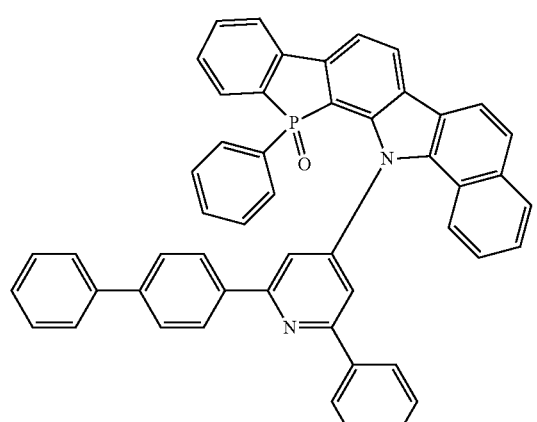
Formula 1-2-173
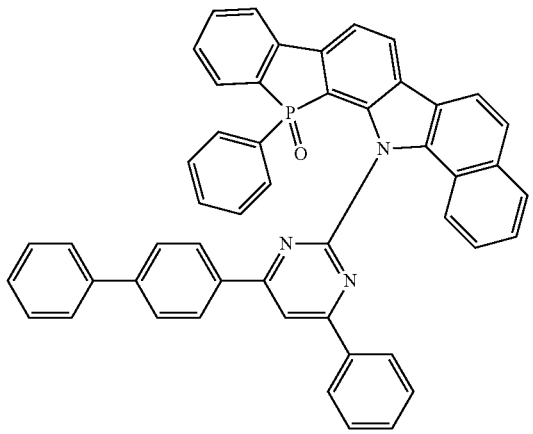
Formula 1-2-174
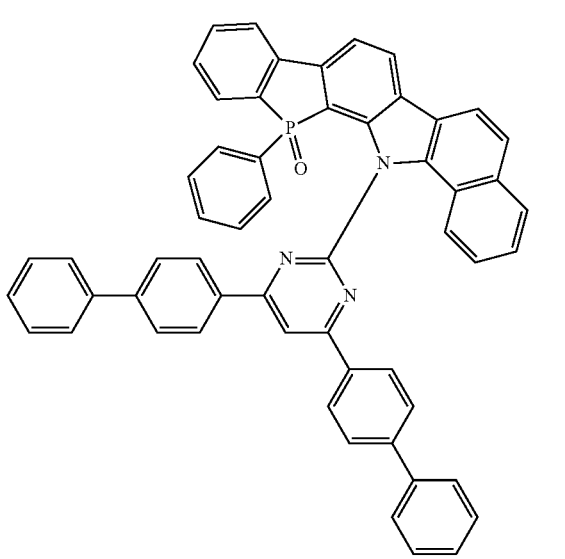
Formula 1-2-175
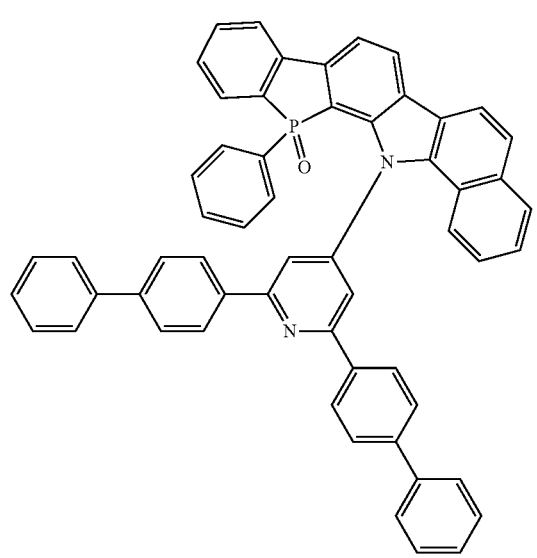

Formula 1-2-176
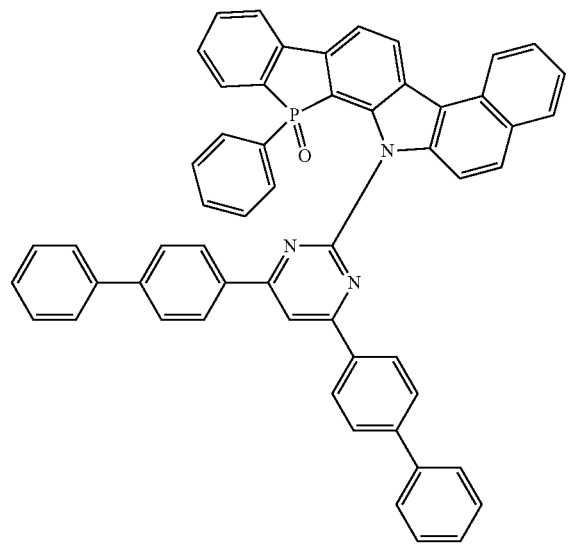
Formula 1-2-177
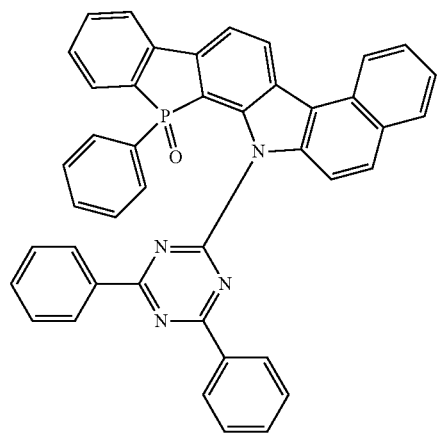
Formula 1-2-178
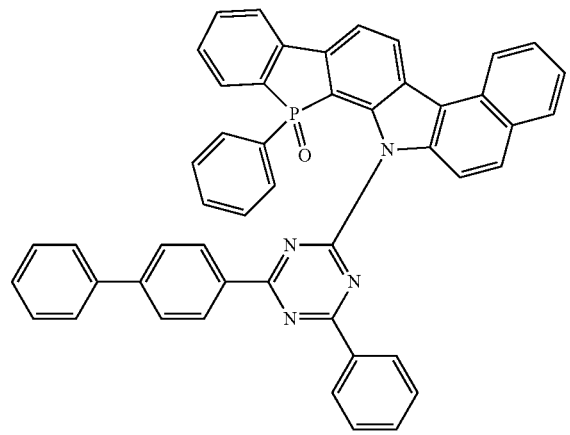
Formula 1-2-179
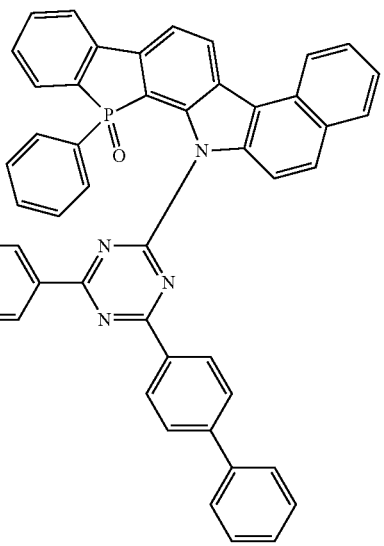
Formula 1-2-180
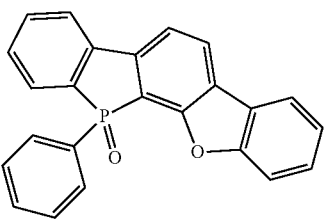
Formula 1-2-181
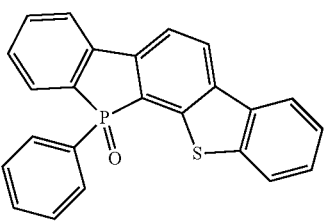
Formula 1-2-182
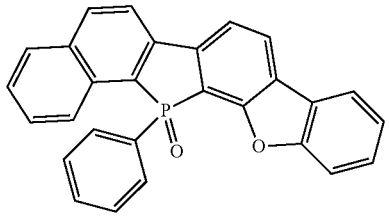
Formula 1-2-183
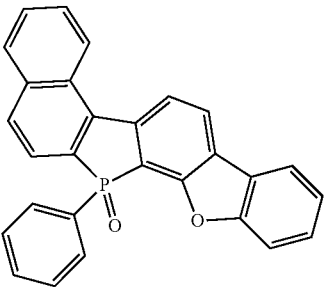

Formula 1-2-184
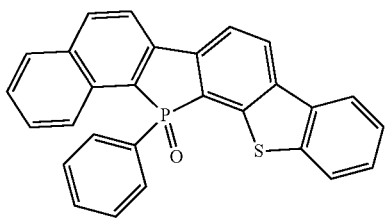
Formula 1-2-185
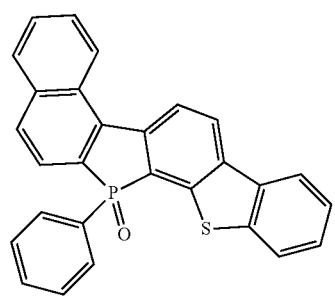
Formula 1-2-186
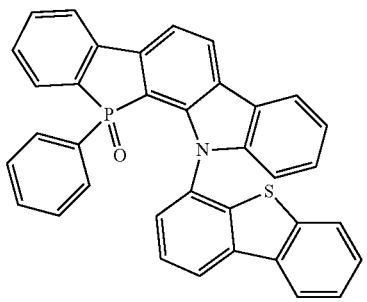
Formula 1-2-187
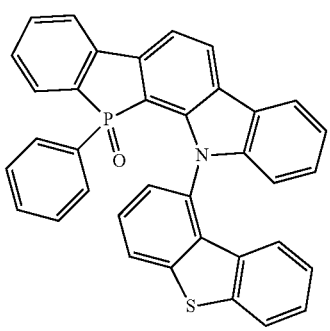
Formula 1-2-188
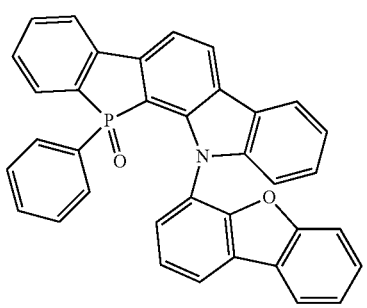
Formula 1-2-189
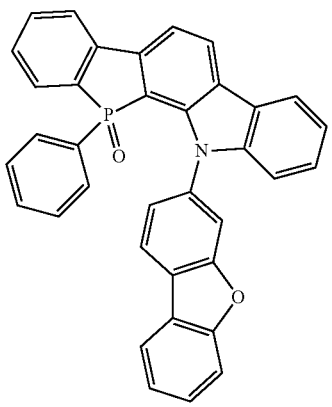
Formula 1-2-190
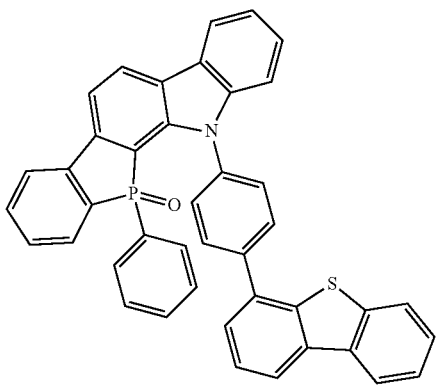
Formula 1-2-191
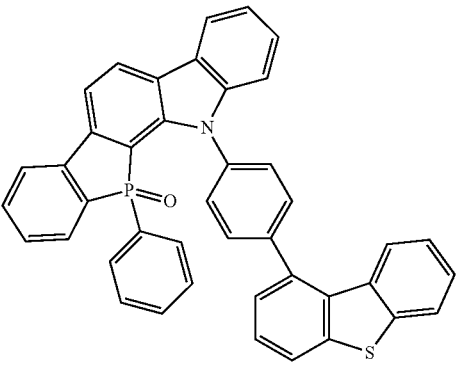
Formula 1-2-192
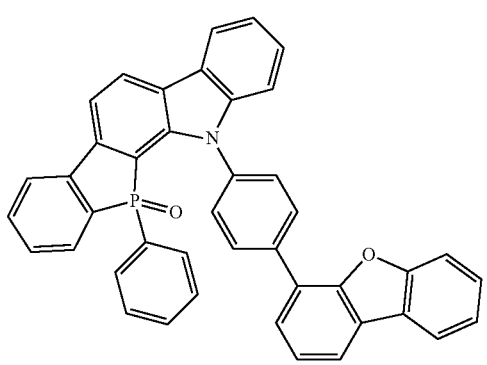

Formula 1-2-193
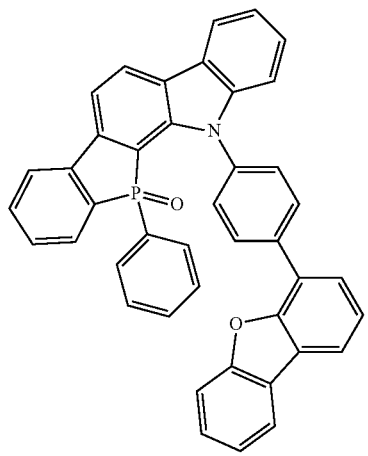
Formula 1-3-1
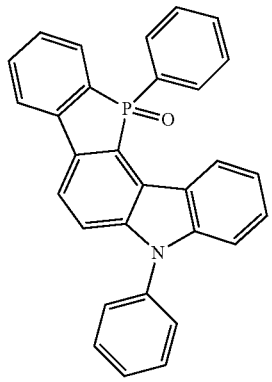
Formula 1-3-2
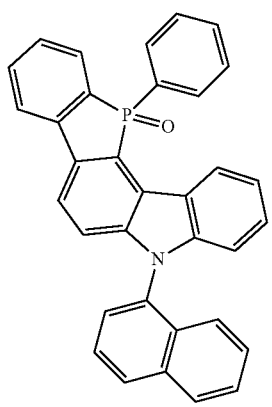
Formula 1-2-194
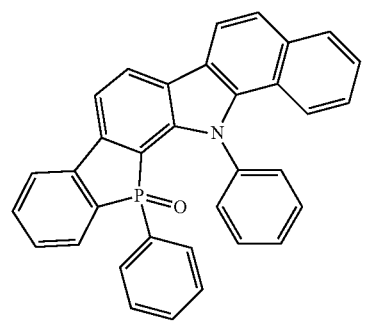
Formula 1-3-3
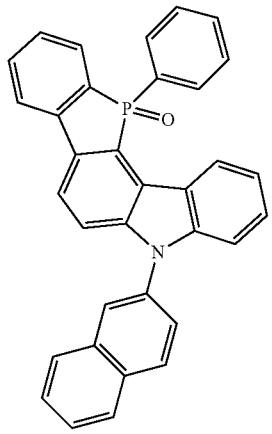
Formula 1-2-195
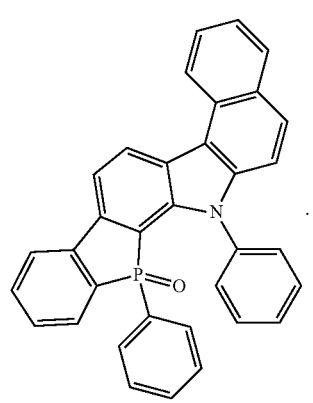
Formula 1-3-4
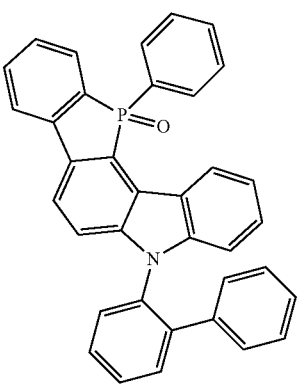
7. The compound of claim 1, wherein the compound represented by Formula 1-3 is represented by any one of the following Formulae 1-3-1 to 1-3-195:

507
-continued
Formula 1-3-5
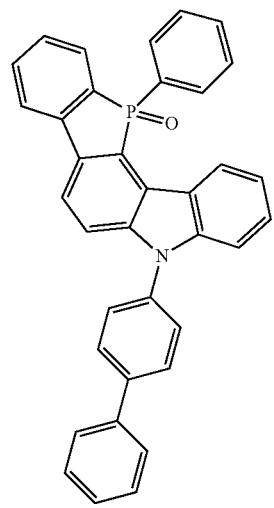
Formula 1-3-6
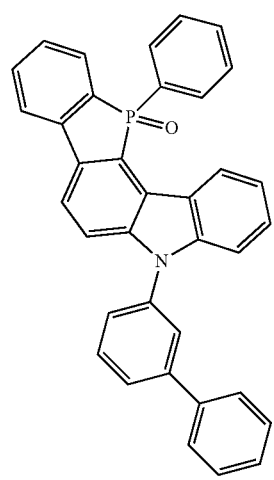
Formula 1-3-7
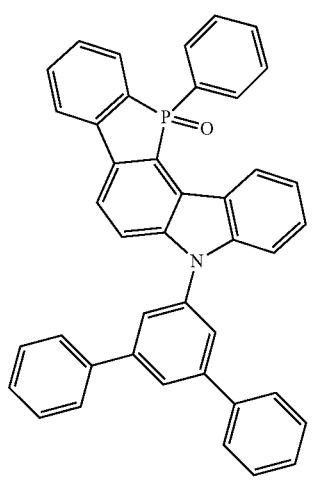
508
-continued
Formula 1-3-8
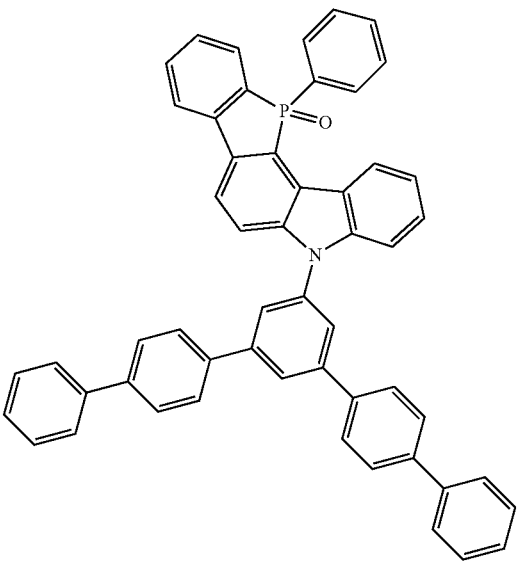
Formula 1-3-9
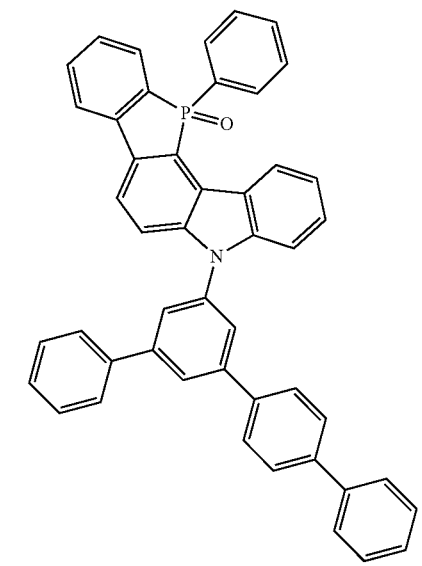

Formula 1-3-10
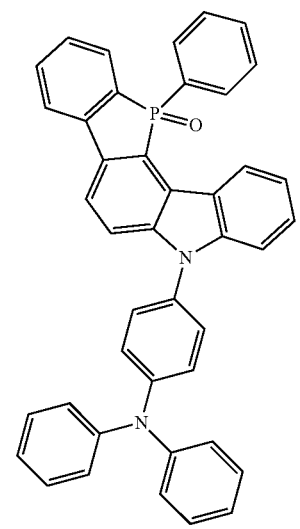
Formula 1-3-11
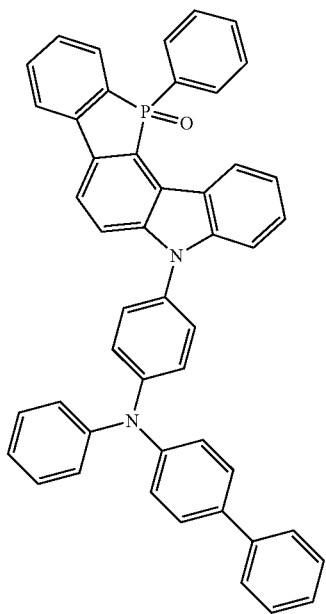
Formula 1-3-12
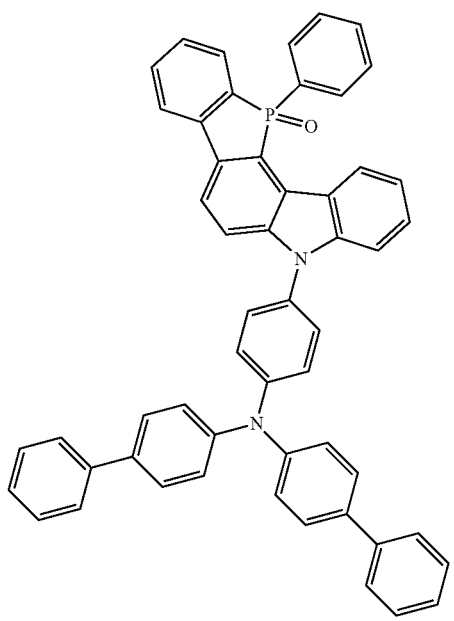
Formula 1-3-13
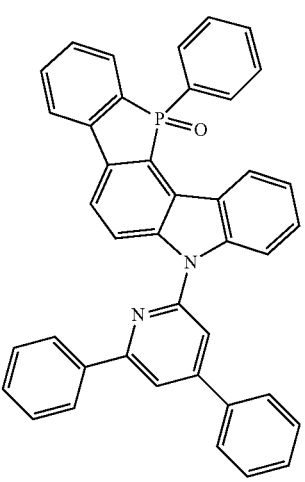
Formula 1-3-14
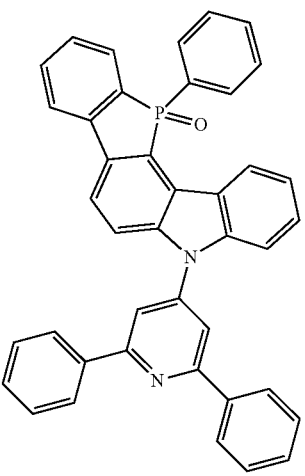

Formula 1-3-15
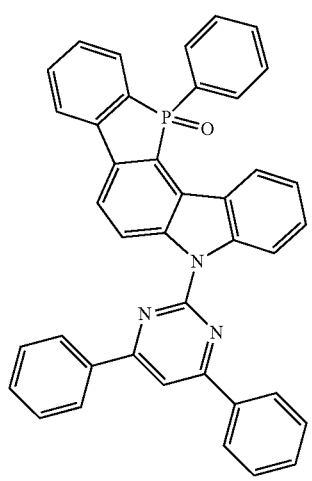
lp;1p
Formula 1-3-16
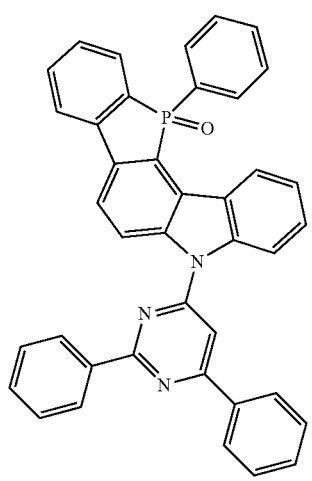
Formula 1-3-17
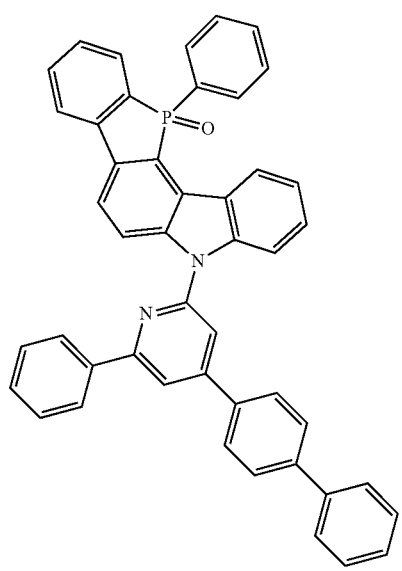
Formula 1-3-18
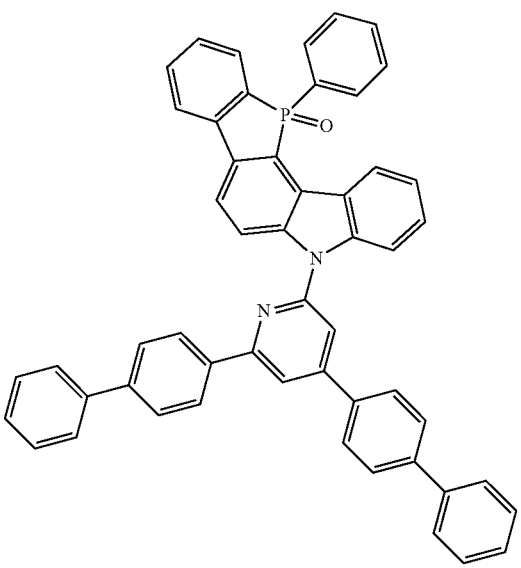
Formula 1-3-19
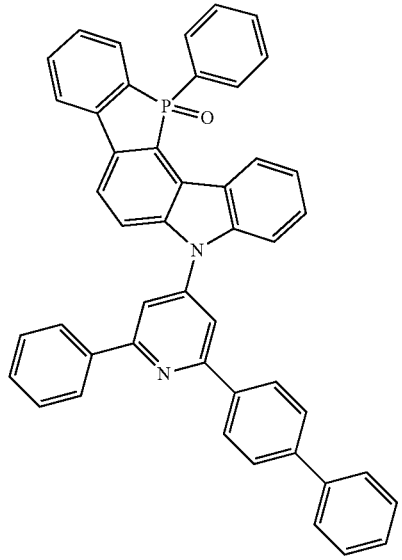

Formula 1-3-20
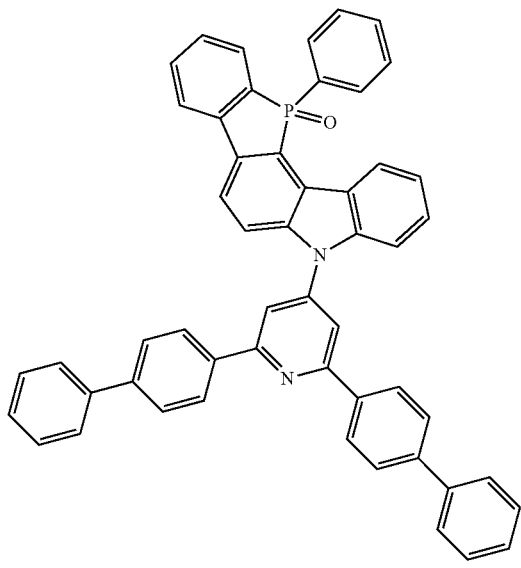
Formula 1-3-21
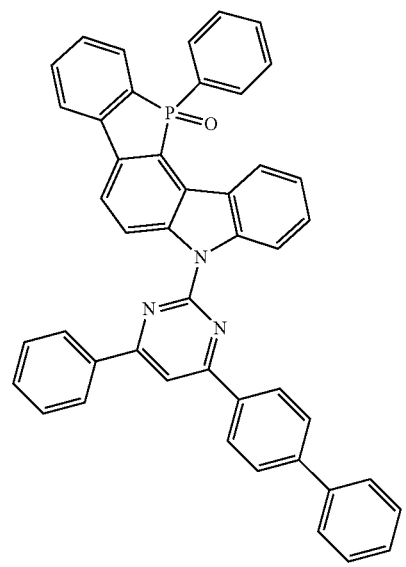
Formula 1-3-22
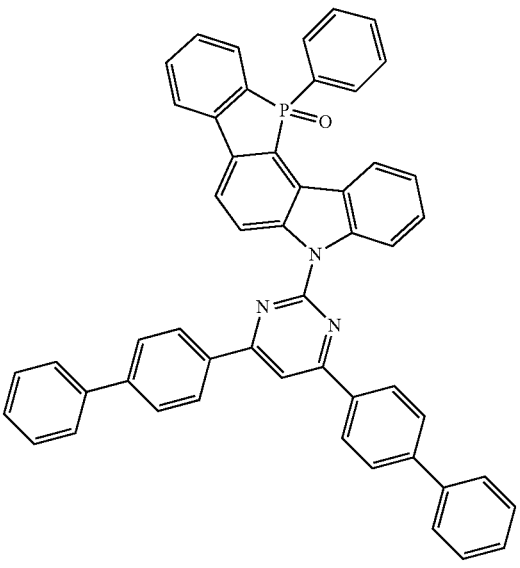
Formula 1-3-23
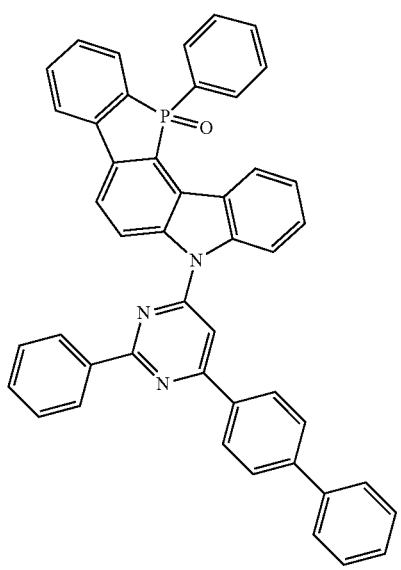

Formula 1-3-24
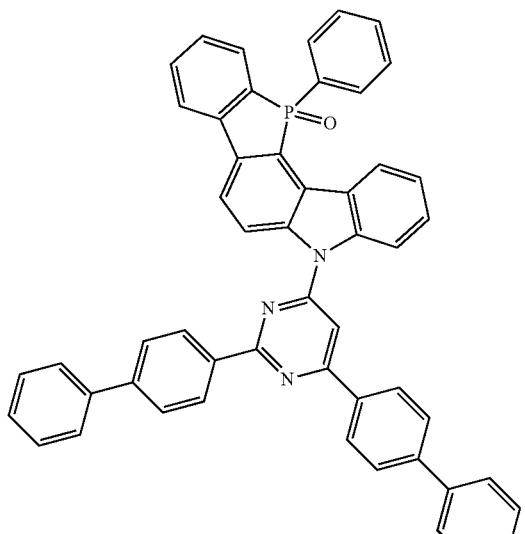
Formula 1-3-25
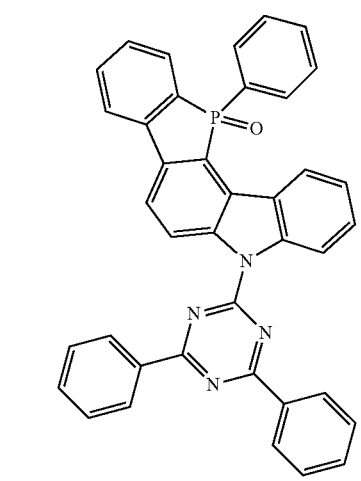
Formula 1-3-26
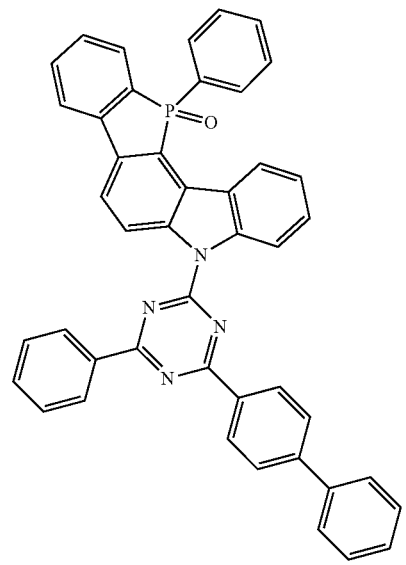
Formula 1-3-27
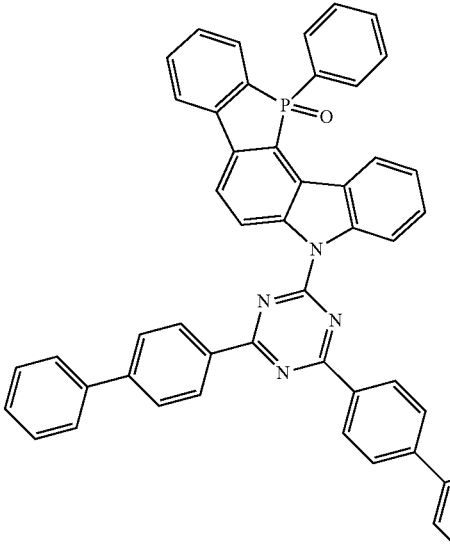
Formula 1-3-28
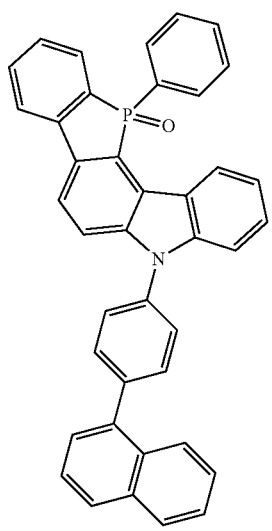
Formula 1-3-29
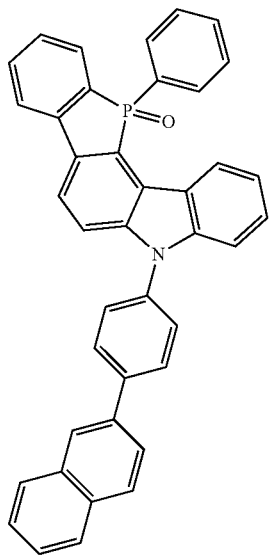

Formula 1-3-30
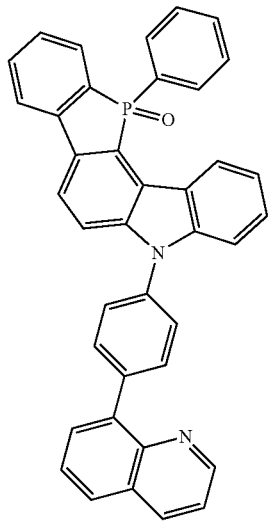
Formula 1-3-31
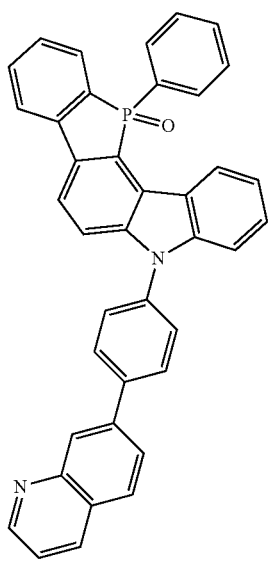
Formula 1-3-32
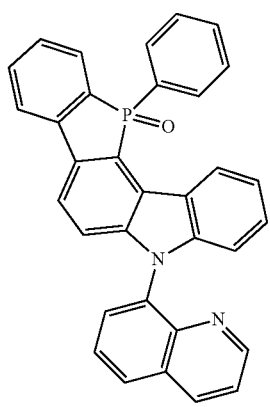
Formula 1-3-33
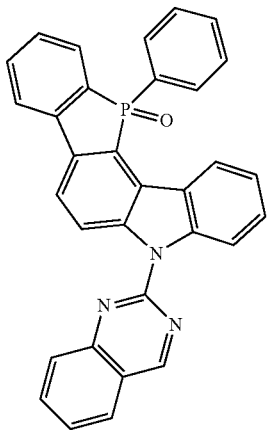
Formula 1-3-34
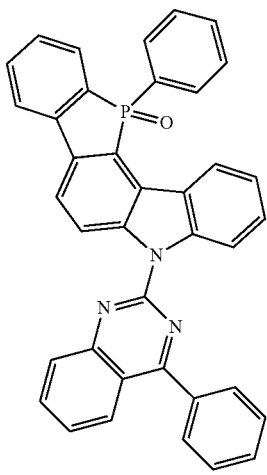
Formula 1-3-35
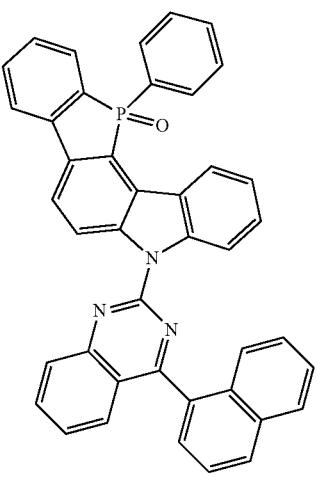

Formula 1-3-36
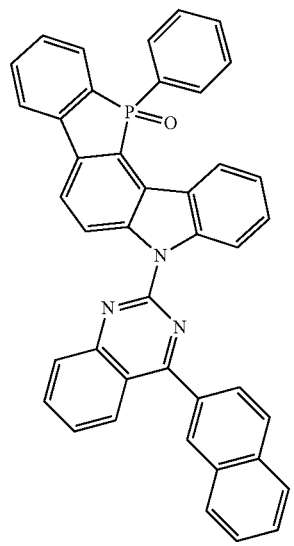
Formula 1-3-38
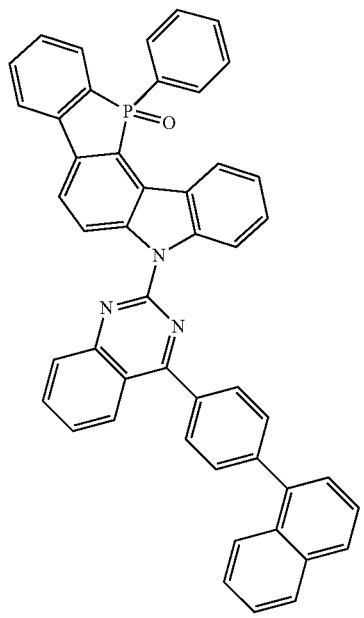
Formula 1-3-37
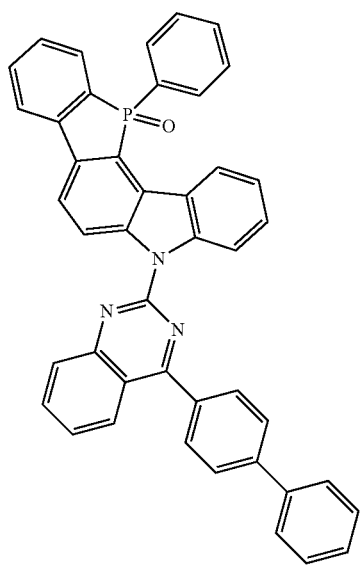
Formula 1-3-39
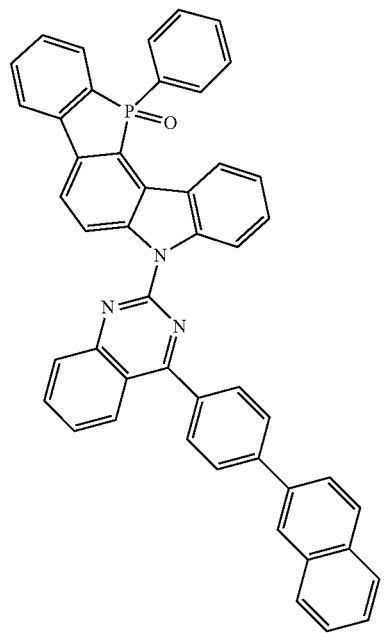

Formula 1-3-40
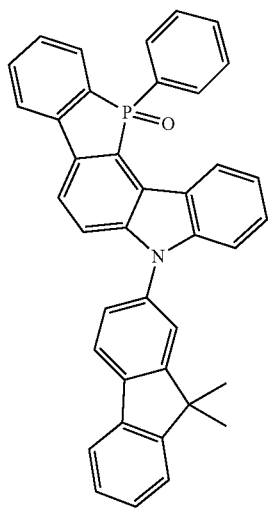
Formula 1-3-41
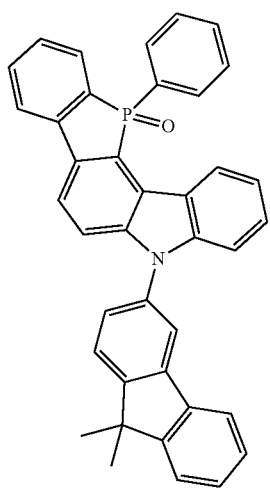
Formula 1-3-42
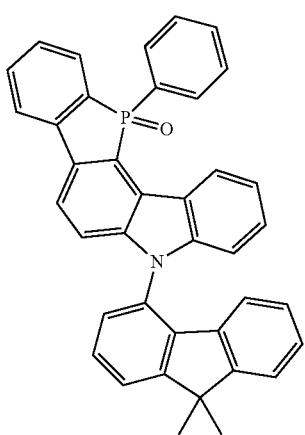
Formula 1-3-43
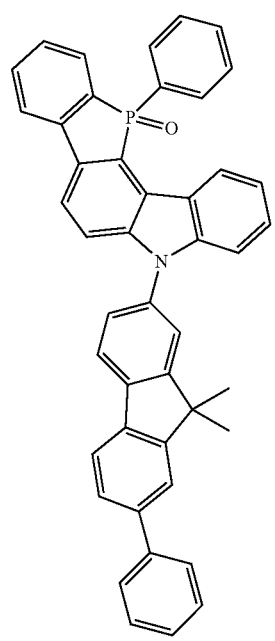
Formula 1-3-44
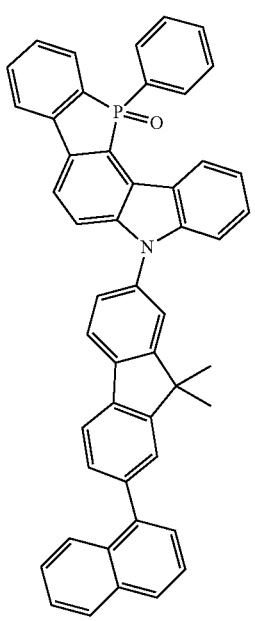

Formula 1-3-45
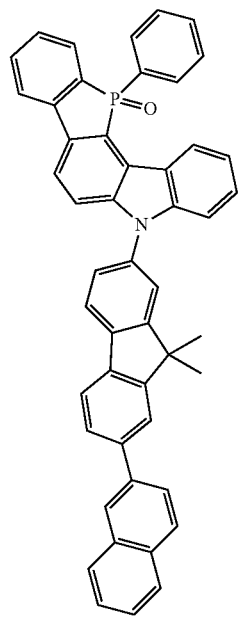
Formula 1-3-46
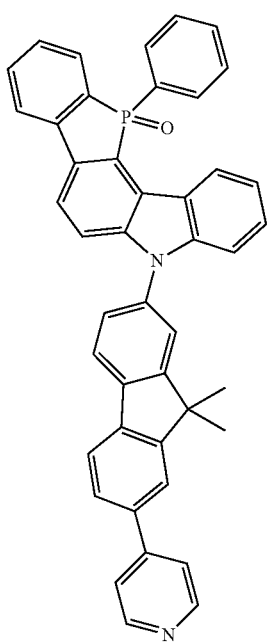
Formula 1-3-47
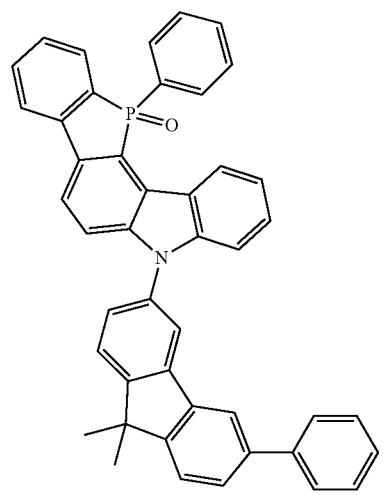
Formula 1-3-48
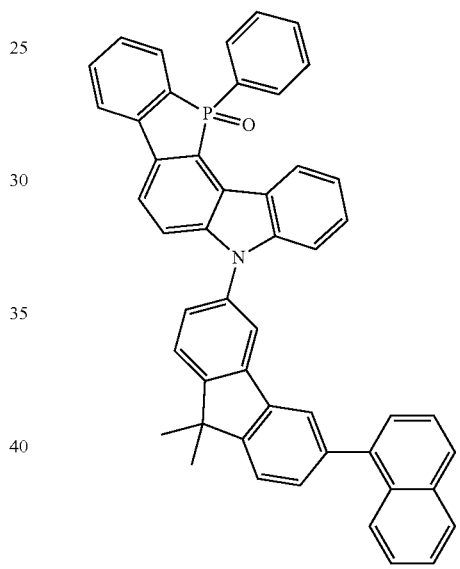
Formula 1-3-49
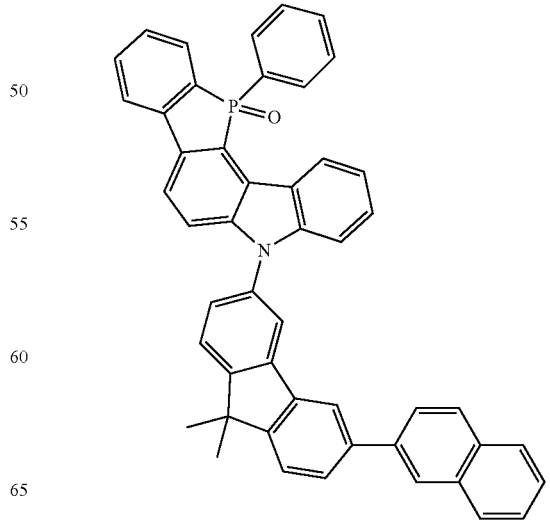

Formula 1-3-50
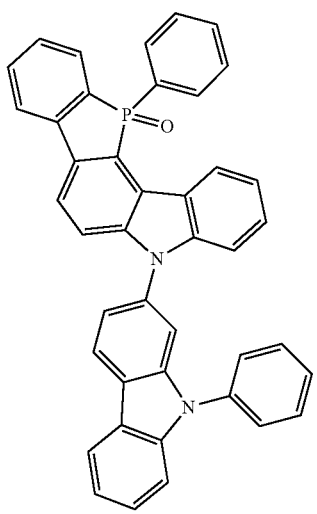
Formula 1-3-51
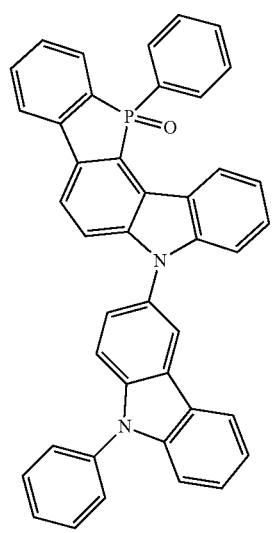
Formula 1-3-52
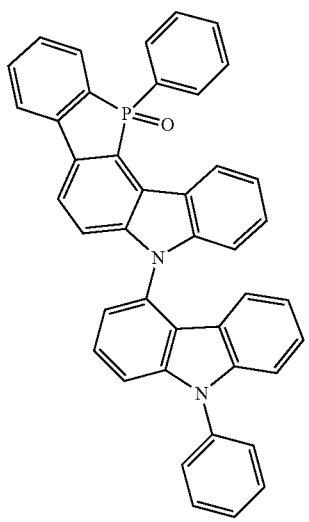
Formula 1-3-53
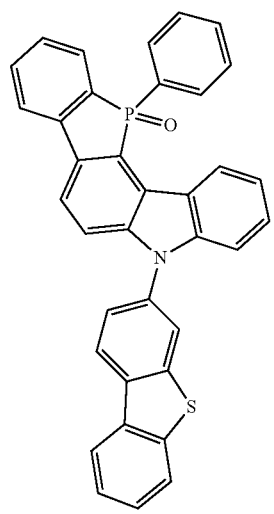
Formula 1-3-54
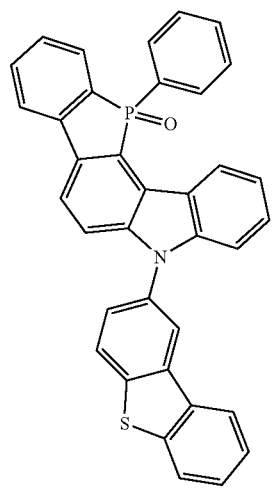
Formula 1-3-55
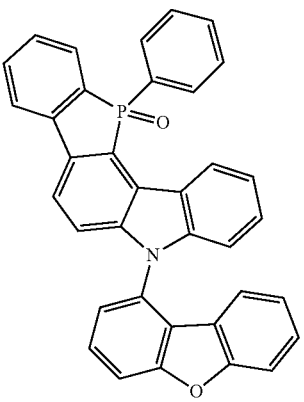

Formula 1-3-56
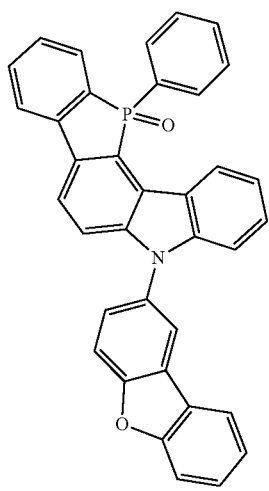
Formula 1-3-57
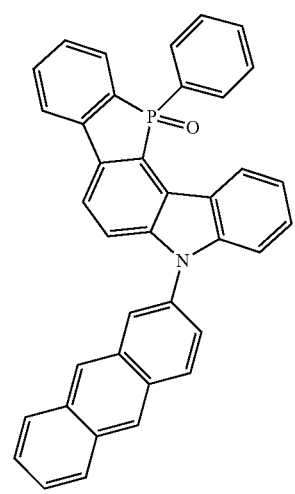
Formula 1-3-58
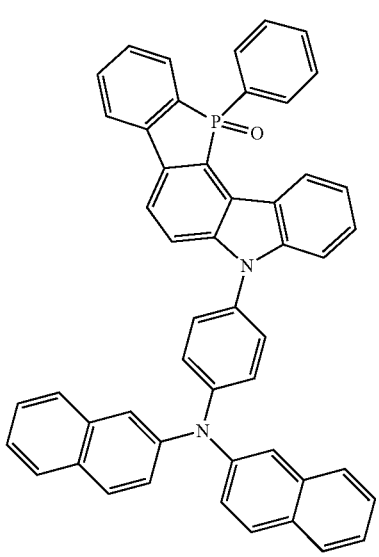
Formula 1-3-59
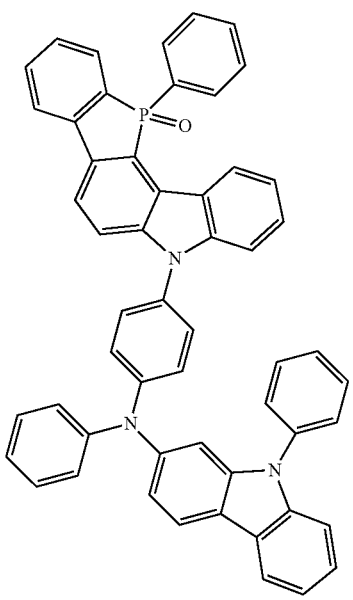
Formula 1-3-60
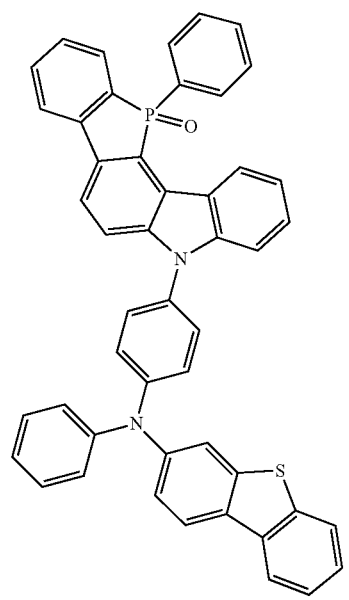

Formula 1-3-61
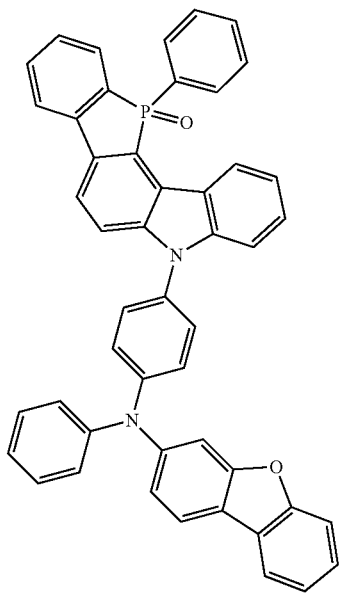
Formula 1-3-63
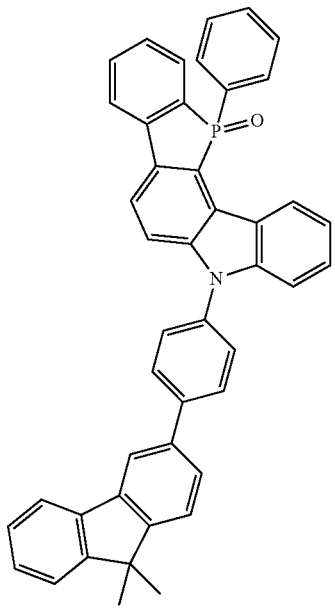
Formula 1-3-62
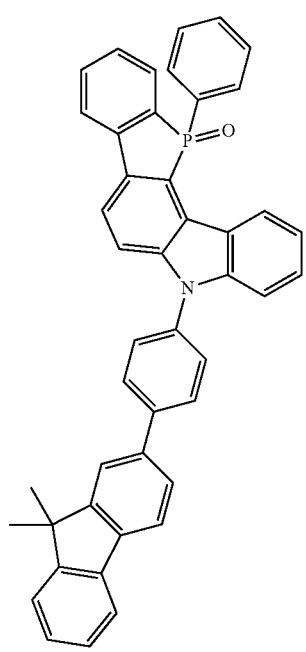
Formula 1-3-64

Formula 1-3-65
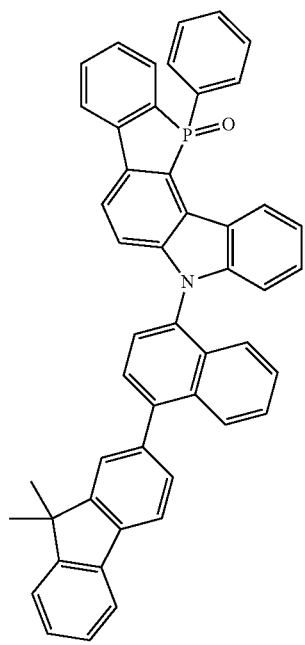
Formula 1-3-67
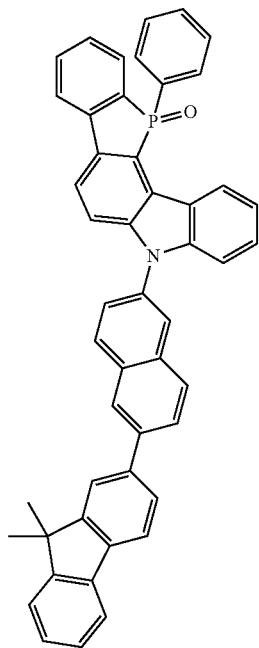
Formula 1-3-66
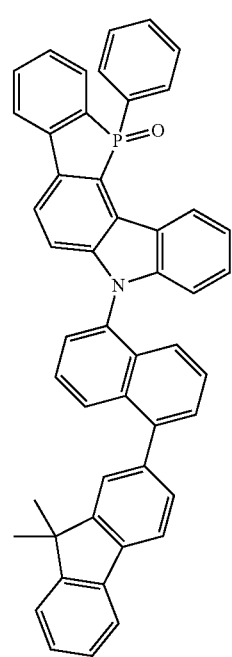
Formula 1-3-68
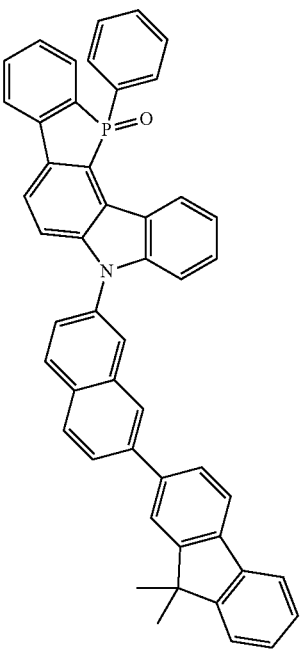

Formula 1-3-69
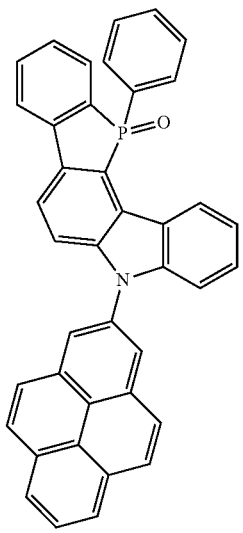
Formula 1-3-70
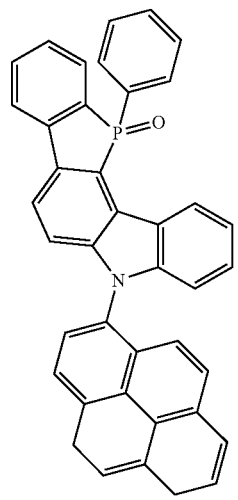
Formula 1-3-71
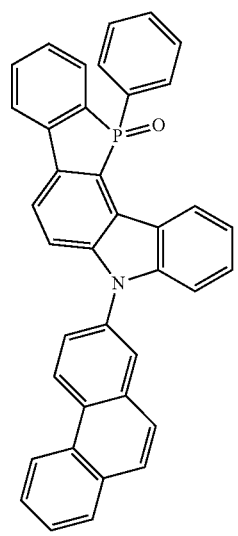
Formula 1-3-72
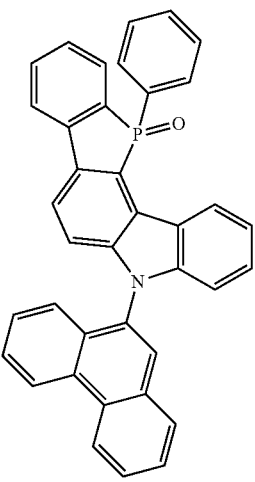
Formula 1-3-73
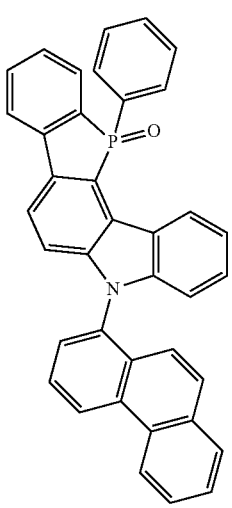
Formula 1-3-74
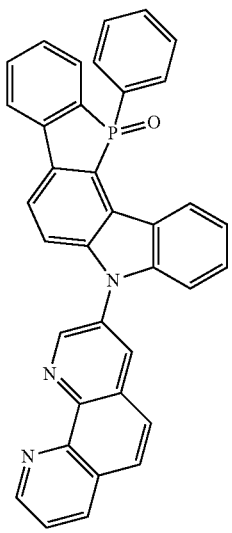

Formula 1-3-75
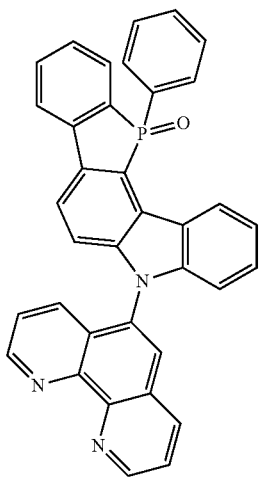
Formula 1-3-76
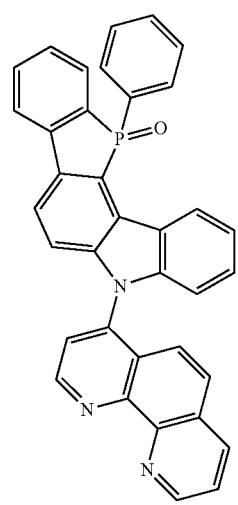
Formula 1-3-77
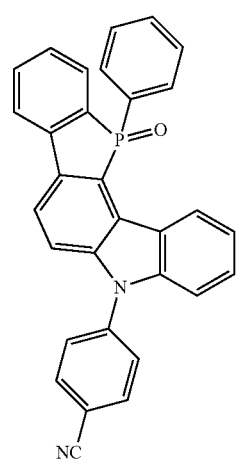
Formula 1-3-78
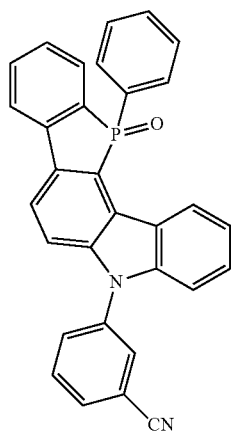
Formula 1-3-79
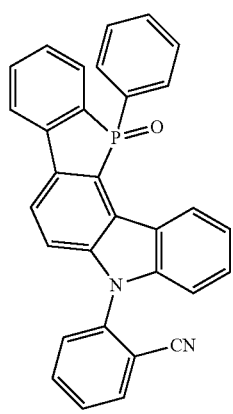
Formula 1-3-80
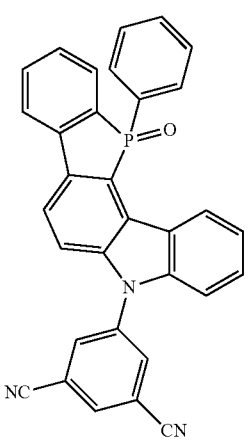

Formula 1-3-81
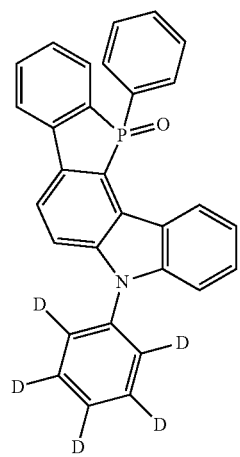
Formula 1-3-82
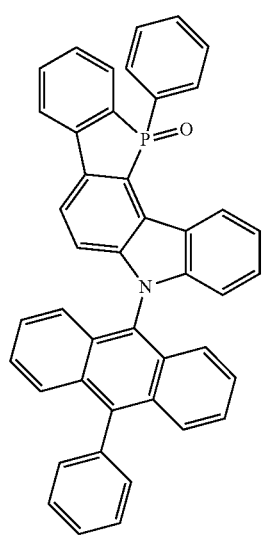
Formula 1-3-83
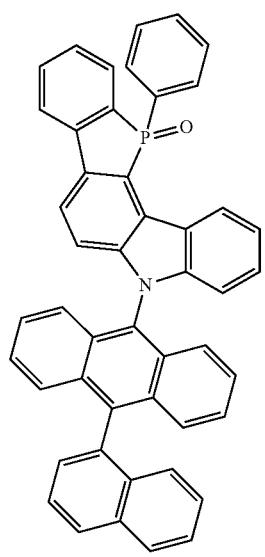
Formula 1-3-84
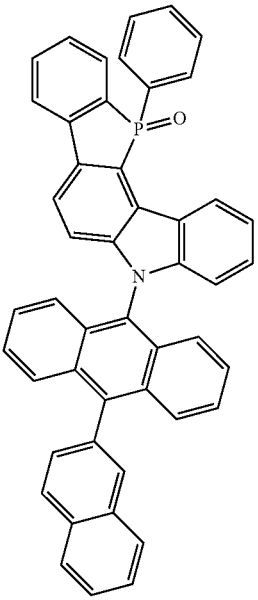
Formula 1-3-85
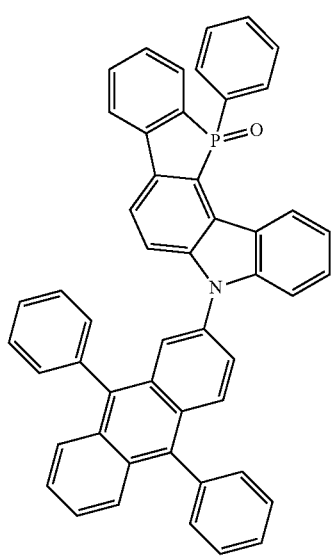

539
-continued
Formula 1-3-86
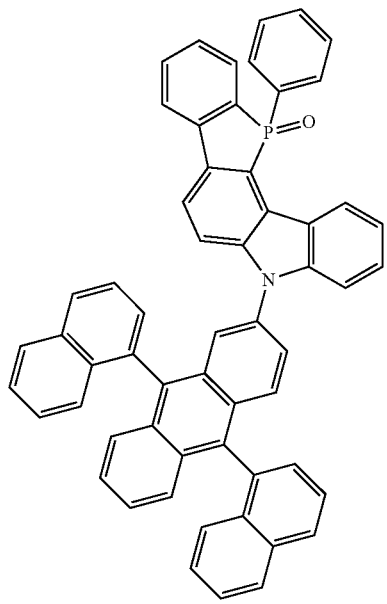
Formula 1-3-87
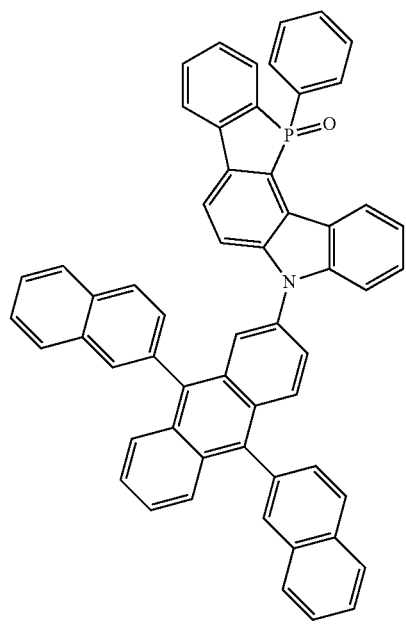
540
-continued
Formula 1-3-88
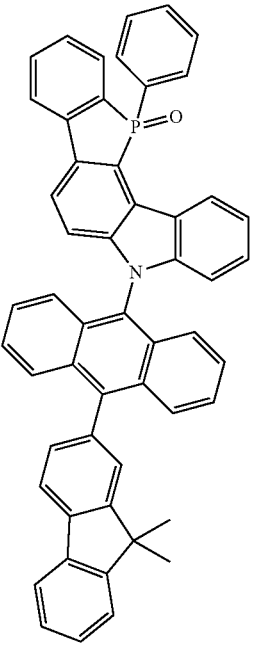
Formula 1-3-89
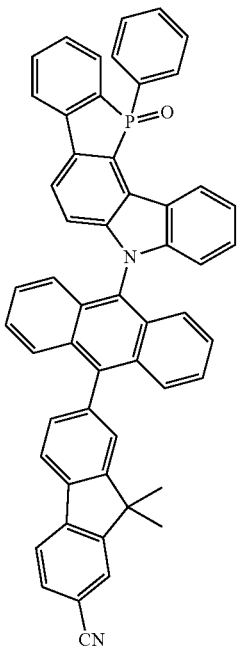

Formula 1-3-90
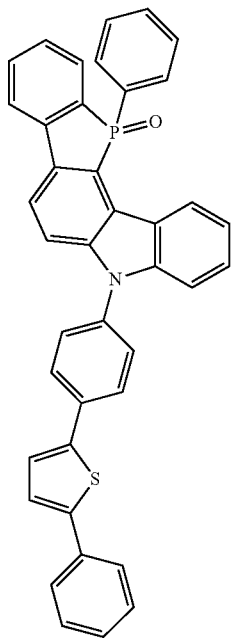
Formula 1-3-92
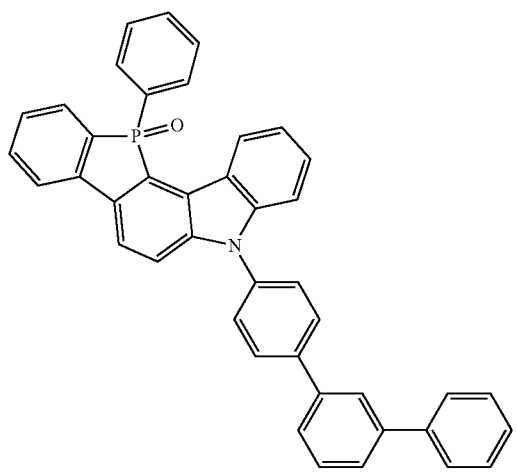
Formula 1-3-91
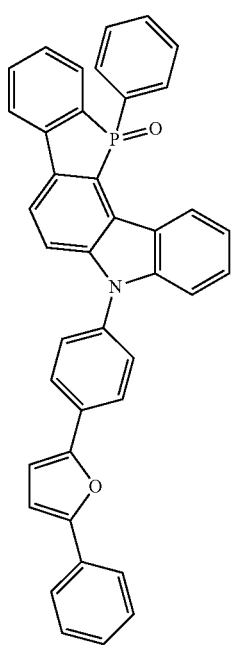
Formula 1-3-93
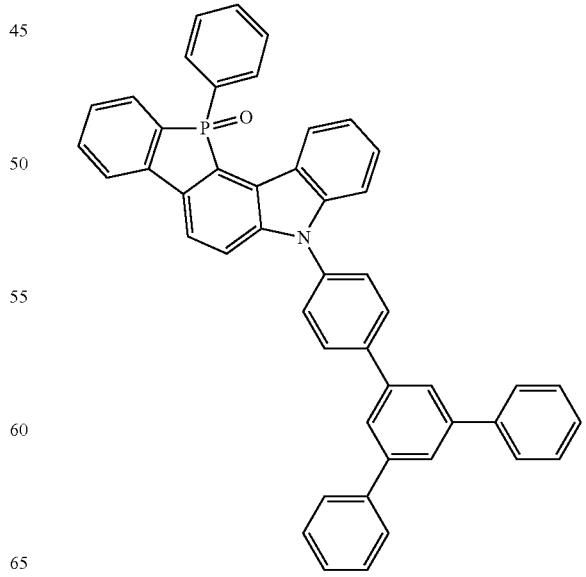

Formula 1-3-94
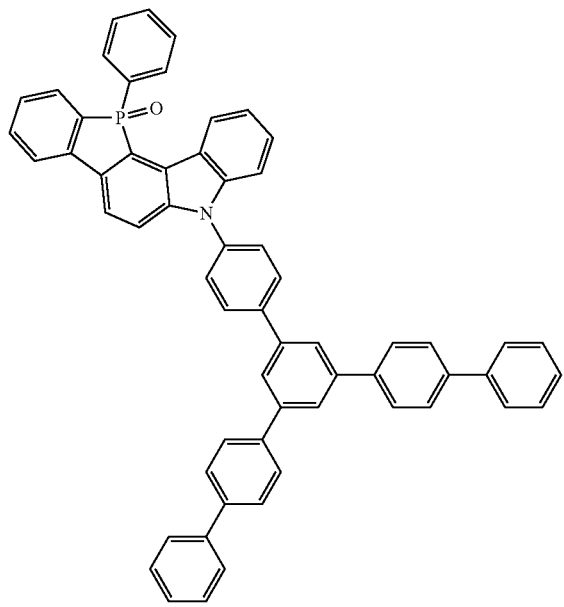
Formula 1-3-96
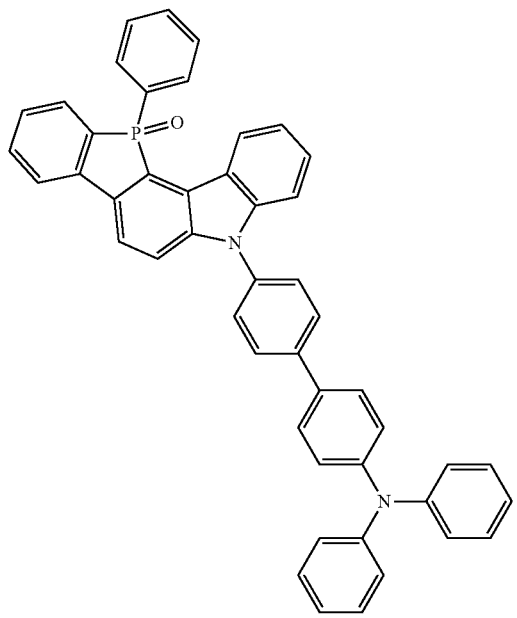
Formula 1-3-95
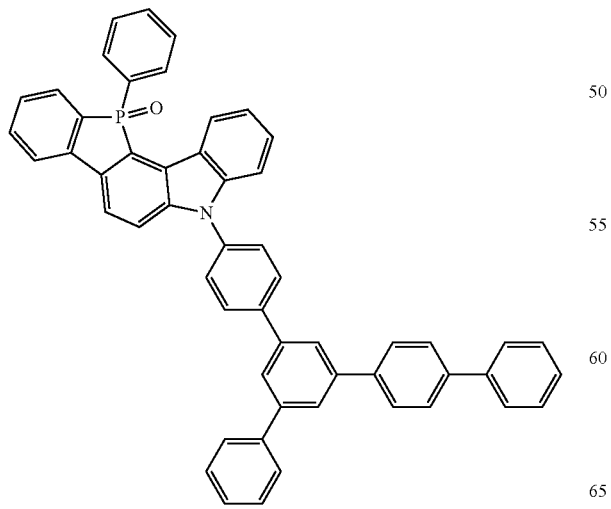
Formula 1-3-97
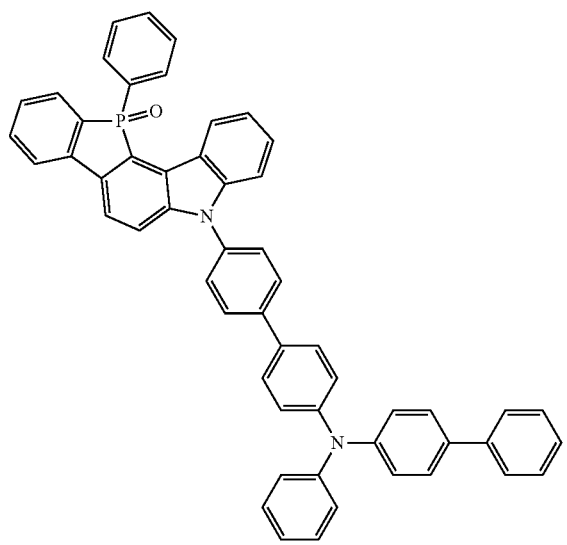

545
-continued
Formula 1-3-98
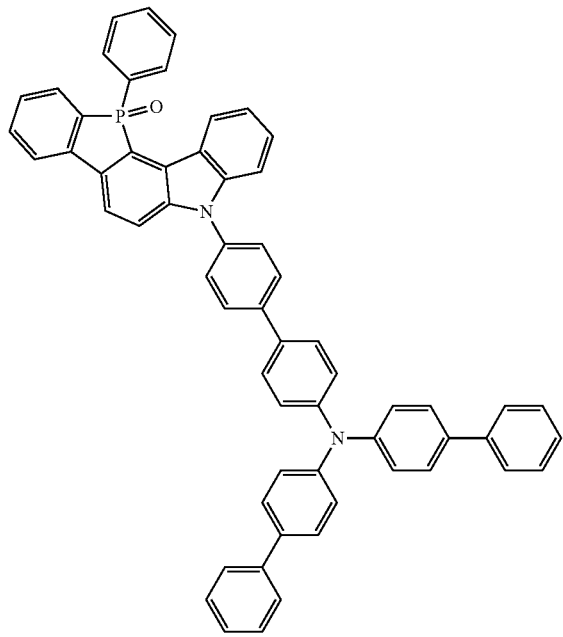
Formula 1-3-99
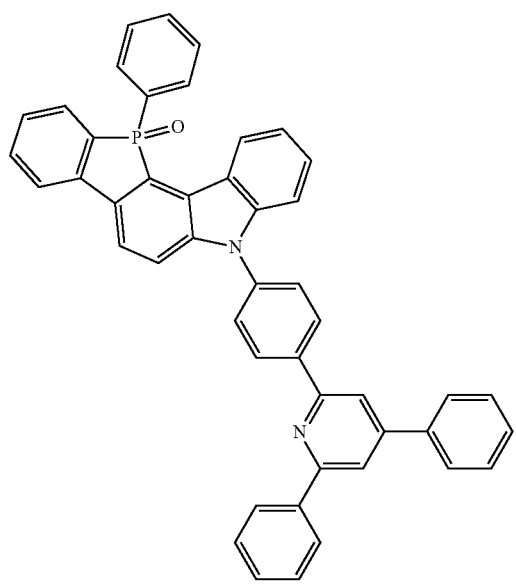
546
-continued
Formula 1-3-100
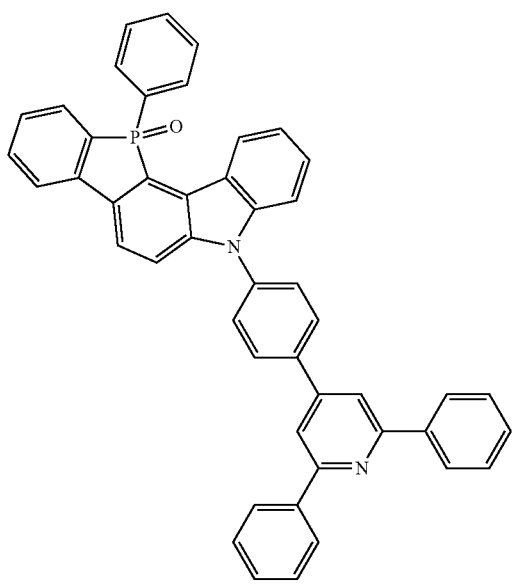
Formula 1-3-101
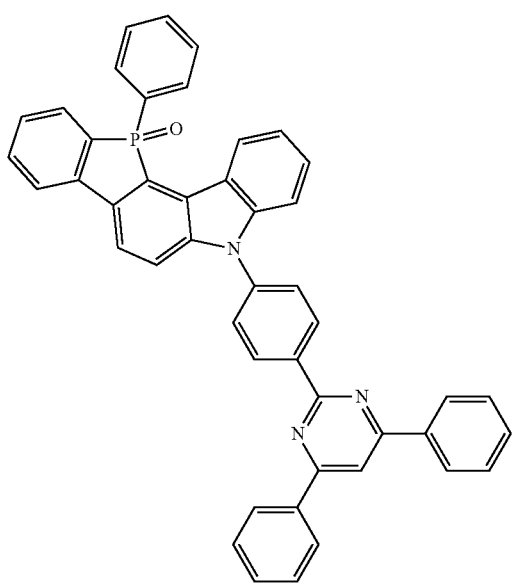

Formula 1-3-102
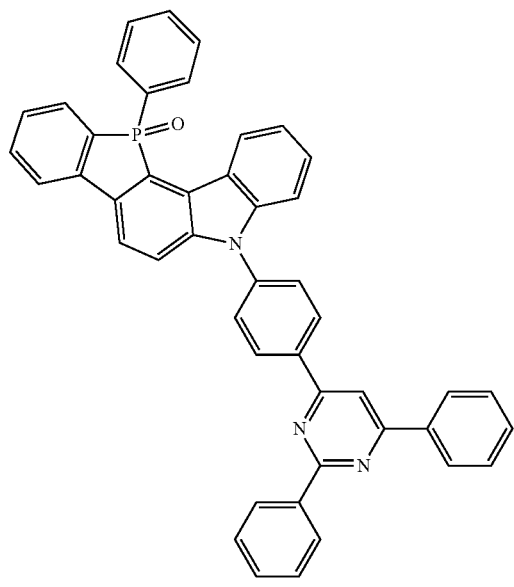
Formula 1-3-104
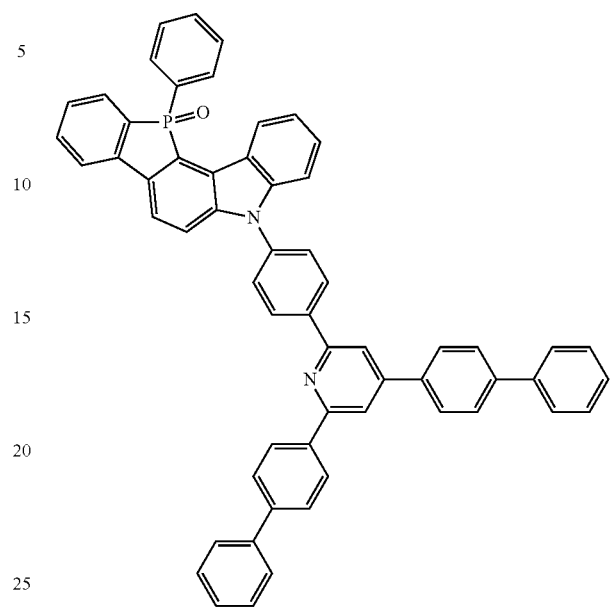
Formula 1-3-103
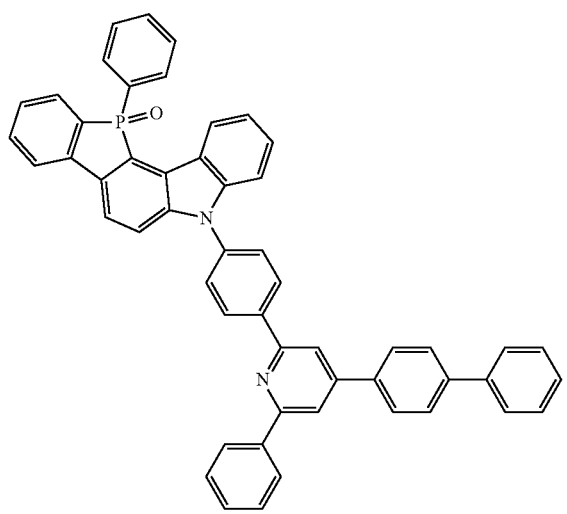
Formula 1-3-105
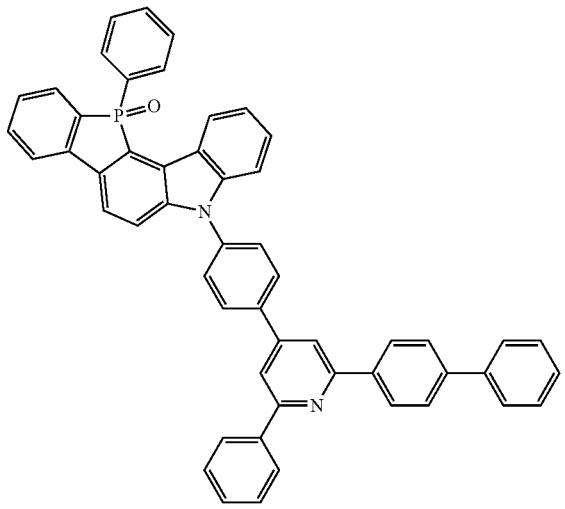

-continued
Formula 1-3-106
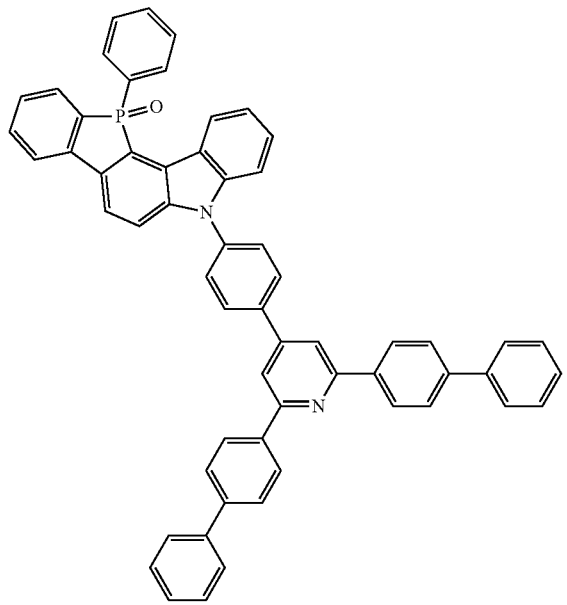
Formula 1-3-107
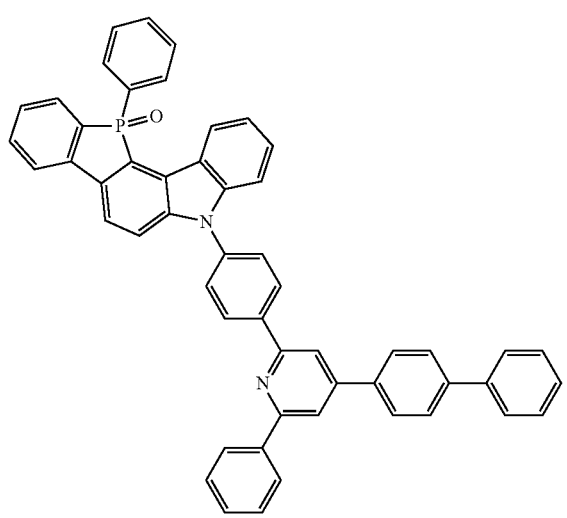
-continued
Formula 1-3-108
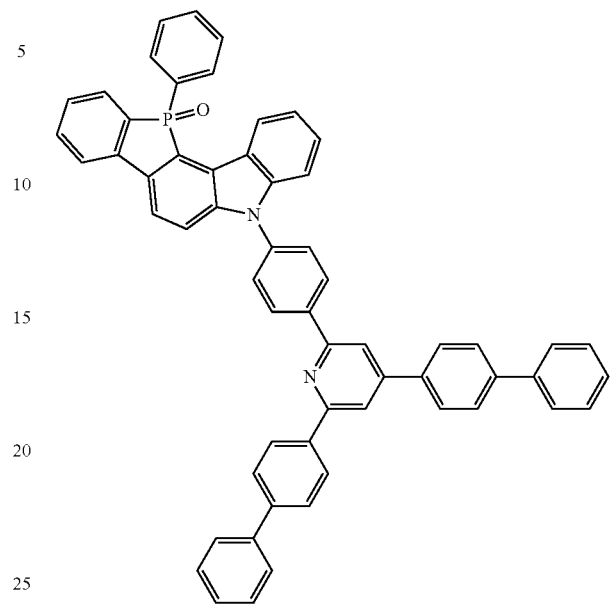
Formula 1-3-109
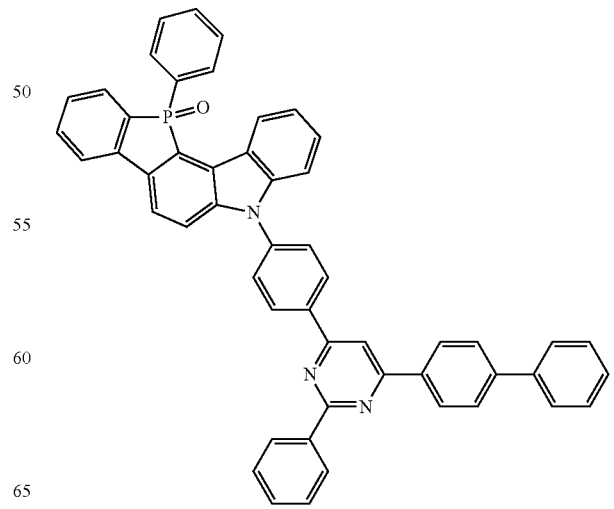

Formula 1-3-110
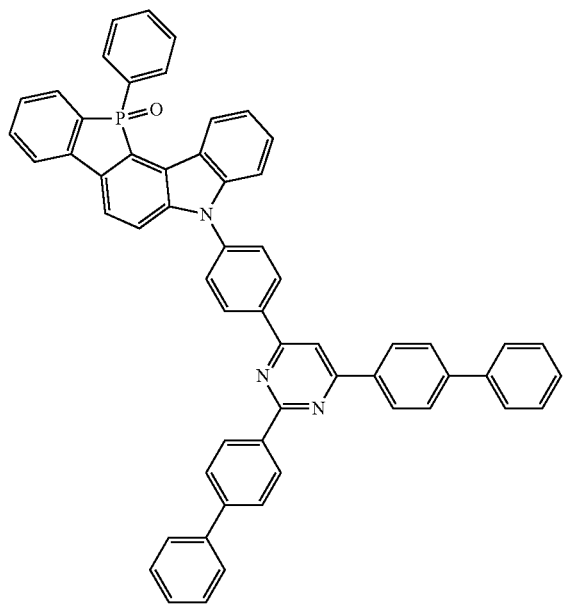
Formula 1-3-112
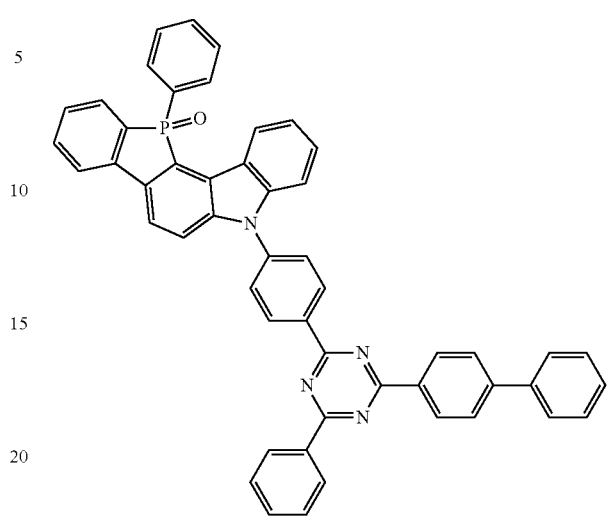
Formula 1-3-111
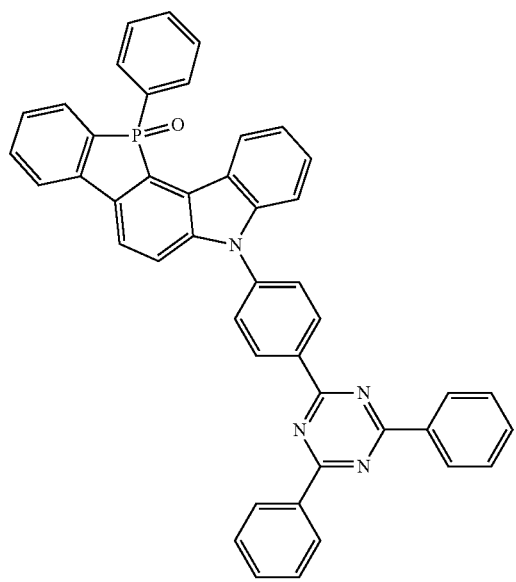
Formula 1-3-113
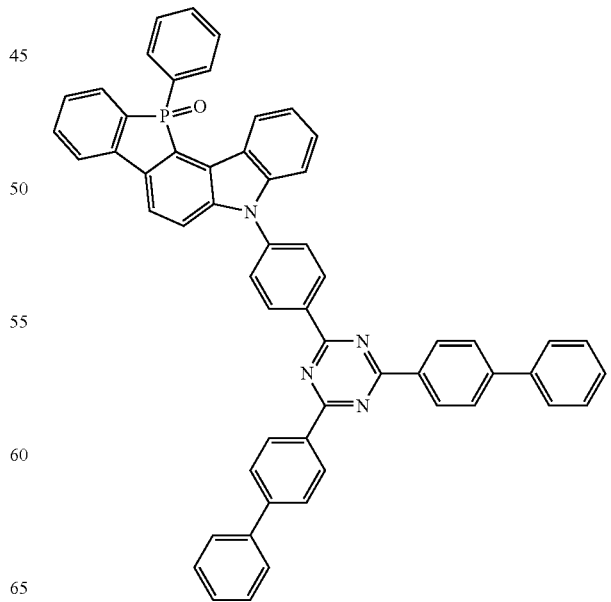

Formula 1-3-114
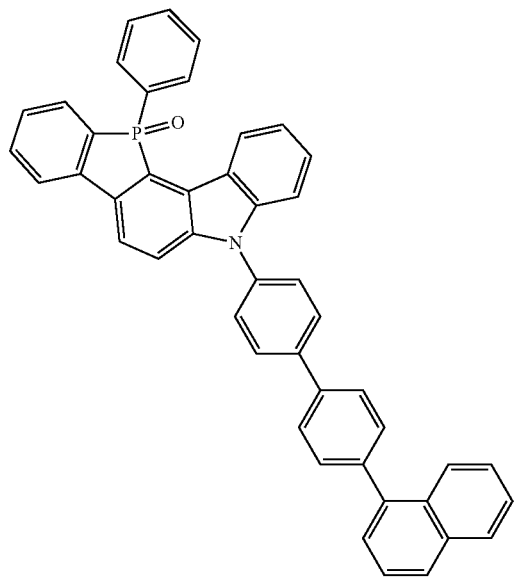
Formula 1-3-116
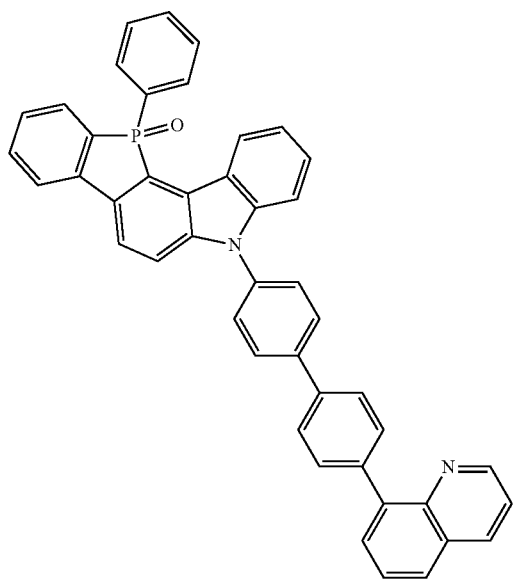
Formula 1-3-115
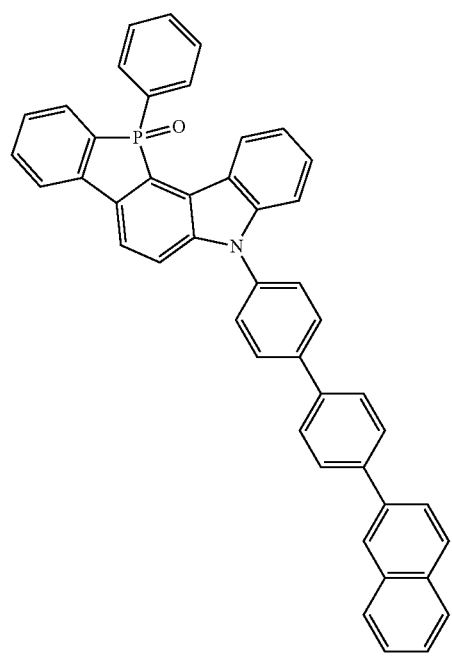
Formula 1-3-117
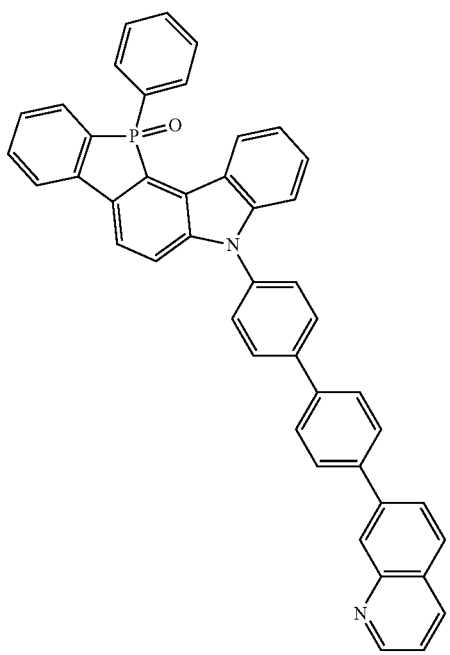

555
-continued
Formula 1-3-118
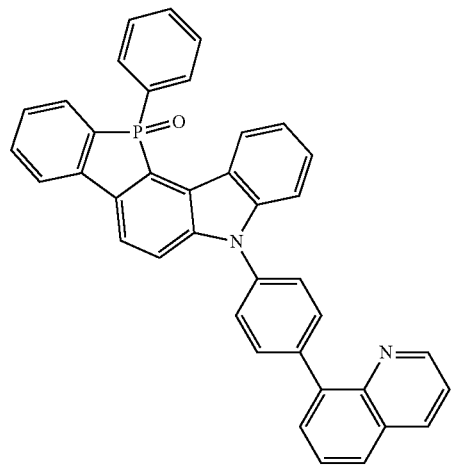
Formula 1-3-119
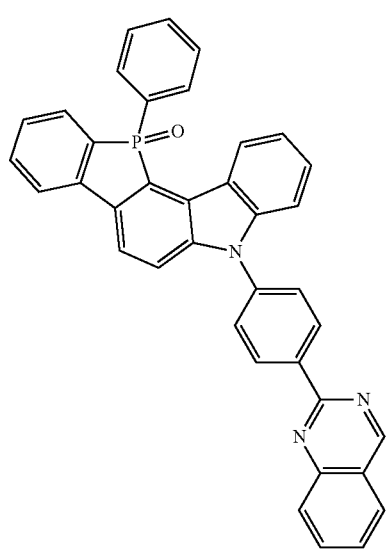
Formula1-3-120
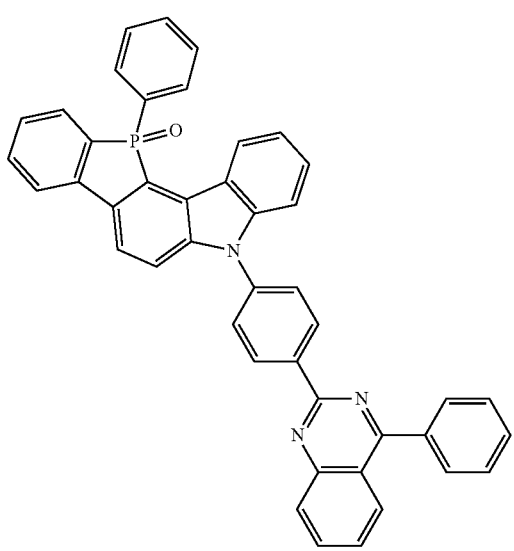
556
-continued
Formula 1-3-121
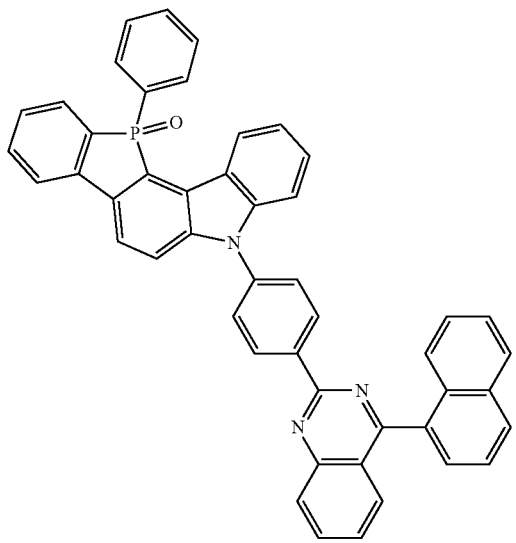
Formula 1-3-122
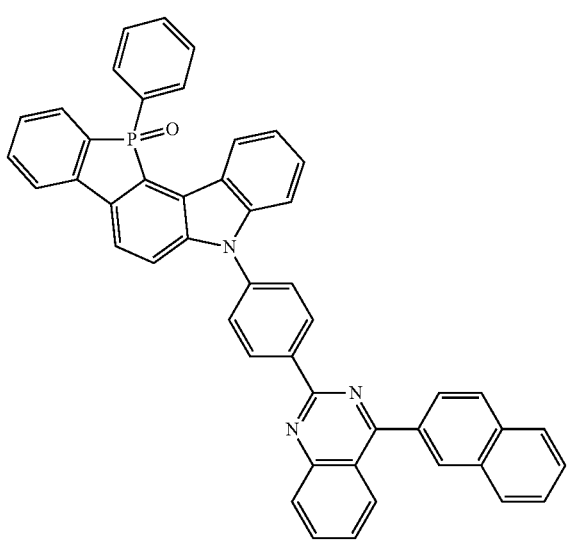
Formula 1-3-123

557
-continued
Formula 1-3-124
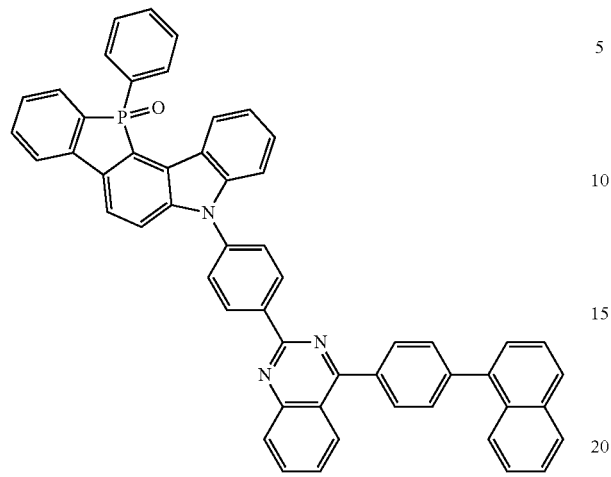
Formula 1-3-125
558
-continued
Formula 1-3-127
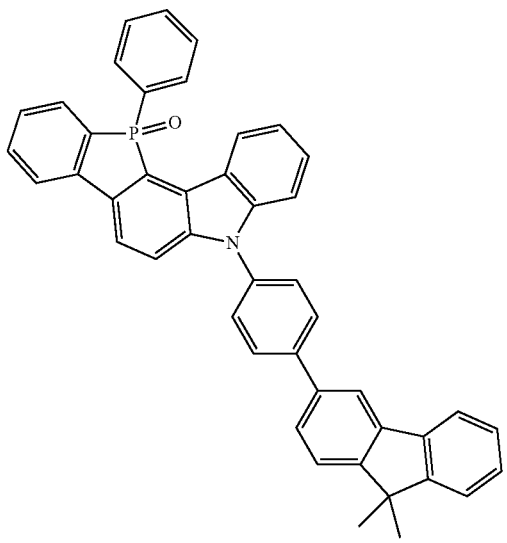
Formula 1-3-126
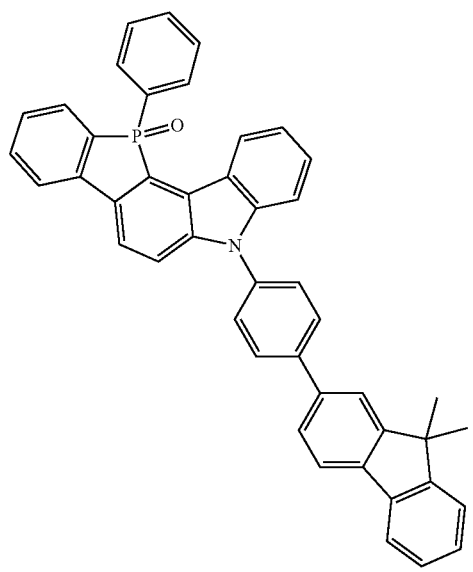
Formula 1-3-128
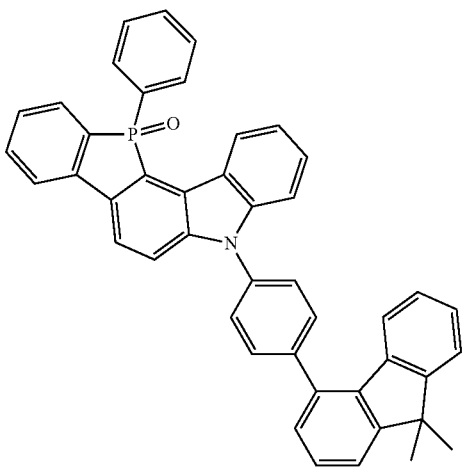

Formula 1-3-129
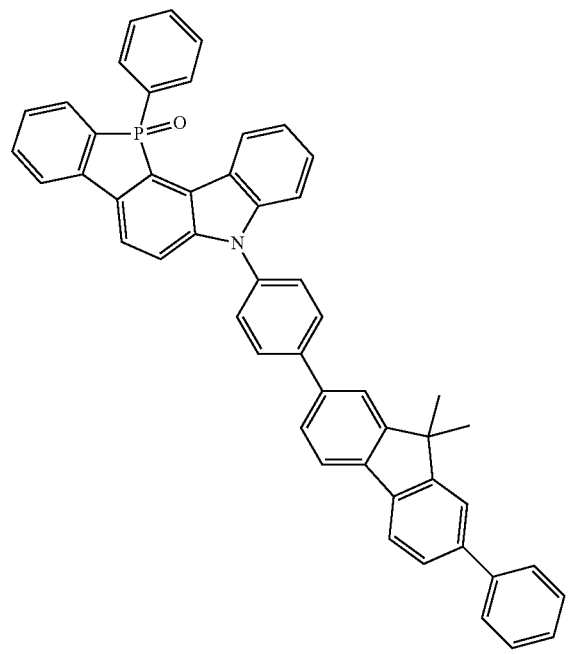
Formula 1-3-130
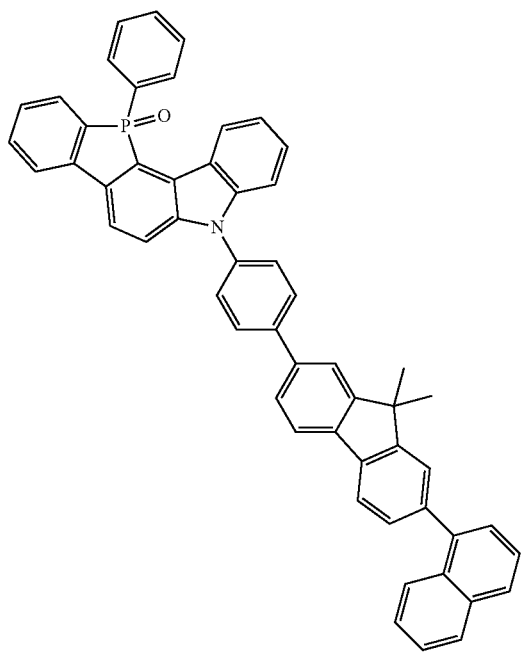
Formula 1-3-131
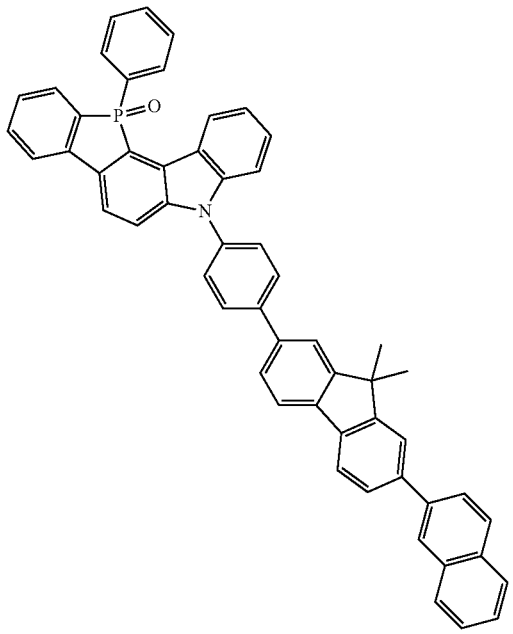
Formula 1-3-132
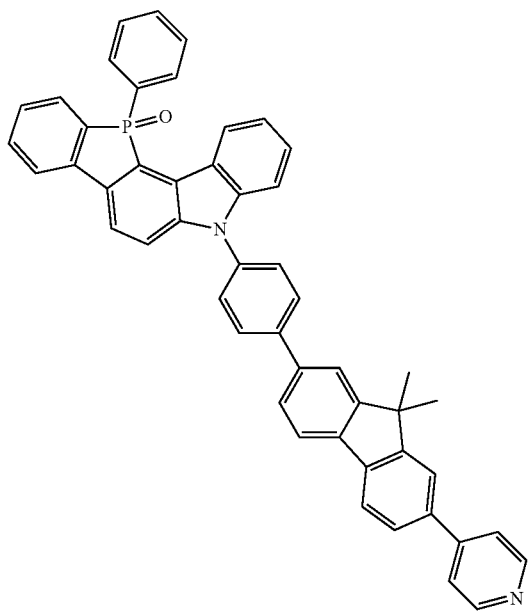

Formula 1-3-133
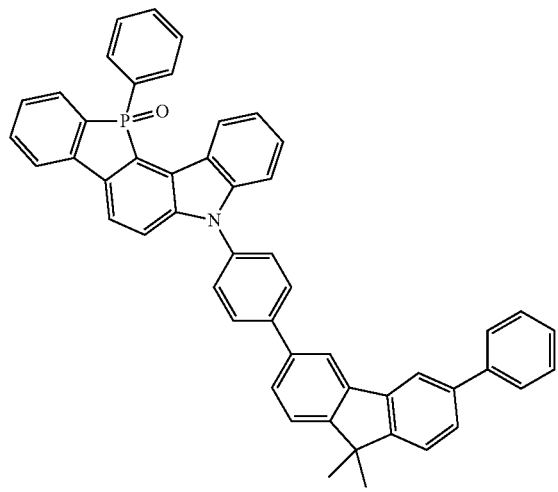
Formula 1-3-134
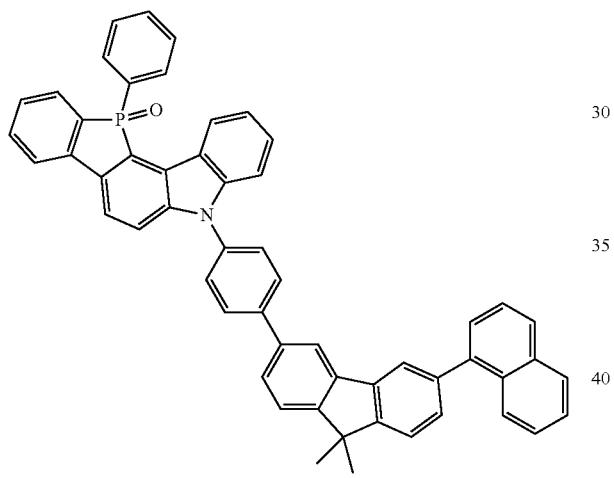
Formula 1-3-135
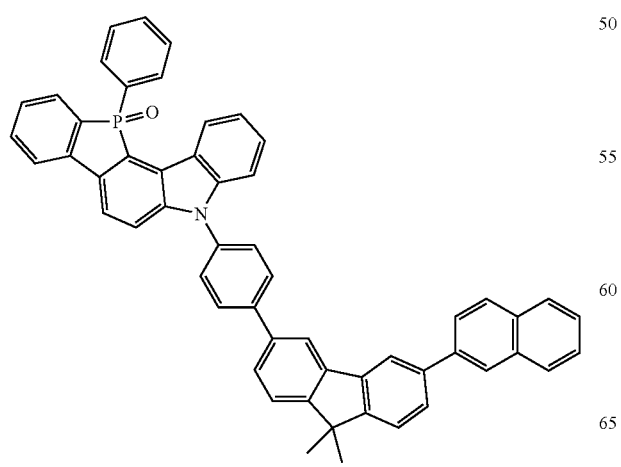
Formula 1-3-136
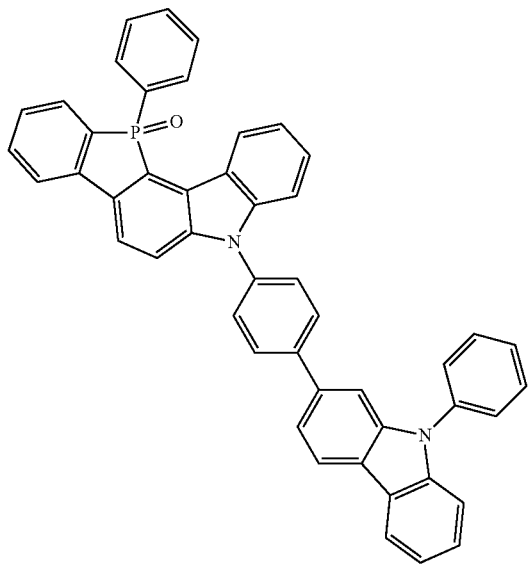
Formula 1-3-137
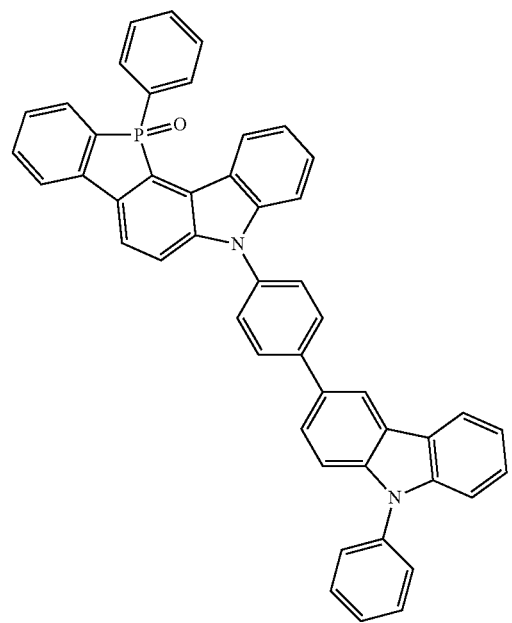

Formula 1-3-138
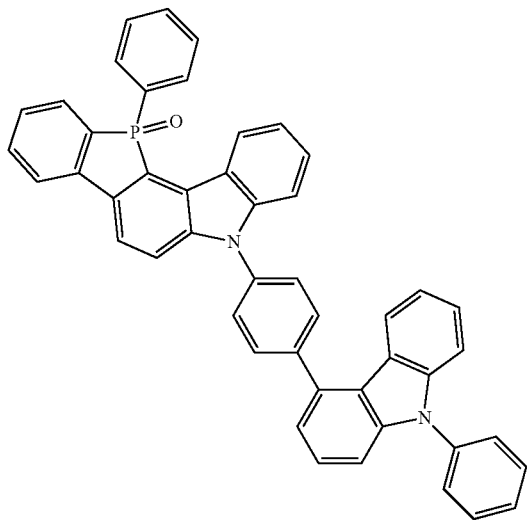
Formula 1-3-139
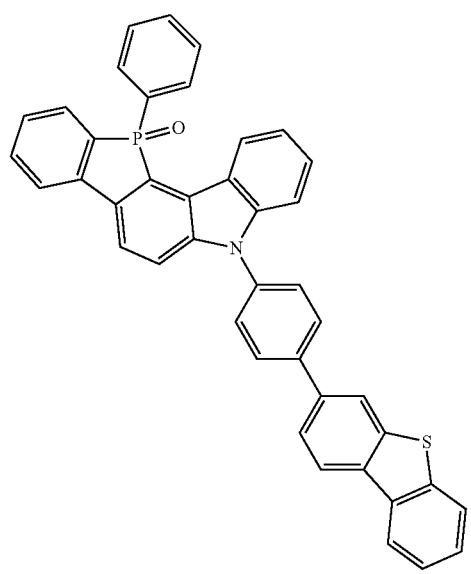
Formula 1-3-140
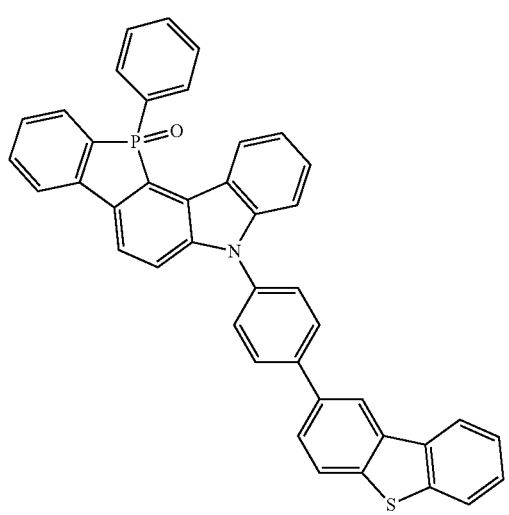
Formula 1-3-141
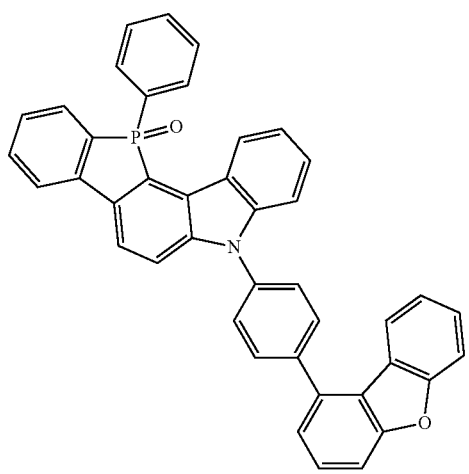
Formula 1-3-142
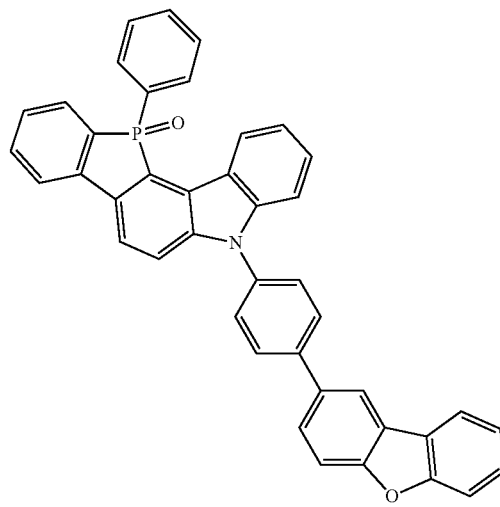
Formula 1-3-143
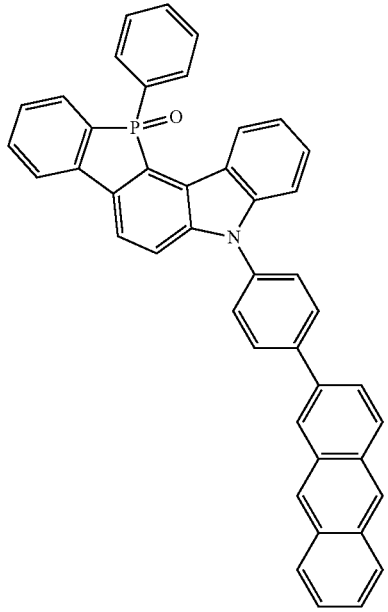

Formula 1-3-144
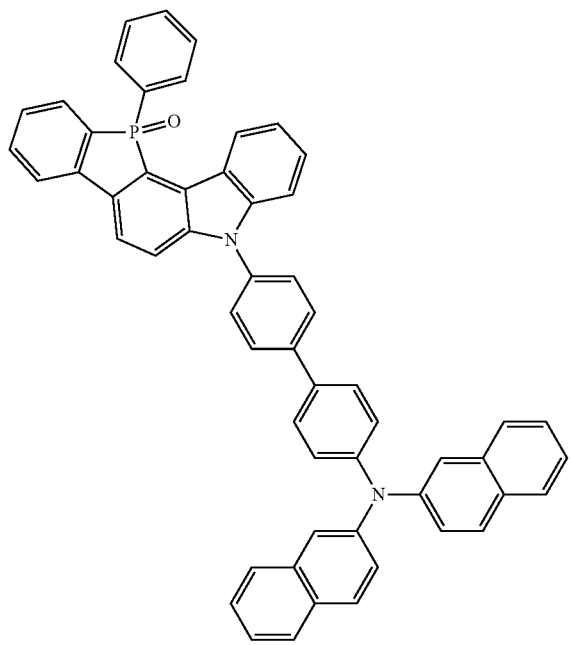
Formula 1-3-145
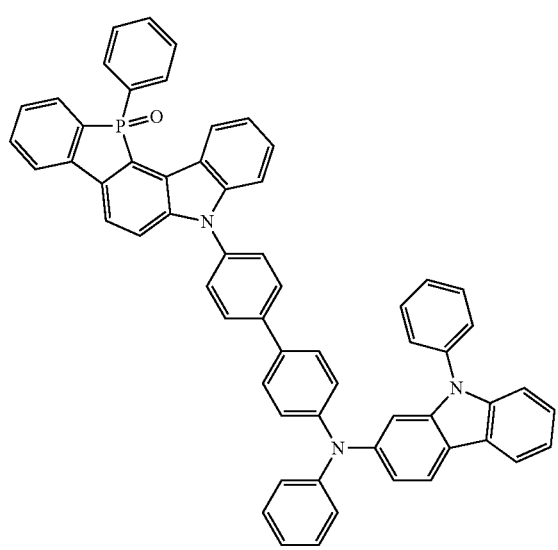
Formula 1-3-146
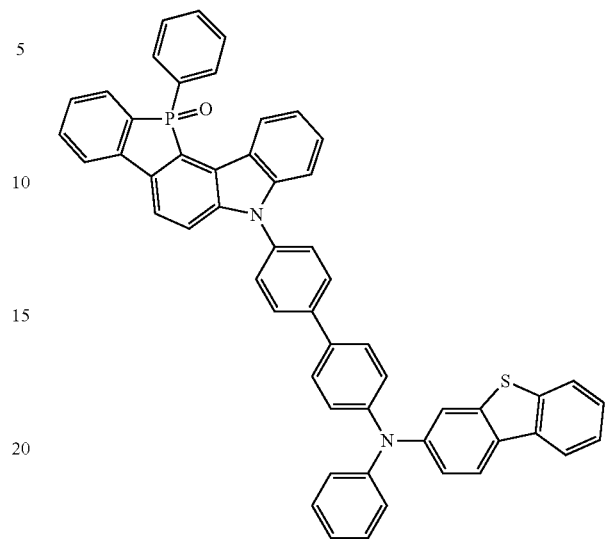
Formula 1-3-147
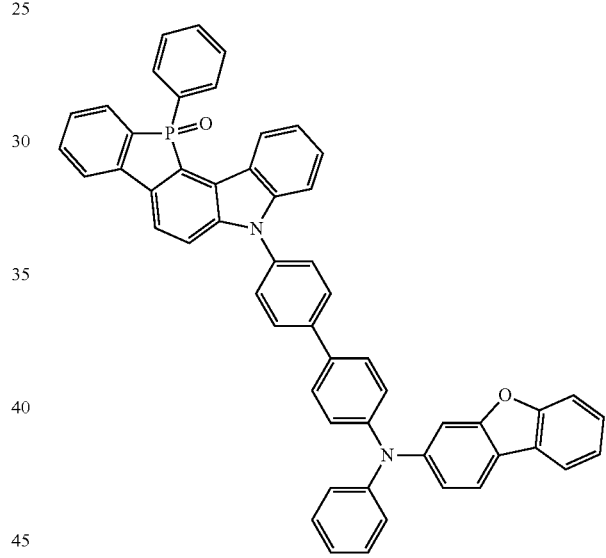
Formula 1-3-148
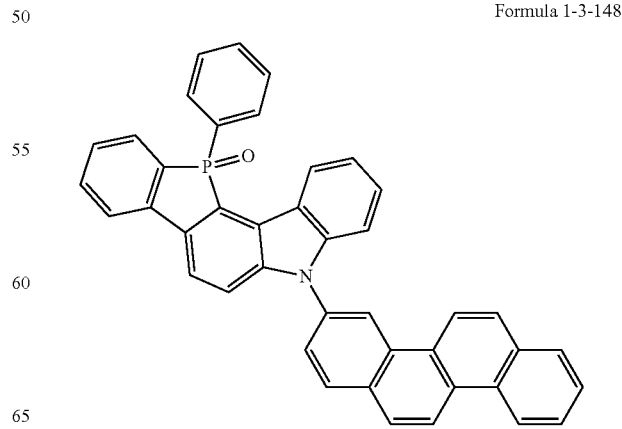

-continued
Formula 1-3-149
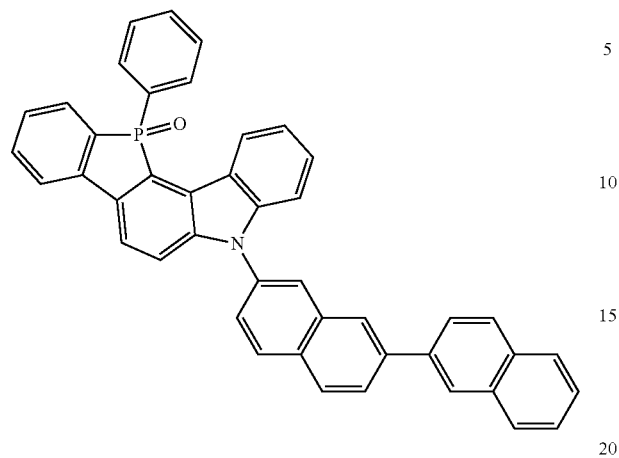
Formula 1-3-150
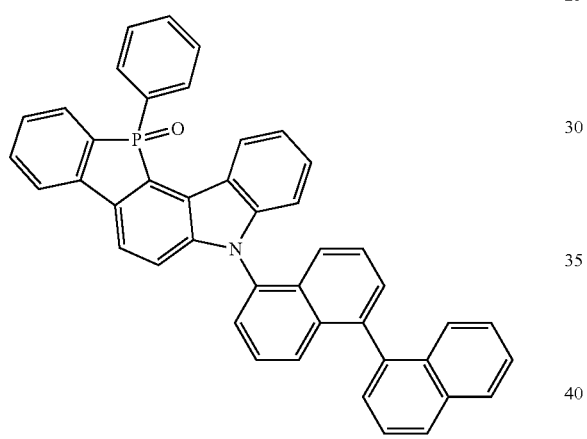
Formula 1-3-151
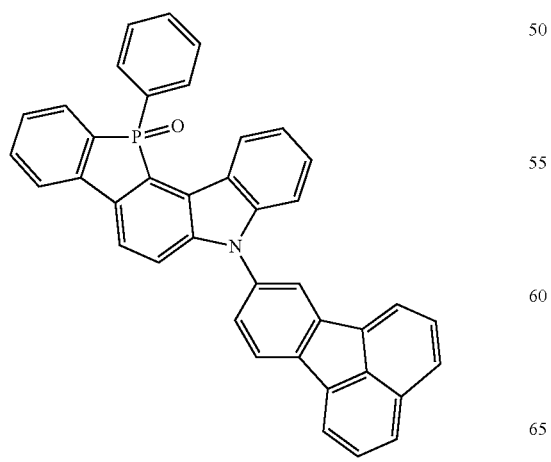
-continued
Formula 1-3-152
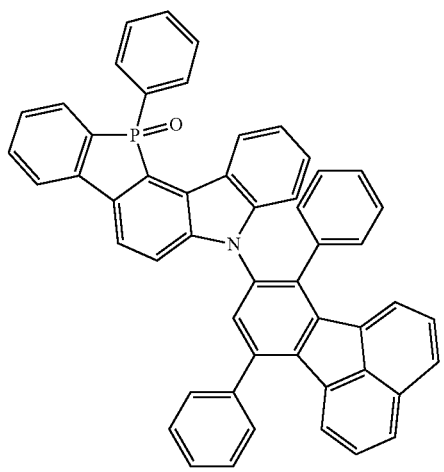
Formula 1-3-153
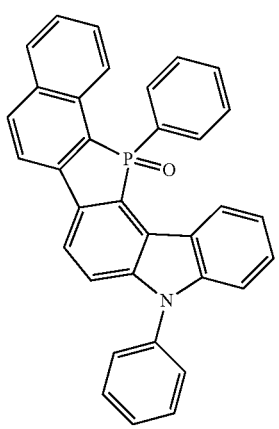
Formula 1-3-154
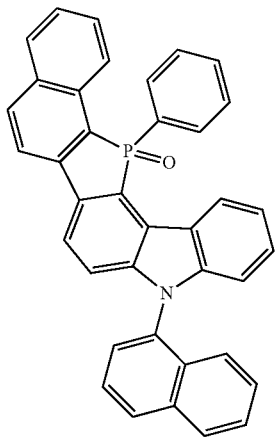

Formula 1-3-155
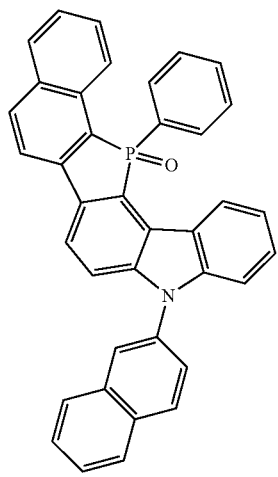
Formula 1-3-158
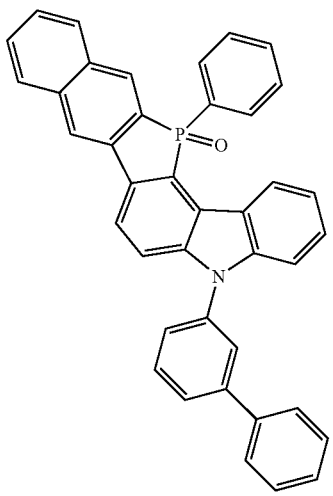
Formula 1-3-156
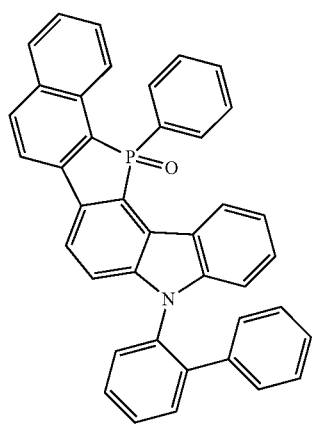
Formula 1-3-159
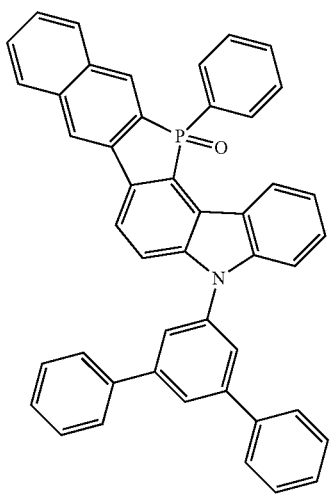
Formula 1-3-157
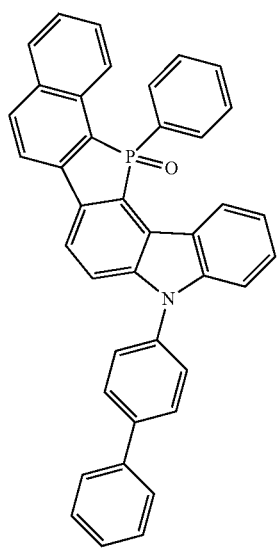
Formula 1-3-160
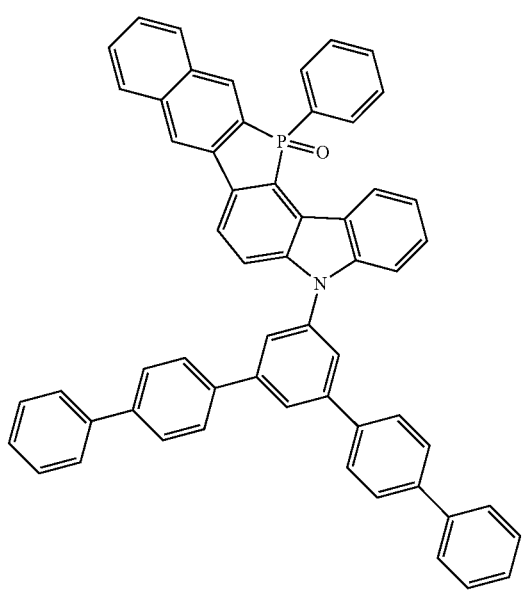

571
-continued
Formula 1-3-161
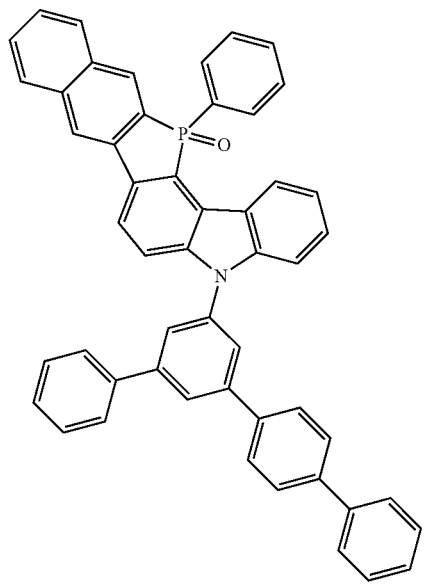
Formula 1-3-162
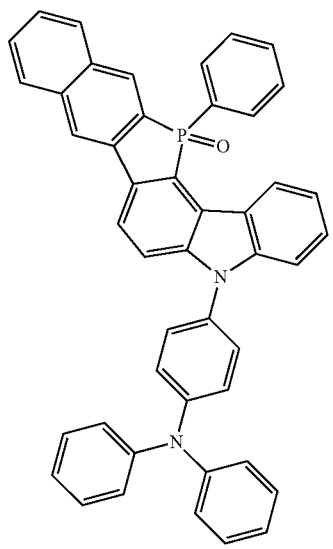
572
-continued
Formula 1-3-163
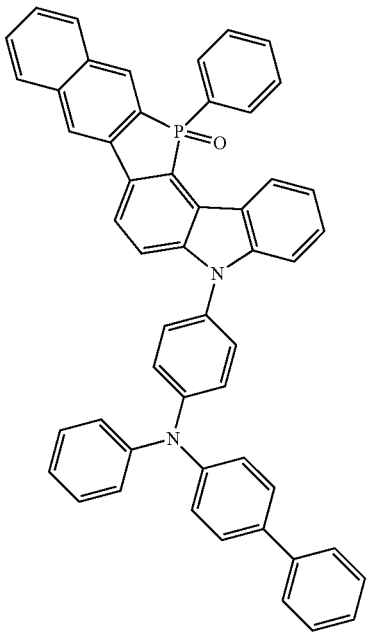
Formula 1-3-164
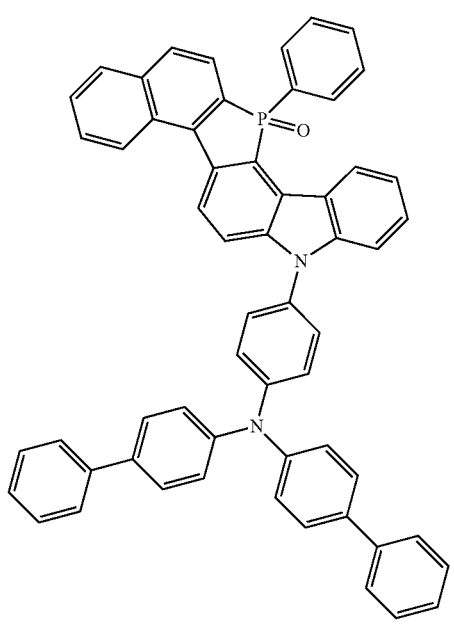

Formula 1-3-165
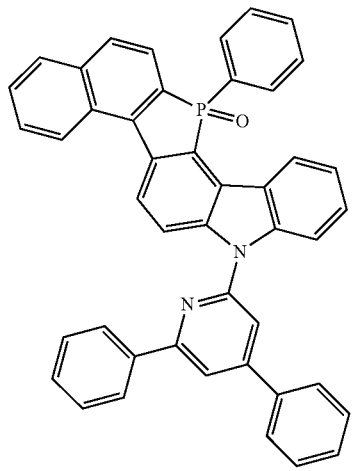
Formula 1-3-166
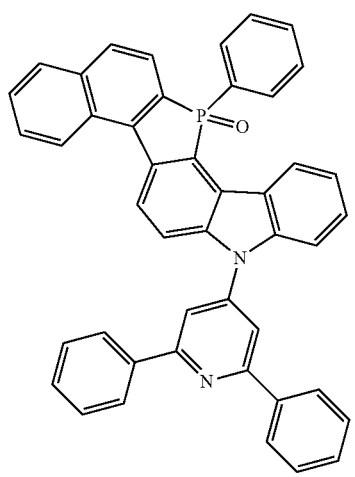
Formula 1-3-167
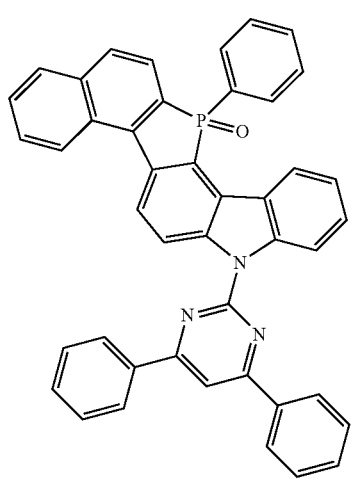
Formula 1-3-168
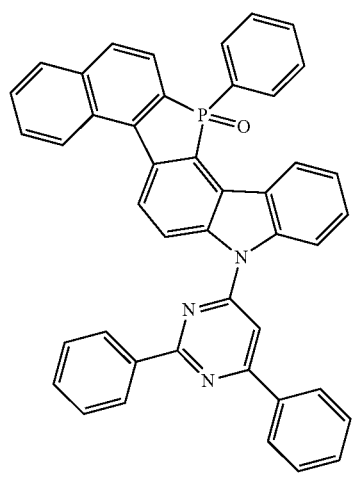
Formula 1-3-169
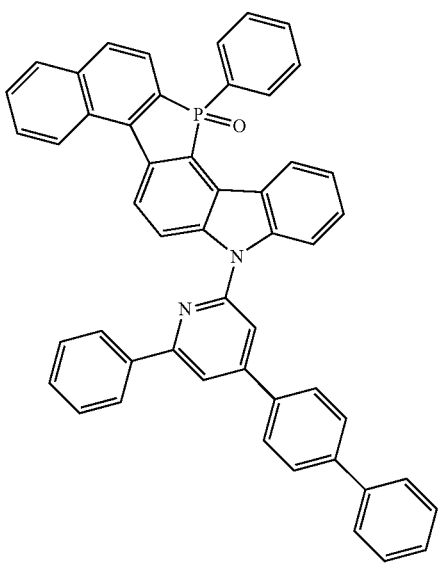
Formula 1-3-170
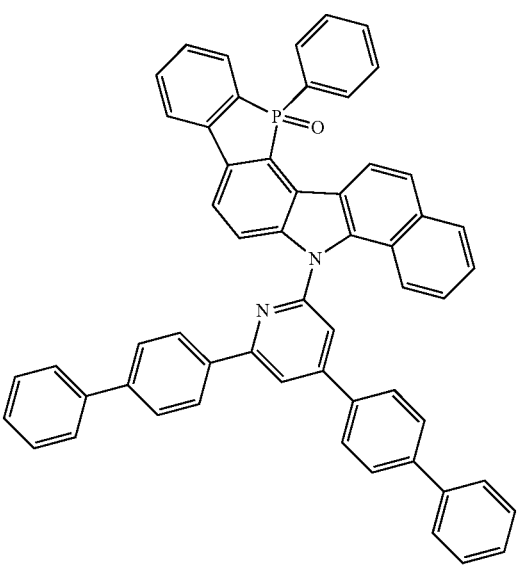

-continued
Formula 1-3-171
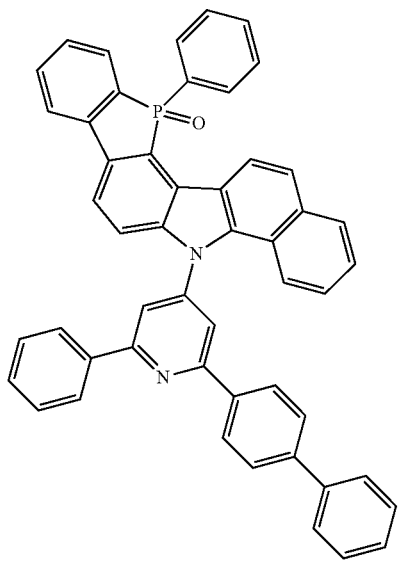
Formula 1-3-172
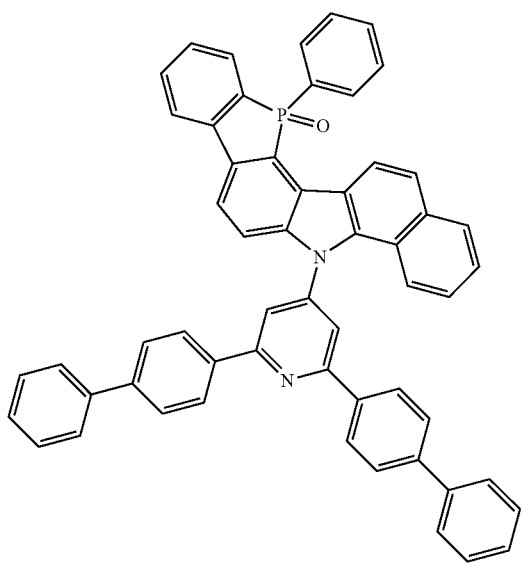
-continued
Formula 1-3-173
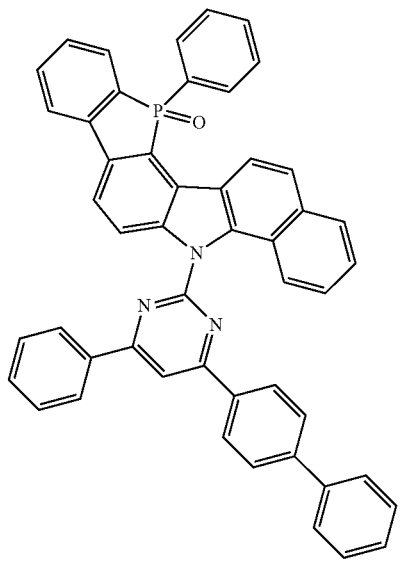
Formula 1-3-174
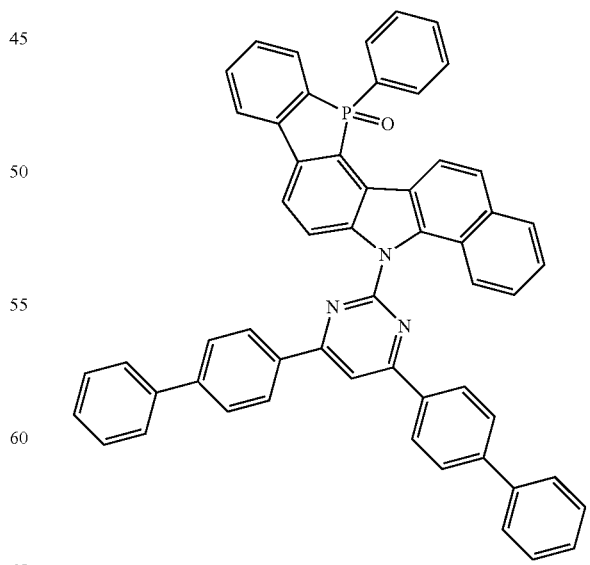

Formula 1-3-175
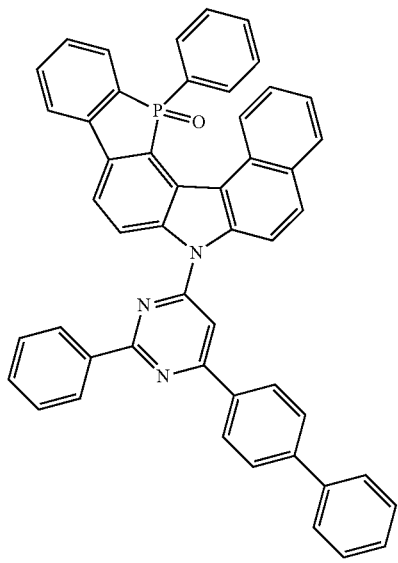
Formula 1-3-176
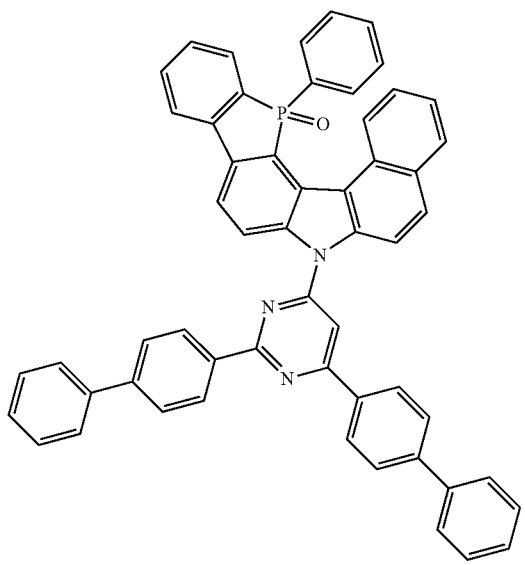
Formula 1-3-177
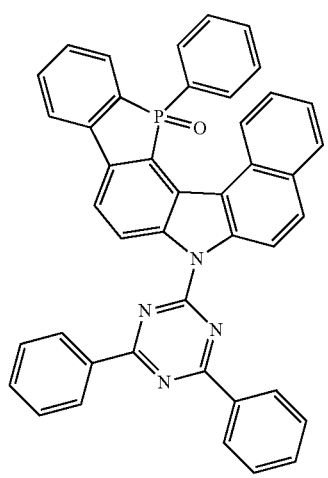
Formula 1-3-178
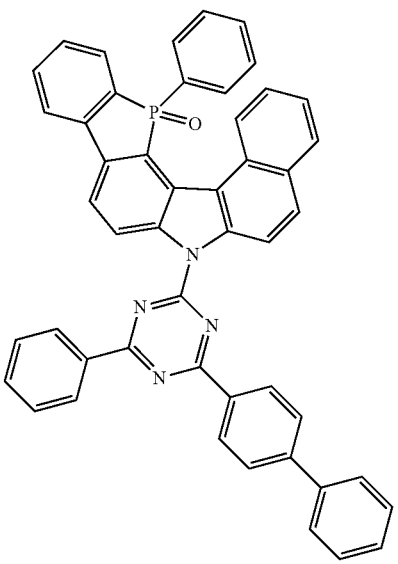
Formula 1-3-179
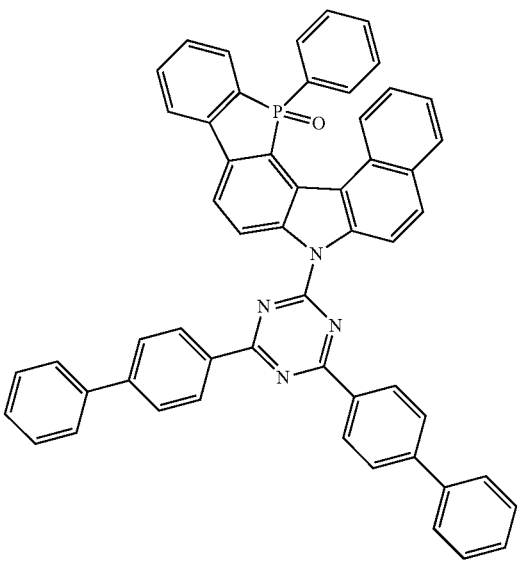
Formula 1-3-180
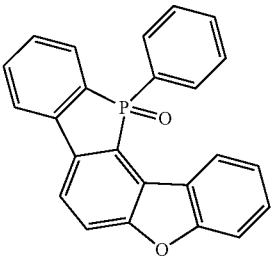

Formula 1-3-181
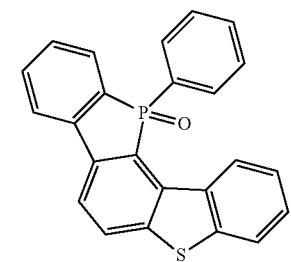
Formula 1-3-182
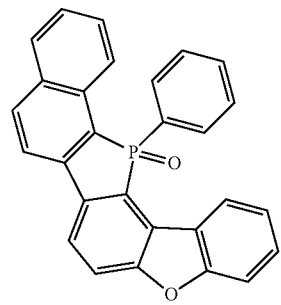
Formula 1-3-183
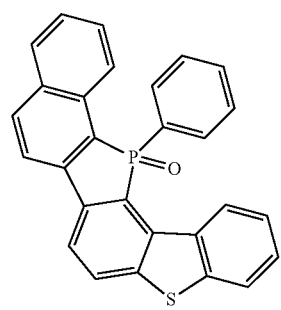
Formula 1-3-184
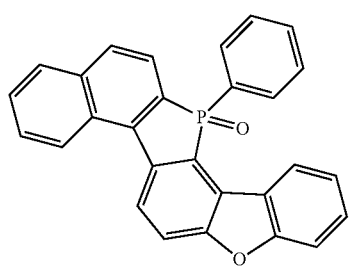
Formula 1-3-185
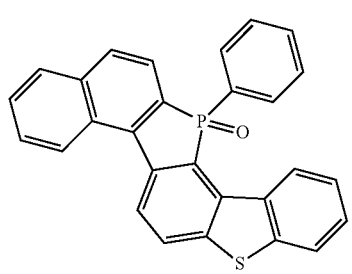
Formula 1-3-186
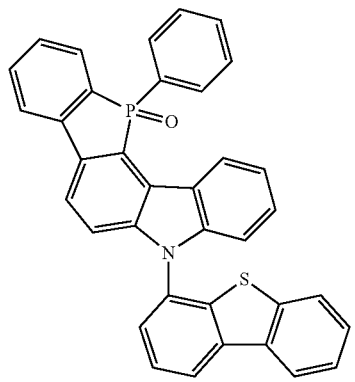
Formula 1-3-187
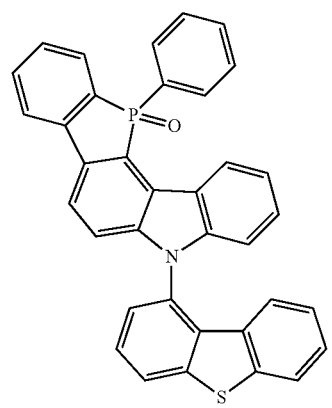
Formula 1-3-188
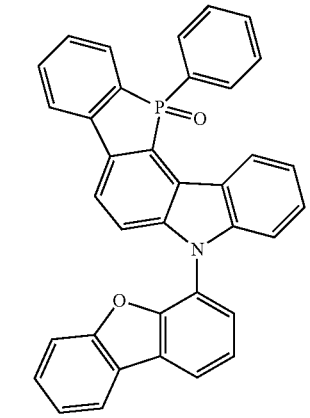
Formula 1-3-189
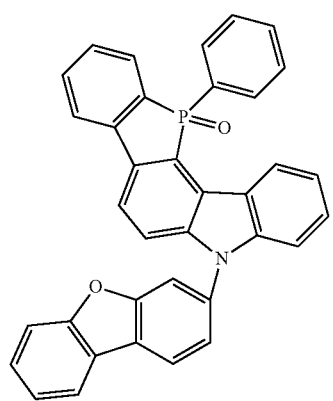

581
-continued
Formula 1-3-190
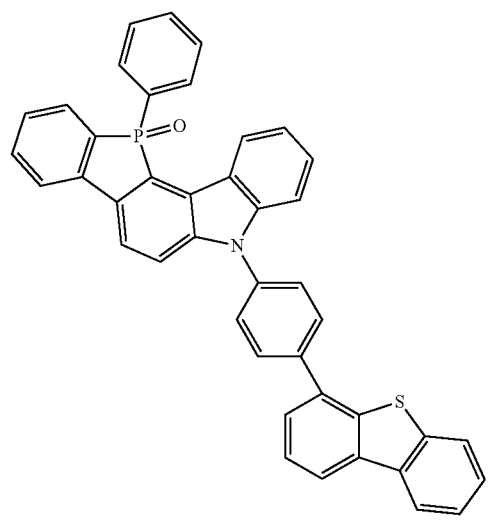
Formula 1-3-191
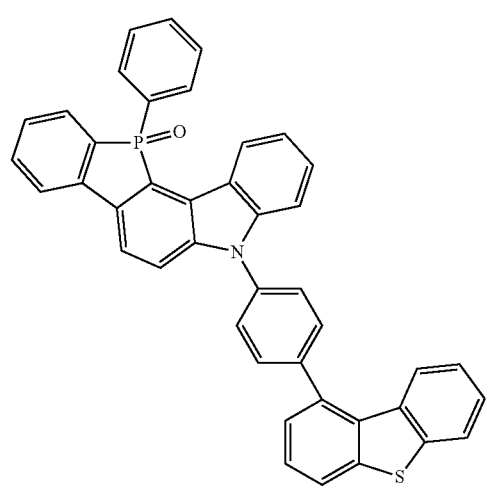
Formula 1-3-192
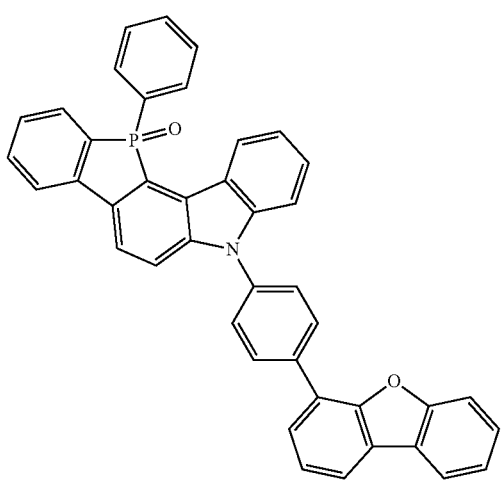
582
-continued
Formula 1-3-193
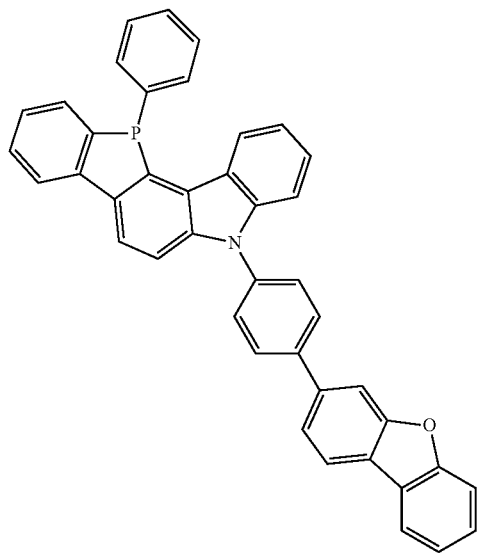
Formula 1-3-194
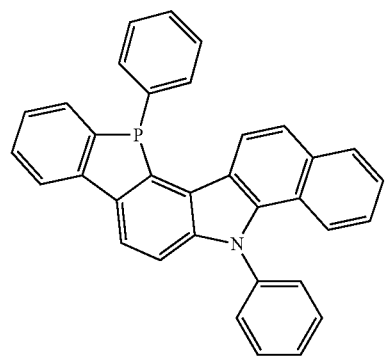
Formula 1-3-195
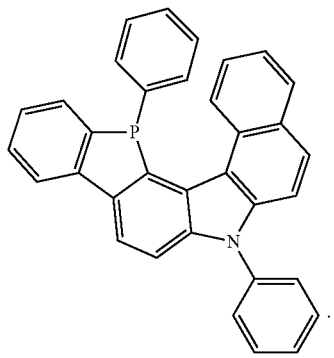
8. The compound of claim 1, wherein the compound represented by Formula 1-4 is represented by any one of the following Formulae 1-4-1 to 1-4-195:

Formula 1-4-1
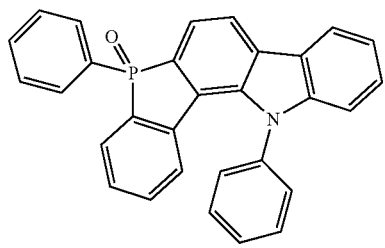
Formula 1-4-2
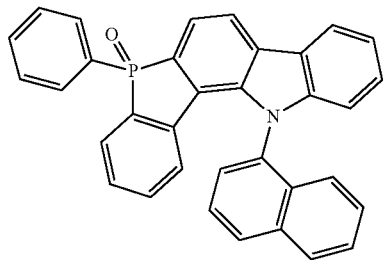
Formula 1-4-3
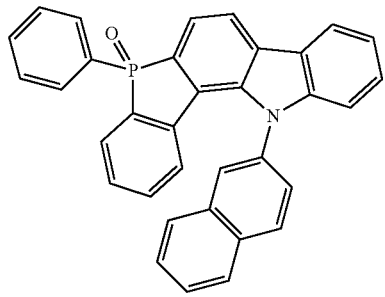
Formula 1-4-4
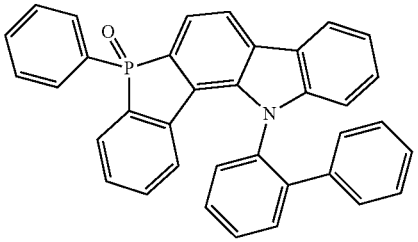
Formula 1-4-5
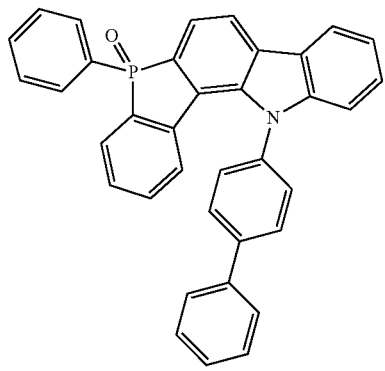
-continued
Formula 1-4-6
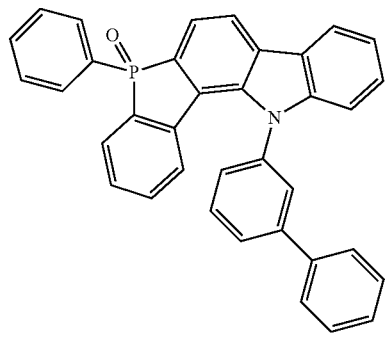
Formula 1-4-7
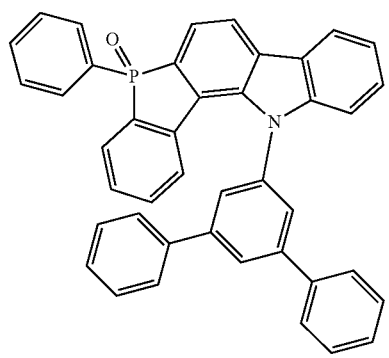
Formula 1-4-8
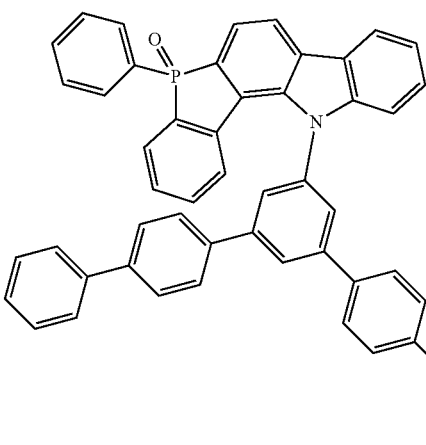
Formula 1-4-9
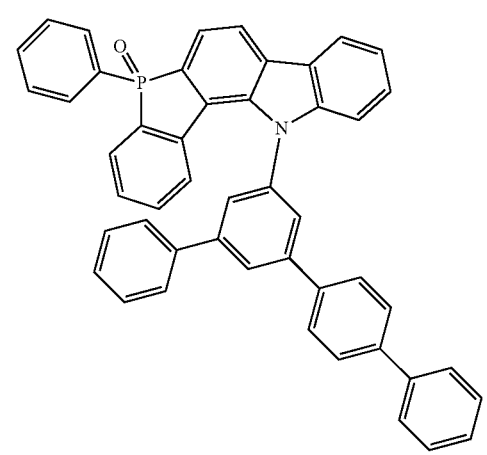

Formula 1-4-10
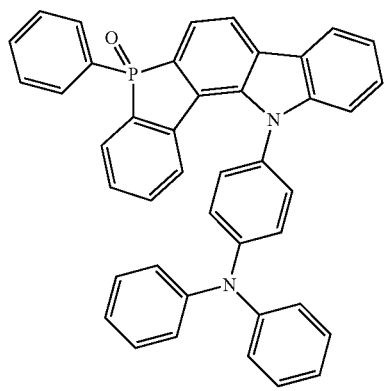
Formula 1-4-11
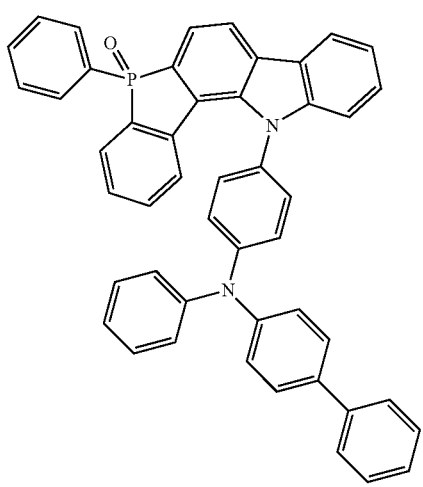
Formula 1-4-12
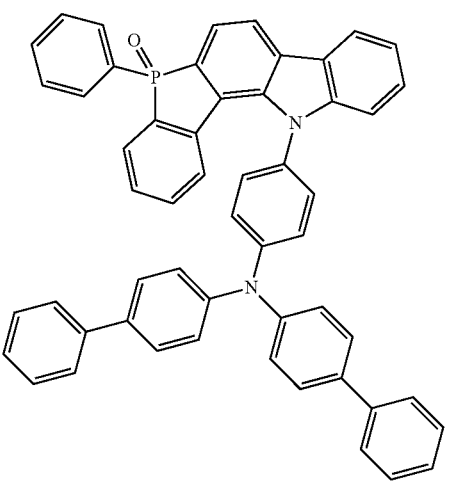
Formula 1-4-13
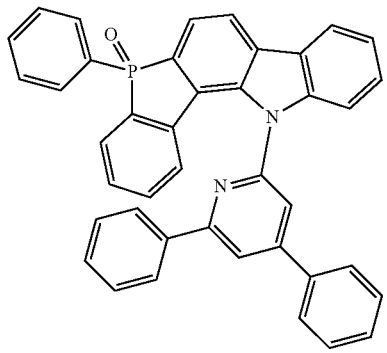
Formula 1-4-14
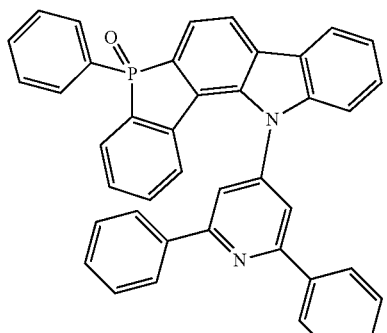
Formula 1-4-15
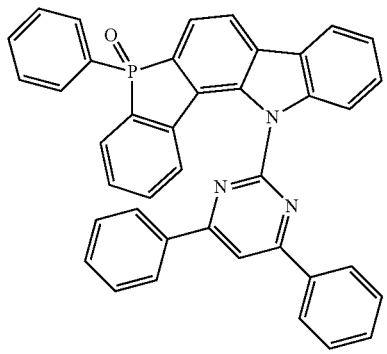
Formula 1-4-16
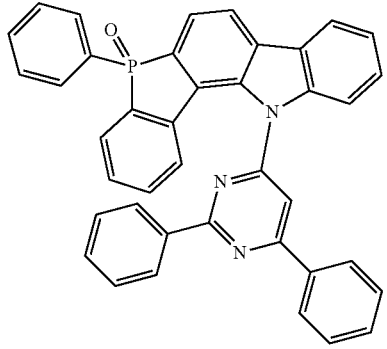

Formula 1-4-17
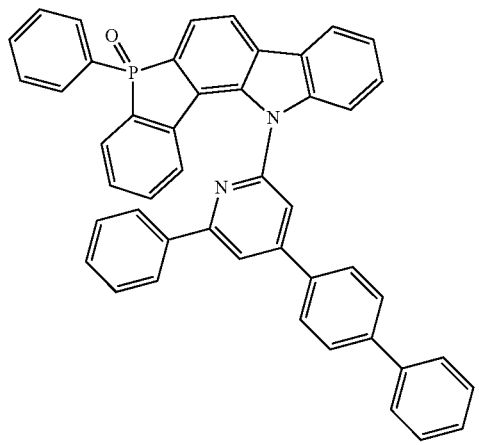
Formula 1-4-18
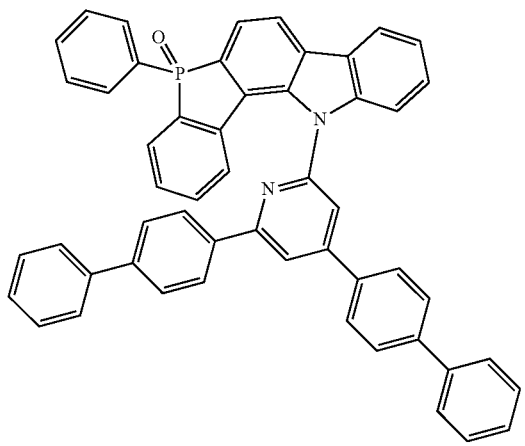
Formula 1-4-19
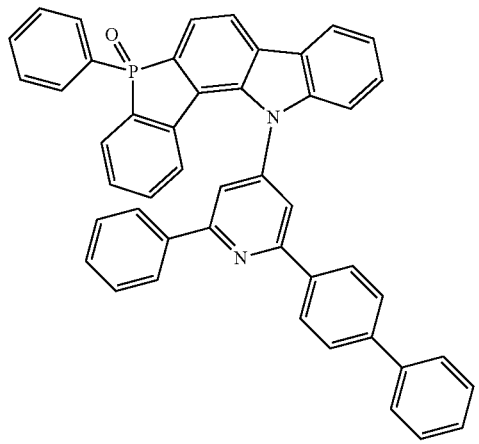
Formula 1-4-20
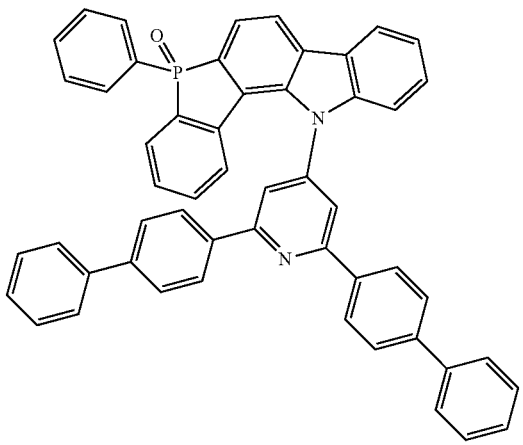
Formula 1-4-21
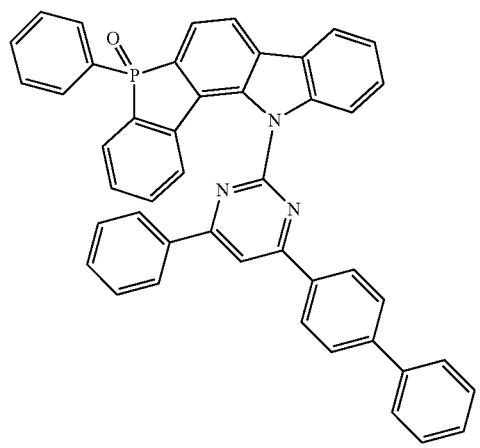
Formula 1-4-22
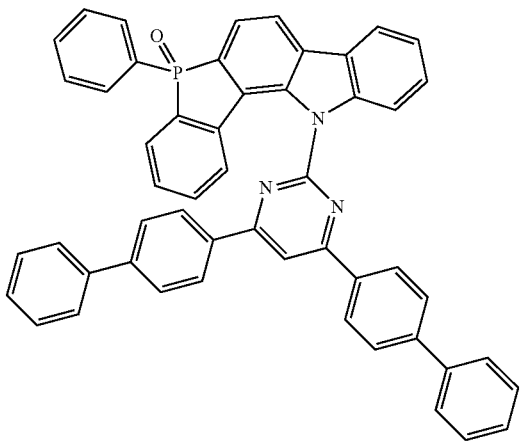

-continued
Formula 1-4-23
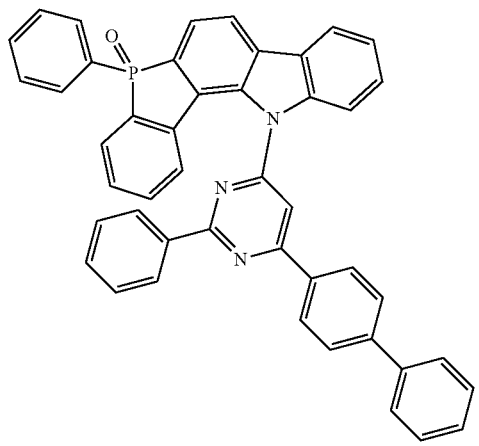
Formula 1-4-24
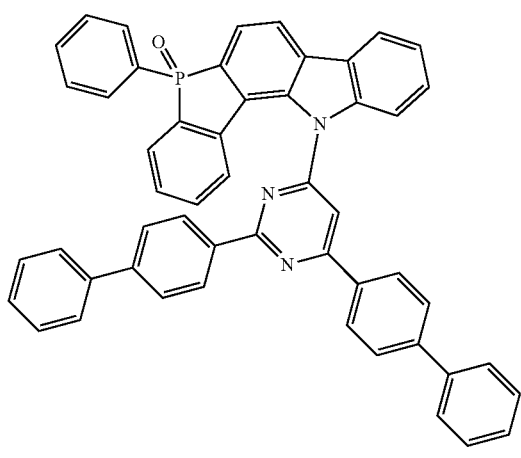
Formula 1-4-25
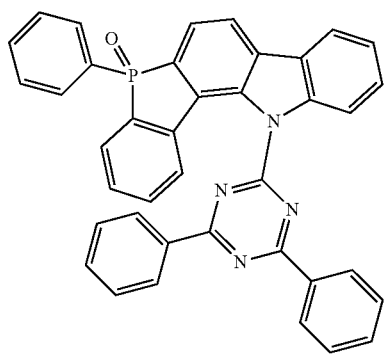
-continued
Formula 1-4-26
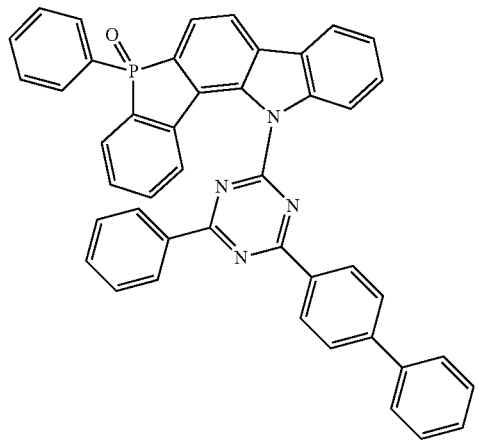
Formula 1-4-27
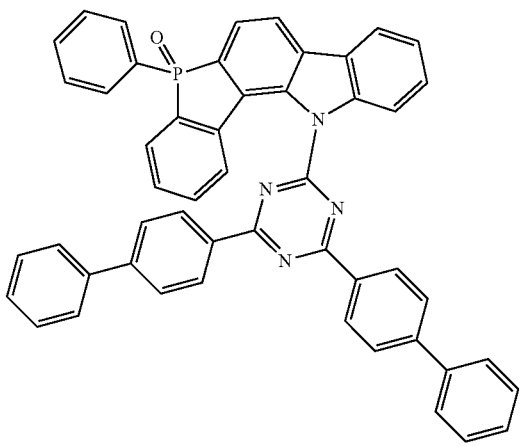
Formula 1-4-28
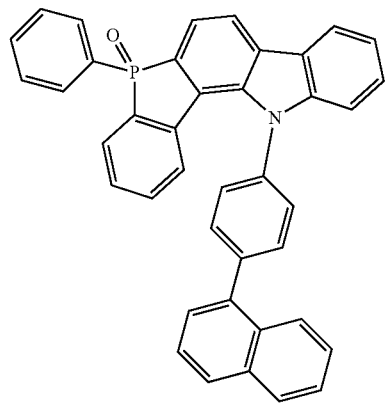

-continued
Formula 1-4-29
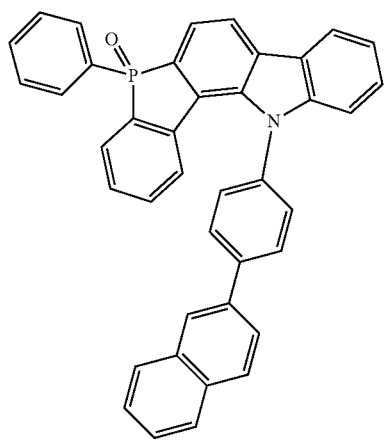
Formula 1-4-30
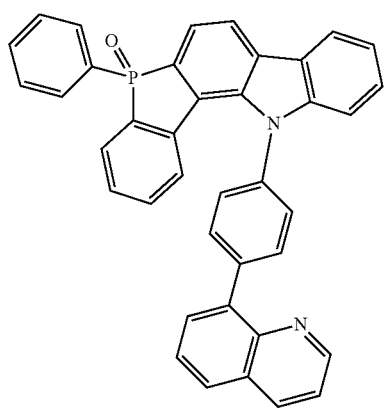
Formula 1-4-31
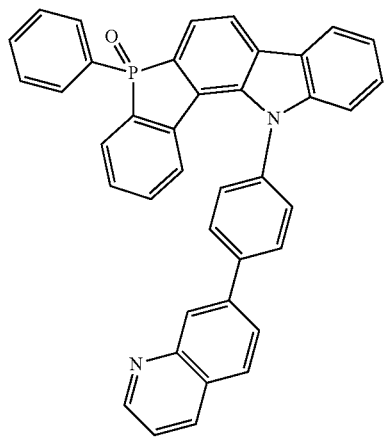
Formula 1-4-32
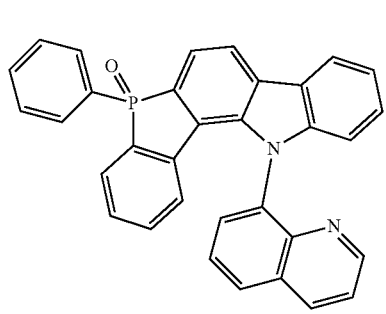
-continued
Formula 1-4-33
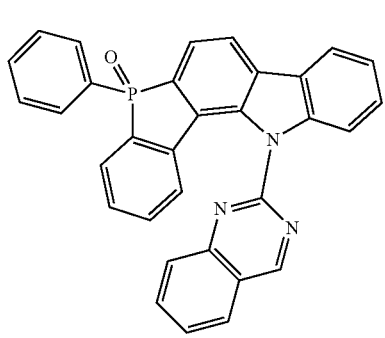
Formula 1-4-34
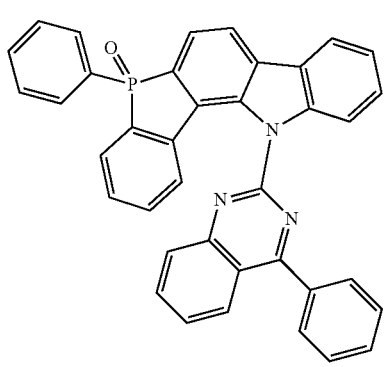
Formula 1-4-35
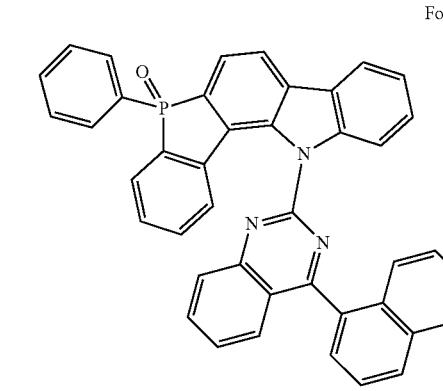
Formula 1-4-36
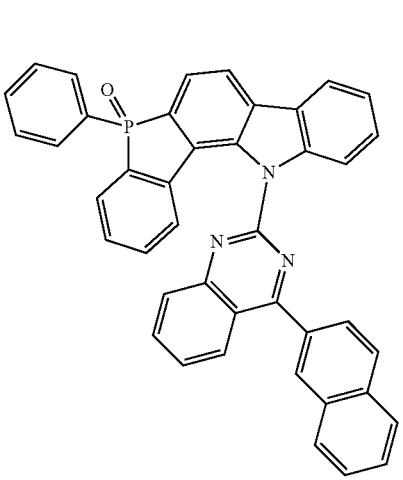

-continued
Formula 1-4-37
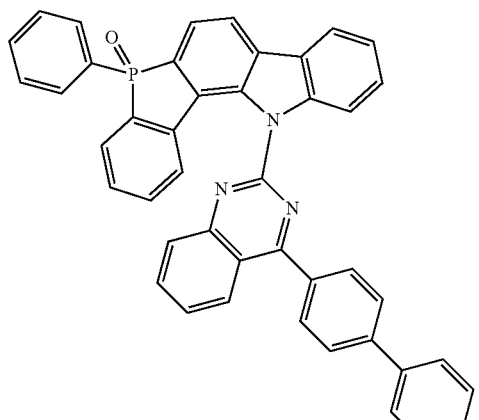
Formula 1-4-38
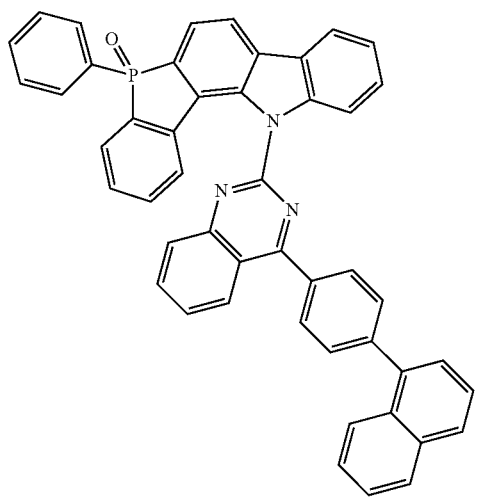
Formula 1-4-39
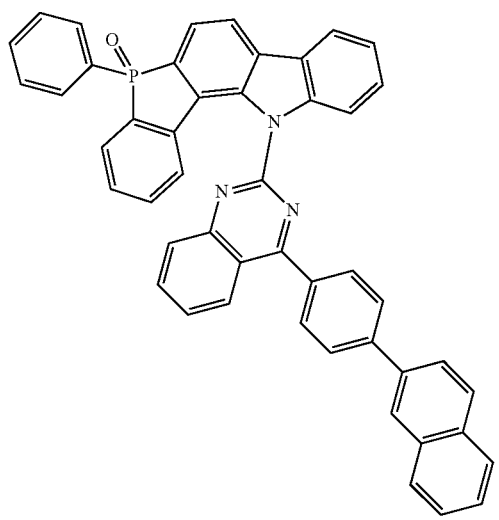
-continued
Formula 1-4-40
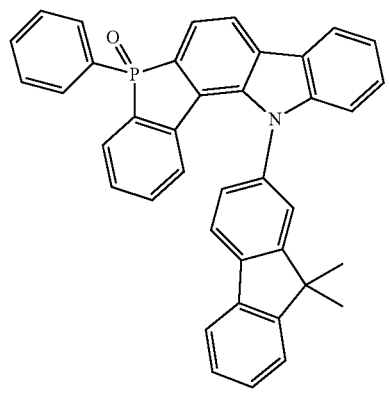
Formula 1-4-41
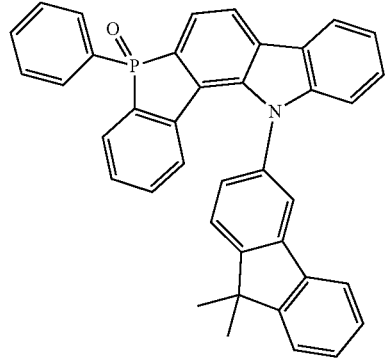
Formula 1-4-42
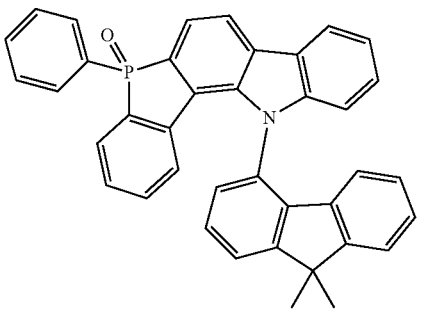
Formula 1-4-43
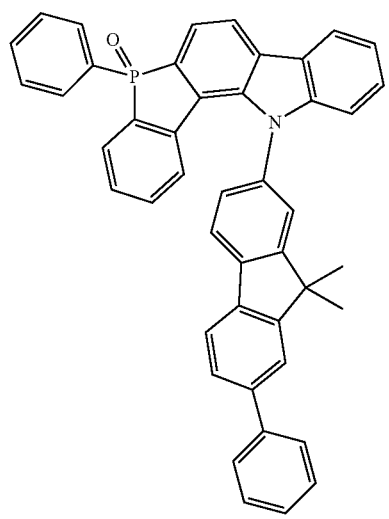

-continued
Formula 1-4-44
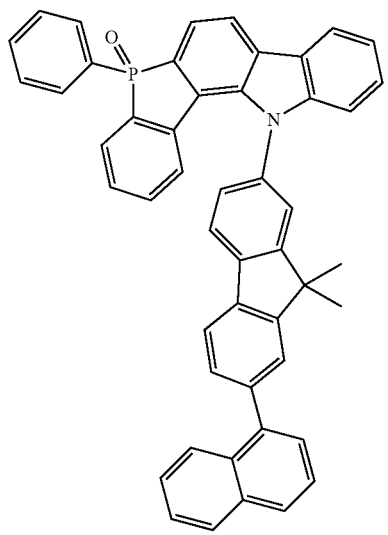
Formula 1-4-45
Formula 1-4-46
-continued
Formula 1-4-47
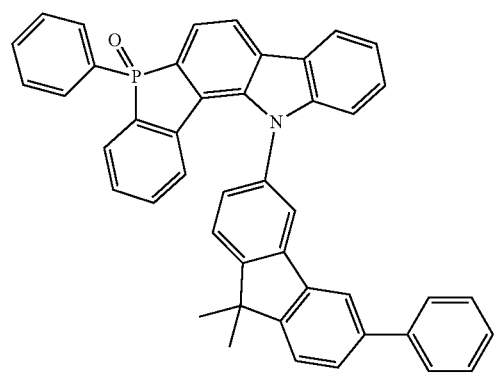
Formula 1-4-48
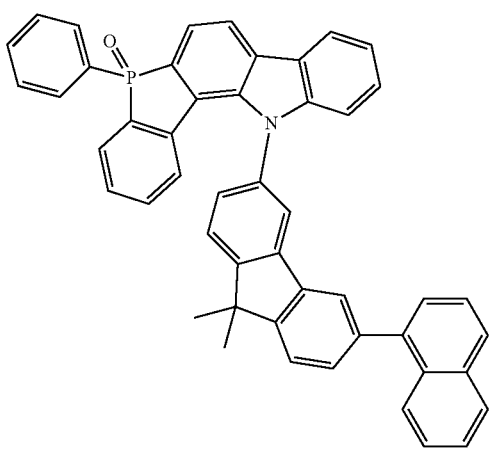
Formula 1-4-49
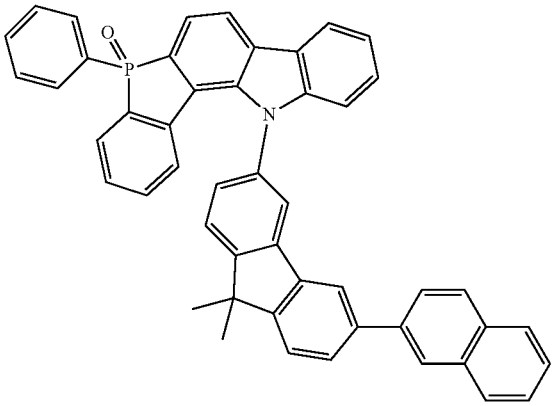

Formula 1-4-50
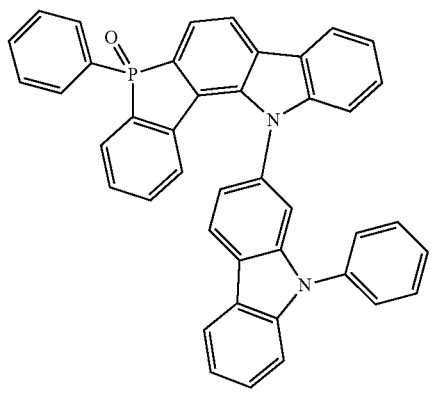
Formula 1-4-51
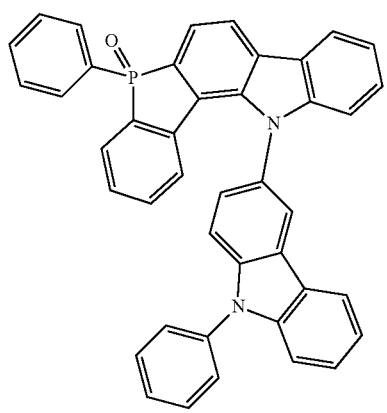
Formula 1-4-52
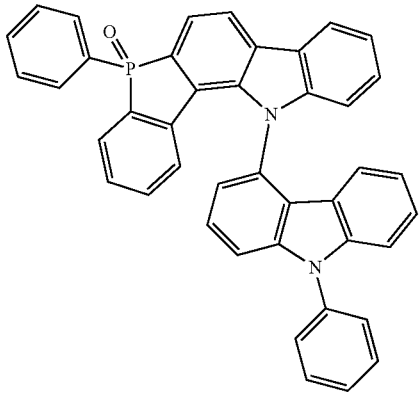
Formula 1-4-53
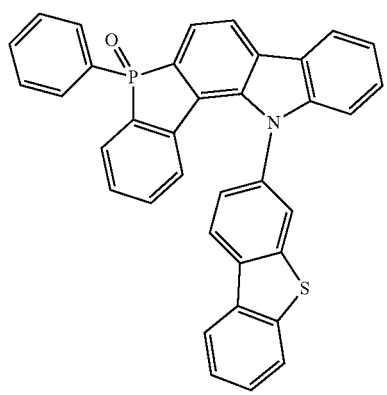
Formula 1-4-54
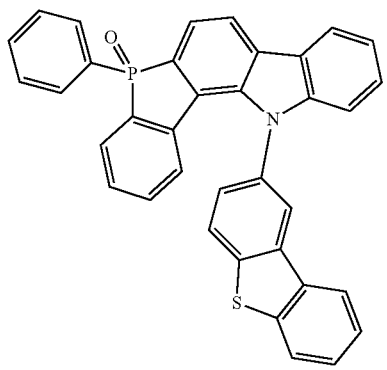
Formula 1-4-55
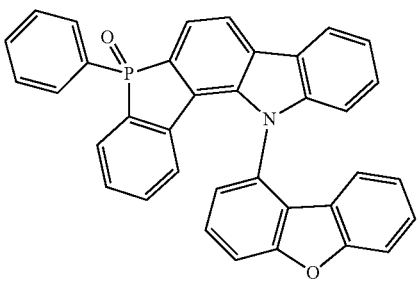
Formula 1-4-56
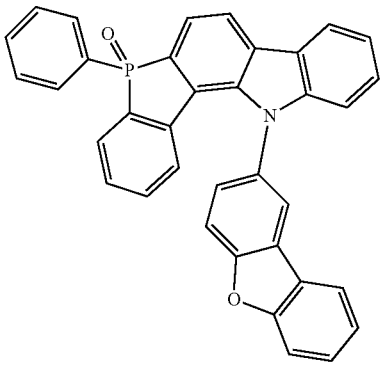
Formula 1-4-57
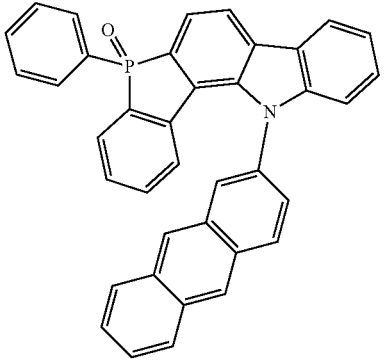

Formula 1-4-58
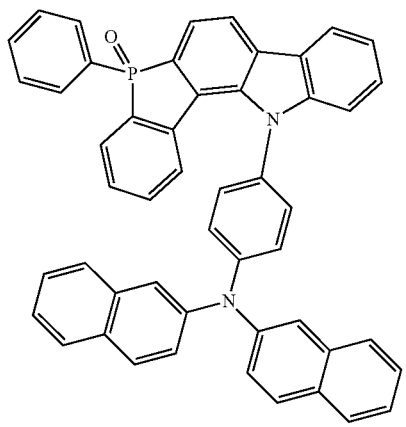
Formula 1-4-59
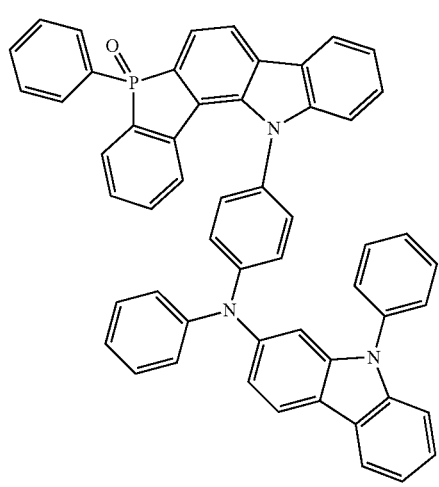
Formula 1-4-60
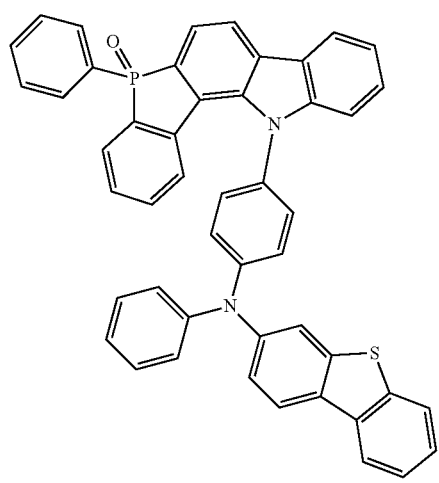
Formula 1-4-61
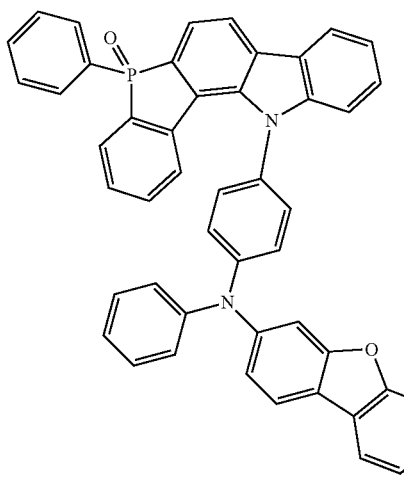
Formula 1-4-62
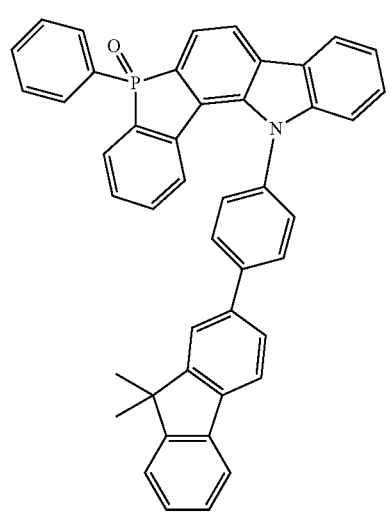
Formula 1-4-63
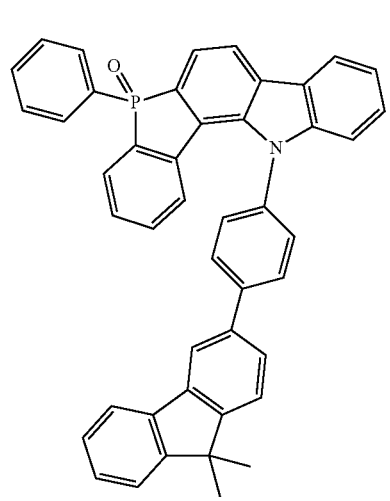

Formula 1-4-64
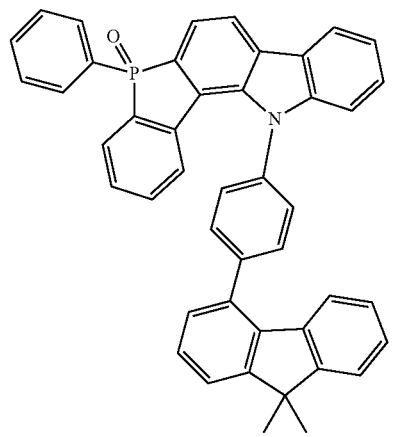
Formula 1-4-65
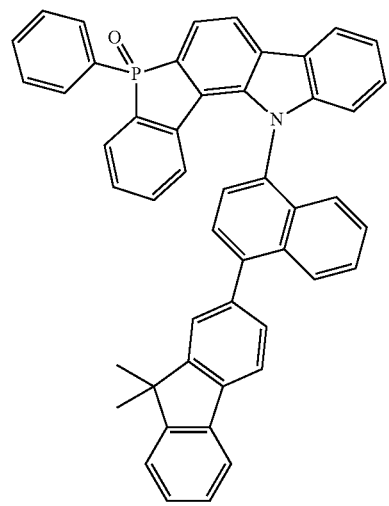
Formula 1-4-66
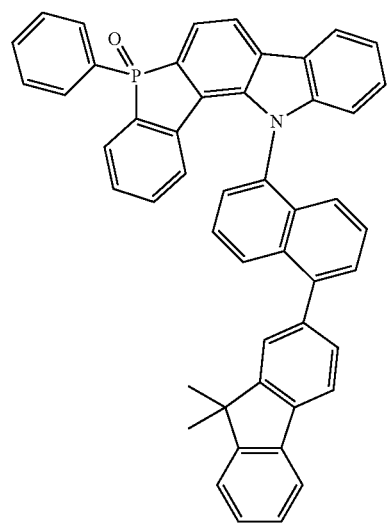
Formula 1-4-67
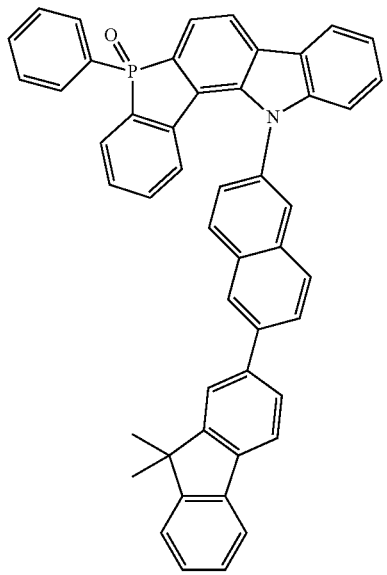
Formula 1-4-68
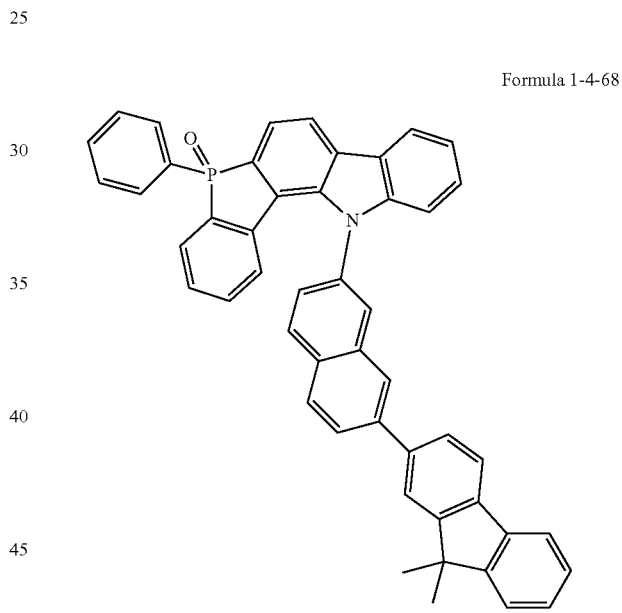
Formula 1-4-69
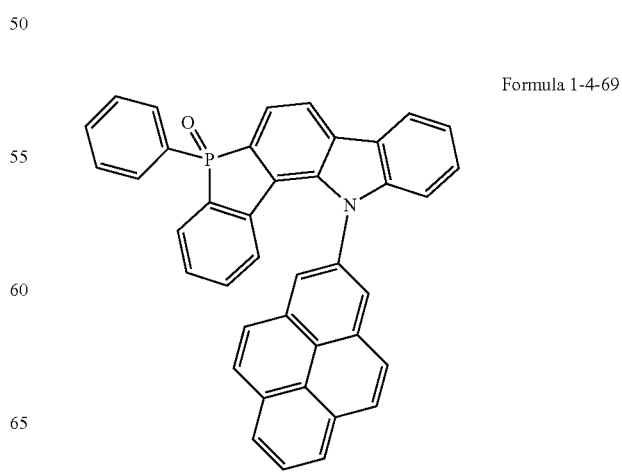

-continued
Formula 1-4-70
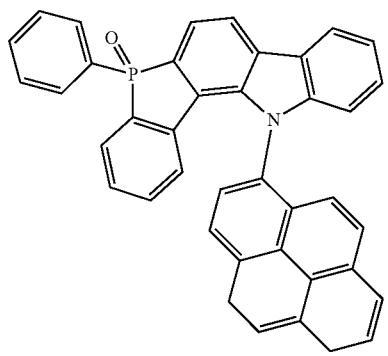
Formula 1-4-71
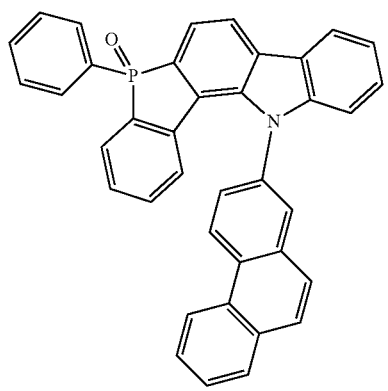
Formula 1-4-72
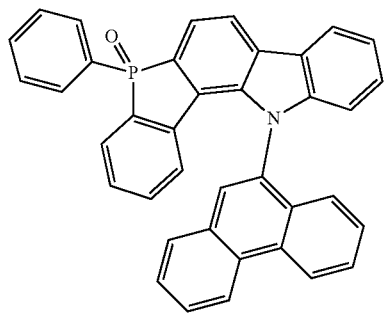
Formula 1-4-73
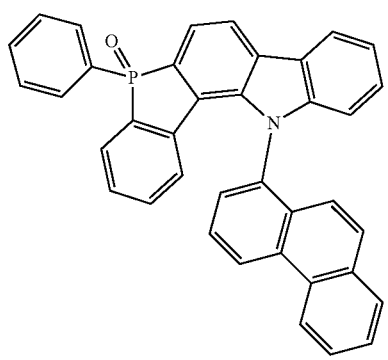
-continued
Formula 1-4-74
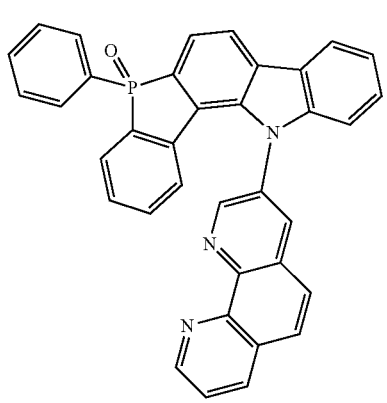
Formula 1-4-75
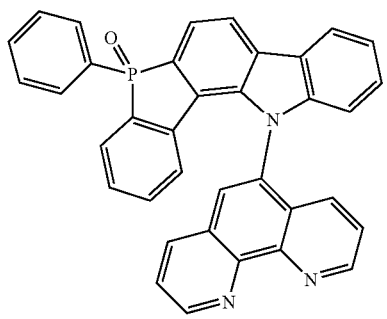
Formula 1-4-76
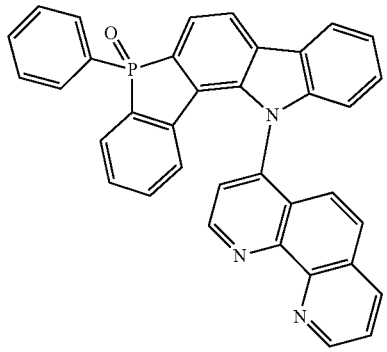
Formula 1-4-77
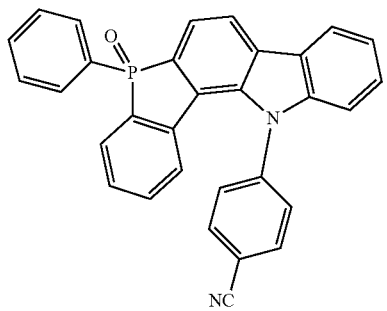

Formula 1-4-78
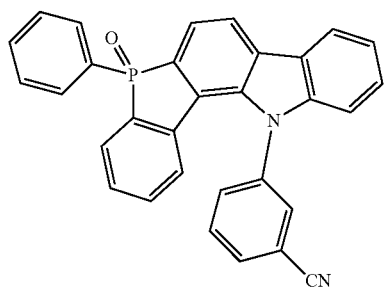
Formula 1-4-79
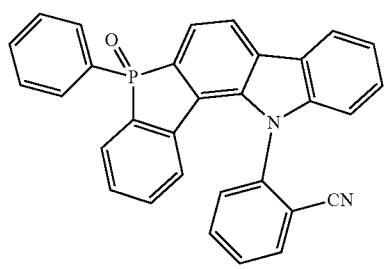
Formula 1-4-80
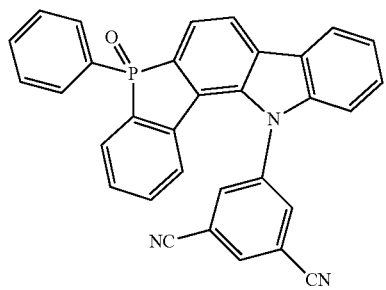
Formula 1-4-81
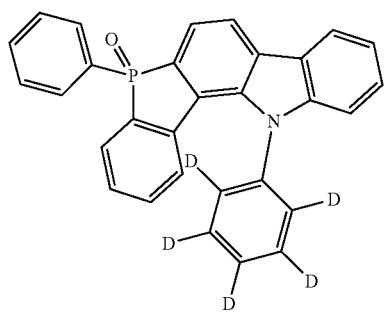
Formula 1-4-82
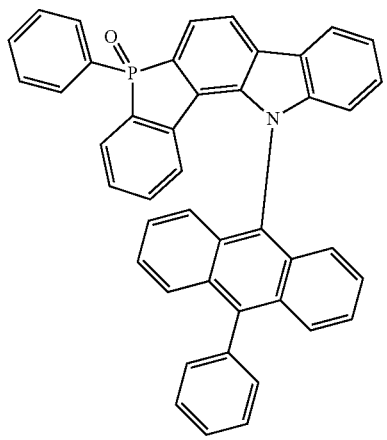
Formula 1-4-83
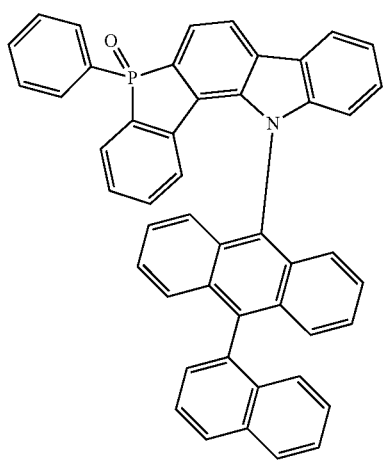
Formula 1-4-84
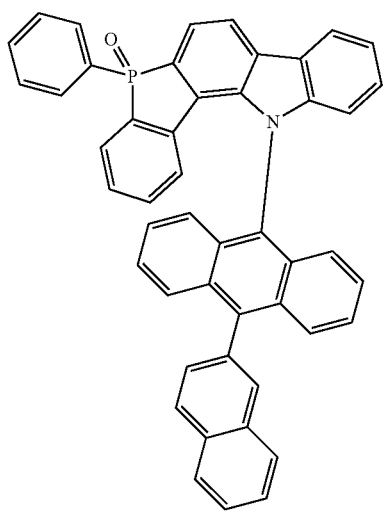

-continued
Formula 1-4-85
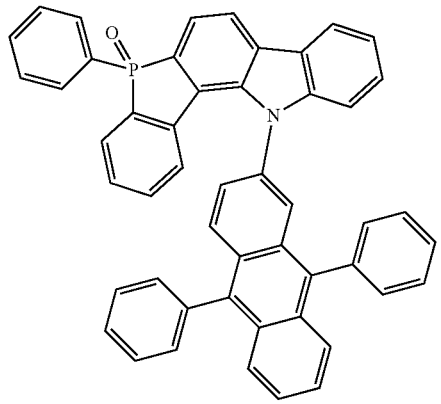
Formula 1-4-86
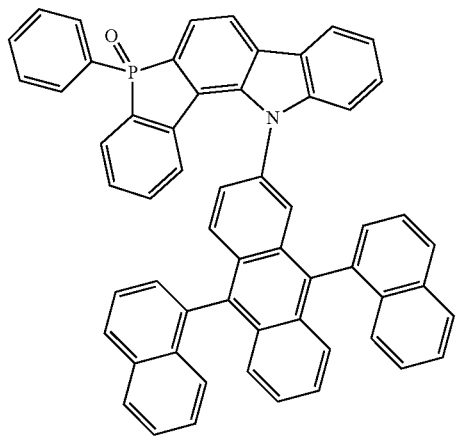
Formula 1-4-87
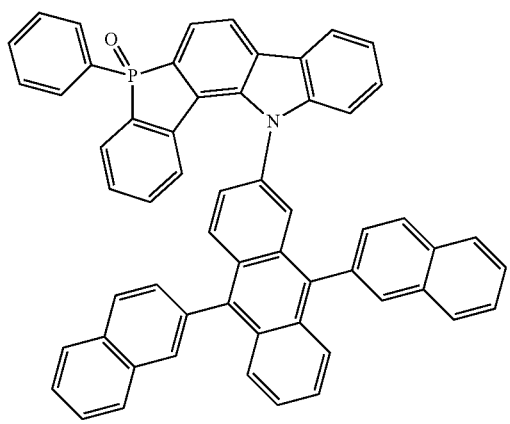
-continued
Formula 1-4-88
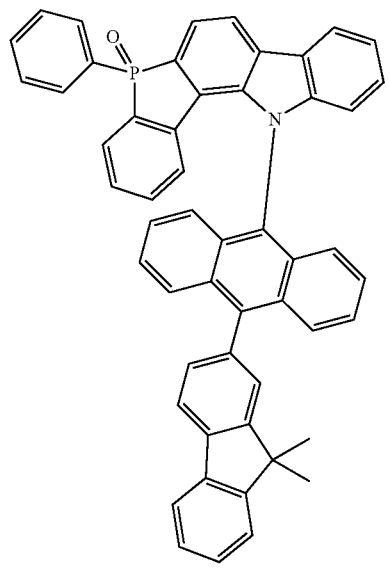
Formula 1-4-89
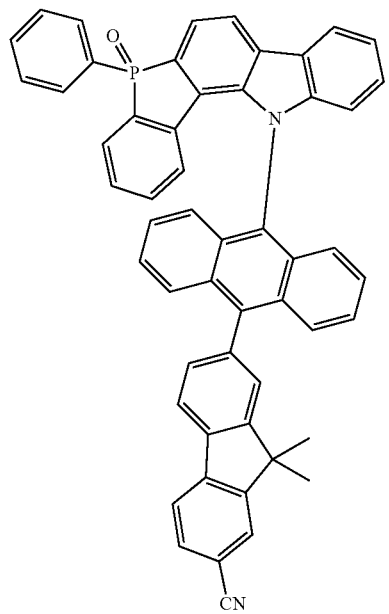

Formula 1-4-90
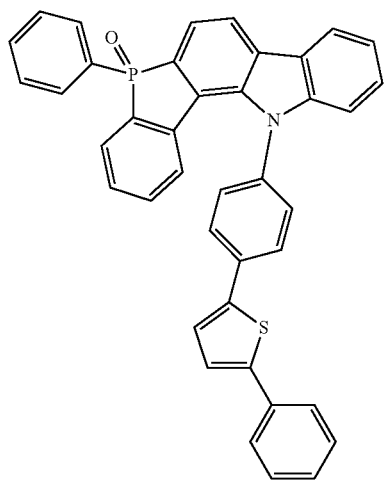
Formula 1-4-93
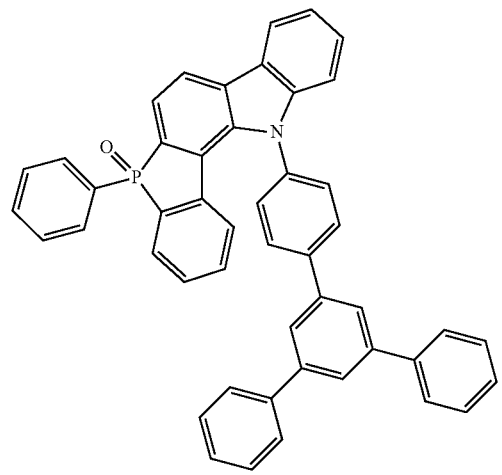
Formula 1-4-91
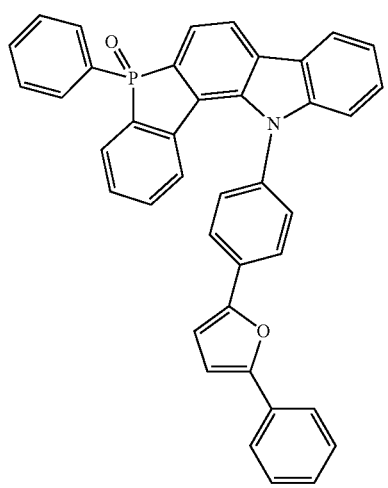
Formula 1-4-94
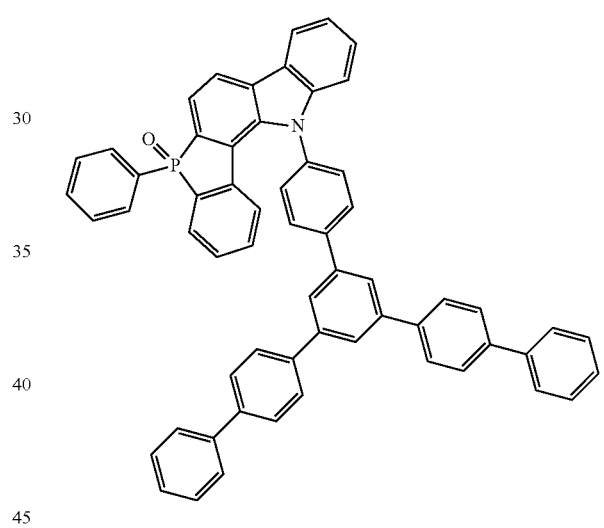
Formula 1-4-92
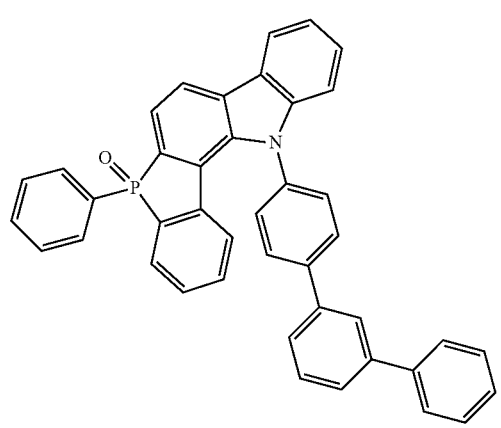
Formula 1-4-95
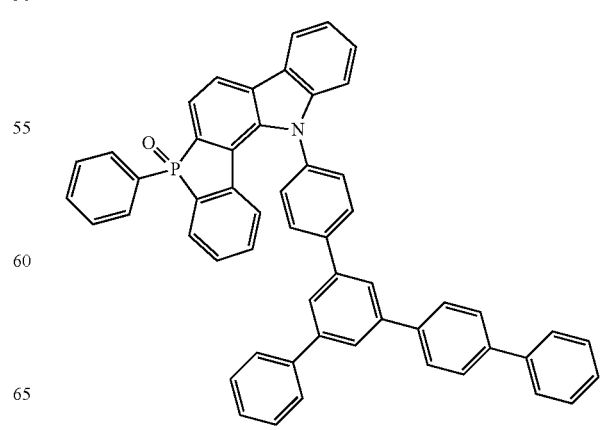

Formula 1-4-96
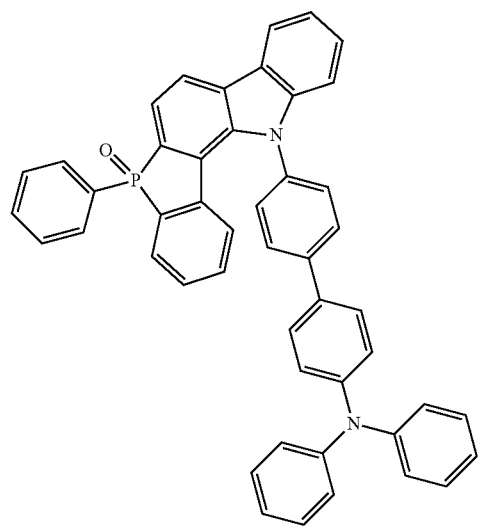
Formula 1-4-97
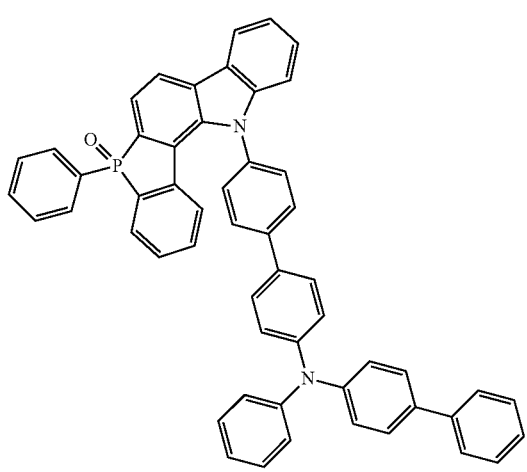
Formula 1-4-98
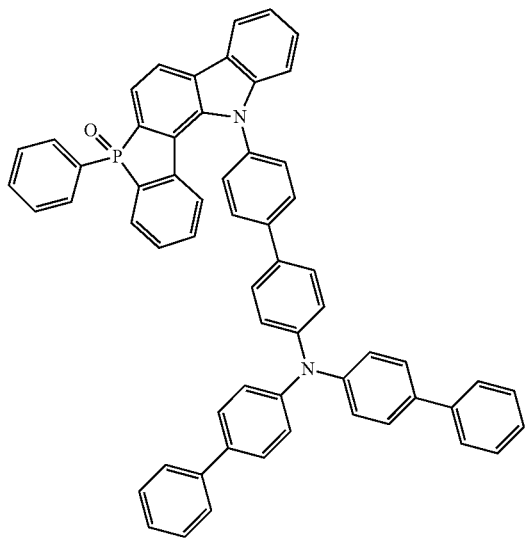
Formula 1-4-99
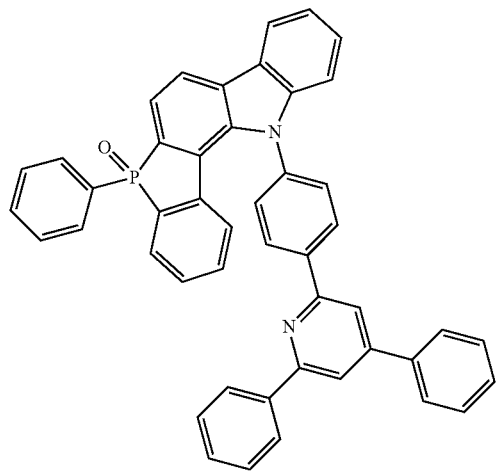
Formula 1-4-100
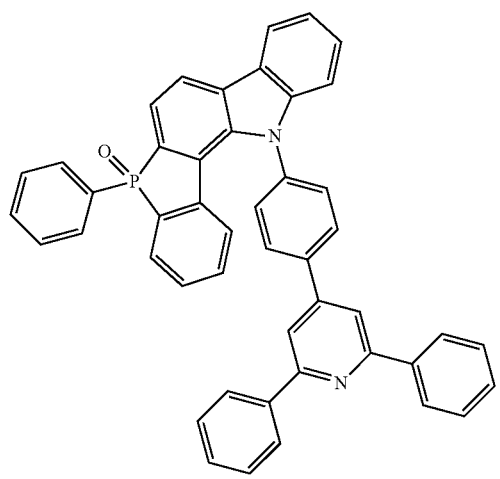
Formula 1-4-101
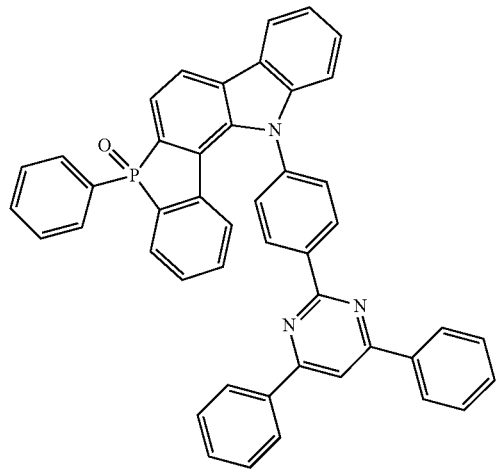

Formula 1-4-102
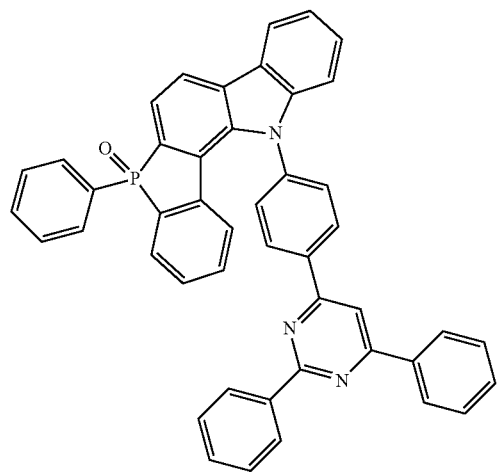
Formula 1-4-105
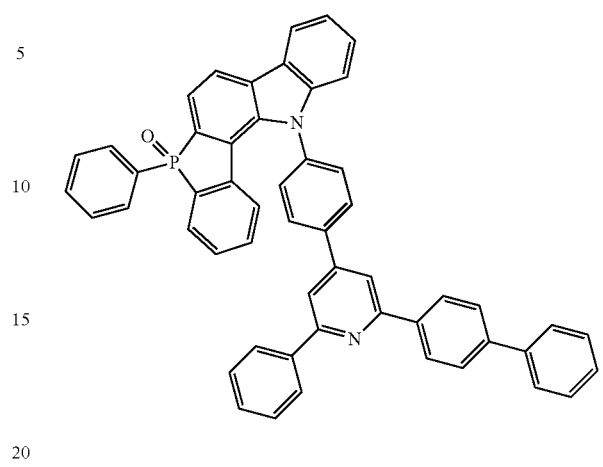
Formula 1-4-103
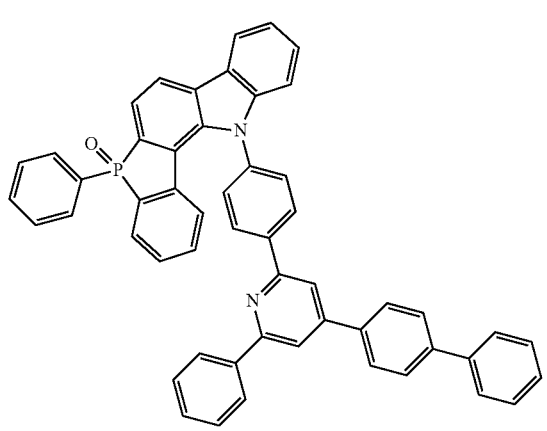
Formula 1-4-106
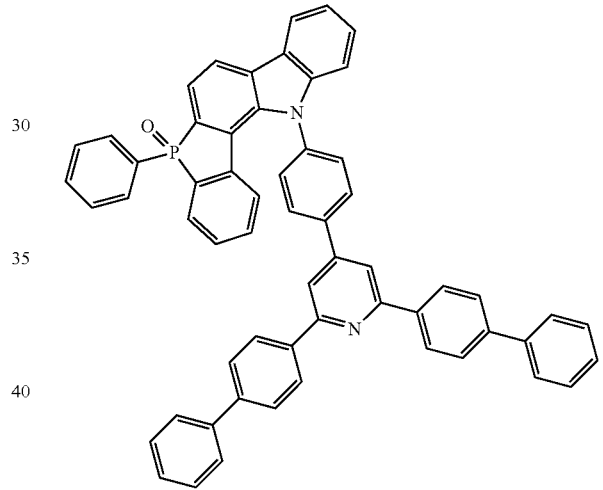
Formula 104-4-104
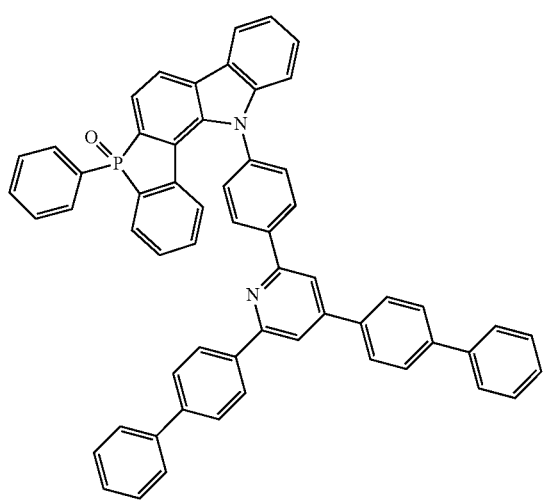
Formula 1-4-107
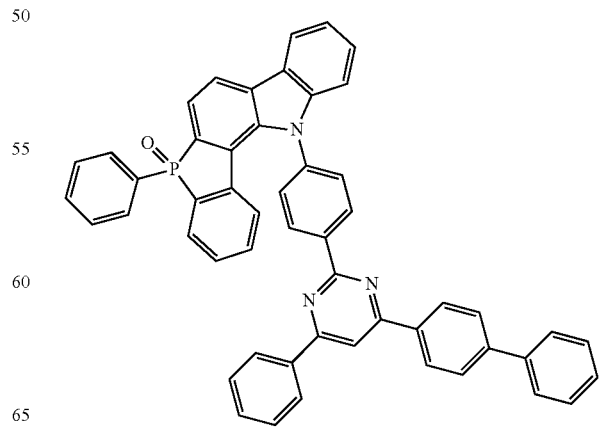

Formula 1-4-108
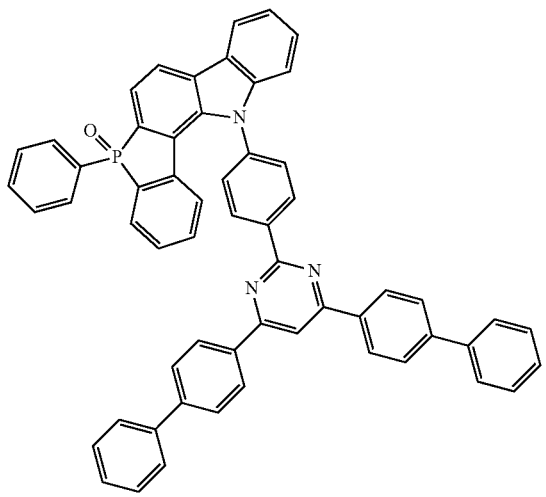
Formula 1-4-111
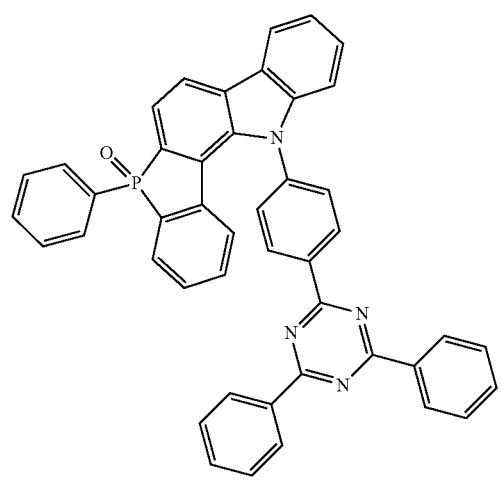
Formula 1-4-109
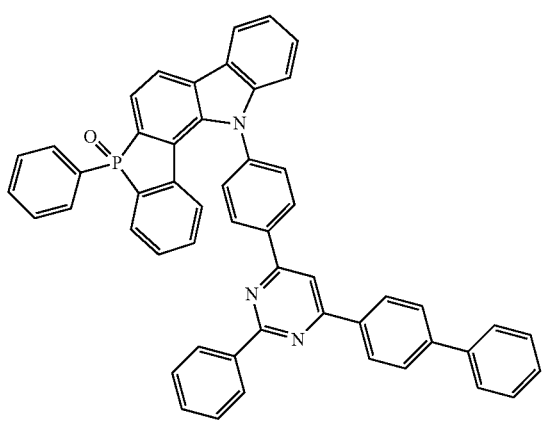
Formula 1-4-112
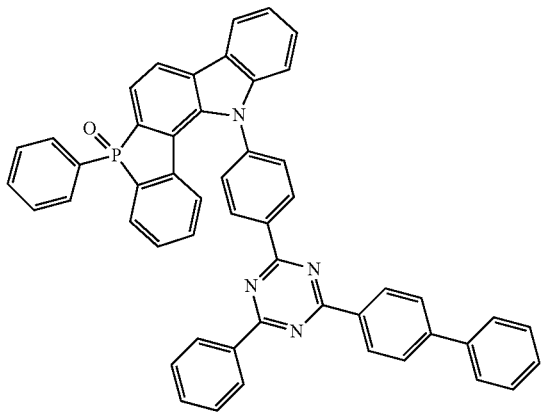
Formula 1-4-110
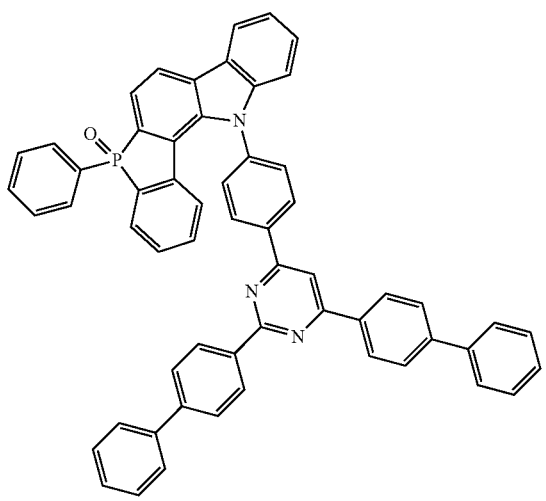
Formula 1-4-113
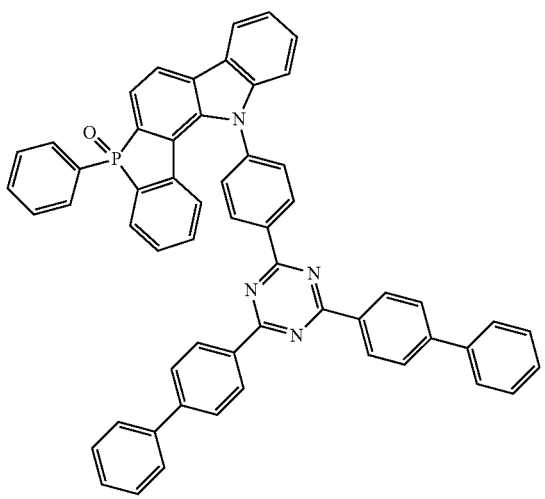

Formula 1-4-114
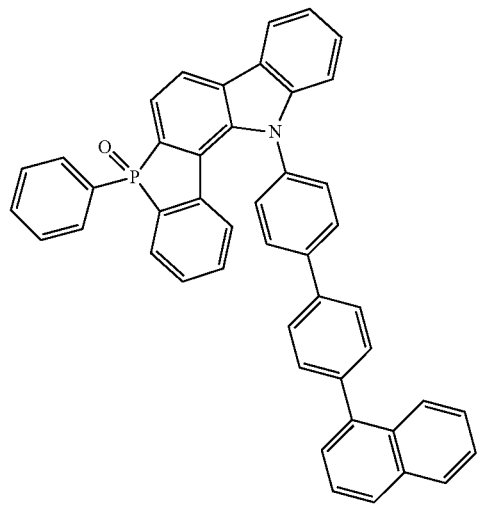
Formula 1-4-115
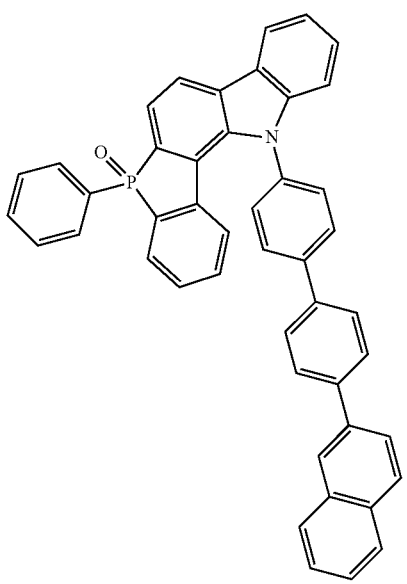
Formula 1-4-116
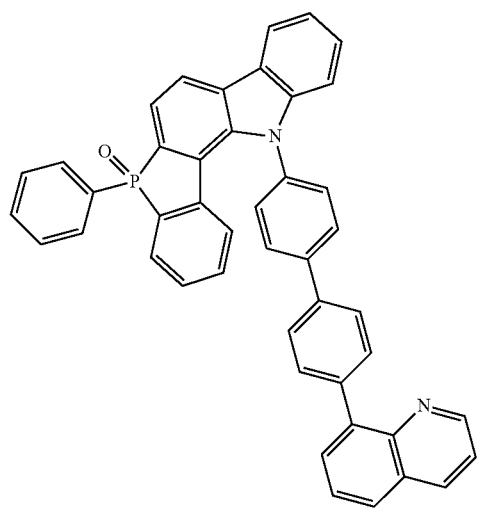
Formula 1-4-117
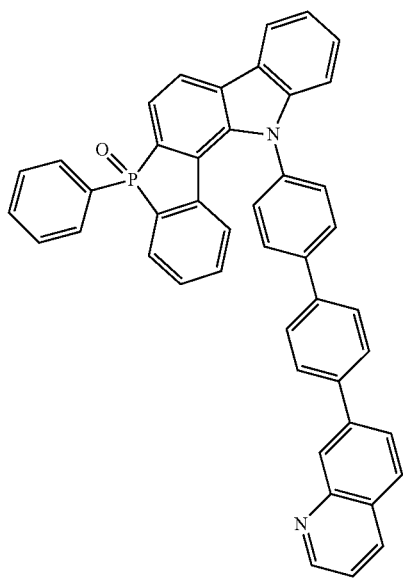
Formula 1-4-118
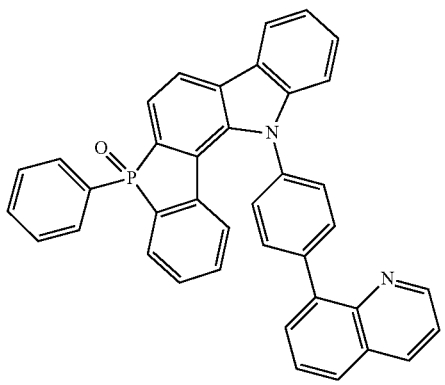
Formula 1-4-119
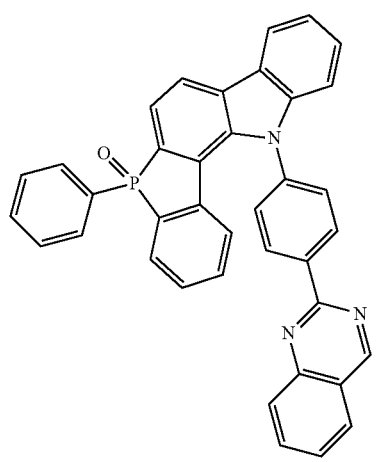

Formula 1-4-120
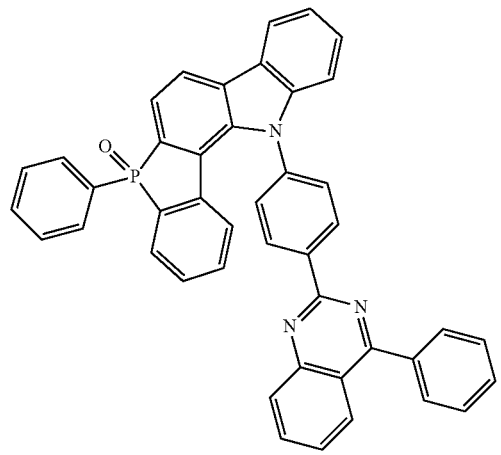
Formula 1-4-123
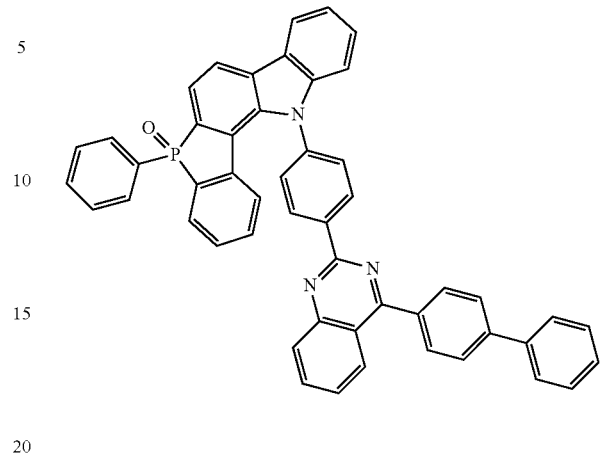
Formula 1-4-121
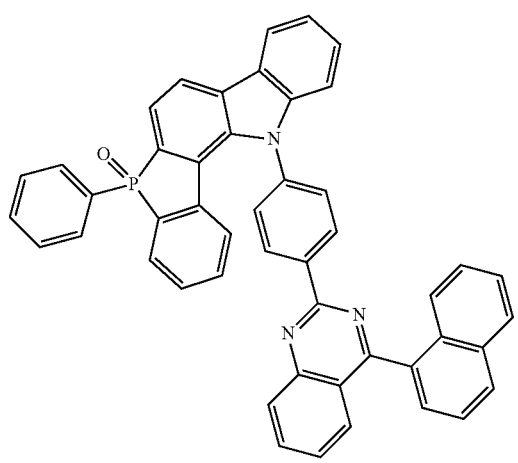
Formula 1-4-124
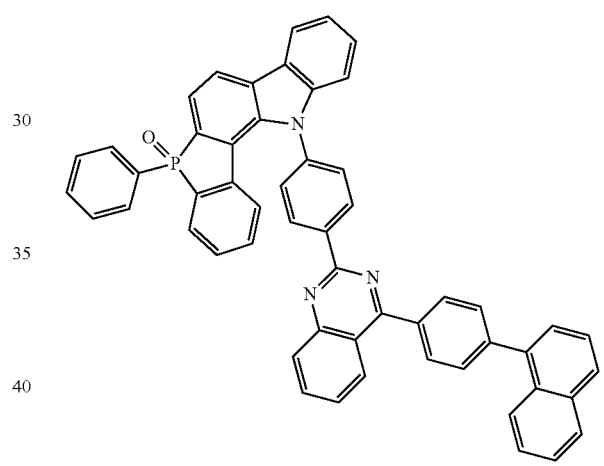
Formula 1-4-122
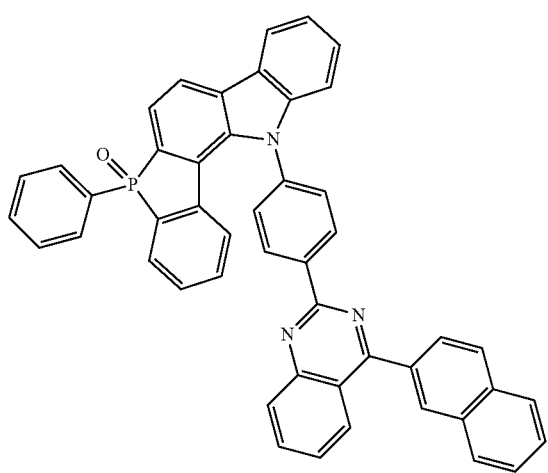
Formula 1-4-125
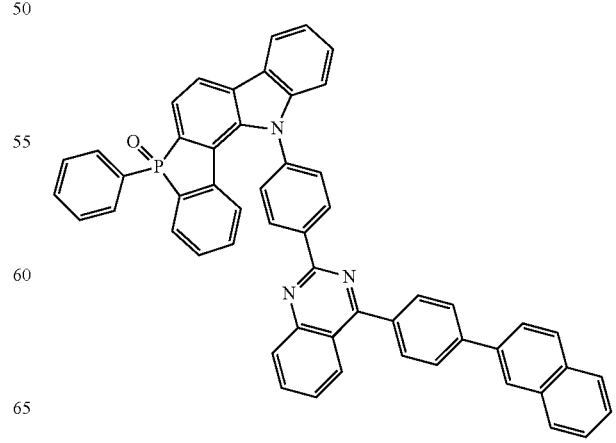

Formula 1-4-126
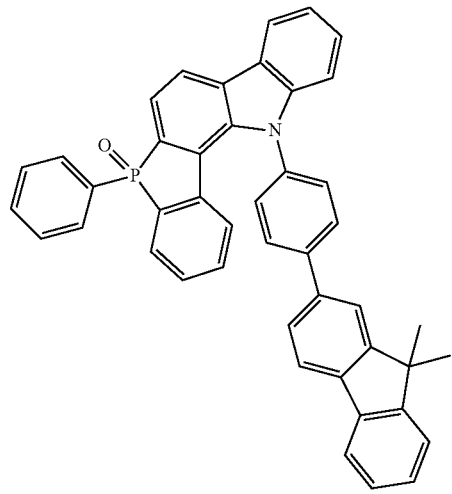
Formula 1-4-127
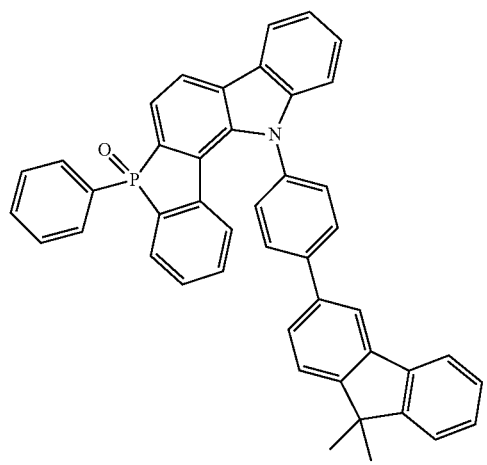
Formula 1-4-128
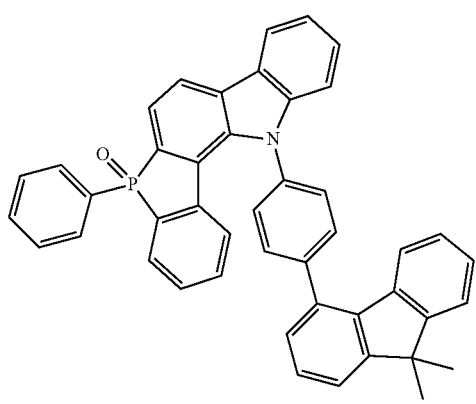
Formula 1-4-129
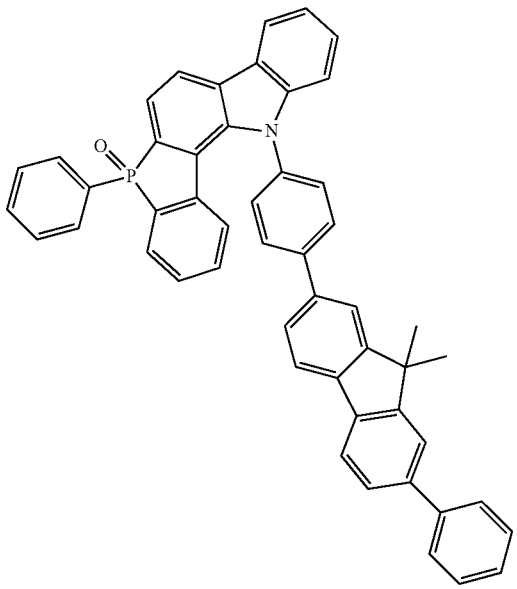
Formula 1-4-130
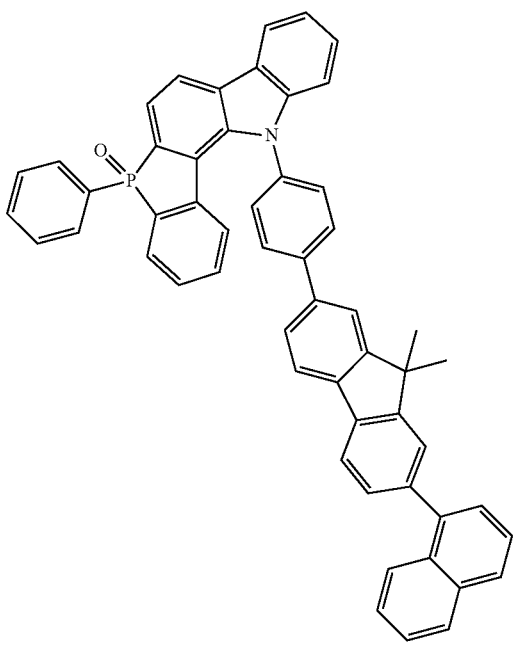

Formula 1-4-131
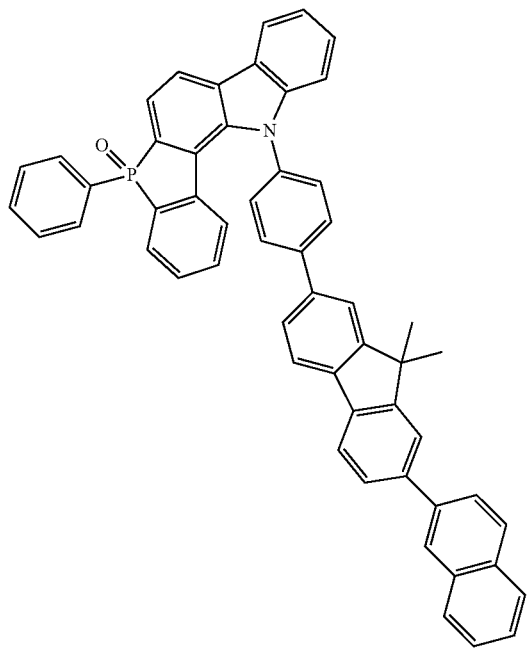
Formula 1-4-132
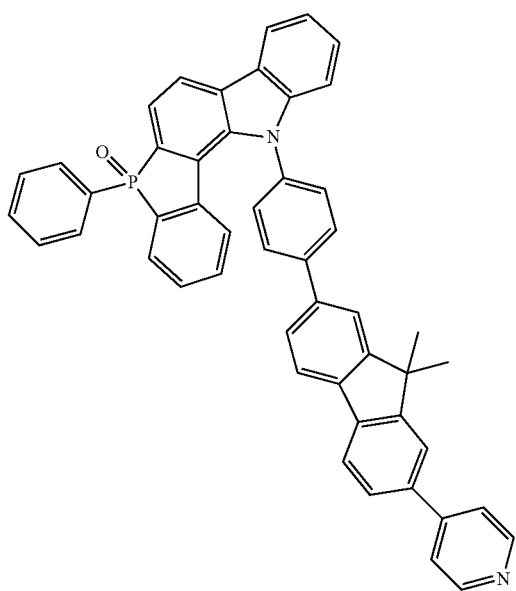
Formula 1-4-133
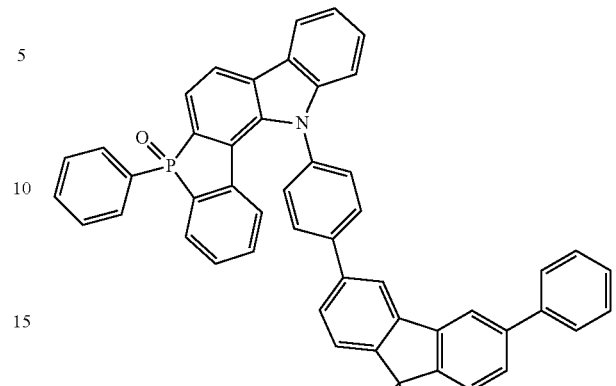
Formula 1-4-134
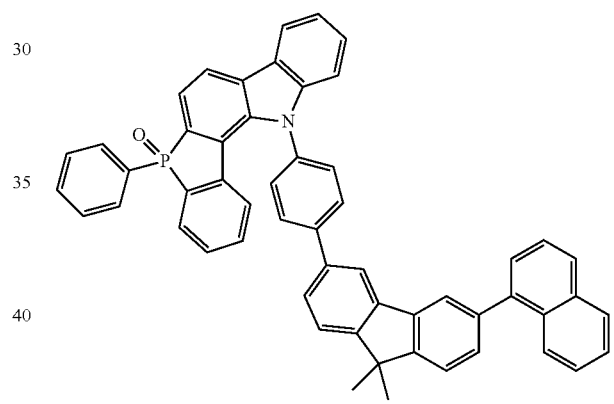
Formula 1-4-135
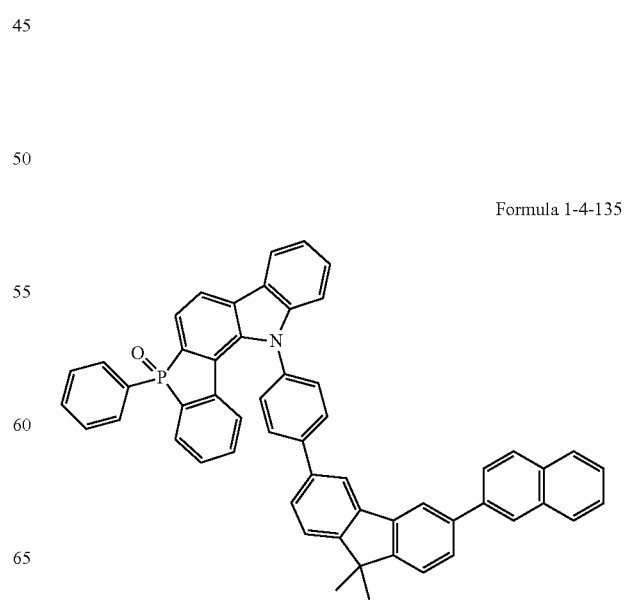

Formula 1-4-136
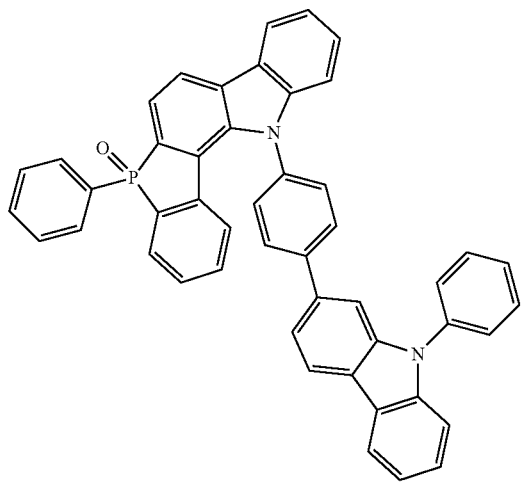
Formula 1-4-137
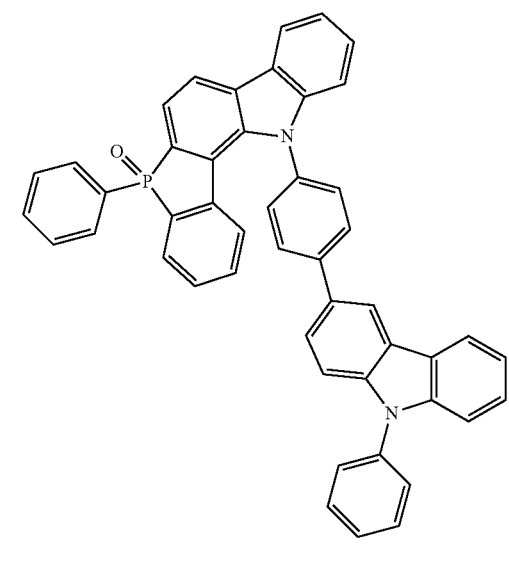
Formula 1-4-138
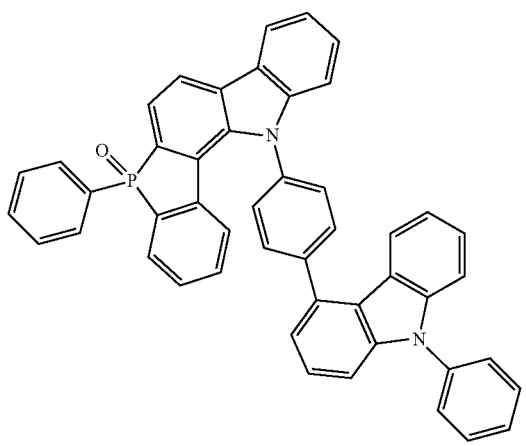
Formula 1-4-139
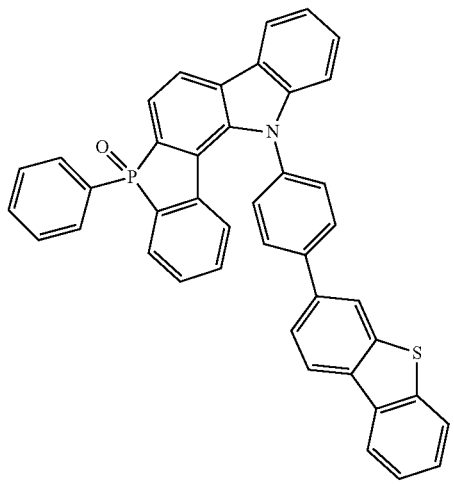
Formula 1-4-140
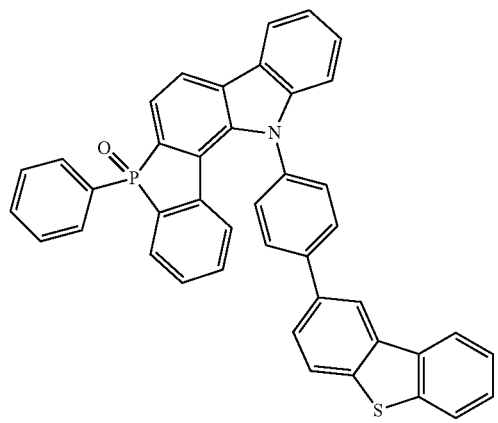
Formula 1-4-141
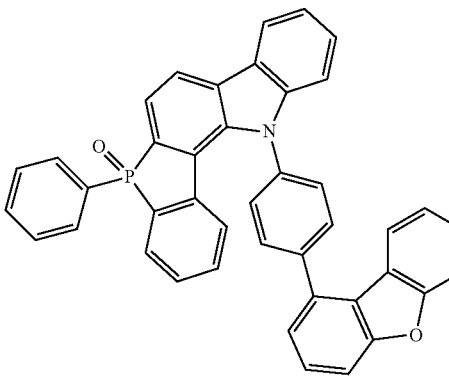

Formula 1-4-142
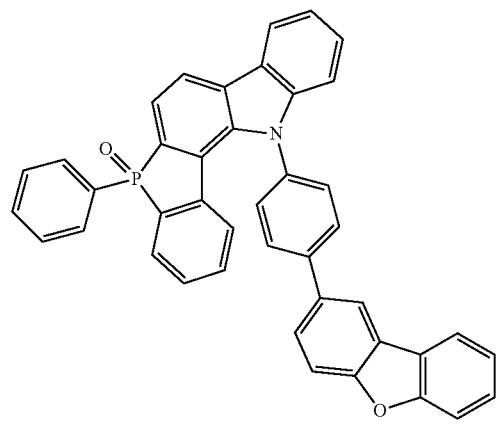
Formula 1-4-143
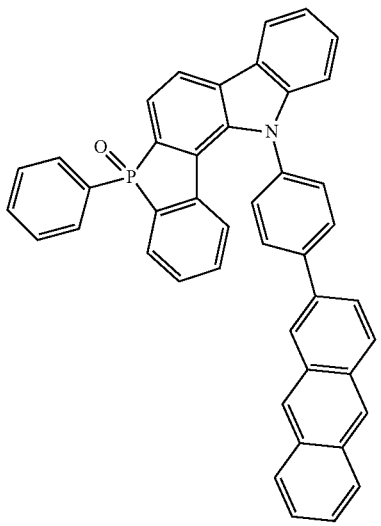
Formula 1-4-144
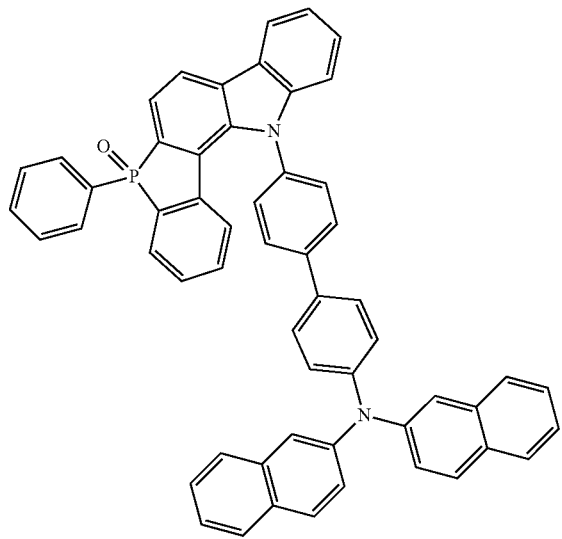
Formula 1-4-145
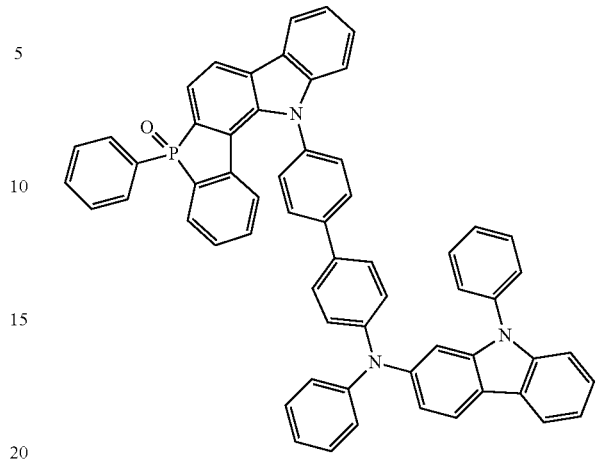
Formula 1-4-146
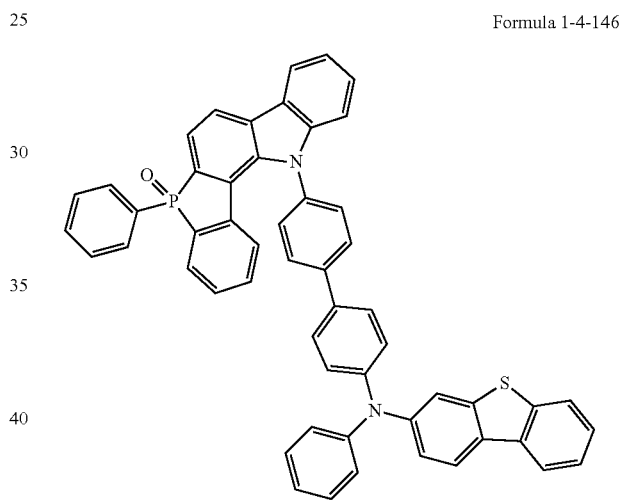
Formula 1-4-147
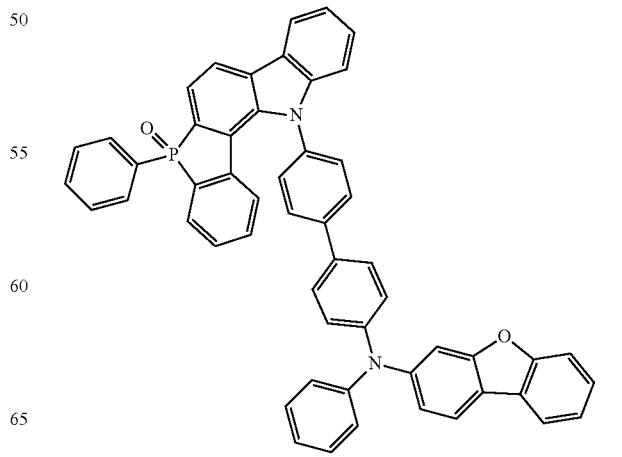

-continued
Formula 1-4-148
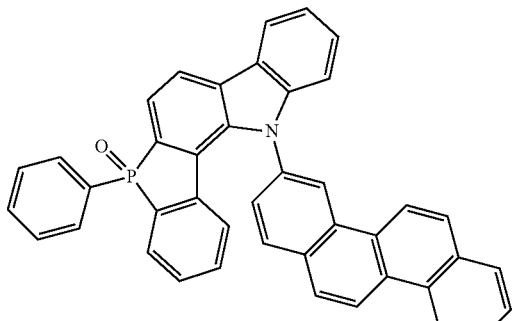
Formula 1-4-149
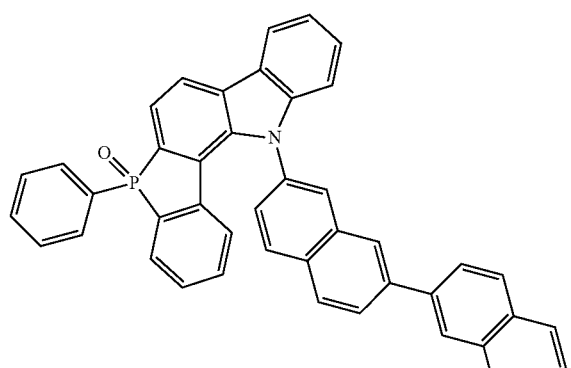
Formula 1-4-150
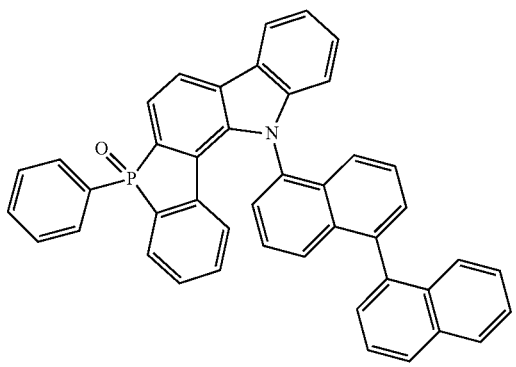
Formula 1-4-151
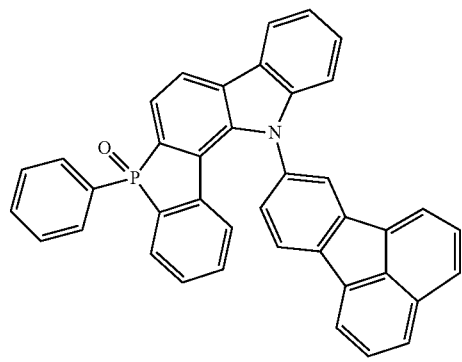
-continued
Formula 1-4-152
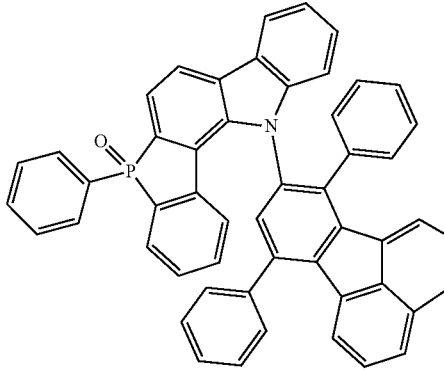
Formula 1-4-153
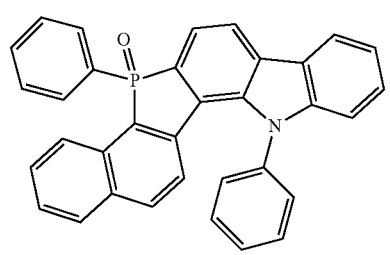
Formula 1-4-154
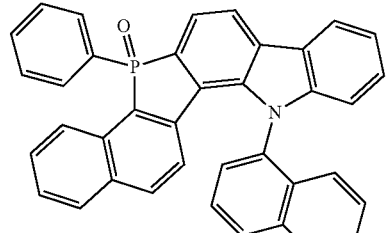
Formula 1-4-155
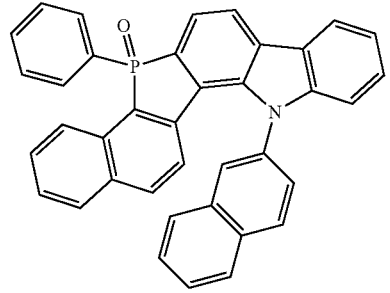
Formula 1-4-156
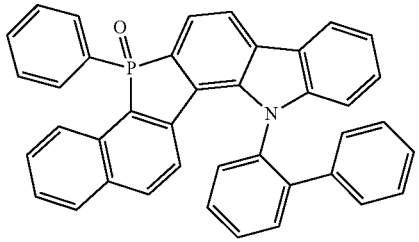

Formula 1-4-157
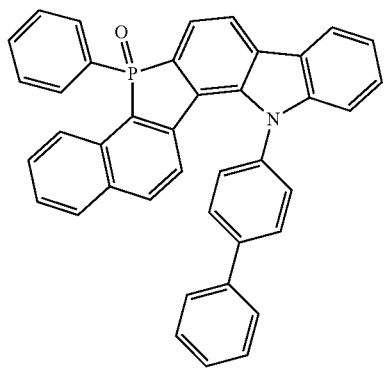
Formula 1-4-160
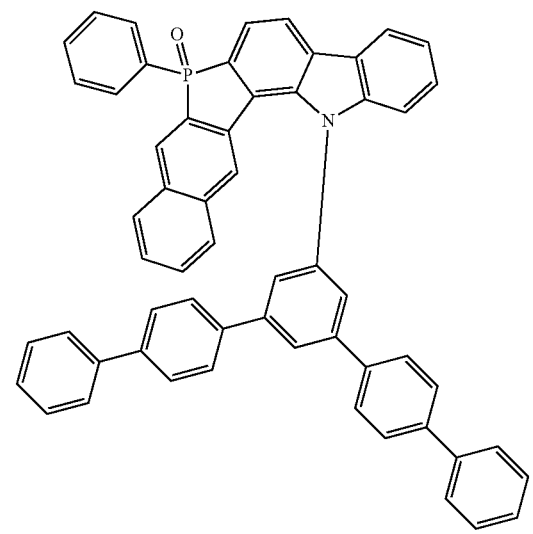
Formula 1-4-158
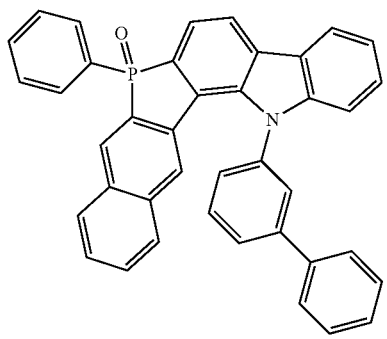
Formula 1-4-161
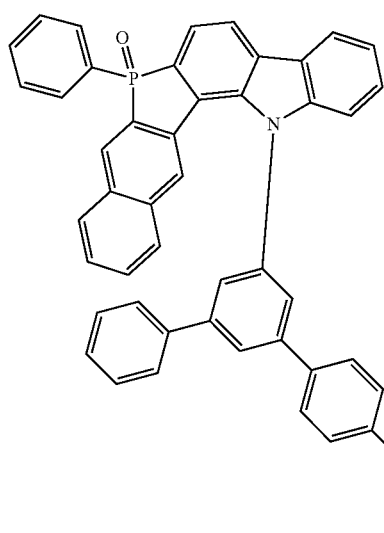
Formula 1-4-159
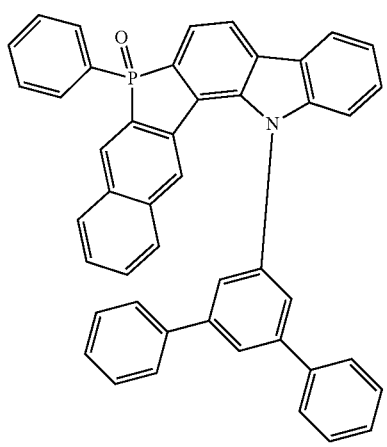
Formula 1-4-162
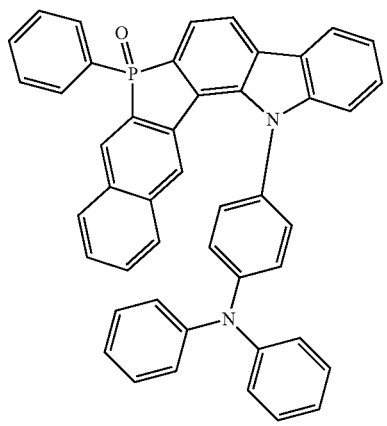

Formula 1-4-163
Formula 1-4-166
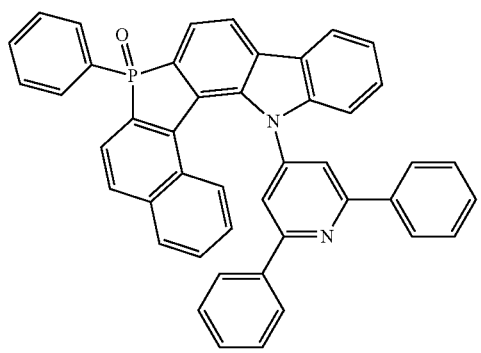
Formula 1-4-167
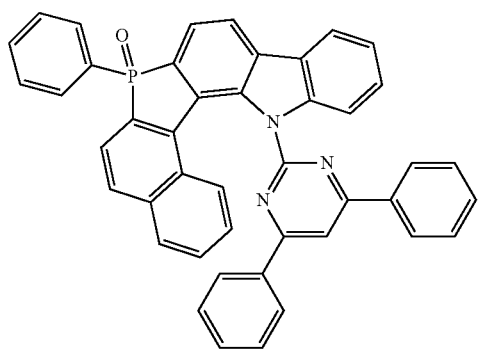
Formula 1-4-164
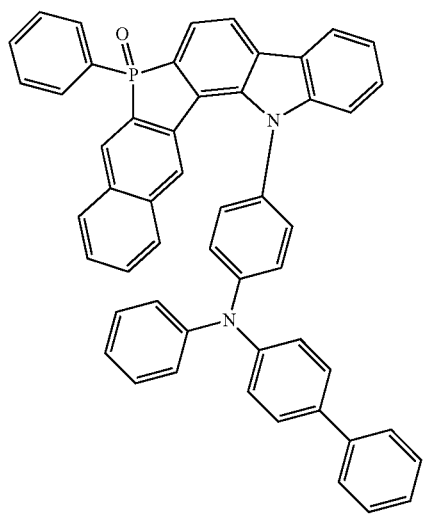
Formula 1-4-168
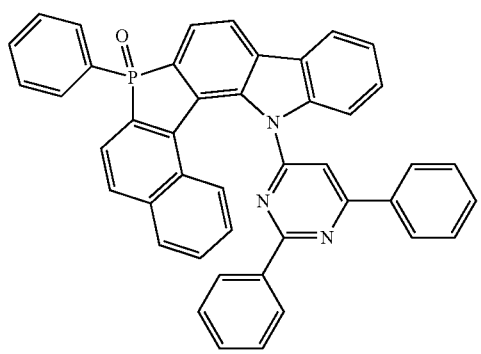
Formula 1-4-165
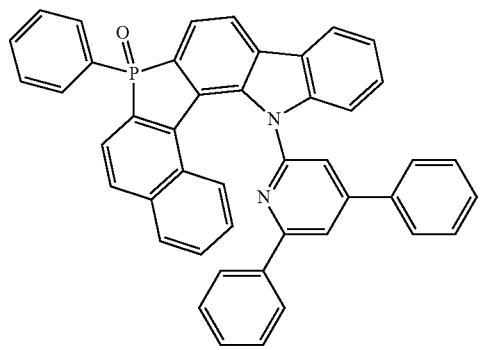
Formula 1-4-169
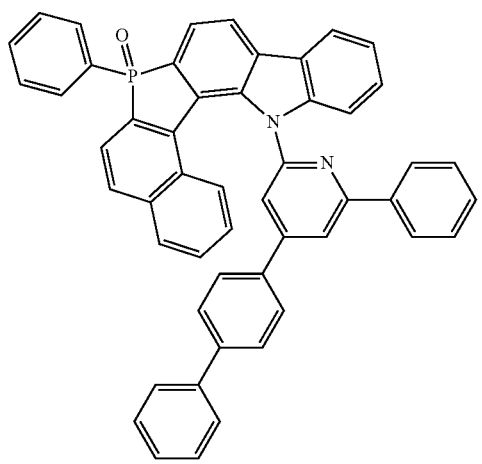

-continued
Formula 1-4-170
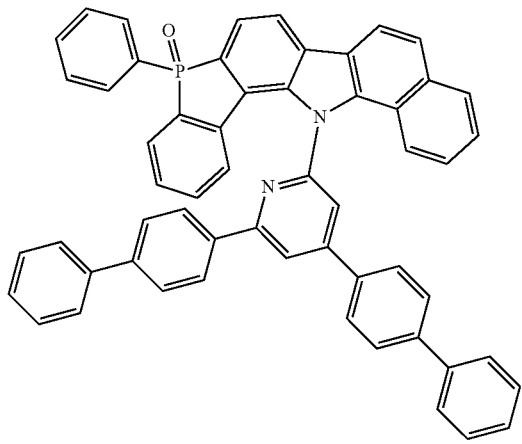
Formula 1-4-171
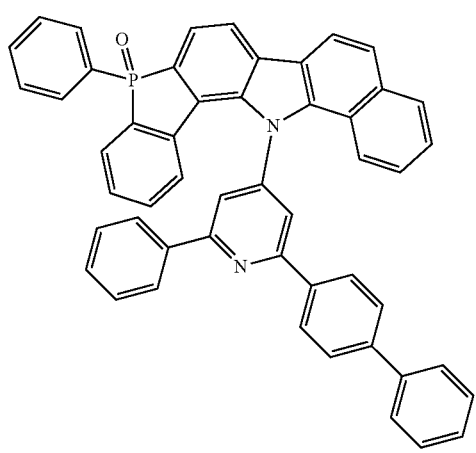
Formula 1-4-172
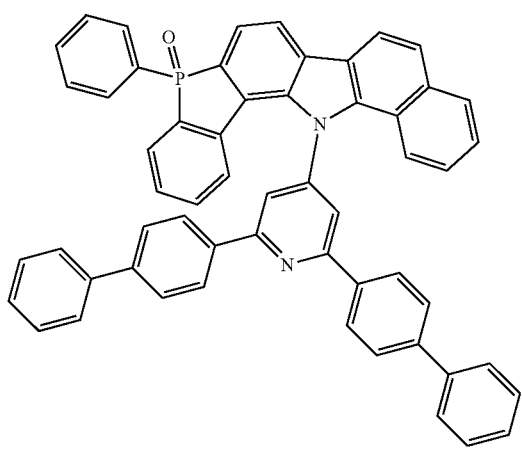
-continued
Formula 1-4-173
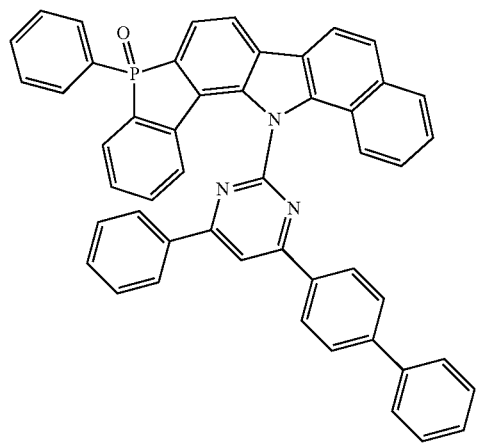
Formula 1-4-174
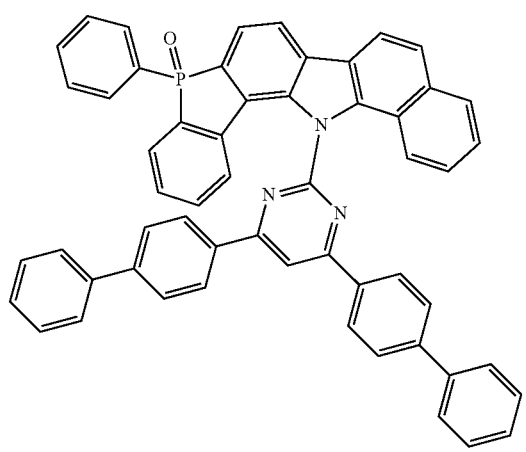
Formula 1-4-175
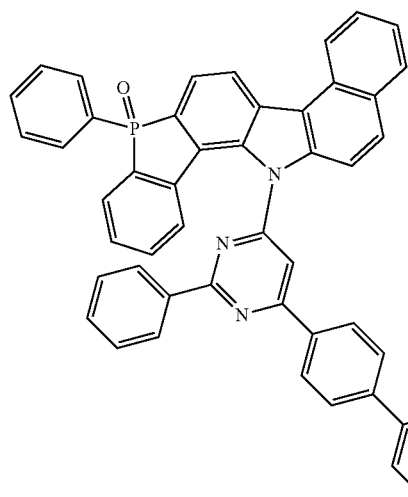

Formula 1-4-176
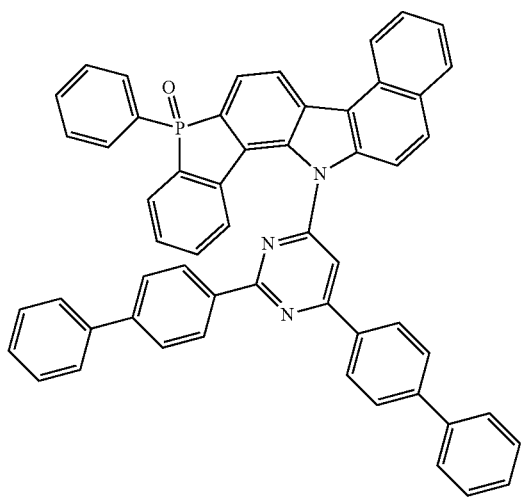
Formula 1-4-177
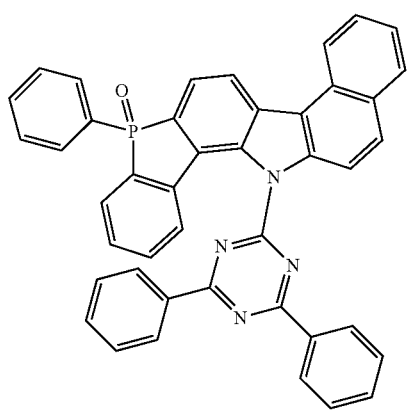
Formula 1-4-178
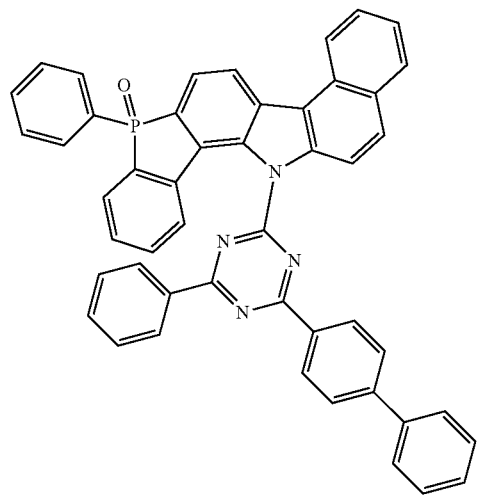
Formula 1-4-179
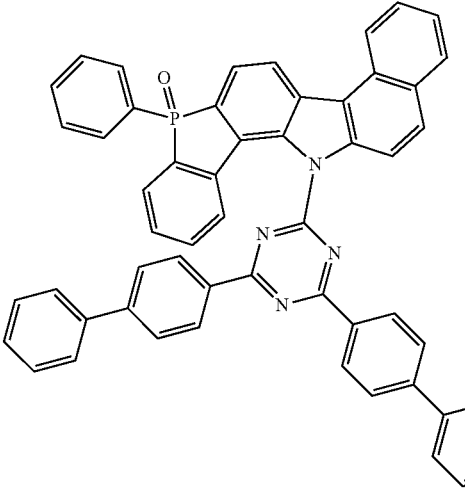
Formula 1-4-180
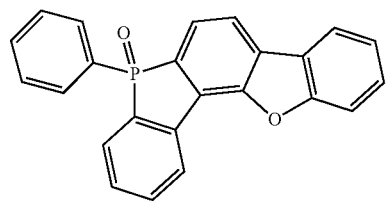
Formula 1-4-181
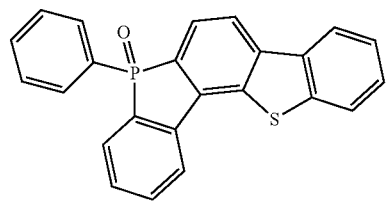
Formula 1-4-182
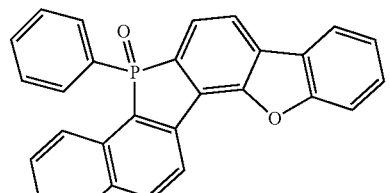
Formula 1-4-183
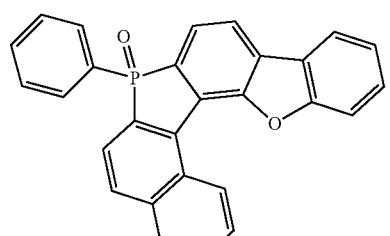
Formula 1-4-184
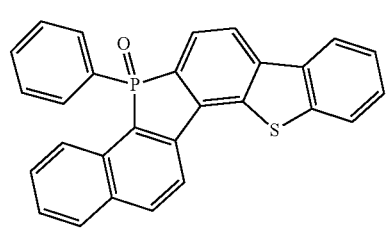

Formula 1-4-185
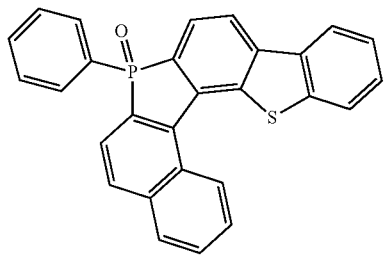
Formula 1-4-186
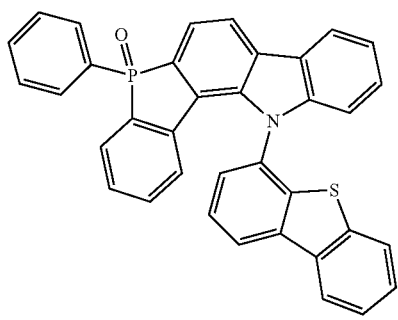
Formula 1-4-187
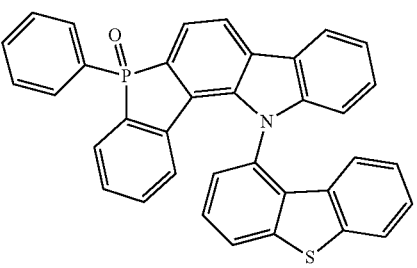
Formula 1-4-188
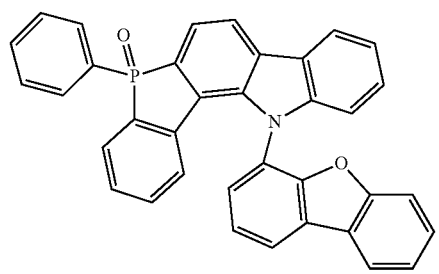
Formula 1-4-189
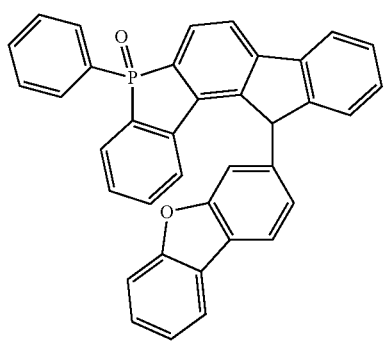
Formula 1-4-190
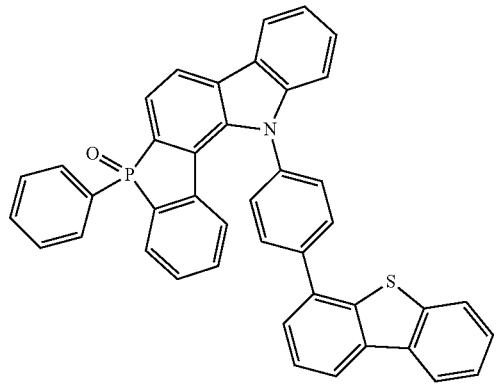
Formula 1-4-191
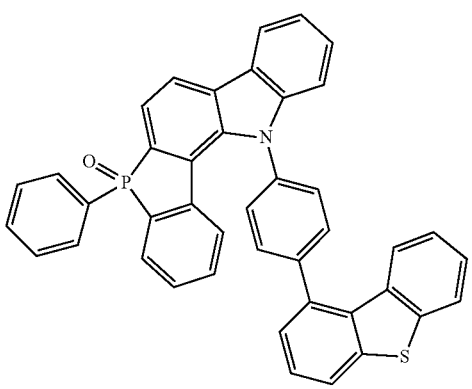
Formula 1-4-192
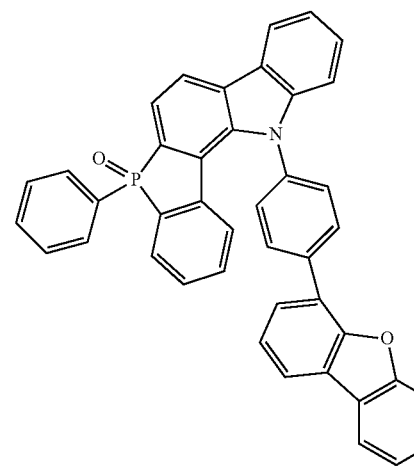

641
-continued

Formula 1-4-193

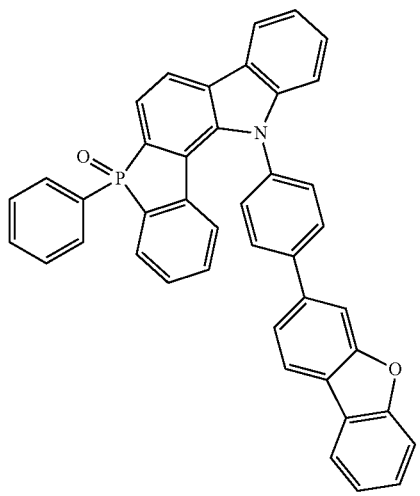

Formula 1-4-194

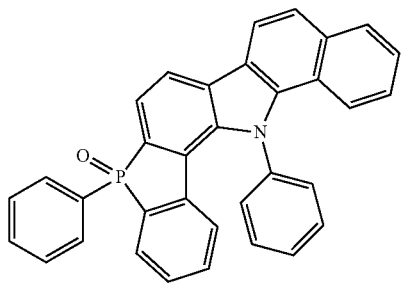

642
-continued

Formula 1-4-195

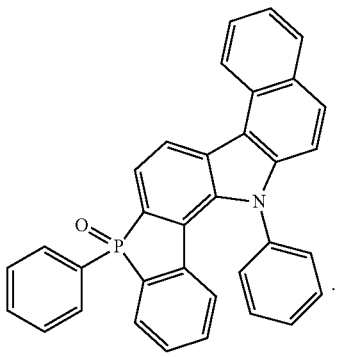

9. An organic electroluminescent device comprising:
a first electrode;
a second electrode provided to face the first electrode; and
one or more organic material layers provided between the first electrode and the second electrode,
wherein one or more layers of the organic material layers comprise the compound of claim 1.

10. The organic electroluminescent device of claim 9, wherein the organic material layer comprising the compound is a light emitting layer.

11. The organic electroluminescent device of claim 9, wherein the compound is a phosphorescent host material or a fluorescent host material.

12. The organic electroluminescent device of claim 9, wherein the organic material layer comprising the compound is an electron injection layer, an electron transporting layer or a layer which injects and transports electrons simultaneously.

13. The organic electroluminescent device of claim 9, wherein the organic material layer comprising the compound is a hole injection layer, a hole transporting layer or a layer which injects and transports holes simultaneously.

* * * * *